United States Patent
Jones et al.

(10) Patent No.: US 11,304,998 B2
(45) Date of Patent: Apr. 19, 2022

(54) COMBINATION IMMUNOTHERAPIES COMPRISING IL-15 SUPERAGONISTS

(71) Applicant: ETUBICS CORPORATION, Seattle, WA (US)

(72) Inventors: Frank R. Jones, Seattle, WA (US);
Adrian Rice, Seattle, WA (US);
Elizabeth Gabitzsch, Seattle, WA (US);
Yvette Latchman, Seattle, WA (US);
Joseph Balint, Seattle, WA (US)

(73) Assignee: Etubics Corporation, Seattle, WA (US)

( * ) Notice: Subject to any disclaimer, the term of this patent is extended or adjusted under 35 U.S.C. 154(b) by 0 days.

(21) Appl. No.: 17/240,285

(22) Filed: Apr. 26, 2021

(65) Prior Publication Data

US 2021/0260175 A1 Aug. 26, 2021

Related U.S. Application Data

(63) Continuation of application No. 16/614,909, filed as application No. PCT/US2018/034780 on May 25, 2018, now Pat. No. 11,020,467.

(60) Provisional application No. 62/511,845, filed on May 26, 2017.

(51) Int. Cl.
| | | |
|---|---|---|
| *A61K 39/00* | (2006.01) | |
| *A61P 35/00* | (2006.01) | |
| *A61K 39/39* | (2006.01) | |
| *C12N 15/86* | (2006.01) | |

(52) U.S. Cl.
CPC ...... *A61K 39/001182* (2018.08); *A61K 39/39* (2013.01); *A61P 35/00* (2018.01); *C12N 15/86* (2013.01); *A61K 2039/5256* (2013.01); *A61K 2039/53* (2013.01); *A61K 2039/55527* (2013.01)

(58) Field of Classification Search
None
See application file for complete search history.

(56) References Cited

U.S. PATENT DOCUMENTS

| | | |
|---|---|---|
| 6,524,587 B1 | 2/2003 | Lyday et al. |
| 2007/0249043 A1 | 10/2007 | Mayall |
| 2015/0374790 A1 | 12/2015 | Liu et al. |
| 2020/0155662 A1 | 5/2020 | Jones et al. |

FOREIGN PATENT DOCUMENTS

| | | |
|---|---|---|
| EP | 3630168 | 4/2020 |
| WO | WO 2016/112195 | 7/2016 |
| WO | WO 2018/218230 | 11/2018 |

OTHER PUBLICATIONS

Genbank Accession No. M29540, 1994, [Retrieved Aug. 20, 2018], 2 pages. Retrieved from: www.ncbi.nlm.nih.gov/nuccore/180222/.
QUILT-3.040: ETBX-011 (Ad5 [E1-, E2b-]-CEA(6D)) Vaccine in Combination With ALT-803 (Super-agonist IL-15) in Subjects Having CEA-Expressing Cancer, [ClinicalTrials.gov Identifier: NCT03127098], 2017, 8 pages. Retrieved from: clinicaltrials.gov/ct2/show/NCT03127098.
QUILT-3.046: NANT Melanoma Vaccine: Combination Immunotherapy in Subjects With Melanoma Who Have Progressed on or After Chemotherapy and PD-1/PD-L1 Therapy, [ClinicalTrials.gov Identifier: NCT03167177], 2017, 11 pages. Retrieved from: clinicaltrials.gov/ct2/show/NCT03167177.
Gabitzsch et al., "The Generation and Analyses of a Novel Combination of Recombinant Adenovirus Vaccines Targeting Three Tumor Antigens as an Immunotherapeutic," Oncotarget, 2015, vol. 6, No. 31, pp. 31344-31359.
Gabitzsch et al., "An Ad5 [E1-E2b-]-HER2/neu vector induces immune responses and inhibits HER2/neu expressing tumor progression in Ad5 immune mice," Cancer Gene Therapy, 2011, vol. 18(5), pp. 326-335.
Han et al., "IL-15:IL-15 receptor alpha superagonist complex: High-level co-expression in recombinant mammalian cells, purification and characterization", Cytokine, 2011, vol. 56, Iss. 3, pp. 804-810.
Kim et al., "IL-15 superagonist/IL-15RαSushi-Fcfusion complex (IL-15SA/IL-15RαSu-Fc; ALT-803) markedly enhances specific subpopulations of NK and memory CD8+ T cells, and mediates potent anti-tumor activity against murine breast and colon carcinomas", Oncotarget, 2016, vol. 7, Iss. 13, pp. 16130-16145.
International Search Report and Written Opinion for International (PCT) Patent Application No. PCT/US2018/034780 dated Sep. 17, 2018, 13 pages.
International Preliminary Report on Patentability for International (PCT) Patent Application No. PCT/US2018/034780 dated Dec. 5, 2019, 10 pages.
Official Action for Australian Patent Application No. 2018272085, dated Oct. 16, 2020 4 pages.
Notice of Allowance for Australian Patent Application No. 2018272085, dated Nov. 12, 2020 3 pages.
Official Action for Canadian Patent Application No. 3,063,735, dated Nov. 10, 2020 5 pages.
Extended European Search Report for European Patent Application No. 18804977.9 dated May 29, 2020, 9 pages.
Official Action for U.S. Appl. No. 16/614,909, dated Nov. 9, 2020 8 pages, Restriction Requirement.
Official Action for U.S. Appl. No. 16/614,909, dated Dec. 24, 2020 10 pages.
Final Action for U.S. Appl. No. 16/614,909, dated Nov. 9, 2020 8 pages.
Notice of Allowance for U.S. Appl. No. 16/614,909, dated Mar. 19, 2021 7 pages.
Official Action for Canadian Patent Application No. 3,063,735, dated Oct. 20, 2021 3 pages.

*Primary Examiner* — Elly-Gerald Stoica
(74) *Attorney, Agent, or Firm* — Sheridan Ross P.C.

(57) ABSTRACT

Methods and compositions for generating enhanced immune responses using adenovirus vectors that allow for multiple vaccinations in combination with an IL-15 superagonist complex in subjects in need thereof are provided.

9 Claims, 3 Drawing Sheets

Specification includes a Sequence Listing.

COMBINATION IMMUNOTHERAPIES COMPRISING IL-15 SUPERAGONISTS

CROSS REFERENCE

This application is a continuation of U.S. patent application Ser. No. 16/614,909, filed Nov. 19, 2019, which is a national stage application under 35 U.S.C. 371 and claims the benefit of PCT Application No. PCT/US2018/034780 having an international filing date of 25 May 2018, which designated the United States, which PCT application claimed the benefit of U.S. Provisional Patent Application No. 62/511,845, filed May 26, 2017, the entire disclosures of each of which are incorporated herein by reference in their entireties.

REFERENCE TO SEQUENCE LISTING

This application contains a Sequence Listing submitted as an electronic text file named "Seq_listing.txt", having a size in bytes of 284000 bytes, and created on May 25, 2018. The information contained in this electronic file is hereby incorporated by reference in its entirety pursuant to 37 CFR § 1.52(e)(5).

BACKGROUND

Vaccines help the body fight disease by training the immune system to recognize and destroy harmful substances and diseased cells. Vaccines can be largely grouped into two types, preventive and treatment vaccines. Preventative vaccines are given to healthy people to prevent the development of specific diseases, while treatment vaccines, also referred to as immunotherapies, are given to a person who has been diagnosed with disease to help stop the disease from growing and spreading or as a preventive. Viral vaccines are currently being developed to help fight infectious diseases and cancers. These viral vaccines work by inducing expression of a small fraction of genes associated with a disease within the host's cells, which in turn, enhance the host's immune system to identify and destroy diseased cells. As such, clinical response of a viral based vaccine can be limited by the ability of vaccine to obtain a high-level immunogenicity and have sustained long-term expression.

Cancer immunotherapy achieved by delivering viral vaccines encoding tumor-associated antigens (TAA) may have survival benefits; however, limitations to these strategies exist and more immunologically potent vaccines are needed. The present invention addresses this limitation by combining the administration of a vaccine with an IL-15 superagonist to enhance the efficacy and effectiveness of a vaccine in a patient.

SUMMARY

In various aspects, the present disclosure provides a composition comprising a first recombinant adenovirus vector comprising a nucleic acid sequence encoding an antigen, and: a) a second recombinant adenovirus vector comprising a nucleic acid sequence encoding an IL-15N72D domain of an interleukin-15 (IL-15) superagonist complex and an IL-15RαSu/Fc fusion domain of the IL-15 superagonist complex; orb) a third recombinant adenovirus vector comprising a nucleic acid sequence encoding an IL-15N72D domain of an IL-15 superagonist complex and fourth recombinant adenovirus vector comprising a nucleic acid sequence encoding an IL-15RαSu/Fc fusion domain of the IL-15 superagonist complex.

In some aspects, the antigen is a CEA antigen. In further aspects, the CEA antigen comprises at least 80%, at least 85%, at least 87%, at least 90%, at least 92%, at least 95%, at least 97%, or at least 99% sequence identity to SEQ ID NO: 3 or SEQ ID NO: 4. In some aspects, the nucleotide sequence encoding the antigen comprises at least 80%, at least 85%, at least 87%, at least 90%, at least 92%, at least 95%, at least 97%, or at least 99% sequence identity to SEQ ID NO: 1 or SEQ ID NO: 100. In some aspects, the first recombinant adenovirus vector comprises a sequence having at least 80%, at least 85%, at least 87%, at least 90%, at least 92%, at least 95%, at least 97% or at least 99% sequence identity to one of: SEQ ID NO: 2; or positions 1057 to 3165 of SEQ ID NO: 2.

In some aspects, the IL-15 superagonist complex is a multimeric protein complex. In some aspects, the multimeric protein complex comprises two IL-15N72D domains and a dimeric IL-15RαSu/Fc fusion domain, and wherein the dimeric IL-15Rα/Fc fusion domain comprises a dimer of an IL-15 Rα domain and an Fc fusion protein. In some aspects, the IL-15Rα domain is a human IL-15RαSu comprising amino acids 1-65 of a mature human IL-15Rα protein. In further aspects, the Fc fusion protein is a human IgG1 Fc protein comprising the CH2-CH3 region of human IgG1. In some aspects the CH2-CH3 region comprises 232 amino acids. In further aspects, the IL-15 superagonist complex is ALT-803.

In some aspects, the nucleic acid sequence encoding the IL-15N72D domain and the IL-15RαSu/Fc fusion domain of the second recombinant adenovirus vector encodes an amino acid sequence comprising at least 80%, at least 85%, at least 87%, at least 90%, at least 92%, at least 95%, at least 97%, or at least 99% sequence identity to SEQ ID NO: 110. In further aspects, the nucleic acid sequence encoding the IL-15N72D domain and the IL-15RαSu/Fc fusion domain of the second recombinant adenovirus vector comprises at least 80%, at least 85%, at least 87%, at least 90%, at least 92%, at least 95%, at least 97%, or at least 99% sequence identity to SEQ ID NO: 109.

In some aspects, the nucleic acid sequence encoding the IL-15N72D domain of the third recombinant adenovirus vector encodes an amino acid sequence comprising at least 80%, at least 85%, at least 87%, at least 90%, at least 92%, at least 95%, at least 97%, or at least 99% sequence identity to SEQ ID NO: 81. In further aspects, the nucleic acid sequence encoding the IL-15N72D domain comprises at least 80%, at least 85%, at least 87%, at least 90%, at least 92%, at least 95%, at least 97%, or at least 99% sequence identity to SEQ ID NO: 107.

In some aspects, the nucleic acid sequence encoding the IL-15RαSu/Fc fusion domain of the fourth recombinant adenovirus vector encodes an amino acid sequence comprising at least 80%, at least 85%, at least 87%, at least 90%, at least 92%, at least 95%, at least 97%, or at least 99% sequence identity to SEQ ID NO: 82. In further aspects, the nucleic acid sequence encoding the IL-15RαSu/Fc fusion domain comprises at least 80%, at least 85%, at least 87%, at least 90%, at least 92%, at least 95%, at least 97%, or at least 99% sequence identity to SEQ ID NO: 108.

In some aspects, the IL-15 superagonist complex exhibits a median effective concentration ($EC_{50}$) for supporting IL-15-dependent cell growth that is greater than 2-fold lower, greater than 3-fold lower, greater than 4-fold lower, greater than 5-fold lower, greater than 6-fold lower, greater than 7-fold lower, greater than 8-fold lower, greater than 9-fold lower, greater than 10-fold lower, greater than 15-fold lower, greater than 20-fold lower, greater than 25-fold lower, greater than 30-fold lower, greater than 35-fold lower, greater than 40-fold lower, greater than 45-fold lower, greater than 50-fold lower, greater than 55-fold lower, greater than 60-fold lower, greater than 65-fold lower, greater than 70-fold lower, greater than 75-fold lower, greater than 80-fold lower, greater than 85-fold lower, greater than 90-fold lower, greater than 95-fold lower, or greater than 100-fold lower than the $EC_{50}$ of a free IL-15 cytokine.

In some aspects, the IL-15 superagonist complex exhibits a median effective concentration ($EC_{50}$) for supporting IL-15-dependent cell growth that is greater than 10-fold lower than the $EC_{50}$ of a free IL-15 cytokine. In some aspects, the first recombinant adenovirus vector, the second recombinant adenovirus vector, the third recombinant adenovirus vector, and the fourth recombinant adenovirus vector comprise recombinant replication defective adenovirus vectors. In some aspects, the recombinant replication defective adenovirus vectors are adenovirus subtype 5 (Ad5)-based vectors. In further aspects, the first recombinant adenovirus vector, the second recombinant adenovirus vector, the third recombinant adenovirus vector, and the fourth recombinant adenovirus vector comprise a deletion in an E1 region, and E2b region, an E3 region, an E4 region, or any combination thereof.

In some aspects, the first recombinant adenovirus vector, the second recombinant adenovirus vector, the third recombinant adenovirus vector, and the fourth recombinant adenovirus vector comprises a deletion in an E1 region. In further aspects, the first recombinant adenovirus vector, the second recombinant adenovirus vector, the third recombinant adenovirus vector, and the fourth recombinant adenovirus vector comprises a deletion in an E1 region and E2b region.

In some aspects, the composition comprises at least $1\times10^9$ viral particles, at least $1\times10^{10}$ viral particles, at least $1\times10^{11}$ viral particles, at least $5\times10^{11}$ viral particles, at least $1\times10^{12}$ viral particles, or at least $5\times10^{12}$ viral particles in a single dose. In further aspects, the composition comprises $1\times10^9$-$5\times10^{12}$ viral particles in a single dose.

In some aspects, the composition further comprises a nucleic acid sequence encoding one or more additional target antigens or immunological epitopes thereof. In some aspects, the recombinant first adenovirus vector further comprises a nucleic acid sequence encoding one or more additional target antigens or immunological epitopes thereof. In some aspects, the composition further comprises a fifth recombinant adenovirus vector comprising a nucleic acid sequence encoding one or more additional target antigens or immunological epitopes thereof. In some aspects, the fifth recombinant adenovirus vector comprises an adenovirus subtype 5 (Ad5)-based vector. In further aspects, the adenovirus subtype 5 (Ad5)-based vector comprises a deletion in an E1 region, an E2b region, an E3 region, an E4 region, or any combination thereof.

In some aspects, the composition further comprises a sixth recombinant adenovirus vector comprising a nucleic acid sequence encoding one or more additional target antigens or immunological epitopes thereof. In some aspects, the sixth recombinant adenovirus vector comprises an adenovirus subtype 5 (Ad5)-based vector. In further aspects, the adenovirus subtype 5 (Ad5)-based vector comprises a deletion in an E1 region, an E2b region, an E3 region, an E4 region, or any combination thereof.

In further aspects, the additional target antigen is a tumor neo-antigen, tumor-neo-epitope, tumor-specific, tumor-specific antigen, tumor-associated antigen, tissue-specific antigen, bacterial antigen, viral antigen, yeast antigen, fungal antigen, protozoan antigen, parasite antigen, mitogen, or a combination thereof.

In further aspects, the additional target antigen is human epidermal growth factor receptor 1 (HER1), human epidermal growth factor receptor 2 (HER2/neu), human epidermal growth factor receptor 3 (HER3), human epidermal growth factor receptor 4 (HER4), prostate-specific antigen (PSA), PSMA, folate receptor alpha, WT1, p53, MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-8, GAGE-3, GAGE-4, GAGE-5, GAGE-6, GAGE-7B, NA88-A, NY-ESO-1, MART-1, MC1R, Gp100, PSA, PSM, Tyrosinase, TRP-1, TRP-2, ART-4, CAMEL, CEA, Cyp-B, BRCA1, Brachyury, Brachyury (TIVS7-2, polymorphism), Brachyury (IVS7 T/C polymorphism), T Brachyury, T, hTERT, hTRT, iCE, MUC1, MUC1 (VNTR polymorphism), MUC1c, MUC1n, MUC2, PRAME, P15, RUL RU2, SART-1, SART-3, AFP, β-catenin/m, Caspase-8/m, CDK-4/m, ELF2M, GnT-V, G250, HSP70-2M, HST-2, KIAAO205, MUM-1, MUM-2, MUM-3, Myosin/m, RAGE, SART-2, TRP-2/INT2, 707-AP, Annexin II, CDC127/m, TPI/mbcr-abl, ETV6/AML, LDLR/FUT, Pml/RARα, HPV E6, HPV E7, and TEL/AML1.

In some aspects, the fifth recombinant adenovirus vector comprises a nucleic acid sequence encoding for a MUC1-C antigen. In further aspects, the MUC1-C antigen comprises at least 80%, at least 85%, at least 87%, at least 90%, at least 92%, at least 95%, at least 97%, or at least 99% sequence identity to SEQ ID NO: 7. In some aspects, the nucleic acid sequence encoding for the MUC1-C antigen comprises at least 80%, at least 85%, at least 87%, at least 90%, at least 92%, at least 95%, at least 97%, or at least 99% sequence identity to SEQ ID NO: 5, SEQ ID NO: 6, or SEQ ID NO: 101.

In still further aspects, the MUC1-C antigen is a modified MUC1 antigen comprising at least 80%, at least 85%, at least 87%, at least 90%, at least 92%, at least 95%, at least 97%, or at least 99% sequence identity to SEQ ID NO: 7. In some aspects, the modified MUC1 antigen is encoded for by a nucleic acid sequence comprising at least 80%, at least 85%, at least 87%, at least 90%, at least 92%, at least 95%, at least 97%, or at least 99% sequence identity to SEQ ID NO: 5, SEQ ID NO: 6, or SEQ ID NO: 101.

In still further aspects, the MUC-1 antigen is a modified antigen having one or more mutations at positions 93, 141-142, 149-151, 392, 404, 406, 422, 430-431, 444-445, or 460 of SEQ ID NO: 7.

In still further aspects, the fifth recombinant adenovirus vector comprises at least 80%, at least 85%, at least 87%, at least 90%, at least 92%, at least 95%, at least 97%, or at least 99% sequence identity to positions 1105-2532 of SEQ ID NO: 8. In some aspects, the fifth recombinant adenovirus vector comprises at least 80%, at least 85%, at least 87%, at least 90%, at least 92%, at least 95%, at least 97%, or at least 99% sequence identity to SEQ ID NO: 8.

In some aspects, the MUC1-C antigen binds to HLA-A2, HLA-A3, HLA-A24, or a combination thereof.

In some aspects, the sixth recombinant adenovirus vector comprises a nucleic acid sequence encoding for a Brachyury antigen. In further aspects, the Brachyury antigen comprises at least 80%, at least 85%, at least 87%, at least 90%, at least 92%, at least 95%, at least 97%, or at least 99% sequence identity to SEQ ID NO: 12 or SEQ ID NO: 14. In some aspects, the nucleic acid sequence encoding for the Brachyury antigen comprises at least 80%, at least 85%, at least 87%, at least 90%, at least 92%, at least 95%, at least 97%, or at least 99% sequence identity to SEQ ID NO: 9, SEQ ID NO: 10, or SEQ ID NO: 102.

In still further aspects, the Brachyury antigen is a modified Brachyury antigen having an amino acid sequence at least 80%, at least 85%, at least 87%, at least 90%, at least 92%, at least 95%, at least 97%, or at least 99% sequence identity to SEQ ID NO: 14 or SEQ ID NO: 102.

In some aspects, the sixth recombinant adenovirus vector comprises at least 80%, at least 85%, at least 87%, at least 90%, at least 92%, at least 95%, at least 97%, or at least 99% sequence identity to positions 1045 to 2277 of SEQ ID NO: 13. In some aspects, the sixth recombinant adenovirus vector comprises at least 80%, at least 85%, at least 87%, at least 90%, at least 92%, at least 95%, at least 97%, or at least 99% sequence identity to SEQ ID NO: 13.

In some aspects, the sixth recombinant adenovirus vector comprises a nucleotide sequence at least 80%, at least 85%, at least 87%, at least 90%, at least 92%, at least 95%, at least 97%, or at least 99% sequence identity to positions 520-1824 of SEQ ID NO: 9. In some aspects, the Brachyury antigen is a modified Brachyury antigen comprising an amino acid sequence set forth in WLLPGTSTV (SEQ ID NO: 15). In some aspects, the Brachyury antigen binds to HLA-A2.

In some aspects, the composition or the first recombinant adenovirus vector further comprises a nucleic acid sequence encoding a costimulatory molecule. In further aspects, the costimulatory molecule comprises B7, ICAM-1, LFA-3, or a combination thereof. In still further aspects, the costimulatory molecule comprises a combination of B7, ICAM-1, and LFA-3. In some aspects, the composition further comprises a plurality of nucleic acid sequences encoding a plurality of costimulatory molecules positioned in the first recombinant adenovirus vector. In some aspects, the composition further comprises a plurality of nucleic acid sequences encoding a plurality of costimulatory molecules positioned in separate recombinant adenovirus vectors.

In some aspects, the composition further comprises an immune pathway checkpoint modulator. In some aspects, the immune pathway checkpoint modulator activates or potentiates an immune response. In other aspects, the immune pathway checkpoint inhibits an immune response. In some aspects, the immune pathway checkpoint modulator targets an endogenous immune pathway checkpoint protein or fragment thereof selected from the group consisting of: PD1, PDL1, PDL2, CD28, CD80, CD86, CTLA4, B7RP1, ICOS, B7RPI, B7-H3, B7-H4, BTLA, HVEM, KIR, TCR, LAG3, CD137, CD137L, OX40, OX40L, CD27, CD70, CD40, CD40L, TIM3, GAL9, ADORA, CD276, VTCN1, IDO1, KIR3DL1, HAVCR2, VISTA, and CD244. In further aspects, the immune pathway checkpoint modulator targets a PD1 protein.

In some aspects, the immune pathway checkpoint modulator comprises siRNAs, antisense, small molecules, mimic, a recombinant form of a ligand, a recombinant form of a receptor, antibodies, or a combination thereof. In some aspects, the immune pathway checkpoint inhibitor is an anti-PD-1 antibody or an anti-PD-L1 antibody. In further aspects, the immune pathway checkpoint inhibitor is Avelumab. In some aspects, the immune response is increased at least 2-, at least 3-, at least 4-, at least 5-, at least 6-, at least 7-, at least 8-, at least 9-, at least 10-, at least 15-, at least 20-, or at least 25-fold.

In some aspects, the composition further comprises an anti-CEA antibody. In further aspects, the anti-CEA antibody is NEO-201, COL1, COL2, COL3, COL4, COLS, COLE, COLT, COLS, COLS, COL10, COL11, COL12, COL13, COL14, COL15, arcitumomab, besilesomab, labetuzumab, or altumomab. In still further aspects, the anti-CEA antibody is NEO-201

In some aspects, the composition further comprises a chemotherapeutic agent. In further aspects, the chemotherapeutic agent is 5-FU, leucovorin, or oxaliplatin, or any combination thereof.

In some aspects, the composition further comprises a population of engineered natural killer (NK) cells. In further aspects, the engineered NK cells comprise one or more NK cells that have been modified as essentially lacking the expression of KIR (killer inhibitory receptors), one or more NK cells that have been modified to express a high affinity CD16 variant, and one or more NK cells that have been modified to express one or more CARs (chimeric antigen receptors), or any combinations thereof. In still further aspects, the engineered NK cells comprise one or more NK cells that have been modified as essentially lacking the expression KIR. In further aspects, the engineered NK cells comprise one or more NK cells that have been modified to express a high affinity CD16 variant. In further aspects, the engineered NK cells comprise one or more NK cells that have been modified to express one or more CARs.

In some aspects, the CAR is a CAR for a tumor neoantigen, tumor neo-epitope, WT1, p53, MAGE-A1, MAGE-A2, MAGE-A3, MAGE-A4, MAGE-A6, MAGE-A10, MAGE-A12, BAGE, DAM-6, DAM-10, Folate receptor alpha, GAGE-1, GAGE-2, GAGE-8, GAGE-3, GAGE-4, GAGE-5, GAGE-6, GAGE-7B, NA88-A, NY-ESO-1, MART-1, MC1R, Gp100, Tyrosinase, TRP-1, TRP-2, ART-4, CAMEL, CEA, Cyp-B, Her2/neu, Her3, BRCA1, Brachyury, Brachyury (TIVS7-2, polymorphism), Brachyury (IVS7 T/C polymorphism), T Brachyury, T, hTERT, hTRT, iCE, MUC1, MUC1 (VNTR polymorphism), MUC1c, MUC1n, MUC2, PRAME, P15, RUL RU2, SART-1, SART-3, AFP, β-catenin/m, Caspase-8/m, CDK-4/m, ELF2M, GnT-V, G250, HSP70-2M, HST-2, KIAAO205, MUM-1, MUM-2, MUM-3, Myosin/m, RAGE, SART-2, TRP-2/INT2, 707-AP, Annexin II, CDC127/m, TP1/mbcr-abl, ETV6/AML, LDLR/FUT, Pml/RARα, TEL/AML1, or any combination thereof.

In various aspects, the present disclosure provides a method of treating a subject in need thereof, the method comprising administering to the subject any one of the above compositions.

In various aspects, the present disclosure provides method of treating a subject in need thereof, the method comprising administering to the subject a first recombinant adenovirus vector comprising a nucleic acid sequence encoding an antigen, and: a) a second recombinant adenovirus vector comprising a nucleic acid sequence encoding an IL-15N72D domain of an interleukin-15 (IL-15) superagonist complex and an IL-15RαSu/Fc fusion domain of the IL-15 superagonist complex; or b) a third recombinant adenovirus vector comprising a nucleic acid sequence encoding an IL-15N72D domain of an IL-15 superagonist complex and fourth recombinant adenovirus vector comprising a nucleic acid sequence encoding an IL-15RαSu/Fc fusion domain of the IL-15 superagonist complex.

In some aspects, the antigen is a CEA antigen. In further aspects, the CEA antigen comprises at least 80%, at least 85%, at least 87%, at least 90%, at least 92%, at least 95%, at least 97%, or at least 99% sequence identity to SEQ ID NO: 3 or SEQ ID NO: 4. In further aspects, the nucleic acid sequence encoding the antigen comprises at least 80%, at least 85%, at least 87%, at least 90%, at least 92%, at least 95%, at least 97% or at least 99% sequence identity to SEQ ID NO: 1 or SEQ ID NO: 100. In still further aspects, the first recombinant adenovirus vector comprises a sequence having at least 80%, at least 85%, at least 87%, at least 90%, at least 92%, at least 95%, at least 97% or at least 99% sequence identity to one of: SEQ ID NO: 2; or positions 1057 to 3165 of SEQ ID NO: 2.

In some aspects, the IL-15 superagonist complex is a multimeric protein complex. In further aspects, the multimeric protein complex comprises two IL-15N72D domains and a dimeric IL-15RαSu/Fc fusion domain, and wherein the dimeric IL-15Rα/Fc fusion domain comprises a dimer of an IL-15 Rα domain and an Fc fusion protein. In still further aspects, the IL-15Rα domain is a human IL-15RαSu comprising amino acids 1-65 of a mature human IL-15Rα protein. In still further aspects, the Fc fusion protein is a human IgG1 Fc protein comprising the CH2-CH3 region of human IgG1. In still further aspects, the CH2-CH3 region comprises 232 amino acids.

In some aspects, the IL-15 superagonist complex is ALT-803.

In some aspects, the nucleic acid sequence encoding the IL-15N72D domain and the IL-15RαSu/Fc fusion domain of the second recombinant adenovirus vector encodes an amino acid sequence comprising at least 80%, at least 85%, at least 87%, at least 90%, at least 92%, at least 95%, at least 97%, or at least 99% sequence identity to SEQ ID NO: 110. In further aspects, the nucleic acid sequence encoding the IL-15N72D domain and the IL-15RαSu/Fc fusion domain of the second recombinant adenovirus vector comprises at least 80%, at least 85%, at least 87%, at least 90%, at least 92%, at least 95%, at least 97%, or at least 99% sequence identity to SEQ ID NO: 109.

In some aspects, the nucleic acid sequence encoding the IL-15N72D domain of the third recombinant adenovirus vector encodes an amino acid sequence comprising at least 80%, at least 85%, at least 87%, at least 90%, at least 92%, at least 95%, at least 97%, or at least 99% sequence identity to SEQ ID NO: 81. In further aspects, the nucleic acid sequence encoding the IL-15N72D domain comprises at least 80%, at least 85%, at least 87%, at least 90%, at least 92%, at least 95%, at least 97%, or at least 99% sequence identity to SEQ ID NO: 107.

In some aspects, the nucleic acid sequence encoding the IL-15RαSu/Fc fusion domain of the fourth recombinant adenovirus vector encodes an amino acid sequence comprising at least 80%, at least 85%, at least 87%, at least 90%, at least 92%, at least 95%, at least 97%, or at least 99% sequence identity to SEQ ID NO: 82. In further aspects, the nucleic acid sequence encoding the IL-15RαSu/Fc fusion domain comprises at least 80%, at least 85%, at least 87%, at least 90%, at least 92%, at least 95%, at least 97%, or at least 99% sequence identity to SEQ ID NO: 108.

In some aspects, the IL-15 superagonist complex exhibits a median effective concentration ($EC_{50}$) for supporting IL-15-dependent cell growth that is greater than 2-fold lower, greater than 3-fold lower, greater than 4-fold lower, greater than 5-fold lower, greater than 6-fold lower, greater than 7-fold lower, greater than 8-fold lower, greater than 9-fold lower, greater than 10-fold lower, greater than 15-fold lower, greater than 20-fold lower, greater than 25-fold lower, greater than 30-fold lower, greater than 35-fold lower, greater than 40-fold lower, greater than 45-fold lower, greater than 50-fold lower, greater than 55-fold lower, greater than 60-fold lower, greater than 65-fold lower, greater than 70-fold lower, greater than 75-fold lower, greater than 80-fold lower, greater than 85-fold lower, greater than 90-fold lower, greater than 95-fold lower, or greater than 100-fold lower than the $EC_{50}$ of a free IL-15 cytokine. In some aspects, the IL-15 superagonist complex exhibits a median effective concentration ($EC_{50}$) for supporting IL-15-dependent cell growth that is greater than 10-fold lower than the $EC_{50}$ of a free IL-15 cytokine.

In some aspects, the first recombinant adenovirus vector, the second recombinant adenovirus vector, the third recombinant adenovirus vector, and the fourth recombinant adenovirus vector comprise recombinant replication defective adenovirus vectors. In some aspects, the recombinant replication defective adenovirus vectors are adenovirus subtype 5 (Ad5)-based vectors. In further aspects, the first recombinant adenovirus vector, the second recombinant adenovirus vector, the third recombinant adenovirus vector, and the fourth recombinant adenovirus vector comprise a deletion in an E1 region, and E2b region, an E3 region, an E4 region, or any combination thereof.

In some aspects, the first recombinant adenovirus vector, the second recombinant adenovirus vector, the third recombinant adenovirus vector, and the fourth recombinant adenovirus vector comprises a deletion in an E1 region. In further aspects, the first recombinant adenovirus vector, the second recombinant adenovirus vector, the third recombinant adenovirus vector, and the fourth recombinant adenovirus vector comprises a deletion in an E1 region and E2b region. In some aspects, the method comprises administering at least $1 \times 10^9$ viral particles, at least $1 \times 10^{10}$ viral particles, at least $1 \times 10^{11}$ viral particles, or $5 \times 10^{11}$ viral particles of the recombinant adenovirus vector in a single dose. In some aspects, the method comprises administering $1 \times 10^9$-$5 \times 10^{11}$ viral particles of the recombinant adenovirus vector in a single dose. In some aspects, the method further comprises administering to the subject a nucleic acid sequence encoding one or more additional target antigens or immunological epitopes thereof. In some aspects, the first recombinant adenovirus vector further comprises a nucleic acid sequence encoding one or more additional target antigens or immunological epitopes thereof.

In some aspects, the method further comprises administering to the subject a fifth recombinant adenovirus vector comprising a nucleic acid sequence encoding one or more additional target antigens or immunological epitopes thereof. In some aspects, the fifth recombinant adenovirus vector comprises an adenovirus subtype 5 (Ad5)-based vector. In further aspects, the adenovirus subtype 5 (Ad5)-based vector comprises a deletion in an E1 region, an E2b region, an E3 region, an E4 region, or any combination thereof.

In some aspects, the method further comprises administering to the subject a sixth recombinant adenovirus vector comprising a nucleic acid sequence encoding one or more additional target antigens or immunological epitopes thereof. In some aspects, the sixth recombinant adenovirus vector comprises an adenovirus subtype 5 (Ad5)-based vector. In further aspects, the adenovirus subtype 5 (Ad5)-based vector comprises a deletion in an E1 region, an E2b region, an E3 region, an E4 region, or any combination thereof.

In some aspects, the additional target antigen is a tumor neo-antigen, tumor-neo-epitope, tumor-specific, tumor-specific antigen, tumor-associated antigen, tissue-specific antigen, bacterial antigen, viral antigen, yeast antigen, fungal antigen, protozoan antigen, parasite antigen, mitogen, or a combination thereof.

In some aspects, the additional target antigen is human epidermal growth factor receptor 1 (HER1), human epidermal growth factor receptor 2 (HER2/neu), human epidermal growth factor receptor 3 (HER3), human epidermal growth factor receptor 4 (HER4), prostate-specific antigen (PSA), PSMA, folate receptor alpha, WT1, p53, MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-8, GAGE-3, GAGE-4, GAGE-5, GAGE-6, GAGE-7B, NA88-A, NY-ESO-1, MART-1, MC1R, Gp100, PSA, PSM, Tyrosinase, TRP-1, TRP-2, ART-4, CAMEL, CEA, Cyp-B, BRCA1, Brachyury, Brachyury (TIVS7-2, polymorphism), Brachyury (IVS7 T/C polymorphism), T Brachyury, T, hTERT, hTRT, iCE, MUC1, MUC1 (VNTR polymorphism), MUC1c, MUC1n, MUC2, PRAME, P15, RU1, RU2, SART-1, SART-3, AFP, β-catenin/m, Caspase-8/m, CDK-4/m, ELF2M, GnT-V, G250, HSP70-2M, HST-2, KIAAO205, MUM-1, MUM-2, MUM-3, Myosin/m, RAGE, SART-2, TRP-2/INT2, 707-AP, Annexin II, CDC127/m, TPI/mbcr-abl, ETV6/AML, LDLR/FUT, Pml/RARα, HPV E6, HPV E7, and TEL/AML1.

In some aspects, the fifth recombinant adenovirus vector comprises a nucleic acid sequence encoding for a MUC1-C antigen. In further aspects, the MUC1-C antigen comprises at least 80%, at least 85%, at least 87%, at least 90%, at least 92%, at least 95%, at least 97%, or at least 99% sequence identity to SEQ ID NO: 7. In further aspects, the nucleic acid sequence encoding for the MUC1-C antigen comprises at least 80%, at least 85%, at least 87%, at least 90%, at least 92%, at least 95%, at least 97%, or at least 99% sequence identity to SEQ ID NO: 5, SEQ ID NO: 6, or SEQ ID NO: 101. In some aspects, the MUC1-C antigen is a modified MUC1 antigen comprising at least 80%, at least 85%, at least 87%, at least 90%, at least 92%, at least 95%, at least 97%, or at least 99% sequence identity to SEQ ID NO: 7. In some aspects, the modified MUC1 antigen is encoded for by a nucleic acid sequence comprising at least 80%, at least 85%, at least 87%, at least 90%, at least 92%, at least 95%, at least 97%, or at least 99% sequence identity to SEQ ID NO: 5, SEQ ID NO: 6, or SEQ ID NO: 101. In some aspects, the MUC-1 antigen is a modified antigen having one or more mutations at positions 94, 141-142, 149-151, 392, 404, 406, 422, 430-431, 444-445, or 460 of SEQ ID NO: 7.

In some aspects, the fifth recombinant adenovirus vector comprises at least 80%, at least 85%, at least 87%, at least 90%, at least 92%, at least 95%, at least 97%, or at least 99% sequence identity to positions 1105-2532 of SEQ ID NO: 8. In some aspects, the fifth recombinant adenovirus vector comprises at least 80%, at least 85%, at least 87%, at least 90%, at least 92%, at least 95%, at least 97%, or at least 99% sequence identity to SEQ ID NO: 8. In some aspects, the MUC1-C antigen binds to HLA-A2, HLA-A3, HLA-A24, or a combination thereof.

In some aspects, the sixth recombinant adenovirus vector comprises a nucleic acid sequence encoding for a Brachyury antigen. In some aspects, the Brachyury antigen comprises at least 80%, at least 85%, at least 87%, at least 90%, at least 92%, at least 95%, at least 97%, or at least 99% sequence identity to SEQ ID NO: 12 or SEQ ID NO: 14. In some aspects, the nucleic acid sequence encoding for the Brachyury antigen comprises at least 80%, at least 85%, at least 87%, at least 90%, at least 92%, at least 95%, at least 97%, or at least 99% sequence identity to SEQ ID NO: 9, SEQ ID NO: 10, or SEQ ID NO: 102. In further aspects, the Brachyury antigen is a modified Brachyury antigen having an amino acid sequence at least 80%, at least 85%, at least 87%, at least 90%, at least 92%, at least 95%, at least 97%, or at least 99% sequence identity to SEQ ID NO: 14 or SEQ ID NO: 102. In some aspects, the sixth recombinant adenovirus vector comprises at least 80%, at least 85%, at least 87%, at least 90%, at least 92%, at least 95%, at least 97%, or at least 99% sequence identity to positions 1045 to 2277 of SEQ ID NO: 13. In further aspects, the sixth recombinant adenovirus vector comprises at least 80%, at least 85%, at least 87%, at least 90%, at least 92%, at least 95%, at least 97%, or at least 99% sequence identity to SEQ ID NO: 13.

In some aspects, the sixth recombinant adenovirus vector comprises a nucleotide sequence at least 80%, at least 85%, at least 87%, at least 90%, at least 92%, at least 95%, at least 97%, or at least 99% sequence identity to positions 520-1824 of SEQ ID NO: 9. In some aspects, the Brachyury antigen is a modified Brachyury antigen comprising an amino acid sequence set forth in WLLPGTSTV (SEQ ID NO: 15).

In some aspects, the Brachyury antigen binds to HLA-A2.

In some aspects, the method further comprises administering the first recombinant adenovirus vector, wherein the first recombinant adenovirus vector further comprises a nucleic acid sequence encoding a costimulatory molecule. In further aspects, the costimulatory molecule comprises B7, ICAM-1, LFA-3, or a combination thereof. In some aspects, the costimulatory molecule comprises a combination of B7, ICAM-1, and LFA-3. In some aspects, the method further comprises administering to the subject a plurality of nucleic acid sequences encoding a plurality of costimulatory molecules positioned in the first recombinant adenovirus vector. In some aspects, the method further comprises administering to the subject a plurality of nucleic acid sequences encoding a plurality of costimulatory molecules positioned in separate recombinant adenovirus vectors.

In some aspects, the method further comprises administering to the subject an immune pathway checkpoint modulator. In further aspects, the immune pathway checkpoint modulator activates or potentiates an immune response. In some aspects, the immune pathway checkpoint inhibits an immune response. In some aspects, the immune pathway checkpoint modulator targets an endogenous immune pathway checkpoint protein or fragment thereof selected from the group consisting of: PD1, PDL1, PDL2, CD28, CD80, CD86, CTLA4, B7RP1, ICOS, B7RPI, B7-H3, B7-H4, BTLA, HVEM, KIR, TCR, LAG3, CD137, CD137L, OX40, OX40L, CD27, CD70, CD40, CD40L, TIM3, GALS, ADORA, CD276, VTCN1, IDO1, KIR3DL1, HAVCR2, VISTA, and CD244.

In some aspects, the immune pathway checkpoint modulator targets a PD1 protein. In some aspects, the immune pathway checkpoint modulator comprises siRNAs, antisense, small molecules, mimic, a recombinant form of a ligand, a recombinant form of a receptor, antibodies, or a combination thereof. In some aspects, the immune pathway checkpoint inhibitor is an anti-PD-1 antibody or an anti-PD-L1 antibody. In some aspects, the immune pathway checkpoint inhibitor is Avelumab. In further aspects, the Avelumab is administered to the subject at least once, at least twice, or at least three times a week. In some aspects, Avelumab is administered on day 1 of week 1, day 1 of week 2, day 1 of week 4, day 1 of week 8, day 1 of week 12, and day 1 of week 16. In further aspects, Avelumab is administered after administration of recombinant adenovirus vector comprising a nucleic acid sequence encoding an antigen. In further aspects, Avelumab is administered to the subject at a dose comprising 1 mg/kg to 20 mg/kg. In still further aspects, the dose comprises 10 mg/kg.

In some aspects, an immune response is increased at least 2, at least 3, at least 4, at least 5, at least 6, at least 7, at least 8, at least 9, at least 10, at least 15, at least 20, or at least 25 fold over basal level. In some aspects, the method further comprises administering to the subject an anti-CEA antibody. In further aspects, the anti-CEA antibody is NEO-201, COL1, COL2, COL3, COL4, COL5, COLE, COLT, COLS, COLS, COL10, COL11, COL12, COL13, COL14, COL15, arcitumomab, besilesomab, labetuzumab, or altumomab. In still further aspects, the anti-CEA antibody is NEO-201. In further aspects, the NEO-201 antibody is administered at a dose comprising 3 mg/kg. In further still aspects, the NEO-201 antibody is administered intravenously on day 1, day 15, and day 22. In some aspects, the method further comprises administering to the subject a chemotherapeutic agent. In further aspects, the chemotherapeutic agent is 5-FU, leucovorin, or oxaliplatin, or any combination thereof.

In some aspects, the method further comprises administering to the subject a population of engineered natural killer (NK) cells. In further aspects, the population of engineered NK cells are infused intravenously on day 9, day 11, day 18, day 22, day 27, day 33, or any combination thereof. In further aspects, the population of engineered NK cells comprises a dose of at least $2 \times 10^9$ engineered NK cells. In further aspects, the engineered NK cells comprise one or more NK cells that have been modified as essentially lacking the expression of KIR (killer inhibitory receptors), one or more NK cells that have been modified to express a high affinity CD16 variant, and one or more NK cells that have been modified to express one or more CARs (chimeric antigen receptors), or any combinations thereof. In further still aspects, the engineered NK cells comprise one or more NK cells that have been modified as essentially lacking the expression KIR. In further still aspects, the engineered NK cells comprise one or more NK cells that have been modified to express a high affinity CD16 variant. In further still aspects, the engineered NK cells comprise one or more NK cells that have been modified to express one or more CARs.

In some aspects, the CAR is a CAR for a tumor neo-antigen, tumor neo-epitope, WT1, p53, MAGE-A1, MAGE-A2, MAGE-A3, MAGE-A4, MAGE-A6, MAGE-A10, MAGE-A12, BAGE, DAM-6, DAM-10, Folate receptor alpha, GAGE-1, GAGE-2, GAGE-8, GAGE-3, GAGE-4, GAGE-5, GAGE-6, GAGE-7B, NA88-A, NY-ESO-1, MART-1, MC1R, Gp100, Tyrosinase, TRP-1, TRP-2, ART-4, CAMEL, CEA, Cyp-B, Her2/neu, Her3, BRCA1, Brachyury, Brachyury (TIVS7-2, polymorphism), Brachyury (IVS7 T/C polymorphism), T Brachyury, T, hTERT, hTRT, iCE, MUC1, MUC1 (VNTR polymorphism), MUC1c, MUC1n, MUC2, PRAME, P15, RU1, RU2, SART-1, SART-3, AFP, β-catenin/m, Caspase-8/m, CDK-4/m, ELF2M, GnT-V, G250, HSP70-2M, HST-2, KIAAO205, MUM-1, MUM-2, MUM-3, Myosin/m, RAGE, SART-2, TRP-2/INT2, 707-AP, Annexin II, CDCl27/m, TP1/mbcr-abl, ETV6/AML, LDLR/FUT, Pml/RARα, TEL/AML1, or any combination thereof.

In some aspects, the administering is of 0.1-5 µg of the IL-15 superagonist complex as a single dose. In further aspects, the administering is of 1 µg of the IL-15 superagonist complex as a single dose. In some aspects, the administering is of the IL-15 superagonist complex is administered within 1 day, within 2 days, within 3 days, within 4 days, within 5 days, or within 6 days of administration of the recombinant adenovirus vector comprising a nucleic acid sequence encoding an antigen. In some aspects, the administering is of the IL-15 superagonist complex is administered 3 days after administration of the recombinant adenovirus vector comprising a nucleic acid sequence encoding an antigen. In some aspects, the administering is of a single dose of the IL-15 superagonist complex is administered more than once over a 21 day period.

In some aspects, the administering is of a single dose of the recombinant adenovirus vector comprising a nucleic acid sequence encoding an antigen is administered more than once over a 21 day period. In some aspects, the administering is of the recombinant adenovirus vector comprising a nucleic acid sequence encoding an antigen is administered on Day 7, Day 14, and Day 21. In some aspects, the administering is of the IL-15 superagonist complex, and is administered on Day 10 and Day 17. In some aspects, the administering comprises administering over an 8-week period.

In some aspects, the recombinant adenovirus vector comprising a nucleic acid sequence encoding an antigen is administered on weeks 3 and 6. In further aspects, the IL-15 superagonist complex is administered on weeks 1, 2, 4, 5, 7, and 8. In some aspects, the administering is of the IL-15 superagonist complex is administered at least once, at least twice, at least three times, at least four times, or at least five times in a dosing regimen. In some aspects, the administering is of the recombinant adenovirus vector comprising a nucleic acid sequence encoding an antigen is administered at least once, at least twice, at least three times, at least four times, or at least five times in a dosing regimen.

In some aspects, the CEA antigen induces an immune response. In further aspects, the immune response is measured as antigen specific antibody response. In further aspects, the immune response is measured as antigen specific cell-mediated immunity (CMI). In further aspects, the immune response is measured as antigen specific IFN-γ secretion. In further aspects, the immune response is measured as antigen specific IL-2 secretion. In further aspects, the immune response against the antigen is measured by ELISpot assay. In further aspects, the immune response is measured by T-cell lysis of CAP-1 pulsed antigen-presenting cells, allogeneic antigen expressing cells from a tumor cell line or from an autologous tumor. In still further aspects, the replication defective adenovirus infects dendritic cells in the subject and wherein the infected dendritic cells present the antigen, thereby inducing the immune response.

In some aspects, the administering comprises subcutaneous, parenteral, intravenous, intramuscular, or intraperitoneal administration. In some aspects, the subject has or does not have a proliferative disease cancer. In some aspects, the subject has colorectal adenocarcinoma, metastatic colorectal cancer, advanced CEA expressing colorectal cancer, breast cancer, lung cancer, bladder cancer, or pancreas cancer. In some aspects, the subject has at least 1, 2, or 3 sites of metastatic disease. In some aspects, the subject comprises cells overexpressing CEA. In further aspects, the cells overexpressing CEA, overexpress CEA by at least 2, 3, 4, 5, 6, 7, 8, 9, or 10 times over a baseline CEA expression in a non-cancer cell. In still further aspects, the cells overexpressing CEA comprise cancer cells.

In some aspects, the subject has a diagnosed disease predisposition. In some aspects, the subject has a stable disease. In some aspects, the subject has a genetic predisposition for a disease. In some aspects, the disease is a cancer. In further aspects, the cancer is selected from the group consisting of prostate cancer, colon cancer, breast cancer, or gastric cancer. In further aspects, the cancer is prostate cancer. In further aspects, the cancer is colon cancer. In some aspects, the subject is a human.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
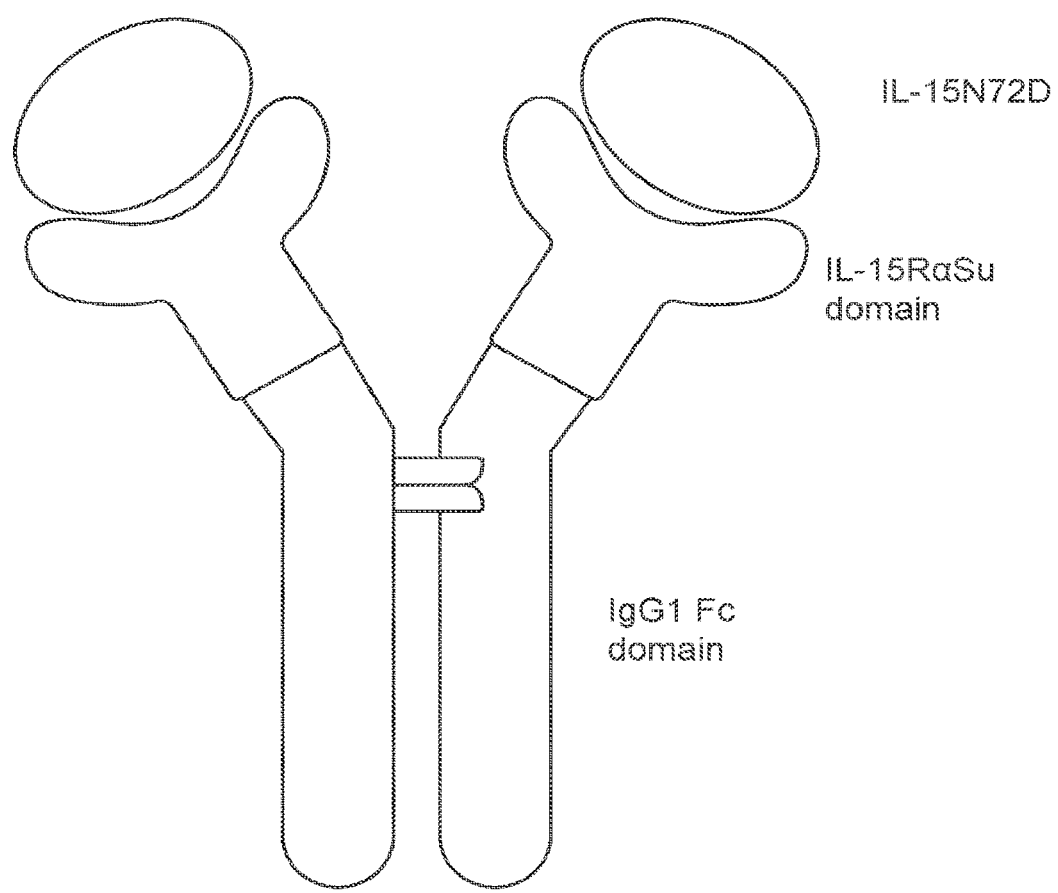
FIG. 1 illustrates a schematic of the ALT-803 superagonist.

The following passages describe different aspects of certain embodiments in greater detail. Each aspect may be combined with any other aspect or aspects unless clearly indicated to the contrary. In particular, any feature indicated as being preferred or advantageous may be combined with any other feature of features indicated as being preferred or advantageous.

Unless otherwise indicated, any embodiment can be combined with any other embodiment. A variety of aspects can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges include the range endpoints.

To address the low immunogenicity of self-tumor antigens, a variety of advanced, multi-component vaccination strategies including combination therapy with an IL-15 superagonist, ALT-803. Some embodiments relate to recombinant viral vectors that provide innate pro-inflammatory signals, while simultaneously engineered to express the antigen of interest, such as CEA. Of particular interest are adenovirus serotype-5 (Ad5)-based immunotherapeutics that can be used in humans to induce robust T-cell-mediated immune (CMI) responses, all while maintaining an extensive safety profile.

Compared to first generation adenovirus vectors, certain embodiments of the Second Generation E2b deleted adenovirus vectors contain additional deletions in the DNA polymerase gene (pol) and deletions of the pre-terminal protein (pTP). E2b deleted vectors have up to a 13 kb gene-carrying capacity as compared to the 5 to 6 kb capacity of First Generation adenovirus vectors, easily providing space for nucleic acid sequences encoding any of a variety of target antigens. The E2b deleted adenovirus vectors also have reduced adverse reactions as compared to first generation adenovirus vectors.

It has been discovered that Ad5 [E1-, E2b-] vectors are not only are safer than, but appear to be superior to Ad5 [E1-] vectors in regard to induction of antigen specific immune responses, making them much better suitable as a platform to deliver CEA vaccines that can result in a clinical response. In other cases, immune induction may take months. Ad5 [E1-, E2b-] vectors not only are safer than, but appear to be superior to Ad5 [E1-] vectors in regard to induction of antigen specific immune responses, making them much better suitable as a platform to deliver CEA vaccines that can result in a clinical response.

Certain embodiments use the new Ad5 [E1-, E2b-] vector system to deliver a long sought-after need for the development of a therapeutic vaccine against CEA, overcome barriers found with other Ad5 systems and permit the immunization of people who have previously been exposed to Ad5.

The innate immune response to wild type Ad can be complex, and it appears that Ad proteins expressed from adenovirus vectors play an important role. Specifically, the deletions of pre-terminal protein and DNA polymerase in the E2b deleted vectors appear to reduce inflammation during the first 24 to 72 h following injection, whereas First Generation adenovirus vectors stimulate inflammation during this period. In addition, it has been reported that the additional replication block created by E2b deletion also leads to a 10,000-fold reduction in expression of Ad late genes, well beyond that afforded by E1, E3 deletions alone. The decreased levels of Ad proteins produced by E2b deleted adenovirus vectors effectively reduce the potential for competitive, undesired, immune responses to Ad antigens, responses that prevent repeated use of the platform in Ad immunized or exposed individuals. The reduced induction of inflammatory response by second generation E2b deleted vectors results in increased potential for the vectors to express desired vaccine antigens during the infection of antigen presenting cells (i.e., dendritic cells), decreasing the potential for antigenic competition, resulting in greater immunization of the vaccine to the desired antigen relative to identical attempts with First Generation adenovirus vectors. E2b deleted adenovirus vectors provide an improved Ad-based vaccine candidate that is safer, more effective, and more versatile than previously described vaccine candidates using First Generation adenovirus vectors.

First generation vectors can have reduced efficacy due to Ad-specific neutralizing antibodies. Without being bound by theory, Ad5-based vectors with deletions of the E1 and the E2b regions (Ad5 [E1-, E2b-]), the latter encoding the DNA polymerase and the pre-terminal protein, for example by virtue of diminished late phase viral protein expression, may avoid immunological clearance and induce more potent immune responses against the encoded tumor antigen transgene in Ad-immune hosts.

Some embodiments relate to methods and compositions (e.g., viral vectors) for generating immune responses against target antigens, in particular, those associated or related to infectious disease or proliferative cell disease such as cancer. Some embodiments relate to methods and compositions for generating immune responses in an individual against target antigens, in particular, those related to cell proliferation diseases such as cancer. In some embodiments, compositions and methods described herein relate to generating an immune response in an individual against cells expressing and/or presenting a target antigen or a target antigen signature comprising at least one target antigen.

The compositions and methods can be used to generate an immune response against a target antigen expressed and/or presented by a cell. For example, the compositions and methods can be used to generate immune responses against a carcinoembryonic antigen (CEA), such as CEA expressed or presented by a cell. For example, the compositions and methods can be used to generate an immune response against CEA(6D) expressed or presented by a cell. For example, the compositions and methods can be used to generate an immune response against Mucin 1 (MUC1) expressed and/or presented by a cell. For example, the compositions and methods can be used to generate an immune response against MUC1c expressed and/or presented by a cell. For example, the compositions and methods can be used to generate an immune response against Brachyury (T protein (T)) expressed and/or presented by a cell.

The compositions and methods can be used to generate an immune response against multiple target antigens expressed and/or presented by a cell. For example, the compositions and methods can be used to generate an immune response against CEA.

A modified form of CEA can be used in a vaccine directed to raising an immune response against CEA or cells expressing and/or presenting CEA. In particular, some embodiments provide an improved Ad-based vaccine such that multiple vaccinations against one or more antigenic target entity can be achieved. In some embodiments, the improved Ad-based vaccine comprises a replication defective adenovirus carrying a target antigen, a fragment, a variant or a variant fragment thereof, such as Ad5 [E1-, E2b-]-CEA(6D). Variants or fragments of target antigens, such as CEA, can be selected based on a variety of factors, including immunogenic potential. A mutant CEA, CEA(6D) can utilized for its increased capability to raise an immune response relative to the CEA(WT). Importantly, vaccination can be performed in the presence of preexisting immunity to the Ad or administered to subjects previously immunized multiple times with the Ad vector as described herein or other Ad vectors. The Ad vectors can be administered to subjects multiple times to induce an immune response against an antigen of interest, such as CEA, including but not limited to, the production of antibodies and CMI responses against one or more target antigens.

As used herein, unless otherwise indicated, the article "a" means one or more unless explicitly otherwise provided for.

As used herein, unless otherwise indicated, terms such as "contain," "containing," "include," "including," and the like mean "comprising." As used herein, unless otherwise indicated, the term "or" can be conjunctive or disjunctive. As used herein, unless otherwise indicated, any embodiment can be combined with any other embodiment.

An "adenovirus" (Ad) refers to non-enveloped DNA viruses from the family Adenoviridae. These viruses can be found in, but are not limited to, human, avian, bovine, porcine and canine species. Some embodiments contemplate the use of any Ad from any of the four genera of the family Adenoviridae (e.g., Aviadenovirus, Mastadenovirus, Atadenovirus and Siadenovirus) as the basis of an E2b deleted virus vector, or vector containing other deletions as described herein. In addition, several serotypes are found in each species. Ad also pertains to genetic derivatives of any of these viral serotypes, including but not limited to, genetic mutations, deletions or transpositions.

A "helper adenovirus" or "helper virus" refers to an Ad that can supply viral functions that a particular host cell cannot (the host may provide Ad gene products such as E1 proteins). This virus is used to supply, in trans, functions (e.g., proteins) that are lacking in a second virus, or helper dependent virus (e.g., a gutted or gutless virus, or a virus deleted for a particular region such as E2b or other region as described herein); the first replication-incompetent virus is said to "help" the second, helper dependent virus thereby permitting the production of the second viral genome in a cell.

An "adenovirus 5 null (Ad5-null)" refers to a non-replicating Ad that does not contain any heterologous nucleic acid sequences for expression.

A "first generation adenovirus" refers to an Ad that has the early region 1 (E1) deleted. In additional cases, the early region 3 (E3) may also be deleted.

"Gutted" or "gutless" refers to an Ad vector that has been deleted of all viral coding regions.

"Transfection" refers to the introduction of foreign nucleic acid into eukaryotic cells. Exemplary means of transfection include calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

"Stable transfection" or "stably transfected" refers to the introduction and integration of foreign nucleic acid, DNA or RNA, into the genome of the transfected cell. The term "stable transfectant" refers to a cell which has stably integrated foreign DNA into the genomic DNA.

A "reporter gene" indicates a nucleotide sequence that encodes a reporter molecule (e.g., an enzyme). A "reporter molecule" is detectable in any of a variety of detection systems, including, but not limited to, enzyme-based detection assays (e.g., ELISA, histochemical assays), fluorescent, radioactive, and luminescent systems. The $E.\ coli$ β-galactosidase gene, green fluorescent protein (GFP), the human placental alkaline phosphatase gene, the chloramphenicol acetyltransferase (CAT) gene; and other reporter genes may be employed.

A "heterologous sequence" refers to a nucleotide sequence that is ligated to, or is manipulated to become ligated to, a nucleic acid sequence to which it is not ligated in nature, or to which it is ligated at a different location in nature. Heterologous nucleic acid may include a naturally occurring nucleotide sequence or some modification relative to the naturally occurring sequence.

A "transgene" refers to any gene coding region, either natural or heterologous nucleic acid sequences or fused homologous or heterologous nucleic acid sequences, introduced into cells or a genome of subject. Transgenes may be carried on any viral vector used to introduce transgenes to the cells of the subject.

A "second generation adenovirus" refers to an Ad that has all or parts of the E1, E2, E3, and, in certain embodiments, E4 DNA gene sequences deleted (removed) from the virus.

A "subject" refers to any animal, including, but not limited to, humans, non-human primates (e.g., rhesus or other types of macaques), mice, pigs, horses, donkeys, cows, sheep, rats and fowls.

An "immunogenic fragment" refers to a fragment of a polypeptide that is specifically recognized (i.e., specifically bound) by a B-cell and/or T-cell surface antigen receptor resulting in a generation of an immune response specifically against a fragment.

A "target antigen" or "target protein" refers to a molecule, such as a protein, against which an immune response is to be directed.

"E2b deleted" refers to a DNA sequence mutated in such a way so as to prevent expression and/or function of at least one E2b gene product. Thus, in certain embodiments, "E2b deleted" is used in relation to a specific DNA sequence that is deleted (removed) from an Ad genome. E2b deleted or "containing a deletion within an E2b region" refers to a deletion of at least one base pair within an E2b region of an Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, a deletion is of more than 150, 160, 170, 180, 190, 200, 250, or 300 base pairs within an E2b region of an Ad genome. An E2b deletion may be a deletion that prevents expression and/or function of at least one E2b gene product and therefore, encompasses deletions within exons of encoding portions of E2b-specific proteins as well as deletions within promoter and leader sequences. In certain embodiments, an E2b deletion is a deletion that prevents expression and/or function of one or both a DNA polymerase and a preterminal protein of an E2b region. In a further embodiment, "E2b deleted" refers to one or more point mutations in a DNA sequence of this region of an Ad genome such that one or more encoded proteins is non-functional. Such mutations include residues that are replaced with a different residue leading to a change in an amino acid sequence that result in a nonfunctional protein.

"E1-deleted" refers to a DNA sequence that is mutated in such a way so as to prevent expression and/or function of at least one E1 gene product. Thus, in certain embodiments, "E1 deleted" is used in relation to a specific DNA sequence that is deleted (removed) from the Ad genome. E1 deleted or "containing a deletion within the E1 region" refers to a deletion of at least one base pair within the E1 region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, the deletion is of more than 150, 160, 170, 180, 190, 200, 250, or 300 base pairs within the E1 region of the Ad genome. An E1 deletion may be a deletion that prevents expression and/or function of at least one E1 gene product and therefore, encompasses deletions within exons of encoding portions of E1-specific proteins as well as deletions within promoter and leader sequences. In certain embodiments, an E1 deletion is a deletion that prevents expression and/or function of one or both of a trans-acting transcriptional regulatory factor of the E1 region. In a further embodiment, "E1 deleted" refers to one or more point mutations in the DNA sequence of this region of an Ad genome such that one or more encoded proteins is non-functional. Such mutations include residues that are replaced with a different residue leading to a change in the amino acid sequence that result in a nonfunctional protein.

"Generating an immune response" or "inducing an immune response" refers to a statistically significant change, e.g., increase or decrease, in the number of one or more immune cells (T-cells, B-cells, antigen-presenting cells, dendritic cells, neutrophils, and the like) or in the activity of one or more of these immune cells (CTL activity, HTL activity, cytokine secretion, change in profile of cytokine secretion, etc.).

The terms "nucleic acid" and "polynucleotide" are used essentially interchangeably herein. Polynucleotides may be single-stranded (coding or antisense) or double-stranded, and may be DNA (e.g. genomic, cDNA, or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide as described herein, and a polynucleotide may, but need not, be linked to other molecules and/or support materials. An isolated polynucleotide, as used herein, means that a polynucleotide is substantially away from other coding sequences. For example, an isolated DNA molecule as used herein does not contain large portions of unrelated coding DNA, such as large chromosomal fragments or other functional genes or polypeptide coding regions. This refers to the DNA molecule as originally isolated, and does not exclude genes or coding regions later added to the segment recombinantly in the laboratory.

As will be understood by those skilled in the art, the polynucleotides can include genomic sequences, extra-genomic and plasmid-encoded sequences and smaller engineered gene segments that express, or may be adapted to express target antigens as described herein, fragments of antigens, peptides and the like. Such segments may be naturally isolated, or modified synthetically by the hand of man.

Typically, polynucleotide variants will contain one or more substitutions, additions, deletions and/or insertions, preferably such that the immunogenicity of the epitope of the polypeptide encoded by the variant polynucleotide or such that the immunogenicity of the heterologous target protein is not substantially diminished relative to a polypeptide encoded by the native polynucleotide sequence. In some cases, the one or more substitutions, additions, deletions and/or insertions may result in an increased immunogenicity of the epitope of the polypeptide encoded by the variant polynucleotide. As described elsewhere herein, the polynucleotide variants can encode a variant of the target antigen, or a fragment (e.g., an epitope) thereof wherein the propensity of the variant polypeptide or fragment (e.g., epitope) thereof to react with antigen-specific antisera and/or T-cell lines or clones is not substantially diminished relative to the native polypeptide. The polynucleotide variants can encode a variant of the target antigen, or a fragment thereof wherein the propensity of the variant polypeptide or fragment thereof to react with antigen-specific antisera and/or T-cell lines or clones is substantially increased relative to the native polypeptide.

The term "variants" should also be understood to encompass homologous genes of xenogenic origin. In particular embodiments, variants or fragments of target antigens are modified such that they have one or more reduced biological activities. For example, an oncogenic protein target antigen may be modified to reduce or eliminate the oncogenic activity of the protein, or a viral protein may be modified to reduce or eliminate one or more activities or the viral protein. An example of a modified CEA protein is a CEA having a N610D mutation, resulting in a variant protein with increased immunogenicity.

When comparing polynucleotide sequences, two sequences are "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned. Optimal alignment of sequences for comparison may be conducted using the Megalign program in the Lasergene suite of bioinformatics software using default parameters. Alternatively, optimal alignment of sequences for comparison may be conducted by the local identity algorithm of Smith and Waterman, Add. APL. Math 2:482 (1981), by the identity alignment algorithm of Needleman and Wunsch, J. Mol. Biol. 48:443 (1970), by the search for similarity methods of Pearson and Lipman, Proc. Natl. Acad. Sci. USA 85: 2444 (1988), by computerized implementations of these algorithms (GAP, BESTFIT, BLAST, FASTA, and TFASTA), or by inspection. One example of algorithms that are suitable for determining percent sequence identity and sequence similarity is the BLAST and BLAST 2.0 algorithms. BLAST and BLAST 2.0 can be used, for example with the parameters described herein, to determine percent sequence identity for the polynucleotides. Software for performing BLAST analysis is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program uses as defaults a word length (W) of 11, and expectation (E) of 10, and the BLOSUM62 scoring matrix alignments, (B) of 50, expectation (E) of 10, M=5, N=−4 and a comparison of both strands.

The "percentage of sequence identity" can be determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence and multiplying the results by 100 to yield the percentage of sequence identity.

It will be appreciated by those of ordinary skill in the art that, as a result of the degeneracy of the genetic code, there are many nucleotide sequences that encode a particular antigen of interest, or fragment thereof, as described herein. Some of these polynucleotides bear minimal homology to the nucleotide sequence of any native gene. Nonetheless, polynucleotides that vary due to differences in codon usage are specifically contemplated. Further, alleles of the genes comprising the polynucleotide sequences provided herein are within the scope of some embodiments. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Viral Vectors for Immunotherapies and Vaccines

Recombinant viral vectors can be used to express protein coding genes or antigens (e.g., TAAs (tumor-associated antigens) and/or IDAAs (infectious-disease associated antigens)). The advantages of recombinant viral vector based vaccines and immunotherapy include high efficiency gene transduction, highly specific delivery of genes to target cells, induction of robust immune responses, and increased cellular immunity. Certain embodiments provide for recombinant adenovirus vectors comprising deletions or insertions of crucial regions of the viral genome. The viral vectors of provided herein can comprise heterologous nucleic acid sequences that encode one or more target antigens of interest, or variants, fragments or fusions thereof, against which it is desired to generate an immune response.

Suitable viral vectors that can be used with the methods and compositions as provided herein, include but are not limited to retroviruses, lentiviruses, provirus, Vaccinia virus, adenoviruses, adeno-associated viruses, self-complementary adeno-associated virus, Cytomegalovirus, Sendai virus, HPV virus, or adenovirus. In some embodiments, the viral vector can be replication-competent. In some embodiments, the viral vector can be replication-defective. Replication-defective viral vectors can be deleted of coding regions that serve to encode for proteins that are involved in replication and packaging. These viruses can infect cells and deliver a payload without killing the cell. Depending on the viral vector, the typical maximum length of an allowable DNA or cDNA insert in a replication-defective viral vector is can be about 8-10 kilobases (kB).

Retroviruses have been used to express antigens, such as an enveloped, single-stranded RNA virus that contains reverse transcriptase. Retrovirus vectors can be replication-defective. Retrovirus vectors can be of murine or avian origin. Retrovirus vectors can be from Moloney murine leukemia virus (MoMLV). Retrovirus vectors can be used that require genome integration for gene expression. Retrovirus vectors can be used to provide long-term gene expression. For example, retrovirus vectors can have a genome size of approximately 7-11 kb and the vector can harbor 7-8 kb long foreign DNA inserts. Retrovirus vectors can be used to display low immunogenicity and most patients do not show pre-existing immunity to retroviral vectors. Retrovirus vectors can be used to infect dividing cells. Retrovirus vectors can be used to not infect non-dividing cells.

Lentivirus vectors can be used to express antigens. Lentiviruses can constitute a subclass of retroviruses. Lentivirus vectors can infect non-dividing cells. Lentivirus vectors can be used to infect dividing cells. Lentivirus vectors can be used to infect both non-dividing and dividing cells. Lentiviruses can exhibit broader tropism than retroviruses. Several proteins such as tat and rev regulate the replication of lentiviruses. These regulatory proteins can be typically absent in retroviruses. HIV is an exemplary lentiviral vector that is genetically modified to deliver a transgene. The advantages of lentivirus vectors are similar to those of retroviral vectors. HIV-based vectors can be generated, for example, by deleting the HIV viral envelope and some of the regulatory genes not required during vector production. Instead of parental envelope, several chimeric or modified envelope vectors are generated because it determines the cell and tissue specificity.

Cytomegalovirus (CMV) vectors have been used to express antigens and are a member of the herpesviruses. Species-specific CMVs can be used (e.g., human CMV (HCMV), e.g., human herpesvirus type 5. HCMV contains a 235-kb double-stranded linear DNA genome surrounded by a capsid. The envelope contains glycoproteins gB and gH, which bind to cellular receptors.

Sendai virus (SeV) vectors have been used to express antigens. The SeV virus is a member of the Paramyxovirus family. SeV is an enveloped, single-stranded RNA virus. The SeV genome encodes six protein and two envelope glycoproteins, HN and F proteins, that mediate cell entry and determine its tropism. SeV vectors that lack F protein can be used as a replication-defective virus to improve the safety of the vector. SeV vector produced in a packaging cell can be used to expresses the F protein. An F gene-deleted and transgene-inserted genome can be transfected into a packaging cell. SeV contains RNA dependent RNA polymerase and viral genome localizes to the cytoplasm. This ensures that fast gene expression occurs soon after infection and the genotoxic advantage of SeV. SeV vectors can be used to exhibit highly efficient gene transfer. SeV vectors can be used to transduce both dividing and non-dividing cells. SeV vectors can be used to transduce non-dividing cells. SeV vectors can be used to transduce dividing cells. SeV vectors can be used, for example, to efficiently transduce human airway epithelial cells. SeV vectors can be, for example, administered by a mucosal (e.g., oral and nasal) route. Intranasal administration can be used to potentially reduce the influence of a pre-existing immunity to SeV, as compared to intramuscular administration. Compared to other viral vectors, its transgene capacity (3.4 kb) is low. SeV is highly homologous to the human parainfluenza type 1 (hPIV-1) virus; thus, a pre-existing immunity against hPIV-1 can work against the use of SeV.

Adenovirus Vectors

In general, adenoviruses are attractive for clinical because they can have a broad tropism, they can infect a variety of dividing and non-dividing cell types and they can be used systemically as well as through more selective mucosal surfaces in a mammalian body. In addition, their relative thermostability further facilitates their clinical use. Adenoviruses are a family of DNA viruses characterized by an icosahedral, non-enveloped capsid containing a linear double-stranded genome. Generally, adenoviruses are found as non-enveloped viruses comprising double-stranded DNA genome approximated ~30-35 kilobases in size. Of the human Ads, none are associated with any neoplastic disease, and only cause relatively mild, self-limiting illness in immunocompetent individuals. The first genes expressed by the virus are the E1 genes, which act to initiate high-level gene expression from the other Ad5 gene promoters present in the wild type genome. Viral DNA replication and assembly of progeny virions occur within the nucleus of infected cells, and the entire life cycle takes about 36 hr with an output of approximately $10^4$ virions per cell. The wild type Ad5 genome is approximately 36 kb, and encodes genes that are divided into early and late viral functions, depending on whether they are expressed before or after DNA replication. The early/late delineation is nearly absolute, since it has been demonstrated that super-infection of cells previously infected with an Ad5 results in lack of late gene expression from the super-infecting virus until after it has replicated its own genome. Without being bound by theory, this is likely due to a replication dependent cis-activation of the Ad5 major late promoter (MLP), preventing late gene expression (primarily the Ad5 capsid proteins) until replicated genomes are present to be encapsulated. The composition and methods as described herein, in some embodiments, take advantage of features in the development of advanced generation Ad vectors/vaccines. The linear genome of the adenovirus can be flanked by two origins for DNA replication (ITRs) and can have eight units for RNA polymerase II-mediated transcription. The genome can carry five early regions including E1A, E1B, E2, E3, E4, and E5, two regions expressed after initiation of viral replication (IX and IVa2), and a single late region (L), which can be subdivided into L1-L5. Some adenoviruses can further encode one or two species of RNA called virus-associated (VA) RNA.

Adenoviruses that induce innate and adaptive immune responses in human patient are provided. By deletion or insertion of crucial regions of the viral genome, recombinant vectors are provided that have been engineered to increase their predictability and reduce unwanted side effects. In some aspects, there is provided an adenovirus vector comprising the genome deletion or insertion selected from the group consisting of: E1A, E1B, E2, E3, E4, E5, IX, IVa2, L1, L2, L3, L4, and L5, and any combination thereof.

Certain embodiments provide recombinant adenovirus vectors comprising an altered capsid. Generally, the capsid of an adenovirus primarily comprises 20 triangular facets of an icosahedron, each icosahedron containing 12 copies of hexon trimers. In addition, there are also other several additional minor capsid proteins, Ma, VI, VIII, and IX.

Certain embodiments provide recombinant adenovirus vectors comprising one or more altered fiber proteins. In general, the fiber proteins, which also form trimers, are inserted at the 12 vertices into the pentameric penton bases. The fiber can comprise of a thin N-terminal tail, a shaft, and a knob domain. The shaft can comprise a variable number of β-strand repeats. The knob can comprise one or more loops A, B, C, D, E, F, G, H, I, J. The fiber knob loops can bind to cellular receptors. Certain embodiments provide adenovirus vectors to be used in vaccine systems for the treatment of cancers and infectious diseases.

Suitable adenoviruses that can be used with the present methods and compositions of the disclosure include but are not limited to species-specific adenovirus including human subgroups A, B1, B2, C, D, E and F or their crucial genomic regions as provided herein, which subgroups can further be classified into immunologically distinct serotypes. Further, suitable adenoviruses that can be used with the present methods and compositions of the disclosure include, but are not limited to, species-specific adenovirus or their crucial genomic regions identified from primates, bovines, fowls, reptiles, or frogs.

Some adenoviruses serotypes preferentially target distinct organs. Serotypes such as AdHu1, AdHu2, and AdHu5 (subgenus C), generally effect the infect upper respiratory, while subgenera A and F effect gastrointestinal organs. Certain embodiments provide recombinant adenovirus vectors to be used in preferentially target distinct organs for the treatment of organ-specific cancers or organ-specific infectious diseases. In some applications, the recombinant adenovirus vector is altered to reduce tropism to a specific organ in a mammal. In some applications, the recombinant adenovirus vector is altered to increase tropism to a specific organ in a mammal.

The tropism of an adenovirus can be determined by their ability to attach to host cell receptors. In some instances, the process of host cell attachment can involve the initial binding of the distal knob domain of the fiber to a host cell surface molecule followed by binding of the RGD motif within the penton base with αV integrins. Certain embodiments provide recombinant adenovirus vectors with altered tropism such that they can be genetic engineered to infect specific cell types of a host. Certain embodiments provide recombinant adenovirus vectors with altered tropism for the treatment of cell-specific cancers or cell-specific infectious diseases. Certain embodiments provide recombinant adenovirus vectors with altered fiber knob from one or more adenoviruses of subgroups A, B, C, D, or F, or a combination thereof or the insertion of RGD sequences. In some applications, the recombinant adenovirus vectors comprising an altered fiber knob results in a vector with reduced tropism for one or more particular cell types. In some applications, the recombinant adenovirus vectors comprising an altered fiber knob results in a vector with enhanced tropism for one or more particular cell types. In some applications, the recombinant adenovirus vectors comprising an altered fiber knob results in a vector with reduced product-specific B or T-cell responses. In some applications, the recombinant adenovirus vectors comprising an altered fiber knob results in a vector with enhanced product-specific B or T-cell responses.

Certain embodiments provide recombinant adenovirus vectors that are coated with other molecules to circumvent the effects of virus-neutralizing antibodies or improve transduction in to a host cell. Certain embodiments provide recombinant adenovirus vectors that are coated with an adaptor molecule that aids in the attachment of the vector to a host cell receptor. By way of example an adenovirus vector can be coated with adaptor molecule that connects coxsackie Ad receptor (CAR) with CD40L resulting in increased transduction of dendritic cells, thereby enhancing immune responses in a subject. Other adenovirus vectors similarly engineered for enhancing the attachment to other target cell types are also contemplated.

Ad5 Vectors

Studies in humans and animals have demonstrated that pre-existing immunity against Ad5 can be an inhibitory factor to commercial use of Ad-based vaccines. The preponderance of humans have antibody against Ad5, the most widely used subtype for human vaccines, with two-thirds of humans studied having lympho-proliferative responses against Ad5. This pre-existing immunity can inhibit immunization or re-immunization using typical Ad5 vaccines and may preclude the immunization of a vaccine against a second antigen, using an Ad5 vector, at a later time. Overcoming the problem of pre-existing anti-vector immunity has been a subject of intense investigation. Investigations using alternative human (non-Ad5 based) Ad5 subtypes or even non-human forms of Ad5 have been examined. Even if these approaches succeed in an initial immunization, subsequent vaccinations may be problematic due to immune responses to the novel Ad5 subtype. To avoid the Ad5 immunization barrier, and improve upon the limited efficacy of first generation Ad5 [E1-] vectors to induce optimal immune responses, some embodiments relate to a next generation Ad5 vector based vaccine platform.

First generation, or E1-deleted adenovirus vectors Ad5 [E1-] are constructed such that a transgene replaces only the E1 region of genes. Typically, about 90% of the wild-type Ad5 genome is retained in the vector. Ad5 [E1-] vectors have a decreased ability to replicate and cannot produce infectious virus after infection of cells that do not express the Ad5 E1 genes. The recombinant Ad5 [E1-] vectors are propagated in human cells (e.g., 293 cells) allowing for Ad5 [E1-] vector replication and packaging. Ad5 [E1-] vectors have a number of positive attributes; one of the most important is their relative ease for scale up and cGMP production. Currently, well over 220 human clinical trials utilize Ad5 [E1-] vectors, with more than two thousand subjects given the virus sc, im, or iv. Additionally, Ad5 vectors do not integrate; their genomes remain episomal. Generally, for vectors that do not integrate into the host genome, the risk for insertional mutagenesis and/or germline transmission is extremely low if at all. Conventional Ad5 [E1-] vectors have a carrying capacity that approaches 7 kb.

Ad5-based vectors with deletions of the E1 and the E2b regions (Ad5 [E1-, E2b-]), the latter encoding the DNA polymerase and the pre-terminal protein, by virtue of diminished late phase viral protein expression, provide an opportunity to avoid immunological clearance and induce more potent immune responses against the encoded tumor antigen transgene in Ad-immune hosts. The new Ad5 platform has additional deletions in the E2b region, removing the DNA polymerase and the preterminal protein genes. The Ad5 [E1-, E2b-] platform has an expanded cloning capacity that is sufficient to allow inclusion of many possible genes. Ad5 [E1-, E2b-] vectors have up to about 12 kb gene-carrying capacity as compared to the 7 kb capacity of Ad5 [E1-] vectors, providing space for multiple genes if needed. In some embodiments, an insert of more than 1, 2, 3, 4, 5, 6, 7, 8, 9, 10, or 11 kb is introduced into an Ad5 vector, such as the Ad5 [E1-, E2b-] vector. Deletion of the E2b region confers advantageous immune properties on the Ad5 vectors, often eliciting potent immune responses to target transgene antigens while minimizing the immune responses to Ad viral proteins.

In various embodiments, Ad5 [E1-, E2b-] vectors induce a potent CMI, as well as antibodies against the vector expressed vaccine antigens even in the presence of Ad immunity. Ad5 [E1-, E2b-] vectors also have reduced adverse reactions as compared to Ad5 [E1-] vectors, in particular the appearance of hepatotoxicity and tissue damage. A key aspect of these Ad5 vectors is that expression of Ad late genes is greatly reduced. For example, production of the capsid fiber proteins could be detected in vivo for Ad5 [E1-] vectors, while fiber expression was ablated from Ad5 [E1-, E2b-] vector vaccines. The innate immune response to wild type Ad is complex. Proteins deleted from the Ad5 [E1-, E2b-] vectors generally play an important role. Specifically, Ad5 [E1-, E2b-] vectors with deletions of preterminal protein or DNA polymerase display reduced inflammation during the first 24 to 72 h following injection compared to Ad5 [E1-] vectors. In various embodiments, the lack of Ad5 gene expression renders infected cells invisible to anti-Ad activity and permits infected cells to express the transgene for extended periods of time, which develops immunity to the target.

Some embodiments contemplate increasing the capability for the Ad5 [E1-, E2b-] vectors to transduce dendritic cells, improving antigen specific immune responses in the vaccine by taking advantage of the reduced inflammatory response against Ad5 [E1-, E2b-] vector viral proteins and the resulting evasion of pre-existing Ad immunity.

Replication Defective Ad5 Vectors

Attempts to overcome anti-Ad immunity have included use of alternative Ad serotypes and/or alterations in the Ad5 viral capsid protein each with limited success and the potential for significantly altering biodistribution of the resultant vaccines. Therefore, a completely novel approach was attempted by further reducing the expression of viral proteins from the E1 deleted Ad5 vectors, proteins known to be targets of pre-existing Ad immunity. Specifically, a novel recombinant Ad5 platform has been described with deletions in the early 1 (E1) gene region and additional deletions in the early 2b (E2b) gene region (Ad5 [E1-, E2b-]). Deletion of the E2b region (that encodes DNA polymerase and the pre-terminal protein) results in decreased viral DNA replication and late phase viral protein expression. This vector platform can be used to induce CMI responses in animal models of cancer and infectious disease and more importantly, this recombinant Ad5 gene delivery platform overcomes the barrier of Ad5 immunity and can be used in the setting of pre-existing and/or vector-induced Ad immunity thus enabling multiple homologous administrations of the vaccine. In particular embodiments, some embodiments relate to a replication defective adenovirus vector of serotype 5 comprising a sequence encoding an immunogenic polypeptide. The immunogenic polypeptide may be a mutant, natural variant, or a fragment thereof.

In some embodiments, the replication defective adenovirus vector comprises a modified sequence encoding a polypeptide with at least 50%, 60%, 65%, 70%, 75%, 80%, 85%, 90%, 95%, 98%, 99%, 99.5%, 99.9%, or 100% identity to a wild-type immunogenic polypeptide or a fragment thereof. In some embodiments, the replication defective adenovirus vector comprises a modified sequence encoding a subunit of a wild-type polypeptide. The compositions and methods, in some embodiments, relate to an adenovirus-derived vector comprising at least 60% sequence identity to SEQ ID NO: 3 or SEQ ID NO: 100.

In some embodiments, an adenovirus-derived vector, optionally relating to a replication defective adenovirus, comprises a sequence with at least 75%, 80%, 85%, 90%, 95%, 98%, 99%, 99.5%, 99.8%, or 99.9% identity to SEQ ID NO: 3 or SEQ ID NO: 100 or a sequence generated from SEQ ID NO: 3 or SEQ ID NO: 100 by alternative codon replacements. In various embodiments, the adenovirus-derived vectors described herein have a deletion in the E2b region, and optionally, in the E1 region, the deletion conferring a variety of advantages to the use of the vectors in immunotherapy as described herein.

In some embodiments, a CEA antigen of the present disclosure can have at least 80%, at least 85%, at least 87%, at least 90%, at least 92%, at least 95%, at least 97%, or at least 99% sequence identity to SEQ ID NO: 3 or SEQ ID NO: 4. In some embodiments, the nucleic acid sequence encoding for a CEA antigen of the present disclosure can have at least 80%, at least 85%, at least 87%, at least 90%, at least 92%, at least 95%, at least 97%, or at least 99% sequence identity to SEQ ID NO: 1, SEQ ID NO: 100, or positions 1057 to 3165 of SEQ ID NO: 2. In some embodiments, a replication defective adenovirus vector (e.g., Ad5 [E1-, E2b-]) encoding for a CEA antigen can have at least 80%, at least 85%, at least 87%, at least 90%, at least 92%, at least 95%, at least 97%, or at least 99% sequence identity to SEQ ID NO: 2 or positions 1057 to 3165 of SEQ ID NO: 2.

Certain regions within the adenovirus genome serve essential functions and may need to be substantially conserved when constructing the replication defective adenovirus vectors. These regions are further described in Lauer et al., J. Gen. Virol., 85, 2615-25 (2004), Leza et al., J. Virol., p. 3003-13 (1988), and Miralles et al., J. Bio Chem., Vol. 264, No. 18, p. 10763-72 (1983), which are incorporated by reference in their entirety. Recombinant nucleic acid vectors comprising a sequence with identity values of at least 50%, 60%, 65%, 70%, 75%, 80%, 85%, 90%, 95%, 98%, 99%, 99.5%, 99.8%, 99.9%, or 100% to a portion of SEQ ID NO: 3 or SEQ ID NO: 100, such as a portion comprising at least about 100, 250, 500, 1000 or more bases of SEQ ID NO: 3 or SEQ ID NO: 100 are used in some embodiments.

Certain embodiments contemplate the use of E2b deleted adenovirus vectors, such as those described in U.S. Pat. Nos. 6,063,622; 6,451,596; 6,057,158; 6,083,750; and 8,298,549, which are each incorporated herein by reference in their entirety. The vectors with deletions in the E2b regions in many cases cripple viral protein expression and/or decrease the frequency of generating replication competent Ad (RCA). Propagation of these E2b deleted adenovirus vectors can be done utilizing cell lines that express the deleted E2b gene products. Such packaging cell lines are provided herein; e.g., E.C7 (formally called C-7), derived from the HEK-2p3 cell line.

Further, the E2b gene products, DNA polymerase and preterminal protein, can be constitutively expressed in E.C7, or similar cells along with the E1 gene products. Transfer of gene segments from the Ad genome to the production cell line has immediate benefits: (1) increased carrying capacity; and, (2) a decreased potential of RCA generation, typically requiring two or more independent recombination events to generate RCA. The E1, Ad DNA polymerase and/or preterminal protein expressing cell lines used in some embodiments can enable the propagation of adenovirus vectors with a carrying capacity approaching 13 kb, without the need for a contaminating helper virus. In addition, when genes critical to the viral life cycle are deleted (e.g., the E2b genes), a further crippling of Ad to replicate or express other viral gene proteins occurs. This can decrease immune recognition of infected cells, and extend durations of foreign transgene expression.

E1, DNA polymerase, and preterminal protein deleted vectors are typically unable to express the respective proteins from the E1 and E2b regions. Further, they may show a lack of expression of most of the viral structural proteins. For example, the major late promoter (MLP) of Ad is responsible for transcription of the late structural proteins L1 through L5. Though the MLP is minimally active prior to Ad genome replication, the highly toxic Ad late genes are primarily transcribed and translated from the mLP only after viral genome replication has occurred. This cis-dependent activation of late gene transcription is a feature of DNA viruses in general, such as in the growth of polyoma and SV-40. The DNA polymerase and preterminal proteins are important for Ad replication (unlike the E4 or protein IX proteins). Their deletion can be extremely detrimental to adenovirus vector late gene expression, and the toxic effects of that expression in cells such as APCs.

The adenovirus vectors can include a deletion in the E2b region of the Ad genome and, optionally, the E1 region. In some cases, such vectors do not have any other regions of the Ad genome deleted. The adenovirus vectors can include a deletion in the E2b region of the Ad genome and deletions in the E1 and E3 regions. In some cases, such vectors have no other regions deleted. The adenovirus vectors can include a deletion in the E2b region of the Ad genome and deletions in the E1, E3 and partial or complete removal of the E4 regions. In some cases, such vectors have no other deletions. The adenovirus vectors can include a deletion in the E2b region of the Ad genome and deletions in the E1 and/or E4 regions. In some cases, such vectors contain no other deletions. The adenovirus vectors can include a deletion in the E2a, E2b and/or E4 regions of the Ad genome. In some cases, such vectors have no other deletions. The adenovirus vectors can have the E1 and/or DNA polymerase functions of the E2b region deleted. In some cases, such vectors have no other deletions. The adenovirus vectors can have the E1 and/or the preterminal protein functions of the E2b region deleted. In some cases, such vectors have no other deletions. The adenovirus vectors can have the E1, DNA polymerase and/or the preterminal protein functions deleted. In some cases, such vectors have no other deletions. The adenovirus vectors can have at least a portion of the E2b region and/or the E1 region. In some cases, such vectors are not gutted adenovirus vectors. In this regard, the vectors may be deleted for both the DNA polymerase and the preterminal protein functions of the E2b region. The adenovirus vectors can have a deletion in the E1, E2b and/or 100K regions of the adenovirus genome. The adenovirus vectors can comprise vectors having the E1, E2b and/or protease functions deleted. In some cases, such vectors have no other deletions. The adenovirus vectors can have the E1 and/or the E2b regions deleted, while the fiber genes have been modified by mutation or other alterations (for example to alter Ad tropism). Removal of genes from the E3 or E4 regions may be added to any of the adenovirus vectors mentioned. In certain embodiments, adenovirus vectors may have a deletion in the E1 region, the E2b region, the E3 region, the E4 region, or any combination thereof. In certain embodiments, the adenovirus vector may be a gutted adenovirus vector.

Other regions of the Ad genome can be deleted. A "deletion" in a particular region of the Ad genome refers to a specific DNA sequence that is mutated or removed in such a way so as to prevent expression and/or function of at least one gene product encoded by that region (e.g., E2b functions of DNA polymerase or preterminal protein function). Deletions can encompass deletions within exons encoding portions of proteins as well as deletions within promoter and leader sequences. A deletion within a particular region refers to a deletion of at least one base pair within that region of the Ad genome. More than one base pair can be deleted. For example, at least 20, 30, 40, 50, 60, 70, 80, 90, 100, 110, 120, 130, 140, or 150 base pairs can be deleted from a particular region. The deletion can be more than 150, 160, 170, 180, 190, 200, 250, or 300 base pairs within a particular region of the Ad genome. These deletions can prevent expression and/or function of the gene product encoded by the region. For example, a particular region of the Ad genome can include one or more point mutations such that one or more encoded proteins is non-functional. Such mutations include residues that are replaced with a different residue leading to a change in the amino acid sequence that result in a nonfunctional protein. Exemplary deletions or mutations in the Ad genome include one or more of E1a, E1b, E2a, E2b, E3, E4, L1, L2, L3, L4, L5, TP, POL, IV, and VA regions. Deleted adenovirus vectors can be made, for example, using recombinant techniques.

Ad vectors in certain embodiments can be successfully grown to high titers using an appropriate packaging cell line that constitutively expresses E2b gene products and products of any of the necessary genes that may have been deleted. HEK-293-derived cells that not only constitutively express the E1 and DNA polymerase proteins, but also the Ad-preterminal protein, can be used. E.C7 cells can be used, for example, to grow high titer stocks of the adenovirus vectors.

To delete critical genes from self-propagating adenovirus vectors, proteins encoded by the targeted genes can first be coexpressed in HEK-293 cells, or similar, along with E1 proteins. For example, those proteins which are non-toxic when coexpressed constitutively (or toxic proteins inducibly-expressed) can be selectively utilized. Coexpression in HEK-293 cells of the E1 and E4 genes is possible (for example utilizing inducible, not constitutive, promoters). The E1 and protein IX genes, a virion structural protein, can be coexpressed. Further coexpression of the E1, E4, and protein IX genes is also possible. E1 and 100K genes can be expressed in trans-complementing cell lines, as can E1 and protease genes.

Cell lines coexpressing E1 and E2b gene products for use in growing high titers of E2b deleted Ad particles can be used. Useful cell lines constitutively express the approximately 140 kDa Ad-DNA polymerase and/or the approximately 90 kDa preterminal protein. Cell lines that have high-level, constitutive coexpression of the E1, DNA polymerase, and preterminal proteins, without toxicity (e.g., E.C7), are desirable for use in propagating Ad for use in multiple vaccinations. These cell lines permit the propagation of adenovirus vectors deleted for the E1, DNA polymerase, and preterminal proteins.

The recombinant Ad can be propagated using, for example, tissue culture plates containing E.C7 cells infected with Ad vector virus stocks at an appropriate MOI (e.g., 5) and incubated at 37° C. for 40-96 h. The infected cells can be harvested, resuspended in 10 mM Tris-Cl (pH 8.0), and sonicated, and the virus can be purified by two rounds of cesium chloride density centrifugation. The virus containing band can be desalted over a column, sucrose or glycerol can be added, and aliquots can be stored at −80° C. Virus can be placed in a solution designed to enhance its stability, such as A195. The titer of the stock can be measured (e.g., by measurement of the optical density at 260 nm of an aliquot of the virus after lysis). Plasmid DNA, either linear or circular, encompassing the entire recombinant E2b deleted adenovirus vector can be transfected into E.C7, or similar cells, and incubated at 37° C. until evidence of viral production is present (e.g., cytopathic effect). Conditioned media from cells can be used to infect more cells to expand the amount of virus produced before purification. Purification can be accomplished, for example, by two rounds of cesium chloride density centrifugation or selective filtration. Virus may be purified by chromatography using commercially available products or custom chromatographic columns.

The compositions as described herein can comprise enough virus to ensure that cells to be infected are confronted with a certain number of viruses. Thus, some embodiments provide a stock of recombinant Ad, such as an RCA-free stock of recombinant Ad. Viral stocks can vary considerably in titer, depending largely on viral genotype and the protocol and cell lines used to prepare them. Viral stocks can have a titer of at least about $10^6$, $10^7$, or $10^8$ pfu/mL, or higher, such as at least about $10^9$, $10^{10}$, $10^{11}$, or $10^{12}$ pfu/mL. Depending on the nature of the recombinant virus and the packaging cell line, a viral stock can have a titer of even about $10^{13}$ particles/ml or higher.

A replication defective adenovirus vector (e.g., SEQ ID NO: 2) can comprise a sequence encoding a target antigen, a fragment thereof, or a variant thereof, at a suitable position. In some embodiments, a replication defective adenovirus vector (e.g., SEQ ID NO: 2) can comprise a sequence encoding a target antigen described herein, or a fragment, a variant, or a variant fragment thereof, at a position replacing the nucleic acid sequence encoding a CEA or a variant CEA (e.g., SEQ ID NO: 1 or SEQ ID NO: 100). In some embodiments, a replication defective adenovirus vector (e.g., SEQ ID NO: 2) can comprise a sequence encoding a target antigen described herein, or a fragment, a variant, or a variant fragment thereof, at a position replacing the nucleic acid sequence encoding a CEA or a variant CEA (e.g., SEQ ID NO: 1, SEQ ID NO: 3, SEQ ID NO: 4, or SEQ ID NO: 100).

Polynucleotides and Variants Encoding Antigen Targets

Certain embodiments provide nucleic acid sequences, also referred to herein as polynucleotides that encode one or more target antigens of interest, or fragments or variants thereof. As such, some embodiments provide polynucleotides that encode target antigens from any source as described further herein, vectors comprising such polynucleotides and host cells transformed or transfected with such expression vectors. In order to express a desired target antigen polypeptide, nucleotide sequences encoding the polypeptide, or functional equivalents, can be inserted into an appropriate Ad vector (e.g., using recombinant techniques). The appropriate adenovirus vector may contain the necessary elements for the transcription and translation of the inserted coding sequence and any desired linkers. Methods which are well known to those skilled in the art may be used to construct these adenovirus vectors containing sequences encoding a polypeptide of interest and appropriate transcriptional and translational control elements. These methods include in vitro recombinant DNA techniques, synthetic techniques, and in vivo genetic recombination.

Polynucleotides may comprise a native sequence (i.e., an endogenous sequence that encodes a target antigen polypeptide/protein/epitope or a portion thereof) or may comprise a sequence that encodes a variant, fragment, or derivative of such a sequence. Polynucleotide sequences can encode target antigen proteins. In some embodiments, polynucleotides represent a novel gene sequence optimized for expression in specific cell types that may substantially vary from the native nucleotide sequence or variant but encode a similar protein antigen.

In other related embodiments, polynucleotide variants have substantial identity to native sequences encoding proteins (e.g., target antigens of interest), for example those comprising at least 70% sequence identity, preferably at least 75%, 80%, 85%, 90%, 95%, 96%, 97%, 98%, or 99% or higher, sequence identity compared to a native polynucleotide sequence encoding the polypeptides (e.g., BLAST analysis using standard parameters). These values can be appropriately adjusted to determine corresponding identity of proteins encoded by two nucleotide sequences by taking into account codon degeneracy, amino acid similarity, reading frame positioning and the like. Polynucleotides can encode a protein comprising for example at least 70% sequence identity, preferably at least 75%, 80%, 85%, 90%, 95%, 96%, 97%, 98%, or 99% or higher, sequence identity compared to a protein sequence encoded by a native polynucleotide sequence.

Polynucleotides can comprise at least about 5, 10, 15, 20, 25, 30, 35, 40, 45, 50, 55, 60, 65, 70, 75, 80, 85, 90, 95, 100, 11, 120, 130, 140, 150, 160, 170, 180, 190, 200, 210, 220, 230, 240, 250, 260, 270, 280, 290, 300, 350, 400, 450, 500, 550, 600, 650, 700, 750, 800, 850, 900, 950, or 1000 or more contiguous nucleotides encoding a polypeptide (e.g., target protein antigens), and all intermediate lengths there between. "Intermediate lengths", in this context, refers to any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. A polynucleotide sequence may be extended at one or both ends by additional nucleotides not found in the native sequence encoding a polypeptide, such as an epitope or heterologous target protein. This additional sequence may consist of 1, 2, 3, 4, 5, 6, 7, 8, 9, 10, 11, 12, 13, 14, 15, 16, 17, 18, 19, or 20 nucleotides or more, at either end of the disclosed sequence or at both ends of the disclosed sequence.

The polynucleotides, regardless of the length of the coding sequence itself, may be combined with other DNA sequences, such as promoters, expression control sequences, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. Illustrative polynucleotide segments with total lengths of about 1000, 2000, 3000, 4000, 5000, 6000, 7000, 8000, 9000, 10,000, about 500, about 200, about 100, about 50 base pairs in length, and the like, (including all intermediate lengths) are contemplated to be useful in many embodiments.

A mutagenesis approach, such as site-specific mutagenesis, can be employed to prepare target antigen sequences. Specific modifications in a polypeptide sequence can be made through mutagenesis of the underlying polynucleotides that encode them. Site-specific mutagenesis can be used to make mutants through the use of oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. For example, a primer comprising about 14 to about 25 nucleotides or so in length can be employed, with about 5 to about 10 residues on both sides of the junction of the sequence being altered. Mutations may be made in a selected polynucleotide sequence to improve, alter, decrease, modify, or otherwise change the properties of the polynucleotide, and/or alter the properties, activity, composition, stability, or primary sequence of the encoded polypeptide.

Mutagenesis of polynucleotide sequences can be used to alter one or more properties of the encoded polypeptide, such as the immunogenicity of an epitope comprised in a polypeptide or the oncogenicity of a target antigen. Assays to test the immunogenicity of a polypeptide include, but are not limited to, T-cell cytotoxicity assays (CTL/chromium release assays), T-cell proliferation assays, intracellular cytokine staining, ELISA, ELISpot, etc. Other ways to obtain sequence variants of peptides and the DNA sequences encoding them can be employed. For example, recombinant vectors encoding the desired peptide sequence may be treated with mutagenic agents, such as hydroxylamine, to obtain sequence variants.

Polynucleotide segments or fragments encoding the polypeptides as described herein may be readily prepared by, for example, directly synthesizing the fragment by chemical means. Fragments may be obtained by application of nucleic acid reproduction technology, such as PCR, by introducing selected sequences into recombinant vectors for recombinant production.

A variety of vector/host systems may be utilized to contain and produce polynucleotide sequences. Exemplary systems include microorganisms such as bacteria transformed with recombinant bacteriophage, plasmid, or cosmid DNA vectors; yeast transformed with yeast vectors; insect cell systems infected with virus vectors (e.g., baculovirus); plant cell systems transformed with virus vectors (e.g., cauliflower mosaic virus, CaMV; tobacco mosaic virus, TMV) or with bacterial vectors (e.g., Ti or pBR322 plasmids); or animal cell systems.

Control elements or regulatory sequences present in an Ad vector may include those non-translated regions of the vector-enhancers, promoters, and 5' and 3' untranslated regions. Such elements may vary in their strength and specificity. Depending on the vector system and host utilized, any number of suitable transcription and translation elements, including constitutive and inducible promoters, may be used. For example, sequences encoding a polypeptide of interest may be ligated into an Ad transcription/translation complex consisting of the late promoter and tripartite leader sequence. Insertion in a non-essential E1 or E3 region of the viral genome may be used to obtain a viable virus which is capable of expressing the polypeptide in infected host cells. In addition, transcription enhancers, such as the Rous sarcoma virus (RSV) enhancer, may be used to increase expression in mammalian host cells.

Specific initiation signals may also be used to achieve more efficient translation of sequences encoding a polypeptide of interest (e.g., ATG initiation codon and adjacent sequences). Exogenous translational elements and initiation codons may be of various origins, both natural and synthetic. The efficiency of expression may be enhanced by the inclusion of enhancers which are appropriate for the particular cell system which is used. Specific termination sequences, either for transcription or translation, may also be incorporated in order to achieve efficient translation of the sequence encoding the polypeptide of choice.

A variety of protocols for detecting and measuring the expression of polynucleotide-encoded products (e.g., target antigens), can be used (e.g., using polyclonal or monoclonal antibodies specific for the product). Examples include enzyme-linked immunosorbent assay (ELISA), radioimmunoassay (MA), and fluorescence activated cell sorting (FACS). A two-site, monoclonal-based immunoassay utilizing monoclonal antibodies reactive to two non-interfering epitopes on a given polypeptide may be preferred for some applications, but a competitive binding assay may also be employed.

The Ad vectors can comprise a product that can be detected or selected for, such as a reporter gene whose product can be detected, such as by fluorescence, enzyme activity on a chromogenic or fluorescent substrate, and the like, or selected for by growth conditions. Exemplary reporter genes include green fluorescent protein (GFP), β-galactosidase, chloramphenicol acetyltransferase (CAT), luciferase, neomycin phosphotransferase, secreted alkaline phosphatase (SEAP), and human growth hormone (HGH). Exemplary selectable markers include drug resistances, such as neomycin (G418), hygromycin, and the like.

The Ad vectors can also comprise a promoter or expression control sequence. The choice of the promoter will depend in part upon the targeted cell type and the degree or type of control desired. Promoters that are suitable include, without limitation, constitutive, inducible, tissue specific, cell type specific, temporal specific, or event-specific. Examples of constitutive or nonspecific promoters include the SV40 early promoter, the SV40 late promoter, CMV early gene promoter, bovine papilloma virus promoter, and adenovirus promoter. In addition to viral promoters, cellular promoters are also amenable and useful in some embodiments. In particular, cellular promoters for the so-called housekeeping genes are useful (e.g., β-actin). Viral promoters are generally stronger promoters than cellular promoters. Inducible promoters may also be used. These promoters include MMTV LTR, inducible by dexamethasone, metallothionein, inducible by heavy metals, and promoters with cAMP response elements, inducible by cAMP, heat shock promoter. By using an inducible promoter, the nucleic acid may be delivered to a cell and will remain quiescent until the addition of the inducer. This allows further control on the timing of production of the protein of interest. Event-type specific promoters (e.g., HIV LTR) can be used, which are active or upregulated only upon the occurrence of an event, such as tumorigenicity or viral infection, for example. The HIV LTR promoter is inactive unless the tat gene product is present, which occurs upon viral infection. Some event-type promoters are also tissue-specific. Preferred event-type specific promoters include promoters activated upon viral infection.

Examples of promoters include promoters for α-fetoprotein, α-actin, myo D, carcinoembryonic antigen, VEGF-receptor; FGF receptor; TEK or tie 2; tie; urokinase receptor; E- and P-selectins; VCAM-1; endoglin; endosialin; αV-β3 integrin; endothelin-1; ICAM-3; E9 antigen; von Willebrand factor; CD44; CD40; vascular-endothelial cadherin; notch 4, high molecular weight melanoma-associated antigen; prostate specific antigen-1, probasin, FGF receptor, VEGF receptor, erb B2; erb B3; erb B4; MUC-1; HSP-27; int-1; int-2, CEA, HBEGF receptor; EGF receptor; tyrosinase, MAGE, IL-2 receptor; prostatic acid phosphatase, probasin, prostate specific membrane antigen, α-crystallin, PDGF receptor, integrin receptor, α-actin, SM1 and SM2 myosin heavy chains, calponin-hl, SM22 α-angiotensin receptor, IL-1, IL-2, IL-3, IL-4, IL-5, IL-6, IL-7, IL-8, IL-9, IL-10, IL-11, IL-12, IL-13, IL-14, immunoglobulin heavy chain, immunoglobulin light chain, and CD4.

Repressor sequences, negative regulators, or tissue-specific silencers may be inserted to reduce non-specific expression of the polynucleotide. Multiple repressor elements may be inserted in the promoter region. Repression of transcription is independent of the orientation of repressor elements or distance from the promoter. One type of repressor sequence is an insulator sequence. Such sequences inhibit transcription and can silence background transcription. Negative regulatory elements can be located in the promoter regions of a number of different genes. The repressor element can function as a repressor of transcription in the absence of factors, such as steroids, as does the NSE in the promoter region of the ovalbumin gene. These negative regulatory elements can bind specific protein complexes from oviduct, none of which are sensitive to steroids. Three different elements are located in the promoter of the ovalbumin gene. In some embodiments, oligonucleotides corresponding to portions of these elements can repress viral transcription of the TK reporter. For example, one such silencer element is TCTCTCCNA (SEQ ID NO: 11), which has sequence identity with silencers that are present in other genes.

Elements that increase the expression of the desired target antigen can be incorporated into the nucleic acid sequence of the Ad vectors described herein. Exemplary elements include internal ribosome binding sites (IRESs). IRESs can increase translation efficiency. As well, other sequences may enhance expression. For some genes, sequences especially at the 5' end may inhibit transcription and/or translation. These sequences are usually palindromes that can form hairpin structures. In some cases, such sequences in the nucleic acid to be delivered are deleted. Expression levels of the transcript or translated product can be assayed to confirm or ascertain which sequences affect expression. Transcript levels may be assayed by any known method, including Northern blot hybridization, RNase probe protection and the like. Protein levels may be assayed by any known method, including ELISA.

Antigen-Specific Immunotherapies and Vaccines

Certain embodiments provide single antigen immunization against CEA utilizing such vectors and other vectors as provided herein. Certain embodiments provide prophylactic vaccines against CEA. Further, in various embodiments, the composition and methods provide herein can lead to clinical responses, such as altered disease progression or life expectancy.

Ad5 [E1-] vectors encoding a variety of antigens can be used to efficiently transduce 95% of ex vivo exposed DC's to high titers of the vector. In certain embodiments, increasing levels of foreign gene expression in the DC was found to correlate with increasing multiplicities of infection (MOI) with the vector. DCs infected with Ad5 [E1-] vectors can encode a variety of antigens (including the tumor antigens MART-1, MAGE-A4, DF3/MUC1, p53, hugp100 melanoma antigen, polyoma virus middle—T antigen) that have the propensity to induce antigen specific CTL responses, have an enhanced antigen presentation capacity, and/or have an improved ability to initiate T-cell proliferation in mixed lymphocyte reactions. Immunization of animals with dendritic cells (DCs) previously transduced by Ad5 vectors encoding tumor specific antigens can be used to induce significant levels of protection for the animals when challenged with tumor cells expressing the respective antigen. Interestingly, intra-tumoral injection of Ads encoding IL-7 is less effective than injection of DCs transduced with IL-7 encoding Ad5 vectors at inducing antitumor immunity. Ex vivo transduction of DCs by Ad5 vectors is contemplated in certain embodiments. Ex vivo DC transduction strategies can been used to induce recipient host tolerance. For example, Ad5 mediated delivery of the CTLA4Ig into DCs can block interactions of the DCs CD80 with CD28 molecules present on T-cells.

Ad5 vector capsid interactions with DCs may trigger several beneficial responses, which may be enhancing the propensity of DCs to present antigens encoded by Ad5 vectors. For example, immature DCs, though specialized in antigen uptake, are relatively inefficient effectors of T-cell activation. DC maturation coincides with the enhanced ability of DCs to drive T-cell immunity. In some instances, the compositions and methods take advantage of an Ad5 infection resulting in direct induction of DC maturation Ad vector infection of immature bone marrow derived DCs from mice may upregulate cell surface markers normally associated with DC maturation (MHC I and II, CD40, CD80, CD86, and ICAM-1) as well as down-regulation of CD11c, an integrin down regulated upon myeloid DC maturation. In some instances, Ad vector infection triggers IL-12 production by DCs, a marker of DC maturation. Without being bound by theory, these events may possibly be due to Ad5 triggered activation of NF-κB pathways. Mature DCs can be efficiently transduced by Ad vectors, and do not lose their functional potential to stimulate the proliferation of naive T-cells at lower MOI, as demonstrated by mature CD83+ human DC (derived from peripheral blood monocytes). However, mature DCs may also be less infectable than immature ones. Modification of capsid proteins can be used as a strategy to optimize infection of DC by Ad vectors, as well as enhancing functional maturation, for example using the CD40L receptor as a viral vector receptor, rather than using the normal CAR receptor infection mechanisms.

In some embodiments, the compositions and methods comprising an Ad5 [E1-, E2b-] vector(s) CEA vaccine have effects of increased overall survival (OS) within the bounds of technical safety. In some embodiments, the compositions and methods comprising an Ad5 [E1-, E2b-] vector(s) CEA vaccine have effects of increased overall survival (OS) within the bounds of technical safety. In certain embodiments, the compositions and methods comprising an Ad5 [E1-, E2b-] vector(s) CEA vaccine have effects of increased overall survival (OS) within the bounds of technical safety.

In some embodiments, the antigen targets are associated with benign tumors. In some embodiments, the antigens targeted are associated with pre-cancerous tumors.

In some embodiments, the antigens targeted are associated with carcinomas, in situ carcinomas, metastatic tumors, neuroblastoma, sarcomas, myosarcoma, leiomyosarcoma, retinoblastoma, hepatoma, rhabdomyosarcoma, plasmocytomas, adenomas, gliomas, thymomas, or osteosarcoma. In some embodiments, the antigens targeted are associated with a specific type of cancer such as neurologic cancers, brain cancer, thyroid cancer, head and neck cancer, melanoma, leukemia, acute lymphoblastic leukemia (ALL), acute myelogenous leukemia (AML), chronic myelogenous leukemia (CML), and chronic lymphocytic leukemia (CLL), non-Hodgkin's lymphoma, multiple myeloma, Hodgkin's disease, breast cancer, bladder cancer, prostate cancer, colorectal cancer, colon cancer, kidney cancer, renal cell carcinoma, pancreatic cancer, esophageal cancer, lung cancer, mesothelioma, ovarian cancer, cervical cancer, endometrial cancer, uterine cancer, germ cell tumors, testicular cancer, gastric cancer, or other cancers, or any clinical (e.g., TNM, Histopathological, Staging or Grading systems or a combination thereof) or molecular subtype thereof. In some embodiments, the antigens targeted are associated with a specific clinical or molecular subtype of cancer. By way of example, breast cancer can be divided into at least four molecular subtypes including Luminal A, Luminal B, Triple negative/basal-like, and HER2 type. By way of example, prostate cancer can be subdivided TNM, Gleason score, or molecular expression of the PSA protein.

As noted above, the adenovirus vectors comprise nucleic acid sequences that encode one or more target proteins or antigens of interest. In this regard, the vectors may contain nucleic acid encoding 1, 2, 3, 4, 5, 6, 7, 8, 9, 10, 11, 12, 13, 14, 15, 16, 17, 18, 19, 20 or more different target antigens of interest. The target antigens may be a full-length protein or may be a fragment (e.g., an epitope) thereof. The adenovirus vectors may contain nucleic acid sequences encoding multiple fragments or epitopes from one target protein of interest or may contain one or more fragments or epitopes from numerous different target proteins of interest. A target antigen may comprise any substance against which it is desirable to generate an immune response but generally, the target antigen is a protein. A target antigen may comprise a full-length protein, a subunit of a protein, an isoform of a protein, or a fragment thereof that induces an immune response (i.e., an immunogenic fragment). A target antigen or fragment thereof may be modified, e.g., to reduce one or more biological activities of the target antigen or to enhance its immunogenicity. The target antigen or target protein can be CEA.

In certain embodiments, immunogenic fragments bind to an MHC class I or class II molecule. An immunogenic fragment may "bind to" an MHC class I or class II molecule if such binding is detectable using any assay known in the art. For example, the ability of a polypeptide to bind to MHC class I may be evaluated indirectly by monitoring the ability to promote incorporation of $^{125}$I labeled β-2-microglobulin (β-2m) into MHC class I/β2m/peptide heterotrimeric complexes. Alternatively, functional peptide competition assays that are known in the art may be employed. Immunogenic fragments of polypeptides may generally be identified using well known techniques. Representative techniques for identifying immunogenic fragments include screening polypeptides for the ability to react with antigen-specific antisera and/or T-cell lines or clones. An immunogenic fragment of a particular target polypeptide is a fragment that reacts with such antisera and/or T-cells at a level that is not substantially less than the reactivity of the full-length target polypeptide (e.g., in an ELISA and/or T-cell reactivity assay). In other words, an immunogenic fragment may react within such assays at a level that is similar to or greater than the reactivity of the full-length polypeptide. Such screens may be performed using methods known in the art.

In some embodiments, the viral vectors comprise heterologous nucleic acid sequences that encode one or more proteins, variants thereof, fusions thereof, or fragments thereof, that can modulate the immune response. In some embodiments, the viral vector encodes one or more antibodies against specific antigens, such as anthrax protective antigen, permitting passive immunotherapy. In some embodiments, the viral vectors comprise heterologous nucleic acid sequences encoding one or more proteins having therapeutic effect (e.g., anti-viral, anti-bacterial, anti-parasitic, or anti-tumor function). In some embodiments, the Second Generation E2b deleted adenovirus vectors comprise a heterologous nucleic acid sequence. In some embodiments, the heterologous nucleic acid sequence is CEA, a variant, a portion, or any combination thereof.

Target antigens include, but are not limited to, antigens derived from a variety of tumor proteins. In some embodiments, parts or variants of tumor proteins are employed as target antigens. In some embodiments, parts or variants of tumor proteins being employed as target antigens have a modified, for example, increased ability to effect and immune response against the tumor protein or cells containing the same. A vaccine can vaccinate against an antigen. A vaccine can also target an epitope. An antigen can be a tumor cell antigen. An epitope can be a tumor cell epitope. Such a tumor cell epitope may be derived from a wide variety of tumor antigens, such as antigens from tumors resulting from mutations, shared tumor specific antigens, differentiation antigens, and antigens overexpressed in tumors. Tumor-associated antigens (TAAs) may be antigens not normally expressed by the host; they can be mutated, truncated, misfolded, or otherwise abnormal manifestations of molecules normally expressed by the host; they can be identical to molecules normally expressed but expressed at abnormally high levels; or they can be expressed in a context or environment that is abnormal. Tumor-associated antigens may be, for example, proteins or protein fragments, complex carbohydrates, gangliosides, haptens, nucleic acids, other biological molecules or any combinations thereof.

Illustrative useful tumor proteins include, but are not limited to any one or more of, CEA, human epidermal growth factor receptor 1 (HER1), human epidermal growth factor receptor 2 (HER2/neu), human epidermal growth factor receptor 3 (HER3), human epidermal growth factor receptor 4 (HER4), MUC1, Prostate-specific antigen (PSA), PSMA, WT1, p53, MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-8, GAGE-3, GAGE-4, GAGE-5, GAGE-6, GAGE-7B, NA88-A, NY-ESO-1, MART-1, MC1R, Gp100, PSA, PSM, Tyrosinase, TRP-1, TRP-2, ART-4, CAMEL, CEA, Cyp-B, BRCA1, Brachyury, Brachyury (TIVS7-2, polymorphism), Brachyury (IVS7 T/C polymorphism), T Brachyury, T, hTERT, hTRT, iCE, MUC1, MUC1 (VNTR polymorphism), MUC1c, MUC1n, MUC2, PRAME, P15, RU1 RU2, SART-1, SART-3, AFP, β-catenin/m, Caspase-8/m, CDK-4/m, ELF2M, GnT-V, G250, HSP70-2M, HST-2, KIAAO205, MUM-1, MUM-2, MUM-3, Myosin/m, RAGE, SART-2, TRP-2/INT2, 707-AP, Annexin II, CDCl27/m, TPI/mbcr-abl, ETV6/AML, LDLR/FUT, Pml/RARα, HPV E6, HPV E7, and TEL/AML1.

In some embodiments, the viral vector comprises a target antigen sequence encoding a modified polypeptide selected from CEA, human epidermal growth factor receptor 1 (HER1), human epidermal growth factor receptor 2 (HER2/neu), human epidermal growth factor receptor 3 (HER3), human epidermal growth factor receptor 4 (HER4), MUC1, Prostate-specific antigen (PSA), PSMA (i.e., PSM), WT1, p53, MAGE-A1, MAGE-A2, MAGE-A3, MAGE-A4, MAGE-A6, MAGE-A10, MAGE-A12, BAGE, DAM-6, DAM-10, GAGE-1, GAGE-2, GAGE-8, GAGE-3, GAGE-4, GAGE-5, GAGE-6, GAGE-7B, NA88-A, NY-ESO-1, MART-1, MC1R, Gp100, Tyrosinase, TRP-1, TRP-2, ART-4, CAMEL, Cyp-B, BRCA1, Brachyury, Brachyury (TIVS7-2, polymorphism), Brachyury (IVS7 T/C polymorphism), T Brachyury, T, hTERT, hTRT, iCE, MUC1 (VNTR polymorphism), MUC1c, MUC1n, MUC2, PRAME, P15, RU1, RU2, SART-1, SART-3, AFP, β-catenin/m, Caspase-8/m, CDK-4/m, ELF2M, GnT-V, G250, HSP70-2M, HST-2, KIAAO205, MUM-1, MUM-2, MUM-3, Myosin/m, RAGE, SART-2, TRP-2/INT2, 707-AP, Annexin II, CDCl27/m, TPI/mbcr-abl, ETV6/AML, LDLR/FUT, Pml/RARα, HPV E6, HPV E7, and TEL/AML1, wherein the polypeptide or a fragment thereof has at least 60%, 65%, 70%, 75%, 80%, 85%, 90%, 95%, 98%, 99%, 99.5%, or 99.9% identity to the corresponding native sequence.

Additional illustrative useful tumor proteins useful include, but are not limited to any one or more of alpha-actinin-4, ARTC1, CAR-ABL fusion protein (b3a2), B-RAF, CASP-5, CASP-8, beta-catenin, Cdc27, CDK4, CDKN2A, COA-1, dek-can fusion protein, EFTUD2, Elongation factor 2, ETV6-AML1 fusion protein, FLT3-ITD, FN1, GPNMB, LDLR-fucosyltransferase fusion protein, HLA-A2d, HLA-A1 1d, hsp70-2, KIAAO205, MART2, ME1, MUM-1f, MUM-2, MUM-3, neo-PAP, Myosin class I, NFYC, OGT, OS-9, p53, pml-RARalpha fusion protein, PRDXS, PTPRK, K-ras, N-ras, RBAF600, SIRT2, SNRPD1, SYT-SSX1- or -SSX2 fusion protein, TGF-betaRII, triosephosphate isomerase, BAGE-1, GnTVf, HERV-K-MEL, KK-LC-1, KM-HN-1, LAGE-1, MAGE-A9, MAGE-C2, mucink, NA-88, NY-ESO-1/LAGE-2, SAGE, Sp17, SSX-2, SSX-4, TAG-1, TAG-2, TRAG-3, TRP2-INT2g, XAGE-1b, gp100/

Pmel17, Kallikrein 4, mammaglobin-A, Melan-A/MART-1, NY-BR-1, OA1, PSA, RAB38NY-MEL-1, TRP-1/gp75, TRP-2, tyrosinase, adipophilin, AIM-2, ALDH1A1, BCLX (L), BCMA, BING-4, CPSF, cyclin D1, DKK1, ENAH (hMena), EP-CAM, EphA3, EZH2, FGF5, G250/MN/ CAIX, IL13Ralpha2, intestinal carboxyl esterase, alpha fetoprotein, M-CSFT, MCSP, mdm-2, MMP-2, PBF, PRAME, RAGE-1, RGS5, RNF43, RU2AS, secernin 1, SOX10, STEAP1, survivin, Telomerase, and/or VEGF.

Tumor-associated antigens may be antigens from infectious agents associated with human malignancies. Examples of infectious agents associated with human malignancies include Epstein-Barr virus, *Helicobacter pylori*, Hepatitis B virus, Hepatitis C virus, Human heresvirus-8, Human immunodeficiency virus, Human papillomavirus, Human T-cell leukemia virus, liver flukes, and *Schistosoma haematobium*.

CEA Antigen Targets

CEA represents an attractive target antigen for immunotherapy since it is over-expressed in nearly all colorectal cancers and pancreatic cancers, and is also expressed by some lung and breast cancers, and uncommon tumors such as medullary thyroid cancer, but is not expressed in other cells of the body except for low-level expression in gastrointestinal epithelium. CEA contains epitopes that may be recognized in an MEW restricted fashion by T-cells.

It was discovered that multiple homologous immunizations with Ad5 [E1-, E2b-]-CEA(6D), encoding the tumor antigen CEA, induced CEA-specific cell-mediated immune (CMI) responses with antitumor activity in mice despite the presence of pre-existing or induced Ad5-neutralizing antibody. In the present phase I/II study, cohorts of patients with advanced colorectal cancer were immunized with escalating doses of Ad5 [E1-, E2b-]-CEA(6D). CEA-specific CMI responses were observed despite the presence of pre-existing Ad5 immunity in a majority (61.3%) of patients. Importantly, there was minimal toxicity, and overall patient survival (48% at 12 months) was similar regardless of pre-existing Ad5 neutralizing antibody titers. The results demonstrate that, in cancer patients, the novel Ad5 [E1-, E2b-] gene delivery platform generates significant CMI responses to the tumor antigen CEA in the setting of both naturally acquired and immunization-induced Ad5 specific immunity.

CEA antigen specific CMI can be, for example, greater than 10, 20, 30, 40, 50, 100, 200, 300, 400, 500, 600, 700, 800, 900, 1000, 5000, 10000, or more IFN-γ spot forming cells (SFC) per $10^6$ peripheral blood mononuclear cells (PBMC). In some embodiments, the immune response is raised in a human subject with a preexisting inverse Ad5 neutralizing antibody titer of greater than 50, 100, 150, 200, 300, 400, 500, 600, 700, 800, 900, 1000, 1500, 2000, 2500, 3000, 3500, 4000, 4500, 5000, 6000, 7000, 8000, 9000, 1000, 12000, 15000 or higher. The immune response may comprise a cell-mediated immunity and/or a humoral immunity as described herein. The immune response may be measured by one or more of intracellular cytokine staining (ICS), ELISpot, proliferation assays, cytotoxic T-cell assays including chromium release or equivalent assays, and gene expression analysis using any number of polymerase chain reaction (PCR) or RT-PCR based assays, as described herein and to the extent they are available to a person skilled in the art, as well as any other suitable assays known in the art for measuring immune response.

In some embodiments, the replication defective adenovirus vector comprises a modified sequence encoding a subunit with at least 75%, 80%, 85%, 90%, 95%, 98%, 99%, 99.5%, or 99.9% identity to a wild-type subunit of the polypeptide.

The immunogenic polypeptide may be a mutant CEA or a fragment thereof. In some embodiments, the immunogenic polypeptide comprises a mutant CEA with an Asn->Asp substitution at position 610. In some embodiments, the replication defective adenovirus vector comprises a sequence encoding a polypeptide with at least 75%, 80%, 85%, 90%, 95%, 98%, 99%, 99.5%, or 99.9% identity to the immunogenic polypeptide. In some embodiments, the sequence encoding the immunogenic polypeptide comprises the sequence of SEQ ID NO: 1 or SEQ ID NO: 100.

In some embodiments, the sequence encoding the immunogenic polypeptide comprises a sequence with at least 70% 75%, 80%, 85%, 90%, 95%, 98%, 99%, 99.5%, or 99.9% identity to SEQ ID NO: 1 or SEQ ID NO: 100 or a sequence generated from SEQ ID NO: 1 or SEQ ID NO: 100 by alternative codon replacements. In some embodiments, the immunogenic polypeptide encoded by the adenovirus vectors comprise up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type human CEA sequence.

In some embodiments, the immunogenic polypeptide comprises a sequence from SEQ ID NO: 2 or a modified version, e.g., comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, of SEQ ID NO: 1 or SEQ ID NO: 100.

Members of the CEA gene family are subdivided into three subgroups based on sequence similarity, developmental expression patterns and their biological functions: the CEA-related Cell Adhesion Molecule (CEACAM) subgroup containing twelve genes (CEACAM1, CEACAM3-CEACAM8, CEACAM16 and CEACAM18-CEACAM21), the Pregnancy Specific Glycoprotein (PSG) subgroup containing eleven closely related genes (PSG1-PSG11) and a subgroup of eleven pseudogenes (CEACAMP1-CEACAMP11). Most members of the CEACAM subgroup have similar structures that consist of an extracellular Ig-like domains composed of a single N-terminal V-set domain, with structural homology to the immunoglobulin variable domains, followed by varying numbers of C2-set domains of A or B subtypes, a transmembrane domain and a cytoplasmic domain. There are two members of CEACAM subgroup (CEACAM16 and CEACAM20) that show a few exceptions in the organization of their structures. CEACAM16 contains two Ig-like V-type domains at its N and C termini and CEACAM20 contains a truncated Ig-like V-type 1 domain. The CEACAM molecules can be anchored to the cell surface via their transmembrane domains (CEACAM5 thought CEACAM8) or directly linked to glycophosphatidylinositol (GPI) lipid moiety (CEACAM5, CEACAM18 thought CEACAM21).

CEA family members are expressed in different cell types and have a wide range of biological functions. CEACAMs are found prominently on most epithelial cells and are present on different leucocytes. In humans, CEACAM1, the ancestor member of CEA family, is expressed on the apical side of epithelial and endothelial cells as well as on lymphoid and myeloid cells. CEACAM1 mediates cell-cell adhesion through hemophilic (CEACAM1 to CEACAM1) as well as heterothallic (e.g., CEACAM1 to CEACAM5) interactions. In addition, CEACAM1 is involved in many other biological processes, such as angiogenesis, cell migration, and immune functions. CEACAM3 and CEACAM4 expression is largely restricted to granulocytes, and they are able to convey uptake and destruction of several bacterial pathogens including Neisseria, Moraxella, and Haemophilus species.

Thus, in various embodiments, compositions and methods relate to raising an immune response against a CEA, selected from the group consisting of CEACAM1, CEACAM3, CEACAM4, CEACAM5, CEACAM6, CEACAM7, CEACAM8, CEACAM16, CEACAM18, CEACAM19, CEACAM20, CEACAM21, PSG1, PSG2, PSG3, PSG4, PSG5, PSG6, PSG7, PSG8, PSG9, and PSG11. An immune response may be raised against cells, e.g. cancer cells, expressing or overexpressing one or more of the CEAs, using the methods and compositions. In some embodiments, the overexpression of the one or more CEAs in such cancer cells is over 5, 10, 20, 30, 40, 50, 60, 70, 80, 90, 100 fold or more compared to non-cancer cells.

In certain embodiments, the CEA antigen used herein is a wild-type CEA antigen or a modified CEA antigen having a least a mutation in YLSGANLNL (SEQ ID NO: 3), a CAP1 epitope of CEA. The mutation can be conservative or non-conservative, substitution, addition, or deletion. In certain embodiments, the CEA antigen used herein has an amino acid sequence set forth in YLSGADLNL (SEQ ID NO: 4), a mutated CAP1 epitope. In further embodiments, the first replication-defective vector or a replication-defective vectors that express CEA has a nucleotide sequence at least 50%, 60%, 65%, 70%, 75%, 80%, 85%, 90%, 95%, 98%, 99%, 99.5%, 99.9%, or 100% identical to any portion of SEQ ID NO: 2 (the predicted sequence of an adenovirus vector expressing a modified CEA antigen), such as positions 1057 to 3165 of SEQ ID NO: 2 or full-length SEQ ID NO: 2.

Mucin Family Antigen Targets

The human mucin family (MUC1 to MUC21) includes secreted and transmembrane mucins that play a role in forming protective mucous barriers on epithelial surfaces in the body. These proteins function in to protecting the epithelia lining the respiratory, gastrointestinal tracts, and lining ducts in important organs such as, for example the mammary gland, liver, stomach, pancreas, and kidneys.

MUC1 (CD227) is a TAA that is over-expressed on a majority of human carcinomas and several hematologic malignancies. MUC1 (GenBank: X80761.1, NCBI: NM 001204285.1) and activates many important cellular pathways known to be involved in human disease. MUC1 is a heterodimeric protein formed by two subunits that is commonly overexpressed in several human cancers. MUC1 undergoes autoproteolysis to generate two subunits MUC1n and MUC1c that, in turn, form a stable noncovalent heterodimer.

The MUC1 C-terminal subunit (MUC1c) can comprise a 58 amino acid extracellular domain (ED), a 28 amino acid transmembrane domain (TM), and a 72 amino acid cytoplasmic domain (CD). The MUC1c also can contain a "CQC" motif that can allow for dimerization of MUC1 and it can also impart oncogenic function to a cell. In some cases, MUC1 can in part oncogenic function through inducing cellular signaling via MUC1c. MUC1c can interact with EGFR, ErbB2 and other receptor tyrosine kinases and contributing to the activation of the PI3K→AKT and MEK→ERK cellular pathways. In the nucleus, MUC1c activates the Wnt/β-catenin, STAT and NF-κB RelA cellular pathways. In some cases, MUC1 can impart oncogenic function through inducing cellular signaling via MUC1n. The MUC1 N-terminal subunit (MUC1n) can comprise variable numbers of 20 amino acid tandem repeats that can be glycosylated. MUC1 is normally expressed at the surface of glandular epithelial cells and is over-expressed and aberrantly glycosylated in carcinomas. MUC1 is a TAA that can be utilized as a target for tumor immunotherapy. Several clinical trials have been and are being performed to evaluate the use of MUC1 in immunotherapeutic vaccines. Importantly, these trials indicate that immunotherapy with MUC1 targeting is safe and may provide survival benefit.

However, clinical trials have also shown that MUC1 is a relatively poor immunogen. To overcome this, the present disclosure provides a T lymphocyte immune enhancer peptide sequence in the C terminus region of the MUC1 oncoprotein (MUC1-C or MUC1c). Compared with the native peptide sequence, the agonist in their modified MUC1-C (a) bound HLA-A2 at lower peptide concentrations, (b) demonstrated a higher avidity for HLA-A2, (c) when used with antigen-presenting cells, induced the production of more IFN-γ by T-cells than with the use of the native peptide, and (d) was capable of more efficiently generating MUC1-specific human T-cell lines from cancer patients. Importantly, T-cell lines generated using the agonist epitope were more efficient than those generated with the native epitope for the lysis of targets pulsed with the native epitope and in the lysis of HLA-A2 human tumor cells expressing MUC1. Additionally, the present disclosure provides additional CD8+ cytotoxic T lymphocyte immune enhancer agonist sequence epitopes of MUC1-C.

Certain embodiments provide a potent MUC1-C modified for immune enhancer capability (mMUC1-C or MUC1-C or MUC1c). Certain embodiments provide a potent MUC1-C modified for immune enhancer capability incorporated it into a recombinant Ad5 [E1-, E2b-] platform to produce a new and more potent immunotherapeutic vaccine. For example, the immunotherapeutic vaccine can be Ad5 [E1-, E2b-]-mMUC1-C for treating MUC1 expressing cancers or infectious diseases.

Post-translational modifications play an important role in controlling protein function in the body and in human disease. For example, in addition to proteolytic cleavage discussed above, MUC1 can have several post-translational modifications such as glycosylation, sialylation, palmitoylation, or a combination thereof at specific amino acid residues. Provided herein are immunotherapies targeting glycosylation, sialylation, phosphorylation, or palmitoylation modifications of MUC1.

MUC1 can be highly glycosylated (N- and O-linked carbohydrates and sialic acid at varying degrees on serine and threonine residues within each tandem repeat, ranging from mono- to penta-glycosylation). Differentially O-glycosylated in breast carcinomas with 3,4-linked GlcNAc. N-glycosylation consists of high-mannose, acidic complex-type and hybrid glycans in the secreted form MUC1/SEC, and neutral complex-type in the transmembrane form, MUC1/TM.4. Certain embodiments provide immunotherapies targeting differentially O-glycosylated forms of MUC1.

Further, MUC1 can be sialylated. Membrane-shed glycoproteins from kidney and breast cancer cells have preferentially sialylated core 1 structures, while secreted forms from the same tissues display mainly core 2 structures. The O-glycosylated content is overlapping in both these tissues with terminal fucose and galactose, 2- and 3-linked galactose, 3- and 3,6-linked GalNAc-ol and 4-linked GlcNAc predominating. Certain embodiments provide immunotherapies targeting various sialylation forms of MUC1. Dual palmitoylation on cysteine residues in the CQC motif is required for recycling from endosomes back to the plasma membrane. Certain embodiments provide for immunotherapies targeting various palmitoylation forms of MUC1.

Phosphorylation can affect MUC1's ability to induce specific cell signaling responses that are important for human health. Certain embodiments provide for immunotherapies targeting various phosphorylated forms of MUC1. For example, MUC1 can be phosphorylated on tyrosine and serine residues in the C-terminal domain. Phosphorylation on tyrosines in the C-terminal domain can increase nuclear location of MUC1 and β-catenin. Phosphorylation by PKC delta can induce binding of MUC1 to β-catenin/CTNNB1 and decrease formation of β-catenin/E-cadherin complexes. Src-mediated phosphorylation of MUC1 can inhibits interaction with GSK3B. Src- and EGFR-mediated phosphorylation of MUC1 on Tyr-1229 can increase binding to β-catenin/CTNNB1. GSK3B-mediated phosphorylation of MUC1 on Ser-1227 can decrease this interaction but restores the formation of the β-cadherin/E-cadherin complex. PDGFR-mediated phosphorylation of MUC1 can increase nuclear colocalization of MUC1CT and CTNNB1. Certain embodiments provide immunotherapies targeting different phosphorylated forms of MUC1, MUC1c and MUC1n known to regulate its cell signaling abilities.

The disclosure provides for immunotherapies that modulate MUC1c cytoplasmic domain and its functions in the cell. The disclosure provides for immunotherapies that comprise modulating a CQC motif in MUC1c. The disclosure provides for immunotherapies that comprise modulating the extracellular domain (ED), the transmembrane domain (TM), the cytoplasmic domain (CD) of MUC1c, or a combination thereof. The disclosure provides for immunotherapies that comprise modulating MUC1c's ability to induce cellular signaling through EGFR, ErbB2 or other receptor tyrosine kinases. The disclosure provides for immunotherapies that comprise modulating MUC1c's ability to induce PI3K→AKT, MEK→ERK, Wnt/β-catenin, STAT, NF-κB RelA cellular pathways, or combination thereof. In some embodiments, the MUC1c immunotherapy can further comprise CEA.

The disclosure also provides for immunotherapies that modulate MUC1n and its cellular functions. The disclosure also provides for immunotherapies comprising tandem repeats of MUC1n, the glycosylation sites on the tandem repeats of MUC1n, or a combination thereof. In some embodiments, the MUC1n immunotherapy further comprises CEA.

The disclosure also provides vaccines comprising MUC1n, MUC1c, CEA, or a combination thereof. The disclosure provides vaccines comprising MUC1c and CEA. The disclosure also provides vaccines targeting MUC1n and CEA. In some embodiments, the antigen combination is contained in one vector as provided herein. In some embodiments, the antigen combination is contained in a separate vector as provided herein.

Some embodiments relate to a replication defective adenovirus vector of serotype 5 comprising a sequence encoding an immunogenic polypeptide. The immunogenic polypeptide may be an isoform of MUC1 or a subunit or a fragment thereof. In some embodiments, the replication defective adenovirus vector comprises a sequence encoding a polypeptide with at least 75%, 80%, 85%, 90%, 95%, 98%, 99%, 99.5%, or 99.9% identity to the immunogenic polypeptide. In some embodiments, the sequence encoding the immunogenic polypeptide comprises the sequence of SEQ ID NO: 102. In some embodiments, the sequence encoding the immunogenic polypeptide comprises the sequence of SEQ ID NO: 5. In some embodiments, the sequence encoding the immunogenic polypeptide comprises the following sequence identified by SEQ ID NO: 6. In some embodiments, the sequence encoding the immunogenic polypeptide comprises the following sequence identified by SEQ ID NO: 9. In some embodiments, the sequence encoding the immunogenic polypeptide comprises the sequence of SEQ ID NO: 102. In some embodiments, the sequence encoding the immunogenic polypeptide comprises a sequence with at least 70%, 75%, 80%, 85%, 90%, 95%, 98%, 99%, 99.5%, 99.9% identity to SEQ ID NO: 5, SEQ ID NO: 6, SEQ ID NO: 101, SEQ ID NO: 9, SEQ ID NO: 102 or a sequence generated from SEQ ID NO: 5, SEQ ID NO: 6, SEQ ID NO: 101, SEQ ID NO: 9 or SEQ ID NO: 102 by alternative codon replacements. In some embodiments, the immunogenic polypeptide encoded by the adenovirus vectors described herein comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type human MUC1 sequence.

In certain embodiments, the MUC1 antigen used herein is a wild-type MUC1 antigen or a modified MUC1 antigen. In certain embodiments, the modified MUC1 antigen has at least 50%, 60%, 65%, 70%, 75%, 80%, 85%, 90%, 95%, 98%, 99%, 99.5%, 99.9%, 100% identity to SEQ ID NO: 7 (a mutated MUC1 protein sequence) or SEQ ID NO: 101 (a modified MUC1 nucleotide sequence). In certain embodiments, the MUC-1 antigen is a modified antigen having one or more mutations at positions 93, 141-142, 149-151, 392, 404, 406, 422, 430-431, 444-445, or 460 of SEQ ID NO: 7. The mutation can be conservative or non-conservative, substitution, addition, or deletion. In further embodiments, the MUC-1 antigen binds to HLA-A2, HLA-A3, HLA-A24, or a combination thereof. In certain embodiments, the third replication-defective vector or a replication-defective vector that express MUC1 has a nucleotide sequence at least 50%, 60%, 65%, 70%, 75%, 80%, 85%, 90%, 95%, 98%, 99%, 99.5%, 99.9%, or 100% identical to SEQ ID NO: 5 (MUC 1 wild-type nucleotide sequence). In further embodiments, the third replication-defective vector or a replication-defective vector that express MUC1 has a nucleotide sequence at least 50%, 60%, 65%, 70%, 75%, 80%, 85%, 90%, 95%, 98%, 99%, 99.5%, 99.9%, or 100% identical to SEQ ID NO: 6 (a mutated MUC1 nucleotide sequence). In further embodiments, the third replication-defective vector or a replication-defective vector that express MUC1 has a nucleotide sequence at least 50%, 60%, 65%, 70%, 75%, 80%, 85%, 90%, 95%, 98%, 99%, 99.5%, 99.9%, or 100% identical to SEQ ID NO: 101 (a modified MUC1 nucleotide sequence, also referred to herein as MUC1-c). In certain embodiments, the third replication-defective vector or a replication-defective vector that express MUC1 has a nucleotide sequence at least 50%, 60%, 65%, 70%, 75%, 80%, 85%, 90%, 95%, 98%, 99%, 99.5%, 99.9%, or 100% identical to any portion of or full-length SEQ ID NO: 8 (the predicted sequence of an adenovirus vector expressing a modified MUC-1 antigen), such as positions 1033-2858 of SEQ ID NO: 8.

In some embodiments, a MUC1 antigen disclosed herein can be a MUC1-C antigen. In some embodiments, the MUC1-C antigen can have at least 80%, at least 85%, at least 87%, at least 90%, at least 92%, at least 95%, at least 97%, or at least 99% sequence identity to SEQ ID NO: 7. In some embodiments, a nucleic acid sequence encoding for a MUC1-C antigen disclosed herein can have at least 80%, at least 85%, at least 87%, at least 90%, at least 92%, at least 95%, at least 97%, or at least 99% sequence identity to SEQ ID NO: 5, SEQ ID NO: 6, SEQ ID NO: 101, or positions 1105-2532 of SEQ ID NO: 8. In some embodiments, the MUC-1C antigen is a modified MUC1 antigen. The modified MUC1 ntigen can have at least 80%, at least 85%, at least 87%, at least 90%, at least 92%, at least 95%, at least 97%, or at least 99% sequence identity to SEQ ID NO: 7. The modified MUC1 antigen can be further encoded for by a nucleic acid sequence having at least 80%, at least 85%, at least 87%, at least 90%, at least 92%, at least 95%, at least 97%, or at least 99% sequence identity to SEQ ID NO: 5, SEQ ID NO: 6, positions 1105-2532 of SEQ ID NO: 8, or SEQ ID NO: 101. The MUC-1 antigen can be modified by having a mutation at any of positions 93, 141-142, 149-151, 392, 404, 406, 422, 430-431, 444-445, or 460 of SEQ ID NO: 7.

In some embodiments, a recombinant adenovirus vector (e.g., Ad5 [E1-, E2b-]) encoding for a MUC-1 antigen of the present disclosure can have at least 80%, at least 85%, at least 87%, at least 90%, at least 92%, at least 95%, at least 97%, or at least 99% sequence identity to SEQ ID NO: 8 or positions 1105-2532 of SEQ ID NO: 8

Brachyury Antigen Targets

Certain embodiments provide immunotherapies that comprise one or more antigens to Brachyury. Brachyury (also known as the "T" protein in humans) is a member of the T-box family of transcription factors that play key roles during early development, mostly in the formation and differentiation of normal mesoderm and is characterized by a highly conserved DNA-binding domain designated as T-domain. The epithelial to mesenchymal transition (EMT) is a key step during the progression of primary tumors into a metastatic state in which Brachyury plays a crucial role. The expression of Brachyury in human carcinoma cells induces changes characteristic of EMT, including up-regulation of mesenchymal markers, down-regulation of epithelial markers, and an increase in cell migration and invasion. Conversely, inhibition of Brachyury resulted in down-regulation of mesenchymal markers and loss of cell migration and invasion and diminished the ability of human tumor cells to form metastases. Brachyury can function to mediate epithelial-mesenchymal transition and promotes invasion.

The disclosure also provides for immunotherapies that modulate Brachyury effect on epithelial-mesenchymal transition function in cell proliferation diseases, such as cancer. The disclosure also provides for immunotherapies that modulate Brachyury's ability to promote invasion in cell proliferation diseases, such as cancer. The disclosure also provides for immunotherapies that modulate the DNA binding function of T-box domain of Brachyury. In some embodiments, the Brachyury immunotherapy can further comprise one or more antigens to CEA or MUC1, MUC1c, or MUC1n.

Brachyury expression is nearly undetectable in most normal human tissues and is highly restricted to human tumors and often overexpressed making it an attractive target antigen for immunotherapy. In human, Brachyury is encoded by the T gene (GenBank: AJ001699.1, NCBI: NM_003181.3). There are at least two different isoforms produced by alternative splicing found in humans. Each isoform has a number of natural variants.

Brachyury is immunogenic and Brachyury-specific CD8+ T-cells expanded in vitro can lyse Brachyury expressing tumor cells. These features of Brachyury make it an attractive TAA for immunotherapy. The Brachyury protein is a T-box transcription factor. It can bind to a specific DNA element, a near palindromic sequence "TCACACCT" through a region in its N-terminus, called the T-box to activate gene transcription when bound to such a site.

The disclosure also provides vaccines comprising Brachyury, CEA, or a combination thereof. In some embodiments, the antigen combination is contained in one vector as provided herein. In some embodiments, the antigen combination is contained in a separate vector as provided herein.

In particular embodiments, there is provided a replication defective adenovirus vector of serotype 5 comprising a sequence encoding an immunogenic polypeptide. The immunogenic polypeptide may be an isoform of Brachyury or a subunit or a fragment thereof. In some embodiments, the replication defective adenovirus vector comprises a sequence encoding a polypeptide with at least 70%, 75%, 80%, 85%, 90%, 95%, 98%, 99%, 99.5%, or 99.9% identity to the immunogenic polypeptide. In some embodiments, the sequence encoding the immunogenic polypeptide comprises the following sequence identified by SEQ ID NO: 101. In some embodiments, the sequence encoding the immunogenic polypeptide comprises the following sequence identified by SEQ ID NO: 7. In some embodiments, the replication defective adenovirus vector comprises a sequence encoding a polypeptide with at least 70%, 75%, 80%, 85%, 90%, 95%, 98%, 99%, 99.5%, or 99.9% identity to the immunogenic polypeptide. In some embodiments, the sequence encoding the immunogenic polypeptide comprises the following sequence identified by SEQ ID NO: 102. In some embodiments, the sequence encoding the immunogenic polypeptide comprises the sequence of SEQ ID NO: 8. In some embodiments, the sequence encoding the immunogenic polypeptide comprises a sequence with at least 70%, 75%, 80%, 85%, 90%, 95%, 98%, 99%, 99.5%, or 99.9% identity to SEQ ID NO: 7, SEQ ID NO: 101, SEQ ID NO: 8 or a sequence generated from SEQ ID NO: 7, SEQ ID NO: 101, or SEQ ID NO: 8 by alternative codon replacements. In some embodiments, the immunogenic polypeptide encoded by the adenovirus vectors described herein comprising up to 1, 2, 3, 4, 5, 6, 7, 8, 9, 10, 11, 12, 13, 14, 15, 16, 17, 18, 19, 20, 25, 30, 35, 40, or more point mutations, such as single amino acid substitutions or deletions, as compared to a wild-type human Brachyury sequence.

In certain embodiments, the Brachyury antigen used herein is a wild-type antigen or a modified antigen. In certain embodiments, the Brachyury antigen binds to HLA-A2. In further embodiments, the Brachyury antigen is a modified Brachyury antigen comprising an amino acid sequence set forth in WLLPGTSTV (SEQ ID NO: 15), a HLA-A2 epitope of Brachyury. In further embodiments, the Brachyury antigen is a modified Brachyury antigen having an amino acid sequence at least 50%, 60%, 65%, 70%, 75%, 80%, 85%, 90%, 95%, 98%, 99%, 99.5%, 99.9%, or 100% identity to SEQ ID NO: 14, a modified Brachyury protein sequence. In certain embodiments, the replication-defective vector has a nucleotide sequence at least 80% identical SEQ ID NO: 10 or positions 1033 to 2283 of SEQ ID NO: 13. In further embodiments, the second replication-defective vector has a nucleotide sequence at least 50%, 60%, 65%, 70%, 75%, 80%, 85%, 90%, 95%, 98%, 99%, 99.5%, 99.9%, or 100% identical to any portion or full-length of SEQ ID NO: 13 (the predicted sequence of an adenovirus vector express a modified Brachyury antigen), such as positions 1033 to 2283 of SEQ ID NO: 13. In some embodiments, the Brachyury antigen is a modified Brachyury antigen having an amino acid sequence at least 80% identical to SEQ ID NO: 12 (another mutated Brachyury protein sequence). In certain embodiments, the second replication-defective vector or a replication-defective vector that express Brachyury has a nucleotide sequence at least 50%, 60%, 65%, 70%, 75%, 80%, 85%, 90%, 95%, 98%, 99%, 99.5%, 99.9%, or 100% identical to positions 520-1824 of SEQ ID NO: 9 (wild-type Brachyury), SEQ ID NO: 9, SEQ ID NO: 10, or SEQ ID NO: 102. In certain embodiments, the second replication-defective vector or a replication-defective vector that express Brachyury has a nucleotide sequence at least 50%, 60%, 65%, 70%, 75%, 80%, 85%, 90%, 95%, 98%, 99%, 99.5%, 99.9%, or 100% identical to SEQ ID NO: 102.

In some embodiments, a Brahcyury antigen of the present disclosure can have at least 80%, at least 85%, at least 87%, at least 90%, at least 92%, at least 95%, at least 97%, or at least 99% sequence identity to SEQ ID NO: 12 or SEQ ID NO: 14. A nucleic acid sequence encoding for a Brachyury antigen of the present disclosure can have at least 80%, at least 85%, at least 87%, at least 90%, at least 92%, at least 95%, at least 97%, or at least 99% sequence identity to SEQ ID NO: 9, SEQ ID NO: 10, positions 1045 to 2277 of SEQ ID NO: 13, or SEQ ID NO: 102. In some embodiments, the Brachyury antigen can be a modified Brachyury antigen. The modified Brachyury antigen can have at least 80%, at least 85%, at least 87%, at least 90%, at least 92%, at least 95%, at least 97%, or at least 99% sequence identity to SEQ ID NO: 14, positions 1045 to 2277 of SEQ ID NO: 13, or SEQ ID NO: 102. In some embodiments, an adenovirus vector (e.g., Ad5 [E1-, E2b-]) encoding for a Brachyury antigen disclosed herein can have at least 80%, at least 85%, at least 87%, at least 90%, at least 92%, at least 95%, at least 97%, or at least 99% sequence identity to SEQ ID NO: 13 or positions 1045 to 2277 of SEQ ID NO: 13.

Infectious Disease-Associated Antigen Targets

Target antigens include, but are not limited to, antigens derived from any of a variety of infectious agents such as parasites, bacteria, virus, prions, and the like. An infectious agent may refer to any living organism capable of infecting a host. Infectious agents include, for example, bacteria, any variety of viruses, such as, single stranded RNA viruses, single stranded DNA viruses, fungi, parasites, and protozoa.

Examples of infectious disease associated target antigens that can be used with the compositions and the methods can be derived from the following: *Actinobacillus* spp., *Actinomyces* spp., Adenovirus (types 1, 2, 3, 4, 5, 6, and 7), Adenovirus (types 40 and 41), *Aerococcus* spp., *Aeromonas hydrophila*, *Ancylostoma duodenale*, *Angiostrongylus cantonensis*, *Ascaris lumbricoides*, *Ascaris* spp., *Aspergillus* spp., *Babesia* spp, *B. microti*, *Bacillus anthracis*, *Bacillus cereus*, *Bacteroides* spp., *Balantidium coli*, *Bartonella baciliformis*, *Blastomyces dermatitidis*, Bluetongue virus, *Bordetella bronchiseptica*, *Bordetella pertussis*, *Borrelia afzelii*, *Borrelia burgdorferi*, *Borrelia garinii*, *Branhamella catarrhalis*, *Brucella* spp. (*B. abortus*, *B. canis*, *B. melitensis*, *B. suis*), *Brugia* spp., *Burkholderia*, (*Pseudomonas*) *mallei*, *Burkholderia* (*Pseudomonas*) *pseudomallei*, California serogroup, *Campylobacter fetus* subsp. Fetus, *Campylobacter jejuni*, *C. coli*, *C. fetus* subsp. Jejuni, *Candida albicans*, *Capnocytophaga* spp., Chikungunya virus, *Chlamydia psittaci*, *Chlamydia trachomatis*, *Citrobacter* spp., *Clonorchis sinensis*, *Clostridium botulinum*, *Clostridium difficile*, *Clostridium perfringens*, *Clostridium tetani*, *Clostridium* spp. (with the exception of those species listed above), *Coccidioides immitis*, Colorado tick fever virus, *Corynebacterium diphtheriae*, *Coxiella burnetii*, Coxsackievirus, Creutzfeldt-Jakob agent, Kuru agent, Crimean-Congo hemorrhagic fever virus, *Cryptococcus neoformans*, *Cryptosporidium parvum*, Cytomegalovirus, *Cyclospora cayatanesis*, Dengue virus (1, 2, 3, 4), Diphtheroids, Eastern (Western) equine encephalitis virus, Ebola virus, *Echinococcus granulosus*, *Echinococcus multilocularis*, Echovirus, *Edwardsiella tarda*, *Entamoeba histolytica*, *Enterobacter* spp., Enterovirus 70, *Epidermophyton floccosum*, *Ehrlichia* spp., *Ehrlichia sennetsu*, *Microsporum* spp., *Trichophyton* spp., Epstein-Barr virus, *Escherichia coli*, enterohemorrhagic, *Escherichia coli*, enteroinvasive, *Escherichia coli*, enteropathogenic, *Escherichia coli*, enterotoxigenic, *Fasciola hepatica*, *Francisella tularensis*, *Fusobacterium* spp., *Gemella haemolysans*, *Giardia lamblia*, Guanarito virus, *Haemophilus ducreyi*, *Haemophilus influenzae* (group b), Hantavirus, Hepatitis A virus, Hepatitis B virus, Hepatitis C virus, Hepatitis D virus, Hepatitis E virus, Herpes simplex virus, Herpesvirus *simiae*, *Histoplasma capsulatum*, Human coronavirus, Human immunodeficiency virus, Human papillomavirus, Human rotavirus, Human T-lymphotrophic virus, Influenza virus including H5N1, Junin virus/Machupo virus, *Klebsiella* spp., Kyasanur Forest disease virus, *Lactobacillus* spp., Lassa virus, *Legionella pneumophila*, *Leishmania major*, *Leishmania infantum*, *Leishmania* spp., *Leptospira interrogans*, *Listeria monocytogenes*, Lymphocytic choriomeningitis virus, Machupo virus, Marburg virus, Measles virus, *Micrococcus* spp., *Moraxella* spp., *Mycobacterium* spp. (other than *M. bovis*, *M. tuberculosis*, *M. avium*, *M. leprae*), *Mycobacterium tuberculosis*, *M. bovis*, *Mycoplasma hominis*, *M. orale*, *M. salivarium*, *M. fermentans*, *Mycoplasma pneumoniae*, *Naegleria fowleri*, *Necator americanus*, *Neisseria gonorrhoeae*, *Neisseria meningitides*, *Neisseria* spp. (other than *N. gonorrhoeae* and *N. meningitidis*), *Nocardia* spp., Norwalk virus, Omsk hemorrhagic fever virus, *Onchocerca volvulus*, *Opisthorchis* spp., Parvovirus B19, *Pasteurella* spp., *Peptococcus* spp., *Peptostreptococcus* spp., *Plasmodium falciparum*, *Plasmodium vivax*, *Plasmodium* spp., *Plesiomonas shigelloides*, Powassan encephalitis virus, *Proteus* spp., *Pseudomonas* spp. (other than *P. mallei*, *P. pseudomallei*), Rabies virus, Respiratory syncytial virus, Rhinovirus, *Rickettsia akari*, *Rickettsia prowazekii*, *R. Canada*, *Rickettsia rickettsii*, Rift Valley virus, Ross river virus/O'Nyong-Nyong virus, Rubella virus, *Salmonella choleraesuis*, *Salmonella paratyphi*, *Salmonella typhi*, *Salmonella* spp. (with the exception of those species listed above), *Schistosoma* spp., Scrapie agent, *Serratia* spp., *Shigella* spp., Sindbis virus, *Sporothrix schenckii*, St. Louis encephalitis virus, Murray Valley encephalitis virus, *Staphylococcus aureus*, *Streptobacillus moniliformis*, *Streptococcus agalactiae*, *Streptococcus faecalis*, *Streptococcus pneumoniae*, *Streptococcus pyogenes*, *Streptococcus salivarius*, *Taenia saginata*, *Taenia solium*, *Toxocara canis*, *T. cati*, *T. cruzi*, *Toxoplasma gondii*, *Treponema pallidum*, *Trichinella* spp., *Trichomonas vaginalis*, *Trichuris trichiura*, *Trypanosoma brucei*, *Trypanosoma cruzi*, *Ureaplasma urealyticum*, Vaccinia virus, Varicella-zoster virus, eastern equine encephalitis virus (EEEV), severe acute respiratory virus (SARS), Venezuelan equine encephalitis virus (VEEV), Vesicular stomatitis virus, *Vibrio cholerae*, serovar 01, *Vibrio parahaemolyticus*, West Nile virus, *Wuchereria bancrofti*, Yellow fever virus, *Yersinia enterocolitica*, *Yersinia pseudotuberculosis*, and *Yersinia pestis*. Target antigens may include proteins, or variants or fragments thereof, produced by any of the infectious organisms.

A number of viruses are associated with viral hemorrhagic fever, including filoviruses (e.g., Ebola, Marburg, and Reston), arenaviruses (e.g. Lassa, Junin, and Machupo), and bunyaviruses. In addition, phleboviruses, including, for example, Rift Valley fever virus, have been identified as etiologic agents of viral hemorrhagic fever. Etiological agents of hemorrhagic fever and associated inflammation may also include paramyxoviruses, particularly respiratory syncytial virus. In addition, other viruses causing hemorrhagic fevers in man have been identified as belonging to the following virus groups: togavirus (Chikungunya), flavivirus (dengue, yellow fever, Kyasanur Forest disease, Omsk hemorrhagic fever), nairovirus (Crimian-Congo hemorrhagic fever) and hantavirus (hemorrhagic fever with renal syndrome, nephropathic epidemia). Furthermore, Sin Nombre virus was identified as the etiologic agent of the 1993 outbreak of hantavirus pulmonary syndrome in the American Southwest.

Target antigens may include viral coat proteins, i.e., influenza neuraminidase and hemagglutinin, HIV gp160 or derivatives thereof, HIV Gag, HIV Nef, HIV Pol, SARS coat proteins, herpes virion proteins, WNV proteins, etc. Target antigens may also include bacterial surface proteins including pneumococcal PsaA, PspA, LytA, surface or virulence associated proteins of bacterial pathogens such as Nisseria gonnorhea, outer membrane proteins or surface proteases.

Personalized Tumor-Associated Antigens

In certain embodiments tumor-associated antigens used with the compositions and methods as described herein may be identified directly from an individual with a proliferative disease or cancer. In certain embodiments, cancers may include benign tumors, metastatic tumors, carcinomas, or sarcomas and the like. In some embodiments, a personalized tumor antigen comprises CEA characterized from a patient and further utilized as the target antigen as a whole, in part or as a variant.

In this regard, screens can be carried out using a variety of known technologies to identify tumor target antigens from an individual. For example, in one embodiment, a tumor biopsy is taken from a patient, RNA is isolated from the tumor cells and screened using a gene chip (for example, from Affymetrix, Santa Clara, Calif.) and a tumor antigen is identified. Once the tumor target antigen is identified, it may then be cloned, expressed, and purified using techniques known in the art.

This target antigen can then linked to one or more epitopes or incorporated or linked to cassettes or viral vectors described herein and administered to the patient in order to alter the immune response to the target molecule isolated from the tumor. In this manner, "personalized" immunotherapy and vaccines are contemplated in certain embodiments. Where cancer is genetic (i.e., inherited), for example, the patient has been identified to have a BRAC1 or BRAC2 mutation, the vaccine can be used prophylactically. When the cancer is sporadic this immunotherapy can be used to reduce the size of the tumor, enhance overall survival and reduce reoccurrence of the cancer in a subject.

Combination Immunotherapy with Ad5-CEA Vaccines and IL-15 Superagonists

Certain embodiments provide combination immunotherapy compositions for the treatment of cancers. In some aspects, combination immunotherapies provided herein can comprise a multi-targeted immunotherapeutic approach against antigens associated with the development of cancer such as tumor associated antigen (TAA) or antigens know to be involved in a particular infectious disease, such as infectious disease associated antigen (IDAA). In some aspects, combination immunotherapies and vaccines provided herein can comprise a multi-targeted antigen signature immunotherapeutic approach against antigens associated with the development of cancer. The compositions and methods, in various embodiments, provide viral based vectors expressing CEA or a variant of CEA for immunization of a disease, as provided herein. These vectors can raise an immune response against CEA.

Ad5-Based Vaccines in Combination Therapy

In some aspects, the vector can comprise at least one antigen, such as CEA. In some aspects, the vector can comprise at least two antigens. In some aspects, the vector can comprise at least three antigens. In some aspects, the vector can comprise more than three antigens. In some aspects, the vaccine formulation can comprise 1:1 ratio of vector to antigen. In some aspects, the vaccine can comprise 1:2 ratio of vector to antigen. In some aspects, the vaccine can comprise 1:3 ratio of vector to antigen. In some aspects, the vaccine can comprise 1:4 ratio of vector to antigen. In some aspects, the vaccine can comprise 1:5 ratio of vector to antigen. In some aspects, the vaccine can comprise 1:6 ratio of vector to antigen. In some aspects, the vaccine can comprise 1:7 ratio of vector to antigen. In some aspects, the vaccine can comprise 1:8 ratio of vector to antigen. In some aspects, the vaccine can comprise 1:9 ratio of vector to antigen. In some aspects, the vaccine can comprise 1:10 ratio of vector to antigen.

In some aspects, the vaccine can be a single-antigen vaccine, for example and Ads[E1-, E2b-]-CEA vaccine. In some aspects, the vaccine can comprise a combination vaccine, wherein the vaccine can comprise at least two vectors each containing at least a single antigen. In some aspects the vaccine can be a combination vaccine, wherein the vaccine can comprise at least three vectors each containing at least a single antigen target. In some aspects the vaccine can comprise a combination vaccine, wherein the vaccine comprises more than three vectors each containing at least a single antigen.

In some aspects, the vaccine can be a combination vaccine, wherein the vaccine can comprise at least two vectors, wherein a first vector of the at least two vectors can comprise at least a single antigen and wherein a second vector of the at least two vectors can comprise at least two antigens. In some aspects, the vaccine can comprise a combination vaccine, wherein the vaccine can comprise at least three vectors, wherein a first vector of the at least three vectors can comprise at least a single antigen and wherein a second vector of the at least three vectors can comprise at least two antigens. In some aspects, the vaccine can be a combination vaccine, wherein the vaccine can comprise three or more vectors, wherein a first vector of the three or more vectors can comprise at least a single antigen and wherein a second vector of the three or more vectors can comprise at least two antigens. In some aspects, the vaccine can be a combination vaccine, wherein the vaccine can comprise more than three vectors each containing at least two antigens.

When a mixture of different antigens are simultaneously administered or expressed from a same or different vector in an individual, they may compete with one another. As a result the formulations comprising different concentration and ratios of expressed antigens in a combination immunotherapy or vaccine must be evaluated and tailored to the individual or group of individuals to ensure that effective and sustained immune responses occur after administration.

Composition that comprises multiple antigens can be present at various ratios. For example, formulations with more than vector can have various ratios. For example, immunotherapies or vaccines can have two different vectors in a stoichiometry of 1:1, 1:2, 1:3, 1:4, 1:5, 1:6, 1:7, 1:8, 1:9, 1:10, 1:15, 1:20, 1:30, 2:1, 2:3, 2:4, 2:5, 2:6, 2:7, 2:8, 3:1, 3:3, 3:4, 3:5, 3:6, 3:7, 3:8, 3:1, 3:3, 3:4, 3:5, 3:6, 3:7, 3:8, 4:1, 4:3, 4:5, 4:6, 4:7, 4:8, 5:1, 5:3, 5:4, 5:6, 5:7, 5:8, 6:1, 6:3, 6:4, 6:5, 6:7, 6:8, 7:1, 7:3, 7:4, 7:5, 7:6, 7:8, 8:1, 8:3, 8:4, 8:5, 8:6, or 8:7. For example, immunotherapies or vaccines can have three different vectors in a stoichiometry of: 1:1:1, 1:2:1, 1:3:1, 1:4:1, 1:5:1, 1:6:1, 1:7:1, 1:8:1, 2:1:1, 2:3:1, 2:4:1, 2:5:1, 2:6:1, 2:7:1, 2:8:1, 3:1, 3:3:1, 3:4:1, 3:5:1, 3:6:1, 3:7:1, 3:8:1, 3:1:1, 3:3:1, 3:4:1, 3:5:1, 3:6:1, 3:7:1, 3:8:1, 4:1:1, 4:3:1, 4:4:1, 4:5:1, 4:6:1, 4:7:1, 4:8:1, 5:1:1, 5:3:1, 5:4:1, 5:5:1, 5:6:1, 5:7:1, 5:8:1, 6:1:1, 6:3:1, 6:4:1, 6:5:1, 6:6:1, 6:7:1, 6:8:1, 7:1:1, 7:3:1, 7:4:1, 7:5:1, 7:6:1, 7:7:1, 7:8:1, 8:1:1, 8:3:1, 8:4:1, 8:5:1, 8:6:1, 8:7:1, 8:8:1, 1:1:2, 1:2:2, 1:3:2, 1:4:2, 1:5:2, 1:6:2, 1:7:2, 1:8:2, 2:1:2, 2:3:2, 2:4:2, 2:5:2, 2:6:2, 2:7:2, 2:8:2, 3:1:2, 3:3:2, 3:4:2, 3:5:2, 3:6:2, 3:7:2, 3:8:2, 3:1:2, 3:3:2, 3:4:2, 3:5:2, 3:6:2, 3:7:2, 3:8:2, 4:1:2, 4:3:2, 4:4:2, 4:5:2, 4:6:2, 4:7:2, 4:8:2, 5:1:2, 5:3:2, 5:4:2, 5:5:2, 5:6:2, 5:7:2, 5:8:2, 6:1:2, 6:3:2, 6:4:2, 6:5:2, 6:6:2, 6:7:2, 6:8:2, 7:1:2, 7:3:2, 7:4:2, 7:5:2, 7:6:2, 7:7:2, 7:8:2, 8:1:2, 8:3:2, 8:4:2, 8:5:2, 8:6:2, 8:7:2, 8:8:2, 1:1:3, 1:2:3, 1:3:3, 1:4:3, 1:5:3, 1:6:3, 1:7:3, 1:8:3, 2:1:3, 2:3:3, 2:4:3, 2:5:3, 2:6:3, 2:7:3, 2:8:3, 3:1:3, 3:3:3, 3:4:3, 3:5:3, 3:6:3, 3:7:3, 3:8:3, 3:1:3, 3:3:3, 3:4:3, 3:5:3, 3:6:3, 3:7:3, 3:8:3, 4:1:3, 4:3:3, 4:4:3, 4:5:3, 4:6:3, 4:7:3, 4:8:3, 5:1:3, 5:3:3, 5:4:3, 5:5:3, 5:6:3, 5:7:3, 5:8:3, 6:1:3, 6:3:3, 6:4:3, 6:5:3, 6:6:3, 6:7:3, 6:8:3, 7:1:3, 7:3:3, 7:4:3, 7:5:3, 7:6:3, 7:7:3, 7:8:3, 8:1:3, 8:3:3, 8:4:3, 8:5:3, 8:6:3, 8:7:3, 8:8:3, 1:1:4, 1:2:4, 1:3:4, 1:4:4, 1:5:4, 1:6:4, 1:7:4, 1:8:4, 2:1:4, 2:3:4, 2:4:4, 2:5:4, 2:6:4, 2:7:4, 2:8:4, 3:1:4, 3:3:4, 3:4:4, 3:5:4, 3:6:4, 3:7:4, 3:8:4, 3:1:4, 3:3:4, 3:4:4, 3:5:4, 3:6:4, 3:7:4, 3:8:4, 4:1:4, 4:3:4, 4:4:4, 4:5:4, 4:6:4, 4:7:4, 4:8:4, 5:1:4, 5:3:4, 5:4:4, 5:5:4, 5:6:4, 5:7:4, 5:8:4, 6:1:4, 6:3:4, 6:4:4, 6:5:4, 6:6:4, 6:7:4, 6:8:4, 7:1:4, 7:3:4, 7:4:4, 7:5:4, 7:6:4, 7:7:4, 7:8:4, 8:1:4, 8:3:4, 8:4:3, 8:5:4, 8:6:4, 8:7:4, 8:8:4, 1:1:5, 1:2:5, 1:3:5, 1:4:5, 1:5:5, 1:6:5, 1:7:5, 1:8:5, 2:1:5, 2:3:5, 2:4:5, 2:5:5, 2:6:5, 2:7:5, 2:8:5, 3:1:5, 3:3:5, 3:4:5, 3:5:5, 3:6:5, 3:7:5, 3:8:5, 3:1:5, 3:3:5, 3:4:5, 3:5:5, 3:6:5, 3:7:5, 3:8:5, 4:1:5, 4:3:5, 4:4:5, 4:5:5, 4:6:5, 4:7:5, 4:8:5, 5:1:5, 5:3:5, 5:4:5, 5:5:5, 5:6:5, 5:7:5, 5:8:5, 6:1:5, 6:3:5, 6:4:5, 6:5:5, 6:6:5, 6:7:5, 6:8:5, 7:1:5, 7:3:5, 7:4:5, 7:5:5, 7:6:5, 7:7:5, 7:8:5, 8:1:5, 8:3:5, 8:4:5, 8:5:5, 8:6:5, 8:7:5, 8:8:5, 1:1:6, 1:2:6, 1:3:6, 1:4:6, 1:5:6, 1:6:6, 1:7:6, 1:8:6, 2:1:6, 2:3:6, 2:4:6, 2:5:6, 2:6:6, 2:7:6, 2:8:6, 3:1:6, 3:3:6, 3:4:6, 3:5:6, 3:6:6, 3:7:6, 3:8:6, 3:1:6, 3:3:6, 3:4:6, 3:5:6, 3:6:6, 3:7:6, 3:8:6, 4:1:6, 4:3:6, 4:4:6, 4:5:6, 4:6:6, 4:7:6, 4:8:6, 5:1:6, 5:3:6, 5:4:6, 5:5:6, 5:6:6, 5:7:6, 5:8:6, 6:1:6, 6:3:6, 6:4:6, 6:5:6, 6:6:6, 6:7:6, 6:8:6, 7:1:6, 7:3:6, 7:4:6, 7:5:6, 7:6:6, 7:7:6, 7:8:6, 8:1:6, 8:3:6, 8:4:6, 8:5:6, 8:6:5, 8:7:6, 8:8:6, 1:1:7, 1:2:7, 1:3:7, 1:4:7, 1:5:7, 1:6:7, 1:7:7, 1:8:7, 2:1:7, 2:3:7, 2:4:7, 2:5:7, 2:6:7, 2:7:7, 2:8:7, 3:1:7, 3:3:7, 3:4:7, 3:5:7, 3:6:7, 3:7:7, 3:8:7, 3:1:7, 3:3:7, 3:4:7, 3:5:7, 3:6:7, 3:7:7, 3:8:7, 4:1:7, 4:3:7, 4:4:7, 4:5:7, 4:6:7, 4:7:7, 4:8:7, 5:1:7, 5:3:7, 5:4:7, 5:5:7, 5:6:7, 5:7:7, 5:8:7, 6:1:7, 6:3:7, 6:4:7, 6:5:7, 6:6:7, 6:7:7, 6:8:7, 7:1:7, 7:3:7, 7:4:7, 7:5:7, 7:6:7, 7:7:7, 7:8:7, 8:1:7, 8:3:7, 8:4:7, 8:5:7, 8:6:5, 8:7:7, or 8:8:7.

Certain embodiments provide combination immunotherapies comprising multi-targeted immunotherapeutic directed TAAs. Certain embodiments provide combination immunotherapies comprising multi-targeted immunotherapeutic directed to IDAAs.

Certain embodiments provide a combination immunotherapies or vaccines comprising: at least two, at least three, or more than three different target antigens comprising a sequence encoding a modified CEA. For example, a combination immunotherapy or vaccine can comprise at least two, at least three, or more than three different target antigens comprising a sequence encoding a modified CEA, wherein the modified CEA comprises a sequence with an identity value of at least 70%, 75%, 80%, 85%, 90%, 95%, 98%, 99%, 99.5%, or 99.9% to SEQ ID NO: 1 or SEQ ID NO: 100. In some embodiments, the modified CEA comprises a sequence with an identity value of at least 70%, 75%, 80%, 85%, 90%, 95%, 98%, 99%, 99.5%, 99.9%, or 100% SEQ ID NO: 1 and has a Asn->Asp substitution at position 610. In some embodiments, the CEA comprises a sequence of YLSGANLNL (SEQ ID NO: 3), a CAP1 epitope of CEA or YLSGADLNL (SEQ ID NO: 4), a mutated CAP1 epitope. The Ad5-CEA expressing vector can have a sequence as set forth in SEQ ID NO: 2.

IL-15 Superagonist in Combination Therapy with Ad5 Vaccines

The present invention provides compositions for combination therapy including an Ad5 [E1-, E2b-]-CEA vaccine and an IL-15 super-agonist complex. In certain embodiments, the present invention provides a method of treating a CEA-expressing cancer in a subject, the method comprising: administering to the individual a first pharmaceutical composition comprising a replication-defective vector comprising a nucleic acid sequence encoding a CEA antigen or any suitable antigen; and administering to the individual an IL-15 super-agonist. In some embodiments, the IL-15 super-agonist is any molecule or molecular complex that binds to and activates IL-15 receptors. In certain embodiments, the IL-15 super-agonist is ALT-803, a molecular complex of IL-15N72D, an IL-15RαSu domain, and an IgG1 Fc domain. The composition of ALT-803 and methods of producing and using ALT-803 are described in U.S. Patent Application Publication 2015/0374790, which is herein incorporated by reference.

Interleukin 15 (IL-15) is a naturally occurring inflammatory cytokine secreted after viral infections. Secreted IL-15 can carry out its function by signaling via its cognate receptor on effector immune cells, and thus, can lead to overall enhancement of effector immune cell activity.

Based on IL-15's broad ability to stimulate and maintain cellular immune responses, it is believed to be a promising immunotherapeutic drug that could potentially cure certain cancers. However, major limitations in clinical development of IL-15 can include low production yields in standard mammalian cell expression systems and short serum half-life. Moreover, the IL-15:IL-15Rα complex, comprising proteins co-expressed by the same cell, rather than the free IL-15 cytokine, can be responsible for stimulating immune effector cells bearing IL-15 βγc receptor.

To contend with these shortcomings, a novel IL-15 super-agonist mutant (IL-15N72D) was identified that has increased ability to bind IL-15βγc and enhanced biological activity. Addition of either mouse or human IL-15Rα and Fc fusion protein (the Fc region of immunoglobulin) to equal molar concentrations of IL-15N72D can provide a further increase in IL-15 biologic activity, such that IL-15N72D:IL-15Rα/Fc super-agonist complex exhibits a median effective concentration ($EC_{50}$) for supporting IL-15-dependent cell growth that was greater than 10-fold lower than that of free IL-15 cytokine.

Thus, in some embodiments, the present disclosure provides a IL-15N72D:IL-15Rα/Fc super-agonist complex with an $EC_{50}$ for supporting IL-15-dependent cell growth that is greater than 2-fold lower, greater than 3-fold lower, greater than 4-fold lower, greater than 5-fold lower, greater than 6-fold lower, greater than 7-fold lower, greater than 8-fold lower, greater than 9-fold lower, greater than 10-fold lower, greater than 15-fold lower, greater than 20-fold lower, greater than 25-fold lower, greater than 30-fold lower, greater than 35-fold lower, greater than 40-fold lower, greater than 45-fold lower, greater than 50-fold lower, greater than 55-fold lower, greater than 60-fold lower, greater than 65-fold lower, greater than 70-fold lower, greater than 75-fold lower, greater than 80-fold lower, greater than 85-fold lower, greater than 90-fold lower, greater than 95-fold lower, or greater than 100-fold lower than that of free IL-15 cytokine.

In some embodiments, the interaction of IL-15N72D, soluble IL-15Rα, and Fc fusion protein have been exploited to create a biologically active protein complex, ALT-803. It is known that a soluble IL-15Rα fragment, containing the so-called "sushi" domain at the N terminus (Su), bears most of the structural elements responsible for high affinity cytokine binding. A soluble fusion protein can be generated by linking the human IL-15RαSu domain (amino acids 1-65 of the mature human IL-15Rα protein) with the human IgG1 CH2-CH3 region containing the Fc domain (232 amino acids). This IL-15RαSu/IgG1 Fc fusion protein has the advantages of dimer formation through disulfide bonding via IgG1 domains and ease of purification using standard Protein A affinity chromatography methods. A diagram of ALT-803 superagonist is presented in FIG. 1.

ALT-803 is a soluble complex consisting of 2 protein subunits of a human IL-15 variant (two IL-15N72D subunits) associated with high affinity to a dimeric IL-15Rα sushi domain/human IgG1 Fcfusion protein and. The IL-15 variant is a 114-amino acid polypeptide comprising the mature human IL-15 cytokine sequence with an Asn to Asp substitution at position 72 of helix C N72D). The human IL-15R sushi domain/human IgG1 Fc fusion protein comprises the sushi domain of the IL-15R subunit (amino acids 1-65 of the mature human IL-15Rα protein) linked with the human IgG1 CH2-CH3 region containing the Fc domain (232 amino acids). Aside from the N72D substitution, all of the protein sequences are human. Based on the amino acid sequence of the subunits, the calculated molecular weight of the complex comprising two IL-15N72D polypeptides and a disulfide linked homodimeric IL-15RαSu/IgG1 Fc protein is 92.4 kDa. Each IL-15N720 polypeptide has a calculated molecular weight of approximately 12.8 kDa and the IL-15RαSu/IgG 1 Fc fusion protein has a calculated molecular weight of approximately 33.4 kDa. Both the IL-15N72D and IL-15RαSu/IgG 1 Fc proteins are glycosylated resulting in an apparent molecular weight of ALT-803 as approximately 114 kDa by size exclusion chromatography. The isoelectric point (pI) determined for ALT-803 can range from approximately 5.6 to 6.5. Thus, the fusion protein can be negatively charged at pH 7. The calculated molar extinction coefficient at A280 for ALT-803 is 116,540 M or, in other words, one OD280 is equivalent to 0.79 mg/mL solution of ALT-803.

Additionally, it has been demonstrated that intracellular complex formation with IL-15Rα prevents IL-15 degradation in the endoplasm reticulum and facilitates its secretion. Using a co-expression strategy in Chinese hamster ovary (CHO) cells, the IL-15N72D and IL-15RαSu/IgG1 Fc proteins can be produced at high levels and formed a soluble, stable complex. The biological activity of CHO-produced ALT-803 complex can be equivalent to in-vitro assembled IL-15N72D1L-15RαSu/IgG1 Fc complexes in standard cell-based potency assays using IL-15-dependent cell lines. The methods provided herein, thus represent a better approach for generating active, fully characterized cGMP grade IL-15:IL-15Rα complex than current strategies employing in vitro assembly of individually produced and, in some cases, refolded proteins.

Recent studies show that ALT-803 (1) can promote the development of high effector NK cells and CD8+ T cell responders of the innate phenotype, (2) can enhance the function of NK cells, and (3) can play a vital role in reducing tumor metastasis and ultimately survival, especially in combination with checkpoint inhibitors, which are further described below.

In some embodiments, an IL-15 super-agonist or an IL-15 super-agonist complex, ALT-803, can be administered parenterally, subcutaneously, intramuscularly, by intravenous infusion, by implantation, intraperitoneally, or intravesicularly. In some embodiments 0.1-5 μg of the IL-15 superagonist can be administered in a single dose. In some embodiments, 0.1-0.2 μg, 0.2-0.3 μg, 0.3-0.4 μg, 0.4-0.5 μg, 0.5-0.6 μg, 0.6-0.7 μg, 0.7-0.8 μg, 0.8-0.9 μg, 0.9-1 μg, 1-1.5 μg, 1.5-2 μg, 2-2.5 μg, 2.5-3 μg, 3-3.5 μg, 3.5-4 μg, 4-4.5 μg, or 4.5-5 μg of the IL-15 superagonistcan be administered in a single dose. In certain embodiments, 1 μg of the ALT-803 can be administered in a single dose. In some embodiments, ALT-803 can be administered at an effective dose of from about 0.1 μg/kg to abut 100 mg/kg body weight, e.g., 0.1, 0.2, 0.3, 0.4, 0.5, 0.6, 0.7, 0.8, 0.9, 1, 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, or 900 μg/kg body weight or 1, 2, 3, 4, 5, 6, 7, 8, 9, 10, 20, 30, 40, 50, 60, 70, 80, 90, 95, 99, or 100 mg/kg body weight. In some embodiments, an IL-15 superagonist can be administered with an Ad5 [E1-, E2b-]-CEA vaccine. In some embodiments, an IL-15 superagonist can be administered as a mixture with the Ad5 [E1-, E2b-]-CEA vaccine. In other embodiments, an IL-15 superagonist can be administered as a separate dose immediately before or after the Ad5 [E1-, E2b-]-CEA vaccine. In other embodiments, an ALT-803 is administered within 1 day, within 2 days, within 3 days, within 4 days, within 5 days, or within 6 days of administration of an Ad5 [E1-, E2b-]-CEA vaccine. In some embodiments, an ALT-803 is administered 3 days after an Ad5 [E1-, E2b-]-CEA vaccine. In some embodiments, ALT-803 is administered continuously or several times per day, e.g., every 1 hour, every 2 hours, every 3 hours, every 4 hours, every 5 hours, every 6 hours, every 7 hours, every 8 hours, every 9 hours, every 10 hours, every 11 hours, or every 12 hours. Daily effective doses of ALT-803 can include from 0.1 μg/kg and 100 μg/kg body weight, e.g., 0.1, 0.3, 0.5, 1, 5, 10, 15, 20, 25, 30, 35, 40, 45, 50, 55, 60, 65, 70, 75, 80, 85, 90, 95, or 99 μg/kg body weight. In some embodiments, ALT-803 is administered once per week, twice per week, three times per week, four times per week, five times per week, six times per week, or seven times per week. Effective weekly doses of ALT-803 include between 0.0001 mg/kg and 4 mg/kg body weight, e.g., 0.001, 0.003, 0.005, 0.01. 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, or 4 mg/kg body weight. ALT-803 can be administered at a dose from from about 0.1 μg/kg body weight to about 5000 μg/kg body weight; or from about 1 μg/kg body weight to about 4000 μg/kg body weight or from about 10 μg/kg body weight to about 3000 μg/kg body weight. In other embodiments, ALT-803 can be administered at a dose of about 0.1, 0.3, 0.5, 1, 3, 5, 10, 25, 50, 75, 100, 150, 200, 250, 300, 350, 400, 450, 500, 550, 600, 650, 700, 750, 800, 850, 900, 950, 1000, 1050, 1100, 1150, 1200, 1250, 1300, 1350, 1400, 1450, 1500, 1600, 1700, 1800, 1900, 2000, 2500, 3000, 3500, 4000, 4500, or 5000 μg/kg. In some embodiments, ALT-803 can be administered at a dose from about 0.5 μg compound/kg body weight to about 20 μg compound/kg body weight. In other embodiments, the doses may be about 0.5, 1, 3, 6, 10, or 20 mg/kg body weight. In some embodiments, or example in parenteral administration, ALT-803 can be administered at a dose of about 0.5 μg/kg-about 15 μg/kg (e.g., 0.5, 1, 3, 5, 10, or 15 μg/kg).

Figures 2, 2A, 2B:
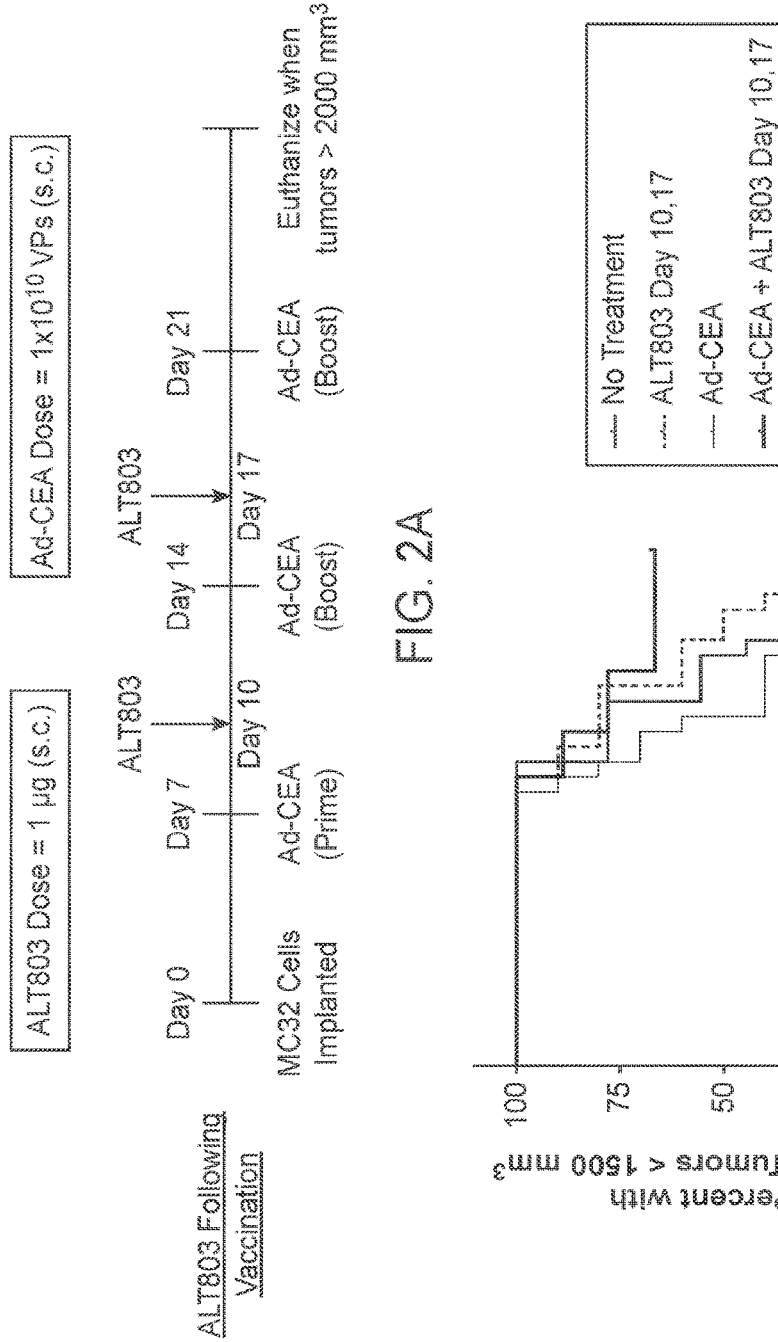
FIG. 2 illustrates study design and results for an Ad5 [E1-]-CEA vaccine in combination with ALT-803 therapy.
FIG. 2A illustrates an administration regimen used to evaluate combination administration of an Ad5 [E1-]-CEA vaccine and ALT-803 therapy in CEA-expressing, tumor-bearing mice.
FIG. 2B illustrates a survival curve showing percent survival in CEA-expressing, tumor-bearing mice which received no treatment, ALT-803 alone on days 10 and 17, an Ad5 [E1-]-CEA vaccine on days 7, 14, and 21, or an Ad5[E1-]-CEA vaccine on days 7, 14, 21 with ALT-803 injections on days 10 and 17.

In some embodiments, a subject in need thereof receiving combination therapy with the Ad5 [E1-, E2b-]-CEA vaccine and ALT-803 is administered one or more dose of the Ad5 [E1-, E2b-]-CEA vaccine and ALT-803 over a 21-day period. For example, as shown in FIG. 2A, a subject in need thereof can be administered the Ad-CEA vaccine on Day 7, Day 14, and Day 21. Additionally, a subject in need thereof can be administered the IL-15 superagonist (ALT-803) on Day 10 and Day 17. In some embodiments, a subject in need thereof receiving combination therapy with the Ad5 [E1-, E2b-]-CEA vaccine and ALT-803 is administered one or more dose of the Ad5 [E1-, E2b-]-CEA vaccine and ALT-803 over an 8-week period. In some embodiments, a subject can be administered the Ad5 [E1-, E2b-]-CEA vaccine on weeks 3 and 6 and can be administered the IL-15 superagonist (ALT-803) on weeks 1, 2, 4, 5, 7, and 8. Thus, in some embodiments, the subject is administered more than one dose of ALT-803 in a complete dosing regimen. In some embodiments, the subject can be administered at least 1 dose, at least 2 doses, at least 3 doses, at least 4 doses, or at least 5 doses of the IL-15 superagonist. In certain embodiments, the subject can be administered one less dose of ALT-803 than the Ad5 [E1-, E2b-]-CEA vaccine.

In some embodiments, the IL-15 superagonist, such as ALT-803, can be encoded as an immunological fusion with the CEA antigen. For example, in some embodiments the Ad5 [E1-, E2b-] vaccine can encode for CEA and ALT-803 (Ad5 [E1-, E2b-]-CEA/ALT-803). In these embodiments, upon administration to a subject in need thereof, Ad5 [E1-, E2b-] vectors encoding for CEA and ALT-803 induce expression of CEA and ALT-803 as an immunological fusion, which is therapeutically active.

Combination therapy with Ad5[E1-, E2b-] vectors encoding for CEA and ALT-803 can result in boosting the immune response, such that the combination of both therapeutic moieties acts to synergistically boost the immune response than either therapy alone. For example, combination therapy with Ad5[E1-, E2b-] vectors encoding for CEA and ALT-803 can result in synergistic enhancement of stimulation of antigen-specific effector CD4+ and CD8+ T cells, stimulation of NK cell response directed towards killing infected cells, stimulation of neutrophils or monocyte cell responses directed towards killing infected cells via antibody dependent cell-mediated cytotoxicity (ADCC) or antibody dependent cellular phagocytosis (ADCP) mechanisms. Combination therapy with Ad5[E1-, E2b-] vectors encoding for CEA and ALT-803 can synergistically boost any one of the above responses, or a combination of the above responses, to vastly improve survival outcomes after administration to a subject in need thereof.

Combination Therapies of Ad5-Vaccines with Further Immunotherapies

In further embodiments, the present invention provides compositions for further combination therapies which include the Ad5 [E1-, E2b-]-CEA vaccine, an IL-15 super-agonist, such as ALT-803, and one or more of the following agents: a chemotherapeutic agent, costimulatory molecules, checkpoint inhibitors, antibodies against a specific antigen (e.g., CEA), engineered NK cells, or any combination thereof. For example, the present invention provides a method of treating a CEA-expressing cancer in an individual in need thereof, the method comprising: administering to the individual a first pharmaceutical composition comprising a replication-defective vector comprising a nucleic acid sequence encoding a CEA antigen or any suitable antigen, administering to the individual an IL-15 superagonist such as ALT-803, and administering to the individual an anti-CEA antibody and engineered NK cells. In some embodiments, the method can further comprise administering to the individual a VEGF inhibitor, a chemotherapy, or a combination thereof. In other embodiments, the method can further comprise administering to the individual engineered NK cells and a checkpoint inhibitor. Any combination of chemotherapeutic agents, costimulatory molecules, checkpoint inhibitors, antibodies against a specific antigen (e.g., CEA), or engineered NK cells can be included in combination therapy with the Ad5 [E1-, E2b-] vaccine encoding for an antigen, such as CEA, and an IL-15 super-agonist or super-agonist complex, such as ALT-803.

In certain embodiments, the chemotherapy used herein is capecitabine, leucovorin, fluorouracil, oxaliplatin, fluoropyrimidine, irinotecan, mitomycin, regorafenib, cetuximab, panitumumab, acetinophen, or a combination thereof. In particular embodiments, the chemotherapy used herein is FOLFOX (leucovorin, fluorouracil and oxaliplatin) or capecitabine. In certain embodiments, the immune checkpoint inhibitor is an anti-PD-1 or anti-PD-L1 antibody, such as avelumab. In certain embodiments, the VEGF inhibitor is an anti-VEGF antibody, such as bevacizumab. The agents which can be used in combination therapy alongside the replication defective vector and ALT-803 are described in further detail below.

FOLFOX (5-Fluorouracil, Leucovorin, Oxaliplatin)

A randomized trial comparing irinotecan and bolus fluorouracil plus leucovorin (IFL, control combination), oxaliplatin and infused fluorouracil plus leucovorin (FOLFOX), or irinotecan and oxaliplatin (IROX) established the FOLFOX combination, given for a total of 6 months, as the standard of care for first line treatment in patients with metastatic colorectal cancer (mCRC). Though multiple infusion schedules of FOLFOX have been validated, typically denominated as 'modified FOLFOX, there are no essential changes in the constituent cytotoxic agents of the regimen. Of these, mFOLFOX6 is one of the most widely used.

Oxaliplatin, however, is very difficult for patients to receive for greater than 6 months (12 cycles) due to progressive neurotoxicity. Though 6 months of combination therapy remains the standard of care in mCRC, clinical judgment may influence the decision to limit the number of oxaliplatin-containing cycles towards the end of treatment Other trials, including the CAIRO3 study, have demonstrated the feasibility and benefit of discontinuation of oxaliplatin after a 3 month "induction" period with continuation of 5-FU and leucovorin as "maintenance" therapy.

Bevacizumab (Avastin®)

Addition of bevacizumab to first-line 5-FU and Oxaliplatin containing regimens was demonstrated to increase time to progression in mCRC patients with a manageable side effect profile and non-overlapping toxicities. Later trials indicated that continuing bevacizumab beyond first progression (in combination with subsequent chemotherapy) improved overall survival in an unselected group of patients by KRAS mutational status, which has led to its approved use in the maintenance setting.

Capecitabine

This agent is a prodrug that is enzymatically converted to 5-fluorouracil by 3 enzymatic steps following oral ingestion. As an orally active fluoropyrimidine, capecitabine has been approved for use in the adjuvant setting. In the advanced colon cancer setting, it has been shown to be equally efficacious as 5-fluorouracil, though with more reported rates of hand-foot syndrome. This agent offers the convenience of the oral route with its benefits of reducing infusion commitments for patients in the maintenance setting, while achieving high concentrations intratumorally, given the higher concentrations of thymidine phosphorylase in tumor as compared to normal tissues.

Costimulatory Molecules

In addition to the use of a recombinant adenovirus-based vector vaccine containing target antigens such as a CEA antigen or epitope, co-stimulatory molecules can be incorporated into said vaccine to increase immunogenicity. Initiation of an immune response requires at least two signals for the activation of naive T cells by APCs (Damle, et al. J Immunol 148: 1985-92 (1992); Guinan, et al. Blood 84: 3261-82 (1994); Hellstrom, et al. Cancer Chemother Pharmacol 38: S40-44 (1996); Hodge, et al. Cancer Res 39: 5800-07 (1999)). An antigen specific first signal is delivered through the T cell receptor (TCR) via the peptide/major histocompatability complex (MHC) and causes the T cell to enter the cell cycle. A second, or costimulatory, signal may be delivered for cytokine production and proliferation.

At least three distinct molecules normally found on the surface of professional antigen presenting cells (APCs) have been reported as capable of providing the second signal critical for T cell activation: B7-1 (CD80), ICAM-1 (CD54), and LFA-3 (human CD58) (Damle, et al. J Immunol 148: 1985-92 (1994); Guinan, et al. Blood 84: 3261-82 (1994); Wingren, et al. Crit Rev Immunol 15: 235-53 (1995); Parra, et al. Scand. J Immunol 38: 508-14 (1993); Hellstrom, et al. Ann NY Acad Sci 690: 225-30 (1993); Parra, et al. J Immunol 158: 637-42 (1997); Sperling, et al. J Immunol 157: 3909-17 (1996); Dubey, et al. J Immunol 155: 45-57 (1995); Cavallo, et al. Eur J Immunol 25: 1154-62 (1995)). These costimulatory molecules have distinct T cell ligands. B7-1 interacts with the CD28 and CTLA-4 molecules, ICAM-1 interacts with the CD11a/CD18 (LFA-1/β2 integrin) complex, and LFA-3 interacts with the CD2 (LFA-2) molecules. Therefore, in a preferred embodiment, it would be desirable to have a recombinant adenovirus vector that contains B7-1, ICAM-1, and LFA-3, respectively, that, when combined with a recombinant adenovirus-based vector vaccine containing one or more nucleic acids encoding target antigens such as a HER2/neu antigen or epitope, will further increase/enhance anti-tumor immune responses directed to specific target antigens.

Natural Killer (NK) Cells

In certain embodiments, native or engineered NK cells may be provided to be administered to a subject in need thereof, in combination with adenoviral vector-based compositions and IL-15 superagonist or other immunotherapies as described herein.

The immune system is a tapestry of diverse families of immune cells each with its own distinct role in protecting from infections and diseases. Among these immune cells are the natural killer, or NK, cells as the body's first line of defense. NK cells have the innate ability to rapidly seek and destroy abnormal cells, such as cancer or virally-infected cells, without prior exposure or activation by other support molecules. In contrast to adaptive immune cells such as T cells, NK cells have been utilized as a cell-based "off-the-shelf" treatment in phase 1 clinical trials, and have demonstrated tumor killing abilities for cancer.

aNK Cells

In addition to native NK cells, there may be provided NK cells for administering to a patient that has do not express Killer Inhibitory Receptors (KIR), which diseased cells often exploit to evade the killing function of NK cells. This unique activated NK, or aNK, cell lack these inhibitory receptors while retaining the broad array of activating receptors which enable the selective targeting and killing of diseased cells. aNK cells also carry a larger pay load of granzyme and perforin containing granules, thereby enabling them to deliver a far greater payload of lethal enzymes to multiple targets.

taNK Cells

Chimeric antigen receptor (CAR) technology is among the most novel cancer therapy approaches currently in development. CARs are proteins that allow immune effector cells to target cancer cells displaying specific surface antigen (target-activated Natural Killer) is a platform in which aNK cells are engineered with one or more CARs to target proteins found on cancers and is then integrated with a wide spectrum of CARs. This strategy has multiple advantages over other CAR approaches using patient or donor sourced effector cells such as autologous T-cells, especially in terms of scalability, quality control and consistency.

Much of the cancer cell killing relies upon ADCC (antibody dependent cell-mediated cytotoxicity) whereupon effector immune cells attach to antibodies, which are in turn bound to the target cancer cell, thereby facilitating killing of the cancer by the effector cell. NK cells are the key effector cell in the body for ADCC and utilize a specialized receptor (CD16) to bind antibodies.

haNK Cells

Studies have shown that perhaps only 20% of the human population uniformly expresses the "high-affinity" variant of CD16, which is strongly correlated with more favorable therapeutic outcomes compared to patients with the "low-affinity" CD16. Additionally, many cancer patients have severely weakened immune systems due to chemotherapy, the disease itself or other factors.

In certain aspects, haNK cells are modified to express high-affinity CD16. As such, haNK cells may potentiate the therapeutic efficacy of a broad spectrum of antibodies directed against cancer cells.

Anti-CEA Antibodies

In some embodiments, compositions are administered with one or more antibodies targeted to CEA, or anti-CEA antibodies. In some embodiments, the composition comprises a replication-defective vector comprising a nucleotide sequence encoding a target antigen, such as CEA, MUC1, Brachyury, or a combination thereof, or any suitable antigens.

Anti-CEA antibodies can be used to generate an immune response against a target antigen expressed and/or presented by a cell. In certain embodiments, the compositions and methods can be used to generate immune responses against a carcinoembryonic antigen (CEA), such as CEA expressed or presented by a cell. For example, the compositions and methods can be used to generate an immune response against CEA(6D) expressed or presented by a cell.

CEA has been shown to be overexpressed on a variety of cancers. In some embodiments, the targeted patient population administered anti-CEA antibody therapy may be individuals with CEA expressing colorectal cancer, head and neck cancer, liver cancer, breast cancer, lung cancer, bladder cancer, or pancreas cancer.

The present invention provides for a novel monoclonal antibody that specifically binds a CPAA. This monoclonal antibody, identified as "16C3", which refers to the number assigned to its hybridoma clone. Herein, 16C3 also refers to the portion of the monoclonal antibody, the paratope or CDRs, that bind specifically with a CPAA epitope identified as 16C3 because of its ability to bind the 16C3 antibody. The several recombinant and humanized forms of 16C3 described herein may be referred to by the same name.

The present invention includes, within its scope, DNA sequences encoding the variable regions of the light and heavy chains of the anti-CPAA antibody of the present invention. A nucleic acid sequence encoding the variable region of the light chain of the 16C3 antibody is presented in SEQ ID NO: 16. A nucleic acid sequence encoding the variable region of the heavy chain of the 16C3 antibody is presented in SEQ ID NO: 17.

The present invention includes, within its scope, a peptide of the 16C3 light chain comprising the amino acid sequence of SEQ ID NO: 18 and SEQ ID NO: 19; and a peptide of the 16C3 heavy chain comprising the amino acid sequence depicted in SEQ ID NO: 99 and SEQ ID NO: 20. Further, the present invention includes the CDR regions depicted for the 16C3 kappa light chain which are the residues underlined in SEQ ID NO: 18, having the amino acids of CDR 1: GASENIYGALN (SEQ ID NO: 21); CDR 2: GASNLAD (SEQ ID NO: 22); and CDR 3: QNVLSSPYT (SEQ ID NO: 23); as well as the amino acids the light chain underlined in SEQ ID NO: 19, which include CDR 1: QASENIYGALN (SEQ ID NO: 24); CDR 2: GASNLAT (SEQ ID NO: 25); and CDR 3: QQVLSSPYT (SEQ ID NO: 26). The invention similarly identifies the CDR regions for the heavy chain, underlined in FIG. 5, which include the amino acids for CDR 1: GYTFTDYAMH (SEQ ID NO: 27); CDR 2: LISTYSGDTKYNQNFKG (SEQ ID NO: 28); and CDR 3: GDYSGSRYWFAY (SEQ ID NO: 29); as well as the amino acids the heavy chain underlined in FIG. 12, which include CDR 1: GYTFTDYAMH (SEQ ID NO: 27); CDR 2: LISTYSGDTKYNQKFQG (SEQ ID NO: 30); and CDR 3: GDYSGSRYWFAY (SEQ ID NO: 31).

In the present application, the 16C3 antibody is also referred to as the NEO-201 antibody.

In certain embodiments, anti-CEA antibodies used can be COL1, COL2, COL3, COL4, COL5, COLE, COLT, COLS, COLS, COL10, COL11, COL12, COL13, COL14, COL15, arcitumomab, besilesomab, labetuzumab, altumomab, or NEO-201. In certain embodiments, the anti-CEA antibody can be murine, chimeric, or humanized.

In certain embodiments, the anti-CEA antibody binds to a CEA overexpressing cell 2, 3, 4, 5, 6, 7, 8, 9, or 10 times or more over a baseline CEA expression in a non-cancer cell.

Immune Pathway Checkpoint Modulators

In some embodiments, compositions are administered with one or more immune checkpoint modulator, such as immune checkpoint inhibitors. In some embodiments, the composition comprises a replication-defective vector comprising a nucleotide sequence encoding a target antigen, such as CEA, or any suitable antigens.

A balance between activation and inhibitory signals regulates the interaction between T lymphocytes and disease cells, wherein T-cell responses are initiated through antigen recognition by the T-cell receptor (TCR). The inhibitory pathways and signals are referred to as immune checkpoints. In normal circumstances, immune checkpoints play a critical role in control and prevention of autoimmunity and also protect from tissue damage in response to pathogenic infection.

In certain aspects, there are provided combination immunotherapies comprising viral vector based vaccines and compositions for modulating immune checkpoint inhibitory pathways for the treatment of cancer and infectious diseases. In some embodiments, modulating is increasing expression or activity of a gene or protein. In some embodiments, modulating is decreasing expression or activity of a gene or protein. In some embodiments, modulating affects a family of genes or proteins.

Certain embodiments provide combination immunotherapies comprising multi-targeted immunotherapeutic directed to TAAs and molecular compositions comprising an immune pathway checkpoint modulator that targets at least one immune checkpoint protein of the immune inhibitory pathway. Certain embodiments provide combination immunotherapies comprising multi-targeted immunotherapeutic directed to IDAAs and molecular compositions comprising an immune pathway checkpoint modulator that targets at least one immune checkpoint protein of the immune inhibitory pathway. Certain embodiments provide a combination immunotherapies or vaccines comprising: at least two, at least three, or more than three different target antigens comprising a sequence encoding a modified CEA, and at least one molecular composition comprising an immune pathway checkpoint modulator. For example, a combination immunotherapy or vaccine can comprise at least two, at least three, or more than three different target antigens comprising a sequence encoding a modified CEA, wherein the modified CEA comprises a sequence with an identity value of at least 70%, 75%, 80%, 85%, 90%, 95%, 98%, 99%, 99.5%, or 99.9% to SEQ ID NO: 1 or SEQ ID NO: 100 and at least one molecular composition comprising an immune pathway checkpoint modulator. In some embodiments, the modified CEA comprises a sequence with an identity value of at least 70%, 75%, 80%, 85%, 90%, 95%, 98%, 99%, 99.5%, 99.9%, or 100% SEQ ID NO: 1 has a Asn->Asp substitution at position 610 or SEQ ID NO: 100.

In general, the immune inhibitory pathways are initiated by ligand-receptor interactions. It is now clear that in diseases, the disease can co-opt immune-checkpoint pathways as mechanism for inducing immune resistance in a subject.

The induction of immune resistance or immune inhibitory pathways in a subject by a given disease can be blocked by molecular compositions such as siRNAs, antisense, small molecules, mimic, a recombinant form of ligand, receptor or protein, or antibodies (which can be an Ig fusion protein) that are known to modulate one or more of the Immune Inhibitory Pathways, or any combination thereof. For example, preliminary clinical findings with blockers of immune-checkpoint proteins, such as Cytotoxic T-lymphocyte-associated antigen 4 (CTLA4) and programmed cell death protein 1 (PD1) have shown promise for enhancing antitumor immunity.

Because diseased cells can express multiple inhibitory ligands, and disease-infiltrating lymphocytes express multiple inhibitory receptors, dual or triple blockade of immune checkpoints proteins may enhance anti-disease immunity. Combination immunotherapies as provide herein can comprise one or more molecular compositions of the following immune-checkpoint proteins: PD1, PDL1, PDL2, CD28, CD80, CD86, CTLA4, B7RP1, ICOS, B7RPI, B7-H3 (also known as CD276), B7-H4 (also known as B7-S1, B7x and VCTN1), BTLA (also known as CD272), HVEM, KIR, TCR, LAG3 (also known as CD223), CD137, CD137L, OX40, OX40L, CD27, CD70, CD40, CD40L, TIM3 (also known as HAVcr2), GALS, and A2aR. In some embodiments, the molecular composition comprises siRNAs. In some embodiments, the molecular composition comprises a small molecule. In some embodiments, the molecular composition comprises a recombinant form of a ligand. In some embodiments, the molecular composition comprises a recombinant form of a receptor. In some embodiments, the molecular composition comprises an antibody. In some embodiments, the combination therapy comprises more than one molecular composition and/or more than one type of molecular composition. As it will be appreciated by those in the art, future discovered proteins of the immune checkpoint inhibitory pathways are also envisioned to be encompassed in certain aspects.

In some embodiments, combination immunotherapies comprise molecular compositions for the modulation of CTLA4. In some embodiments, combination immunotherapies comprise molecular compositions for the modulation PD1. In some embodiments, combination immunotherapies comprise molecular compositions for the modulation PDL1. In some embodiments, combination immunotherapies comprise molecular compositions for the modulation LAG3. In some embodiments, combination immunotherapies comprise molecular compositions for the modulation B7-H3. In some embodiments, combination immunotherapies comprise molecular compositions for the modulation B7-H4. In some embodiments, combination immunotherapies comprise molecular compositions for the modulation TIM3. In some embodiments, modulation is an increase or enhancement of expression. In other embodiments, modulation is the decrease of absence of expression.

Two exemplary immune checkpoint inhibitors include the cytotoxic T lymphocyte associated antigen-4 (CTLA-4) and the programmed cell death protein-1 (PD1). CTLA-4 can be expressed exclusively on T-cells where it regulates early stages of T-cell activation. CTLA-4 interacts with the co-stimulatory T-cell receptor CD28 which can result in signaling that inhibits T-cell activity. Once TCR antigen recognition occurs, CD28 signaling may enhance TCR signaling, in some cases leading to activated T-cells, and CTLA-4 inhibits the signaling activity of CD28. Certain embodiments provide immunotherapies as provided herein in combination with anti-CTLA-4 monoclonal antibody for the treatment of proliferative disease and cancer. Certain embodiments provide immunotherapies as provided herein in combination with CTLA-4 molecular compositions for the treatment of proliferative disease and cancer.

Programmed death cell protein ligand-1 (PDL1) is a member of the B7 family and is distributed in various tissues and cell types. PDL1 can interact with PD1 inhibiting T-cell activation and CTL mediated lysis. Significant expression of PDL1 has been demonstrated on various human tumors and PDL1 expression is one of the key mechanisms in which tumors evade host antitumor immune responses. Programmed death-ligand 1 (PDL1) and programmed cell death protein-1 (PD1) interact as immune checkpoints. This interaction can be a major tolerance mechanism which results in the blunting of anti-tumor immune responses and subsequent tumor progression. PD1 is present on activated T cells and PDL1, the primary ligand of PD1, is often expressed on tumor cells and antigen-presenting cells (APC) as well as other cells, including B cells. PDL1 interacts with PD1 on T cells inhibiting T cell activation and cytotoxic T lymphocyte (CTL) mediated lysis. Certain embodiments provide immunotherapies as provided herein in combination with anti-PD1 or anti-PDL1 monoclonal antibody for the treatment of proliferative disease and cancer. Certain embodiments provide immunotherapies as provided herein in combination with PD1 or anti-PDL1 molecular compositions for the treatment of proliferative disease and cancer. Certain embodiments provide immunotherapies as provided herein in combination with anti-CTLA-4 and anti-PD1 monoclonal antibodies for the treatment of proliferative disease and cancer. Certain embodiments provide immunotherapies as provided herein in combination with anti-CTLA-4 and PDL1 monoclonal antibodies for the treatment of proliferative disease and cancer. Certain embodiments provide immunotherapies as provided herein in combination with anti-CTLA-4, anti-PD1, PDL1, monoclonal antibodies, or a combination thereof, for the treatment of proliferative disease and cancer.

Certain embodiments provide immunotherapies as provided herein in combination with several antibodies directed against the PD-L1/PD-1 pathway that are in clinical development for cancer treatment. In certain embodiments, anti-PD-L1 antibodies may be used. Compared with anti-PD-1 antibodies that target T-cells, anti-PDL1 antibodies that target tumor cells are expected to have less side effects, including a lower risk of autoimmune-related safety issues, as blockade of PD-L1 leaves the PD-L2/PD-1 pathway intact to promote peripheral self-tolerance.

To this end, avelumab, a fully human IgG1 anti-PDL1 antibody (drug code MSB0010718C) has been produced. Avelumab selectively binds to PD-L1 and competitively blocks its interaction with PD-1.

Avelumab is also cross-reactive with murine PD-L1, thus allowing in vivo pharmacology studies to be conducted in normal laboratory mice. However, due to immunogenicity directed against the fully human avelumab molecule, the dosing regimen was limited to three doses given within a week. In some embodiments, avelumab can be administered at a dose of 1 mg/kg-20 mg/kg. In some embodiments, avelumab can also be administered at 1 mg/kg, 3 mg/kg, 10 mg/kg, and 20 mg/kg. In some embodiments, the addition of Avelumab, or any other immune pathway checkpoint modulator, in the dosing regimen can increase the immune response by at least 2, at least 3, at least 4, at least 5, at least 6, at least 7, at least 8, at least 9, at least 10, at least 15, at least 20, or at least 25-fold. In some embodiments, Aveluman is administered to a subject at least once, at least twice, or at least three times a week. In some embodiments, Avelumab is administered on day 1 of week 1, day 1 of week 2, day 1 of week 4, day 1 of week 8, day 1 of week 12, and day 1 of week 16. Avelumab can be administered on the same day as immunization with the Ad5 [E1-, E2b-]-CEA vaccine of the present disclosure. In these instances, Avelumab infusion occurs after immunization with the Ad5 [E1-, E2b-]-CEA vaccine.

The key preclinical pharmacology findings for avelumab are summarized below. Avelumab showed functional enhancement of primary T cell activation in vitro in response to antigen-specific and antigen non-specific stimuli; and significant inhibition of in vivo tumor growth (PD-L1 expressing MC38 colon carcinoma) as a monotherapy. Its in vivo efficacy is driven by CD8+ T cells, as evidenced by complete abrogation of anti-tumor activity when this cell type was systemically depleted. Its combination with localized, fractionated radiotherapy resulted in complete regression of established tumors with generation of anti-tumor immune memory. Its use in chemotherapy combinations also showed promising activity: additive combination effect when partnered with oxaliplatin and 5-fluorouracil (5-FU) (core components of FOLFOX [oxaliplatin, 5-FU, and folinic acid]) against MC38 colon tumors; significant increase in survival when partnered with gemcitabine against PANC02 pancreatic tumors. Its antibody-dependent cell-mediated cytotoxicity (ADCC) was demonstrated against human tumor cells in vitro; furthermore, studies in ADCC deficient settings in vivo support a contribution of ADCC to anti-tumor efficacy. Additional findings of Avelumab include: no complement-dependent cytotoxicity was observed in vitro. Immunomonitoring assays with translational relevance for the clinic further support an immunological mechanism of action: consistent increases in CD8+

PD-1+ T cells and CD8+ effector memory T cells as measured by fluorescence-activated cell sorter (FACS); enhanced tumor-antigen specific CD8+ T cell responses as measured by pentamer staining and enzyme-linked immunosorbent spot (ELISPOT) assays.

Despite reports indicating that anti-tumor radiographic responses were unlikely using agents that interfere with PD-1-PD-L1 binding in colorectal cancer, there have been reports of radiographic responses. Additionally, a correlation has been demonstrated in multiple clinical trials indicating that PD-L1 expression levels on tumor tissue predict the likelihood of radiographic response. However, it has become clear that PD-L1 expression, as it is currently measured, is not a definitive requirement for anti-tumor efficacy. It has been noted that colorectal tumors rarely express PD-L1 compared with other tumors that are more likely to respond to PD-1-PD-L1 blockade. However, it is known that a strong anti-tumor T cell response, producing IFN-gamma, will induce PD-L1 expression.

In some embodiments, without being bound by theory, it was contemplated that an underlying immune response is necessary for PD-1-PD-L1 blockade to have an anti-tumor effect. Without being bound by theory, it was further contemplated that this combination of an immune checkpoint inhibitor with the standard therapy and an adenoviral vector composition such as Ad-CEA immunizations or Ad-CEA immunizations may be capable of induction of PD-L1 expression and thereby increase the anti-tumor activity of PD-1-PD-L1 blockade.

Immune checkpoint molecules can be expressed by T cells. Immune checkpoint molecules can effectively serve as "brakes" to down-modulate or inhibit an immune response. Immune checkpoint molecules include, but are not limited to Programmed Death 1 (PD1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as HAVCR2, GenBank accession number: JX049979.1), BTLA (also known as CD272, accession number: NM_181780.3), BY55 (also known as CD160, GenBank accession number: CR541888.1), TIGIT (also known as IVSTM3, accession number: NM_173799), LAIR1 (also known as CD305, GenBank accession number: CR542051.1), SIGLECIO (GeneBank accession number: AY358337.1), 2B4 (also known as CD244, accession number: NM_001166664.1), PPP2CA, PPP2CB, PTPN6, PTPN22, CD96, CRTAM, SIGLEC7, SIGLEC9, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, ILIORA, IL10RB, HMOX2, IL6R, IL6ST, EIF2AK4, CSK, PAG1, SIT1, FOXP3, PRDM1, BATF, GUCY1A2, GUCY1A3, GUCY1B2, GUCY1B3 which directly inhibit immune cells. For example, PD1 can be combined with an adenoviral vaccine to treat a patient in need thereof. TABLE 1, without being exhaustive, shows exemplary immune checkpoint genes that can be inactivated to improve the efficiency of the adenoviral vaccine. Immune checkpoints gene can be selected from such genes listed in TABLE 1 and others involved in co-inhibitory receptor function, cell death, cytokine signaling, arginine tryptophan starvation, TCR signaling, Induced T-reg repression, transcription factors controlling exhaustion or anergy, and hypoxia mediated tolerance.

TABLE 1

Exemplary Immune Checkpoint Genes

| Gene Symbol | NCBI # (GRCh38.p2) | Start | Stop | Genome location |
|---|---|---|---|---|
| ADORA2A | 135 | 24423597 | 24442360 | 22q11.23 |
| CD276 | 80381 | 73684281 | 73714518 | 15q23-q24 |
| VTCN1 | 79679 | 117143587 | 117270368 | 1p13.1 |
| BTLA | 151888 | 112463966 | 112499702 | 3q13.2 |
| CTLA4 | 1493 | 203867788 | 203873960 | 2q33 |
| IDO1 | 3620 | 39913809 | 39928790 | 8p12-p11 |
| KIR3DL1 | 3811 | 54816438 | 54830778 | 19q13.4 |
| LAG3 | 3902 | 6772483 | 6778455 | 12p13.32 |
| PDCD1 | 5133 | 241849881 | 241858908 | 2q37.3 |
| HAVCR2 | 84868 | 157085832 | 157109237 | 5q33.3 |
| VISTA | 64115 | 71747556 | 71773580 | 10q22.1 |
| CD244 | 51744 | 160830158 | 160862902 | 1q23.3 |
| CISH | 1154 | 50606454 | 50611831 | 3p21.3 |

The combination of an adenoviral-based vaccine and an immune pathway checkpoint modulator may result in reduction in cancer recurrences in treated patients, as compared to either agent alone. In yet another embodiment the combination of an adenoviral-based vaccine and an immune pathway checkpoint modulator may result in reduction in the presence or appearance of metastases or micro metastases in treated patients, as compared to either agent alone. In another embodiment, the combination of an adenoviral-based vaccine and an immune pathway checkpoint modulator may result improved overall survival of treated patients, as compared to either agent alone. In some cases, the combination of an adenoviral vaccine and an immune pathway checkpoint modulator may increase the frequency or intensity of tumor-specific T cell responses in patients compared to either agent alone.

Some embodiments also disclose the use of immune checkpoint inhibition to improve performance of an adenoviral vector-based vaccine. The immune checkpoint inhibition may be administered at the time of the vaccine. The immune checkpoint inhibition may also be administered after a vaccine. Immune checkpoint inhibition may occur simultaneously to an adenoviral vaccine administration. Immune checkpoint inhibition may occur 1, 2, 3, 4, 5, 6, 7, 8, 9, 10, 15, 20, 30, 40, 50, or 60 minutes after vaccination. Immune checkpoint inhibition may also occur 1, 2, 3, 4, 5, 6, 7, 8, 9, 10, 11, 12, 13, 14, 15, 16, 17, 18, 19, 20, 21, 22, 23, or 24 hours post vaccination. In some cases, immune inhibition may occur 1, 2, 3, 4, 5, 6, or 7 days after vaccination. Immune checkpoint inhibition may occur at any time before or after vaccination.

In another aspect, there is provided a vaccine comprising an antigen and an immune pathway checkpoint modulator. Some embodiments pertain to a method for treating a subject having a condition that would benefit from downregulation of an immune checkpoint, PD1 for example, and its natural binding partner(s) on cells of the subject.

An immune pathway checkpoint modulator may be combined with an adenoviral vaccine comprising nucleotide sequences encoding any antigen. For example, an antigen can be MUC1c, HER3, Brachyury, HER2NEU, CEA, PMSA, or PSA. An immune pathway checkpoint modulator may produce a synergistic effect when combined with a vaccine. An immune pathway checkpoint modulator may also produce an additive effect when combined with a vaccine.

In particular embodiments, a checkpoint immune inhibitor may be combined with a vector comprising nucleotide sequences encoding any antigen, optionally with a chemotherapy or any other cancer care or therapy, such as VEGF inhibitors, angiogenesis inhibitors, radiation, other immune therapy, or any suitable cancer care or therapy.

Immunological Fusion Partner Antigen Targets

The viral vectors or composition described herein may further comprise nucleic acid sequences that encode proteins, or an "immunological fusion partner," that can increase the immunogenicity of the target antigen such as a tumor neo-antigen or neo-epitope. In this regard, the protein produced following immunization with the viral vector containing such a protein may be a fusion protein comprising the target antigen of interest fused to a protein that increases the immunogenicity of the target antigen of interest.

In one embodiment, such an immunological fusion partner is derived from a *Mycobacterium* sp., such as a *Mycobacterium tuberculosis*-derived Ra12 fragment. The immunological fusion partner derived from *Mycobacterium* sp. can be any one of the sequences set forth in SEQ ID NO: 32-SEQ ID NO: 40. Ra12 compositions and methods for their use in enhancing the expression and/or immunogenicity of heterologous polynucleotide/polypeptide sequences are described in U.S. Pat. No. 7,009,042, which is herein incorporated by reference in its entirety. Briefly, Ra12 refers to a polynucleotide region that is a subsequence of a *Mycobacterium tuberculosis* MTB32A nucleic acid. MTB32A is a serine protease of 32 kDa encoded by a gene in virulent and avirulent strains of *M. tuberculosis*. The nucleotide sequence and amino acid sequence of MTB32A have been described (see, e.g., U.S. Pat. No. 7,009,042; Skeiky et al., Infection and Immun. 67:3998-4007 (1999), incorporated herein by reference in their entirety). C-terminal fragments of the MTB32A coding sequence can be expressed at high levels and remain as soluble polypeptides throughout the purification process. Moreover, Ra12 may enhance the immunogenicity of heterologous immunogenic polypeptides with which it is fused. A Ra12 fusion polypeptide can comprise a 14 kDa C-terminal fragment corresponding to amino acid residues 192 to 323 of MTB32A. Other Ra12 polynucleotides generally can comprise at least about 15, 30, 60, 100, 200, 300, or more nucleotides that encode a portion of a Ra12 polypeptide. Ra12 polynucleotides may comprise a native sequence (i.e., an endogenous sequence that encodes a Ra12 polypeptide or a portion thereof) or may comprise a variant of such a sequence. Ra12 polynucleotide variants may contain one or more substitutions, additions, deletions and/or insertions such that the biological activity of the encoded fusion polypeptide is not substantially diminished, relative to a fusion polypeptide comprising a native Ra12 polypeptide. Variants can have at least about 70%, 80%, or 90% identity, or more, to a polynucleotide sequence that encodes a native Ra12 polypeptide or a portion thereof.

In certain aspects, an immunological fusion partner can be derived from protein D, a surface protein of the gramnegative bacterium *Haemophilus influenzae* B. The immunological fusion partner derived from protein D can be the sequence set forth in SEQ ID NO: 41. In some cases, a protein D derivative comprises approximately the first third of the protein (e.g., the first N-terminal 100-110 amino acids). A protein D derivative may be lipidated. Within certain embodiments, the first 109 residues of a Lipoprotein D fusion partner is included on the N-terminus to provide the polypeptide with additional exogenous T-cell epitopes, which may increase the expression level in *E. coli* and may function as an expression enhancer. The lipid tail may ensure optimal presentation of the antigen to antigen presenting cells. Other fusion partners can include the non-structural protein from influenza virus, NS1 (hemagglutinin). Typically, the N-terminal 81 amino acids are used, although different fragments that include T-helper epitopes may be used.

In certain aspects, the immunological fusion partner can be the protein known as LYTA, or a portion thereof (particularly a C-terminal portion). The immunological fusion partner derived from LYTA can the sequence set forth in SEQ ID NO: 42. LYTA is derived from *Streptococcus pneumoniae*, which synthesizes an N-acetyl-L-alanine amidase known as amidase LYTA (encoded by the LytA gene). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus can be employed. Within another embodiment, a repeat portion of LYTA may be incorporated into a fusion polypeptide. A repeat portion can, for example, be found in the C-terminal region starting at residue 178. One particular repeat portion incorporates residues 188-305.

In some embodiments, the target antigen is fused to an immunological fusion partner, also referred to herein as an "immunogenic component," comprising a cytokine selected from the group of IFN-γ, TNFα, IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-IRA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. The target antigen fusion can produce a protein with substantial identity to one or more of IFN-γ, TNFα IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. The target antigen fusion can encode a nucleic acid encoding a protein with substantial identity to one or more of IFN-γ, TNFα, IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. In some embodiments, the target antigen fusion further comprises one or more immunological fusion partner, also referred to herein as an "immunogenic components," comprising a cytokine selected from the group of IFN-γ, TNFα, IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. The sequence of IFN-γ can be, but is not limited to, a sequence as set forth in SEQ ID NO: 43. The sequence of TNFα can be, but is not limited to, a sequence as set forth in SEQ ID NO: 44. The sequence of IL-2 can be, but is not limited to, a sequence as set forth in SEQ ID NO: 45. The sequence of IL-8 can be, but is not limited to, a sequence as set forth in SEQ ID NO: 46. The sequence of IL-12 can be, but is not limited to, a sequence as set forth in SEQ ID NO: 47. The sequence of IL-18 can be, but is not limited to, a sequence as set forth in SEQ ID NO: 48. The sequence of IL-7 can be, but is not limited to, a sequence as set forth in SEQ ID NO: 49. The sequence of IL-3 can be, but is not limited to, a sequence as set forth in SEQ ID NO: 50. The sequence of IL-4 can be, but is not limited to, a sequence as set forth in SEQ ID NO: 51. The sequence of IL-5 can be, but is not limited to, a sequence as set forth in SEQ ID NO: 52. The sequence of IL-6 can be, but is not limited to, a sequence as set forth in SEQ ID NO: 53. The sequence of IL-9 can be, but is not limited to, a sequence as set forth in SEQ ID NO: 54. The sequence of IL-10 can be, but is not limited to, a sequence as set forth in SEQ ID NO: 55. The sequence of IL-13 can be, but is not limited to, a sequence as set forth in SEQ ID NO: 56. The sequence of IL-15 can be, but is not limited to, a sequence as set forth in SEQ ID NO: 57. The sequence of IL-16 can be, but is not limited to, a sequence as set forth in SEQ ID NO: 103. The sequence of IL-17 can be, but is not limited to, a sequence as set forth in SEQ ID NO: 104. The sequence of IL-23 can be, but is not limited to, a sequence as set forth in SEQ ID NO: 105. The sequence of IL-32 can be, but is not limited to, a sequence as set forth in SEQ ID NO: 106.

In some embodiments, the target antigen is fused or linked to an immunological fusion partner, also referred to herein as an "immunogenic component," comprising a cytokine selected from the group of IFN-γ, TNFα IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-10, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. In some embodiments, the target antigen is co-expressed in a cell with an immunological fusion partner, also referred to herein as an "immunogenic component," comprising a cytokine selected from the group of IFN-γ, TNFα IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-10, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, CD30 ligand, 4-1BBL, Trail, OPG-L, APRIL, LIGHT, TWEAK, BAFF, TGF-β1, and MIF. In some embodiments, the immunogenic component is selected from the group consisting of IL-7, a nucleic acid encoding IL-7, a protein with substantial identity to IL-7, and a nucleic acid encoding a protein with substantial identity to IL-7. In some embodiments, the adjuvant is selected from the group consisting of IL-15, a nucleic acid encoding IL-15, a protein with substantial identity to IL-15, and a nucleic acid encoding a protein with substantial identity to IL-15.

In some embodiments, the target antigen is fused or linked to an immunological fusion partner, comprising CpG ODN (a non-limiting example sequence is shown in SEQ ID NO: 58), cholera toxin (a non-limiting example sequence is shown in SEQ ID NO: 59), a truncated A subunit coding region derived from a bacterial ADP-ribosylating exotoxin (a non-limiting example sequence is shown in (a non-limiting example sequence is shown in SEQ ID NO: 60), a truncated B subunit coding region derived from a bacterial ADP-ribosylating exotoxin (a non-limiting example sequence is shown in SEQ ID NO: 61), Hp91 (a non-limiting example sequence is shown in SEQ ID NO: 62), CCL20 (a non-limiting example sequence is shown in SEQ ID NO: 63), CCL3 (a non-limiting example sequence is shown in SEQ ID NO: 64), GM-CSF (a non-limiting example sequence is shown in SEQ ID NO: 65), G-CSF (a non-limiting example sequence is shown in SEQ ID NO: 66), LPS peptide mimic (non-limiting example sequences are shown in SEQ ID NO: 67-SEQ ID NO: 78), shiga toxin (a non-limiting example sequence is shown in SEQ ID NO: 79), diphtheria toxin (a non-limiting example sequence is shown in SEQ ID NO: 80), or $CRM_{197}$ (a non-limiting example sequence is shown in SEQ ID NO: 83).

In some embodiments, the target antigen (e.g., CEA) is fused or linked to an immunological fusion partner comprising an IL-15 superagonist complex, in which both the target antigen and immunological fusion partner (e.g., an IL-15 superagonist complex) are encoded together in one adenovirus vector (e.g., an Ad5 [E1-, E2b-]). In some embodiments, an adenovirus vector encoding for the target antigen is codelivered with a separate adenovirus vector encoding for the immunological fusion partner (e.g., the domains of the IL-15 superagonist complex). In some embodiments, the IL-15 superagonist can be a novel IL-15 superagonist mutant (IL-15N72D). In certain embodiments, addition of either mouse or human IL-15Rα and Fc fusion protein (the Fc region of immunoglobulin) to equal molar concentrations of IL-15N72D can provide a further increase in IL-15 biologic activity, such that IL-15N72D1L-15Rα/Fc super-agonist complex exhibits a median effective concentration ($EC_{50}$) for supporting IL-15-dependent cell growth that can be greater than 10-fold lower than that of free IL-15 cytokine.

In some embodiments, the IL-15 super agonist is a biologically active protein complex of IL-15N72D, soluble IL-15Rα, and Fc fusion protein, also known as ALT-803. It is known that a soluble IL-15Rα fragment, containing the so-called "sushi" domain at the N terminus (Su), can bear most of the structural elements responsible for high affinity cytokine binding. A soluble fusion protein can be generated by linking the human IL-15RαSu domain (amino acids 1-65 of the mature human IL-15Rα protein) with the human IgG1 CH2-CH3 region containing the Fc domain (232 amino acids). This IL-15RαSu/IgG1 Fc fusion protein can have the advantages of dimer formation through disulfide bonding via IgG1 domains and ease of purification using standard Protein A affinity chromatography methods.

In some embodiments, ALT-803 can have a soluble complex consisting of 2 protein subunits of a human IL-15 variant associated with high affinity to a dimeric IL-15Rα sushi domain/human IgG1 Fc fusion protein. The IL-15 variant is a 114 amino acid polypeptide comprising the mature human IL-15 cytokine sequence with an Asn to Asp substitution at position 72 of helix C N72D). The human IL-15R sushi domain/human IgG1 Fc fusion protein comprises the sushi domain of the IL-15R subunit (amino acids 1-65 of the mature human IL-15Rα protein) linked with the human IgG1 CH2-CH3 region containing the Fc domain (232 amino acids). Aside from the N72D substitution, all of the protein sequences are human. Based on the amino acid sequence of the subunits, the calculated molecular weight of the complex comprising two IL-15N72D polypeptides (an example IL-15N72D amino acid sequence is shown in SEQ ID NO: 81 and an example IL-15N72D nucleotide sequence is shown in SEQ ID NO: 107) and a disulfide linked homodimeric IL-15RαSu/IgG1 Fc protein (an example amino acid sequence of the IL-15RαSu/Fc domain is shown in SEQ ID NO: 82 and an example nucleotide sequence of the IL-15 RαSu/Fc domain is shown in SEQ ID NO: 108) is 92.4 kDa. In some embodiments the two chains of IL-15 RαSu/Fc dimerize.

In some embodiments, a recombinant vector described herein (e.g., an Ad5 [E1-, E2b-]) can encode for each domain of an IL-15 superagonist complex. For example, an IL-15N72D polypeptide chain can be encoded for in an adenovirus vector (e.g., an Ad5 [E1-, E2b-]), wherein the adenovirus vector encodes for a sequence comprising at least 80%, at least 85%, at least 90%, at least 92%, at least 95%, at least 97%, or at least 99% sequence identity to SEQ ID NO: 107. Separately an IL-15RαSu/IgG1 Fc protein can be encoded for in a different adenovirus vector (e.g., an Ad5 [E1-, E2b-]), wherein the adenovirus vector encodes for a sequence comprising at least 80%, at least 85%, at least 90%, at least 92%, at least 95%, at least 97%, or at least 99% sequence identity to SEQ ID NO: 108. These adenovirus vectors can be delivered together alongside a separate adenovirus vector (e.g., an Ad5 [E1-, E2b-]) encoding for CEA. Upon expression in a cell, two IL-15N72D polypeptides and two IL-15RαSu/IgG1 Fc proteins can come together to form the IL-15 superagonist complex (ALT-803).

In other embodiments, a single recombinant vector described herein (e.g., an Ad5 [E1-, E2b-]) can encode for an IL-15N72D and IL-15RαSu/IgG1 Fc, separated by a Gly-Ser-Gly linker and a 2A sequence from Thosea asigna virus (EGRGSLLTCGDVEENPGP; SEQ ID NO: 111). This adenovirus vector can be delivered together alongside a separate adenovirus vector (e.g., an Ad5 [E1-, E2b-]) encoding for CEA. Upon expression in a cell, two IL-15N72D polypeptides and two IL-15RαSu/IgG1 Fc protein can come together to form the IL-15 superagonist complex (ALT-803).

Each IL-15N720 polypeptide has a calculated molecular weight of approximately 12.8 kDa and the IL-15RαSu/IgG 1 Fc fusion protein has a calculated molecular weight of approximately 33.4 kDa. Both the IL-15N72D and IL-15RαSu/IgG 1 Fc proteins can be glycosylated resulting in an apparent molecular weight of ALT-803 of approximately 114 kDa by size exclusion chromatography. The isoelectric point (pI) determined for ALT-803 can range from approximately 5.6 to 6.5. Thus, the fusion protein can be negatively charged at pH 7.

Any of the immunogenicity enhancing agents described herein can be fused or linked to a target antigen by expressing the immunogenicity enhancing agents and the target antigen in the same recombinant vector, using any recombinant vector described herein.

Nucleic acid sequences that encode for such immunogenicity enhancing agents can be any one of SEQ ID NO: 32-SEQ ID NO: 83 and SEQ ID NO: 103-SEQ ID NO: 110 and are summarized in TABLE 2.

TABLE 2

Sequences of Immunogenicity Enhancing Agents

| SEQ ID NO | Sequence |
|---|---|
| SEQ ID NO: 32 | TAASDNFQLSQGGQGFAIPIGQAMAIAGQIRSGGGSPTVHIGPTAFL<br>GLGVVDNNGNGARVQRVVGSAPAASLGISTGDVITAVDGAPINSAT<br>AMADALNGHHPGDVISVTWQTKSGGTRTGNVTLAEGPPA |
| SEQ ID NO: 33 | MHHHHHHTAASDNFQLSQGGQGFAIPIGQAMAIAGQIRSGGGSPTV<br>HIGPTAFLGLGVVDNNGNGARVQRVVGSAPAASLGISTGDVITAVD<br>GAPINSATAMADALNGHHPGDVISVTWQTKSGGTRTGNVTLAEGP<br>PAEFDDDDKDPPDPHQPDMTKGYCPGGRWGFGDLAVCDGEKYPD<br>GSFWHQWMQTWFTGPQFYFDCVSGGEPLPGPPPPGGCGGAIPSEQP<br>NAP |
| SEQ ID NO: 34 | MHHHHHHTAASDNFQLSQGGQGFAIPIGQAMAIAGQIRSGGGSPTV<br>HIGPTAFLGLGVVDNNGNGARVQRVVGSAPAASLGISTGDVITAVD<br>GAPINSATAMADALNGHHPGDVISVTWQTKSGGTRTGNVTLAEGP<br>PAEFPLVPRGSPMGSDVRDLNALLPAVPSLGGGGGCALPVSGAAQ<br>WAPVLDFAPPGASAYGSLGGPAPPPAPPPPPPPPPHSFIKQEPSWGGA<br>EPHEEQCLSAFTVHFSGQFTGTAGACRYGPFGPPPPSQASSGQARMF<br>PNAPYLPSCLESQPAIRNQGYSTVTFDGTPSYGHTPSHHAAQFPNHS<br>FKHEDPMGQQGSLGEQQYSVPPPVYGCHTPTDSCTGSQALLLRTPY<br>SSDNLYQMTSQLECMTWNQMNLGATLKGHSTGYESDNHTTPILCG<br>AQYRIHTHGVFRGIQDVRRVPGVAPTLVRSASETSEKRPFMCAYSG<br>CNKRYFKLSHLQMHSRKHTGEKPYQCDFKDCERRFFRSDQLKRHQ<br>RRHTGVKPFQCKTCQRKFSRSDHLKTHTRTHTGEKPFSCRWPSCQK<br>KFARSDELVRHHNMHQRNMTKLQLAL |
| SEQ ID NO: 35 | MHHHHHHTAASDNFQLSQGGQGFAIPIGQAMAIAGQIRSGGGSPTV<br>HIGPTAFLGLGVVDNNGNGARVQRVVGSAPAASLGISTGDVITAVD<br>GAPINSATAMADALNGHHPGDVISVTWQTKSGGTRTGNVTLAEGP<br>PAEFIEGRGSGCPLLENVISKTINPQVSKTEYKELLQEFIDDNATTNAI<br>DELKECFLNQTDETLSNVEVFMQLIYDSSLCDLF |
| SEQ ID NO: 36 | MHHHHHHTAASDNFQLSQGGQGFAIPIGQAMAIAGQIRSGGGSPTV<br>HIGPTAFLGLGVVDNNGNGARVQRVVGSAPAASLGISTGDVITAVD<br>GAPINSATAMADALNGHHPGDVISVTWQTKSGGTRTGNVTLAEGP<br>PAEFMVDFGALPPEINSARMYAGPGSASLVAAAQMWDSVASDLFS<br>AASAFQSVVWGLTVGSWIGSSAGLMVAAASPYVAWMSVTAGQAE |

TABLE 2-continued

Sequences of Immunogenicity Enhancing Agents

| SEQ ID NO | Sequence |
|---|---|
| | LTAAQVRVAAAAYETAYGLTVPPPVIAENRAELMILIATNLLGQNT PAIAVNEAEYGEMWAQDAAAMFGYAAATATATATLLPFEEAPEMT SAGGLLEQAAAVEEASDTAAANQLMNNVPQALQQLAQPTQGTTPS SKLGGLWKTVSPHRSPISNMVSMANNHMSMTNSGVSMTNTLSSML KGFAPAAAAQAVQTAAQNGVRAMSSLGSSLGSSGLGGGVAANLG RAASVGSLSVPQAWAAANQAVTPAARALPLTSLTSAAERGP TABLE 2-continued Sequences of Immunogenicity Enhancing Agents

| SEQ ID NO | Sequence |
|---|---|
| | APGTEVTYRLQLHMLSCPCKAKATRTLHLGKMPYLSGAAYNVAVI SSNQFGPGLNQTWHIPADTHTEPVALNISVGTNGTTMYWPARAQS MTYCIEWQPVGQDGGLATCSLTAPQDPDPAGMATYSWSRESGAM GQEKCYYITIFASAHPEKLTLWSTVLSTYHFGGNASAAGTPHHVSV KNHSLDSVSVDWAPSLLSTCPGVLKEYVVRCRDEDSKQVSEHPVQP TETQVTLSGLRAGVAYTVQVRADTAWLRGVWSQPQRFSIEVQVSD WLIFFASLGSFLSILLVGVLGYLGLNRAARHLCPPLPTPCASSAIEFPG GKETWQWINPVDFQEEASLQEALVVEMSWDKGERTEPLEKTELPE GAPELALDTELSLEDGDRCKAKM |
| SEQ ID NO: 48 | MAAEPVEDNCINFVAMKFIDNTLYFIAEDDENLESDYFGKLESKLSV IRNLNDQVLFIDQGNRPLFEDMTDSDCRDNAPRTIFIISMYKDSQPRG MAVTISVKCEKISTLSCENKIISFKEMNPPDNIKDTKSDIIFFQRSVPG HDNKMQFESSSYEGYFLACEKERDLFKLILKKEDELGDRSIMFTVQ NED |
| SEQ ID NO: 49 | MFHVSFRYIFGLPPLILVLLPVASSDCDIEGKDGKQYESVLMVSIDQL LDSMKEIGSNCLNNEFNFFKRHICDANKEGMFLFRAARKLRQFLKM NSTGDFDLHLLKVSEGTTILLNCTGQVKGRKPAALGEAQPTKSLEE NKSLKEQKKLNDLCFLKRLLQEIKTCWNKILMGTKEH |
| SEQ ID NO: 50 | MSRLPVLLLLQLLVRPGLQAPMTQTTSLKTSWVNCSNMIDEIITHLK QPPLPLLDFNNLNGEDQDILMENNLRRPNLEAFNRAVKSLQNASAIE SILKNLLPCLPLATAAPTRHPIHIKDGDWNEFRRKLTFYLKTLENAQ AQQTTLSLAIF |
| SEQ ID NO: 51 | MGLTSQLLPPLFFLLACAGNFVHGHKCDITLQEIIKTLNSLTEQKTLC TELTVTDIFAASKNTTEKETFCRAATVLRQFYSHHEKDTRCLGATA QQFHRHKQLIRFLKRLDRNLWGLAGLNSCPVKEANQSTLENFLERL KTIMREKYSKCSS |
| SEQ ID NO: 52 | MRMLLHLSLLALGAAYVYAIPTEIPTSALVKETLALLSTHRTLLIAN ETLRIPVPVHKNHQLCTEEIFQGIGTLESQTVQGGTVERLFKNLSLIK KYIDGQKKKCGEERRRVNQFLDYLQEFLGVMNTEWIIES |
| SEQ ID NO: 53 | MNSFSTSAFGPVAFSLGLLLVLPAAFPAPVPPGEDSKDVAAPHRQPL TSSERIDKQIRYILDGISALRKETCNKSNMCESSKEALAENNLNLPK MAEKDGCFQSGFNEETCLVKIITGLLEFEVYLEYLQNRFESSEEQAR AVQMSTKVLIQFLQKKAKNLDAITTPDPTTNASLLTKLQAQNQWLQ DMTTHLILRSFKEFLQSSLRALRQM |
| SEQ ID NO: 54 | MVLTSALLLCSVAGQGCPTLAGILDINFLINKMQEDPASKCHCSAN VTSCLCLGIPSDNCTRPCFSERLSQMTNTTMQTRYPLIFSRVKKSVE VLKNNKCPYFSCEQPCNQTTAGNALTFLKSLLEIFQKEKMRGMRGK I |
| SEQ ID NO: 55 | MHSSALLCCLVLLTGVRASPGQGTQSENSCTHFPGNLPNMLRDLRD AFSRVKTFFQMKDQLDNLLLKESLLEDFKGYLGCQALSEMIQFYLE EVMPQAENQDPDIKAHVNSLGENLKTLRLRLRRCHRFLPCENKSKA VEQVKNAFNKLQEKGIYKAMSEFDIFINYIEAYMTMKIRN |
| SEQ ID NO: 56 | MALLLTTVIALTCLGGFASPGPVPPSTALRELIEELVNITQNQKAPLC NGSMVWSINLTAGMYCAALESLINVSGCSAIEKTQRMLSGFCPHKV SAGQFSSLHVRDTKIEVAQFVKDLLLHLKKLFREGQFNRNFESIIICR DRT |
| SEQ ID NO: 57 | MDFQVQIFSFLLISASVIMSRANWVNVISDLKKIEDLIQSMHIDATLY TESDVHPSCKVTAMKCFLLELQVISLESGDASIHDTVENLIILANNSL SSNGNVTESGCKECEELEEKNIKEFLQSFVHIVQMFINTS |
| SEQ ID NO: 58 | MEGDGSDPEPPDAGEDSKSENGENAPIYCICRKPDINCFMIGCDNCN EWFHGDCIRITEKMAKAIREWYCRECREKDPKLEIRYRHKKSRERD GNERDSSEPRDEGGGRKRPVPDPNLQRRAGSGTGVGAMLARGSAS PHKSSPQPLVATPSQHHQQQQQQIKRSARMCGECEACRRTEDCGHC DFCRDMKKFGGPNKIRQKCRLRQCQLRARESYKYFPSSLSPVTPSES LPRPRRPLPTQQQPQPSQKLGRIREDEGAVASSTVKEPPEATATPEPL SDEDLPLDPDLYQDFCAGAFDDNGLPWMSDTEESPFLDPALRKRAV KVKHVKRREKKSEKKKEERYKRHRQKQKHKDKWKHPERADAKD PASLPQCLGPGCVRPAQPSSKYCSDDCGMKLAANRIYEILPQRIQQW QQSPCIAEEHGKKLLERIRREQQSARTRLQEMERRFHELEAIILRAKQ QAVREDEESNEGDSDDTDLQIFCVSCGHPINPRVALRHMERCYAKY ESQTSFGSMYPTRIEGATRLFCDVYNPQSKTYCKRLQVLCPEHSRDP KVPADEVCGCPLVRDVFELTGDFCRLPKRQCNRHYCWEKLRRAEV DLERVRVWYKLDELFEQERNVRTAMTNRAGLLALMLHQTIQHDPL TTDLRSSADR |

TABLE 2-continued

Sequences of Immunogenicity Enhancing Agents

| SEQ ID NO | Sequence |
| --- | --- |
| SEQ ID NO: 59 | MIKLKFGVFFTVLLSSAYAHGTPQNITDLCAEYHNTQIYTLNDKIFS YTESLAGKREMAIITFKNGAIFQVEVPGSQHIDSQKKAIERMKDTLRI AYLTEAKVEKLCVWNNKTPHAIAAISMAN |
| SEQ ID NO: 60 | MVKIIFVFFIFLSSFSYANDDKLYRADSRPPDEIKQSGGLMPRGQNEY FDRGTQMNINLYDHARGTQTGFVRHDDGYVSTSISLRSAHLVGQTI LSGHSTYYIYVIATAPNMFNVNDVLGAYSPHPDEQEVSALGGIPYSQ IYGWYRVHFGVLDEQLHRNRGYRDRYYSNLDIAPAADGYGLAGFP PEHRAWREEPWIHHAPPGCGNAPRSSMSNTCDEKTQSLGVKFLDEY QSKVKRQIFSGYQSDIDTHNRIKDEL |
| SEQ ID NO: 61 | MIKLKFGVFFTVLLSSAYAHGTPQNITDLCAEYHNTQIHTLNDKILS YTESLAGNREMAIITFKNGATFQVEVPGSQHIDSQKKAIERMKDTLR IAYLTEAKVEKLCVWNNKTPHAIAAISMAN |
| SEQ ID NO: 62 | DPNAPKRPPSAFFLFCSE |
| SEQ ID NO: 63 | MCCTKSLLLAALMSVLLLHLCGESEAASNFDCCLGYTDRILHPKFIV GFTRQLANEGCDINAIIFHTKKKLSVCANPKQTWVKYIVRLLSKKV KNM |
| SEQ ID NO: 64 | MQVSTAALAVLLCTMALCNQFSASLAADTPTACCFSYTSRQIPQNFI ADYFETSSQCSKPGVIFLTKRSRQVCADPSEEWVQKYVSDLELSA |
| SEQ ID NO: 65 | MWLQSLLLLGTVACSISAPARSPSPSTQPWEHVNAIQEARRLLNLSR DTAAEMNETVEVISEMFDLQEPTCLQTRLELYKQGLRGSLTKLKGP LTMMASHYKQHCPPTPETSCATQIITFESFKENLKDFLLVIPFDCWEP VQE |
| SEQ ID NO: 66 | MAGPATQSPMKLMALQLLLWHSALWTVQEATPLGPASSLPQSFLL KCLEQVRKIQGDGAALQEKLCATYKLCHPEELVLLGHSLGIPWAPL SSCPSQALQLAGCLSQLHSGLFLYQGLLQALEGISPELGPTLDTLQL DVADFATTIWQQMEELGMAPALQPTQGAMPAFASAFQRRAGGVL VASHLQSFLEVSYRVLRHLAQP |
| SEQ ID NO: 67 | QEINSSY |
| SEQ ID NO: 68 | SHPRLSA |
| SEQ ID NO: 69 | SMPNPMV |
| SEQ ID NO: 70 | GLQQVLL |
| SEQ ID NO: 71 | HELSVLL |
| SEQ ID NO: 72 | YAPQRLP |
| SEQ ID NO: 73 | TPRTLPT |
| SEQ ID NO: 74 | APVHSSI |
| SEQ ID NO: 75 | APPHALS |
| SEQ ID NO: 76 | TFSNRFI |
| SEQ ID NO: 77 | VVPTPPY |
| SEQ ID NO: 78 | ELAPDSP |
| SEQ ID NO: 79 | TPDCVTGKVEYTKYNDDDTFTVKVGDKELFTNRWNLQSLLLSAQIT GMTVTIKQNACHNGGGFSEVIFR |
| SEQ ID NO: 80 | MSRKLFASILIGALLGIGAPPSAHAGADDVVDSSKSFVMENFSSYHG TKPGYVDSIQKGIQKPKSGTQGNYDDDWKGFYSTDNKYDAAGYSV DNENPLSGKAGGVVKVTYPGLTKVLALKVDNAETIKKELGLSLTEP LMEQVGTEEFIKRFGDGASRVVLSLPFAEGSSSVEYINNWEQAKALS VELEINFETRGKRGQDAMYEYMAQACAGNRVRRSVGSSLSCINLD WDVIRDKTKTKIESLKEHGPIKNKMSESPNKTVSEEKAKQYLEEFH QTALEHPELSELKTVTGTNPVFAGANYAAWAVNVAQVIDSETADN LEKTTAALSILPGIGSVMGIADGAVHHNTEEIVAQSIALSSLMVAQAI PLVGELVDIGFAAYNFVESIINLFQVVHNSYNRPAYSPGHKTQPFLH DGYAVSWNTVEDSIIRTGFQGESGHDIKITAENTPLPIAGVLLPTIPG KLDVNKSKTHISVNGRKIRMRCRAIDGDVTFCRPKSPVYVGNVHA NLHVAFHRSSSEKIHSNEISSDSIGVLGYQKTVDHTKVNSKLSLFFEI KS |

TABLE 2-continued

Sequences of Immunogenicity Enhancing Agents

| SEQ ID NO | Sequence |
| --- | --- |
| SEQ ID NO: 81 | NWVNVISDLKKIEDLIQSMHIDATLYTESDVHPSCKVTAMKCFLLEL<br>QVISLESGDASIHDTVENLIILANDSLSSNGNVTESGCKECEELEEKNI<br>KEFLQSFVHIVQMFINTS |
| SEQ ID NO: 82 | ITCPPPMSVEHADIWVKSYSLYSRERYICNSGFKRKAGTSSLTECVL<br>NKATNVAHWTTPSLKCIREPKSCDKTHTCPPCPAPELLGGPSVFLFP<br>PKPKDTLMISRTPEVTCVVVDVSHEDPEVKFNWYVDGVEVHNAKT<br>KPREEQYNSTYRVVSVLTVLHQDWLNGKEYKCKVSNKALPAPIEK<br>TISKAKGQPREPQVYTLPPSRDELTKNQVSLTCLVKGFYPSDIAVEW<br>ESNGQPENNYKTTPPVLDSDGSFFLYSKLTVDKSRWQQGNVFSCSV<br>MHEALHNHYTQKSLSLSPGK |
| SEQ ID NO: 83 | GADDVVDSSKSFVMENFSSYHGTKPGYVDSIQKGIQKPKSGTQGNY<br>DDDWKEFYSTDNKYDAAGYSVDNENPLSGKAGGVVKVTYPGLTK<br>VLALKVDNAETIKKELGLSLTEPLMEQVGTEEFIKRFDGASRVVLS<br>LPFAEGSSSVEYINNWEQAKALSVELEINFETRGKRGQDAMYEYMA<br>QACAGNRVRRSVGSSLSCINLDWDVIRDKTKTKIESLKEHGPIKNK<br>MSESPNKTVSEEKAKQYLEEFHQTALEHPELSELKTVTGTNPVFAG<br>ANYAAWAVNVAQVIDSETADNLEKTTAALSILPGIGSVMGIADGAV<br>HHNTEEIVAQSIALSSLMVAQAIPLVGELVDIGFAAYNFVESIINLFQ<br>VVHNSYNRPAYSPGHKTQPFLHDGYAVSWNTVEDSIIRTGFQGESG<br>HDIKITAENTPLPIAGVLLPTIPGKLDVNKSKTHISVNGRKIRMRCRAI<br>DGDVTFCRPKSPVYVGNGVHANLHVAFHRSSSEKIHSNEISSDSIGV<br>LGYQKTVDHTKVNSKLSLFFEIKS |
| SEQ ID NO: 103 | MESHSRAGKSRKSAKFRSISRSLMLCNAKTSDDGSSPDEKYPDPFEI<br>SLAQGKEGIFHSSVQLADTSEAGPSSVPDLALASEAAQLQAAGNDR<br>GKTCRRIFFMKESSTASSREKPGKLEAQSSNFLFPKACHQRARSNST<br>SVNPYCTREIDFPMTKKSAAPTDRQPYSLCSNRKSLSQQLDCPAGK<br>AAGTSRPTRSLSTAQLVQPSGGLQASVISNIVLMKGQAKGLGFSIVG<br>GKDSIYGPIGIYVKTIFAGGAAAADGRLQEGDEILELNGESMAGLTH<br>QDALQKFKQAKKGLLTLTVRTRLTAPPSLCSHLSPPLCRSLSSSTCIT<br>KDSSSFALESPSAPISTAKPNYRIMVEVSLQKEAGVGLGIGLCSVPYF<br>QCISGIFVHTLSPGSVAHLDGRLRCGDEIVEISDSPVHCLTLNEVYTIL<br>SRCDPGPVPIIVSRHPDPQVSEQQLKEAVAQAVENTKFGKERHQWS<br>LEGVKRLESSWHGRPTLEKEREKNSAPPHRRAQKVMIRSSSDSSYM<br>SGSPGGSPGSGSAEKPSSDVDISTHSPSLPLAREPVVLSIASSRLPQES<br>PPLPESRDSHPPLRLKKSFEILVRKPMSSKPKPPPRKYFKSDSDPQKS<br>LEERENSSCSSGHTPPTCGQEARELLPLLLPQEDTAGRSPSASAGCPG<br>PGIGPQTKSSTEGEPGWRRASPVTQTSPIKHPLLKRQARMDYSFDTT<br>AEDPWVRISDCIKNLFSPIMSENHGHMPLQPNASLNEEEGTQGHPDG<br>TPPKLDTANGTPKVYKSADSSTVKKGPPVAPKPAWFRQSLKGLRNR<br>ASDPRGLPDPALSTQPAPASREHLGSHIRASSSSSSIRQRISSFETFGSS<br>QLPDKGAQRLSLQPSSGEAAKPLGKHEEGRFSGLLGRGAAPTLVPQ<br>QPEQVLSSGSPAASEARDPGVSESPPPGRQPNQKTLPPGPDPLLRLLS<br>TQAEESQGPVLKMPSQRARSFPLTRSQSCETKLLLDEKTSKLYSISSQ<br>VSSAVMKSLLCLPSSISCAQTPCIPKEGASPTSSSNEDSAANGSAETS<br>ALDTGFSLNLSELREYTEGLTEAKEDDDGDHSSLQSGQSVISLLSSEE<br>LKKLIEEVKVLDEATLKQLDGIHVTILHKEEGAGLGFSLAGGADLEN<br>KVITVHRVFPNGLASQEGTIQKGNEVLSINGKSLKGTTHHDALAILR<br>QAREPRQAVIVTRKLTPEAMPDLNSSTDSAASASAASDVSVESTEAT<br>VCTVTLEKMSAGLGFSLEGGKGSLHGDKPLTINRIFKGAASEQSETV<br>QPGDEILQLGGTAMQGLTRFEAWNIIKALPDGPVTIVIRRKSLQSKE<br>TTAAGDS |
| SEQ ID NO: 104 | MTPGKTSLVSLLLLLSLEAIVKAGITIPRNPGCPNSEDKNFPRTVMVN<br>LNIHNRNTNTNPKRSSDYYNRSTSPWNLHRNEDPERYPSVIWEAKC<br>RHLGCINADGNVDYHMNSVPIQQEILVLRREPPHCPNSFRLEKILVS<br>VGCTCVTPIVHHVA |
| SEQ ID NO: 105 | RAVPGGSSPAWTQCQQLSQKLCTLAWSAHPLVGHMDLREEGDEET<br>TNDVPHIQCGDGCDPQGLRDNSQFCLQRIHQGLIFYEKLLGSDIFTG<br>EPSLLPDSPVGQLHASLLGLSQLLQPEGHHWETQQIPSLSPSQPWQR<br>LLLRFKILRSLQAFVAVAARVFAHGAATLSPIWELKKDVYVVELDW<br>YPDAPGEMVVLTCDTPEEDGITWTLDQSSEVLGSGKTLTIQVKEFG<br>DAGQYTCHKGGEVLSHSLLLLHKKEDGIWSTDILKDQKEPKNKTFL<br>RCEAKNYSGRFTCWWLTTISTDLTFSVKSSRGSSDPQGVTCGAATL<br>SAERVRGDNKEYEYSVECQEDSACPAAEEESLPIEVMVDAVHKLKYE<br>NYTSSFFIRDIIKPDPPKNLQLKPLKNSRQVEVSWEYPDTWSTPHSYF<br>SLTFCVQVQGKSKREKKDRVFTDKTSATVICRKNASISVRAQDRYY<br>SSSWSEWASVPCS |

TABLE 2-continued

Sequences of Immunogenicity Enhancing Agents

| SEQ ID NO | Sequence |
|---|---|
| SEQ ID NO: 106 | MCFPKVLSDDMKKLKARMVMLLPTSAQGLGAWVSACDTEDTVGH<br>LGPWRDKDPALWCQLCLSSQHQAIERFYDKMQNAESGRGQVMSSL<br>AELEDDFKEGYLETVAAYYEEQHPELTPLLEKERDGLRCRGNRSPV<br>PDVEDPATEEPGESFCDKVMRWFQAMLQRLQTWWHGVLAWVKE<br>KVVALVHAVQALWKQFQSFCCSLSELFMSSFQSYGAPRGDKEELTP<br>QKCSEPQSSK |
| SEQ ID NO: 107 | AACTGGGTGAATGTAATAAGTGATTTGAAAAAAATTGAAGATCT<br>TATTCAATCTATGCATATTGATGCTACTTTATATACGGAAAGTGA<br>TGTTCACCCCAGTTGCAAAGTAACAGCAATGAAGTGCTTTCTCTT<br>GGAGTTACAAGTTATTTCACTTGAGTCCGGAGATGCAAGTATTCA<br>TGATACAGTAGAAAATCTGATCATCCTAGCAAACGACAGTTTGT<br>CTTCTAATGGGAATGTAACAGAATCTGGATGCAAAGAATGTGAG<br>GAACTGGAGGAAAAAATATTAAAGAATTTTTGCAGAGTTTTGT<br>ACATATTGTCCAAATGTTCATCAACACTTCTTAA |
| SEQ ID NO: 108 | ATCACGTGCCCTCCCCCCATGTCCGTGGAACACGCAGACATCTG<br>GGTCAAGAGCTACAGCTTGTACTCCAGGGAGCGGTACATTTGTA<br>ACTCTGGTTTCAAGCGTAAAGCCGGCACGTCCAGCCTGACGGAG<br>TGCGTGTTGAACAAGGCCACGAATGTCGCCCACTGGACAACCCC<br>CAGTCTCAAATGTATTAGAGAGCCCAAATCTTGTGACAAAACTC<br>ACACATGCCCACCGTGCCCAGCACCTGAACTCCTGGGGGGACCG<br>TCAGTCTTCCTCTTCCCCCCAAAACCCAAGGACACCCTCATGATC<br>TCCCGGACCCCTGAGGTCACATGCGTGGTGGTGGACGTGAGCCA<br>CGAAGACCCTGAGGTCAAGTTCAACTGGTACGTGGACGGCGTGG<br>AGGTGCATAATGCCAAGACAAAGCCGCGGGAGGAGCAGTACAA<br>CAGCACGTACCGTGTGGTCAGCGTCCTCACCGTCCTGCACCAGG<br>ACTGGCTGAATGGCAAGGAGTACAAGTGCAAGGTCTCCAACAAA<br>GCCCTCCCAGCCCCCATCGAGAAAACCATCTCCAAAGCCAAGG<br>GCAGCCCCGAGAACCACAGGTGTACACCCTGCCCCCATCCCGGG<br>ATGAGCTGACCAAGAACCAGGTCAGCCTGACCTGCCTGGTCAAA<br>GGCTTCTATCCCAGCGACATCGCCGTGGAGTGGGAGAGCAATGG<br>GCAGCCGGAGAACAACTACAAGACCACGCCTCCCGTGCTGGACT<br>CCGACGGCTCCTTCTTCCTCTACAGCAAGCTCACCGTGGACAAGA<br>GCAGGTGGCAGCAGGGGAACGTCTTCTCATGCTCCGTGATGCAT<br>GAGGCTCTGCACAACCACTACACGCAGAAGAGCCTCTCCCTGTC<br>TCCGGGTAAATAA |
| SEQ ID NO: 109 | ATGGAAACCGACACCCTGCTGCTGTGGGTGCTGCTGCTGTGGGT<br>GCCAGGCAGCACAGGCAACTGGGTCAACGTGATCAGCGACCTGA<br>AGAAGATCGAGGACCTGATCCAGAGCATGCACATCGACGCCACC<br>CTGTACACCGAGAGCGACGTGCACCCCAGCTGCAAAGTGACCGC<br>CATGAAGTGCTTTCTGCTGGAACTGCAAGTGATCAGCCTGGAAA<br>GCGGCGACGCCAGCATCCACGACACCGTGGAAAACCTGATCATC<br>CTGGCCAACGACAGCCTGAGCAGCAACGGCAACGTGACCGAGTC<br>CGGCTGCAAAGAGTGCGAGGAACTGGAAGAGAAGAATATCAAA<br>GAGTTCCTGCAGAGCTTCGTGCACATCGTGCAGATGTTCATCAAC<br>ACCAGCGGCTCTGGCGAGGGCAGAGGCAGCCTGCTGACATGCGG<br>AGATGTGGAAGAGAACCCTGGCCCCATGGACCGGCTGACCAGCT<br>CTTTTCTGCTGCTGATCGTGCCCGCCTACGTGCTGAGCATCACCT<br>GTCCCCCACCCATGAGCGTGGAACACGCCGACATCTGGGTCAAG<br>AGCTACAGCCTGTACAGCCGGGAACGGTACATCTGCAACAGCGG<br>CTTCAAGCGGAAGGCCGGCACCAGCAGCCTGACCGAGTGTGTGC<br>TGAACAAGGCCACCAACGTGGCCCACTGGACCACCCCTAGCCTG<br>AAGTGCATCAGAGAGCCCAAGAGCTGCGACAAGACCCACACAT<br>GCCCCCCTTGTCCTGCCCCTGAACTGCTGGGAGGCCCTAGCGTGT<br>TCCTGTTCCCCCCAAAGCCCAAGGACACCCTGATGATCAGCCGG<br>ACCCCCGAAGTGACCTGCGTGGTGGTGGATGTGTCCCACGAGGA<br>CCCTGAAGTGAAGTTCAATTGGTACGTGGACGGCGTGGAAGTGC<br>ACAACGCCAAGACCAAGCCCAGAGAGGAACAGTACAACAGCAC<br>CTACCGGGTGGTGTCCGTGCTGACCGTGCTGCACCAGGACTGGC<br>TGAACGGCAAAGAGTACAAGTGCAAGGTGTCCAACAAGGCCCTG<br>CCTGCCCCCATCGAGAAAACCATCAGCAAGGCCAAGGGCCAGCC<br>CCGCGAACCCCAGGTGTACACACTGCCCCCTAGCAGGGACGAGC<br>TGACCAAGAACCAGGTGTCCCTGACCTGTCTCGTGAAGGGCTTCT<br>ACCCCAGCGACATTGCCGTGGAATGGGAGAGCAACGGCCAGCCC<br>GAGAACAACTACAAGACCACCCCCCCTGTGCTGGACAGCGACGG<br>CTCATTCTTCCTGTACTCCAAGCTGACAGTGGACAAGAGCCGGTG<br>GCAGCAGGGCAACGTGTTCAGCTGCAGCGTGATGCACGAGGCCC<br>TGCACAACCACTACACCCAGAAGTCCCTGAGCCTGAGCCCCGGC<br>AAATGA |
| SEQ ID NO: 110 | METDTLLLWVLLLWVPGSTGNWVNVISDLKKIEDLIQSMHIDATLY<br>TESDVHPSCKVTAMKCFLLELQVISLESGDASIHDTVENLIILANDSL<br>SSNGNVTESGCKECEELEEKNIKEFLQSFVHIVQMFINTSGSGEGRGS<br>LLTCGDVEENPGPMDRLTSSFLLLIVPAYVLSITCPPPMSVEHADIW |

TABLE 2-continued

Sequences of Immunogenicity Enhancing Agents

| SEQ ID NO | Sequence |
|---|---|
| | VKSYSLYSRERYICNSGFKRKAGTSSLTECVLNKATNVAHWTTPSL
KCIREPKSCDKTHTCPPCPAPELLGGPSVFLFPPKPKDTLMISRTPEV
TCVVVDVSHEDPEVKFNWYVDGVEVHNAKTKPREEQYNSTYRVV
SVLTVLHQDWLNGKEYKCKVSNKALPAPIEKTISKAKGQPREPQVY
TLPPSRDELTKNQVSLTCLVKGFYPSDIAVEWESNGQPENNYKTTPP
VLDSDGSFFLYSKLTVDKSRWQQGNVFSCSVMHEALHNHYTQKSL
SLSPGK |

In some embodiments, the nucleic acid sequences for the target antigen and the immunological fusion partner are not separated by any nucleic acids. In other embodiments, a nucleic acid sequence that encodes for a linker can be inserted between the nucleic acid sequence encoding for any target antigen described herein and the nucleic acid sequence encoding for any immunological fusion partner described herein. Thus, in certain embodiments, the protein produced following immunization with the viral vector containing a target antigen, a linker, and an immunological fusion partner can be a fusion protein comprising the target antigen of interest followed by the linker and ending with the immunological fusion partner, thus linking the target antigen to an immunological fusion partner that increases the immunogenicity of the target antigen of interest via a linker. In some embodiments, the sequence of linker nucleic acids can be from about 1 to about 150 nucleic acids long, from about 5 to about 100 nucleic acids along, or from about 10 to about 50 nucleic acids in length. In some embodiments, the nucleic acid sequences may encode one or more amino acid residues. In some embodiments, the amino acid sequence of the linker can be from about 1 to about 50, or about 5 to about 25 amino acid residues in length. In some embodiments, the sequence of the linker comprises less than 10 amino acids. In some embodiments, the linker can be a polyalanine linker, a polyglycine linker, or a linker with both alanines and glycines.

Nucleic acid sequences that encode for such linkers can be any one of SEQ ID NO: 84-SEQ ID NO: 98 and are summarized in TABLE 3.

TABLE 3

Sequences of Linkers

| SEQ ID NO | Sequence |
|---|---|
| SEQ ID NO: 84 | MAVPMQLSCSR |
| SEQ ID NO: 85 | RSTG |
| SEQ ID NO: 86 | TR |
| SEQ ID NO: 87 | RSQ |
| SEQ ID NO: 88 | RSAGE |
| SEQ ID NO: 89 | RS |
| SEQ ID NO: 90 | GG |
| SEQ ID NO: 91 | GSGGSGGSG |
| SEQ ID NO: 92 | GGSGGSGGSGG |
| SEQ ID NO: 93 | GGSGGSGGSGGSGG |
| SEQ ID NO: 94 | GGSGGSGGSGGSGGSGG |

TABLE 3-continued

Sequences of Linkers

| SEQ ID NO | Sequence |
|---|---|
| SEQ ID NO: 95 | GGSGGSGGSGGSGGSGGSGG |
| SEQ ID NO: 96 | GGSGGSGGSGGSGGSGGSGGSGG |
| SEQ ID NO: 97 | GGSGGSGGSGGSGGSG |
| SEQ ID NO: 98 | GSGGSGGSGGSGGSGG |

Formulations of Vaccines or ALT-803

Some embodiments provide pharmaceutical compositions comprising a vaccination and ALT-803 regimen that can be administered either alone or together with a pharmaceutically acceptable carrier or excipient, by any routes, and such administration can be carried out in both single and multiple dosages. More particularly, the pharmaceutical composition can be combined with various pharmaceutically acceptable inert carriers in the form of tablets, capsules, lozenges, troches, hand candies, powders, sprays, aqueous suspensions, injectable solutions, elixirs, syrups, in drug delivery devices for implantation and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. The compositions described throughout can be formulated into a pharmaceutical medicament and be used to treat a human or mammal, in need thereof, diagnosed with a disease, e.g., cancer.

For administration, viral vector or ALT-803 stock can be combined with an appropriate buffer, physiologically acceptable carrier, excipient or the like. In certain embodiments, an appropriate number of virus vector particles (VP) or ALT-803 proteins are administered in an appropriate buffer, such as, sterile PBS or saline. In certain embodiment, vector compositions and ALT-803 compositions disclosed herein are provided in specific formulations for subcutaneously, parenterally, intravenously, intramuscularly, or even intraperitoneally administration. In certain embodiments, formulations in a solution of the active compounds as free base or pharmacologically acceptable salts may be prepared in water suitably mixed with a surfactant, such as hydroxypropylcellulose. Dispersions may also be prepared in glycerol, liquid polyethylene glycols, squalene-based emulsion, Squalene-based oil-in-water emulsions, water-in-oil emulsions, oil-in-water emulsions, nonaqueous emulsions, water-in-paraffin oil emulsion, and mixtures thereof and in oils. In other embodiments, viral vectors may are provided in specific formulations for pill form administration by swallowing or by suppository.

Illustrative pharmaceutical forms suitable for injectable use include sterile aqueous solutions or dispersions and sterile powders for the extemporaneous preparation of sterile injectable solutions or dispersions (see, e.g., U.S. Pat. No. 5,466,468). Fluid forms to the extent that easy syringability exists may be preferred. Forms that are stable under the conditions of manufacture and storage are provided in some embodiments. In various embodiments, forms are preserved against the contaminating action of microorganisms, such as bacteria, molds and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, and thimerosal. It may be suitable to include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution can be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see, e.g., "Remington's Pharmaceutical Sciences" 15th Edition, pages 1035-1038 and 1570-1580). Some variation in dosage may occur depending on the condition of the subject being treated.

Carriers of formulation can comprise any and all solvents, dispersion media, vehicles, coatings, diluents, antibacterial and antifungal agents, isotonic and absorption delaying agents, buffers, carrier solutions, suspensions, colloids, suspending agents, solubilizing agents, stabilizing agents, pH-adjusting agent (such as hydrochloric id, sodium hydroxide or a suitable buffer, 1,3-butanediol, Ringer's solution, and isotonic sodium chloride solution and dextrose solution), tonicity adjusting agents, preservatives (e.g., methyl, ethyl or n-propyl p-hydroxybenzoate) and the like. Except insofar as any conventional media or agent is incompatible with the active ingredient, its use in the therapeutic compositions is contemplated. Supplementary active ingredients can also be incorporated into the compositions.

Pharmaceutical formulations can be provided as a unit dose, (e.g., in single-dose ampoules, syringes or bags), or in vials containing several doses and in which a suitable preservative may be added (see below). Therapeutic moieties can be formulated in microspheres, microcapsules, nanoparticles, or liposomes.

Formulation of Viral Vectors with Immunostimulants

In certain embodiments, the viral vectors may be administered in conjunction with one or more immunostimulants, such as an adjuvant. An immunostimulant refers to essentially any substance that enhances or potentiates an immune response (antibody and/or cell-mediated) to an antigen. One type of immunostimulant comprises an adjuvant. Many adjuvants contain a substance designed to protect the antigen from rapid catabolism, such as aluminum hydroxide or mineral oil, and a stimulator of immune responses, such as lipid A, Bortadella pertussis or *Mycobacterium tuberculosis* derived proteins. Certain adjuvants are commercially available as, for example, Freund's Incomplete Adjuvant and Complete Adjuvant (Difco Laboratories); Merck Adjuvant 65 (Merck and Company, Inc.) AS-2 (SmithKline Beecham); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, IFN-$\gamma$, TNF$\alpha$, IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-$\alpha$, IFN-$\beta$, IL-1$\alpha$, IL-1$\beta$, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36$\alpha,\beta,\lambda$, IL-36Ra, IL-37, TSLP, LIF, OSM, LT-$\alpha$, LT-$\beta$, CD40 ligand, Fas ligand, CD27 ligand, CD30 ligand, 4-1BBL, Trail, OPG-L, APRIL, LIGHT, TWEAK, BAFF, TGF-$\beta$1, MIF and others, like growth factors, may also be used as adjuvants.

In some embodiments, the adjuvant is selected from the group consisting of IL-15, a nucleic acid encoding IL-15, a protein with substantial identity to IL-15, and a nucleic acid encoding a protein with substantial identity to IL-15.

Within certain embodiments, the adjuvant composition can be one that induces an immune response predominantly of the Th1 type. High levels of Th1-type cytokines (e.g., IFN-$\gamma$, TNF$\alpha$, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient may support an immune response that includes Th1- and/or Th2-type responses. Within certain embodiments, in which a response is predominantly Th1-type, the level of Th1-type cytokines will increase to a greater extent than the level of Th2-type cytokines. The levels of these cytokines may be readily assessed using standard assays. Thus, various embodiments relate to therapies raising an immune response against a target antigen, for example CEA, using cytokines, e.g., IFN-$\gamma$, TNF$\alpha$, IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-$\alpha$, IFN-$\beta$, IL-1$\alpha$, IL-1$\beta$, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36$\alpha,\beta,\lambda$, IL-36Ra, IL-37, TSLP, LIF, OSM, LT-$\alpha$, LT-$\beta$, CD40 ligand, Fas ligand, CD27 ligand, CD30 ligand, 4-1BBL, Trail, OPG-L, APRIL, LIGHT, TWEAK, BAFF, TGF-$\beta$1, and/or MIF supplied concurrently with a replication defective viral vector treatment. In some embodiments, a cytokine or a nucleic acid encoding a cytokine, is administered together with a replication defective viral described herein. In some embodiments, cytokine administration is performed prior or subsequent to viral vector administration. In some embodiments, a replication defective viral vector capable of raising an immune response against a target antigen, for example CEA, further comprises a sequence encoding a cytokine.

Certain illustrative adjuvants for eliciting a predominantly Th1-type response include, for example, a combination of monophosphoryl lipid A, such as 3-de-O-acylated monophosphoryl lipid A, together with an aluminum salt. MPL® adjuvants are commercially available (see, e.g., U.S. Pat. Nos. 4,436,727; 4,877,611; 4,866,034 and 4,912,094). CpG-containing oligonucleotides (in which the CpG dinucleotide is unmethylated) also induce a predominantly Th1 response. (see, e.g., WO 96/02555, WO 99/33488 and U.S. Pat. Nos. 6,008,200 and 5,856,462). Immunostimulatory DNA sequences can also be used. Another adjuvant for use comprises a saponin, such as Quil A, or derivatives thereof, including QS21 and QS7 (Aquila Biopharmaceuticals Inc.), Escin; Digitonin; or *Gypsophila* or *Chenopodium quinoa* saponins. Other formulations may include more than one saponin in the adjuvant combinations, e.g., combinations of at least two of the following group comprising QS21, QS7, Quil A, β-escin, or digitonin.

In some embodiments, the compositions may be delivered by intranasal sprays, inhalation, and/or other aerosol delivery vehicles. The delivery of drugs using intranasal microparticle resins and lysophosphatidyl-glycerol compounds can be employed (see, e.g., U.S. Pat. No. 5,725,871). Likewise, illustrative transmucosal drug delivery in the form of a polytetrafluoroetheylene support matrix can be employed (see, e.g., U.S. Pat. No. 5,780,045).

Liposomes, nanocapsules, microparticles, lipid particles, vesicles, and the like, can be used for the introduction of the compositions into suitable hot cells/organisms. Compositions as described herein may be formulated for delivery either encapsulated in a lipid particle, a liposome, a vesicle, a nanosphere, or a nanoparticle or the like. Alternatively, compositions as described herein can be bound, either covalently or non-covalently, to the surface of such carrier vehicles. Liposomes can be used effectively to introduce genes, various drugs, radiotherapeutic agents, enzymes, viruses, transcription factors, allosteric effectors and the like, into a variety of cultured cell lines and animals. Furthermore, the use of liposomes does not appear to be associated with autoimmune responses or unacceptable toxicity after systemic delivery. In some embodiments, liposomes are formed from phospholipids dispersed in an aqueous medium and spontaneously form multilamellar concentric bilayer vesicles (i.e. multilamellar vesicles (MLVs).

In some embodiments, pharmaceutically-acceptable nanocapsule formulations of the compositions are provided. Nanocapsules can generally entrap compounds in a stable and reproducible way. To avoid side effects due to intracellular polymeric overloading, such ultrafine particles (sized around 0.1 µm) may be designed using polymers able to be degraded in vivo.

The compositions in some embodiments comprise or are administered with a chemotherapeutic agent (e.g., a chemical compound useful in the treatment of cancer). Chemotherapeutic cancer agents that can be used in combination with the disclosed T cell include, but are not limited to, mitotic inhibitors (*vinca* alkaloids), such as vincristine, vinblastine, vindesine and Navelbine™ (vinorelbine, 5′-noranhydroblastine); topoisomerase I inhibitors, such as camptothecin compounds (e.g., Camptosar™ (irinotecan HCL), Hycamtin™ (topotecan HCL) and other compounds derived from camptothecin and its analogues); podophyllotoxin derivatives, such as etoposide, teniposide and mitopodozide; alkylating agents such as cisplatin, cyclophosphamide, nitrogen mustard, trimethylene thiophosphoramide, carmustine, busulfan, chlorambucil, belustine, uracil mustard, chlomaphazin, and dacarbazine; antimetabolites such as cytosine arabinoside, fluorouracil, methotrexate, mercaptopurine, azathioprime, and procarbazine; antibiotics, such as doxorubicin, bleomycin, dactinomycin, daunorubicin, mithramycin, mitomycin, mytomycin C, and daunomycin; anti-tumor antibodies; dacarbazine; azacytidine; amsacrine; melphalan; ifosfamide; and mitoxantrone.

Compositions disclosed herein can be administered in combination with other anti-tumor agents, including cytotoxic/antineoplastic agents and anti-angiogenic agents. Cytotoxic/anti-neoplastic agents can be defined as agents who attack and kill cancer cells. Some cytotoxic/anti-neoplastic agents can be alkylating agents, which alkylate the genetic material in tumor cells, e.g., cis-platin, cyclophosphamide, nitrogen mustard, trimethylene thiophosphoramide, carmustine, busulfan, chlorambucil, belustine, uracil mustard, chlomaphazin, and dacabazine. Other cytotoxic/anti-neoplastic agents can be antimetabolites for tumor cells, e.g., cytosine arabinoside, fluorouracil, methotrexate, mercaptopuirine, azathioprime, and procarbazine. Other cytotoxic/anti-neoplastic agents can be antibiotics, e.g., doxorubicin, bleomycin, dactinomycin, daunorubicin, mithramycin, mitomycin, mytomycin C, and daunomycin. There are numerous liposomal formulations commercially available for these compounds. Still other cytotoxic/anti-neoplastic agents can be mitotic inhibitors (*vinca* alkaloids). These include vincristine, vinblastine and etoposide. Miscellaneous cytotoxic/anti-neoplastic agents include taxol and its derivatives, L-asparaginase, anti-tumor antibodies, dacarbazine, azacytidine, amsacrine, melphalan, VM-26, ifosfamide, mitoxantrone, and vindesine.

Anti-angiogenic agents can also be used. Suitable anti-angiogenic agents for use in the disclosed methods and compositions include anti-VEGF antibodies, including humanized and chimeric antibodies, anti-VEGF aptamers and anti sense oligonucleotides. Other inhibitors of angiogenesis include angiostatin, endostatin, interferons, interleukin 1 (including α and β) interleukin 12, retinoic acid, and tissue inhibitors of metalloproteinase-1 and -2 (TIMP-1 and -2). Small molecules, including topoisomerases such as razoxane, a topoisomerase II inhibitor with anti-angiogenic activity, can also be used.

Methods of Preparation of Ad5 Vaccines

In some embodiments, compositions and methods make use of human cytolytic T-cells (CTLs), such as those that recognize CEAs epitopes which bind to selected MEW molecules, e.g. HLA-A2, A3, and A24. Individuals expressing MEW molecules of certain serotypes, e.g. HLA-A2, A3, and A24 may be selected for therapy using the methods and compositions as described herein. For example, individuals expressing MEW molecules of certain serotypes, e.g. HLA-A2, A3, and A24, may be selected for a therapy including raising an immune response against CEAs, using the methods and compositions described herein.

In various embodiments, these T-cells can be generated by in vitro cultures using antigen-presenting cells pulsed with the epitope of interest to stimulate peripheral blood mononuclear cells. In addition, T-cell lines can also be generated after stimulation with CEA latex beads, CEA protein-pulsed plastic adherent peripheral blood mononuclear cells, or DCs sensitized with CEAsRNA. T-cells can also be generated from patients immunized with a vaccine vector encoding CEAs immunogen. HLA A2-presented peptides from CEAs can further be found in primary gastrointestinal tumors.

Some embodiments relate to an HLA A2 restricted epitope of CEAs, CAP-1, a nine amino acid sequence (YLSGANLNL; SEQ ID NO: 3), with ability to stimulate CTLs from cancer patients immunized with vaccine-CEAs. Cap-1(6D) (YLSGADLNL; SEQ ID NO: 4) is a peptide analog of CAP-1. Its sequence includes a heteroclitic (nonanchor position) mutation, resulting in an amino acid change from Asn to Asp, enhancing recognition by the T-cell receptor. The Asn to Asp mutation appears to not cause any change in the binding of the peptide to HLA A2. Compared with the non-mutated CAP-1 epitope, Cap-1(6D) can enhance the sensitization of CTLs by 100 to 1,000 times. CTL lines can be elicited from peripheral blood mononuclear cells of healthy volunteers by in vitro sensitization to the Cap-1(6D) peptide, but not significantly to the CAP-1 peptide. These cell lines can lyse human tumor cells expressing endogenous CEA. Thus, polypeptide sequences comprising CAP-1 or CAP-1(6D), nucleic acid sequences encoding such sequences, an adenovirus vectors; for example replication defective adenovirus vectors, comprising such nucleic acid sequences are provided in some embodiments.

Methods of Treatment with Ad5 Vaccines

The adenovirus vectors can be used in a number of vaccine settings for generating an immune response against one or more target antigens as described herein. Some embodiments provide methods of generating an immune response against any target antigen, such as those described elsewhere herein. The adenovirus vectors are of particular importance because of the unexpected finding that they can be used to generate immune responses in subjects who have preexisting immunity to Ad and can be used in vaccination regimens that include multiple rounds of immunization using the adenovirus vectors, regimens not possible using previous generation adenovirus vectors.

In some embodiments, a first or a second replication defective adenovirus infects dendritic cells in the human and wherein the infected dendritic cells present the antigen, thereby inducing the immune response.

Generally, generating an immune response comprises an induction of a humoral response and/or a cell-mediated response. It may desirable to increase an immune response against a target antigen of interest. Generating an immune response may involve a decrease in the activity and/or number of certain cells of the immune system or a decrease in the level and/or activity of certain cytokines or other effector molecules. Any suitable methods for detecting alterations in an immune response (e.g., cell numbers, cytokine expression, cell activity) can be used in some embodiments. Illustrative methods useful in this context include intracellular cytokine staining (ICS), ELISpot, proliferation assays, cytotoxic T-cell assays including chromium release or equivalent assays, and gene expression analysis using any number of polymerase chain reaction (PCR) or RT-PCR based assays.

Generating an immune response can comprise an increase in target antigen-specific CTL activity of between 1.5 and 5-fold in a subject administered the adenovirus vectors as described herein as compared to a control. In another embodiment, generating an immune response comprises an increase in target-specific CTL activity of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject administered the adenovirus vectors as compared to a control.

Generating an immune response can comprise an increase in target antigen-specific HTL activity, such as proliferation of helper T-cells, of between 1.5 and 5-fold in a subject administered the adenovirus vectors that comprise nucleic acid encoding the target antigen as compared to an appropriate control. In another embodiment, generating an immune response comprises an increase in target-specific HTL activity of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold as compared to a control. In this context, HTL activity may comprise an increase as described above, or decrease, in production of a particular cytokine, such as interferon-γ (IFN-γ), interleukin-1 (IL-1), IL-2, IL-3, IL-6, IL-7, IL-12, IL-15, tumor necrosis factor-α (TNF-α), granulocyte macrophage colony-stimulating factor (GM-CSF), granulocyte-colony stimulating factor (G-CSF), or other cytokines. In this regard, generating an immune response may comprise a shift from a Th2 type response to a Th1 type response or in certain embodiments a shift from a Th1 type response to a Th2 type response. In other embodiments, generating an immune response may comprise the stimulation of a predominantly Th1 or a Th2 type response.

Generating an immune response can comprise an increase in target-specific antibody production of between 1.5 and 5-fold in a subject administered the adenovirus vectors as compared to an appropriate control. In another embodiment, generating an immune response comprises an increase in target-specific antibody production of about 2, 2.5, 3, 3.5, 4, 4.5, 5, 5.5, 6, 6.5, 7, 7.5, 8, 8.5, 9, 9.5, 10, 10.5, 11, 11.5, 12, 12.5, 15, 16, 17, 18, 19, 20, or more fold in a subject administered the adenovirus vector as compared to a control.

In some embodiments, the recombinant viral vector affects overexpression of the antigen in transfected cells. In some embodiments, the recombinant viral induces a specific immune response against cells expressing the antigen in a human that is at least 2, 3, 4, 5, 6, 7, 8, 9, 10, 15, 20, or 25-fold over basal. In some embodiments, the human has an inverse Ad5 neutralizing antibody titer of greater than 50, 75, 100, 125, 150, 160, 175, 200, 225, 250, 275, or 300 prior to the administering step. In some embodiments, the human has an inverse Ad5 neutralizing antibody titer of greater than 250, 500, 750, 1000, 1500, 2000, 2500, 3000, 3500, 4000, 4500, or 4767. In some embodiments, the immune response is measured as antigen specific antibody response.

In some embodiments, the immune response is measured as antigen specific cell-mediated immunity (CMI). In some embodiments, the immune response is measured as antigen specific IFN-γ secretion. In some embodiments, the immune response is measured as antigen specific IL-2 secretion. In some embodiments, the immune response against the antigen is measured by ELISpot assay. In some embodiments, the antigen specific CMI is greater than 25, 50, 75, 100, 150, 200, 250, or 300 IFN-γ spot forming cells (SFC) per $10^6$ peripheral blood mononuclear cells (PBMC). In some embodiments, the immune response is measured by T-cell lysis of CAP-1 pulsed antigen-presenting cells, allogeneic antigen expressing cells from a tumor cell line or from an autologous tumor.

Thus, some embodiments provide methods for generating an immune response against a target antigen of interest comprising administering to the individual an adenovirus vector comprising: a) a replication defective adenovirus vector, wherein the adenovirus vector has a deletion in the E2b region, and b) a nucleic acid encoding the target antigen; and readministering the adenovirus vector at least once to the individual; thereby generating an immune response against the target antigen. In certain embodiments, the vector administered to the individual is not a gutted vector. In particular embodiments, the target antigen may be a wild-type protein, a fragment, a variant, or a variant fragment thereof. In some embodiments, the target antigen comprises CEA, a fragment, a variant, or a variant fragment thereof.

In a further embodiment, there is provided methods for generating an immune response against a target antigen in an individual, wherein the individual has preexisting immunity to Ad, by administering to the individual an adenovirus vector comprising: a) a replication defective adenovirus vector, wherein the adenovirus vector has a deletion in the E2b region, and b) a nucleic acid encoding the target antigen; and readministering the adenovirus vector at least once to the individual; thereby generating an immune response against the target antigen. In particular embodiments, the target antigen may be a wild-type protein, a fragment, a variant, or a variant fragment thereof. In some embodiments, the target antigen comprises CEA, a fragment, a variant, or a variant fragment thereof.

With regard to preexisting immunity to Ad, this can be determined using any suitable methods, such as antibody-based assays to test for the presence of Ad antibodies. Further, in certain embodiments, the methods include first determining that an individual has preexisting immunity to Ad then administering the E2b deleted adenovirus vectors as described herein.

One embodiment provides a method of generating an immune response against one or more target antigens in an individual comprising administering to the individual a first adenovirus vector comprising a replication defective adenovirus vector, wherein the adenovirus vector has a deletion in the E2b region, and a nucleic acid encoding at least one target antigen; administering to the individual a second adenovirus vector comprising a replication defective adenovirus vector, wherein the adenovirus vector has a deletion in the E2b region, and a nucleic acid encoding at least one target antigen, wherein the at least one target antigen of the second adenovirus vector is the same or different from the at least one target antigen of the first adenovirus vector. In particular embodiments, the target antigen may be a wild-type protein, a fragment, a variant, or a variant fragment thereof. In some embodiments, the target antigen comprises CEA, a fragment, a variant, or a variant fragment thereof.

Thus, multiple immunizations with the same E2b deleted adenovirus vector or multiple immunizations with different E2b deleted adenovirus vectors are contemplated in some embodiments. In each case, the adenovirus vectors may comprise nucleic acid sequences that encode one or more target antigens as described elsewhere herein. In certain embodiments, the methods comprise multiple immunizations with an E2b deleted adenovirus encoding one target antigen, and re-administration of the same adenovirus vector multiple times, thereby inducing an immune response against the target antigen. In some embodiments, the target antigen comprises CEA, a fragment, a variant, or a variant fragment thereof.

In a further embodiment, the methods comprise immunization with a first adenovirus vector that encodes one or more target antigens, and then administration with a second adenovirus vector that encodes one or more target antigens that may be the same or different from those antigens encoded by the first adenovirus vector. In this regard, one of the encoded target antigens may be different or all of the encoded antigens may be different, or some may be the same and some may be different. Further, in certain embodiments, the methods include administering the first adenovirus vector multiple times and administering the second adenovirus multiple times. In this regard, the methods comprise administering the first adenovirus vector 1, 2, 3, 4, 5, 6, 7, 8, 9, 10, 11, 12, 13, 14, 15, or more times and administering the second adenovirus vector 1, 2, 3, 4, 5, 6, 7, 8, 9, 10, 11, 12, 13, 14, 15, or more times. The order of administration may comprise administering the first adenovirus one or multiple times in a row followed by administering the second adenovirus vector one or multiple times in a row. In certain embodiments, the methods include alternating administration of the first and the second adenovirus vectors as one administration each, two administrations each, three administrations each, and so on. In certain embodiments, the first and the second adenovirus vectors are administered simultaneously. In other embodiments, the first and the second adenovirus vectors are administered sequentially. In some embodiments, the target antigen comprises CEA, a fragment, a variant, or a variant fragment thereof.

As would be readily understood by the skilled artisan, more than two adenovirus vectors may be used in the methods. Three, 4, 5, 6, 7, 8, 9, 10, or more different adenovirus vectors may be used in the methods as described herein. In certain embodiments, the methods comprise administering more than one E2b deleted adenovirus vector at a time. In this regard, immune responses against multiple target antigens of interest can be generated by administering multiple different adenovirus vectors simultaneously, each comprising nucleic acid sequences encoding one or more target antigens.

The adenovirus vectors can be used to generate an immune response against a cancer, such as carcinomas or sarcomas (e.g., solid tumors, lymphomas and leukemia). The adenovirus vectors can be used to generate an immune response against an infectious disease, such as a cancer, such as any CEA-expressing cancer, Brachyury-expressing cancer, MUC1-expessing cancer, an epithelial cancer, a neurologic cancer, melanoma, non-Hodgkin's lymphoma, Hodgkin's disease, leukemia, plasmocytomas, adenomas, gliomas, thymomas, breast cancer, prostate cancer, colorectal cancer, kidney cancer, renal cell carcinoma, uterine cancer, pancreatic cancer, esophageal cancer, lung cancer, ovarian cancer, cervical cancer, testicular cancer, gastric cancer, multiple myeloma, hepatoma, acute lymphoblastic leukemia (ALL), acute myelogenous leukemia (AML), chronic myelogenous leukemia (CML), and chronic lymphocytic leukemia (CLL), gastrointestinal cancer, or other cancers.

In one aspect, a method of selecting a human for administration of the compositions is provided comprising: determining a HLA subtype of the human; and administering the composition to the human, if the HLA subtype is determined to be one of a preselected subgroup of HLA subtypes. In some embodiments, the preselected subgroup of HLA subtypes comprises one or more of HLA-A2, HLA-A3, and HLA-A24.

In some embodiments, the human is not concurrently being treated by any one of steroids, corticosteroids, and immunosuppressive agents. In some embodiments, the human does not have an autoimmune disease. In some embodiments, the human does not have inflammatory bowel disease, systemic lupus erythematosus, ankylosing spondylitis, scleroderma, multiple sclerosis, viral hepatitis, or HIV. In some embodiments, the human has or may have in the future an infectious disease. In some embodiments, the human has autoimmune related thyroid disease or vitiligo. In some embodiments, the human has or may have in the future a proliferative disease cancer. In some embodiments, the human has colorectal adenocarcinoma, metastatic colorectal cancer, advanced CEA expressing colorectal cancer, advanced MUC1-C, Brachyury, or CEA expressing colorectal cancer, breast cancer, lung cancer, bladder cancer, or pancreas cancer. In some embodiments, the human has at least 1, 2, or 3 sites of metastatic disease. In some embodiments, the human comprises cells overexpressing CEA. In some embodiments, the cells overexpressing CEA, overexpress the CEA by at least 2, 3, 4, 5, 6, 7, 8, 9, or 10 times over a baseline CEA expression in a non-cancer cell. In some embodiments, the cells overexpressing CEA comprise cancer cells. In some embodiments, the human comprises cells overexpressing MUC1-C, Brachyury, or CEA. In some embodiments, the cells overexpressing MUC1-C, Brachyury, or CEA, overexpress the MUC1-C, Brachyury, or CEA by at least 2, 3, 4, 5, 6, 7, 8, 9, or 10 times over a baseline MUC1-C, Brachyury, or CEA expression in a non-cancer cell. In some embodiments, the cells overexpressing MUC1-C, Brachyury, or CEA comprise cancer cells. In some embodiments, the subject has a diagnosed disease predisposition. In some embodiments, the subject has a stable disease. In some embodiments, the subject has a genetic predisposition for a disease. In some embodiments, the disease is a cancer. In some embodiments, the cancer is selected from the group consisting of prostate cancer, colon cancer, breast cancer, or gastric cancer. In some embodiments, the cancer is prostate cancer.

Some embodiments provide combination multi-targeted vaccines, immunotherapies and methods for enhanced therapeutic response to complex diseases such as infectious diseases and cancers. For example, in some embodiments, a subject can be administered a combination Ad5 vaccine as apart of the immunization strategy during treatment. For example, in some embodiments, a first and second replication defective adenovirus vector can be administered, each encoding for a different antigen. In some embodiments, the first or the second replication defective adenovirus vector comprises a sequence with at least 80% sequence identity to SEQ ID NO: 2. In some embodiments, the first or the second replication defective adenovirus vector comprises a region with at least 80% sequence identity to a region in SEQ ID NO: 2 selected from 26048-26177, 26063-26141, 1-103, 54-103, 32214-32315, and 32214-32262. In some embodiments, the first or the second replication defective adenovirus vector comprises a region with at least 80% sequence identity to a region in SEQ ID NO: 2 between positions 1057 and 3165. In some embodiments, the first or second replication defective adenovirus vector comprises a sequence encoding a MUC1-C, Brachyury, or CEA antigen; wherein the MUC1-C antigen is encoded by a sequence with at least 80% sequence identity to SEQ ID NO: 5, SEQ ID NO: 6, or SEQ ID NO: 101; wherein the Brachyury antigen is encoded by a sequence with at least 80% sequence identity to SEQ ID NO: 9, SEQ ID NO: 10, or SEQ ID NO: 102; wherein the CEA antigen is encoded by a sequence with at least 80% sequence identity to SEQ ID NO: 1, SEQ ID NO: 2, or SEQ ID NO: 100.

Methods are also provided for treating or ameliorating the symptoms of any of the infectious diseases or cancers as described herein. The methods of treatment comprise administering the adenovirus vectors one or more times to individuals suffering from or at risk from suffering from an infectious disease or cancer as described herein. As such, some embodiments provide methods for vaccinating against infectious diseases or cancers in individuals who are at risk of developing such a disease. Individuals at risk may be individuals who may be exposed to an infectious agent at some time or have been previously exposed but do not yet have symptoms of infection or individuals having a genetic predisposition to developing a cancer or being particularly susceptible to an infectious agent. Individuals suffering from an infectious disease or cancer described herein may be determined to express and/or present a target antigen, which may be use to guide the therapies herein. For example, an example can be found to express and/or present a target antigen and an adenovirus vector encoding the target antigen, a variant, a fragment or a variant fragment thereof may be administered subsequently.

Some embodiments contemplate the use of adenovirus vectors for the in vivo delivery of nucleic acids encoding a target antigen, or a fragment, a variant, or a variant fragment thereof. Once injected into a subject, the nucleic acid sequence is expressed resulting in an immune response against the antigen encoded by the sequence. The adenovirus vector vaccine can be administered in an "effective amount", that is, an amount of adenovirus vector that is effective in a selected route or routes of administration to elicit an immune response as described elsewhere herein. An effective amount can induce an immune response effective to facilitate protection or treatment of the host against the target infectious agent or cancer. The amount of vector in each vaccine dose is selected as an amount which induces an immune, immunoprotective or other immunotherapeutic response without significant adverse effects generally associated with typical vaccines. Once vaccinated, subjects may be monitored to determine the efficacy of the vaccine treatment. Monitoring the efficacy of vaccination may be performed by any method known to a person of ordinary skill in the art. In some embodiments, blood or fluid samples may be assayed to detect levels of antibodies. In other embodiments, ELISpot assays may be performed to detect a cell-mediated immune response from circulating blood cells or from lymphoid tissue cells.

Routes and frequency of administration of the therapeutic compositions described herein, as well as dosage, may vary from individual to individual, and from disease to disease, and may be readily established using standard techniques. In general, the pharmaceutical compositions and vaccines may be administered by injection (e.g., intracutaneous, intramuscular, intravenous or subcutaneous), intranasally (e.g., by aspiration), in pill form (e.g., swallowing, suppository for vaginal or rectal delivery). In certain embodiments, between 1 and 10 doses may be administered over a 52-week period. In certain embodiments, 6 doses are administered, at intervals of 1 month, and further booster vaccinations may be given periodically thereafter. Alternate protocols may be appropriate for individual patients. As such, 1, 2, 3, 4, 5, 6, 7, 8, 9, 10, 11, 12, 13, 14, 15, 16, 17, 18, 19, 20, or more doses may be administered over a 1 year period or over shorter or longer periods, such as over 35, 40, 45, 50, 55, 60, 65, 70, 75, 80, 85, 90, 95, or 100 week periods. Doses may be administered at 1, 2, 3, 4, 5, or 6 week intervals or longer intervals.

A vaccine can be infused over a period of less than about 4 hours, and more preferably, over a period of less than about 3 hours. For example, the first 25-50 mg could be infused within 30 minutes, preferably within 15 min, and the remainder infused over the next 2-3 hrs. More generally, the dosage of an administered vaccine construct may be administered as one dosage every 2 or 3 weeks, repeated for a total of at least 3 dosages. Or, the construct may be administered twice per week for 4-6 weeks. The dosing schedule can optionally be repeated at other intervals and dosage may be given through various parenteral routes, with appropriate adjustment of the dose and schedule. Compositions can be administered to a patient in conjunction with (e.g., before, simultaneously, or following) any number of relevant treatment modalities.

A suitable dose is an amount of an adenovirus vector that, when administered as described above, is capable of promoting a target antigen immune response as described elsewhere herein. In certain embodiments, the immune response is at least 10-50% above the basal (i.e., untreated)

level. In certain embodiments, the immune response is at least 2, 3, 4, 5, 6, 7, 8, 9, 10, 12, 15, 20, 25, 30, 35, 40, 45, 50, 55, 60, 65, 70, 75, 80, 85, 90, 100, 110, 125, 150, 200, 250, 300, 400, 500, or more over the basal level. Such response can be monitored by measuring the target antigen(s) antibodies in a patient or by vaccine-dependent generation of cytolytic effector cells capable of killing patient tumor or infected cells in vitro, or other methods known in the art for monitoring immune responses. Such vaccines should also be capable of causing an immune response that leads to an improved clinical outcome of the disease in question in vaccinated patients as compared to non-vaccinated patients. In some embodiments, the improved clinical outcome comprises treating disease, reducing the symptoms of a disease, changing the progression of a disease, or extending life.

In general, an appropriate dosage and treatment regimen provides the adenovirus vectors in an amount sufficient to provide therapeutic and/or prophylactic benefit. Such a response can be monitored by establishing an improved clinical outcome for the particular disease being treated in treated patients as compared to non-treated patients. The monitoring data can be evaluated over time. The progression of a disease over time can be altered. Such improvements in clinical outcome would be readily recognized by a treating physician. Increases in preexisting immune responses to a target protein can generally correlate with an improved clinical outcome. Such immune responses may generally be evaluated using standard proliferation, cytotoxicity or cytokine assays, which may be performed using samples obtained from a patient before and after treatment.

While one advantage is the capability to administer multiple vaccinations with the same or different adenovirus vectors, particularly in individuals with preexisting immunity to Ad, the adenoviral vaccines may also be administered as part of a prime and boost regimen. A mixed modality priming and booster inoculation scheme may result in an enhanced immune response. Thus, one aspect is a method of priming a subject with a plasmid vaccine, such as a plasmid vector comprising a target antigen of interest, by administering the plasmid vaccine at least one time, allowing a predetermined length of time to pass, and then boosting by administering the adenovirus vector. Multiple primings, e.g., 1-4, may be employed, although more may be used. The length of time between priming and boost may typically vary from about four months to a year, but other time frames may be used. In certain embodiments, subjects may be primed 1, 2, 3, 4, 5, 6, 7, 8, 9, 10, or more times with plasmid vaccines, and then boosted 4 months later with the adenovirus vector.

Any of the compositions provided herein may be administered to an individual. "Individual" may be used interchangeably with "subject" or "patient." An individual may be a mammal, for example a human or animal such as a non-human primate, a rodent, a rabbit, a rat, a mouse, a horse, a donkey, a goat, a cat, a dog, a cow, a pig, or a sheep. In embodiments, the individual is a human. In embodiments, the individual is a fetus, an embryo, or a child. In some cases, the compositions provided herein are administered to a cell ex vivo. In some cases, the compositions provided herein are administered to an individual as a method of treating a disease or disorder. In some embodiments, the individual has a genetic disease. In some cases, the individual is at risk of having the disease, such as any of the diseases described herein. In some embodiments, the individual is at increased risk of having a disease or disorder caused by insufficient amount of a protein or insufficient activity of a protein. If an individual is "at an increased risk" of having a disease or disorder, the method involves preventative or prophylactic treatment. For example, an individual can be at an increased risk of having such a disease or disorder because of family history of the disease. Typically, individuals at an increased risk of having such a disease or disorder benefit from prophylactic treatment (e.g., by preventing or delaying the onset or progression of the disease or disorder).

In some cases, a subject does not have a disease. In some cases, the treatment is administered before onset of a disease. A subject may have undetected disease. A subject may have a low disease burden. A subject may also have a high disease burden. In certain cases, a subject may be administered a treatment as described herein according to a grading scale. A grading scale can be a Gleason classification. A Gleason classification reflects how different tumor tissue is from normal prostate tissue. It uses a scale from 1 to 5. A physician gives a cancer a number based on the patterns and growth of the cancer cells. The lower the number, the more normal the cancer cells look and the lower the grade. The higher the number, the less normal the cancer cells look and the higher the grade. In certain cases, a treatment may be administered to a patient with a low Gleason score. Particularly, a patient with a Gleason score of 3 or below may be administered a treatment as described herein. In some embodiments, the subject has a Gleason score of 6 or less. In some embodiments, the subject has a Gleason score greater than 6.

Various embodiments relate to compositions and methods for raising an immune response against CEA antigens in selected patient populations. Accordingly, methods and compositions may target patients with a cancer including, but not limited to, carcinomas or sarcomas such as neurologic cancers, melanoma, non-Hodgkin's lymphoma, Hodgkin's disease, leukemia, plasmocytomas, adenomas, gliomas, thymomas, breast cancer, gastrointestinal cancer, prostate cancer, colorectal cancer, kidney cancer, renal cell carcinoma, uterine cancer, pancreatic cancer, esophageal cancer, lung cancer, ovarian cancer, cervical cancer, testicular cancer, gastric cancer, multiple myeloma, hepatoma, acute lymphoblastic leukemia (ALL), acute myelogenous leukemia (AML), chronic myelogenous leukemia (CML), and chronic lymphocytic leukemia (CLL), or other cancers can be targeted for therapy. In some cases, the targeted patient population may be limited to individuals having colorectal adenocarcinoma, metastatic colorectal cancer, advanced CEA expressing colorectal cancer, head and neck cancer, liver cancer, breast cancer, lung cancer, bladder cancer, or pancreas cancer. A histologically confirmed diagnosis of a selected cancer, for example colorectal adenocarcinoma, may be used. A particular disease stage or progression may be selected, for example, patients with one or more of a metastatic, recurrent, stage III, or stage IV cancer may be selected for therapy with the methods and compositions. In some embodiments, patients may be required to have received and, optionally, progressed through other therapies including but not limited to fluoropyrimidine, irinotecan, oxaliplatin, bevacizumab, cetuximab, or panitumumab containing therapies. In some cases, individual's refusal to accept such therapies may allow the patient to be included in a therapy eligible pool with methods and compositions. In some embodiments, individuals to receive therapy using the methods and compositions may be required to have an estimated life expectancy of at least, 1, 2, 3, 4, 5, 6, 7, 8, 9, 10, 11, 12, 14, 15, 18, 21, or 24 months. The patient pool to receive a therapy using the methods and compositions may be limited by age. For example, individuals who are older than 2, 3, 4, 5, 6, 7, 8, 9, 10, 11, 12, 13, 14, 15, 16, 17, 18, 19, 20, 21, 25, 30, 35, 40, 50, 60, or more years old can be eligible for therapy with methods and compositions. For another example, individuals who are younger than 75, 70, 65, 60, 55, 50, 40, 35, 30, 25, 20, or fewer years old can be eligible for therapy with methods and compositions.

In some embodiments, patients receiving therapy using the methods and compositions are limited to individuals with adequate hematologic function, for example with one or more of a WBC count of at least 1000, 1500, 2000, 2500, 3000, 3500, 4000, 4500, 5000 or more per microliter, a hemoglobin level of at least 5, 6, 7, 8, 9, 10, 11, 12, 13, 14 or higher g/dL, a platelet count of at least 50,000; 60,000; 70,000; 75,000; 90,000; 100,000; 110,000; 120,000; 130,000; 140,000; 150,000 or more per microliter; with a PT-INR value of less than or equal to 0.8, 1.0, 1.2, 1.3, 1.4, 1.5, 1.6, 1.8, 2.0, 2.5, 3.0, or higher, a PTT value of less than or equal to 1.2, 1.4, 1.5, 1.6, 1.8, 2.0×ULN or more. In various embodiments, hematologic function indicator limits are chosen differently for individuals in different gender and age groups, for example 0-5, 5-10, 10-15, 15-18, 18-21, 21-30, 30-40, 40-50, 50-60, 60-70, 70-80, or older than 80.

In some embodiments, patients receiving therapy using the methods and compositions are limited to individuals with adequate renal and/or hepatic function, for example with one or more of a serum creatinine level of less than or equal to 0.8, 0.9, 1.0, 1.1, 1.2, 1.3, 1.4, 1.5, 1.6, 1.7, 1.8, 1.9, 2.0, 2.1, 2.2 mg/dL or more, a bilirubin level of 0.8, 0.9, 1.0, 1.1, 1.2, 1.3, 1.4, 1.5, 1.6, 1.7, 1.8, 1.9, 2.0, 2.1, 2.2 mg/dL or more, while allowing a higher limit for Gilbert's syndrome, for example, less than or equal to 1.5, 1.6, 1.8, 1.9, 2.0, 2.1, 2.2, 2.3, or 2.4 mg/dL, an ALT and AST value of less than or equal to less than or equal to 1.5, 2.0, 2.5, 3.0× upper limit of normal (ULN) or more. In various embodiments, renal or hepatic function indicator limits are chosen differently for individuals in different gender and age groups, for example 0-5, 5-10, 10-15, 15-18, 18-21, 21-30, 30-40, 40-50, 50-60, 60-70, 70-80, or older than 80.

In some embodiments, the K-ras mutation status of individuals who are candidates for a therapy using the methods and compositions as described herein can be determined. Individuals with a preselected K-ras mutational status can be included in an eligible patient pool for therapies using the methods and compositions as described herein.

In various embodiments, patients receiving therapy using the methods and compositions as described herein are limited to individuals without concurrent cytotoxic chemotherapy or radiation therapy, a history of, or current, brain metastases, a history of autoimmune disease, such as but not restricted to, inflammatory bowel disease, systemic lupus erythematosus, ankylosing spondylitis, scleroderma, multiple sclerosis, thyroid disease and vitiligo, serious intercurrent chronic or acute illness, such as cardiac disease (NYHA class III or IV), or hepatic disease, a medical or psychological impediment to probable compliance with the protocol, concurrent (or within the last 5 years) second malignancy other than non-melanoma skin cancer, cervical carcinoma in situ, controlled superficial bladder cancer, or other carcinoma in situ that has been treated, an active acute or chronic infection including: a urinary tract infection, HIV (e.g., as determined by ELISA and confirmed by Western Blot), and chronic hepatitis, or concurrent steroid therapy (or other immuno-suppressives, such as azathioprine or cyclosporin A). In some cases, patients with at least 3, 4, 5, 6, 7, 8, 9, or 10 weeks of discontinuation of any steroid therapy (except that used as pre-medication for chemotherapy or contrast-enhanced studies) may be included in a pool of eligible individuals for therapy using the methods and compositions as described herein.

In some embodiments, patients receiving therapy using the methods and compositions as described herein include individuals with thyroid disease and vitiligo.

In various embodiments, samples, for example serum or urine samples, from the individuals or candidate individuals for a therapy using the methods and compositions as described herein may be collected. Samples may be collected before, during, and/or after the therapy for example, within 2, 4, 6, 8, 10 weeks prior to the start of the therapy, within 1 week, 10 day, 2 weeks, 3 weeks, 4 weeks, 6 weeks, 8 weeks, or 12 weeks from the start of the therapy, within 2, 4, 6, 8, 10 weeks prior to the start of the therapy, within 1 week, 10 day, 2 weeks, 3 weeks, 4 weeks, 6 weeks, 8 weeks, 9 weeks, or 12 weeks from the start of the therapy, in 1 week, 10 day, 2 weeks, 3 weeks, 4 weeks, 6 weeks, 8 weeks, 9 weeks, or 12 weeks intervals during the therapy, in 1 month, 3 month, 6 month, 1 year, 2 year intervals after the therapy, within 1 month, 3 months, 6 months, 1 year, 2 years, or longer after the therapy, for a duration of 6 months, 1, 2, 3, 4, 5, 6, 7, 8, 9, 10 years, or longer. The samples may be tested for any of the hematologic, renal, or hepatic function indicators described herein as well as suitable others known in the art, for example a ß-HCG for women with childbearing potential. In that regard, hematologic and biochemical tests, including cell blood counts with differential, PT, INR and PTT, tests measuring Na, K, Cl, $CO_2$, BUN, creatinine, Ca, total protein, albumin, total bilirubin, alkaline phosphatase, AST, ALT and glucose may be used in some embodiments. In some embodiments, the presence or the amount of HIV antibody, Hepatitis BsAg, or Hepatitis C antibody are determined in a sample from individuals or candidate individuals for a therapy using the methods and compositions as described herein. Biological markers, such as antibodies to CEA or the neutralizing antibodies to Ad5 vector can be tested in a sample, such as serum, from individuals or candidate individuals for a therapy using the methods and compositions as described herein. In some cases, one or more samples, such as a blood sample can be collected and archived from an individuals or candidate individuals for a therapy using the methods and compositions as described herein. Collected samples can be assayed for immunologic evaluation. Individuals or candidate individuals for a therapy using the methods and compositions as described herein can be evaluated in imaging studies, for example using CT scans or MRI of the chest, abdomen, or pelvis. Imaging studies can be performed before, during, or after therapy using the methods and compositions as described herein, during, and/or after the therapy, for example, within 2, 4, 6, 8, 10 weeks prior to the start of the therapy, within 1 week, 10 day, 2 weeks, 3 weeks, 4 weeks, 6 weeks, 8 weeks, or 12 weeks from the start of the therapy, within 2, 4, 6, 8, 10 weeks prior to the start of the therapy, within 1 week, 10 day, 2 weeks, 3 weeks, 4 weeks, 6 weeks, 8 weeks, 9 weeks, or 12 weeks from the start of the therapy, in 1 week, 10 day, 2 week, 3 week, 4 week, 6 week, 8 week, 9 week, or 12 week intervals during the therapy, in 1 month, 3 month, 6 month, 1 year, 2 year intervals after the therapy, within 1 month, 3 months, 6 months, 1 year, 2 years, or longer after the therapy, for a duration of 6 months, 1, 2, 3, 4, 5, 6, 7, 8, 9, 10 years, or longer.

With regard to treatment of a condition with Ad5 vectors encoding for CEA, MUC1-C, and Brachyury, in one aspect, a method of generating an immune response in a human to each antigen, or any combination thereof is provided comprising administering to the human the composition. In some embodiments, the administering step is repeated at least once. In some embodiments, the administering step is repeated after about 2, 3, 4, 5, or 6 weeks following a previous administering step. In some embodiments, the administering step is repeated after about 2, 3, 4, 5, or 6 months following a previous administering step. In some embodiments, the administering step is repeated twice.

In one aspect, a method of treatment is provided comprising: selecting a first phase of treatment and a second phase of treatment; during the first phase, administering to a human a total of 3 times, in about 3 week intervals, a first composition comprising a first replication defective adenovirus vector encoding a MUC1-C antigen; and during the second phase, administering to the human a total of 3 times, in about 3 month intervals, a second composition comprising a second replication defective adenovirus vector encoding an antigen that induces an immune response in a human against cells expressing the MUC1-C antigen.

In one aspect, a method of treatment is provided comprising: selecting a first phase and a second phase of treatment; during the first phase, administering to a human a total of 3 times, in about 3 week intervals, a first composition comprising a first replication defective adenovirus vector encoding a Brachyury antigen; and during the second phase, administering to the human a total of 3 times, in about 3 month intervals, a second composition comprising a second replication defective adenovirus vector encoding an antigen that induces an immune response in a human against cells expressing the Brachyury antigen.

In one aspect, a method of treatment is provided comprising: selecting a first phase of treatment and a second phase of treatment; during the first phase, administering to a human a total of 3 times, in about 3 week intervals, a first composition comprising a first replication defective adenovirus vector encoding at least two antigens selected from the group consisting of a MUC1-C antigen, a Brachyury antigen, and a CEA antigen; and during the second phase, administering to the human a total of 3 times, in about 3 month intervals, a second composition comprising a second replication defective adenovirus vector encoding an antigen that induces an immune response in a human against cells expressing the at least two antigens. In some embodiments, the second phase starts about 3 months after the end of the first phase.

In one aspect, a method of treatment is provided comprising: selecting a first phase of treatment and a second phase of treatment; during the first phase, administering to a human, a total of n times, a first composition comprising a first replication defective adenovirus vector encoding a Brachyury antigen; during the second phase, administering the human, a total of m times, a second composition comprising a second replication defective adenovirus vector encoding an antigen that induces an immune response in a human against cells expressing the Brachyury antigen.

In one aspect, a method of treatment is provided comprising: selecting a first phase of treatment and a second phase of treatment; during the first phase, administering to a human, a total of n times, a first composition comprising a first replication defective adenovirus vector encoding a MUC1-C antigen; during the second phase, administering the human, a total of m times, a second composition comprising a second replication defective adenovirus vector encoding an antigen that induces an immune response in a human against cells expressing the MUC1-C antigen.

In one aspect, a method of treatment is provided comprising: selecting a first phase of treatment and a second phase of treatment; during the first phase, administering to a human, a total of n times, a first composition comprising a first replication defective adenovirus vector encoding at least two antigens selected from the group consisting of a MUC1-C antigen, a Brachyury antigen, and a CEA antigen; during the second phase, administering the human, a total of m times, a second composition comprising a second replication defective adenovirus vector encoding the at least two antigens that induces an immune response in a human against cells expressing the at least two antigens. In some embodiments, n is greater than 1. In some embodiments, n is 3. In some embodiments, m is greater than 1. In some embodiments, m is 3. In some embodiments, the first phase is at least 2, 3, 4, 5, 6, 7, or 8 weeks. In some embodiments, the second phase is at least 2, 3, 4, 5, 6, 7, or 8 months. In some embodiments, the second phase starts 3-16 weeks after first phase ends. In some embodiments, in the first phase two administrations of the replication defective adenovirus are at least 18 days apart. In some embodiments, in the first phase two administrations of the replication defective adenovirus are about 21 days apart. In some embodiments, in the first phase two administrations of the replication defective adenovirus are at most 24 days apart. In some embodiments, in the second phase two administrations of the replication defective adenovirus are at least 10 weeks apart. In some embodiments, in the second phase two administrations of the replication defective adenovirus are about 13 weeks apart. In some embodiments, in the second phase two administrations of the replication defective adenovirus are at most 16 weeks apart. In some embodiments, the method further comprises administering a molecular composition comprising an immune pathway checkpoint modulator.

In one aspect, a method of treatment is provided comprising: selecting a first phase of treatment and a second phase of treatment; during the first phase, administering to a human, a total of n times, a first composition comprising a first replication defective adenovirus vector encoding an antigen that induces an immune response in a human against cells expressing a MUC1-C, Brachyury, or CEA antigen; and during the second phase, administering the human, a total of m times, a second composition comprising a second replication defective adenovirus vector encoding an antigen that is capable of inducing an immune response directed towards cells expressing MUC1-C, Brachyury, or CEA antigen in a human; wherein a molecular composition comprising and an immune pathway checkpoint modulator is administered during the first phase, the second phase, or both.

In one aspect, a method of treating a subject in need thereof is provided, comprising administering to the subject: (a) a recombinant replication deficient adenovirus vector encoding (i) a MUC1-C antigen, (ii) a Brachyury antigen, or (iii) at least two antigens selected from the group consisting of a MUC1-C antigen, a Brachyury antigen, and a CEA antigen; and (b) a molecular composition comprising an immune pathway checkpoint modulator; thereby generating an immune response in the subject. In some embodiments, (a) and (b) are administered in series. In some embodiments, (a) and (b) are administered at the same time. In some embodiments, (a) and (b) are administered a month apart.

Dosages and Administration of Ad5 Vaccines

Compositions and methods as described herein contemplate various dosage and administration regimens during therapy. Patients may receive one or more replication defective adenovirus or adenovirus vector, for example Ad5 [E1-, E2B-]-CEA(6D), that is capable of raising an immune response in an individual against a target antigen described herein. Patients can also receive one or more replication defective adenovirus or adenovirus vector, for example Ad5 [E1-, E2B-]-CEA(6D), Ad5 [E1-, E2b-]-MUC1, Ad5 [E1-, E2b-]-MUC1c, Ad5 [E1-, E2b-]-MUC1n, or Ad5 [E1-, E2b-]-T (i.e., Ad5 [E1-, E2b-]-Brachyury) that is capable of raising an immune response in an individual against a target antigen described herein. In various embodiments, the replication defective adenovirus is administered at a dose that suitable for effecting such immune response. In some cases, the replication defective adenovirus is administered at a dose that is greater than or equal to $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $1.5\times10^{12}$, $2\times10^{12}$, $3\times10^{12}$, $4\times10^{12}$, $5\times10^{12}$ or more virus particles (VP) per immunization. In some cases, the replication defective adenovirus is administered at a dose that is less than or equal to $1\times10^9$ $2\times10^9$ $3\times10^9$ $4\times10^9$ $5\times10^9$ $6\times10^9$ $7\times10^9$ $8\times10^9$ $9\times10^9$ $1\times10^{10}$ $2\times10^{10}$ $3\times10^{10}$ $4\times10^{10}$ $5\times10^{10}$ $6\times10^{10}$ $7\times10^{10}$ $8\times10^{10}$ $9\times10^{10}$ $1\times10^{11}$ $2\times10^{11}$ $3\times10^{11}$ $4\times10^{11}$ $5\times10^{11}$ $6\times10^{11}$, $7\times10^{11}$, $8\times10^{11}$, $9\times10^{11}$, $1\times10^{12}$, $1.5\times10^{12}$, $2\times10^{12}$, $3\times10^{12}$, $4\times10^{12}$, $5\times10^{12}$, or more virus particles per immunization. In some embodiments, the replication defective adenovirus is administered at a dose of $1\times10^9$-$5\times10^{12}$ virus particles per immunization. In some embodiments, the composition comprises at least $1.0\times10^{11}$, $2.0\times10^{11}$, $3.0\times10^{11}$, $3.5\times10^{11}$, $4.0\times10^{11}$, $4.5\times10^{11}$, $4.8\times10^{11}$, $4.9\times10^{11}$, $4.95\times10^{11}$, or $4.99\times10^{11}$ virus particles comprising the recombinant nucleic acid vector. In some embodiments, the composition comprises at most $7.0\times10^{11}$, $6.5\times10^{11}$, $6.0\times10^{11}$, $5.5\times10^{11}$, $5.2\times10^{11}$, $5.1\times10^{11}$, $5.05\times10^{11}$, or $5.01\times10^{11}$ virus particles. In some embodiments, the composition comprises $1.0\times10^{11}$-$7.0\times10^{11}$ or $1.0$-$5.5\times10^{11}$ virus particles. In some embodiments, the composition comprises $4.5\times10^{11}$-$5.5\times10^{11}$ virus particles. In some embodiments, the composition comprises $4.8\times10^{11}$-$5.2\times10^{11}$ virus particles. In some embodiments, the composition comprises $4.9\times10^{11}$-$5.1\times10^{11}$ virus particles. In some embodiments, the composition comprises $4.95\times10^{11}$-$5.05\times10^{11}$ virus particles. In some embodiments, the composition comprises $4.99\times10^{11}$-$5.01\times10^{11}$ virus particles.

In various embodiments, a desired dose described herein is administered in a suitable volume of formulation buffer, for example a volume of about 0.1-10 mL, 0.2-8 mL, 0.3-7 mL, 0.4-6 mL, 0.5-5 mL, 0.6-4 mL, 0.7-3 mL, 0.8-2 mL, 0.9-1.5 mL, 0.95-1.2 mL, or 1.0-1.1 mL. Those of skill in the art appreciate that the volume may fall within any range bounded by any of these values (e.g., about 0.5 mL to about 1.1 mL). Administration of virus particles can be through a variety of suitable paths for delivery, for example it can be by injection (e.g., intradermally, intracutaneously, intramuscularly, intravenously or subcutaneously), intranasally (e.g., by aspiration), in pill form (e.g. swallowing, suppository for vaginal or rectal delivery. In some embodiments, a subcutaneous delivery may be preferred and can offer greater access to dendritic cells.

Administration of virus particles to an individual may be repeated. Repeated deliveries of virus particles may follow a schedule or alternatively, may be performed on an as needed basis. For example, an individual's immunity against a target antigen, for example CEA, may be tested and replenished as necessary with additional deliveries. In some embodiments, schedules for delivery include administrations of virus particles at regular intervals. Joint delivery regimens may be designed comprising one or more of a period with a schedule and/or a period of need based administration assessed prior to administration. For example, a therapy regimen may include an administration, such as subcutaneous administration once every three weeks then another immunotherapy treatment every three months until removed from therapy for any reason including death. Another example regimen comprises three administrations every three weeks then another set of three immunotherapy treatments every three months. Another example regimen comprises a first period with a first number of administrations at a first frequency, a second period with a second number of administrations at a second frequency, a third period with a third number of administrations at a third frequency, etc., and optionally one or more periods with undetermined number of administrations on an as needed basis. The number of administrations in each period can be independently selected and can for example be 1, 2, 3, 4, 5, 6, 7, 8, 9, 10, 11, 12, 13, 14, 15, 16, 17, 18, 19, 20, or more. The frequency of the administration in each period can also be independently selected, can for example be about every day, every other day, every third day, twice a week, once a week, once every other week, every three weeks, every month, every six weeks, every other month, every third month, every fourth month, every fifth month, every sixth month, once a year, etc. The therapy can take a total period of up to 1, 2, 3, 4, 5, 6, 7, 8, 9, 10, 11, 12, 13, 14, 15, 16, 17, 18, 19, 20, 21, 22, 23, 24, 30, 36 months, or more. The scheduled interval between immunizations may be modified so that the interval between immunizations is revised by up to a fifth, a fourth, a third, or half of the interval. For example, for a 3-week interval schedule, an immunization may be repeated between 20 and 28 days (3 weeks-1 day to 3 weeks+7 days). For the first 3 immunizations, if the second and/or third immunization is delayed, the subsequent immunizations may be shifted allowing a minimum amount of buffer between immunizations. For example, for a three week interval schedule, if an immunization is delayed, the subsequent immunization may be scheduled to occur no earlier than 17, 18, 19, or 20 days after the previous immunization.

Compositions, such as Ad5 [E1-, E2B-]-CEA(6D) virus particles, can be provided in various states, for example, at room temperature, on ice, or frozen. Compositions may be provided in a container of a suitable size, for example a vial of 2 mL vial. In one embodiment, a 2-ml vial with 1.0 mL of extractable vaccine contains $5\times10^{11}$ total virus particles/ mL. Storage conditions including temperature and humidity may vary. For example, compositions for use in therapy may be stored at room temperature, 4° C., −20° C., or lower.

In various embodiments, general evaluations are performed on the individuals receiving treatment according to the methods and compositions as described herein. One or more of any tests may be performed as needed or in a scheduled basis, such as on weeks 0, 3, 6, etc. A different set of tests may be performed concurrent with immunization vs. at time points without immunization.

General evaluations may include one or more of medical history, ECOG Performance Score, Karnofsky performance status, and complete physical examination with weight by the attending physician. Any other treatments, medications, biologics, or blood products that the patient is receiving or has received since the last visit may be recorded. Patients may be followed at the clinic for a suitable period, for example approximately 30 minutes, following receipt of vaccine to monitor for any adverse reactions. Local and systemic reactogenicity after each dose of vaccine will may be assessed daily for a selected time, for example for 3 days (on the day of immunization and 2 days thereafter). Diary cards may be used to report symptoms and a ruler may be used to measure local reactogenicity. Immunization injection sites may be assessed. CT scans or MM of the chest, abdomen, and pelvis may be performed.

In various embodiments, hematological and biochemical evaluations are performed on the individuals receiving treatment according to the methods and compositions as described herein. One or more of any tests may be performed as needed or in a scheduled basis, such as on weeks 0, 3, 6, etc. A different set of tests may be performed concurrent with immunization vs. at time points without immunization. Hematological and biochemical evaluations may include one or more of blood test for chemistry and hematology, CBC with differential, Na, K, Cl, $CO_2$, BUN, creatinine, Ca, total protein, albumin, total bilirubin, alkaline phosphatase, AST, ALT, glucose, and ANA In various embodiments, biological markers are evaluated on individuals receiving treatment according to the methods and compositions as described herein. One or more of any tests may be performed as needed or in a scheduled basis, such as on weeks 0, 3, 6, etc. A different set of tests may be performed concurrent with immunization vs. at time points without immunization.

Biological marker evaluations may include one or more of measuring antibodies to CEA or the Ad5 vector, from a serum sample of adequate volume, for example about 5 ml Biomarkers (e.g., CEA or CA15-3) may be reviewed if determined and available.

In various embodiments, an immunological assessment is performed on individuals receiving treatment according to the methods and compositions as described herein. One or more of any tests may be performed as needed or in a scheduled basis, such as on weeks 0, 3, 6, etc. A different set of tests may be performed concurrent with immunization vs. at time points without immunization.

Peripheral blood, for example about 90 mL may be drawn prior to each immunization and at a time after at least some of the immunizations, to determine whether there is an effect on the immune response at specific time points during the study and/or after a specific number of immunizations. Immunological assessment may include one or more of assaying peripheral blood mononuclear cells (PBMC) for T-cell responses to CEA using ELISpot, proliferation assays, multi-parameter flow cytometric analysis, and cytoxicity assays. Serum from each blood draw may be archived and sent and determined.

In various embodiments, a tumor assessment is performed on individuals receiving treatment according to the methods and compositions as described herein. One or more of any tests may be performed as needed or in a scheduled basis, such as prior to treatment, on weeks 0, 3, 6 etc. A different set of tests may be performed concurrent with immunization vs. at time points without immunization. Tumor assessment may include one or more of CT or MRI scans of chest, abdomen, or pelvis performed prior to treatment, at a time after at least some of the immunizations and at approximately every three months following the completion of a selected number, for example 2, 3, or 4, of first treatments and for example until removal from treatment.

Immune responses against a target antigen described herein, such as CEA, may be evaluated from a sample, such as a peripheral blood sample of an individual using one or more suitable tests for immune response, such as ELISpot, cytokine flow cytometry, or antibody response. A positive immune response can be determined by measuring a T-cell response. A T-cell response can be considered positive if the mean number of spots adjusted for background in six wells with antigen exceeds the number of spots in six control wells by 10 and the difference between single values of the six wells containing antigen and the six control wells is statistically significant at a level of $p \leq 0.05$ using the Student's t-test. Immunogenicity assays may occur prior to each immunization and at scheduled time points during the period of the treatment. For example, a time point for an immunogenicity assay at around week 1, 2, 3, 4, 5, 6, 7, 8, 9, 10, 11, 12, 13, 14, 15, 18, 20, 24, 30, 36, or 48 of a treatment may be scheduled even without a scheduled immunization at this time. In some cases, an individual may be considered evaluable for immune response if they receive at least a minimum number of immunizations, for example 1, 2, 3, 4, 5, 6, 7, 8, 9, or more immunizations.

In some embodiments, disease progression or clinical response determination is made according to the RECIST 1.1 criteria among patients with measurable/evaluable disease. In some embodiments, therapies using the methods and compositions as described herein affect a Complete Response (CR; disappearance of all target lesions for target lesions or disappearance of all non-target lesions and normalization of tumor marker level for non-target lesions) in an individual receiving the therapy. In some embodiments, therapies using the methods and compositions affect a Partial Response (PR; at least a 30% decrease in the sum of the LD of target lesions, taking as reference the baseline sum LD for target lesions) in an individual receiving the therapy.

In some embodiments, therapies using the methods and compositions affect a Stable Disease (SD; neither sufficient shrinkage to qualify for PR nor sufficient increase to qualify for PD, taking as reference the smallest sum LD since the treatment started for target lesions) in an individual receiving the therapy. In some embodiments, therapies using the methods and compositions as described herein affect an Incomplete Response/Stable Disease (SD; persistence of one or more non-target lesion(s) or/and maintenance of tumor marker level above the normal limits for non-target lesions) in an individual receiving the therapy. In some embodiments, therapies using the methods and compositions as described herein affect a Progressive Disease (PD; at least a 20% increase in the sum of the LD of target lesions, taking as reference the smallest sum LD recorded since the treatment started or the appearance of one or more new lesions for target lesions or persistence of one or more non-target lesion(s) or/and maintenance of tumor marker level above the normal limits for non-target lesions) in an individual receiving the therapy.

Kits for Combination Therapy Using Ad5 Vaccines and ALT-803

The compositions, immunotherapy, or vaccines may be supplied in the form of a kit. Certain embodiments provide compositions, methods and kits for generating an immune response in an individual to fight infectious diseases and cancer. Certain embodiments provide compositions, methods and kits for generating an immune response against a target antigen or cells expressing or presenting a target antigen or a target antigen signature comprising at least one target antigen. The kits may further comprise instructions regarding the dosage and or administration including treatment regimen information. In some embodiments, the instructions are for the treatment of a proliferative disease or cancer. In some embodiments, the instructions are for the treatment of an infectious disease.

In some embodiments, kits comprise the compositions and methods for providing combination Ad5-CEA vaccines and ALT-803. In some embodiment's kits may further comprise components useful in administering the kit components and instructions on how to prepare the components. In some embodiments, the kit can further comprise software for conducting monitoring patient before and after treatment with appropriate laboratory tests, or communicating results and patient data with medical staff. In some embodiments, the kit comprises multiple effective doses of Ad5[E1-, E2b-]-CEA vaccines and multiple effective doses of ALT-803.

In one aspect, a kit for inducing an immune response in a human is provided comprising: a composition comprising a therapeutic solution of a volume in the range of 0.8-1.2 mL, the therapeutic solution comprising at least $1.0 \times 10^{11}$ virus particles; wherein the virus particles comprise a recombinant replication defective adenovirus vector; a composition comprising of a therapeutic solution of a molecular composition comprising an immune pathway checkpoint modulator and; instructions.

In some embodiments, the therapeutic solution comprises $1.0 \times 10^{11}$-$5.5 \times 10^{11}$ virus particles. In some embodiments, adenovirus vector is capable of effecting overexpression of the modified CEA in transfected cells. In some embodiments, therapeutic solution comprises a first, second and third replication defective adenovirus vector each comprising an antigen selected from the group consisting of a CEA antigen, and combinations thereof. In some embodiments, the adenovirus vector comprises a nucleic acid sequence encoding an antigen that induces a specific immune response against CEA expressing cells in a human.

In some embodiments, the kit further comprises an immunogenic component. In some embodiments, the immunogenic component comprises a cytokine selected from the group of IFN-γ, TNFα IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Rα, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. In some embodiments, the immunogenic component is selected from the group consisting of IL-7, a nucleic acid encoding IL-7, a protein with substantial identity to IL-7, and a nucleic acid encoding a protein with substantial identity to IL-7. In some embodiments, the kit further comprises IL-15, a nucleic acid encoding for IL-15, a protein with substantial identity to IL-14, or a nucleic acid encoding a protein with substantial identity to IL-15.

The components comprising the kit may be in dry or liquid form. If they are in dry form, the kit may include a solution to solubilize the dried material. The kit may also include transfer factor in liquid or dry form. If the transfer factor is in dry form, the kit will include a solution to solubilize the transfer factor. The kit may also include containers for mixing and preparing the components. The kit may also include instrument for assisting with the administration such for example needles, tubing, applicator, inhalant, syringe, pipette, forceps, measured spoon, eye dropper or any such medically approved delivery vehicle. In some embodiments, the kits or drug delivery systems as described herein also include a means for containing compositions disclosed herein in close confinement for commercial sale and distribution.

EXAMPLES

The following examples are included to further describe some aspects of the present disclosure, and should not be used to limit the scope of the invention.

Example 1

Peptides and Vectors

This example describes peptides and vectors. The following HLA-A2 and HLA-A24 binding peptides were used in this and other examples: (a) the HLA-A2 binding CEA agonist peptide CAP1-6D (YLSGADLNL (SEQ ID NO: 4)). All peptides were greater than 96% pure.

Ad5 [E1-, E2b-]-CEA was constructed and produced. Briefly, the transgene was sub-cloned into the E1 region of the Ad5 [E1-, E2b-] vector using a homologous recombination-based approach. The replication deficient virus was propagated in the E.C7 packaging cell line, $CsCl_2$ purified, and titered. Viral infectious titer was determined as plaque-forming units (PFUs) on an E.C7 cell monolayer. The VP concentration was determined by sodium dodecyl sulfate (SDS) disruption and spectrophotometry at 260 nm and 280 nm. The CEA transgene also contained a modified CEA containing the highly immunogenic epitope CAP1-6D.

Example 2

GLP Production of Clinical Grade Multi-Targeted Vaccine

This example shows the production of clinical-grade multi-target vaccine using good laboratory practice (GLP) standards. Previously, the Ad5 [E1-, E2b-]-CEA(6D) product was produced using a 5 L Cell Bioreactor under GLP conditions in accordance with good manufacturing practice standards. This example shows that the Ad5 [E1-, E2b-]-mMUC1-C and the Ad5 [E1-, E2b-]-Brachyury products can be produced in a 5 L Cell Bioreactor using a similar approach.

Briefly, vials of the E.C7 manufacturing cell line are thawed, transferred into a T225 flask, and initially cultured at 37° C. in 5% $CO_2$ in DMEM containing 10% FBS/4 mM L-glutamine. After expansion, the E.C7 cells will be expanded using 10-layered CellSTACKS (CS-10) and transitioned to FreeStyle serum-free medium (SFM). The E.C7 cells will be cultured in SFM for 24 hours at 37° C. in 5% $CO_2$ to a target density of $5 \times 10^5$ cells/mL in the Cell Bioreactor. The E.C7 cells will then be infected with Ad5 [E1-, E2b-]-mMUC1-C or Ad5 [E1-, E2b-]-Brachyury, respectively, and cultured for 48 hours.

Mid-stream processing will be performed in an identical manner as that used to prepare clinical grade Ad5 [E1-, E2b-]-CEA(6D) product under IND14325. Thirty minutes before harvest, Benzonase nuclease will be added to the culture to promote better cell pelleting for concentration. After pelleting by centrifugation, the supernatant will be discarded and the pellets re-suspended in Lysis Buffer containing 1% Polysorbate-20 for 90 minutes at room temperature. The lysate will then be treated with Benzonase and the reaction quenched by addition of 5M NaCl. The slurry will be centrifuged and the pellet discarded. The lysate will be clarified by filtration and subjected to a two-column ion exchange procedure.

To purify the vaccine products, a two-column anion exchange procedure will be performed. A first column will be packed with Q Sepharose XL resin, sanitized, and equilibrated with loading buffer. The clarified lysate will be loaded onto the column and washed with loading buffer. The vaccine product will be eluted and the main elution peak (eluate) containing Ad5 [E1-, E2b-]-mMUC1-C or Ad5 [E1-, E2b-]-Brachyury is carried forward to the next step. A second column will be packed with Source 15Q resin, sanitized, and equilibrated with loading buffer. The eluate from the first anion exchange column will be loaded onto the second column and the vaccine product eluted with a gradient starting at 100% Buffer A (20 mM Tris, 1 mM $MgCl_2$, pH 8.0) running to 50% Buffer B (20 mM Tris, 1 mM $MgCl_2$, 2M NaCl, pH 8.0). The elution peak containing Ad5 [E1-, E2b-]-mMUC1-C or Ad5 [E1-, E2b-]-Brachyury will be collected and stored overnight at 2-8° C. The peak elution fraction will be processed through a tangential flow filtration (TFF) system for concentration and diafiltration against formulation buffer (20 mM Tris, 25 mM NaCl, 2.5% (v/v) glycerol, pH 8.0). After processing, the final vaccine product will be sterile filtered, dispensed into aliquots, and stored at ≤−60° C. A highly purified product approaching 100% purity is typically produced and similar results for these products are predicted.

The concentration and total number of VP product produced will be determined spectrophotometrically. Product purity is assessed by HPLC. Infectious activity is determined by performing an Ad5 hexon-staining assay for infectious particles using kits.

Western blots will be performed using lysates from vector transfected A549 cells to verify mMUC1-C or Brachyury expression. Quality control tests will be performed to determine that the final vaccine products are mycoplasma-free, have no microbial bioburden, and exhibit endotoxin levels less than 2.5 endotoxin units (EU) per mL. To confirm immunogenicity, the individual vectors will tested in mice as described below (Example 8).

Example 3

Pre-Clinical Studies of Ad5 [E1-]-CEA(6D) Vaccine in Combination with ALT-803 Therapy This example describes pre-clinical studies of Ad5 [E1-]-CEA(6D) vaccine in combination with ALT-803 therapy. A commercially obtained Ad5-based vector containing CEA (Ad5 [E1-]-CEA) combined with ALT-803 injections in CEA transgenic mice bearing CEA expressing tumors was evaluated. FIG. 2A illustrates the tumor implantation and dosing regimen used in this study. Groups of mice were implanted with CEA expressing murine MC32-CEA tumor cells (Day 0). One group received no treatment. A second group received injections with ALT-803 (1 µg SC) alone on days 10 and 17, respectively. A third group received injections with Ad5 [E1-]-CEA ($1 \times 10^{10}$ VP SC) on days 7, 14, and 21, respectively. A fourth group received injections with (A) Ad5 [E1-]-CEA on days 7, 14, and 21 and (B) with ALT-803 on days 10 and 17, respectively.

All mice were monitored for tumor growth and tumor volumes were measured over the course of 35 days. When tumors reached a volume of greater than 2000 mm³, mice were euthanized. As shown in FIG. 2B, when mice were injected with ALT-803 alone on days 10 and 17, there was no difference in survival as compared to untreated control mice. Similarly, when mice were injected with Ad5 [E1-]-CEA alone on days 7, 14, and 21, there was no difference in survival as compared to untreated control mice. However, when mice were injected first with Ad5 [E1-]-CEA on days 7, 14, and 21 and then subsequently injected with ALT-803 on days 10 and 17, a difference in survival was observed. Twenty percent (20%) of untreated control mice survived at 35 days as compared to 60% of the Ad5 [E1-]-CEA/ALT-803 treated mice. These results indicate that an anti-tumor immune responses can be augmented by first immunizing with an Ad5 [E1-]-CEA vaccine to induce a CEA directed anti-tumor immune response and then treating with ALT-803.

Example 4

Pre-Clinical Studies of Ad5 [E1-, E2b-]-CEA(6D) Vaccine in Combination with ALT-803 Therapy This example describes pre-clinical studies of Ad5 [E1-, E2b-]-CEA(6D) vaccine in combination with ALT-803 therapy. An Ad5-based vector containing CEA (Ad5 [E1-, E2b-]-CEA) combined with ALT-803 injections in CEA transgenic mice bearing CEA expressing tumors was evaluated. Groups of mice were implanted with $10^6$ CEA expressing murine MC38-CEA tumor cells (Day 0). Mice were separated into four separate groups (n=10 per group). One group received administration of an Ads[E1-, E2b-]-Null vector containing no antigen at a dose of $1 \times 10^{10}$ VPs subcutaneously (SC) on days 1, 7, and 14. A second group received injections with an Ad5[E1-, E2b-]-Null vector containing no antigen at a dose of $1 \times 10^{10}$ VPs SC on days 1, 7, and 14 and ALT-803 (4 µg SC) alone on days 4, 11, and 18, respectively. A third group received injections with an Ad5[E1-, E2b-]-CEA vector at a dose of $1 \times 10^{10}$ VPs SC on days 1, 7, and 14. A fourth group received injections with an Ad5[E1-, E2b-]-CEA vector at a dose of $1 \times 10^{10}$ VPs SC on days 1, 7, and 14 and ALT-803 (1 µg SC) alone on days 4, 11, and 18, respectively.

Figure 3:
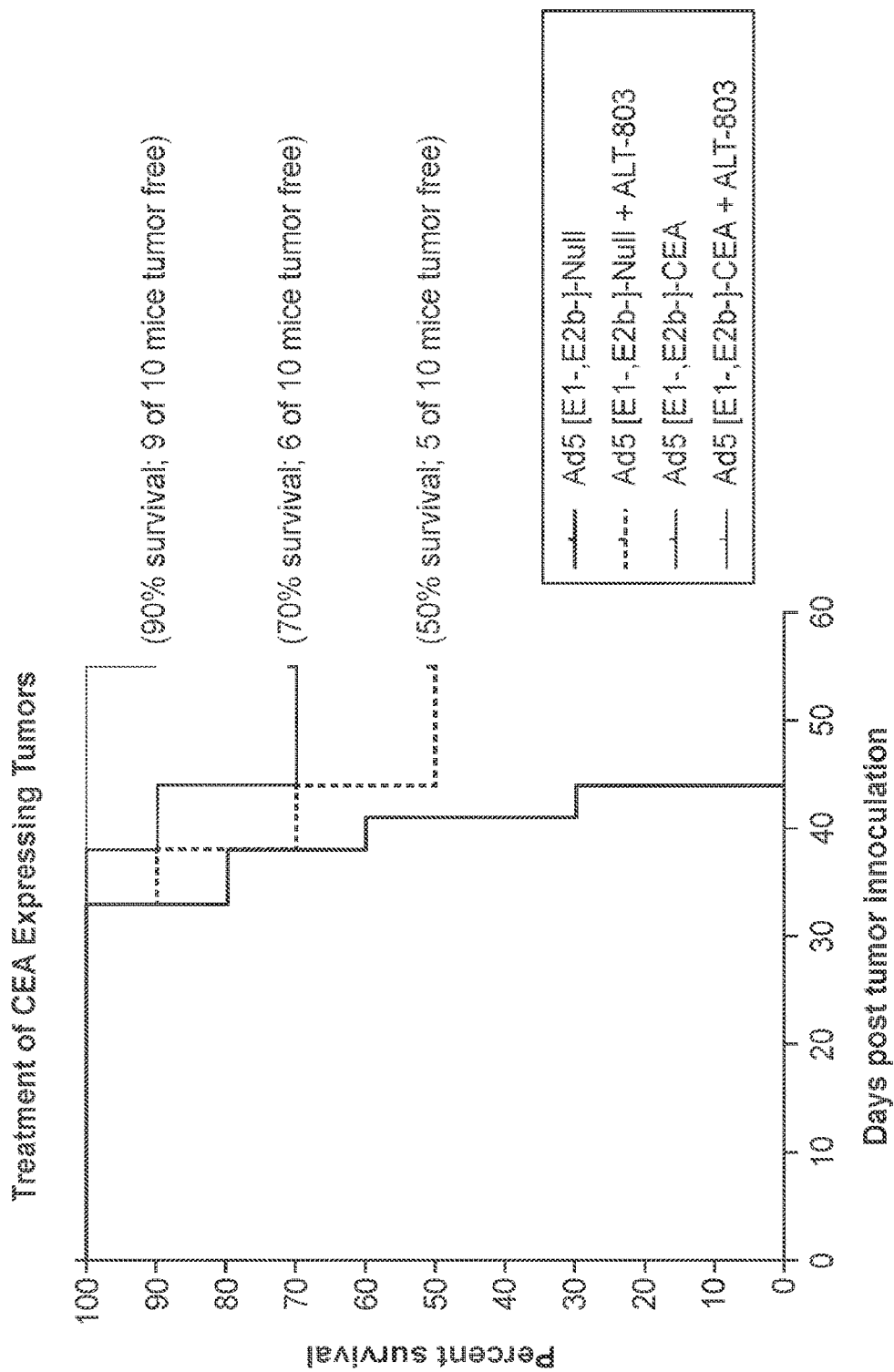
FIG. 3 illustrates a survival curve showing percent survival in CEA-expressing, tumor-bearing mice which received Ad5 [E1-, E2b-]-Null vaccine alone, Ad5 [E1-, E2b-]-Null vaccine with ALT-803, Ad5 [E1-, E2b-]-CEA vaccine alone, or Ad5 [E1-, E2b-]-CEA vaccine with ALT-803.

Ad5[E1-, E2b-]-Null and Ad59E1-, E2b-]-CEA vaccines were administered on days 1, 7, and 14, respectively. ALT-803 was administered on days 4, 11, and 18, respectively. All mice were monitored for tumor growth and tumor volumes were measured over the course of 35 days. When tumors reached a volume of greater than 1500 mm³, mice were euthanized. Percent survival is shown in FIG. 3 over a 55-day period. Percent survival for the group administered the Ad5[E1-, E2b-]-Null vaccine with ALT-803 was 50%. Percent survival for the group administered the Ad5[E1-, E2b-]-CEA vaccine alone was 70%. Percent survival for the group administered the Ads[E1-, E2b-]-CEA vaccine with ALT-803 was the highest at 90%. These results indicate that a immune responses can be augmented by first immunizing with an Ad5 [E1-, E2b-]-CEA vaccine to induce a CEA directed anti-tumor immune response and then treating with ALT-803.

Example 5

Phase 1b and Phase 2 Clinical Studies of Ad5 [E1-, E2b-]-CEA(6D) Vaccine in Combination with ALT-803 Therapy This example describes Phase 1b and Phase 2 clinical studies evaluating combination therapy with Ad5 [E1-, E2b-]-CEA(6D) vaccine and ALT-803, an IL-15 super-agonist. Subjects enrolled in clinical studies have carcinoembryonic antigen (CEA)-expressing cancers. Subjects previously have been treated for locally advanced or metastatic CEA-expressing cancer. The clinical study includes a Phase 1b arm in which the Ad5 [E1-, E2b-]-CEA(6D)

vaccine is given at a fixed dose and dose-esclation is performed with ALT-803 unless de-esclaration is required. The Phase 2 arm will include additional safety studies for the maximum tolerated dose (MTD) and preliminary efficacy data in several indications known to express CEA. The primary objective of the Phase 1b study is to determine the dose-limiting toxicities (DLTs) and maximum tolerated dose (MTD) of Ad5 [E1-, E2b-]-CEA(6D) vaccine and ALT-803 combination treatment in subjects with CEA-expressing cancers whose tumor has recurred after standard-of-care treatment. The primary objectives of the Phase 2 study is to determine the overall safety and tolerability profile for the MTD dose of the Ad5 [E1-, E2b-]-CEA(6D) vaccine plus ALT-803 combination treatment in subjects with CEA expressing cancers whose tumor has recurred after standard-of-care treatment. Preliminary evaluation of the overall response rate (ORR) for the MTD dose of the Ad5 [E1-, E2b-]-CEA(6D) vaccine plus ALT-803 combination treatment in the following indications known to express CEA: (1) histologically confirmed unresectable locally advanced or metastatic medullary thyroid cancer that expresses CEA and have progressed on at least cabozantinib or vandetanib, (2) histologically confirmed unresectable locally advanced or metastatic colon cancer that expresses CEA and have progressed on at least one prior standard-of-care treatment with a FOLFIRI- or FOLFOX-based combination therapy, (3) histologically confirmed unresectable locally advanced or metastatic ovarian cancer that expresses CEA and have progressed on at least one prior standard-of-care-based combination therapy, (4) histologically confirmed unresectable locally advanced or metastatic breast cancer that expresses CEA and have progressed on at least one prior standard-of-care-based combination therapy, (5) histologically confirmed unresectable locally advanced or metastatic lung cancer that expresses CEA and have progressed on at least one prior standard-of-care-based combination therapy, (6) histologically confirmed unresectable locally advanced or metastatic pancreatic cancer that expresses CEA and have progressed on at least one prior standard-of-care-based combination therapy, and (7) other histologically confirmed unresectable locally advanced or metastatic cancers that express CEA and have progressed on at least one prior standard-of-care-based combination therapy.

Secondary objectives of the clinical studies include preliminary evaluation of duration of response, progression-free survival (PFS), and overall survival (OS) for the MTD dose of the Ad5 [E1-, E2b-]-CEA(6D) vaccine plus ALT-803 combination treatment in the indications outlined above. Exploratory objectives of the clinical studies include evaluating the immunogenicity against CEA over the course of treatment with combined Ad5 [E1-, E2b-]-CEA(6D) vaccine plus ALT-803 and determining the genomic, transcriptomic, and proteomic profile of subjects' tumors to identify gene mutations, gene amplifications, RNA-expression levels, and protein-expression levels. Correlations between genomic, transcriptomic, and proteomic profiles and efficacy outcome are assessed. Additional exploratory objectives include determining the tumor molecular profiles and correlation to safety and efficacy, as well as assessing changes in circulating tumor DNA (ctDNA) and circulating tumor RNA (ctRNA) using a genomics panel.

Dose Escalation. Studies are conducted in conformity with Good Clinical Practice and involves a previously determined safe dose of the Ad5 [E1-, E2b-]-CEA(6D) vaccine ($5 \times 10^{11}$ virus particles (VPs)/dose). In the Phase 1b study, the ALT-803 dose is escalated using the standard 3+3 design. Dose levels include (1) Level 1: Ad5 [E1-, E2b-]-CEA(6D) vaccine ($5 \times 10^{11}$ VP/dose) and ALT-803 (10 μg/kg/dose) and (2) Level 2: Ad5 [E1-, E2b-]-CEA(6D) vaccine ($5 \times 10^{11}$ VP/dose) and ALT-803 (15 μg/kg/dose). If needed, the dose of the Ad5 [E1-, E2b-]-CEA(6D) vaccine is de-escalated to $1 \times 10^{11}$ VP/dose. If needed, the dose of ALT-803 is de-escalated to 6 μg/kg/dose.

Three to six subjects are sequentially enrolled with a fixed dose of the Ad5 [E1-, E2b-]-CEA(6D) vaccine and escalating doses of ALT-803. Two ALT-803 dose levels are planned, 10 ug/kg/dose, and 15 ug/kg/dose (with a de-escalation dose if required). During each cohort enrollment, there are a minimum of 7 days between enrolling successive subjects. DLTs are monitored continuously during treatments. In Phase 2, subjects with CEA-expressing indications are treated at the MTD.

Endpoints. The primary endpoints for the Phase 1b study includes DLTs and the MTD. The primary endpoints for the Phase 2 study includes treatment-emergent adverse events (AEs) and serious adverse events (SAEs), clinically significant changes in safety laboratory tests, physical examinations, electrocardiograms (ECGs), and vital signs. Secondary endpoints include duration of response, PFS, and OS. Exploratory endpoints include assessing immunenicity of the Ad5 [E1-, E2b-]-CEA(6D) vaccine by flow cytometric and ELISpot analysis of T-cell frequency, activation status, cytokine profiles, and CEA antibody, adenovirus antibody levels, and potential antibody development against the IL-15N72D:IL-15RαSu/IgG1 Fc complex, correlation of tumor molecular profiles (genomic, transcriptomic, and proteomic) with safety and efficacy, and assessment of changes in circulating tumor DNA (ctDNA) and circulating tumor RNA (ctRNA) with a genomics panel.

Number of Subjects. Up to 12 subjects are enrolled in the Phase 1b study with 3 to 6 subjects sequentially enrolled starting at Dose Level 1. In the Phase 2 study, up to 20 subjects for each indication are enrolled and treated at the MTD determined in Phase 1b. Subjects from the Phase 1b study who were treated at the MTD are included in the Phase 2 enrollment targets as appropriate.

Duration of Treatment. Subjects receive treatments during three-week cycles for a planned three cycles (eight weeks total). Subjects receive treatment unless they experience progressive disease (PD), DLT, withdraw consent, or if it is determined it is no longer in their best medical interest to continue treatment.

Evaluation of Endpoints. Safety endpoints include assessment of DLT and MTD, treatment-emergent AE, SAE, and clinically significant changes in safety laboratory tests, such as changes in ECG, physical examinations, and vital signs. Toxicities are determined using the National Cancer Institute (NCI) Common Terminology Criteria for Adverse Events (CTCAE) Version 4.03.

Tumor response is determined according to the Response Evaluation Criteria In Solid Tumors (RECIST) Version 1.1; duration of response, PFS, and OS are also evaluated. Exploratory immune analysis includes detection and quantification of T-cell immune responses by flow cytometry and ELISpot. CEA, adenoviral antibody levels, and potential antibody development against the IL-15N72D1L-15RαSu/ IgG1 Fc complex are determined by enzyme-linked immunosorbent assay (ELISA). Molecular profiling and analysis is carried out as follows. Genomic sequencing of tumor cells from tissue relative to non-tumor cells from whole blood is profiled to identify the genomic variances that may contribute to response or disease progression and provide an understanding of molecular abnormalities. RNA sequencing is conducted to provide expression data and give relevance to DNA mutations. Quantitative proteomics analysis is conducted to determine the exact amounts of specific proteins and to confirm expression of genes that are correlative of response and disease progression. All genomic, transcriptomic, and proteomic molecular analyses are retrospective and exploratory. Plasma is collected and PCR is used to assess expression levels, and directly measure fusion genes and mutations in circulating DNA and RNA.

Subject Eligibility

Subject eligibility is defined by inclusion criteria and exclusion criteria. Inclusion criteria include the following conditions: (1) age≥18 years, (2) subjects with a histologically confirmed diagnosis of locally advanced or metastatic malignancy who were previously treated with at least one method of standard therapy known to have a possible survival benefit or refused such therapy, (3) the tumor must express CEA as defined by immunohistochemical staining (at least 50% of the tumor with at least moderate intensity of staining) or must be known to be universally CEA positive (i.e., colon and rectal cancer). For inclusion criteria (3), if the CEA-expressing cancer is colorectal cancer, pathologic or clinical confirmation of adenocarcinoma is required. Data should be derived from the primary site or most recent metastatic biopsy sample available. Importantly, subjects must (4): have a recent FFPE tumor biopsy specimen that was obtained following the conclusion of the most recent anticancer treatment and be willing to release the specimen for tumor molecular profiling analysis. If an historic specimen is not available, the subject must be willing to undergo a biopsy during the screening period. Collection of tumor tissue and whole blood for genomics at screening is optional for Phase 1b and mandatory for Phase 2 of this study. Further inclusion criteria include the following conditions: (5) subjects who have received prior CEA-targeted immunotherapy (e.g., vaccine or antibody) are eligible for this trial if this treatment was discontinued at least 3 months prior to enrollment, (6) resolution of all toxic side effects of prior chemotherapy, radiotherapy, or surgical procedures to NCI CTCAE grade≤1, (7) ability to understand and provide signed informed consent that fulfills Institutional Review Board (IRB)'s guidelines, (8): an ECOG performance status of 0 or 1, (9) subjects who are taking medications that do not have a known history of immunosuppression are eligible for this trial, (10) adequate hematologic function at screening, as follows: WBC count≥3000/microliter, hemoglobin≥9 g/dL (may not transfuse or use erythropoietin to achieve this level), platelets≥75,000/microliter, prothrombin (PT)-international normalized ratio (INR)<1.5, and partial thromboplastin time (PTT)<1.5× upper limit of normal (ULN), and (11) adequate renal and hepatic function at screening, as follows: serum creatinine<2.0 mg/dL, bilirubin<1.5 mg/dL (except for Gilbert's syndrome which will allow bilirubin≤2.0 mg/dL), alanine aminotransferase (ALT)≤2.5× ULN, and aspartate aminotransferase (AST)≤2.5× ULN. Inclusion crieteria (12) includes the condition that female subjects of childbearing potential and women<12 months since the onset of menopause must agree to use acceptable contraceptive methods for the duration of the study and for 7 months following the last injection of study medication. If employing contraception, two of the following precautions must be used: vasectomy of partner, tubal ligation, vaginal diaphragm, intrauterine device, condom and spermicidal (gel/foam/cream/vaginal suppository), or total abstinence. Male subjects must be surgically sterile or must agree to use a condom and acceptable contraceptive method with their partner. Female subjects who are post-menopausal are defined as those with an absence of menses for >12 consecutive months. Finally, inclusion criterion (13) requires that subjects must have the ability to attend required study visits and return for adequate follow-up, as required by this protocol.

Exclusion criteria include following conditions: (1) participation in an investigational drug or device study within 30 days of screening for this study, (2) pregnant and nursing women, (3) subjects with ongoing everolimus or other cancer therapy that interferes with the induction of immune responses, and (4) subjects with concurrent cytotoxic chemotherapy or radiation therapy. Regarding condition (4), there must be at least one month between any other prior chemotherapy (or radiotherapy) and study treatment. Any prior CEA-targeted immunotherapy (vaccine) must have been discontinued at least 3 months before initiation of study treatment. Subjects must have recovered from all acute toxicities from prior treatment prior to screening for this study. Further exclusion criteria include (5) active brain or central nervous system metastasis, seizures requiring anticonvulsant treatment, cerebrovascular accident (<6 months), or transient ischemic attack, (6) subjects with a history of autoimmune disease (active or past), such as but not restricted to inflammatory bowel disease, systemic lupus erythematosus, ankylosing spondylitis, scleroderma, or multiple sclerosis (autoimmune-related thyroid disease and vitiligo are permitted), (7) subjects with serious intercurrent chronic or acute illness, such as cardiac or pulmonary disease, hepatic disease, or other illness considered by the Investigator as high risk for investigational drug treatment, (8) subjects with a history of heart disease, such as congestive heart failure (class II, III, or IV defined by the New York Heart Association functional classification), history of unstable or poorly controlled angina, or history (<1 year) of ventricular arrhythmia, (9) subjects with a medical or psychological impediment that would impair the ability of the subject to receive therapy per protocol or impact ability to comply with the protocol or protocol-required visits and procedures, (10) history of malignancy except for the following: adequately treated non-melanoma skin cancer, cervical carcinoma in situ, superficial bladder cancer, or other carcinoma that has been in complete remission without treatment for more than 5 years, (11) presence of a known active acute or chronic infection, including human immunodeficiency virus (HIV, as determined by enzyme-linked immunosorbent assay [ELISA] and confirmed by western blot) and hepatitis B and hepatitis C virus (HBV/HCV, as determined by HBsAg and hepatitis C serology), and (12) subjects on systemic intravenous or oral steroid therapy (or other immunosuppressives, such as azathioprine or cyclosporin A) are excluded on the basis of potential immune suppression. Regarding exclusion criterion (12), subjects must have had at least 6 weeks of discontinuation of any steroid therapy (except that used as premedication for chemotherapy or contrast-enhanced studies) prior to enrollment. Exclusion criteria also include (13) subjects with known allergy or hypersensitivity to any component of the investigational product are excluded, (14) subjects with acute or chronic skin disorders that will interfere with injection into the skin of the extremities or subsequent assessment of potential skin reactions, and (15) subjects vaccinated with a live (attenuated) vaccine (e.g., FluMist) or a killed (inactivated)/subunit vaccine (e.g., PNEU-MOVAX®, Fluzone®) within 28 days or 14 days, respectively, of the first planned dose of Ad5 [E1-, E2b-]-CEA(6D) vaccine or ALT 803.

Treatment Procedures

The Ad5 [E1-, E2b-]-CEA(6D) vaccine is provided in 2-mL single-dose vials. Each single-dose vial contains a sterile suspension of the Ad5 [E1-, E2b-]-CEA(6D) vaccine at $5 \times 10^{11}$ VP intended for single dose administration and contains ARM formulation buffer (20 mM TRIS, 25 mM NaCl, 2.5% glycerol, pH 8.0). Each vial contains approximately 1.3 mL of the vaccine.

ALT-803 is supplied as a sterile solution for subcutaneous injection. ALT-803 is provided at a concentration of 1.2 mg per 1 mL (1.2 mg/mL) and contains Phosphate Buffered Saline (Sodium Chloride (USP) 8.18 g/1; Sodium Phosphate Dibasic (USP) 1.43 g/L; Potassium Phosphate Monobasic (NF) 1.36 g/L, pH 7.4). Each vial contains approximately 1.2 mL of ALT-803. The product is stored at 2-8° C. until used.

Storage. The Ad5 [E1-, E2b-]-CEA(6D) vaccine is stored in freezer conditions of ≤−20° C. until used. ALT-803 is stored at 2-8° C. until used.

Dose Preparation. The dose of Ad5 [E1-, E2b-]-CEA(6D) vaccine to be injected is $5 \times 10^{11}$ VP (Cohort 1 and 2) or $1 \times 10^{11}$ VP (dose level −1) per 1 mL. Prior to injection, the appropriate vial is removed from the freezer and allowed to thaw at controlled room temperature (20-25° C.) for at least 20 minutes and not more than 30 minutes, after which it is kept at 2-8° C. Each vial is sealed with a rubber stopper and has a white flip-off seal. The rubber stopper is secured to the vial with an aluminum-crimped seal. The thawed vial is swirled and then, using aseptic technique, the appropriate volume is withdrawn from the appropriate vial using a 1-mL syringe. The vaccine dose is injected as soon as possible using a 1 to ½ inch, 20 to 25-gauge needle. Storage of the vaccine in the vial at 2-8° C. does not exceed 12 hours and once the vaccine is thawed, it is not refrozen.

Dose Preparation—$5 \times 10^{11}$ Virus Particles. 1 mL of contents is withdrawn from the vial, and the injection site is prepared with alcohol. The dose is administered to the subject by subcutaneous (SC) injection in the thigh without any further manipulation.

Dose Preparation—$1 \times 10^{11}$ Virus Particles. From a 5.0-mL vial of 0.9% sterile saline, 1 mL of fluid is removed using a 1.0 mL tuberculin syringe, leaving 4 mL. Then, using another 1.0 mL tuberculin syringe, 1 mL is removed from the vial containing the Ad5 [E1-, E2b-]-CEA(6D) vaccine, and added into the 4 mL of sterile saline remaining in the 5-mL sterile saline vial. The contents are mixed by inverting the 5 mL solution of diluted Ad5 [E1-, E2b-]-CEA(6D) vaccine. 1 mL of the diluted Ad5 [E1-, E2b-]-CEA(6D) vaccine is withdrawn and the injection site is prepared with alcohol, and administered to the subject by SC injection in the thigh.

ALT-803 Dose Preparation. ALT-803 dose calculation is based on actual body weight. The calculated amount of ALT-803 is drawn into a syringe/or subcutaneous injection. The stock concentration is 1 mg/mL. Doses are drawn directly into the syringe for injection.

Administration. The Ad5 [E1-, E2b-]-CEA(6D) vaccine is administered on weeks 0, 3, and 6 for a total of three (3) immunizations on an outpatient basis. All study drug administration treatment occurs within ±5 days of the planned visit date. All immunizations of the vaccine are given by SC injection in the thigh after preparation of the site with alcohol. Injection site reactions were reported in previous Phase 1/2 studies with the Ad5 [E1-, E2b-]-CEA(6D) and are monitored during the study. Either thigh is used for the initial injection. Subsequent injections are given in the same thigh as the initial injection and are separated by at least 5 cm. Subjects remain in the clinic for a minimum of 60 minutes after the first injection and 30 minutes after subsequent injections to allow for the evaluation of vital signs and for monitoring of injection site reactions. For the first injection, vital signs are assessed 30 and 60 minutes after the injection. Vital signs are assessed 30 minutes after the subsequent injections. ALT-803 is administered once a week for two weeks following treatment with the Ad5 [E1-, E2b-]-CEA(6D) vaccine. A window of −1/+3 days for weekly ALT-803 dosing is allowed in the event of scheduling issues (i.e., holiday, bad weather or other scheduling issues). Any dose that cannot be accommodated within this window is skipped and the dose not made up. Injection sites should be in a different limb than the Ad5 [E1-, E2b-]-CEA (6D) vaccine and, and each injection site should be separated by at least 5 cm. Doses of ALT-803 are administered on an outpatient basis. If the first dose of the first cycle is well tolerated after 2 hours of monitoring, subsequent doses are administered with 30-minute post treatment monitoring. Both the Ad5 [E1-, E2b-]-CEA(6D) vaccine and ALT-803 are administer by subcutaneous (SC) injection.

Dose Limiting Toxicity and Maximum Tolerated Dose

A DLT is defined as: (1) any grade 3 or greater toxicity as defined by the National Cancer Institute (NCI) Common Terminology Criteria for Adverse Events (CTCAE) Version 4.03 or (2) any grade 2 or higher autoimmune reaction or immediate hypersensitivity reaction. In addition, the following criteria will apply: any toxicity that is not clearly unrelated to the study treatment that is of grade 3 and does not resolve to grade 1 or lower (or to baseline or lower, if a subject enters the study with a toxicity that is grade 2 or higher) within a week despite the use of medical intervention, or that is of grade 4, but with exceptions as follows: (1) any grade 3 or 4 lymphopenia, leukopenia, and neutropenia that recovers within 14 days is not a DLT, (2) grade≥3 neutropenia with infection is a DLT, (3) any grade 3 or 4 thrombocytopenia or anemia that recovers within 14 days is not a DLT, (4) a grade 4 thrombocytopenia (without clinical sequalae) of less than or equal to 1 week duration and/or return to grade 2 or less will not trigger DLT (5) grade≥3 thrombocytopenia with bleeding is a DLT, (6) nausea or vomiting controllable with anti-emetics within 72 hours is not a DLT, (7) hypotension (systolic pressure<90 mm Hg) of grade<3 that is of limited duration (less than 72 hours) or can be managed with hydration measures as described in Section 5.9.1 is not a DLT, (8) hypotension of grade 3 that persists for >4 hours and requires hospitalization is a DLT. A precautionary admission for observation after grade 3 hypotension that persists for ≤4 hours is not a DLT, (9) grade>3 arrhythmia of any kind is a DLT, (10) absolute lymphocyte count (ALC)≥50,000/4, sustained for 14 days is a DLT, and (11) white blood cell (WBC) count≥60,000/4, sustained for 14 days is a DLT. The MTD is defined as the highest dose level with an observed incidence of DLT in <33% of subjects enrolled in a cohort.

Dose Escalation. Dose escalation is performed as shown in TABLE 4.

TABLE 4

| Dose Levels | |
| --- | --- |
| Cohort | ALT-803 |
| 1 | 10 µg/kg/dose |
| 2 | 15 µg/kg/dose |
| Dose level (−1) | 6 µg/kg/dose |

TABLE 4-continued

| Cohort | Ad5 [E1-, E2b-]-CEA(6D) vaccine |
|---|---|
| 1 and 2 | $5 \times 10^{11}$ VP/dose |
| Dose level (−1) | $1 \times 10^{11}$ VP/dose |

Cohort 1 Ad5 [E1-, E2b-]-CEA(6D) vaccine at $5 \times 10^{11}$ VP plus ALT-803 10 µg/kg/dose. If none of the initial 3 subjects experience a DLT, dose escalation to Cohort 2 is initiated. If 1 of the initial 3 subjects experiences a DLT, 3 additional subjects are enrolled into Cohort 1 for a total of 6 subjects. If ≤1 of 6 subjects experience a DLT, escalation to Cohort 2 is initiated. If ≥2 of the initial 3 subjects or of the 6 total subjects experience a DLT, enrollment into the de-escalation Cohort-1 is initiated.

Cohort 2 Ad5 [E1-, E2b-]-CEA(6D) vaccine at $5 \times 10^{11}$ VP plus ALT-803 at 15 µg/kg/dose. If ≤1 of the initial 3 subjects experience a DLT, 3 additional subjects are enrolled into Cohort 2 for a total of 6 subjects. If ≤1 of 6 subjects experience a DLT, this dose level is defined as the MTD. If ≥2 of the initial 3 subjects, or if ≥2 of a total 6 subjects experience a DLT, enrollment into the next lower dose level is resumed: (1) if six subjects have been already treated in Cohort 1, that dose is defined as the MTD, (2) if three subjects have been treated in Cohort 1, 3 additional subjects are enrolled at this dose level for a total of 6 subjects. If ≤1 of 6 subjects experience a DLT, that dose is defined as the MTD. If ≥2 of 6 subjects experience a DLT, enrollment into the de-escalation Cohort-1 is initiated. If a DLT is related to the Ad5 [E1-, E2b-]-CEA(6D) vaccine, then the dose is reduced to $1 \times 10^{11}$ VP/dose. If a DLT is related to ALT-803, then the dose is reduced to 6 µg/kg/dose.

Efficacy Assessments

Survival. After the subject completes or withdraws from the study, all subjects are followed for survival every 3 months for 12 months and then approximately every 6 months thereafter for an additional 12 months.

Antitumor Response. Tumor assessments may include the following evaluations: physical examination (with photograph and measurement of skin lesions, as applicable); cross-sectional imaging using computed tomography (CT) or magnetic resonance imaging (Mill) scan of the chest, abdomen, and pelvis (pelvis scan is optional unless known pelvic disease is present at baseline); nuclear bone scan for subjects with known/suspected bone lesions; and CT or MRI scan of the brain (only as clinically warranted based on symptoms/findings). The preferred method of disease assessment is CT with contrast. If CT with contrast is contraindicated, CT of the chest without contrast and MRI scan of the abdomen/pelvis with contrast is preferred. At baseline, tumor lesions are selected and categorized as target or non-target lesions. Target lesions include those lesions that can be accurately measured in at least 1 dimension as ≥20 mm with conventional techniques or ≥10 mm with CT scan. Malignant lymph nodes with a short axis diameter≥15 mm can be considered target lesions. Up to a maximum of 2 target lesions per organ and 5 target lesions in total are identified at baseline. These lesions should be representative of all involved organs and selected based on their size (those with the longest diameter) and their suitability for accurate repeated measurements. A sum of the longest lesion diameter (LLD) for all target lesions is calculated and reported as the baseline sum LLD. For malignant lymph nodes identified as target lesions, the short axis diameter is used in the sum of LLD calculation. All other lesions (or sites of disease) should be identified as non-target lesions (including bone lesions). All post-baseline response assessments follow the same lesions identified at baseline. The same mode of assessment (e.g., CT) used to identify/evaluate lesions at baseline is used throughout the course of the study unless subject safety necessitates a change (e.g., allergic reaction to contrast media).

RECIST Response Criteria. Antitumor activity is evaluated with target and/or non-target lesions according to RECIST Version 1.1as summarized below.

Target Response. Percentage change in target lesion size is evaluated by the following formulae: (1) when determining complete response or partial response: [(Post value−Baseline value)/Baseline value]×100, (2) when determining progressive disease: [(Post value−Smallest value since treatment started)/(Smallest value since treatment started)]×100. Target response is classified according to the RECIST Version 1.1 Target Lesion Response Criteria in TABLE 5.

TABLE 5

RECIST Target Response Criteria

| Target Response Criteria | Definition |
|---|---|
| Complete Response (CR) | Disappearance of all target lesions. Any pathological lymph nodes (whether target or non-target) must have reduction in short axis to <10 mm. |
| Partial Response (PR) | At least a 30% decrease in the sum of diameters of target lesions, taking as reference the baseline sum diameters. |
| Stable Disease (SD) | Neither sufficient shrinkage to qualify for PR nor sufficient increase to qualify for PD, taking as reference the smallest sum diameters while on study. |
| Progressive Disease (PD) | At least a 20% increase in the sum of diameters of target lesions, taking as reference the smallest sum diameters while on study (this includes the baseline sum if that is the smallest on study). In addition to the relative increase of 20%, the sum must also demonstrate an absolute increase of 5 mm. (Note: the appearance of one or more lesions is also considered progression). |

Non-target response is classified according to the RECIST Version 1.1 Non-Target Lesion Response Criteria in TABLE 6.

TABLE 6

RECIST Non-Target Response Criteria

| Non-Target Response Criteria | Definition |
|---|---|
| CR | Disappearance of all non-target lesions and normalization of tumor marker level. All lymph nodes must be non-pathological in size (<10 mm short axis). |
| Non-CR/ Non-PD | Persistence of one or more non-target lesion(s) and/or maintenance of tumor marker level above the normal limits. |
| PD | Unequivocal progression of existing non-target lesions. (Note: the appearance of one or more new lesions is also considered progression). |

Overall response is classified according to the RECIST Version 1.1 Overall Response Criteria in TABLE 7.

TABLE 7

RECIST Overall Response Criteria

| Target Lesions | Non-Target Lesions | New Lesions | Overall Response |
|---|---|---|---|
| CR | CR | No | CR |
| CR | Non-CR/Non-PD | No | PR |
| CR | Not Evaluated | No | PR |
| PR | Non-PD or not all evaluated | No | PR |
| SD | Non-PD or not all evaluated | No | SD |
| Not all evaluated | Non-PD | No | Inevaluable |
| PD | Any | Yes or No | PD |
| Any | PD | Yes or No | PD |
| Any | Any | Yes | PD |

Exploratory Pharmacodynamic Assessments

Peripheral Blood Collection. Subjects have approximately 90 mL of peripheral blood drawn to evaluate the study drug's effect on the immune response at specific time points during the study and/or after a specified injection. Immune monitoring blood draws is done at baseline, and at weeks 3, 6, 8, 9, 18, or any combination thereof.

Samples Collected. Five to six, 10-mL green top heparin tubes for PBMC samples and two 8-mL red top tubes for serum samples are drawn. Samples are processed for subsequent analyses.

Immune Sample Analysis. Analyses of PBMCs in blood are performed as follows. Pre- and post-therapy PBMCs, isolated by Ficoll-Hypaque density gradient separation, are analyzed for antigen-specific immune responses using ELISpot assays for IFN-γ or granzyme B secretion after exposure to CEA peptides. Flow cytometry is utilized to assess T cell responses using intracellular cytokine staining assay for IFN-γ or TNF-α expression after exposure to CEA peptides. Flow cytometry analysis for the expression of CD107a on cells is utilized to test for degranulating cells such as CD8+ T cells and NK cells, for example, activated NK cells. PBMCs are stimulated in vitro with overlapping 15-mer peptide pools encoding the tumor-associated antigen CEA. Control peptide pools involve the use of irrelevant antigen peptide pools as a negative control and CEFT peptide mix as a positive control. CEFT is a mixture of peptides of CMV, Epstein-Barr virus, influenza, and tetanus toxin. Post-stimulation analyses of CD4 and CD8 T cells will involve the production of IFN-γ, TNF-α, and CD107a expression. Sera is analyzed pre- and post-therapy for CEA directed antibody, neutralizing antibody titer to adenovirus (serotype 5), and for potential antibody development against the IL-15N72D1L-15RαSu/IgG1 Fc complex.

Genomics, Transcriptomics, and Proteomics Molecular Analysis

Rationale for Tumor Molecular Profiling. Genomic sequencing of tumor cells from tissue relative to non-tumor cells from whole blood is profiled to identify the genomic variances that may contribute to response or disease progression and provide an understanding of molecular abnormalities. RNA sequencing is conducted to provide expression data and give relevance to DNA mutations. Quantitative proteomics analysis is conducted to determine the exact amounts of specific proteins and to confirm expression of genes that are correlative of response and disease progression. All genomic, transcriptomic, and proteomic molecular analyses are retrospective and exploratory.

Sample Collection and Analysis. Exploratory genomics, transcriptomics, and proteomics molecular profiling are performed on formalin-fixed, paraffin-embedded (FFPE) tumor tissue and whole blood (subject matched normal comparator against the tumor tissue) by next-generation sequencing and mass spectrometry-based quantitative proteomics. Collection of tumor tissue and whole blood at screening is optional for Phase 1b and mandatory for Phase 2 of this study. Tumor tissue and whole blood samples are collected according to the instruction cards included in the Tissue Specimen Kit and Blood Specimen Kit. The kits include the materials necessary to collect and ship FFPE tumor tissue and whole blood samples.

A single FFPE tumor tissue block is required for the extraction of tumor DNA, tumor RNA, and tumor protein (TABLE 8). A whole blood sample is required for the extraction of subject normal DNA.

Circulating Tumor DNA and RNA Assays. Blood-based ctRNA and ctDNA testing identify targets and monitor changes in targets. During treatment, 20 mL of whole blood are collected at baseline and weeks 3, 6, and 8 for analysis of circulating DNA and RNA. Whole blood is drawn into Cell-Free RNA BCT® tubes or Cell-Free DNA BCT® tubes containing RNA or DNA stabilizers, respectively (TABLE 8).

TABLE 8

Schedule of Collection for Exploratory Molecular Profiling

| Exploratory Molecular Profiling | Baseline | Weeks 3, 6, and 8 |
|---|---|---|
| Whole blood (normal comparator against tumor) | | |
| 1 PAXgene Blood DNA tube (2.5 mL)[a] | X | |
| 1 Streck Cell-Free RNA BCT ® (10.0 mL) | X | X |
| 1 Streck Cell-Free DNA BCT ® (10.0 mL) | X | X |
| Formalin-fixed, paraffin-embedded tumor tissue[b] | | |
| A minimum tissue surface area of 25 mm², 75 μm thick, with at least 30% malignant tissue | X | |

[a]Whole blood to be collected at screening only for genomic sequencing. Requires 2.5 mL of subject's whole blood in 1 PAXgene Blood DNA tube, provided in the Blood Specimen Kit.
[b]FFPE tissue block to be collected at screening for genomic sequencing, RNA sequencing, and proteomic analysis. A single block meeting the minimum requirements for genomics, transcriptomics, and proteomics is required. A historic FFPE tissue block is acceptable if the specimen was taken following the completion of the subject's most recent anti-cancer therapy. Otherwise, a fresh biopsy specimen will need to be obtained and prepared as an FFPE tissue block, and collected per local pathology laboratory procedures. Optional tissue will be requested at week 8.

Statistical Considerations

Safety Analysis. DLTs are evaluated continuously in a cohort. An overall assessment of whether to escalate to the next dose level is made at least 3 weeks after the last subject in the previous cohort has received their first injection. A dose level is considered safe if <33% of subjects treated at a dose level experience a DLT (i.e., 0 of 3, ≤1 of 6, ≤2 of 9, ≤3 of 12, ≤4 of 15, or ≤5 of 18 subjects). Safety is evaluated in 3 or 6 subjects at each dose level in the dose escalation component of the study. Safety will continue to be monitored among additional subjects treated at the MTD in the dose expansion component of the study. A subject is considered evaluable for safety if treated with at least one injection. DLTs are observed through 9 weeks to accommodate the safety evaluation of multiple treatments.

Overall safety is assessed by descriptive analyses using tabulated frequencies of AEs by grade using CTCAE Version 4.03 within dose cohorts and for the overall study population in terms of treatment-emergent AEs, SAES, and clinically significant changes in safety laboratory tests, physical examinations, ECGs, vital signs.

Efficacy Analysis—Obejctive Tumor Response and Disease Control Rate. The percentage of subjects that achieve an objective confirmed complete or partial overall tumor response using RECIST Version 1.1 is evaluated by dose cohort and overall. The 95% confidence interval of the response rate is evaluated. Disease control (confirmed response or SD lasting for at least 4 months) is analyzed in a similar manner.

Efficacy Analysis—Duration of Response. The duration of the overall response is evaluated by dose cohort and overall. The duration of overall response is measured from the time measurement criteria are met for CR or PR (whichever is first recorded) until the first date that recurrent or PD is objectively documented (taking as reference for PD the smallest measurements recorded since the treatment started).

Efficacy Analysis—Progression-Free Survival. PFS is evaluated by dose cohort and overall using Kaplan-Meier methods. PFS is defined as the time from the date of first treatment to the date of disease progression or death (any cause) whichever occurs first. Subjects who do not have disease progression or have not died at the end of follow up are censored at the last known date the subject was progression free.

Efficacy Analysis—Overall Survival. OS is evaluated by dose cohort and overall using the Kaplan-Meier method. OS is defined as the time from the date of first treatment to the date of death from any cause. Subjects who are alive at the end of follow up are censored at the last known date alive.

Efficacy Analysis—Exploratory Immune Response Analysis. The percentage of subjects with a positive immune response is evaluated by dose cohorts and overall. A positive immune response is defined by flow cytometric readout (cytokine production or CD107a expression) or ELISpot analysis or CMI reactivity in ex vivo stimulation assays.

Efficacy Analysis—Statistical Power and Analysis Plan. For ELISpot CMI studies, groups of at least five total PBMC samples from individual patients in the phase 1 cohorts appropriately power the studies. Assuming non-specific and/or background activity results in 10 (±10 SD) IFN-γ spot forming cells (SFC) from baseline PBMC samples versus a minimum of 50 (±10 SD) SFC observed from treatment PBMC samples in ELISpot CMI determinations, the statistical power is >95% for a 95% confidence interval. In flow cytometry studies and based on prior studies with mouse spleen cell samples, a TNF-α and/or IFN-γ expressing cell has an assumed background response of approximately 0.1% (±0.4 SD) for $CD4^+/CD8^+$ lymphocytes from PBMC baseline samples. After treatments, a TNF-α, IFN-γ, and/or CD107a expression of at least 0.6% (±0.4 SD) is detected. Groups of at least 5 total samples from individual patients in the phase 1 cohorts for these flow cytometry studies will give a statistical power of 80% for a 95% confidence interval.

Statistical analyses of data are performed. For ELISpot analyses on individual PBMC samples, Student T tests (PRISM software) are performed among the treatment samples to determine any significant differences. For flow cytometry analyses on individual PBMC samples, Student T tests are performed on percentages of TNF-α, INF-γ, and/or CD107a and/or IFN-γ expressing cells among the treatment samples to determine any significant differences in cell populations.

Determination of Sample Size. It is expected that up to 12 subjects are enrolled in the Phase 1b study with three to six subjects sequentially enrolled starting at dose level 1. In the Phase 2 study, 20 subjects for each indication are enrolled and treated at the MTD determined in Phase 1b. Subjects from the Phase 1b study who were treated at the MTD are included in the Phase 2 enrollment targets.

Example 6

Treatment of Cancer with Ad5 [E1-E2b-]-CEA(6D) Vaccine in Combination with ALT-803 Therapy This example describes treatment of cancer in a subject in need thereof with Ad5 [E1-, E2b-]-CEA(6D) vaccine in combination with ALT-803 therapy. Subjects with CEA-expressing tumors are immunized with the Ad5[E1-, E2b-]-CEA vaccine. The Ad5[E1-, E2b-]-CEA vaccine is administered at a dose of $5 \times 10^{11}$ virus particles (VPs) by subcutaneous (SC) injection. Vaccinations are repeated up to 3 times total over a 3-week period. The Ad5[E1-, E2b-]-CEA vaccine is administered on days 7, 14, and 21, respectively. Subjects are also administered a super-agonist/super-agonist complex, such as ALT-803, at a dose of 1 μg SC on days 10 and 17, respectively.

Subjects in need thereof have CEA-expressing cancer cells, such as CEA-expressing colorectal cancer. Subjects are any mammal, such as a human or a non-human primate.

Example 7

Treatment of Cancer with Ad5 [E1-E2b-]-CEA(6D) Vaccine in Combination with ALT-803 Therapy and Engineered NK Cells This example describes treatment of cancer in a subject in need thereof with Ad5 [E1-, E2b-]-CEA(6D) vaccine in combination with ALT-803 therapy and engineered NK cells. Subjects with CEA-expressing tumors are immunized with the Ad5[E1-, E2b-]-CEA vaccine. The Ad5[E1-, E2b-]-CEA vaccine is administered at a dose of $5 \times 10^{11}$ virus particles (VPs) by subcutaneous (SC) injection. The Ad5 [E1-, E2b-]-CEA vaccine is administered on days 7, 14, and 21, respectively. Subjects are also administered ALT-803 at a dose of 1 μg SC on days 10 and 17, respectively.

Subjects are additionally administered aNK cells. aNK cells are infused intravenously on days 9, 11, 18, 22, 27, and 33 at a dose of $2 \times 10^9$ cells per treatment. Subjects in need thereof have CEA-expressing cancer cells, such as colorectal cancer. Subjects are any mammal, such as a human or a non-human primate.

Example 8

Treatment of Cancer with Ad5 [E1-E2b-]-CEA(6D) Vaccine in Combination with ALT-803 Therapy and an Anti-CEA Antibody This example describes treatment of cancer in a subject in need thereof with Ad5 [E1-, E2b-]-CEA(6D) vaccine in combination with ALT-803 therapy and an anti-CEA antibody. Subjects with CEA-expressing tumors are immunized with the Ad5[E1-, E2b-]-CEA vaccine. The Ad5 [E1-, E2b-]-CEA vaccine is administered at a dose of $5 \times 10^{11}$ virus particles (VPs) by subcutaneous (SC) injection. The Ad5 [E1-, E2b-]-CEA vaccine is administered on days 7, 14, and 21, respectively. Subjects are also administered ALT-803 at a dose of 1 μg SC on days 10 and 17, respectively.

Subjects are additionally administered an anti-CEA antibody, such as a NEO-201 antibody. NEO-201 antibody is infused in subjects at a dose of 3 mg/kg administered IV every on days 1, 15, and 22. This occurs over a 2 to 3-month period. Subjects in need thereof have CEA-expressing cancer cells, such as colorectal cancer. Subjects are any mammal, such as a human or a non-human primate.

Example 9

Treatment of Cancer with Ad5 [E1-, E2b-]-CEA(6D) Vaccine in Combination with ALT-803 Therapy and FOLFOX-B, Avelumab, and NK Cell Therapy This example describes treatment of cancer with Ad5 [E1-, E2b-]-CEA(6D) vaccine in combination with ALT-803 therapy and FOLFOX-B, Avelumab, NEO-201 antibody, and NK cell therapy. Subjects with CEA-expressing tumors are immunized with the Ad5 [E1-, E2b-]-CEA vaccine. The Ad5[E1-, E2b-]-CEA vaccine is administered at a dose of $5\times10^{11}$ virus particles (VPs) by subcutaneous (SC) injection. Vaccinations are repeated up to 3 times total over a 3-week period. The Ad5[E1-, E2b-]-CEA vaccine is administered on days 7, 14, and 21, respectively. Subjects are also administered a super-agonist/super-agonist complex, such as ALT-803, at a dose of 1 µg SC on days 10 and 17, respectively. Anti-PD-1 monoclonal antibody, a checkpoint inhibitor, is (avelumab) infused in in order to enhance the vaccine effect. As a routine precaution, subjects enrolled in this trial are observed for 1 hour post infusion, in an area with resuscitation equipment and emergency agents. At all times during avelumab treatment, immediate emergency treatment of an infusion-related reaction or a severe hypersensitivity reaction according to institutional standards must be assured. In order to treat possible anaphylactic reactions, for instance, dexamethasone 10 mg and epinephrine in a 1:1000 dilution or equivalents are available along with equipment for assisted ventilation. Subjects receive intravenous infusion of avelumab over 1 hour (−10 minutes/+20 minutes, i.e., 50 to 80 minutes) as applicable at a dose of 10 mg/kg. Treatment with avelumab starts on the second vaccine treatment 3 weeks after the first vaccine injection. Alternatively, treatment with avelumab starts concurrently with the first vaccine treatment. An immune response against the CEA tumor-associated antigens (TAAs) is induced and then enhanced by injections with anti-PD-1 that will interfere with the inhibitory effect of the immune checkpoint pathway. Anti-PD-1 antibody is injected into subjects at a dose of 3 mg/kg administered IV after a vaccination beginning on week 3. This infusion (injection) procedure is repeated on weeks 9 and 12.

Following Avelumab administration, FOLFOX therapy is administered intravenously. Oxaliplatin 85 mg/m² is administered IV over 2 hours on day 1 or 2, Leucovorin* 400 mg/m² is administered IV over 2 hours on day 1 or 2, 5-FU* 400 mg/m² is administered IV bolus on day 1 or 2, and 5-FU* 2400 mg/m² is administered IV over 46 hours to start on day 1 or 2. 5-Fluorouracil and leucovorin should be administered separately to avoid the formation of a precipitate. Per package insert, leucovorin is administered first.

Engineered NK cells, specifically aNK cells, are infused on days 9, 11, 18, 22, 27, and 33 at a dose of $2\times10^9$ cells per treatment.

A NEO-201 antibody is infused in subjects at a dose of 3 mg/kg administered IV on days 1, 15, and 22 after infusions with haNK cells delivered to patients above. This occurs over a 2- to 3-month period.

A subject in need thereof has any stage of disease progression, including metastatic colorectal cancer or advanced stage colorectal cancer. Subjects are any mammal, such as a human or a non-human primate. Administration is performed intravenously by infusion or subcutaneously. Administration of each therapy is given or days, weeks, or months. Therapies are administered once or multiple types, depending on the agent being delivered.

Example 10

Treatment of Cancer with Ad5 [E1-, E2b-]-CEA (6D) Vaccine and ALT-803 Therapy in Combination with Ad5 [E1-, E2b-]-Brachyury and Ad5 [E1-, E2b-]-MUC1

This example describes treatment of cancer with Ad5 [E1-, E2b-]-CEA(6D) Vaccine and ALT-803 therapy in combination with Ad5 [E1-, E2b-]-Brachyury and Ad5 [E1-, E2b-]-MUC1. The following HLA-A2 and HLA-A24 binding peptides were used in this and other examples: (a) the HLA-A2 binding CEA agonist peptide CAP1-6D (YLSGADLNL (SEQ ID NO: 4)), (b) the HLA-A2 MUC1 agonist peptide P93L (ALWGQDVTSV (SEQ ID NO: 112)), (c) the HLA-A24 binding MUC1 agonist peptide C6A (KYHPMSEYAL (SEQ ID NO: 113)), and (d) the HLA-A2 binding brachyury agonist peptide (WLLPGTSTV (SEQ ID NO: 15)). All peptides were greater than 96% pure. Ad5 [E1-, E2b-]-brachyury, Ad5 [E1-, E2b-]-CEA and Ad5 [E1-, E2b-]-MUC1 were constructed and produced. Briefly, the transgenes were sub-cloned into the E1 region of the Ad5 [E1-, E2b-] vector using a homologous recombination-based approach. The replication deficient virus was propagated in the E.C7 packaging cell line, $CsCl_2$ purified, and titered. Viral infectious titer was determined as plaque-forming units (PFUs) on an E.C7 cell monolayer. The VP concentration was determined by sodium dodecyl sulfate (SDS) disruption and spectrophotometry at 260 nm and 280 nm. The CEA transgene also contained a modified CEA containing the highly immunogenic epitope CAP1-6D. The sequence encoding for the human Brachyury protein (T, NM_003181.3) was modified by introducing the enhancer T-cell HLA-A2 epitope (WLLPGTSTV; SEQ ID NO: 15) and removal of a 25-amino acid fragment involved in DNA binding. The resulting construct was subsequently sub-cloned into the Ad5 vector to generate the Ad5 [E1-, E2b-]-Brachyury construct. The MUC1 molecule consisted of two regions: the N-terminus (MUC1-n), which is the large extracellular domain of MUC1, and the C-terminus (MUC1-c), which has three regions: a small extracellular domain, a single transmembrane domain, and a cytoplasmic tail. The cytoplasmic tail contained sites for interaction with signaling proteins and acts as an oncogene and a driver of cancer motility, invasiveness and metastasis. For construction of the Ad5 [E1-, E2b-]-MUC1, the entire MUC1 transgene, including eight agonist epitopes, was subcloned into the Ad5 vector. The agonist epitopes included in the Ad5 [E1-, E2b-]-MUC1 vector bind to HLA-A2 (epitope P93L in the N-terminus, V1A and V2A in the VNTR region, and C1A, C2A and C3A in the C-terminus), HLA-A3 (epitope C5A), and HLA-A24 (epitope C6A in the C-terminus). The Tri-Ad5 vaccine was produced by combining of $10^{10}$ VP of Ad5 [E1-, E2b-]-Brachyury, Ad5 [E1-, E2b-]-CEA and Ad5 [E1-, E2b-]-MUC1 at a ratio of 1:1:1 ($3\times10^{10}$ VP total).

Subjects with CEA-expressing tumors are immunized by subcutaneous injection with a mixture of $5\times10^{11}$ virus particles (VPs) of the Ad5[E1-, E2b-]-CEA vaccine, $5\times10^{11}$ VPs of the Ad5[E1-, E2b-]-Brachyury vaccine, and $5\times10^{11}$ VPs of the Ad5[E1-, E2b-]-MUC1 vaccine. Vaccinations are repeated up to 3 times total over a 3-week period. The Ad5[E1-, E2b-]-CEA, Ad5[E1-, E2b-]-Brachyury, Ad5[E1-, E2b-]-MUC1 vaccine mixture is administered on days 7, 14, and 21, respectively. Subjects are also administered a super-agonist/super-agonist complex, such as ALT-803, at a dose of 1 μg SC on days 10 and 17, respectively. Subjects in need thereof have CEA-expressing cancer cells, such as CEA-expressing colorectal cancer. Subjects are any mammal, such as a human or a non-human primate.

Example 11

Treatment of Cancer with Ad5 [E1-, E2b-]-CEA(6D) Vaccine in Combination with ALT-803 and a Checkpoint Inhibitor This example describes treatment of cancer with Ad5 [E1-, E2b-]-CEA(6D) vaccine in combination with ALT-803 therapy and a checkpoint inhibitor. Subjects with CEA-expressing tumors are immunized with the Ad5 [E1-, E2b-]-CEA vaccine. The Ad5[E1-, E2b-]-CEA vaccine is administered at a dose of $5 \times 10^{11}$ virus particles (VPs) by subcutaneous (SC) injection. Vaccinations are repeated up to 3 times total over a 3-week period. The Ad5 [E1-, E2b-]-CEA vaccine is administered on days 7, 14, and 21, respectively. Subjects are also administered a super-agonist/super-agonist complex, such as ALT-803, at a dose of 1 μg SC on days 10 and 17, respectively.

The checkpoint inhibitor administered in combination therapy is an anti-PD-1 monoclonal antibody, such as Avelumab. An anti-PD-1 monoclonal antibody (avelumab) is infused in in order to enhance the vaccine effect. As a routine precaution, subjects enrolled in this trial are observed for 1 hour post infusion, in an area with resuscitation equipment and emergency agents. At all times during avelumab treatment, immediate emergency treatment of an infusion-related reaction or a severe hypersensitivity reaction according to institutional standards must be assured. In order to treat possible anaphylactic reactions, for instance, dexamethasone 10 mg and epinephrine in a 1:1000 dilution or equivalents are available along with equipment for assisted ventilation. Subjects receive intravenous infusion of avelumab over 1 hour (–10 minutes/+20 minutes, i.e., 50 to 80 minutes) as applicable at a dose of 10 mg/kg. Treatment with avelumab starts on the second vaccine treatment 3 weeks after the first vaccine injection. Alternatively, treatment with avelumab starts concurrently with the first vaccine treatment. An immune response against the CEA tumor-associated antigens (TAAs) is induced and then enhanced by injections with anti-PD-1 that will interfere with the inhibitory effect of the immune checkpoint pathway. Anti-PD-1 antibody is injected into subjects at a dose of 3 mg/kg administered IV after a vaccination beginning on week 3. This infusion (injection) procedure is repeated on weeks 9 and 12.

A subject in need thereof has any stage of disease progression, including metastatic colorectal cancer or advanced stage colorectal cancer. Subjects are any mammal, such as a human or a non-human primate. Administration is performed intravenously by infusion or subcutaneously. Administration of each therapy is given or days, weeks, or months. Therapies are administered once or multiple types, depending on the agent being delivered.

Example 12

Treatment of Cancer with Ad5 [E1-, E2b-]-CEA(6D) Vaccine in Combination with ALT-803, Low Dose Chemotherapy, and Low Dose Irradiation This example describes treatment of cancer with Ad5 [E1-, E2b-]-CEA(6D) vaccine in combination with ALT-803 therapy, low dose chemotherapy, and low dose irradiation. Subjects with CEA-expressing tumors are immunized with the Ad5 [E1-, E2b-]-CEA vaccine. The Ad5[E1-, E2b-]-CEA vaccine is administered at a dose of $5 \times 10^{11}$ virus particles (VPs) by subcutaneous (SC) injection. Vaccinations are repeated up to 3 times total over a 3-week period. The Ad5 [E1-, E2b-]-CEA vaccine is administered on days 7, 14, and 21, respectively. Subjects are also administered a super-agonist/super-agonist complex, such as ALT-803, at a dose of 1 SC on days 10 and 17, respectively.

Subjects are also administered low dose chemotherapy. The chemotherapy is cyclophosphamide. The chemotherapy is administered, orally or intravenously, at a dose that is lower than the clinical standard of care dosing. For example, the chemotherapy is administered at 50 mg twice a day (BID) on days 1-5 and 8-12 every 2 weeks for a total of 8 weeks.

Subjects are also, optionally, administered low dose radiation. The low dose radiation is administered at a dose that is lower than the clinical standard of care dosing. Concurrent sterotactic body radiotherapy (SBRT) at 8 Gy is given on day 8, 22, 36, 50 (every 2 weeks for 4 doses). Radiation is administered to all feasible tumor sites using SBRT. Subjects in need thereof have CEA-expressing cancer, and the cancer is eliminated. Subjects are any mammal, such as a human or a non-human animal.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

| SEQ ID NO | Sequence |
|---|---|
| SEQ ID NO: 1 | ATGGAGTCTCCCTCGGCCCCTCCCCACAGATGGTGCATCCCCTG |
| | GCAGAGGCTCCTGCTCACAGCCTCACTTCTAACCTTCTGGAACC |
| | CGCCCACCACTGCCAAGCTCACTATTGAATCCACGCCGTTCAAT |
| | GTCGCAGAGGGGAAGGAGGTGCTTCTACTTGTCCACAATCTGCC |
| | CCAGCATCTTTTTGGCTACAGCTGGTACAAAGGTGAAAGAGTGG |
| | ATGGCAACCGTCAAATTATAGGATATGTAATAGGAACTCAACA |
| | AGCTACCCCAGGGCCCGCATACAGTGGTCGAGAGATAATATAC |
| | CCCAATGCATCCCTGCTGATCCAGAACATCATCCAGAATGACAC |
| | AGGATTCTACACCCTACACGTCATAAAGTCAGATCTTGTGAATG |
| | AAGAAGCAACTGGCCAGTTCCGGGTATACCCGGAGCTGCCCAA |

| SEQ ID NO | Sequence |
|---|---|
| | GCCCTCCATCTCCAGCAACAACTCCAAACCCGTGGAGGACAAG<br>GATGCTGTGGCCTTCACCTGTGAACCTGAGACTCAGGACGCAAC<br>CTACCTGTGGTGGGTAAACAATCAGAGCCTCCCGGTCAGTCCCA<br>GGCTGCAGCTGTCCAATGGCAACAGGACCCTCACTCTATTCAAT<br>GTCACAAGAAATGACACAGCAAGCTACAAATGTGAAACCCAGA<br>ACCCAGTGAGTGCCAGGCGCAGTGATTCAGTCATCCTGAATGTC<br>CTCTATGGCCCGGATGCCCCCACCATTTCCCCTCTAAACACATCT<br>TACAGATCAGGGGAAAATCTGAACCTCTCCTGCCACGCAGCCTC<br>TAACCCACCTGCACAGTACTCTTGGTTTGTCAATGGGACTTTCCA<br>GCAATCCACCCAAGAGCTCTTTATCCCCAACATCACTGTGAATA<br>ATAGTGGATCCTATACGTGCCAAGCCCATAACTCAGACACTGGC<br>CTCAATAGGACCACAGTCACGACGATCACAGTCTATGCAGAGCC<br>ACCCAAACCCTTCATCACCAGCAACAACTCCAACCCCGTGGAGG<br>ATGAGGATGCTGTAGCCTTAACCTGTGAACCTGAGATTCAGAAC<br>ACAACCTACCTGTGGTGGGTAAATAATCAGAGCCTCCCGGTCAG<br>TCCCAGGCTGCAGCTGTCCAATGACAACAGGACCCTCACTCTAC<br>TCAGTGTCACAAGGAATGATGTAGGACCCTATGAGTGTGGAATC<br>CAGAACGAATTAAGTGTTGACCACAGCGACCCAGTCATCCTGAA<br>TGTCCTCTATGGCCCAGACGACCCCACCATTTCCCCCTCATACAC<br>CTATTACCGTCCAGGGGTGAACCTCAGCCTCTCCTGCCATGCAG<br>CCTCTAACCCACCTGCACAGTATTCTTGGCTGATTGATGGGAAC<br>ATCCAGCAACACACACAAGAGCTCTTTATCTCCAACATCACTGA<br>GAAGAACAGCGGACTCTATACCTGCCAGGCCAATAACTCAGCC<br>AGTGGCCACAGCAGGACTACAGTCAAGACAATCACAGTCTCTG<br>CGGAGCTGCCCAAGCCCTCCATCTCCAGCAACAACTCCAAACCC<br>GTGGAGGACAAGGATGCTGTGGCCTTCACCTGTGAACCTGAGGC<br>TCAGAACACAACCTACCTGTGGTGGGTAAATGGTCAGAGCCTCC<br>CAGTCAGTCCCAGGCTGCAGCTGTCCAATGGCAACAGGACCCTC<br>ACTCTATTCAATGTCACAAGAAATGACGCAAGAGCCTATGTATG<br>TGGAATCCAGAACTCAGTGAGTGCAAACCGCAGTGACCCAGTC<br>ACCCTGGATGTCCTCTATGGGCCGGACACCCCCATCATTTCCCC<br>CCCAGACTCGTCTTACCTTTCGGGAGCGAACCTCAACCTCTCCT<br>GCCACTCGGCCTCTAACCCATCCCCGCAGTATTCTTGGCGTATC<br>AATGGGATACCGCAGCAACACACACAAGTTCTCTTTATCGCCAA<br>AATCACGCCAAATAATAACGGGACCTATGCCTGTTTTGTCTCTA<br>ACTTGGCTACTGGCCGCAATAATTCCATAGTCAAGAGCATCACA<br>GTCTCTGCATCTGGAACTTCTCCTGGTCTCTCAGCTGGGGCCACT<br>GTCGGCATCATGATTGGAGTGCTGGTTGGGGTTGCTCTGATATA<br>G |
| SEQ ID NO: 2 | CATCATCAATAATATACCTTATTTTGGATTGAAGCCAATATGAT<br>AATGAGGGGGTGGAGTTTGTGACGTGGCGCGGGGCGTGGGAAC<br>GGGGCGGGTGACGTAGTAGTGTGGCGGAAGTGTGATGTTGCAA<br>GTGTGGCGGAACACATGTAAGCGACGGATGTGGCAAAAGTGAC<br>GTTTTTGGTGTGCGCCGGTGTACACAGGAAGTGACAATTTTCGC<br>GCGGTTTTAGGCGGATGTTGTAGTAAATTTGGGCGTAACCGAGT<br>AAGATTTGGCCATTTTCGCGGGAAAACTGAATAAGAGGAAGTG<br>AAATCTGAATAATTTTGTGTTACTCATAGCGCGTAATACTGTAA<br>TAGTAATCAATTACGGGGTCATTAGTTCATAGCCCATATATGGA<br>GTTCCGCGTTACATAACTTACGGTAAATGGCCCGCCTGGCTGAC<br>CGCCCAACGACCCCCGCCCATTGACGTCAATAATGACGTATGTT<br>CCCATAGTAACGCCAATAGGGACTTTCCATTGACGTCAATGGGT<br>GGAGTATTTACGGTAAACTGCCCACTTGGCAGTACATCAAGTGT<br>ATCATATGCCAAGTACGCCCCCTATTGACGTCAATGACGGTAAA<br>TGGCCCGCCTGGCATTATGCCCAGTACATGACCTTATGGGACTT<br>TCCTACTTGGCAGTACATCTACGTATTAGTCATCGCTATTACCAT<br>GGTGATGCGGTTTTGGCAGTACATCAATGGGCGTGGATAGCGGT<br>TTGACTCACGGGGATTTCCAAGTCTCCACCCCATTGACGTCAAT<br>GGGAGTTTGTTTTGGCACCAAAATCAACGGGACTTTCCAAAATG<br>TCGTAACAACTCCGCCCCATTGACGCAAATGGGCGGTAGGCGTG<br>TACGGTGGGAGGTCTATATAAGCAGAGCTGGTTTAGTGAACCGT<br>CAGATCCGCTAGAGATCTGGTACCGTCGACGCGGCCGCTCGAGC<br>CTAAGCTTGGTACCGAGCTCGGATCCACTAGTAACGGCCGCCAG<br>TGTGCTGGAATTCGGCTTAAAGGTACCCAGAGCAGACAGCCGCC<br>ACCATGGAGTCTCCCTCGGCCCCTCCCCACAGATGGTGCATCCC<br>CTGGCAGAGGCTCCTGCTCACAGCCTCACTTCTAACCTTCTGGA<br>ACCCGCCCACCACTGCCAAGCTCACTATTGAATCCACGCCGTTC<br>AATGTCGCAGAGGGGAAGGAGGTGCTTCTACTTGTCCACAATCT<br>GCCCCAGCATCTTTTTGGCTACAGCTGGTACAAAGGTGAAAGAG<br>TGGATGGCAACCGTCAAATTATAGGATATGTAATAGGAACTCAA<br>CAAGCTACCCCAGGGCCCGCATACAGTGGTCGAGAGATAATAT<br>ACCCCAATGCATCCCTGCTGATCCAGAACATCATCCAGAATGAC<br>ACAGGATTCTACACCCTACACGTCATAAAGTCAGATCTTGTGAA<br>TGAAGAAGCAACTGGCCAGTTCCGGGTATACCCGGAGCTGCCC<br>AAGCCCTCCATCTCCAGCAACAACTCCAAACCCGTGGAGGACA<br>AGGATGCTGTGGCCTTCACCTGTGAACCTGAGACTCAGGACGCA<br>ACCTACCTGTGGTGGGTAAACAATCAGAGCCTCCCGGTCAGTCC |

| SEQ ID NO | Sequence |
|---|---|
| | CAGGCTGCAGCTGTCCAATGGCAACAGGACCCTCACTCTATTCA
ATGTCACAAGAAATGACACAGCAAGCTACAAATGTGAAACCCA
GAACCCAGTGAGTGCCAGGCGCAGTGATTCAGTCATCCTGAATG
TCCTCTATGGCCCGGATGCCCCCACCATTTCCCCTCTAAACACAT
CTTACAGATCAGGGGAAAATCTGAACCTCTCCTGCCACGCAGCC
TCTAACCCACCTGCACAGTACTCTTGGTTTGTCAATGGGACTTTC
CAGCAATCCACCCAAGAGCTCTTTATCCCCAACATCACTGTGAA
TAATAGTGGATCCTATACGTGCCAAGCCCATAACTCAGACACTG
GCCTCAATAGGACCACAGTCACGACGATCACAGTCTATGCAGA
GCCACCCAAACCCTTCATCACCAGCAACAACTCCAACCCCGTGG
AGGATGAGGATGCTGTAGCCTTAACCTGTGAACCTGAGATTCAG
AACACAACCTACCTGTGGTGGGTAAATAATCAGAGCCTCCCGGT
CAGTCCCAGGCTGCAGCTGTCCAATGACAACAGGACCCTCACTC
TACTCAGTGTCACAAGGAATGATGTAGGACCCTATGAGTGTGGA
ATCCAGAACGAATTAAGTGTTGACCACAGCGACCCAGTCATCCT
GAATGTCCTCTATGGCCCAGACGACCCCACCATTTCCCCCTCAT
ACACCTATTACCGTCCAGGGGTGAACCTCAGCCTCTCCTGCCAT
GCAGCCTCTAACCCACCTGCACAGTATTCTTGGCTGATTGATGG
GAACATCCAGCAACACACACAAGAGCTCTTTATCTCCAACATCA
CTGAGAAGAACAGCGGACTCTATACCTGCCAGGCCAATAACTC
AGCCAGTGGCCACAGCAGGACTACAGTCAAGACAATCACAGTC
TCTGCGGAGCTGCCCAAGCCCTCCATCTCCAGCAACAACTCCAA
ACCCGTGGAGGACAAGGATGCTGTGGCCTTCACCTGTGAACCTG
AGGCTCAGAACACAACCTACCTGTGGTGGGTAAATGGTCAGAG
CCTCCCAGTCAGTCCCAGGCTGCAGCTGTCCAATGGCAACAGGA
CCCTCACTCTATTCAATGTCACAAGAAATGACGCAAGAGCCTAT
GTATGTGGAATCCAGAACTCAGTGAGTGCAAACCGCAGTGACC
CAGTCACCCTGGATGTCCTCTATGGGCCGGACACCCCCATCATT
TCCCCCCCAGACTCGTCTTACCTTTCGGGAGCGGACCTCAACCT
CTCCTGCCACTCGGCCTCTAACCCATCCCCGCAGTATTCTTGGCG
TATCAATGGGATACCGCAGCAACACACAAGTTCTCTTTATCG
CCAAAATCACGCCAAATAATAACGGGACCTATGCCTGTTTTGTC
TCTAACTTGGCTACTGGCCGCAATAATTCCATAGTCAAGAGCAT
CACAGTCTCTGCATCTGGAACTTCTCCTGGTCTCTCAGCTGGGGC
CACTGTCGGCATCATGATTGGAGTGCTGGTTGGGGTTGCTCTGA
TATAGCAGCCCTGGTGTAGTTTCTTCATTTCAGGAAGACTGACA
GTTGTTTTGCTTCTTCCTTAAAGCATTTGCAACAGCTACAGTCTA
AAAATTGCTTCTTTACCAAGGATATTTACAGAAAAGACTCTGACC
AGAGATCGAGACCATCCTCTAGATAAGATATCCGATCCACCGGA
TCTAGATAACTGATCATAATCAGCCATACCACATTTGTAGAGGT
TTTACTTGCTTTAAAAAAACCTCCCACACCTCCCCCTGAACCTGAA
ACATAAAATGAATGCAATTGTTGTTGTTAACTTGTTTATTGCAGC
TTATAATGGTTACAAATAAAGCAATAGCATCACAAATTTCACAA
ATAAAGCATTTTTTTCACTGCATTCTAGTTGTGGTTTGTCCAAAC
TCATCAATGTATCTTAACGCGGATCTGGGCGTGGTTAAGGGTGG
GAAAGAATATATAAGGTGGGGGTCTTATGTAGTTTTGTATCTGT
TTTGCAGCAGCCGCCGCCGCCATGAGCACCAACTCGTTTGATGG
AAGCATTGTGAGCTCATATTTGACAACGCGCATGCCCCCATGGG
CCGGGGTGCGTCAGAATGTGATGGGCTCCAGCATTGATGGTCGC
CCCGTCCTGCCCGCAAACTCTACTACCTTGACCTACGAGACCGT
GTCTGGAACGCCGTTGGAGACTGCAGCCTCCGCCGCCGCTTCAG
CCGCTGCAGCCACCGCCCGCGGGATTGTGACTGACTTTGCTTTC
CTGAGCCCGCTTGCAAGCAGTGCAGCTTCCCGTTCATCCGCCCG
CGATGACAAGTTGACGGCTCTTTTGGCACAATTGGATTCTTTGA
CCCGGGAACTTAATGTCGTTTCTCAGCAGCTGTTGGATCTGCGC
CAGCAGGTTTCTGCCCTGAAGGCTTCCTCCCCCTCCCAATGCGGTT
TAAAACATAAATAAAAAACCAGACTCTGTTTGGATTTGGATCAA
GCAAGTGTCTTGCTGTCTTTATTTAGGGGTTTTGCGCGCGCGGTA
GGCCCGGGACCAGCGGTCTCGGTCGTTGAGGGTCCTGTGTATTT
TTTCCAGGACGTGGTAAAGGTGACTCTGGATGTTCAGATACATG
GGCATAAGCCCGTCTCTGGGGTGGAGGTAGCACCACTGCAGAG
CTTCATGCTGCGGGGTGGTGTTGTAGATGATCCAGTCGTAGCAG
GAGCGCTGGGCGTGGTGCCTAAAAATGTCTTTCAGTAGCAAGCT
GATTGCCAGGGGCAGGCCCTTGGTGTAAGTGTTTACAAAGCGGT
TAAGCTGGGATGGGTGCATACGTGGGGATATGAGATGCATCTTG
GACTGTATTTTTAGGTTGGCTATGTTCCCAGCCATATCCCTCCGG
GGATTCATGTTGTGCAGAACCACCAGCACAGTGTATCCGGTGCA
CTTGGGAAATTTGTCATGTAGCTTAGAAGGAAATGCGTGGAAGA
ACTTGGAGACGCCCTTGTGACCTCCAAGATTTTCCATGCATTCGT
CCATAATGATGGCAATGGGCCCACGGGCGGCGGCCTGGGCGAA
GATATTTCTGGGATCACTAACGTCATAGTTGTGTTCCAGGATGA
GATCGTCATAGGCCATTTTTACAAAGCGCGGGCGGAGGGTGCCA
GACTGCGGTATAATGGTTCCATCCGGCCCAGGGGCGTAGTTACC
CTCACAGATTTGCATTTCCCACGCTTTGAGTTCAGATGGGGGGA
TCATGTCTACCTGCGGGCGATGAAGAAAACGGTTTCCGGGGTA
GGGGAGATCAGCTGGAAGAAAGCAGGTTCCTGAGCAGCTGCG
ACTTACCGCAGCCGGTGGGCCCGTAAATCACACCTATTACCGGC |

| SEQ ID NO | Sequence |
| --- | --- |
| | TGCAACTGGTAGTTAAGAGAGCTGCAGCTGCCGTCATCCCTGAG |
| | CAGGGGGGCCACTTCGTTAAGCATGTCCCTGACTCGCATGTTTT |
| | CCCTGACCAAATCCGCCAGAAGGCGCTCGCCGCCCAGCGATAG |
| | CAGTTCTTGCAAGGAAGCAAAGTTTTTCAACGGTTTGAGACCGT |
| | CCGCCGTAGGCATGCTTTTGAGCGTTTGACCAAGCAGTTCCAGG |
| | CGGTCCCACAGCTCGGTCACCTGCTCTACGGCATCTCGATCCAG |
| | CATATCTCCTCGTTTCGCGGGTTGGGGCGGCTTTCGCTGTACGGC |
| | AGTAGTCGGTGCTCGTCCAGACGGGCCAGGGTCATGTCTTTCCA |
| | CGGGCGCAGGGTCCTCGTCAGCGTAGTCTGGGTCACGGTGAAG |
| | GGGTGCGCTCCGGGCTGCGCGCTGGCCAGGGTGCGCTTGAGGCT |
| | GGTCCTGCTGGTGCTGAAGCGCTGCCGGTCTTCGCCCTGCGCGT |
| | CGGCCAGGTAGCATTTGACCATGGTGTCATAGTCCAGCCCCTCC |
| | GCGGCGTGGCCCTTGGCGCGCAGCTTGCCCTTGGAGGAGGCGCC |
| | GCACGAGGGGCAGTGCAGACTTTTGAGGGCGTAGAGCTTGGGC |
| | GCGAGAAATACCGATTCCGGGGAGTAGGCATCCGCGCCGCAGG |
| | CCCCGCAGACGGTCTCGCATTCCACGAGCCAGGTGAGCTCTGGC |
| | CGTTCGGGGTCAAAAACCAGGTTTCCCCCATGCTTTTTGATGCG |
| | TTTCTTACCTCTGGTTTCCATGAGCCGGTGTCCACGCTCGGTGAC |
| | GAAAAGGCTGTCCGTGTCCCCGTATACAGACTTGAGAGGCCTGT |
| | CCTCGAGCGGTGTTCCGCGGTCCTCCTCGTATAGAAACTCGGAC |
| | CACTCTGAGACAAAGGCTCGCGTCCAGGCCAGCACGAAGGAGG |
| | CTAAGTGGGAGGGGTAGCGGTCGTTGTCCACTAGGGGTCCACT |
| | CGCTCCAGGGTGTGAAGACACATGTCGCCCTCTTCGGCATCAAG |
| | GAAGGTGATTGGTTTGTAGGTGTAGGCCACGTGACCGGGTGTTC |
| | CTGAAGGGGGCTATAAAAGGGGGTGGGGGCGCGTTCGTCCTC |
| | ACTCTCTTCCGCATCGCTGTCTGCGAGGGCCAGCTGTTGGGGTG |
| | AGTACTCCCTCTGAAAAGCGGGCATGACTTCTGCGCTAAGATTG |
| | TCAGTTTCCAAAAACGAGGAGGATTTGATATTCACCTGGCCCGC |
| | GGTGATGCCTTTGAGGGTGGCCGCATCCATCTGGTCAGAAAAGA |
| | CAATCTTTTTGTTGTCAAGCTTGGTGGCAAACGACCCGTAGAGG |
| | GCGTTGGACAGCAACTTGGCGATGGAGCGCAGGGTTTGGTTTTT |
| | GTCGCGATCGGCGCGCTCCTTGGCCGCGATGTTTAGCTGCACGT |
| | ATTCGCGCGCAACGCACCGCCATTCGGGAAAGACGGTGGTGCG |
| | CTCGTCGGGCACCAGGTGCACGCGCCAACCGCGGTTGTGCAGG |
| | GTGACAAGGTCAACGCTGGTGGCTACCTCTCCGCGTAGGCGCTC |
| | GTTGGTCCAGCAGAGGCGGCCGCCCTTGCGCGAGCAGAATGGC |
| | GGTAGGGGGTCTAGCTGCGTCTCGTCCGGGGGGTCTGCGTCCAC |
| | GGTAAAGACCCCGGGCAGCAGGCGCGCGTCGAAGTAGTCTATC |
| | TTGCATCCTTGCAAGTCTAGCGCCTGCTGCCATGCGCGGGCGGC |
| | AAGCGCGCGCTCGTATGGGTTGAGTGGGGGACCCCATGGCATG |
| | GGGTGGGTGAGCGCGGAGGCGTACATGCCGCAAATGTCGTAAA |
| | CGTAGAGGGGCTCTCTGAGTATTCCAAGATATGTAGGGTAGCAT |
| | CTTCCACCGCGGATGCTGGCGCGCACGTAATCGTATAGTTCGTG |
| | CGAGGGAGCGAGGAGGTCGGGACCGAGGTTGCTACGGGCGGGC |
| | TGCTCTGCTCGGAAGACTATCTGCCTGAAGATGGCATGTGAGTT |
| | GGATGATATGGTTGGACGCTGGAAGACGTTGAAGCTGGCGTCTG |
| | TGAGACCTACCGCGTCACGCACGAAGGAGGCGTAGGAGTCGCG |
| | CAGCTTGTTGACCAGCTCGGCGGTGACCTGCACGTCTAGGGCGC |
| | AGTAGTCCAGGGTTTCCTTGATGATGTCATACTTATCCTGTCCCT |
| | TTTTTTTTCCACAGCTCGCGGTTGAGGACAAACTCTTCGCGGTCTT |
| | TCCAGTACTCTTGGATCGGAAACCCGTCGGCCTCCGAACGGTAA |
| | GAGCCTAGCATGTAGAACTGGTTGACGGCCTGGTAGGCGCAGC |
| | ATCCCTTTTCTACGGGTAGCGCGTATGCCTGCGCGGCCTTCCGG |
| | CATGACCAGCATGAAGGGCACGAGCTGCTTCCCAAAGGCCCCC |
| | ATCCAAGTATAGGTCTCTACATCGTAGGTGACAAAGAGACGCTC |
| | GGTGCGAGGATGCGAGCCGATCGGGAAGAACTGGATCTCCCGC |
| | CACCAATTGGAGGAGTGGCTATTGATGTGGTGAAAGTAGAAGT |
| | CCCTGCGACGGGCCGAACACTCGTGCTGGCTTTTGTAAAAACGT |
| | GCGCAGTACTGGCAGCGGTGCACGGGCTGTACATCCTGCACGA |
| | GGTTGACCTGACGACCGCGCACAAGGAAGCAGAGTGGGAATTT |
| | GAGCCCCTCGCCTGGCGGGTTTGGCTGGTGGTCTTCTACTTCGG |
| | CTGCTTGTCCTTGACCGTCTGGCTGCTCGAGGGGAGTTACGGTG |
| | GATCGGACCACCACGCCGCGCGAGCCCAAAGTCCAGATGTCCG |
| | CGCGCGGCGGTCGGAGCTTGATGACAACATCGCGCAGATGGGA |
| | GCTGTCCATGGTCTGGAGCTCCCGCGGCGTCAGGTCAGGCGGGA |
| | GCTCCTGCAGGTTTACCTCGCATAGACGGGTCAGGGCGGGGCT |
| | AGATCCAGGTGATACCTAATTTCCAGGGGCTGGTTGGTGGCGGC |
| | GTCGATGGCTTGCAAGAGGCCGCATCCCCGCGGCGCGACTACG |
| | GTACCGCGCGGCGGGCGGTGGGCCGCGGGGTGTCCTTGGATG |
| | ATGCATCTAAAAGCGGTGACGCGGGCGAGCCCCCGGAGGTAGG |
| | GGGGGCTCCGGACCCGCCGGGAGGGGGCAGGGGCACGTCGG |
| | CGCCGCGCGCGGGCAGGAGCTGGTGCTGCGCGCGTAGGTTGCT |
| | GGCGAACGCGACGACGCGGCGGTTGATCTCCTGAATCTGGCGCC |
| | TCTGCGTGAAGACGACGGGCCCGGTGAGCTTGAACCTGAAAGA |
| | GAGTTCGACAGAATCAATTTCGGTGTCGTTGACGGCGGCCTGGC |
| | GCAAAATCTCCTGCACGTCTCCTGAGTTGTCTTGATAGGCGATC |
| | TCGGCCATGAACTGCTCGATCTCTTCCTCCTGGAGATCTCCGCGT |

| SEQ ID NO | Sequence |
|---|---|
| | CCGGCTCGCTCCACGGTGGCGGCGAGGTCGTTGGAAATGCGGG |
| | CCATGAGCTGCGAGAAGGCGTTGAGGCCTCCCTCGTTCCAGACG |
| | CGGCTGTAGACCACGCCCCCTTCGGCATCGCGGGCGCGCATGAC |
| | CACCTGCGCGAGATTGAGCTCCACGTGCCGGGCGAAGACGGCG |
| | TAGTTTCGCAGGCGCTGAAAGAGGTAGTTGAGGGTGGTGGCGG |
| | TGTGTTCTGCCACGAAGAAGTACATAACCCAGCGTCGCAACGTG |
| | GATTCGTTGATAATTGTTGTGTAGGTACTCCGCCGCCGAGGGAC |
| | CTGAGCGAGTCCGCATCGACCGGATCGGAAAACCTCTCGAGAA |
| | AGGCGTCTAACCAGTCACAGTCGCAAGGTAGGCTGAGCACCGT |
| | GGCGGGCGGCAGCGGGCGGCGGTCGGGGTTGTTTCTGGCGGAG |
| | GTGCTGCTGATGATGTAATTAAAGTAGGCGGTCTTGAGACGGCG |
| | GATGGTCGACAGAAGCACCATGTCCTTGGGTCCGGCCTGCTGAA |
| | TGCGCAGGCGGTCGGCCATGCCCCAGGCTTCGTTTTGACATCGG |
| | CGCAGGTCTTTGTAGTAGTCTTGCATGAGCCTTTCTACCGGCACT |
| | TCTTCTTCTCCTTCCTCTTGTCCTGCATCTCTTGCATCTATCGCTG |
| | CGGCGGCGGCGGAGTTTGGCCGTAGGTGGCGCCCTCTTCCTCCC |
| | ATGCGTGTGACCCCGAAGCCCCTCATCGGCTGAAGCAGGGCTAG |
| | GTCGGCGACAACGCGCTCGGCTAATATGGCCTGCTGCACCTGCG |
| | TGAGGGTAGACTGGAAGTCATCCATGTCCACAAAGCGGTGGTAT |
| | GCGCCCGTGTTGATGGTGTAAGTGCAGTTGGCCATAACGGACCA |
| | GTTAACGGTCTGGTGACCCGGCTGCGAGAGCTCGGTGTACCTGA |
| | GACGCGAGTAAGCCCTCGAGTCAAATACGTAGTCGTTGCAAGTC |
| | CGCACCAGGTACTGGTATCCCACCAAAAAGTGCGGCGGCGGCT |
| | GGCGGTAGAGGGGCCAGCGTAGGGTGGCCGGGGCTCCGGGGGC |
| | GAGATCTTCCAACATAAGGCGATGATATCCGTAGATGTACCTGG |
| | ACATCCAGGTGATGCCGGCGGCGGTGGTGGAGGCGCGCGGAAA |
| | GTCGCGGACGCGGTTCCAGATGTTGCGCAGCGGCAAAAAGTGC |
| | TCCATGGTCGGGACGCTCTGGCCGGTCAGGCGCGCAATCGTT |
| | GACGCTCTAGCGTGCAAAAGGAGAGCCTGTAAGCGGGCACTCT |
| | TCCGTGGTCTGGTGGATAAATTCGCAAGGGTATCATGGCGGACG |
| | ACCGGGGTTCGAGCCCCGTATCCGGCCGTCCGCCGTGATCCATG |
| | CGGTTACCGCCCGCGTGTCGAACCCAGGTGTGCGACGTCAGACA |
| | ACGGGGGAGTGCTCCTTTTGGCTTCCTTCCAGGCGCGGCGGCTG |
| | CTGCGCTAGCTTTTTTGGCCACTGGCCGCGCGCAGCGTAAGCGG |
| | TTAGGCTGGAAAGCGAAAGCATTAAGTGGCTCGCTCCCTGTAGC |
| | CGGAGGGTTATTTTCCAAGGGTTGAGTCGCGGGACCCCCGGTTC |
| | GAGTCTCGGACCGGCCGGACTGCGGCGAACGGGGGTTTGCCTCC |
| | CCGTCATGCAAGACCCCGCTTGCAAATTCCTCCGGAAACAGGGA |
| | CGAGCCCCTTTTTTGCTTTTCCCAGATGCATCCGGTGCTGCGGCA |
| | GATGCGCCCCCCTCCTCAGCAGCGGCAAGAGCAAGAGCAGCGG |
| | CAGACATGCAGGGCACCCTCCCCTCCTCCTACCGCGTCAGGAGG |
| | GGCGACATCCGCGGTTGACGCGGCAGCAGATGGTGATTACGAA |
| | CCCCCGCGGCGCCGGGCCCGGCACTACCTGGACTTGGAGGAGG |
| | GCGAGGGCCTGGCGCGGCTAGGAGCGCCCTCTCCTGAGCGGCA |
| | CCCAAGGGTGCAGCTGAAGCGTGATACGCGTGAGGCGTACGTG |
| | CCGCGGCAGAACCTGTTTCGCGACCGCGAGGGAGAGGAGCCCG |
| | AGGAGATGCGGGATCGAAAGTTCCACGCAGGGCGCGAGCTGCG |
| | GCATGGCCTGAATCGCGAGCGGTTGCTGCGCGAGGAGGACTTTG |
| | AGCCCGACGCGCGAACCGGGATTAGTCCCGCGCGCGCACACGT |
| | GGCGGCCGCCGACCTGGTAACCGCATACGAGCAGACGGTGAAC |
| | CAGGAGATTAACTTTCAAAAAAGCTTTAACAACCACGTGCGTAC |
| | GCTTGTGGCGCGCGAGGAGGTGGCTATAGGACTGATGCATCTGT |
| | GGGACTTTGTAAGCGCGCTGGAGCAAAACCCAAATAGCAAGCC |
| | GCTCATGGCGCAGCTGTTCCTTATAGTGCAGCACAGCAGGGACA |
| | ACGAGGCATTCAGGGATGCGCTGCTAAACATAGTAGAGCCCGA |
| | GGGGCCGCTGGCTGCTCGATTTGATAAACATCCTGCAGAGCATAG |
| | TGGTGCAGGAGCGCAGCTTGAGCCTGGCTGACAAGGTGGCCGC |
| | CATCAACTATTCCATGCTTAGCCTGGGCAAGTTTTACGCCCGCA |
| | AGATATACCATACCCCTTACGTTCCATAGACAAGGAGGTAAAG |
| | ATCGAGGGGTTCTACATGCGCATGGCGCTGAAGGTGCTTACCTT |
| | GAGCGACGACCTGGGCGTTTATCGCAACGAGCGCATCCACAAG |
| | GCCGTGAGCGTGAGCCGGCGGCGCGAGCTCAGCGACCGCGAGC |
| | TGATGCACAGCCTGCAAAGGGCCCTGGCTGGCACGGGCAGCGG |
| | CGATAGAGAGGCCGAGTCCTACTTTGACGCGGGCGCTGACCTGC |
| | GCTGGGCCCCAAGCCGACGCGCCCTGGAGGCAGCTGGGGCCGG |
| | ACCTGGGCTGGCGGTGGCACCCGCGCGCGCTGGCAACGTCGGC |
| | GGCGTGGAGGAATATGACGAGGACGATGAGTACGAGCCAGAGG |
| | ACGGCGAGTACTAAGCGGTGATGTTTCTGATCAGATGATGCAAG |
| | ACGCAACGGACCCGGCGGTGCGGGCGGCGCTGCAGAGCCAGCC |
| | GTCCGGCCTTAACTCCACGGACGACTGGCGCCAGGTCATGGACC |
| | GCATCATGTCGCTGACTGCGCGCAATCCTGACGCGTTCCGGCAG |
| | CAGCCGCAGGCCAACCGGCTCTCCGCAATTCTGGAAGCGGTGGT |
| | CCCGGCGCGCGCAAACCCCACGCACGAGAAGGTGCTGGCGATC |
| | GTAAACGCGCTGGCCGAAAACAGGGCCATCCGGCCCGACGAGG |
| | CCGGCCTGGTCTACGACGCGCTGCTTCAGCGCGTGGCTCGTTAC |
| | AACAGCGGCAACGTGCAGACCAACCTGGACCGGCTGGTGGGGG |
| | ATGTGCGCGAGGCCGTGGCGCAGCGTGAGCGCGCGCAGCAGCA |

| SEQ ID NO | Sequence |
|---|---|
| | GGGCAACCTGGGCTCCATGGTTGCACTAAACGCCTTCCTGAGTA |
| | CACAGCCCGCCAACGTGCCGCGGGACAGGAGGACTACACCAA |
| | CTTTGTGAGCGCACTGCGGCTAATGGTGACTGAGACACCGCAA |
| | GTGAGGTGTACCAGTCTGGGCCAGACTATTTTTTCCAGACCAGT |
| | AGACAAGGCCTGCAGACCGTAAACCTGAGCCAGGCTTTCAAAA |
| | ACTTGCAGGGGCTGTGGGGGGTGCGGGCTCCCACAGGCGACCG |
| | CGCCGACCGTGTCTAGCTTGCTGACGCCCAACTCGCGCCTGTTGC |
| | TGCTGCTAATAGCGCCCTTCACGGACAGTGGCAGCGTGTCCCGG |
| | GACACATACCTAGGTCACTTGCTGACACTGTACCGCGAGGCCAT |
| | AGGTCAGGCGCATGTGGACGAGCATACTTTCCAGGAGATTACA |
| | AGTGTCAGCCGCGCGCTGGGCAGGAGGACACGGGCAGCCTGG |
| | AGGCAACCCTAAACTACCTGCTGACCAACCGGCGGCAGAAGAT |
| | CCCCTCGTTGCACAGTTTAAACAGCGAGGAGGAGCGCATTTTGC |
| | GCTACGTGCAGCAGAGCGTGAGCCTTAACCTGATGCGCGACGG |
| | GGTAACGCCCAGCGTGGCGCTGGACATGACCGCGCGCAACATG |
| | GAACCGGGCATGTATGCCTCAAACCGGCCGTTTATCAACCGCCT |
| | AATGGACTACTTGCATCGCGCGGCCGCCGTGAACCCCGAGTATT |
| | TCACCAATGCCATCTTGAACCCGCACTGGCTACCGCCCCTGGT |
| | TTCTACACCGGGGGATTCGAGGTGCCCGAGGGTAACGATGGATT |
| | CCTCTGGGACGACATAGACGACAGCGTGTTTTCCCCGCAACCGC |
| | AGACCCTGCTAGAGTTGCAACAGCGCGAGCAGGCAGAGGCGGC |
| | GCTGCGAAAGGAAAGCTTCCGCAGGCCAAGCAGCTTGTCCGAT |
| | CTAGGCGCTGCGGCCCCGCGGTCAGATGCTAGTAGCCCATTTCC |
| | AAGCTTGATAGGGTCTCTTACCAGCACTCGCACCACCCGCCCGC |
| | GCCTGCTGGGCGAGGAGGAGTACCTAAACAACTCGCTGCTGCA |
| | GCCGCAGCGCGAAAAAAACCTGCCTCCGGCATTTCCCAACAAC |
| | GGGATAGAGAGCCTAGTGGACAAGATGAGTAGATGGAAGACGT |
| | ACGCGCAGGAGCACAGGGACGTGCCAGGCCCGCGCCCGCCCAC |
| | CCGTCGTCAAAGGCACGACCGTCAGCGGGGTCTGGTGTGGGAG |
| | GACGATGACTCGGCAGACGACAGCAGCGTCCTGGATTTGGGAG |
| | GGAGTGGCAACCCGTTTGCGCACCTTCGCCCCAGGCTGGGGAGA |
| | ATGTTTTAAAAAAAAAAAAGCATGATGCAAAATAAAAAACTCA |
| | CCAAGGCCATGGCACCGAGCGTTGGTTTTCTTGTATTCCCCTTAG |
| | TATGCGGCGCGCGGCGATGTATGAGGAAGGTCCTCCTCCCTCCT |
| | ACGAGAGTGTGGTGAGCGCGGCGCCAGTGGCGGCGGCGCTGGG |
| | TTCTCCCTTCGATGCTCCCCTGGACCCGCCGTTTGTGCCTCCGCG |
| | GTACCTGCGGCCTACCGGGGGGAGAAACAGCATCCGTTACTCTG |
| | AGTTGGCACCCCTATTCGACACCACCCGTGTGTACCTGGTGGAC |
| | AACAAGTCAACGGATGTGGCATCCCTGAACTACCAGAACGACC |
| | ACAGCAACTTTCTGACCACGGTCATTCAAAACAATGACTACAGC |
| | CCGGGGGAGGCAAGCACACAGACCATCAATCTTGACGACCGGT |
| | CGCACTGGGGCGGCGACCTGAAAACCATCCTGCATACCAACAT |
| | GCCAAATGTGAACGAGTTCATGTTTACCAATAAGTTTAAGGCGC |
| | GGGTGATGGTGTCGCGCTTGCCTACTAAGGACAATCAGGTGGAG |
| | CTGAAATACGAGTGGGTGGAGTTCACGCTGCCCGAGGGCAACT |
| | ACTCCGAGACCATGACCATAGACCTTATGAACAACGCGATCGTG |
| | GAGCACTACTTGAAAGTGGGCAGACAGAACGGGGTTCTGGAAA |
| | GCGACATCGGGGTAAAGTTTGACACCCGCAACTTCAGACTGGG |
| | GTTTGACCCCGTCACTGGTCTTGTCATGCCTGGGGTATATACAA |
| | ACGAAGCCTTCCATCCAGACATCATTTTGCTGCCAGGATGCGGG |
| | GTGGACTTCACCCACAGCCGCCTGAGCAACTTGTTGGGCATCCG |
| | CAAGCGGCAACCCTTCCAGGAGGGCTTTAGGATCACCTACGATG |
| | ATCTGGAGGGTGGTAACATTCCCGCACTGTTGGATGTGGACGCC |
| | TACCAGGCGAGCTTGAAAGATGACACCGAACAGGGCGGGGGTG |
| | GCGCAGGCGGCAGCAACAGCAGTGGCAGCGGCGCGGAAGAGA |
| | ACTCCAACGCGGCAGCCGCGGCAATGCAGCCGGTGGAGGACAT |
| | GAACGATCATGCCATTCGCGGCGACACCTTTGCCACACGGGCTG |
| | AGGAGAAGCGCGCTGAGGCCGAAGCAGCGGCCGAAGCTGCCGC |
| | CCCCGCTGCGCAACCCGAGGTCGAGAAGCCTCAGAAGAAACCG |
| | GTGATCAAACCCCTGACAGAGGACAGCAAGAAACGCAGTTACA |
| | ACCTAATAAGCAATGACAGCACCTTCACCCAGTACCGCAGCTGG |
| | TACCTTGCATACAACTACGGCGACCCTCAGACCGGAATCCGCTC |
| | ATGGACCCTGCTTTGCACTCCTGACGTAACCTGCGGCTCGGAGC |
| | AGGTCTACTGGTCGTTGCCAGACATGATGCAAGACCCCGTGACC |
| | TTCCGCTCCACGCGCCAGATCAGCAACTTTCCGGTGGTGGGCGC |
| | CGAGCTGTTGCCCGTGCACTCCAAGAGCTTCTACAACGACCAGG |
| | CCGTCTACTCCCAACTCATCCGCCAGTTTACCTCTCTGACCCACG |
| | TGTTCAATCGCTTTCCCGAGAACCAGATTTTGGCGCGCCCGCCA |
| | GCCCCCACCATCACCACCGTCAGTGAAAACGTTCCTGCTCTCAC |
| | AGATCACGGGACGCTACCGCTGCGCAACAGCATCGGAGGAGTC |
| | CAGCGAGTGACCATTACTGACGCCAGACGCCGCACCTGCCCCTA |
| | CGTTTACAAGGCCCTGGGCATAGTCTCGCCGCGCGTCCTATCGA |
| | GCCGCACTTTTTGAGCAAGCATGTCCATCCTTATATCGCCCAGC |
| | AATAACACAGGCTGGGGCCTGCGCTTCCCAAGCAAGATGTTTGG |
| | CGGGGCCAAGAAGCGCTCCGACCAACACCCAGTGCGCGTGCGC |
| | GGGCACTACCGCGCGCCCTGGGGCGCGCACAAACGCGGCCGCA |
| | CTGGGCGCACCACCGTCGATGACGCCATCGACGCGGTGGTGGA |

| SEQ ID NO | Sequence |
|---|---|
| | GGAGGCGCGCAACTACACGCCCACGCCGCCACCAGTGTCCACA |
| | GTGGACGCGGCCATTCAGACCGTGGTGCGCGGAGCCCGGCGCT |
| | ATGCTAAAATGAAGAGACGGCGGAGGCGCGTAGCACGTCGCCA |
| | CCGCCGCCGACCCGGCACTGCCGCCCAACGCGCGGCGGCGGCC |
| | CTGCTTAACCGCGCACGTCGCACCGGCCGACGGGCGGCCATGCG |
| | GGCCGCTCGAAGGCTGGCCGCGGGTATTGTCACTGTGCCCCCCA |
| | GGTCCAGGCGACGAGCGGCCGCCGCAGCAGCCGCGGCCATTAG |
| | TGCTATGACTCAGGGTCGCAGGGGCAACGTGTATTGGGTGCGCG |
| | ACTCGGTTAGCGGCCTGCGCGTGCCCGTGCGCACCCGCCCCCCG |
| | CGCAACTAGATTGCAAGAAAAAACTACTTAGACTCGTACTGTTG |
| | TATGTATCCAGCGGCGGCGGCGCGCAACGAAGCTATGTCCAAG |
| | CGCAAAATCAAAGAAGAGATGCTCCAGGTCATCGCGCCGGAGA |
| | TCTATGGCCCCCGAAGAAGGAAGAGCAGGATTACAAGCCCCG |
| | AAAGCTAAAGCGGGTCAAAAAGAAAAAGAAAGATGATGATGAT |
| | GAACTTGACGACGAGGTGGAACTGCTGCACGCTACCGCGCCCA |
| | GGCGACGGGTACAGTGGAAAGGTCGACGCGTAAAACGTGTTTT |
| | GCGACCCGGCACCACCGTAGTCTTTACGCCCGGTGAGCGCTCCA |
| | CCCGCACCTACAAGCGCGTGTATGATGAGGTGTACGGCGACGA |
| | GGACCTGCTTGAGCAGGCCAACGAGCGCCTCGGGGAGTTTGCCT |
| | ACGGAAAGCGGCATAAGGACATGCTGGCGTTGCCGCTGGACGA |
| | GGGCAACCCAACACCTAGCCTAAAGCCCGTAACACTGCAGCAG |
| | GTGCTGCCCGCGCTTGCACCGTCCGAAGAAAAGCGCGGCCTAA |
| | AGCGCGAGTCTGGTGACTTGGCACCCACCGTGCAGCTGATGGTA |
| | CCCAAGCGCCAGCGACTGGAAGATGTCTTGGAAAAAATGACCG |
| | TGGAACCTGGGCTGGAGCCCGAGGTCCGCGTGCGGCCAATCAA |
| | GCAGGTGGCGCCGGGACTGGGCGTGCAGACCGTGGACGTTCAG |
| | ATACCCACTACCAGTAGCACCAGTATTGCCACCGCCACAGAGGG |
| | CATGGAGACACAAACGTCCCCGGTTGCCTCAGCGGTGGCGGAT |
| | GCCGCGGTGCAGGCGGTCGCTGCGGCCGCGTCCAAGACCTCTAC |
| | GGAGGTGCAAACGGACCCGTGGATGTTTCGCGTTTCAGCCCCCC |
| | GGCGCCCGCGCCGTTCGAGGAAGTACGGCGCCGCCAGCGCGCT |
| | ACTGCCCGAATATGCCCTACATCCTTCCATTGCGCCTACCCCCG |
| | GCTATCGTGGCTACACCTACCGCCCCAGAAGACGAGCAACTACC |
| | CGACGCCGAACCACCACTGGAACCCGCCGCCGCCGTCGCCGTCG |
| | CCAGCCCGTGCTGGCCCCGATTTCCGTGCGCAGGGTGGCTCGCG |
| | AAGGAGGCAGGACCCTGGTGCTGCCAACAGCGCGCTACCACCC |
| | CAGCATCGTTTAAAAGCCGGTCTTTGTGGTTCTTGCAGATATGG |
| | CCCTCACCTGCCGCCTCCGTTTCCCGGTGCCGGGATTCCGAGGA |
| | AGAATGCACCGTAGGAGGGGCATGGCCGGCCACGGCCTGACGG |
| | GCGGCATGCGTCGTGCGCACCACCGGCGGCGGCGCGCGTCGCA |
| | CCGTCGCATGCGCGGCGGTATCCTGCCCCTCCTTATTCCACTGAT |
| | CGCCGCGGCGATTGGCGCCGTGCCCGGAATTGCATCCGTGGCCT |
| | TGCAGGCGCAGAGACACTGATTAAAAACAAGTTGCATGTGGAA |
| | AAATCAAAATAAAAAGTCTGGACTCTCACGCTCGCTTGGTCCTG |
| | TAACTATTTTGTAGAATGGAAGACATCAACTTTGCGTCTCTGGC |
| | CCCGCGACACGGCTCGCGCCCGTTCATGGGAAACTGGCAAGAT |
| | ATCGGCACCAGCAATATGAGCGGTGGCGCCTTCAGCTGGGGCTC |
| | GCTGTGGAGCGGCATTAAAAATTTCGGTTCCACCGTTAAGAACT |
| | ATGGCAGCAAGGCCTGGAACAGCAGCACAGGCCAGATGCTGAG |
| | GGATAAGTTGAAAGAGCAAAATTTCCAACAAAAGGTGGTAGAT |
| | GGCCTGGCCTCTGGCATTAGCGGGGTGGTGGACCTGGCCAACCA |
| | GGCAGTGCAAAATAAGATTAACAGTAAGCTTGATCCCCGCCCTC |
| | CCGTAGAGGAGCCTCCACCGGCCGTGGAGACAGTGTCTCCAGA |
| | GGGGCGTGGCGAAAAGCGTCCGCGCCCCGACAGGGAAGAAACT |
| | CTGGTGACGCAAATAGACGAGCCTCCCTCGTACGAGGAGGCAC |
| | TAAAGCAAGGCCTGCCCACCACCCGTCCCATCGCGCCCATGGCT |
| | ACCGGAGTGCTGGGCCAGCACACACCCGTAACGCTGGACCTGC |
| | CTCCCCCCGCCGACACCCAGCAGAAACCTGTGCTGCCAGGCCCG |
| | ACCGCCGTTGTTGTAACCCGTCCTAGCCGCGCGTCCCTGCGCCG |
| | CGCCGCCAGCGGTCCGCGATCGTTGCGGCCCGTAGCCAGTGGCA |
| | ACTGGCAAAGCACACTGAACAGCATCGTGGGTCTGGGGGTGCA |
| | ATCCCTGAAGCGCCGACGATGCTTCTGATAGCTAACGTGTCGTA |
| | TGTGTGTCATGTATGCGTCCATGTCGCCGCCAGAGGAGCTGCTG |
| | AGCCGCCGCGCGCCCGCTTTCCAAGATGGCTACCCCTTCGATGA |
| | TGCCGCAGTGGTCTTACATGCACATCTCGGGCCAGGACGCCTCG |
| | GAGTACCTGAGCCCCGGGCTGGTGCAGTTTGCCCGCGCCACCGA |
| | GACGTACTTCAGCCTGAATAACAAGTTTAGAAACCCCACGGTGG |
| | CGCCTACGCACGACGTGACCACAGACCGGTCCCAGCGTTTGACG |
| | CTGCGGTTCATCCCTGTGGACCGTGAGGATACTGCGTACTCGTA |
| | CAAGGCGCGGTTCACCCTAGCTGTGGGTGATAACCGTGTGCTGG |
| | ACATGGCTTCCACGTACTTTGACATCCGCGGCGTGCTGGACAGG |
| | GGCCCTACTTTTAAGCCCTACTCTGGCACTGCCTACAACGCCCT |
| | GGCTCCCAAGGGTGCCCCAAATCCTTGCGAATGGGATGAAGCTG |
| | CTACTGCTCTTGAAATAAACCTAGAAGAAGAGGACGATGACAA |
| | CGAAGACGAAGTAGACGAGCAAGCTGAGCAGCAAAAAACTCAC |
| | GTATTTGGGCAGGCGCCTTATTCTGGTATAAATATTACAAAGGA |
| | GGGTATTCAAATAGGTGTCGAAGGTCAAACACCTAAATATGCCG |

| SEQ ID NO | Sequence |
| --- | --- |
| | ATAAAACATTTCAACCTGAACCTCAAATAGGAGAATCTCAGTGG |
| | TACGAAACAGAAATTAATCATGCAGCTGGGAGAGTCCTAAAAA |
| | AGACTACCCCAATGAAACCATGTTACGGTTCATATGCAAAACCC |
| | ACAAATGAAAATGGAGGGCAAGGCATTCTTGTAAAGCAACAAA |
| | ATGGAAAGCTAGAAAGTCAAGTGGAAATGCAATTTTTCTCAACT |
| | ACTGAGGCAGCCGCAGGCAATGGTGATAACTTGACTCCTAAAGT |
| | GGTATTGTACAGTGAAGATGTAGATATAGAAACCCCAGACACTC |
| | ATATTTCTTACATGCCCACTATTAAGGAAGGTAACTCACGAGAA |
| | CTAATGGGCCAACAATCTATGCCCAACAGGCCTAATTACATTGC |
| | TTTTAGGGACAATTTTATTGGTCTAATGTATTACAACAGCACGG |
| | GTAATATGGGTGTTCTGGCGGGCCAAGCATCGCAGTTGAATGCT |
| | GTTGTAGATTTGCAAGACAGAAACACAGAGCTTTCATACCAGCT |
| | TTTGCTTGATTCCATTGGTGATAGAACCAGGTACTTTTCTATGTG |
| | GAATCAGGCTGTTGACAGCTATGATCCAGATGTTAGAATTATTG |
| | AAAATCATGGAACTGAAGATGAACTTCCAAATTACTGCTTTCCA |
| | CTGGGAGGTGTGATTAATACAGAGACTCTTACCAAGGTAAAACC |
| | TAAAACAGGTCAGGAAAATGGATGGGAAAAAGATGCTACAGAA |
| | TTTTCAGATAAAAATGAAATAAGAGTTGGAAATAATTTTGCCAT |
| | GGAAATCAATCTAAATGCCAACCTGTGGAGAAATTTCCTGTACT |
| | CCAACATAGCGCTGTATTTGCCCGACAAGCTAAAGTACAGTCCT |
| | TCCAACGTAAAAATTTCTGATAACCCAAACACCTACGACTACAT |
| | GAACAAGCGAGTGGTGGCTCCCGGGCTAGTGGACTGCTACATTA |
| | ACCTTGGAGCACGCTGGTCCCTTGACTATATGGACAACGTCAAC |
| | CCATTTAACCACCACCGCAATGCTGGCCTGCGCTACCGCTCAAT |
| | GTTGCTGGGCAATGGTCGCTATGTGCCCTTCCACATCCAGGTGC |
| | CTCAGAAGTTCTTTGCCATTAAAAACCTCCTTCTCCTGCCGGGCT |
| | CATACACCTACGAGTGGAACTTCAGGAAGGATGTTAACATGGTT |
| | CTGCAGAGCTCCCTAGGAAATGACCTAAGGGTTGACGGAGCCA |
| | GCATTAAGTTTGATAGCATTTGCCTTTACGCCACCTTCTTCCCCA |
| | TGGCCCACAACACCGCCTCCACGCTTGAGGCCATGCTTAGAAAC |
| | GACACCAACGACCAGTCCTTTAACGACTATCTCTCCGCCGCCAA |
| | CATGCTCTACCCTATACCCGCCAACGCTACCAACGTGCCCATAT |
| | CCATCCCCTCCCGCAACTGGGCGGCTTTCCGCGGCTGGGCCTTC |
| | ACGCGCCTTAAGACTAAGGAAACCCCATCACTGGGCTCGGGCTA |
| | CGACCCTTATTACACCTACTCTGGCTCTATACCCTACCTAGATGG |
| | AACCTTTTACCTCAACCACACCTTTAAGAAGGTGGCCATTACCT |
| | TTGACTCTTCTGTCAGCTGGCCTGGCAATGACCGCCTGCTTACCC |
| | CCAACGAGTTTGAAATTAAGCGCTCAGTTGACGGGGAGGGTTAC |
| | AACGTTGCCCAGTGTAACATGACCAAAGACTGGTTCCTGGTACA |
| | AATGCTAGCTAACTATAACATTGGCTACCAGGGCTTCTATATCC |
| | CAGAGAGCTACAAGGACCGCATGTACTCCTTCTTTAGAAACTTC |
| | CAGCCCATGAGCCGTCAGGTGGTGGATGATACTAAATACAAGG |
| | ACTACCAACAGGTGGGCATCCTACACCAACACAACAACTCTGG |
| | ATTTGTTGGCTACCTTGCCCCCACCATGCGCGAAGGACAGGCCT |
| | ACCCTGCTAACTTCCCCTATCCGCTTATAGGCAAGACCGCAGTT |
| | GACAGCATTACCCAGAAAAAGTTTCTTTGCGATCGCACCCTTTG |
| | GCGCATCCCATTCTCCAGTAACTTTATGTCCATGGGCGCACTCA |
| | CAGACCTGGGCCAAAACCTTCTCTACGCCAACTCCGCCCACGCG |
| | CTAGACATGACTTTTGAGGTGGATCCCATGGACGAGCCCACCCT |
| | TCTTTATGTTTTGTTTGAAGTCTTTGACGTGGTCCGTGTGCACCA |
| | GCCGCACCGCGGCGTCATCGAAACCGTGTACCTGCGCACGCCCT |
| | TCTCGGCCGGCAACGCCACAACATAAAGAAGCAAGCAACATCA |
| | ACAACAGCTGCCGCCATGGGCTCCAGTGAGCAGGAACTGAAAG |
| | CCATTGTCAAAGATCTTGGTTGTGGGCCATATTTTTTGGGCACCT |
| | ATGACAAGCGCTTTCCAGGCTTTGTTTCTCCACACAAGCTCGCCT |
| | GCGCCATAGTCAATACGGCCGGTCGCGAGACTGGGGGCGTACA |
| | CTGGATGGCCTTTGCCTGGAACCCGCACTCAAAAACATGCTACC |
| | TCTTTGAGCCCTTTGGCTTTTCTGACCAGCGACTCAAGCAGGTTT |
| | ACCAGTTTGAGTACGAGTCACTCCTGCGCCGTAGCGCCATTGCT |
| | TCTTCCCCCGACCGCTGTATAACGCTGGAAAAGTCCACCCAAAG |
| | CGTACAGGGGCCCAACTCGGCCGCCTGTGGACTATTCTGCTGCA |
| | TGTTTCTCCACGCCTTTGCCAACTGGCCCCAAACTCCCATGGATC |
| | ACAACCCCACCATGAACCTTATTACCGGGGTACCCAACTCCATG |
| | CTCAACAGTCCCCAGGTACAGCCCACCCTGCGTCGCAACCAGGA |
| | ACAGCTCTACAGCTTCCTGGAGCGCCACTCGCCCTACTTCCGCA |
| | GCCACAGTGCGCAGATTAGGAGCGCCACTTCTTTTTGTCACTTG |
| | AAAAACATGTAAAAATAATGTACTAGAGACACTTTCAATAAAG |
| | GCAAATGCTTTTATTTGTACACTCTCGGGTGATTATTTACCCCCA |
| | CCCTTGCCGTCTGCGCCGTTTAAAAATCAAGGGGTTCTGCCGC |
| | GCATCGCTATGCGCCACTGGCAGGGACACGTTGCGATACTGGTG |
| | TTTAGTGCTCCACTTAAACTCAGGCACAACCATCCGCGGCAGCT |
| | CGGTGAAGTTTTCACTCCACAGGCTGCGCACCATCACCAACGCG |
| | TTTAGCAGGTCGGGCGCCGATATCTTGAAGTCGCAGTTGGGGCC |
| | TCCGCCCTGCGCGCGCGAGTTGCGATACACAGGGTTGCAGCACT |
| | GGAACACTATCAGCGCCGGGTGGTGCACGCTGGCCAGCACGCT |
| | CTTGTCGGAGATCAGATCCGCGTCCAGGTCCTCCGCGTTGCTCA |
| | GGGCGAACGGAGTCAACTTTGGTAGCTGCCTTCCCAAAAAGGG |

| SEQ ID NO | Sequence |
|---|---|
| | CGCGTGCCCAGGCTTTGAGTTGCACTCGCACCGTAGTGGCATCA<br>AAAGGTGACCGTGCCCGGTCTGGGCGTTAGGATACAGCGCCTGC<br>ATAAAAGCCTTGATCTGCTTAAAAGCCACCTGAGCCTTTGCGCC<br>TTCAGAGAAGAACATGCCGCAAGACTTGCCGGAAAACTGATTG<br>GCCGGACAGGCCGCGTCGTGCACGCAGCACCTTGCGTCGGTGTT<br>GGAGATCTGCACCACATTTCGGCCCCACCGGTTCTTCACGATCT<br>TGGCCTTGCTAGACTGCTCCTTCAGCGCGCGCTGCCCGTTTTCGC<br>TCGTCACATCCATTTCAATCACGTGCTCCTTATTTATCATAATGC<br>TTCCGTGTAGACACTTAAGCTCGCCTTCGATCTCAGCGCAGCGG<br>TGCAGCCACAACGCGCAGCCCGTGGGCTCGTGATGCTTGTAGGT<br>CACCTCTGCAAACGACTGCAGGTACGCCTGCAGGAATCGCCCCA<br>TCATCGTCACAAAGGTCTTGTTGCTGGTGAAGGTCAGCTGCAAC<br>CCGCGGTGCTCCTCGTTCAGCCAGGTCTTGCATACGGCCGCCAG<br>AGCTTCCACTTGGTCAGGCAGTAGTTTGAAGTTCGCCTTTAGAT<br>CGTTATCCACGTGGTACTTGTCCATCAGCGCGCGCGCAGCCTCC<br>ATGCCCTTCTCCCACGCAGACACGATCGGCACACTCAGCGGGTT<br>CATCACCGTAATTTCACTTTCCGCTTCGCTGGGCTCTTCCTCTTC<br>CTCTTGCGTCCGCATACCACGCGCCACTGGGTCGTCTTCATTCAG<br>CCGCCGCACTGTGCGCTTACCTCCTTTGCCATGCTTGATTAGCAC<br>CGGTGGGTTGCTGAAACCCACCATTTGTAGCGCCACATCTTCTC<br>TTTCTTCCTCGCTGTCCACGATTACCTCTGGTGATGGCGGGCGCT<br>CGGGCTTGGGAGAAGGGCGCTTCTTTTTCTTCTTGGGCGCAATG<br>GCCAAATCCGCCGCCGAGGTCGATGGCCGCGGGCTGGGTGTGC<br>GCGGCACCCAGCGCGTCTTGTGATGAGTCTTCCTCGTCCTCGGAC<br>TCGATACGCCGCCTCATCCGCTTTTTTGGGGGCGCCCGGGGAGG<br>CGGCGGCGACGGGGACGGGGACGACACGTCCTCCATGGTTGGG<br>GGACGTCGCGCCGCACCGCGTCCGCGCTCGGGGGTGGTTTCGCG<br>CTGCTCCTCTTCCCGACTGGCCATTTCCTTCTCCTATAGGCAGAA<br>AAAGATCATGGAGTCAGTCGAGAAGAAGGACAGCCTAACCGCC<br>CCCTCTGAGTTCGCCACCACCGCCTCCACCGATGCCGCCAACGC<br>GCCTACCACCTTCCCCGTCGAGGCACCCCCGCTTGAGGAGGAGG<br>AAGTGATTATCGAGCAGGACCCAGGTTTTTGTAAGCGAAGACGA<br>CGAGGACCGCTCAGTACCAACAGAGGATAAAAAGCAAGACCAG<br>GACAACGCAGAGGCAAACGAGGAACAAGTCGGGCGGGGGGAC<br>GAAAGGCATGGCGACTACCTAGATGTGGGAGACGACGTGCTGT<br>TGAAGCATCTGCAGCGCCAGTGCGCCATTATCTGCGACGCGTTG<br>CAAGAGCGCAGCGATGTGCCCCTCGCCATAGCGGATGTCAGCCT<br>TGCCTACGAACGCCACCTATTCTCACCGCGCGTACCCCCCAAAC<br>GCCAAGAAAACGGCACATGCGAGCCCAACCCGCGCCTCAACTT<br>CTACCCCGTATTTGCCGTGCCAGAGGTGCTTGCCACCTATCACA<br>TCTTTTTCCAAAACTGCAAGATACCCCTATCCTGCCGTGCCAACC<br>GCAGCCGAGCGGACAAGCAGCTGGCCTTGCGGCAGGGCGCTGT<br>CATACCTGATATCGCCTCGCTCAACGAAGTGCCAAAAATCTTTG<br>AGGGTCTTGGACGCGACGAGAAGCGCGCGGCAAACGCTCTGCA<br>ACAGGAAAACAGCGAAAATGAAAGTCACTCTGGAGTGTTGGTG<br>GAACTCGAGGGTGACAACGCGCGCCTAGCCGTACTAAAACGCA<br>GCATCGAGGTCACCCACTTTGCCTACCCGGCACTTAACCTACCC<br>CCCAAGGTCATGAGCACAGTCATGAGTGAGCTGATCGTGCGCCG<br>TGCGCAGCCCCTGGGAGAGGGATGCAAATTTGCAAGAACAAACA<br>GAGGAGGGCCTACCCGCAGTTGGCGACGAGCAGCTAGCGCGCT<br>GGCTTCAAACGCGCGAGCCTGCCGACTTGGAGGAGCGACGCAA<br>ACTAATGATGGCCGCAGTGCTCGTTACCGTGGAGCTTGAGTGCA<br>TGCAGCGGTTCTTTGCTGACCCGGAGATGCAGCGCAAGCTAGAG<br>GAAACATTGCACTACACCTTTCGACAGGGCTACGTACGCCAGGC<br>CTGCAAGATCTCCAACGTGGAGCTCTGCAACCTGGTCTCCTACC<br>TTGGAATTTTGCACGAAAACCGCCTTGGGCAAAACGTGCTTCAT<br>TCCACGCTCAAGGGCGAGGCGCCGCGACTACGTCCGCGACT<br>GCGTTTACTTATTTCTATGCTACACCTGGCAGACGGCCATGGGC<br>GTTTGGCAGCAGTGCTTGGAGGAGTGCAACCTCAAGGAGCTGC<br>AGAAACTGCTAAAGCAAAACTTGAAGGACCTATGGACGGCCTTT<br>CAACGAGCGCTCCGTGGCCGCGCACCTGGCGGACATCATTTTCC<br>CCGAACGCCTGCTTAAAACCCTGCAACAGGGTCTGCCAGACTTC<br>ACCAGTCAAAGCATGTTGCAGAACTTTAGGAACTTTATCCTAGA<br>GCGCTCAGGAATCTTGCCCGCCACCTGCTGTGCACTTCCTAGCG<br>ACTTTGTGCCCATTAAGTACCGCGAATGCCCTCCGCCGCTTTGG<br>GGCCACTGCTACCTTCTGCAGCTAGCCAACTACCTTGCCTACCA<br>CTCTGACATAATGGAAGACGTGAGCGGTGACGGTCTACTGGAGT<br>GTCACTGTCGCTGCAACCTATGCACCCCGCACCGCTCCCTGGTTT<br>GCAATTCGCAGCTGCTTAACGAAAGTCAAATTATCGGTACCTTT<br>GAGCTGCAGGGTCCCTCGCCTGACGAAAAGTCCGCGGCTCCGG<br>GGTTGAAACTCACTCCGGGGCTGTGGACGTCGGCTTACCTTCGC<br>AAATTTGTACCTGAGGACTACCACGCCCACGAGATTAGGTTCTA<br>CGAAGACCAATCCCGCCCGCCTAATGCGGAGCTTACCGCCTGCG<br>TCATTACCCAGGGCCACATTCTTGGCCAATTGCAAGCCATCAAC<br>AAAGCCCGCCAAGAGTTTCTGCTACGAAAGGGACGGGGGGTTT<br>ACTTGGACCCCCAGTCCGGCGAGGAGCTCAACCCAATCCCCCCG<br>CCGCCGCAGCCCTATCAGCAGCAGCCGCGGGCCCTTGCTTCCCA |

| SEQ ID NO | Sequence |
| --- | --- |
| | GGATGGCACCCAAAAAGAAGCTGCAGCTGCCGCCGCCACCCAC<br>GGACGAGGAGGAATACTGGGACAGTCAGGCAGAGGAGGTTTTG<br>GACGAGGAGGAGGAGGACATGATGGAAGACTGGGAGAGCCTA<br>GACGAGGAAGCTTCCGAGGTCGAAGAGGTGTCAGACGAAACAC<br>CGTCACCCTCGGTCGCATTCCCCTCGCCGGCGCCCCAGAAATCG<br>GCAACCGGTTCCAGCATGGCTACAACCTCCGCTCCTCAGGCGCC<br>GCCGGCACTGCCCGTTCGCCGACCCAACCGTAGATGGGACACCA<br>CTGGAACCAGGGCCGGTAAGTCCAAGCAGCCGCCGCCGTTAGC<br>CCAAGAGCAACAACAGCGCCAAGGCTACCGCTCATGGCGCGGG<br>CACAAGAACGCCATAGTTGCTTGCTTGCAAGACTGTGGGGCAA<br>CATCTCCTTCGCCCGCCGCTTTCTTCTCTACCATCACGGCGTGGC<br>CTTCCCCCGTAACATCCTGCATTACTACCGTCATCTCTACAGCCC<br>ATACTGCACCGGCGGCAGCGGCAGCAACAGCAGCGGCCACACA<br>GAAGCAAAGGCGACCGGATAGCAAGACTCTGACAAAGCCCAAG<br>AAATCCACAGCGGCGGCAGCAGCAGGAGGAGGAGCGCTGCGTC<br>TGGCGCCCAACGAACCCGTATCGACCCGCGAGCTTAGAAACAG<br>GATTTTTCCCACTCTGTATGCTATATTTCAACAGAGCAGGGGCC<br>AAGAACAAGAGCTGAAAATAAAAAACAGGTCTCTGCGATCCCT<br>CACCCGCAGCTGCCTGTATCACAAAAGCGAAGATCAGCTTCGGC<br>GCACGCTGGAAGACGCGGAGGCTCTCTTCAGTAAATACTGCGCG<br>CTGACTCTTAAGGACTAGTTTCGCGCCCTTTCTCAAATTTAAGCG<br>CGAAAACTACGTCATCTCCAGCGGCCACACCCGGCGCCAGCACC<br>TGTTGTCAGCGCCATTATGAGCAAGGAAATTCCCACGCCCTACA<br>TGTGGAGTTACCAGCCACAAATGGGACTTGCGGCTGGAGCTGCC<br>CAAGACTACTCAACCCGAATAAACTACATGAGCGCGGGACCCC<br>ACATGATATCCCGGGTCAACGGAATACGCGCCCACCGAAACCG<br>AATTCTCCTGGAACAGGCGGCTATTACCACCACACCTCGTAATA<br>ACCTTAATCCCCGTAGTTGGCCCGCTGCCCTGGTGTACCAGGAA<br>AGTCCCGCTCCCACCACTGTGGTACTTCCCAGAGACGCCCAGGC<br>CGAAGTTCAGATGACTAACTCAGGGGCGCAGCTTGCGGGCGGC<br>TTTCGTCACAGGGTGCGGTCGCCCGGGCAGGGTATAACTCACCT<br>GACAATCAGAGGGCGAGGTATTCAGCTCAACGACGAGTCGGTG<br>AGCTCCTCGCTTGGTCTCCGTCCGACGGGACATTTCAGATCGG<br>CGGCGCCGGCCGCTCTTCATTCACGCCTCGTCAGGCAATCCTAA<br>CTCTGCAGACCTCGTCCTCTGAGCCGCGCTCTGGAGGCATTGGA<br>ACTCTGCAATTTATTGAGGAGTTTGTGCCATCGGTCTACTTTAAC<br>CCCTTCTCGGGACCTCCCGGCCACTATCCGGATCAATTTATTCCT<br>AACTTTGACGCGGTAAAGGACTCGGCGGACGGCTACGACTGAA<br>TGTTAAGTGGAGAGGCAGAGCAACTGCGCCTGAAACACCTGGT<br>CCACTGTCGCCGCCACAAGTGCTTTGCCCGCGACTCCGGTGAGT<br>TTTGCTACTTTGAATTGCCCGAGGATCATATCGAGGGCCCGGCG<br>CACGGCGTCCGGCTTACCGCCCAGGGAGAGCTTGCCCGTAGCCT<br>GATTCGGGAGTTTACCCAGCGCCCCCTGCTAGTTGAGCGGGACA<br>GGGGACCCTGTGTTCTCACTGTGATTTGCAACTGTCCTAACCCTG<br>GATTACATCAAGATCCTCTAGTTAATGTCAGGTCGCCTAAGTCG<br>ATTAACTAGAGTACCCGGGGATCTTATTCCCTTTAACTAATAAA<br>AAAAAATAATAAAGCATCACTTACTTAAAATCAGTTAGCAAATT<br>TCTGTCCAGTTTATTCAGCAGCACCTCCTTGCCCTCCTCCCAGCT<br>CTGGTATTGCAGCTTCCTCCTGGCTGCAAACTTTCTCCACAATCT<br>AAATGGAATGTCAGTTTCCTCCTGTTCCTGTCCATCCGCACCCAC<br>TATCTTCATGTTGTTGCAGATGAAGCGCGCAAGACCGTCTGAAG<br>ATACCTTCAACCCCGTGTATCCATATGACACGGAAACCGGTCCT<br>CCAACTGTGCCTTTTCTTACTCCTCCCTTTGTATCCCCCAATGGG<br>TTTCAAGAGAGTCCCCCTGGGGTACTCTCTTTGCGCCTATCCGA<br>ACCTCTAGTTACCTCCAATGGCATGCTTGCGCTCAAAATGGGCA<br>ACGGCCTCTCTCTGGACGAGGCCGGCAACCTTACCTCCCAAAAT<br>GTAACCACTGTGAGCCCACCTCTCAAAAAAACCAAGTCAAACAT<br>AAACCTGGAAATATCTGCACCCCTCACAGTTACCTCAGAAGCCC<br>TAACTGTGGCTGCCGCCGCACCTCTAATGGTCGCGGGCAACACA<br>CTCACCATGCAATCACAGGCCCCGCTAACCGTGCACGACTCCAA<br>ACTTAGCATTGCCACCCAAGGACCCCTCACAGTGTCAGAAGGAA<br>AGCTAGCCCTGCAAACATCAGGCCCCCTCACCACCACCGATAGC<br>AGTACCCTTACTATCACTGCCTCACCCCCTCTAACTACTGCCACT<br>GGTAGCTTGGGCATTGACTTGAAAGAGCCCATTTATACACAAA<br>TGGAAAACTAGGACTAAAGTACGGGGCTCCTTTGCATGTAACAG<br>ACGACCTAAACACTTTGACCGTAGCAACTGGTCCAGGTGTGACT<br>ATTAATAATACTTCCTTGCAAACTAAAGTTACTGGAGCCTTGGG<br>TTTTGATTCACAAGGCAATATGCAACTTAATGTAGCAGGAGGAC<br>TAAGGATTGATTCTCAAAACAGACGCCTTATACTTGATGTTAGT<br>TATCCGTTTGATGCTCAAAACCAACTAAATCTAAGACTAGGACA<br>GGGCCCTCTTTTTATAAACTCAGCCCACAACTTGGATATTAACT<br>ACAACAAAGGCCTTTACTTGTTTACAGCTTCAAACAATTCCAAA<br>AAGCTTGAGGTTAACCTAAGCACTGCCAAGGGGTTGATGTTTGA<br>CGCTACAGCCATAGCCATTAATGCAGGAGATGGGCTTGAATTTG<br>GTTCACCTAATGCACCAAACACAAATCCCCTCAAAACAAAAATT<br>GGCCATGGCCTAGAATTTGATTCAAACAAGGCTATGGTTCCTAA<br>ACTAGGAACTGGCCTTAGTTTTGACAGCACAGGTGCCATTACAG |

| SEQ ID NO | Sequence |
|---|---|
| | TAGGAAACAAAAATAATGATAAGCTAACTTTGTGGACCACACC |
| | AGCTCCATCTCCTAACTGTAGACTAAATGCAGAGAAAGATGCTA |
| | AACTCACTTTGGTCTTAACAAAATGTGGCAGTCAAATACTTGCT |
| | ACAGTTTCAGTTTTGGCTGTTAAAGGCAGTTTGGCTCCAATATCT |
| | GGAACAGTTCAAAGTGCTCATCTTATTATAAGATTTGACGAAAA |
| | TGGAGTGCTACTAAACAATTCCTTCCTGGACCCAGAATATTGGA |
| | ACTTTAGAAATGGAGATCTTACTGAAGGCACAGCCTATACAAAC |
| | GCTGTTGGATTTATGCCTAACCTATCAGCTTATCCAAAATCTCAC |
| | GGTAAAACTGCCAAAAGTAACATTGTCAGTCAAGTTTACTTAAA |
| | CGGAGACAAAACTAAACCTGTAACACTAACCATTACACTAAAC |
| | GGTACACAGGAAACAGGAGACACAACTCCAAGTGCATACTCTA |
| | TGTCATTTTCATGGGACTGGTCTGGCCACAACTACATTAATGAA |
| | ATATTTGCCACATCCTCTTACACTTTTTCATACATTGCCCAAGAA |
| | TAAAGAATCGTTTGTGTTATGTTTCAACGTGTTTATTTTTCAATT |
| | GCAGAAAATTTCAAGTCATTTTTCATTCAGTAGTATAGCCCCAC |
| | CACCACATAGCTTATACAGATCACCGTACCTTAATCAAACTCAC |
| | AGAACCCTAGTATTCAACCTGCCACCTCCCTCCCAACACACAGA |
| | GTACACAGTCCTTTCTCCCCGGCTGGCCTTAAAAAGCATCATAT |
| | CATGGGTAACAGACATATTCTTAGGTGTTATATTCCACACGGTT |
| | TCCTGTCGAGCCAAACGCTCATCAGTGATATTAATAAACTCCCC |
| | GGGCAGCTCACTTAAGTTCATGTCGCTGTCCAGCTGCTGAGCCA |
| | CAGGCTGCTGTCCAACTTGCGGTTGCTTAACGGGCGGCGAAGGA |
| | GAAGTCCACGCCTACATGGGGGTAGAGTCATAATCGTGCATCAG |
| | GATAGGGCGGTGGTGCTGCAGCAGCGCGCGAATAAACTGCTGC |
| | CGCCGCCGCTCCGTCCTGCAGGAATACAACATGGCAGTGGTCTC |
| | CTCAGCGATGATTCGCACCGCCCGCAGCATAAGGCGCCTTGTCC |
| | TCCGGGCACAGCAGCGCACCCTGATCTCACTTAAATCAGCACAG |
| | TAACTGCAGCACAGCACCACAATATTGTTCAAAATCCCACAGTG |
| | CAAGGCGCTGTATCCAAAGCTCATGGCGGGGACCACAGAACCC |
| | ACGTGGCCATCATACCACAAGCGCAGGTAGATTAAGTGGCGAC |
| | CCCTCATAAACACGCTGGACATAAACATTACCTCTTTTGGCATG |
| | TTGTAATTCACCACCTCCCGGTACCATATAAACCTCTGATTAAA |
| | CATGGCGCCATCCACCACCATCCTAAACCAGCTGGCCAAAACCT |
| | GCCCGCCGGCTATACACTGCAGGGAACCGGGACTGGAACAATG |
| | ACAGTGGAGAGCCCAGGACTCGTAACCATGGATCATCATGCTCG |
| | TCATGATATCAATGTTGGCACAACACAGGCACACGTGCATACAC |
| | TTCCTCAGGATTACAAGCTCCTCCCGCGTTAGAACCATATCCCA |
| | GGGAACAACCCATTCCTGAATCAGCGTAAATCCCACACTGCAGG |
| | GAAGACCTCGCACGTAACTCACGTTGTGCATTGTCAAAGTGTTA |
| | CATTCGGGCAGCAGCGGATGATCCTCCAGTATGGTAGCGCGGGT |
| | TTCTGTCTCAAAAGGAGGTAGACGATCCCTACTGTACGGAGTGC |
| | GCCGAGACAACCGAGATCGTGTTGGTCGTAGTGTCATGCCAAAT |
| | GGAACGCCGGACGTAGTCATATTTCCTGAAGCAAAACCAGGTG |
| | CGGGCGTGACAAACAGATCTGCGTCTCCGGTCTCGCCGCTTAGA |
| | TCGCTCTGTGTAGTAGTTGTAGTATATCCACTCTCTCAAAGCATC |
| | CAGGCGCCCCCTGGCTTCGGGTTCTATGTAAACTCCTTCATGCG |
| | CCGCTGCCCTGATAACATCCACCACCGCAGAATAAGCCACACCC |
| | AGCCAACCTACACATTCGTTCTGCGAGTCACACACGGGAGGAGC |
| | GGGAAGAGCTGGAAGAACCATGTTTTTTTTTTTATTCCAAAAGA |
| | TTATCCAAAACCTCAAAATGAAGATCTATTAAGTGAACGCGCTC |
| | CCCTCCGGTGGCGTGGTCAAACTCTACAGCCAAAGAACAGATA |
| | ATGGCATTTGTAAGATGTTGCACAATGGCTTCCAAAAGGCAAAC |
| | GGCCCTCACGTCCAAGTGGACGTAAAGGCTAAACCCTTCAGGGT |
| | GAATCTCCTCTATAAACATTCCAGCACCTTCAACCATGCCCAAA |
| | TAATTCTCATCTCGCCACCTTCTCAATATATCTCTAAGCAAATCC |
| | CGAATATTAAGTCCGGCCATTGTAAAAATCTGCTCCAGAGCGCC |
| | CTCCACCTTCAGCCTCAAGCAGCGAATCATGATTGCAAAAATTC |
| | AGGTTCCTCACAGACCTGTATAAGATTCAAAAGCGGAACATTAA |
| | CAAAAATACCGCGATCCCGTAGGTCCCTTCGCAGGGCCAGCTGA |
| | ACATAATCGTGCAGGTCTGCACGGACCAGCGCGGCCACTTCCCC |
| | GCCAGGAACCATGACAAAAGAACCCACACTGATTATGACACGC |
| | ATACTCGGAGCTATGCTAACCAGCGTAGCCCCGATGTAAGCTTG |
| | TTGCATGGGCGGCGATATAAAATGCAAGGTGCTGCTCAAAAAA |
| | TCAGGCAAAGCCTCGCGCAAAAAAGAAAGCACATCGTAGTCAT |
| | GCTCATGCAGATAAAGGCAGGTAAGCTCCGGAACCACCACAGA |
| | AAAAGACACCATTTTTCTCTCAAACATGTCTGCGGGTTTCTGCAT |
| | AAACACAAAATAAAATAACAAAAAAACATTTAAACATTAGAAG |
| | CCTGTCTTACAACAGGAAAAACAACCCTTATAAGCATAAGACG |
| | GACTACGGCCATGCCGGCGTGACCGTAAAAAAACTGGTCACCG |
| | TGATTAAAAAGCACCACCGACAGCTCCTCGGTCATGTCCGGAGT |
| | CATAATGTAAGACTCGGTAAACACATCAGGTTGATTCACATCGG |
| | TCAGTGCTAAAAAGCGACCGAAATAGCCCGGGGGAATACATAC |
| | CCGCAGGCGTAGAGACAACATTACAGCCCCCATAGGAGGTATA |
| | ACAAAATTAATAGGAGAGAAAAACATAAACACCTGAAAAAC |
| | CCTCCTGCCTAGGCAAAATAGCACCCTCCCGCTCCAGAACAACA |
| | TACAGCGCTTCCACAGCGGCAGCCATAACAGTCAGCCTTACCAG |
| | TAAAAAAGAAAACCTATTAAAAAAACACCACTCGACACGGCAC |

| SEQ ID NO | Sequence |
|---|---|
| | CAGCTCAATCAGTCACAGTGTAAAAAAGGGCCAAGTGCAGAGC<br>GAGTATATATAGGACTAAAAAATGACGTAACGGTTAAAGTCCA<br>CAAAAAACACCCAGAAAACCGCACGCGAACCTACGCCCAGAAA<br>CGAAAGCCAAAAAACCCACAACTTCCTCAAATCGTCACTTCCGT<br>TTTCCCACGTTACGTCACTTCCCATTTTAAGAAAACTACAATTCC<br>CAACACATACAAGTTACTCCGCCCTAAAACCTACGTCACCCGCC<br>CCGTTCCCACGCCCCGCGCCACGTCACAAACTCCACCCCCTCAT<br>TATCATATTGGCTTCAATCCAAAATAAGGTATATTATTGATGAT |
| SEQ ID NO: 3 | YLSGANLNL |
| SEQ ID NO: 4 | YLSGADLNL |
| SEQ ID NO: 5 | CGCTCCACCTCTCAAGCAGCCAGCGCCTGCCTGAATCTGTTCTG<br>CCCCCTCCCCACCCATTTCACCACCACCATGACACCGGGCACCC<br>AGTCTCCTTTCTTCCTGCTGCTGCTCCTCACAGTGCTTACAGTTG<br>TTACGGGTTCTGGTCATGCAAGCTCTACCCCAGGTGGAGAAAAG<br>GAGACTTCGGCTACCCAGAGAAGTTCAGTGCCCAGCTCTACTGA<br>GAAGAATGCTGTGAGTATGACCAGCAGCGTACTCTCCAGCCACA<br>GCCCCGGTTCAGGCTCCTCCACCACTCAGGGACAGGATGTCACT<br>CTGGCCCCGGCCACGGAACCAGCTTCAGGTTCAGCTGCCACCTG<br>GGGACAGGATGTCACCTCGGTCCCAGTCACCAGGCCAGCCCTGG<br>GCTCCACCACCCCGCCAGCCCACGATGTCACCTCAGCCCCGGAC<br>AACAAGCCAGCCCCGGGCTCCACCGCCCCCCAGCCCACGGTGT<br>CACCTCGGCCCCGGACACCAGGCCGGCCCCGGGCTCCACCGCCC<br>CCCCAGCCCATGGTGTCACCTCGGCCCCGGACAACAGGCCCGCC<br>TTGGGCTCCACCGCCCCTCCAGTCCACAATGTCACCTCGGCCTC<br>AGGCTCTGCATCAGGCTCAGCTTCTACTCTGGTGCACAACGGCA<br>CCTCTGCCAGGGCTACCACAACCCCAGCCAGCAAGAGCACTCCA<br>TTCTCAATTCCCAGCCACCACTCTGATACTCCTACCACCCTTGCC<br>AGCCATAGCACCAAGACTGATGCCAGTAGCACTCACCATAGCA<br>CGGTACCTCCTCTCACCTCCTCCAATCACAGCACTTCTCCCCAGT<br>TGTCTACTGGGGTCTCTTTCTTTTTCCTGTCTTTTCACATTTCAAA<br>CCTCCAGTTTAATTCCTCTCTGGAAGATCCCAGCACCGACTACT<br>ACCAAGAGCTGCAGAGAGACATTTCTGAAATGTTTTTGCAGATT<br>TATAAACAAGGGGGTTTTCTGGGCCTCTCCAATATTAAGTTCAG<br>GCCAGGATCTGTGGTGGTACAATTGACTCTGGCCTTCCGAGAAG<br>GTACCATCAATGTCCACGACGTGGAGACACAGTTCAATCAGTAT<br>AAAACGGAAGCAGCCTCTCGATATAACCTGACGATCTCAGACGT<br>CAGCGTGAGTGATGTGCCATTTCCTTTCTCTGCCCAGTCTGGGGC<br>TGGGGTGCCAGGCTGGGGCATCGCGCTGCTGGTGCTGGTCTGTG<br>TTCTGGTTGCGCTGGCCATTGTCTATCTCATTGCCTTGGCTGTCT<br>GTCAGTGCCGCCGAAAGAACTACGGGCAGCTGGACATCTTTCCA<br>GCCCGGGATACCTACCATCCTATGAGCGAGTACCCCACCTACCA<br>CACCCATGGGCGCTATGTGCCCCCTAGCAGTACCGATCGTAGCC<br>CCTATGAGAAGGTTTCTGCAGGTAATGGTGGCAGCAGCCTCTCT<br>TACACAAACCCAGCAGTGGCAGCCACTTCTGCCAACTTGTAGGG<br>GCACGTCGCCCGCTGAGCTGAGTGGCCAGCCAGTGCCATTCCAC<br>TCCACTCAGGTTCTTCAGGGCCAGAGCCCCTGCACCCTGTTTGG<br>GCTGGTGAGCTGGGAGTTCAGGTGGGCTGCTCACAGCCTCCTTC<br>AGAGGCCCCACCAATTTCTCGGACACTTCTCAGTGTGTGGAAGC<br>TCATGTGGGCCCCTGAGGGCTCATGCCTGGGAAGTGTTGTGGTG<br>GGGGCTCCCAGGAGGACTGGCCCAGAGAGCCCTGAGATAGCGG<br>GGATCCTGAACTGGACTGAATAAAACGTGGTCTCCCACTGCGCC<br>AAAAAAAAAAAAAAAA |
| SEQ ID NO: 6 | CGCTCCACCTCTCAAGCAGCCAGCGCCTGCCTGAATCTGTTCTG<br>CCCCCTCCCCACCCATTTCACCACCACCATGACACCGGGCACCC<br>AGTCTCCTTTCTTCCTGCTGCTGCTCCTCACAGTGCTTACAGTTG<br>TTACGGGTTCTGGTCATGCAAGCTCTACCCCAGGTGGAGAAAAG<br>GAGACTTCGGCTACCCAGAGAAGTTCAGTGCCCAGCTCTACTGA<br>GAAGAATGCTGTGAGTATGACCAGCAGCGTACTCTCCAGCCACA<br>GCCCCGGTTCAGGCTCCTCCACCACTCAGGGACAGGATGTCACT<br>CTGGCCCCGGCCACGGAACCAGCTTCAGGTTCAGCTGCCCTTTG<br>GGGACAGGATGTCACCTCGGTCCCAGTCACCAGGCCAGCCCTGG<br>GCTCCACCACCCCGCCAGCCCACGATGTCACCTCAGCCCCGGAC<br>AACAAGCCAGCCCCGGGCTCCACCGCCCCCCAGCCCACGGTGT<br>CACCTCGTATCTTGACACCAGGCCGGCCCCGGTTTATCTTGCCCC<br>CCCAGCCCATGGTGTCACCTCGGCCCCGGACAACAGGCCCGCCT<br>TGGGCTCCACCGCCCCTCCAGTCCACAATGTCACCTCGGCCTCA<br>GGCTCTGCATCAGGCTCAGCTTCTACTCTGGTGCACAACGGCAC<br>CTCTGCCAGGGCTACCACAACCCCAGCCAGCAAGAGCACTCCAT<br>TCTCAATTCCCAGCCACCACTCTGATACTCCTACCACCCTTGCCA<br>GCCATAGCACCAAGACTGATGCCAGTAGCACTCACCATAGCAC<br>GGTACCTCCTCTCACCTCCTCCAATCACAGCACTTCTCCCCAGTT<br>GTCTACTGGGGTCTCTTTCTTTTTCCTGTCTTTTCACATTTCAAAC<br>CTCCAGTTTAATTCCTCTCTGGAAGATCCCAGCACCGACTACTA |

| SEQ ID NO | Sequence |
|---|---|
| | CCAAGAGCTGCAGAGAGACATTTCTGAAATGTTTTTGCAGATTT<br>ATAAACAAGGGGGTTTTCTGGGCCTCTCCAATATTAAGTTCAGG<br>CCAGGATCTGTGGTGGTACAATTGACTCTGGCCTTCCGAGAAGG<br>TACCATCAATGTCCACGACGTGGAGACACAGTTCAATCAGTATA<br>AAACGGAAGCAGCCTCTCGATATAACCTGACGATCTCAGACGTC<br>AGCGTGAGTGATGTGCCATTTCCTTTCTCTGCCCAGTCTGGGGCT<br>GGGGTGCCAGGCTGGGGCATCGCGCTGCTGGTGCTGGTCTGTGT<br>TCTGGTTTATCTGGCCATTGTCTATCTCATTGCCTTGGCTGTCGC<br>TCAGGTTCGCCGAAAGAACTACGGGCAGCTGGACATCTTTCCAG<br>CCCGGGATAAATACCATCCTATGAGCGAGTACGCTCTTTACCAC<br>ACCCATGGGCGCTATGTGCCCCCTAGCAGTCTTTTCCGTAGCCC<br>CTATGAGAAGGTTTCTGCAGGTAATGGTGGCAGCTATCTCTCTT<br>ACACAAACCCAGCAGTGGCAGCCGCTTCTGCCAACTTGTAGGGG<br>CACGTCGCCCGCTGAGCTGAGTGGCCAGCCAGTGCCATTCCACT<br>CCACTCAGGTTCTTCAGGGCCAGAGCCCCTGCACCCTGTTTGGG<br>CTGGTGAGCTGGGAGTTCAGGTGGGCTGCTCACAGCCTCCTTCA<br>GAGGCCCCACCAATTTCTCGGACACTTCTCAGTGTGTGGAAGCT<br>CATGTGGGCCCCTGAGGGCTCATGCCTGGGAAGTGTTGTGGTGG<br>GGGCTCCCAGGAGGACTGGCCCAGAGAGCCCTGAGATAGCGGG<br>GATCCTGAACTGGACTGAATAAAACGTGGTCTCCCACTGCGCCA<br>AAAAAAAAAAAAAAAA |
| SEQ ID NO: 7 | MTPGTQSPFFLLLLLTVLTVVTGSGHASSTPGGEKETSATQRSSVPS<br>STEKNAVSMTSSVLSSHSPGSGSSTTQGQDVTLAPATEPASGSAAL<br>WGQDVTSVPVTRPALGSTTPPAHDVTSAPDNKPAPGSTAPPAHGV<br>TSYLDTRPAPVYLAPPAHGVTSAPDNRPALGSTAPPVHNVTSASGS<br>ASGSASTLVHNGTSARATTTPASKSTPFSIPSHHSDTPTTLASHSTKT<br>DASSTHHSTVPPLTSSNHSTSPQLSTGVSFFFLSFHISNLQFNSSLED<br>STDYYQELQRDISEMFLQIYKQGGFLGLSNIKFRPGSVVVQLTLAFR<br>EGTINVHDVETQFNQYKTEAASRYNLTISDVSVSDVPFPFSAQSGA<br>GVPGWGIALLVLVCVLVYLAIVYLIALAVAQVRRKNYGQLDIFPA<br>RDKYHPMSEYALYHTHGRYVPPSSLFRSPYEKVSAGNGGSYLSYT<br>NPAVAAASANL |
| SEQ ID NO: 8 | CATCATCAATAATATACCTTATTTTGGATTGAAGCCAATATGAT<br>AATGAGGGGGTGGAGTTTGTGACGTGGCGCGGGGCGTGGGAAC<br>GGGGCGGGTGACGTAGTAGTGTGGCGGAAGTGTGATGTTGCAA<br>GTGTGGCGGAACACATGTAAGCGACGGATGTGGCAAAAGTGAC<br>GTTTTTGGTGTGCGCCGGTGTACACAGGAAGTGACAATTTTCGC<br>GCGGTTTTAGGCGGATGTTGTAGTAAATTTGGGCGTAACCGAGT<br>AAGATTTGGCCATTTTCGCGGGAAAACTGAATAAGAGGAAGTG<br>AAATCTGAATAATTTTGTGTTACTCATAGCGCGTAATACTGTAA<br>TAGTAATCAATTACGGGGTCATTAGTTCATAGCCCATATATGGA<br>GTTCCGCGTTACATAACTTACGGTAAATGGCCCGCCTGGCTGAC<br>CGCCCAACGACCCCCGCCCATTGACGTCAATAATGACGTATGTT<br>CCCATAGTAACGCCAATAGGGACTTTCCATTGACGTCAATGGGT<br>GGAGTATTTACGGTAAACTGCCCACTTGGCAGTACATCAAGTGT<br>ATCATATGCCAAGTACGCCCCCTATTGACGTCAATGACGGTAAA<br>TGGCCCGCCTGGCATTATGCCCAGTACATGACCTTATGGGACTT<br>TCCTACTTGGCAGTACATCTACGTATTAGTCATCGCTATTACCAT<br>GGTGATGCGGTTTTGGCAGTACATCAATGGGCGTGGATAGCGGT<br>TTGACTCACGGGGATTTCCAAGTCTCCACCCCATTGACGTCAAT<br>GGGAGTTTGTTTTGGCACCAAAATCAACGGGACTTTCCAAAATG<br>TCGTAACAACTCCGCCCCATTGACGCAAATGGGCGGTAGGCGTG<br>TACGGTGGGAGGTCTATATAAGCAGAGCTGGTTTAGTGAACCGT<br>CAGATCCGCTAGAGATCTGGTACCGTCGACGCGGCCGCTCGAGC<br>CTAAGCTTCTAGATGCATGCTCGAGCGGCCGCCAGTGTGATGGA<br>TATCTGCAGAATTCGCCCTTGCTCGCTCCACCTCTCAAGCAGCC<br>AGCGCCTGCCTGAATCTGTTCTGCCCCCTCCCCACCCATTTCACC<br>ACCACCATGACACCGGGCACCCAGTCTCCTTTCTTCCTGCTGCTG<br>CTCCTCACAGTGCTTACAGTTGTTACGGGTTCTGGTCATGCAAG<br>CTCTACCCCAGGTGGAGAAAAGGAGACTTCGGCTACCAGAGA<br>AGTTCAGTGCCCAGCTCTACTGAGAAGAATGCTGTGAGTATGAC<br>CAGCAGCGTACTCTCCAGCCACAGCCCCGGTTCAGGCTCCTCCA<br>CCACTCAGGGACAGGATGTCACTCTGGCCCCGGCCACGGAACC<br>AGCTTCAGGTTCAGCTGCCCTTTGGGGACAGGATGTCACCTCGG<br>TCCCAGTCACCAGGCCAGCCCTGGGCTCCACCACCCCGCCAGCC<br>CACGATGTCACCTCAGCCCCGGACAACAAGCCAGCCCCGGGCTC<br>CACCGCCCCCCCAGCCCACGGTGTCACCTCGTATCTTGACACCA<br>GGCCGGCCCCGGTTTATCTTGCCCCCCCAGCCCATGGTGTCACC<br>TCGGCCCCGGACAACAGGCCCGCCTTGGGCTCCACCGCCCCTCC<br>AGTCCACAATGTCACCTCGGCCTCAGGCTCTGCATCAGGCTCAG<br>CTTCTACTCTGGTGCACAACGGCACCTCTGCCAGGGCTACCACA<br>ACCCCAGCCAGCAAGAGCACTCCATTCTCAATTCCCAGCCACCA<br>CTCTGATACTCCTACCACCCTTGCCAGCCATAGCACCAAGACTG<br>ATGCCAGTAGCACTCACCATAGCACGGTACCTCCTCTCACCTCC<br>TCCAATCACAGCACTTCTCCCCAGTTGTCTACTGGGGTCTCTTTC |

| SEQ ID NO | Sequence |
|---|---|
| | TTTTTCCTGTCTTTTCACATTTCAAACCTCCAGTTTAATTCCTCTC<br>TGGAAGATCCCAGCACCGACTACTACCAAGAGCTGCAGAGAGA<br>CATTTCTGAAATGTTTTTGCAGATTTATAAACAAGGGGGTTTTCT<br>GGGCCTCTCCAATATTAAGTTCAGGCCAGGATCTGTGGTGGTAC<br>AATTGACTCTGGCCTTCCGAGAAGGTACCATCAATGTCCACGAC<br>GTGGAGACACAGTTCAATCAGTATAAAACGGAAGCAGCCTCTC<br>GATATAACCTGACGATCTCAGACGTCAGCGTGAGTGATGTGCCA<br>TTTCCTTTCTCTGCCCAGTCTGGGGCTGGGGTGCCAGGCTGGGG<br>CATCGCGCTGCTGGTGCTGGTCTGTGTTCTGGTTTATCTGGCCAT<br>TGTCTATCTCATTGCCTTGGCTGTCGCTCAGGTTCGCCGAAAGA<br>ACTACGGGCAGCTGGACATCTTTCCAGCCCGGGATAAATACCAT<br>CCTATGAGCGAGTACGCTCTTTACCACACCCATGGGCGCTATGT<br>GCCCCCTAGCAGTCTTTTCCGTAGCCCCTATGAGAAGGTTTCTGC<br>AGGTAATGGTGGCAGCTATCTCTCTTACACAAACCCAGCAGTGG<br>CAGCCGCTTCTGCCAACTTGTAGGGGCACGTCGCCCGCTGAGCT<br>GAGTGGCCAGCCAGTGCCATTCCACTCCACTCAGGTTCTTCAGG<br>GCCAGAGCCCTGCACCCTGTTTGGGCTGGTGAGCTGGGAGTTC<br>AGGTGGGCTGCTCACAGCCTCCTTCAGAGGCCCCACCAATTTCT<br>CGGACACTTCTCAGTGTGTGGAAGCTCATGTGGGCCCTGAGGG<br>CTCATGCCTGGGAAGTGTTGTGGTGGGGCTCCCAGGAGGACTG<br>GCCCAGAGAGCCCTGAGATAGCGGGGATCCTGAACTGGACTGA<br>ATAAAACGTGGTCTCCCACTGCGCCAAAAAAAAAAAAAAAAC<br>GATCCACCGGATCTAGATAACTGATCATAATCAGCCATACCACA<br>TTTGTAGAGGTTTTACTTGCTTTAAAAAACCTCCCACACCTCCC<br>CTGAACCTGAAACATAAAATGAATGCAATTGTTGTTGTTAACTT<br>GTTTATTGCAGCTTATAATGGTTACAAATAAAGCAATAGCATCA<br>CAAATTTCACAAATAAAGCATTTTTTTCACTGCATTCTAGTTGTG<br>GTTTGTCCAAACTCATCAATGTATCTTAACGCGGATCTGGAAGG<br>TGCTGAGGTACGATGAGACCCGCACCAGGTGCAGACCCTGCGA<br>GTGTGGCGGTAAACATATTAGGAACCAGCCTGTGATGCTGGATG<br>TGACCGAGGAGCTGAGGCCCGATCACTTGGTGCTGGCCTGCACC<br>CGCGCTGAGTTTGGCTCTAGCGATGAAGATACAGATTGAGGTAC<br>TGAAATGTGTGGGCGTGGCTTAAGGGTGGGAAGAATATATAA<br>GGTGGGGGTCTTATGTAGTTTTGTATCTGTTTTGCAGCAGCCGCC<br>GCCGCCATGAGCACCAACTCGTTTGATGGAAGCATTGTGAGCTC<br>ATATTTGACAACGCGCATGCCCCCATGGGCCGGGGTGCGTCAGA<br>ATGTGATGGGCTCCAGCATTGATGGTCGCCCCGTCCTGCCCGCA<br>AACTCTACTACCTTGACCTACGAGACCGTGTCTGGAACGCCGTT<br>GGAGACTGCAGCCTCCGCCGCCGCTTCAGCCGCTGCAGCCACCG<br>CCCGCGGGATTGTGACTGACTTTGCTTTCCTGAGCCCGCTTGCA<br>AGCAGTGCAGCTTCCCGTTCATCCGCCCGCGATGACAAGTTGAC<br>GGCTCTTTTGGCACAATTGGATTCTTTGACCCGGGAACTTAATGT<br>CGTTTCTCAGCAGCTGTTGGATCTGCGCCAGCAGGTTTCTGCCCT<br>GAAGGCTTCCTCCCCTCCCAATGCGGTTTAAAACATAAATAAAA<br>AACCAGACTCTGTTTGGATTTGGATCAAGCAAGTGTCTTGCTGT<br>CTTTATTTAGGGGTTTTGCGCGCGCGGTAGGCCCGGGACCAGCG<br>GTCTCGGTCGTTGAGGGTCCTGTGTATTTTTTCCAGGACGTGGTA<br>AAGGTGACTCTGGATGTTCAGATACATGGGCATAAGCCCGTCTC<br>TGGGGTGGAGGTAGCACCACTGCAGAGCTTCATGCTGCGGGGT<br>GGTGTTGTAGATGATCCAGTCGTAGCAGGAGCGCTGGGCGTGGT<br>GCCTAAAAATGTCTTTCAGTAGCAAGCTGATTGCCAGGGGCAGG<br>CCCTTGGTGTAAGTGTTTACAAAGCGGTTAAGCTGGGATGGGTG<br>CATACGTGGGGATATGAGATGCATCTTGGACTGTATTTTTAGGT<br>TGGCTATGTTCCCAGCCATATCCCTCCGGGGATTCATGTTGTGCA<br>GAACCACCAGCACAGTGTATCCGGTGCACTTGGGAAATTTGTCA<br>TGTAGCTTAGAAGGAAATGCGTGGAAGAACTTGGAGACGCCCT<br>TGTGACCTCCAAGATTTTCCATGCATTCGTCCATAATGATGGCA<br>ATGGGCCCACGGGCGGCGGCCTGGGCGAAGATATTTCTGGGAT<br>CACTAACGTCATAGTTGTGTTCCAGGATGAGATCGTCATAGGCC<br>ATTTTTACAAAGCGCGGGCGGAGGGTGCCAGACTGCGGTATAAT<br>GGTTCCATCCGGCCCAGGGGCGTAGTTACCCTCACAGATTTGCA<br>TTTCCCACGCTTTGAGTTCAGATGGGGGGATCATGTCTACCTGC<br>GGGGCGATGAAGAAAACGGTTTCCGGGGTAGGGGAGATCAGCT<br>GGGAAGAAAGCAGGTTCCTGAGCAGCTGCGACTTACCGCAGCC<br>GGTGGGCCCGTAAATCACACCTATTACCGGCTGCAACTGGTAGT<br>TAAGAGAGCTGCAGCTGCCGTCATCCCTGAGCAGGGGGGCCAC<br>TTCGTTAAGCATGTCCCTGACTCGCATGTTTTCCCTGACCAAATC<br>CGCCAGAAGGCGCTCGCCGCCCAGCGATAGCAGTTCTTGCAAG<br>GAAGCAAAGTTTTTCAACGGTTTGAGACCGTCCGCCGTAGGCAT<br>GCTTTTGAGCGTTTGACCAAGCAGTTCCAGGCGGTCCCACAGCT<br>CGGTCACCTGCTCTACGGCATCTCGATCCAGCATATCTCCTCGTT<br>TCGCGGGTTGGGGCGGCTTTCGCTGTACGGCAGTAGTCGGTGCT<br>CGTCCAGACGGGCCAGGGTCATGTCTTTCCACGGGCGCAGGGTC<br>CTCGTCAGCGTAGTCTGGGTCACGGTGAAGGGGTGCGCTCCGGG<br>CTGCGCGCTGGCCAGGGTGCGCTTGAGGCTGGTCCTGCTGGTGC<br>TGAAGCGCTGCCGGTCTTCGCCCTGCGCGTCGGCCAGGTAGCAT<br>TTGACCATGGTGTCATAGTCCAGCCCCTCCGCGGCGTGGCCCTT |

| SEQ ID NO | Sequence |
| --- | --- |
| | GGCGCGCAGCTTGCCCTTGGAGGAGGCGCCGCACGAGGGGCAG |
| | TGCAGACTTTTGAGGGCGTAGAGCTTGGGCGCGAGAAATACCG |
| | ATTCCGGGGAGTAGGCATCCGCGCCGCAGGCCCCGCAGACGGT |
| | CTCGCATTCCACGAGCCAGGTGAGCTCTGGCCGTTCGGGGTCAA |
| | AAACCAGGTTTCCCCCATGCTTTTTGATGCGTTTCTTACCTCTGG |
| | TTTTCCATGAGCCGGTGTCCACGCTCGGTGACGAAAAGGCTGTCC |
| | GTGTCCCCGTATACAGACTTGAGAGGCCTGTCCTCGAGCGGTGT |
| | TCCGCGGTCCTCCTCGTATAGAAACTCGGACCACTCTGAGACAA |
| | AGGCTCGCGTCCAGGCCAGCACGAAGGAGGCTAAGTGGGAGGG |
| | GTAGCGGTCGTTGTCCACTAGGGGGTCCACTCGCTCCAGGGTGT |
| | GAAGACACATGTCGCCCTCTTCGGCATCAAGGAAGGTGATTGGT |
| | TTGTAGGTGTAGGCCACGTGACCGGGTGTTCCTGAAGGGGGGCT |
| | ATAAAAGGGGGTGGGGGCGCGTTCGTCCTCACTCTCTTCCGCAT |
| | CGCTGTCTGCGAGGGCCAGCTGTTGGGGTGAGTACTCCCTCTGA |
| | AAAGCGGGCATGACTTCTGCGCTAAGATTGTCAGTTTCCAAAAA |
| | CGAGGAGGATTTGATATTCACCTGGCCCGCGGTGATGCCTTTGA |
| | GGGTGGCCGCATCCATCTGGTCAGAAAAGACAATCTTTTTGTTG |
| | TCAAGCTTGGTGGCAAACGACCCGTAGAGGGCGTTGGACAGCA |
| | ACTTGGCGATGGAGCGCAGGGTTTGGTTTTTGTCGCGATCGGCG |
| | CGCTCCTTGGCCGCGATGTTTAGCTGCACGTATTCGCGCGCAAC |
| | GCACCGCCATTCGGGAAAGACGGTGGTGCGCTCGTCGGGCACC |
| | AGGTGCACGCGCCAACCGCGGTTGTGCAGGGTGACAAGGTCAA |
| | CGCTGGTGGCTACCTCTCCGCGTAGGCGCTCGTTGGTCCAGCAG |
| | AGGCGGCCGCCCTTGCGCGAGCAGAATGGCGGTAGGGGGTCTA |
| | GCTGCGTCTCGTCCGGGGGGTCTGCGTCCACGGTAAAGACCCCG |
| | GGCAGCAGGCGCGCGTCGAAGTAGTCTATCTTGCATCCTTGCAA |
| | GTCTAGCGCCTGCTGCCATGCGCGGGCGGCAAGCGCGCGCTCGT |
| | ATGGGTTGAGTGGGGGACCCCATGGCATGGGGTGGGTGAGCGC |
| | GGAGGCGTACATGCCGCAAATGTCGTAAACGTAGAGGGGCTCT |
| | CTGAGTATTCCAAGATATGTAGGGTAGCATCTTCCACCGCGGAT |
| | GCTGGCGCGCACGTAATCGTATAGTTCGTGCGAGGGAGCGAGG |
| | AGGTCGGGACCGAGGTTGCTACGGGCGGGCTGCTCTGCTCGGA |
| | AGACTATCTGCCTGAAGATGGCATGTGAGTTGGATGATATGGTT |
| | GGACGCTGGAAGACGTTGAAGCTGGCGTCTGTGAGACCTACCG |
| | CGTCACGCACGAAGGAGGCGTAGGAGTCGCGCAGCTTGTTGAC |
| | CAGCTCGGCGGTGACCTGCACGTCTAGGGCGCAGTAGTCCAGG |
| | GTTTCCTTGATGATGTCATACTTATCCTGTCCCTTTTTTTTCCACA |
| | GCTCGCGGTTGAGGACAAACTCTTCGCGGTCTTTCCAGTACTCTT |
| | GGATCGGAAACCCGTCGGCCTCCGAACGGTAAGAGCCTAGCAT |
| | GTAGAACTGGTTGACGGCCTGGTAGGCGCAGCATCCCTTTTCTA |
| | CGGGTAGCGCGTATGCCTGCGCGGCCTTCCGGCATGACCAGCAT |
| | GAAGGGCACGAGCTGCTTCCCAAAGGCCCCCATCCAAGTATAG |
| | GTCTCTACATCGTAGGTGACAAAGAGACGCTCGGTGCGAGGAT |
| | GCGAGCCGATCGGGAAGAACTGGATCTCCCGCCACCAATTGGA |
| | GGAGTGGCTATTGATGTGGTGAAAGTAGAAGTCCCTGCGACGG |
| | GCCGAACACTCGTGCTGGCTTTTGTAAAAACGTGCGCAGTACTG |
| | GCAGCGGTGCACGGGCTGTACATCCTGCACGAGGTTGACCTGAC |
| | GACCGCGCACAAGGAAGCAGAGTGGGAATTTGAGCCCCTCGCC |
| | TGGCGGGTTTGGCTGGTGGTCTTCTACTTCGGCTGCTTGTCCTTG |
| | ACCGTCTGGCTGCTCGAGGGGAGTTACGGTGGATCGGACCACCA |
| | CGCCGCGCGAGCCCAAAGTCCAGATGTCCGCGCGCGGCGGTCG |
| | GAGCTTGATGACAACATCGCGCAGATGGGAGCTGTCCATGGTCT |
| | GGAGCTCCCGCGGCGTCAGGTCAGGCGGGAGCTCCTGCAGGTTT |
| | ACCTCGCATAGACGGGTCAGGGCGCGGGCTAGATCCAGGTGAT |
| | ACCTAATTTCCAGGGGCTGGTTGGTGGCGGCGTCGATGGCTTGC |
| | AAGAGGCCGCATCCCCGCGGCGCGACTACGGTACCGCGCGGCG |
| | GGCGGTGGGCCGCGGGGGTGTCCTTGGATGATGCATCTAAAAG |
| | CGGTGACGCGGGCGAGCCCCCGGAGGTAGGGGGGGCTCCGGAC |
| | CCGCCGGGAGAGGGGCAGGGGCACGTCGGCGCCGCGCGGGG |
| | CAGGAGCTGGTGCTGCGCGTAGGTTGCTGGCGAACGCGACG |
| | ACGCGGCGGTTGATCTCCTGAATCTGGCGCCTCTGCGTGAAGAC |
| | GACGGGCCCGGTGAGCTTGAACCTGAAAGAGAGTTCGACAGAA |
| | TCAATTTCGGTGTCGTTGACGGCGGCCTGGCGCAAAATCTCCTG |
| | CACGTCTCCTGAGTTGTCTTGATAGGCGATCTCGGCCATGAACT |
| | GCTCGATCTCTTCCTCCTGGAGATCTCCGCGTCCGGCTCGCTCCA |
| | CGGTGGCGGCGAGGTCGTTGGAAATGCGGGCCATGAGCTGCGA |
| | GAAGGCGTTGAGGCCTCCCTCGTTCCAGACGCGGCTGTAGACCA |
| | CGCCCCCTTCGGCATCGCGGGCGCGCATGACCACCTGCGCGAGA |
| | TTGAGCTCCACGTGCCGGGCGAAGACGCGTAGTTTCGCAGGCG |
| | CTGAAAGAGGTAGTTGAGGGTGGTGGCGGTGTGTTCTGCCACGA |
| | AGAAGTACATAACCCAGCGTCGCAACGTGGATTCGTTGATAATT |
| | GTTGTGTAGGTACTCCGCCGCCGAGGGACCTGAGCGAGTCCGCA |
| | TCGACCGGATCGGAAAACCTCTCGAGAAAGGCGTCTAACCAGT |
| | CACAGTCGCAAGGTAGGCTGAGCACCGTGGCGGGCGGCAGCGG |
| | GCGGCGGTCGGGGTTGTTTCTGGCGGAGGTGCTGCTGATGATGT |
| | AATTAAAGTAGGCGGTCTTGAGACGGCGGATGGTCGACAGAAG |
| | CACCATGTCCTTGGGTCCGGCCTGCTGAATGCGCAGGCGGTCGG |

| SEQ ID NO | Sequence |
|---|---|
| | CCATGCCCCAGGCTTCGTTTTGACATCGGCGCAGGTCTTTGTAGT |
| | AGTCTTGCATGAGCCTTTCTACCGGCACTTCTTCTTCTCCTTCCT |
| | CTTGTCCTGCATCTCTTGCATCTATCGCTGCGGCGGCGGCGGAG |
| | TTTGGCCGTAGGTGGCGCCCTCTTCCTCCCATGCGTGTGACCCCG |
| | AAGCCCCTCATCGGCTGAAGCAGGGCTAGGTCGGCGACAACGC |
| | GCTCGGCTAATATGGCCTGCTGCACCTGCGTGAGGGTAGACTGG |
| | AAGTCATCCATGTCCACAAAGCGGTGGTATGCGCCCGTGTTGAT |
| | GGTGTAAGTGCAGTTGGCCATAACGGACCAGTTAACGGTCTGGT |
| | GACCCGGCTGCGAGAGCTCGGTGTACCTGAGACGCGAGTAAGC |
| | CCTCGAGTCAAATACGTAGTCGTTGCAAGTCCGCACCAGGTACT |
| | GGTATCCCACCAAAAAGTGCGGCGGCGGCTGGCGGTAGAGGGG |
| | CCAGCGTAGGGTGGCCGGGGCTCCGGGGGCGAGATCTTCCAAC |
| | ATAAGGCGATGATATCCGTAGATGTACCTGGACATCCAGGTGAT |
| | GCCGGCGGCGGTGGTGGAGGCGCGCGGAAAGTCGCGGACGCGG |
| | TTCCAGATGTTGCGCAGCGGCAAAAAGTGCTCCATGGTCGGGAC |
| | GCTCTGGCCGGTCAGGCGCGCGCAATCGTTGACGCTCTAGCGTG |
| | CAAAAGGAGAGCCTGTAAGCGGGCACTCTTCCGTGGTCTGGTGG |
| | ATAAATTCGCAAGGGTATCATGGCGGACGACCGGGGTTCGAGC |
| | CCCGTATCCGGCCGTCCGCCGTGATCCATGCGGTTACCGCCCGC |
| | GTGTCGAACCCAGGTGTGCGACGTCAGACAACGGGGGAGTGCT |
| | CCTTTTGGCTTCCTTCCAGGCGCGGCGGCTGCTGCGCTAGCTTTT |
| | TTGGCCACTGGCCGCGCGCAGCGTAAGCGGTTAGGCTGGAAAG |
| | CGAAAGCATTAAGTGGCTCGCTCCCTGTAGCCGGAGGGTTATTT |
| | TCCAAGGGTTGAGTCGCGGGACCCCCGGTTCGAGTCTCGGACCG |
| | GCCGGACTGCGGCGAACGGGGGTTTGCCTCCCCGTCATGCAAGA |
| | CCCCGCTTGCAAATTCCTCCGGAAACAGGGACGAGCCCCTTTTT |
| | TGCTTTTCCCAGATGCATCCGGTGCTGCGGCAGATGCGCCCCCC |
| | TCCTCAGCAGCGGCAAGAGCAAGAGCAGCGGCAGACATGCAGG |
| | GCACCCTCCCCTCCTCCTACCGCGTCAGGAGGGGCGACATCCGC |
| | GGTTGACGCGGCAGCAGATGGTGATTACGAACCCCGCGGCGC |
| | CGGGCCCGGCACTACCTGGACTTGGAGGAGGGCGAGGGCCTGG |
| | CGCGGCTAGGAGCGCCCTCTCCTGAGCGGCACCCAAGGGTGCA |
| | GCTGAAGCGTGATACGCGTGAGGCGTACGTGCCGCGGCAGAAC |
| | CTGTTTCGCGACCGCGAGGGAGAGGAGCCCGAGGAGATGCGGG |
| | ATCGAAAGTTCCACGCAGGGCGCGAGCTGCGGCATGGCCTGAA |
| | TCGCGAGCGGTTGCTGCGCGAGGAGGACTTTGAGCCCGACGCG |
| | CGAACCGGGATTAGTCCCGCGCGCACACGTGGCGGCCGCCG |
| | ACCTGGTAACCGCATACGAGCAGACGGTGAACCAGGAGATTAA |
| | CTTTCAAAAAGCTTTAACAACCACGTGCGTACGCTTGTGGCGC |
| | GCGAGGAGGTGGCTATAGGACTGATGCATCTGTGGGACTTTGTA |
| | AGCGCGCTGGAGCAAAACCCAAATAGCAAGCCGCTCATGGCGC |
| | AGCTGTTCCTTATAGTGCAGCACAGCAGGGACAACGAGGCATTC |
| | AGGGATGCGCTGCTAAACATAGTAGAGCCCGAGGGCCGCTGGC |
| | TGCTCGATTTGATAAACATCCTGCAGAGCATAGTGGTGCAGGAG |
| | CGCAGCTTGAGCCTGGCTGACAAGGTGGCCGCCATCAACTATTC |
| | CATGCTTAGCCTGGGCAAGTTTTACGCCCGCAAGATATACCATA |
| | CCCCTTACGTTCCCATAGACAAGGAGGTAAAGATCGAGGGGTTC |
| | TACATGCGCATGGCGCTGAAGGTGCTTACCTTGAGCGACGACCT |
| | GGGCGTTTATCGCAACGAGCGCATCCACAAGGCCGTGAGCGTG |
| | AGCCGGCGGCGCGAGCTCAGCGACCGCGAGCTGATGCACAGCC |
| | TGCAAAGGGCCCTGGCTGGCACGGGCAGCGGCGATAGAGAGGC |
| | CGAGTCCTACTTTGACGCGGGCGCTGACCTGCGCTGGGCCCCAA |
| | GCCGACGCGCCCTGGAGGCAGCTGGGGCCGGACCTGGGCTGGC |
| | GGTGGCACCCGCGCGCGCTGGCAACGTCGGCGGCGTGGAGGAA |
| | TATGACGAGGACGATGAGTACGAGCCAGAGGACGGCGAGTACT |
| | AAGCGGTGATGTTTCTGATCAGATGATGCAAGACGCAACGGAC |
| | CCGGCGGTGCGGGCGGCGCTGCAGAGCCAGCCGTCCGGCCTTA |
| | ACTCCACGGACGACTGGCGCCAGGTCATGGACCGCATCATGTCG |
| | CTGACTGCGCGCAATCCTGACGCGTTCCGGCAGCAGCCGCAGGC |
| | CAACCGGCTCTCCGCAATTCTGGAAGCGGTGGTCCCGGCGCGCG |
| | CAAACCCCACGCACGAGAAGGTGCTGGCGATCGTAAACGCGCT |
| | GGCCGAAAACAGGGCCATCCGGCCCGACGAGGCCGGCCTGGTC |
| | TACGACGCGCTGCTTCAGCGCGTGGCTCGTTACAACAGCGGCAA |
| | CGTGCAGACCAACCTGGACCGGCTGGTGGGGATGTGCGCGAG |
| | GCCGTGGCGCAGCGTGAGCGCGCGCAGCAGCAGGGCAACCTGG |
| | GCTCCATGGTTGCACTAAACGCCTTCCTGAGTACACAGCCCGCC |
| | AACGTGCCGCGGGGACAGGAGGACTACACCAACTTTGTGAGCG |
| | CACTGCGGCTAATGGTGACTGAGACACCGCAAAGTGAGGTGTA |
| | CCAGTCTGGGCCAGACTATTTTTTCCAGACCAGTAGACAAGGCC |
| | TGCAGACCGTAAACCTGAGCCAGGCTTTCAAAAACTTGCAGGG |
| | GCTGTGGGGGTGCGGGCTCCCACAGGCGACCGCGCGACCGTG |
| | TCTAGCTTGCTGACGCCCAACTCGCGCCTGTTGCTGCTGCTAATA |
| | GCGCCCTTCACGGACAGTGGCAGCGTGTCCCGGGACACATACCT |
| | AGGTCACTTGCTGACACTGTACCGCGAGGCCATAGGTCAGGCGC |
| | ATGTGGACGAGCATACTTTCCAGGAGATTACAAGTGTCAGCCGC |
| | GCGCTGGGGCAGGAGGACACGGGCAGCCTGGAGGCAACCCTAA |
| | ACTACCTGCTGACCAACCGGCGGCAGAAGATCCCCTCGTTGCAC |

| SEQ ID NO | Sequence |
|---|---|
| | AGTTTAAACAGCGAGGAGGAGCGCATTTTGCGCTACGTGCAGC<br>AGAGCGTGAGCCTTAACCTGATGCGCGACGGGGTAACGCCCAG<br>CGTGGCGCTGGACATGACCGCGCGCAACATGGAACCGGGCATG<br>TATGCCTCAAACCGGCCGTTTATCAACCGCCTAATGGACTACTT<br>GCATCGCGCGGCCGCCGTGAACCCCGAGTATTTCACCAATGCCA<br>TCTTGAACCCGCACTGGCTACCGCCCCCTGGTTTCTACACCGGG<br>GGATTCGAGGTGCCCGAGGGTAACGATGGATTCCTCTGGGACG<br>ACATAGACGACAGCGTGTTTTCCCCGCAACCGCAGACCCTGCTA<br>GAGTTGCAACAGCGCGAGCAGGCAGAGGCGGCGCTGCGAAAGG<br>AAAGCTTCCGCAGGCCAAGCAGCTTGTCCGATCTAGGCGCTGCG<br>GCCCCGCGGTCAGATGCTAGTAGCCCATTTCCAAGCTTGATAGG<br>GTCTCTTACCAGCACTCGCACCACCCGCCCGCGCCTGCTGGGCG<br>AGGAGGAGTACCTAAACAACTCGCTGCTGCAGCCGCAGCGCGA<br>AAAAAACCTGCCTCCGGCATTTCCCAACAACGGGATAGAGAGC<br>CTAGTGGACAAGATGAGTAGATGGAAGACGTACGCGCAGGAGC<br>ACAGGGACGTGCCAGGCCCGCGCCCGCCCACCCGTCGTCAAAG<br>GCACGACCGTCAGCGGGGTCTGGTGTGGGAGGACGATGACTCG<br>GCAGACGACAGCAGCGTCCTGGATTTGGGAGGGAGTGGCAACC<br>CGTTTGCGCACCTTCGCCCCAGGCTGGGGAGAATGTTTTAAAAA<br>AAAAAAAGCATGATGCAAAATAAAAAACTCACCAAGGCCATGG<br>CACCGAGCGTTGGTTTTCTTGTATTCCCCTTAGTATGCGGCGCGC<br>GGCGATGTATGAGGAAGGTCCTCCTCCCTCCTACGAGAGTGTGG<br>TGAGCGCGGCGCCAGTGGCGGCGGCGCTGGGTTCTCCCTTCGAT<br>GCTCCCCTGGACCCGCCGTTTGTGCCTCCGCGGTACCTGCGGCC<br>TACCGGGGGGAGAAACAGCATCCGTTACTCTGAGTTGGCACCCC<br>TATTCGACACCACCCGTGTGTACCTGGTGGACAACAAGTCAACG<br>GATGTGGCATCCCTGAACTACCAGAACGACCACAGCAACTTTCT<br>GACCACGGTCATTCAAAACAATGACTACAGCCCGGGGGAGGCA<br>AGCACACAGACCATCAATCTTGACGACCGGTCGCACTGGGGCG<br>GCGACCTGAAAACCATCCTGCATACCAACATGCCAAATGTGAAC<br>GAGTTCATGTTTACCAATAAGTTTAAGGCGCGGGTGATGGTGTC<br>GCGCTTGCCTACTAAGGACAATCAGGTGGAGCTGAAATACGAG<br>TGGGTGGAGTTCACGCTGCCCGAGGGCAACTACTCCGAGACCAT<br>GACCATAGACCTTATGAACAACGCGATCGTGGAGCACTACTTGA<br>AAGTGGGCAGACAGAACGGGGTTCTGGAAAGCGACATCGGGGT<br>AAAGTTTGACACCCGCAACTTCAGACTGGGGTTTGACCCCGTCA<br>CTGGTCTTGTCATGCCTGGGGTATATACAAACGAAGCCTTCCAT<br>CCAGACATCATTTTGCTGCCAGGATGCGGGGTGGACTTCACCCA<br>CAGCCGCCTGAGCAACTTGTTGGGCATCCGCAAGCGGCAACCCT<br>TCCAGGAGGGCTTTAGGATCACCTACGATGATCTGGAGGGTGGT<br>AACATTCCCGCACTGTTGGATGTGGACGCCTACCAGGCGAGCTT<br>GAAAGATGACACCGAACAGGGCGGGGGTGGCGCAGGCGGCAG<br>CAACAGCAGTGGCAGCGGCGCGGAAGAGAACTCCAACGCGGCA<br>GCCGCGGCAATGCAGCCGGTGGAGGACATGAACGATCATGCCA<br>TTCGCGGCGACACCTTTGCCACACGGGCTGAGGAGAAGCGCGCT<br>GAGGCCGAAGCAGCGGCCGAAGCTGCCGCCCCCGCTGCGCAAC<br>CCGAGGTCGAGAAGCCTCAGAAGAAACCGGTGATCAAACCCCT<br>GACAGAGGACAGCAAGAAACGCAGTTACAACCTAATAAGCAAT<br>GACAGCACCTTCACCCAGTACCGCAGCTGGTACCTTGCATACAA<br>CTACGGCGACCCTCAGACCGGAATCCGCTCATGGACCCTGCTTT<br>GCACTCCTGACGTAACCTGCGGCTCGGAGCAGGTCTACTGGTCG<br>TTGCCAGACATGATGCAAGACCCCGTGACCTTCCGCTCCACGCG<br>CCAGATCAGCAACTTTCCGGTGGTGGGCGCCGAGCTGTTGCCCG<br>TGCACTCCAAGAGCTTCTACAACGACCAGGCCGTCTACTCCCAA<br>CTCATCCGCCAGTTTACCTCTCTGACCCACGTGTTCAATCGCTTT<br>CCCGAGAACCAGATTTTGGCGCGCCCGCCAGCCCCCACCATCAC<br>CACCGTCAGTGAAAACGTTCCTGCTCTCACAGATCACGGGACGC<br>TACCGCTGCGCAACAGCATCGGAGGAGTCCAGCGAGTGACCAT<br>TACTGACGCCAGACGCCGCACCTGCCCCTACGTTTACAAGGCCC<br>TGGGCATAGTCTCGCCGCGCGTCCTATCGAGCCGCACTTTTTGA<br>GCAAGCATGTCCATCCTTATATCGCCCAGCAATAACACAGGCTG<br>GGGCCTGCGCTTCCCAAGCAAGATGTTTGGCGGGGCCAAGAAG<br>CGCTCCGACCAACACCCAGTGCGCGTGCGCGGGCACTACCGCGC<br>GCCCTGGGGCGCGCACAAACGCGGCCGCACTGGGCGCACCACC<br>GTCGATGACGCCATCGACGCGGTGGTGGAGGAGGCGCGCAACT<br>ACACGCCCACGCCGCCACCAGTGTCCACAGTGGACGCGGCCATT<br>CAGACCGTGGTGCGCGGAGCCCGGCGCTATGCTAAAATGAAGA<br>GACGGCGGAGGCGCGTAGCACGTCGCCACCGCCGCCGACCCGG<br>CACTGCCGCCCAACGCGCGGCGGCGGCCCTGCTTAACCGCGCAC<br>GTCGCACCGGCCGACGGGCGGCCATGCGGGCCGCTCGAAGGCT<br>GGCCGCGGGTATTGTCACTGTGCCCCCCAGGTCCAGGCGACGAG<br>CGGCCGCCGCAGCAGCCGCGGCCATTAGTGCTATGACTCAGGGT<br>CGCAGGGGCAACGTGTATTGGGTGCGCGACTCGGTTAGCGGCCT<br>GCGCGTGCCCGTGCGCACCCGCCCCCCGCGCAACTAGATTGCAA<br>GAAAAAACTACTTAGACTCGTACTGTTGTATGTATCCAGCGGCG<br>GCGGCGCGCAACGAAGCTATGTCCAAGCGCAAAATCAAAGAAG<br>AGATGCTCCAGGTCATCGCGCCGGAGATCTATGGCCCCCCGAAG |

-continued

| SEQ ID NO | Sequence |
|---|---|
| | AAGGAAGAGCAGGATTACAAGCCCCGAAAGCTAAAGCGGGTCA |
| | AAAAGAAAAAGAAAGATGATGATGATGAACTTGACGACGAGGT |
| | GGAACTGCTGCACGCTACCGCGCCCAGGCGACGGGTACAGTGG |
| | AAAGGTCGACGCGTAAAACGTGTTTTGCGACCCGGCACCACCGT |
| | AGTCTTTACGCCCGGTGAGCGCTCCACCCGCACCTACAAGCGCG |
| | TGTATGATGAGGTGTACGGCGACGAGGACCTGCTTGAGCAGGC |
| | CAACGAGCGCCTCGGGGAGTTTGCCTACGGAAAGCGGCATAAG |
| | GACATGCTGGCGTTGCCGCTGGACGAGGGCAACCCAACACCTA |
| | GCCTAAAGCCCGTAACACTGCAGCAGGTGCTGCCCGCGCTTGCA |
| | CCGTCCGAAGAAAAGCGCGGCCTAAAGCGCGAGTCTGGTGACT |
| | TGGCACCCACCGTGCAGCTGATGGTACCCAAGCGCCAGCGACTG |
| | GAAGATGTCTTGGAAAAAATGACCGTGGAACCTGGGCTGGAGC |
| | CCGAGGTCCGCGTGCGGCCAATCAAGCAGGTGGCGCCGGGACT |
| | GGGCGTGCAGACCGTGGACGTTCAGATACCCACTACCAGTAGC |
| | ACCAGTATTGCCACCGCCACAGAGGGCATGGAGACACAAACGT |
| | CCCCGGTTGCCTCAGCGGTGGCGGATGCCGCGGTGCAGGCGGTC |
| | GCTGCGGCCGCGTCCAAGACCTCTACGGAGGTGCAAACGGACC |
| | CGTGGATGTTTCGCGTTTCAGCCCCCCGGCGCCCGCGCCGTTCG |
| | AGGAAGTACGGCGCCGCCAGCGCGCTACTGCCCGAATATGCCCT |
| | ACATCCTTCCATTGCGCCTACCCCCGGCTATCGTGGCTACACCTA |
| | CCGCCCCAGAAGACGAGCAACTACCCGACGCCGAACCACCACT |
| | GGAACCCGCCGCCGCCGTCGCCGTCGCCAGCCCGTGCTGGCCCC |
| | GATTTCCGTGCGCAGGGTGGCTCGCGAAGGAGGCAGGACCCTG |
| | GTGCTGCCAACAGCGCGCTACCACCCCAGCATCGTTTAAAAGCC |
| | GGTCTTTGTGGTTCTTGCAGATATGGCCCTCACCTGCCGCCTCCG |
| | TTTCCCGGTGCCGGGATTCCGAGGAAGAATGCACCGTAGGAGG |
| | GGCATGGCCGGCCACGGCCTGACGGGCGGCATGCGTCGTGCGC |
| | ACCACCGGCGGCGGCGCGTCGCACCGTCGCATGCGCGGCGG |
| | TATCCTGCCCCTCCTTATTCCACTGATCGCCGCGGCGATTGGCGC |
| | CGTGCCCGGAATTGCATCCGTGCCTTGCAGGCGCAGAGACACT |
| | GATTAAAAACAAGTTGCATGTGGAAAAATCAAAATAAAAAGTC |
| | TGGACTCTCACGCTCGCTTGGTCCTGTAACTATTTTGTAGAATGG |
| | AAGACATCAACTTTGCGTCTCTGGCCCCGCGACACGGCTCGCGC |
| | CCGTTCATGGGAAACTGGCAAGATATCGGCACCAGCAATATGA |
| | GCGGTGGCGCCTTCAGCTGGGGCTCGCTGTGGAGCGGCATTAAA |
| | AATTTCGGTTCCACCGTTAAGAACTATGGCAGCAAGGCCTGGAA |
| | CAGCAGCACAGGCCAGATGCTGAGGGATAAGTTGAAAGAGCAA |
| | AATTTCCAACAAAAGGTGGTAGATGGCCTGGCCTCTGGCATTAG |
| | CGGGGTGGTGGACCTGGCCAACCAGGCAGTGCAAAATAAGATT |
| | AACAGTAAGCTTGATCCCCGCCCTCCCGTAGAGGAGCCTCCACC |
| | GGCCGTGGAGACAGTGTCTCCAGAGGGGCGTGGCGAAAAGCGT |
| | CCGCGCCCCGACAGGGAAGAAACTCTGGTGACGCAAATAGACG |
| | AGCCTCCCTCGTACGAGGAGGCACTAAAGCAAGGCCTGCCCAC |
| | CACCCGTCCCATCGCGCCCATGGCTACCGGAGTGCTGGGCCAGC |
| | ACACCACCCGTAACGCTGGACCTGCCTCCCCCCGCCGACACCCAG |
| | CAGAAACCTGTGCTGCCAGGCCCGACCGCCGTTGTTGTAACCCG |
| | TCCTAGCCGCGCGTCCCTGCGCCGCGCCGCCAGCGGTCCGCGAT |
| | CGTTGCGGCCCGTAGCCAGTGGCAACTGGCAAAGCACACTGAA |
| | CAGCATCGTGGGTCTGGGGGTGCAATCCCTGAAGCGCCGACGAT |
| | GCTTCTGATAGCTAACGTGTCGTATGTGTGTCATGTATGCGTCCA |
| | TGTCGCCGCCAGAGGAGCTGCTGAGCCGCCGCGCGCCCGCTTTC |
| | CAAGATGGCTACCCCTTCGATGATGCCGCAGTGGTCTTACATGC |
| | ACATCTCGGGCCAGGACGCCTCGGAGTACCTGAGCCCCGGGCTG |
| | GTGCAGTTTGCCCGCGCCACCGAGACGTACTTCAGCCTGAATAA |
| | CAAGTTTAGAAACCCCACGGTGGCGCCTACGCACGACGTGACC |
| | ACAGACCGGTCCCAGCGTTTGACGCTGCGGTTCATCCCTGTGGA |
| | CCGTGAGGATACTGCGTACTCGTACAAGGCGCGGTTCACCCTAG |
| | CTGTGGGTGATAACCGTGTGCTGGACATGGCTTCCACGTACTTT |
| | GACATCCGCGGCGTGCTGGACAGGGGCCCTACTTTTAAGCCCTA |
| | CTCTGGCACTGCCTACAACGCCCTGGCTCCCAAGGGTGCCCCAA |
| | ATCCTTGCGAATGGGATGAAGCTGCTACTGCTCTTGAAATAAAC |
| | CTAGAAGAAGAGGACGATGACAACGAAGACGAAGTAGACGAG |
| | CAAGCTGAGCAGCAAAAAACTCACGTATTTGGGCAGGCGCCTT |
| | ATTCTGGTATAAATATTACAAAGGAGGGTATTCAAATAGGTGTC |
| | GAAGGTCAAACACCTAAATATGCCGATAAAACATTTCAACCTGA |
| | ACCTCAAATAGGAGAATCTCAGTGGTACGAAACAGAAATTAAT |
| | CATGCAGCTGGGAGAGTCCTAAAAAAGACTACCCCAATGAAAC |
| | CATGTTACGGTTCATATGCAAAACCCACAAATGAAAATGGAGG |
| | GCAAGGCATTCTTGTAAAGCAACAAAATGGAAAGCTAGAAAGT |
| | CAAGTGGAAATGCAATTTTTCTCAACTACTGAGGCAGCCGCAGG |
| | CAATGGTGATAACTTGACTCCTAAAGTGGTATTGTACAGTGAAG |
| | ATGTAGATATAGAAACCCCAGACACTCATATTTCTTACATGCCC |
| | ACTATTAAGGAAGGTAACTCACGAGAACTAATGGGCCAACAAT |
| | CTATGCCCAACAGGCCTAATTACATTGCTTTTAGGGACAATTTT |
| | ATTGGTCTAATGTATTACAACAGCACGGGTAATATGGGTGTTCT |
| | GGCGGGCCAAGCATCGCAGTTGAATGCTGTTGTAGATTTGCAAG |
| | ACAGAAACACAGAGCTTTCATACCAGCTTTTGCTTGATTCCATT |

| SEQ ID NO | Sequence |
|---|---|
| | GGTGATAGAACCAGGTACTTTTCTATGTGGAATCAGGCTGTTGA |
| | CAGCTATGATCCAGATGTTAGAATTATTGAAAATCATGGAACTG |
| | AAGATGAACTTCCAAATTACTGCTTTCCACTGGGAGGTGTGATT |
| | AATACAGAGACTCTTACCAAGGTAAAACCTAAAACAGGTCAGG |
| | AAAATGGATGGGAAAAAGATGCTACAGAATTTTCAGATAAAAA |
| | TGAAATAAGAGTTGGAAATAATTTTGCCATGGAAATCAATCTAA |
| | ATGCCAACCTGTGGAGAAATTTCCTGTACTCCAACATAGCGCTG |
| | TATTTGCCCGACAAGCTAAAGTACAGTCCTTCCAACGTAAAAAT |
| | TTCTGATAACCCAAACACCTACGACTACATGAACAAGCGAGTGG |
| | TGGCTCCCGGGCTAGTGGACTGCTACATTAACCTTGGAGCACGC |
| | TGGTCCCTTGACTATATGGACAACGTCAACCCATTTAACCACCA |
| | CCGCAATGCTGGCCTGCGCTACCGCTCAATGTTGCTGGGCAATG |
| | GTCGCTATGTGCCCTTCCACATCCAGGTGCCTCAGAAGTTCTTTG |
| | CCATTAAAAACCTCCTTCTCCTGCCGGGCTCATACACCTACGAG |
| | TGGAACTTCAGGAAGGATGTTAACATGGTTCTGCAGAGCTCCCT |
| | AGGGAAATGACCTAAGGGTTGACGGAGCCAGCATTAAGTTTGAT |
| | AGCATTTGCCTTTACGCCACCTTCTTCCCCATGGCCCACAACACC |
| | GCCTCCACGCTTGAGGCCATGCTTAGAAACGACACCAACGACCA |
| | GTCCTTTAACGACTATCTCTCCGCCGCCAACATGCTCTACCCTAT |
| | ACCCGCCAACGCTACCAACGTGCCCATATCCATCCCCTCCCGCA |
| | ACTGGGCGGCTTTCCGCGGCTGGGCCTTCACGCGCCTTAAGACT |
| | AAGGAAACCCCATCACTGGGCTCGGGCTACGACCCTTATTACAC |
| | CTACTCTGGCTCTATACCCTACCTAGATGGAACCTTTTACCTCAA |
| | CCACACCTTTAAGAAGGTGGCCATTACCTTTGACTCTTCTGTCAG |
| | CTGGCCTGGCAATGACCGCCTGCTTACCCCCAACGAGTTTGAAA |
| | TTAAGCGCTCAGTTGACGGGAGGGTTACAACGTTGCCCAGTGT |
| | AACATGACCAAAGACTGGTTCCTGGTACAAATGCTAGCTAACTA |
| | TAACATTGGCTACCAGGGCTTCTATATCCCAGAGAGCTACAAGG |
| | ACCGCATGTACTCCTTCTTTAGAAACTTCCAGCCCATGAGCCGT |
| | CAGGTGGTGGATGATACTAAATACAAGGACTACCAACAGGTGG |
| | GCATCCTACACCAACACAACAACTCTGGATTTGTTGGCTACCTT |
| | GCCCCCACCATGCGCGAAGGACAGGCCTACCCTGCTAACTTCCC |
| | CTATCCGCTTATAGGCAAGACCGCAGTTGACAGCATTACCCAGA |
| | AAAAGTTTCTTTGCGATCGCACCCTTTGGCGCATCCCATTCTCCA |
| | GTAACTTTATGTCCATGGGCGCACTCACAGACCTGGGCCAAAAC |
| | CTTCTCTACGCCAACTCCGCCCACGCGCTAGACATGACTTTTGA |
| | GGTGGATCCCATGGACGAGCCCACCCTTCTTTATGTTTTGTTTGA |
| | AGTCTTTGACGTGGTCCGTGTGCACCAGCCGCACCGCGGCGTCA |
| | TCGAAACCGTGTACCTGCGCACGCCCTTCTCGGCCGGCAACGCC |
| | ACAACATAAAGAAGCAAGCAACATCAACAACAGCTGCCGCCAT |
| | GGGCTCCAGTGAGCAGGAACTGAAAGCCATTGTCAAAGATCTT |
| | GGTTGTGGGCCATATTTTTTGGGCACCTATGACAAGCGCTTTCC |
| | AGGCTTTGTTTCTCCACACAAGCTCGCCTGCGCCATAGTCAATA |
| | CGGCCGGTCGCGAGACTGGGGCGTACACTGGATGGCCTTTGCC |
| | TGGAACCCGCACTCAAAAACATGCTACCTCTTTGAGCCCTTTGG |
| | CTTTTCTGACCAGCGACTCAAGCAGGTTTACCAGTTTGAGTACG |
| | AGTCACTCCTGCGCCGTAGCGCCATTGCTTCTTCCCCCGACCGCT |
| | GTATAACGCTGGAAAAGTCCACCCAAAGCGTACAGGGGCCCAA |
| | CTCGGCCGCCTGTGGACTATTCTGCTGCATGTTTCTCCACGCCTT |
| | TGCCAACTGGCCCCAAACTCCCATGGATCACAACCCCACCATGA |
| | ACCTTATTACCGGGGTACCCAACTCCATGCTCAACAGTCCCCAG |
| | GTACAGCCCACCCTGCGTCGCAACCAGGAACAGCTCTACAGCTT |
| | CCTGGAGCGCCACTCGCCCTACTTCCGCAGCCACAGTGCGCAGA |
| | TTAGGAGCGCCACTTCTTTTTGTCACTTGAAAAACATGTAAAAA |
| | TAATGTACTAGAGACACTTTCAATAAAGGCAAATGCTTTTATTT |
| | GTACACTCTCGGGTGATTATTTACCCCCACCCTTGCCGTCTGCGC |
| | CGTTTAAAAATCAAAGGGGTTCTGCCGCGCATCGCTATGCGCCA |
| | CTGGCAGGGACACGTTGCGATACTGGTGTTTAGTGCTCCACTTA |
| | AACTCAGGCACAACCATCCGCGGCAGCTCGGTGAAGTTTTCACT |
| | CCACAGGCTGCGCACCATCACCAACGCGTTTAGCAGGTCGGGCG |
| | CCGATATCTTGAAGTCGCAGTTGGGGCCTCCGCCCTGCGCGCGC |
| | GAGTTGCGATACACAGGGTTGCAGCACTGGAACACTATCAGCG |
| | CCGGGTGGTGCACGCTGGCCAGCACGCTCTTGTCGGAGATCAGA |
| | TCCGCGTCCAGGTCCTCCGCGTTGCTCAGGGCGAACGGAGTCAA |
| | CTTTGGTAGCTGCCTTCCCAAAAAGGGCGCGTGCCCAGGCTTTG |
| | AGTTGCACTCGCACCGTAGTGGCATCAAAAGGTGACCGTGCCCG |
| | GTCTGGGCGTTAGGATACAGCGCCTGCATAAAAGCCTTGATCTG |
| | CTTAAAAGCCACCTGAGCCTTTGCGCCTTCAGAGAAGAACATGC |
| | CGCAAGACTTGCCGGAAAACTGATTGGCCGGACAGGCCGCGTC |
| | GTGCACGCAGCACCTTGCGTCGGTGTTGGAGATCTGCACCACAT |
| | TTCGGCCCCACCGGTTCTTCACGATCTTGGCCTTGCTAGACTGCT |
| | CCTTCAGCGCGCGCTGCCCGTTTTCGCTCGTCACATCCATTTCAA |
| | TCACGTGCTCCTTATTTATCATAATGCTTCCGTGTAGACACTTAA |
| | GCTCGCCTTCGATCTCAGCCAGCGGTGCAGCCACAACGCGCAG |
| | CCCGTGGGCTCGTGATGCTTGTAGGTCACCTCTGCAAACGACTG |
| | CAGGTACGCCTGCAGGAATCGCCCCATCATCGTCACAAAGGTCT |
| | TGTTGCTGGTGAAGGTCAGCTGCAACCCGCGGTGCTCCTCGTTC |

| SEQ ID NO | Sequence |
|---|---|
| | AGCCAGGTCTTGCATACGGCCGCCAGAGCTTCCACTTGGTCAGG |
| | CAGTAGTTTGAAGTTCGCCTTTAGATCGTTATCCACGTGGTACTT |
| | GTCCATCAGCGCGCGCGCAGCCTCCATGCCCTTCTCCCACGCAG |
| | ACACGATCGGCACACTCAGCGGGTTCATCACCGTAATTTCACTT |
| | TCCGCTTCGCTGGGCTCTTCCTCTTCCTCTTGCGTCCGCATACCA |
| | CGCGCCACTGGGTCGTCTTCATTCAGCCGCCGCACTGTGCGCTT |
| | ACCTCCTTTGCCATGCTTGATTAGCACCGGTGGGTTGCTGAAAC |
| | CCACCATTTGTAGCGCCACATCTTCTCTTTCTTCCTCGCTGTCCA |
| | CGATTACCTCTGGTGATGGCGGGCGCTCGGGCTTGGGAGAAGG |
| | GCGCTTCTTTTTCTTCTTGGGCGCAATGGCCAAATCCGCCGCCGA |
| | GGTCGATGGCCGCGGGCTGGGTGTGCGCGGCACCAGCGCGTCTT |
| | GTGATGAGTCTTCCTCGTCCTCGGACTCGATACGCCGCCTCATCC |
| | GCTTTTTTGGGGGCGCCCGGGGAGGCGGCGGCGACGGGGACGG |
| | GGACGACACGTCCTCCATGGTTGGGGACGTCGCGCCGCACCGC |
| | GTCCGCGCTCGGGGGTGGTTTCGCGCTGCTCCTCTTCCCGACTG |
| | GCCATTTCCTTCTCCTATAGGCAGAAAAAGATCATGGAGTCAGT |
| | CGAGAAGAAGGACAGCCTAACCGCCCCCTCTGAGTTCGCCACC |
| | ACCGCCTCCACCGATGCCGCCAACGCGCCTACCACCTTCCCCGT |
| | CGAGGCACCCCCGCTTGAGGAGGAGGAAGTGATTATCGAGCAG |
| | GACCCAGGTTTTGTAAGCGAAGACGACGAGGACCGCTCAGTAC |
| | CAACAGAGGATAAAAAGCAAGACCAGGACAACGCAGAGGCAA |
| | ACGAGGAACAAGTCGGGCGGGGGGACGAAAGGCATGGCGACT |
| | ACCTAGATGTGGGAGACGACGTGCTGTTGAAGCATCTGCAGCGC |
| | CAGTGCGCCATTATCTGCGACGCGTTGCAAGAGCGCAGCGATGT |
| | GCCCCTCGCCATAGCGGATGTCAGCCTTGCCTACGAACGCCACC |
| | TATTCTCACCGCGCGTACCCCCCAAACGCCAAGAAAACGGCACA |
| | TGCGAGCCCAACCCGCGCCTCAACTTCTACCCCGTATTTGCCGT |
| | GCCAGAGGTGCTTGCCACCTATCACATCTTTTTCCAAAACTGCA |
| | AGATACCCCTATCCTGCCGTGCCAACCGCAGCCGAGCGGACAA |
| | GCAGCTGGCCTTGCGGCAGGGCGCTGTCATACCTGATATCGCCT |
| | CGCTCAACGAAGTGCCAAAAATCTTTGAGGGTCTTGGACGCGAC |
| | GAGAAGCGCGCGGCAAACGCTCTGCAACAGGAAAACAGCGAAA |
| | ATGAAAGTCACTCTGGAGTGTTGGTGGAACTCGAGGGTGACAA |
| | CGCGCGCCTAGCCGTACTAAAACGCAGCATCGAGGTCACCCACT |
| | TTGCCTACCCGGCACTTAACCTACCCCCCAAGGTCATGAGCACA |
| | GTCATGAGTGAGCTGATCGTGCGCCGTGCGCAGCCCCTGGAGAG |
| | GGATGCAAATTTGCAAGAACAAACAGAGGAGGGCCTACCCGCA |
| | GTTGGCGACGAGCAGCTAGCGCGCTGGCTTCAAACGCGCGAGC |
| | CTGCCGACTTGGAGGAGCGACGCAAACTAATGATGGCCGCAGT |
| | GCTCGTTACCGTGGAGCTTGAGTGCATGCAGCGGTTCTTTGCTG |
| | ACCCGGAGATGCAGCGCAAGCTAGAGGAAACATTGCACTACAC |
| | CTTTCGACAGGGCTACGTACGCCAGGCCTGCAAGATCTCCAACG |
| | TGGAGCTCTGCAACCTGGTCTCCTACCTTGGAATTTTGCACGAA |
| | AACCGCCTTGGGCAAAACGTGCTTCATTCCACGCTCAAGGGCGA |
| | GGCGCCGCGACTACGTCCGCGACTGCGTTTACTTATTTCTAT |
| | GCTACACCTGGCAGACGGCCATGGGCGTTTGGCAGCAGTGCTTG |
| | GAGGAGTGCAACCTCAAGGAGCTGCAGAAACTGCTAAAGCAAA |
| | ACTTGAAGGACCTATGGACGGCCTTCAACGAGCGCTCCGTGGCC |
| | GCGCACCTGGCGGACATCATTTTCCCCGAACGCCTGCTTAAAAC |
| | CCTGCAACAGGGTCTGCCAGACTTCACCAGTCAAAGCATGTTGC |
| | AGAACTTTAGGAACTTTATCCTAGAGCGCTCAGGAATCTTGCCC |
| | GCCACCTGCTGTGCACTTCCTAGCGACTTTGTGCCCATTAAGTAC |
| | CGCGAATGCCCTCCGCCGCTTTGGGGCCACTGCTACCTTCTGCA |
| | GCTAGCCAACTACCTTGCCTACCACTCTGACATAATGGAAGACG |
| | TGAGCGGTGACGGTCTACTGGAGTGTCACTGTCGCTGCAACCTA |
| | TGCACCCCGCACCGCTCCCTGGTTTGCAATTCGCAGCTGCTTAA |
| | CGAAAGTCAAATTATCGGTACCTTTGAGCTGCAGGGTCCCTCGC |
| | CTGACGAAAAGTCCGCGGCTCCGGGGTTGAAACTCACTCCGGG |
| | GCTGTGGACGTCGGCTTACCTTCGCAAATTTGTACCTGAGGACT |
| | ACCACGCCCACGAGATTAGGTTCTACGAAGACCAATCCCGCCCG |
| | CCTAATGCGGAGCTTACCGCCTGCGTCATTACCCAGGGCCACAT |
| | TCTTGGCCAATTGCAAGCCATCAACAAAGCCCGCCAAGAGTTTC |
| | TGCTACGAAAGGGACGGGGGGTTTACTTGGACCCCCAGTCCGGC |
| | GAGGAGCTCAACCCAATCCCCCCGCCGCCAGCCCTATCAGCA |
| | GCAGCCGCGGGCCCTTGCTTCCCAGGATGGCACCCAAAAAGAA |
| | GCTGCAGCTGCCGCCGCCACCCACGGACGAGGAGGAATACTGG |
| | GACAGTCAGGCAGAGGAGGTTTTGGACGAGGAGGAGGAGGACA |
| | TGATGGAAGACTGGGAGAGCCTAGACGAGGAAGCTTCCGAGGT |
| | CGAAGAGGTGTCAGACGAAACACCGTCACCCTCGGTCGCATTCC |
| | CCTCGCCGGCGCCCCAGAAATCGGCAACCGGTTCCAGCATGGCT |
| | ACAACCTCCGCTCCTCAGGCGCCGCCGGCACTGCCCGTTCGCCG |
| | ACCCAACCGTAGATGGGACACCACTGGAACCAGGGCCGGTAAG |
| | TCCAAGCAGCCGCCGCCGTTAGCCCAAGAGCAACAACAGCGCC |
| | AAGGCTACCGCTCATGGCGCGGGCACAAGAACGCCATAGTTGC |
| | TTGCTTGCAAGACTGTGGGGCAACATCTCCTTCGCCCGCCGCT |
| | TTCTTCTCTACCATCACGGCGTGGCCTTCCCCGTAACATCCTGC |
| | ATTACTACCGTCATCTCTACAGCCCATACTGCACCGGCGGCAGC |

| SEQ ID NO | Sequence |
|---|---|
| | GGCAGCAACAGCAGCGGCCACACAGAAGCAAAGGCGACCGGAT
AGCAAGACTCTGACAAAGCCCAAGAAATCCACAGCGGCGGCAG
CAGCAGGAGGAGGAGCGCTGCGTCTGGCGCCCAACGAACCCGT
ATCGACCCGCGAGCTTAGAAACAGGATTTTTCCCACTCTGTATG
CTATATTTCAACAGAGCAGGGGCCAAGAACAAGAGCTGAAAAT
AAAAAACAGGTCTCTGCGATCCCTCACCCGCAGCTGCCTGTATC
ACAAAAGCGAAGATCAGCTTCGGCGCACGCTGGAAGACGCGGA
GGCTCTCTTCAGTAAATACTGCGCGCTGACTCTTAAGGACTAGT
TTCGCGCCCTTTCTCAAATTTAAGCGCGAAAACTACGTCATCTCC
AGCGGCCACACCCGGCGCCAGCACCTGTTGTCAGCGCCATTATG
AGCAAGGAAATTCCCACGCCCTACATGTGGAGTTACCAGCCACA
AATGGGACTTGCGGCTGGAGCTGCCCAAGACTACTCAACCCGA
ATAAACTACATGAGCGCGGGACCCCACATGATATCCCGGGTCA
ACGGAATACGCGCCCACCGAAACCGAATTCTCCTGGAACAGGC
GGCTATTACCACCACACCTCGTAATAACCTTAATCCCCGTAGTT
GGCCCGCTGCCCTGGTGTACCAGGAAAGTCCCGCTCCCACCACT
GTGGTACTTCCCAGAGACGCCCAGGCCGAAGTTCAGATGACTAA
CTCAGGGGCGCAGCTTGCGGGCGGCTTTCGTCACAGGGTGCGGT
CGCCCGGGCAGGGTATAACTCACCTGACAATCAGAGGGCGAGG
TATTCAGCTCAACGACGAGTCGGTGAGCTCCTCGCTTGGTCTCC
GTCCGGACGGGACATTTCAGATCGGCGGCGCCGGCCGCTCTTCA
TTCACGCCTCGTCAGGCAATCCTAACTCTGCAGACCTCGTCCTCT
GAGCCGCGCTCTGGAGGCATTGGAACTCTGCAATTTATTGAGGA
GTTTGTGCCATCGGTCTACTTTAACCCCTTCTCGGGACCTCCCGG
CCACTATCCGGATCAATTTATTCCTAACTTTGACGCGGTAAAGG
ACTCGGCGGACGGCTACGACTGAATGTTAAGTGGAGAGGCAGA
GCAACTGCGCCTGAAACACCTGGTCCACTGTCGCCGCCACAAGT
GCTTTGCCCGCGACTCCGGTGAGTTTTGCTACTTTGAATTGCCCG
AGGATCATATCGAGGGCCCGGCGCACGGCGTCCGGCTTACCGCC
CAGGGAGAGCTTGCCCGTAGCCTGATTCGGGAGTTTACCCAGCG
CCCCCTGCTAGTTGAGCGGGACAGGGGACCCTGTGTTCTCACTG
TGATTTGCAACTGTCCTAACCCTGGATTACATCAAGATCCTCTA
GTTAATGTCAGGTCGCCTAAGTCGATTAACTAGAGTACCCGGGG
ATCTTATTCCCTTTAACTAATAAAAAAAATAATAAAGCATCAC
TTACTTAAAATCAGTTAGCAAATTTCTGTCCAGTTTATTCAGCAG
CACCTCCTTGCCCTCCTCCCAGCTCTGGTATTGCAGCTTCCTCCT
GGCTGCAAACTTTCTCCACAATCTAAATGGAATGTCAGTTTCCT
CCTGTTCCTGTCCATCCGCACCCACTATCTTCATGTTGTTGCAGA
TGAAGCGCGCAAGACCGTCTGAAGATACCTTCAACCCCGTGTAT
CCATATGACACGGAAACCGGTCCTCCAACTGTGCCTTTTCTTACT
CCTCCCTTTGTATCCCCCAATGGGTTTCAAGAGAGTCCCCCTGG
GGTACTCTCTTTGCGCCTATCCGAACCTCTAGTTACCTCCAATGG
CATGCTTGCGCTCAAAATGGGCAACGGCCTCTCTCTGGACGAGG
CCGGCAACCTTACCTCCCAAAATGTAACCACTGTGAGCCCACCT
CTCAAAAAAACCAAGTCAAACATAAACCTGGAAATATCTGCAC
CCCTCACAGTTACCTCAGAAGCCCTAACTGTGGCTGCCGCCGCA
CCTCTAATGGTCGCGGGCAACACACTCACCATGCAATCACAGGC
CCCGCTAACCGTGCACGACTCCAAACTTAGCATTGCCACCCAAG
GACCCCTCACAGTGTCAGAAGGAAAGCTAGCCCTGCAAACATC
AGGCCCCCTCACCACCACCGATAGCAGTACCCTTACTATCACTG
CCTCACCCCCTCTAACTACTGCCACTGGTAGCTTGGGCATTGACT
TGAAAGAGCCCATTTATACACAAAATGGAAAACTAGGACTAAA
GTACGGGGCTCCTTTGCATGTAACAGACGACCTAAACACTTTGA
CCGTAGCAACTGGTCCAGGTGTGACTATTAATAATACTTCCTTG
CAAACTAAAGTTACTGGAGCCTTGGGTTTTGATTCACAAGGCAA
TATGCAACTTAATGTAGCAGGAGGACTAAGGATTGATTCTCAAA
ACAGACGCCTTATACTTGATGTTAGTTATCCGTTTGATGCTCAAA
ACCAACTAAATCTAAGACTAGGACAGGGCCCTCTTTTTATAAAC
TCAGCCCACAACTTGGATATTAACTACAACAAAGGCCTTTACTT
GTTTACAGCTTCAAACAATTCCAAAAAGCTTGAGGTTAACCTAA
GCACTGCCAAGGGGTTGATGTTTGACGCTACAGCCATAGCCATT
AATGCAGGAGATGGGCTTGAATTTGGTTCACCTAATGCACCAAA
CACAAATCCCCTCAAAACAAAAATTGGCCATGGCCTAGAATTTG
ATTCAAACAAGGCTATGGTTCCTAAACTAGGAACTGGCCTTAGT
TTTGACAGCACAGGTGCCATTACAGTAGGAAACAAAAATAATG
ATAAGCTAACTTTGTGGACCACACCAGCTCCATCTCCTAACTGT
AGACTAAATGCAGAGAAAGATGCTAAACTCACTTTGGTCTTAAC
AAAATGTGGCAGTCAAATACTTGCTACAGTTTCAGTTTTGGCTG
TTAAAGGCAGTTTGGCTCCAATATCTGGAACAGTTCAAAGTGCT
CATCTTATTATAAGATTTGACGAAAATGGAGTGCTACTAAACAA
TTCCTTCCTGGACCCAGAATATTGGAACTTTAGAAATGGAGATC
TTACTGAAGGCACAGCCTATACAAACGCTGTTGGATTTATGCCT
AACCTATCAGCTTATCCAAAATCTCACGGTAAAACTGCCAAAAG
TAACATTGTCAGTCAAGTTTACTTAAACGGAGACAAAACTAAAC
CTGTAACACTAACCATTACACTAAACGGTACACAGGAAACAGG
AGACACAACTCCAAGTGCATACTCTATGTCATTTTCATGGGACT
GGTCTGGCCACAACTACATTAATGAAATATTTGCCACATCCTCT |

| SEQ ID NO | Sequence |
|---|---|
| | TACACTTTTTCATACATTGCCCAAGAATAAAGAATCGTTTGTGTT<br>ATGTTTCAACGTGTTTATTTTTCAATTGCAGAAAATTTCAAGTCA<br>TTTTTCATTCAGTAGTATAGCCCCACCACCACATAGCTTATACAG<br>ATCACCGTACCTTAATCAAACTCACAGAACCCTAGTATTCAACC<br>TGCCACCTCCCTCCCAACACACAGAGTACACAGTCCTTTCTCCC<br>CGGCTGGCCTTAAAAAGCATCATATCATGGGTAACAGACATATT<br>CTTAGGTGTTATATTCCACACGGTTTCCTGTCGAGCCAAACGCTC<br>ATCAGTGATATTAATAAACTCCCCGGGCAGCTCACTTAAGTTCA<br>TGTCGCTGTCCAGCTGCTGAGCCACAGGCTGCTGTCCAACTTGC<br>GGTTGCTTAACGGGCGGCGAAGGAGAAGTCCACGCCTACATGG<br>GGGTAGAGTCATAATCGTGCATCAGGATAGGGCGGTGGTGCTG<br>CAGCAGCGCGCGAATAAACTGCTGCCGCCGCCGCTCCGTCCTGC<br>AGGAATACAACATGGCAGTGGTCTCCTCAGCGATGATTCGCACC<br>GCCCGCAGCATAAGGCGCCTTGTCCTCCGGGCACAGCAGCGCAC<br>CCTGATCTCACTTAAATCAGCACAGTAACTGCAGCACAGCACCA<br>CAATATTGTTCAAAATCCCACAGTGCAAGGCGCTGTATCCAAAG<br>CTCATGGCGGGGACCACAGAACCCACGTGGCCATCATACCACA<br>AGCGCAGGTAGATTAAGTGGCGACCCCTCATAAACACGCTGGA<br>CATAAACATTACCTCTTTTGGCATGTTGTAATTCACCACCTCCCG<br>GTACCATATAAACCTCTGATTAAACATGGCGCCATCCACCACCA<br>TCCTAAACCAGCTGGCCAAAACCTGCCCGCCGGCTATACACTGC<br>AGGGAACCGGGACTGGAACAATGACAGTGGAGAGCCCAGGACT<br>CGTAACCATGGATCATCATGCTCGTCATGATATCAATGTTGGCA<br>CAACACAGGCACACGTGCATACACTTCCTCAGGATTACAAGCTC<br>CTCCCGCGTTAGAACCATATCCCAGGGAACAACCCATTCCTGAA<br>TCAGCGTAAATCCCACACTGCAGGGAAGACCTCGCACGTAACTC<br>ACGTTGTGCATTGTCAAAGTGTTACATTCGGGCAGCAGCGGATG<br>ATCCTCCAGTATGGTAGCGCGGGTTTCTGTCTCAAAAGGAGGTA<br>GACGATCCCTACTGTACGGAGTGCGCCGAGACAACCGAGATCG<br>TGTTGGTCGTAGTGTCATGCCAAATGGAACGCCGGACGTAGTCA<br>TATTTCCTGAAGCAAAACCAGGTGCGGGCGTGACAAACAGATCT<br>GCGTCTCCGGTCTCGCCGCTTAGATCGCTCTGTGTAGTAGTTGTA<br>GTATATCCACTCTCTCAAAGCATCCAGGCGCCCCCTGGCTTCGG<br>GTTCTATGTAAACTCCTTCATGCGCCGCTGCCCTGATAACATCCA<br>CCACCGCAGAATAAGCCACACCCAGCCAACCTACACATTCGTTC<br>TGCGAGTCACACACGGGAGGAGCGGGAAGAGCTGGAAGAACCA<br>TGTTTTTTTTTTATTCCAAAAGATTATCCAAAACCTCAAAATGA<br>AGATCTATTAAGTGAACGCGCTCCCCTCCGGTGGCGTGGTCAAA<br>CTCTACAGCCAAAGAACAGATAATGGCATTTGTAAGATGTTGCA<br>CAATGGCTTCCAAAAGGCAAACGGCCCTCACGTCCAAGTGGAC<br>GTAAAGGCTAAACCCTTCAGGGTGAATCTCCTCTATAAACATTC<br>CAGCACCTTCAACCATGCCCAAATAATTCTCATCTCGCCACCTTC<br>TCAATATATCTCTAAGCAAATCCCGAATATTAAGTCCGGCCATT<br>GTAAAAATCTGCTCCAGAGCGCCCTCCACCTTCAGCCTCAAGCA<br>GCGAATCATGATTGCAAAAATTCAGGTTCCTCACAGACCTGTAT<br>AAGATTCAAAAGCGGAACATTAACAAAAATACCGCGATCCCGT<br>AGGTCCCTTCGCAGGGCCAGCTGAACATAATCGTGCAGGTCTGC<br>ACGGACCAGCGCGGCCACTTCCCCGCCAGGAACCATGACAAAA<br>GAACCCACACTGATTATGACACGCATACTCGGAGCTATGCTAAC<br>CAGCGTAGCCCCGATGTAAGCTTGTTGCATGGGCGGCGATATAA<br>AATGCAAGGTGCTGCTCAAAAAATCAGGCAAAGCCTCGCGCAA<br>AAAAGAAAGCACATCGTAGTCATGCTCATGCAGATAAAGGCAG<br>GTAAGCTCCGGAACCACCACAGAAAAAGACACCATTTTTCTCTC<br>AAACATGTCTGCGGGTTTCTGCATAAACACAAAATAAAATAACA<br>AAAAAACATTTAAACATTAGAAGCCTGTCTTACAACAGGAAAA<br>ACAACCCTTATAAGCATAAGACGGACTACGGCCATGCCGGCGT<br>GACCGTAAAAAAAACTGGTCACCGTGATTAAAAAGCACCACCGA<br>CAGCTCCTCGGTCATGTCCGGAGTCATAATGTAAGACTCGGTAA<br>ACACATCAGGTTGATTCACATCGGTCAGTGCTAAAAAGCGACCG<br>AAATAGCCCGGGGGAATACATACCCGCAGGCGTAGAGACAACA<br>TTACAGCCCCCATAGGAGGTATAACAAAATTAATAGGAGAGAA<br>AAACACATAAACACCTGAAAAACCCTCCTGCCTAGGCAAAATA<br>GCACCCTCCCGCTCCAGAACAACATACAGCGCTTCCACAGCGGC<br>AGCCATAACAGTCAGCCTTACCAGTAAAAAAGAAAACCTATTA<br>AAAAAACACCACTCGACACGGCACCAGCTCAATCAGTCACAGT<br>GTAAAAAAGGGCCAAGTGCAGAGCGAGTATATATAGGACTAAA<br>AAATGACGTAACGGTTAAAGTCCACAAAAAACACCCAGAAAAC<br>CGCACGCGAACCTACGCCCAGAAACGAAAGCCAAAAAACCCAC<br>AACTTCCTCAAATCGTCACTTCCGTTTTCCCACGTTACGTCACTT<br>CCCATTTTAAGAAAACTACAATTCCCAACACATACAAGTTACTC<br>CGCCCTAAAACCTACGTCACCCGCCCCGTTCCCACGCCCCGCGC<br>CACGTCACAAACTCCACCCCCTCATTATCATATTGGCTTCAATCC<br>AAAATAAGGTATATTATTGATGAT |
| SEQ ID NO: 9 | GGAGGACACTTCTCAGAAGGGGTTGTTTTGCTTTTGCTTATTTCC<br>GTCCATTTCCCTCTCTGCGCGCGGACCTTCCTTTTCCAGATGGTG<br>AGAGCCGCGGGGACACCCGACGCCGGGGCAGGCTGATCCACGA |

| SEQ ID NO | Sequence |
|---|---|
| | TCCTGGGTGTGCGTAACGCCGCCTGGGGCTCCGTGGGCGAGGGA<br>CGTGTGGGACAGGTGCACCGGAAACTGCCAGACTGGAGAGTT<br>GAGGCATCGGAGGCGCGAGAACAGCACTACTACTGCGGCGAGA<br>CGAGCGCGGCGCATCCCAAAGCCCGGCCAAATGCGCTCGTCCCT<br>GGGAGGGGAGGGAGGCGCGCCTGGAGCGGGGACAGTCTTGGTC<br>CGCGCCCTCCTCCCGGGTCTGTGCCGGGACCCGGGACCCGGGAG<br>CCGTCGCAGGTCTCGGTCCAAGGGGCCCCTTTTCTCGGAAGGGC<br>GGCGGCCAAGAGCAGGGAAGGTGGATCTCAGGTAGCGAGTCTG<br>GGCTTCGGGGACGGCGGGGAGGGGAGCCGGACGGGAGGATGA<br>GCTCCCCTGGCACCGAGAGCGCGGGAAAGAGCCTGCAGTACCG<br>AGTGGACCACCTGCTGAGCGCCGTGGAGAATGAGCTGCAGGCG<br>GGCAGCGAGAAGGGCGACCCCACAGAGCGCGAACTGCGCGTGG<br>GCCTGGAGGAGAGCGAGCTGTGGCTGCGCTTCAAGGAGCTCAC<br>CAATGAGATGATCGTGACCAAGAACGGCAGGAGGATGTTTCCG<br>GTGCTGAAGGTGAACGTGTCTGGCCTGGACCCCAACGCCATGTA<br>CTCCTTCCTGCTGGACTTCGTGGCGGCGGACAACCACCGCTGGA<br>AGTACGTGAACGGGGAATGGGTGCCGGGGGGCAAGCCGGAGCC<br>GCAGGCGCCCAGCTGCGTCTACATCCACCCCGACTCGCCCAACT<br>TCGGGGCCCACTGGATGAAGGCTCCCGTCTCCTTCAGCAAAGTC<br>AAGCTCACCAACAAGCTCAACGGAGGGGGCCAGATCATGCTGA<br>ACTCCTTGCATAAGTATGAGCCTCGAATCCACATAGTGAGAGTT<br>GGGGGTCCACAGCGCATGATCACCAGCCACTGCTTCCCTGAGAC<br>CCAGTTCATAGCGGTGACTGCTTATCAGAACGAGGAGATCACAG<br>CTCTTAAAATTAAGTACAATCCATTTGCAAAAGCTTTCCTTGATG<br>CAAAGGAAAGAAGTGATCACAAAGAGATGATGGAGGAACCCG<br>GAGACAGCCAGCAACCTGGGTACTCCCAATGGGGGTGGCTTCTT<br>CCTGGAACCAGCACCCTGTGTCCACCTGCAAATCCTCATCCTCA<br>GTTTGGAGGTGCCCTCTCCCTCCCCTCCACGCACAGCTGTGACA<br>GGTACCCAACCCTGAGGAGCCACCGGTCCTCACCCTACCCCAGC<br>CCCTATGCTCATCGGAACAATTCTCCAACCTATTCTGACAACTC<br>ACCTGCATGTTTATCCATGCTGCAATCCCATGACAATTGGTCCA<br>GCCTTGGAATGCCTGCCCATCCCAGCATGCTCCCCGTGAGCCAC<br>AATGCCAGCCCACCTACCAGCTCCAGTCAGTACCCCAGCCTGTG<br>GTCTGTGAGCAACGGCGCCGTCACCCCGGGCTCCCAGGCAGCA<br>GCCGTGTCCAACGGGCTGGGGGCCCAGTTCTTCCGGGGCTCCCC<br>CGCGCACTACACACCCCTCACCCATCCGGTCTCGGCGCCCTCTT<br>CCTCGGGATCCCCACTGTACGAAGGGGCGGCCGCGGCCACAGA<br>CATCGTGGACAGCCAGTACGACGCCGCAGCCCAAGGCCGCCTC<br>ATAGCCTCATGGACACCTGTGTCGCCACCTTCCATGTGAAGCAG<br>CAAGGCCCAGGTCCCGAAAGATGCAGTGACTTTTTTGTCGTGGCA<br>GCCAGTGGTGACTGGATTGACCTACTAGGTACCCAGTGGCAGTC<br>TCAGGTTAAGAAGGAAATGCAGCCTCAGTAACTTCCTTTTCAAA<br>GCAGTGGAGGAGCACACGGCACCTTTCCCCAGAGCCCCAGCAT<br>CCCCTTGCTCACACCTGCAGTAGCGGTGCTGTCCCAGGTGGCTTA<br>CAGATGAACCCAACTGTGGAGATGATGCAGTTGGCCCAACCTCA<br>CTGACGGTGAAAAAATGTTTGCCAGGGTCCAGAAACTTTTTTTG<br>GTTTATTTCTCATACAGTGTATTGGCAACTTTGGCACACCAGAAT<br>TTGTAAACTCCACCAGTCCTACTTTAGTGAGATAAAAAGCACAC<br>TCTTAATCTTCTTCCTTGTTGCTTTCAAGTAGTTAGAGTTGAGCT<br>GTTAAGGACAGAATAAAATCATAGTTGAGGACAGCAGGTTTTA<br>GTTGAATTGAAAATTTGACTGCTCTGCCCCCTAGAATGTGTGTA<br>TTTTAAGCATATGTAGCTAATCTCTTGTGTTGTTAAACTATAACT<br>GTTTCATATTTTTCTTTTGACAAAGTAGCCAAAGACAATCAGCA<br>GAAAGCATTTTCTGCAAAATAAACGCAATATGCAAAAAAAAAA<br>AAAAAAAA |
| SEQ ID NO: 10 | TCTAGAGCCACCATGAGCTCCCCTGGCACCGAGAGCGCGGGAA<br>AGAGCCTGCAGTACCGAGTGGACCACCTGCTGAGCGCCGTGGA<br>GAATGAGCTGCAGGCGGGCAGCGAGAAGGGCGACCCCACAGAG<br>CGCGAACTGCGCGTGGGCCTGGAGGAGAGCGAGCTGTGGCTGC<br>GCTTCAAGGAGCTCACCAATGAGATGATCGTGACCAAGAACGG<br>CAGGAGGATGTTTCCGGTGCTGAAGGTGAACGTGTCTGGCCTGG<br>ACCCCAACGCCATGTACTCCTTCCTGCTGGACTTCGTGGCGGCG<br>GACAACCACCGCTGGAAGTACGTGAACGGGGAATGGGTGCCGG<br>GGGGCAAGCCGGAGCCGCAGGCGCCCAGCTGCGTCTACATCCA<br>CCCCGACTCGCCCAACTTCGGGGCCCACTGGATGAAGGCTCCCG<br>TCTCCTTCAGCAAAGTCAAGCTCACCAACAAGCTCAACGGAGGG<br>GGCCAGATCATGCTGAACTCCTTGCATAAGTATGAGCCTCGAAT<br>CCACATAGTGAGAGTTGGGGGTCCACAGCGCATGATCACCAGC<br>CACTGCTTCCCTGAGACCCAGTTCATAGCGGTGACTGCTAGAAG<br>TGATCACAAAGAGATGATGGAGGAACCCGGAGACAGCCAGCA<br>CCTGGGTACTCCCAATGGGGGTGGCTTCTTCCTGGAACCAGCAC<br>CGTGTGTCCACCTGCAAATCCTCATCCTCAGTTTGGAGGTGCCCT<br>CTCCCTCCCCTCCACGCACAGCTGTGACAGGTACCCAACCCTGA<br>GGAGCCACCGGTCCTCACCCTACCCCAGCCCCTATGCTCATCGG<br>AACAATTCTCCAACCTATTCTGACAACTCACCTGCATGTTTATCC<br>ATGCTGCAATCCCATGACAATTGGTCCAGCCTTGGAATGCCTGC |

| SEQ ID NO | Sequence |
| --- | --- |
| | CCATCCCAGCATGCTCCCCGTGAGCCACAATGCCAGCCCACCTA<br>CCAGCTCCAGTCAGTACCCCAGCCTGTGGTCTGTGAGCAACGGC<br>GCCGTCACCCCGGGCTCCCAGGCAGCAGCCGTGTCCAACGGGCT<br>GGGGGCCCAGTTCTTCCGGGGCTCCCCCGCGCACTACACACCCC<br>TCACCCATCCGGTCTCGGCGCCCTCTTCCTCGGGATCCCCACTGT<br>ACGAAGGGGCGGCCGCGGCCACAGACATCGTGGACAGCCAGTA<br>CGACGCCGCAGCCCAAGGCCGCCTCATAGCCTCATGGACACCTG<br>TGTCGCCACCTTCCATGTGAGATATC |
| SEQ ID NO: 11 | TCTCTCCNA |
| SEQ ID NO: 12 | MSSPGTESAGKSLQYRVDHLLSAVENELQAGSEKGDPTERELRVG<br>LEESELWLRFKELTNEMIVTKNGRRMFPVLKVNVSGLDPNAMYSF<br>LLDFVAADNHRWKYVNGEWVPGGKPEPQAPSCVYIHPDSPNFGA<br>HWMKAPVSFSKVKLTNKLNGGGQIMLNSLHKYEPRIHIVRVGDPQ<br>RMITSHCFPETQFIAVTAYQNEEITALKIKYNPFAKAFLDAKERSDH<br>KEMMEEPGDSQQPGYSQWGWLLPGTSTLCPPANPHPQFGGALSLP<br>STHSCDRYPTLRSHRSSPYPSPYAHRNNSPTYSDNSPACLSMLQSH<br>DNWSSLGMPAHPSMLPVSHNASPPTSSSQYPSLWSVSNGAVTPGS<br>QAAAVTNGLGAQFFRGSPAHYTPLTHPVSAPSSSGSPLYEGAAAAT<br>NIVDSQYDAAAQGRLIASWTPVSPPSM |
| SEQ ID NO: 13 | CATCATCAATAATATACCTTATTTTGGATTGAAGCCAATATGAT<br>AATGAGGGGGTGGAGTTTGTGACGTGGCGCGGGGCGTGGGAAC<br>GGGGCGGGTGACGTAGTAGTGTGGCGGAAGTGTGATGTTGCAA<br>GTGTGGCGGAACACATGTAAGCGACGGATGTGGCAAAAGTGAC<br>GTTTTTGGTGTGCGCCGGTGTACACAGGAAGTGACAATTTTCGC<br>GCGGTTTTAGGCGGATGTTGTAGTAAATTTGGGCGTAACCGAGT<br>AAGATTTGGCCATTTTCGCGGGAAAACTGAATAAGAGGAAGTG<br>AAATCTGAATAATTTTGTGTTACTCATAGCGCGTAATACTGTAA<br>TAGTAATCAATTACGGGGTCATTAGTTCATAGCCCATATATGGA<br>GTTCCGCGTTACATAACTTACGGTAAATGGCCCGCCTGGCTGAC<br>CGCCCAACGACCCCCGCCCATTGACGTCAATAATGACGTATGTT<br>CCCATAGTAACGCCAATAGGGACTTTCCATTGACGTCAATGGGT<br>GGAGTATTTACGGTAAACTGCCCACTTGGCAGTACATCAAGTGT<br>ATCATATGCCAAGTACGCCCCCTATTGACGTCAATGACGGTAAA<br>TGGCCCGCCTGGCATTATGCCCAGTACATGACCTTATGGGACTT<br>TCCTACTTGGCAGTACATCTACGTATTAGTCATCGCTATTACCAT<br>GGTGATGCGGTTTTGGCAGTACATCAATGGGCGTGGATAGCGGT<br>TTGACTCACGGGGATTTCCAAGTCTCCACCCCATTGACGTCAAT<br>GGGAGTTTGTTTTGGCACCAAAATCAACGGGACTTTCCAAAATG<br>TCGTAACAACTCCGCCCCATTGACGCAAATGGGCGGTAGGCGTG<br>TACGGTGGGAGGTCTATATAAGCAGAGCTGGTTTAGTGAACCGT<br>CAGATCCGCTAGAGATCTGGTACCGTCGACGCGGCCGCTCGAGC<br>CTAAGCTTCTAGATGCATGCTCGAGCGGCCGCCAGTGTGATGGA<br>TATCTGCAGAATTCGCCCTTGCTTCTAGAGCCACCATGAGCTCC<br>CCTGGCACCGAGAGCGCGGGAAAGAGCCTGCAGTACCGAGTGG<br>ACCACCTGCTGAGCGCCGTGGAGAATGAGCTGCAGGCGGGCAG<br>CGAGAAGGGCGACCCCACAGAGCGCGAACTGCGCGTGGGCCTG<br>GAGGAGAGCGAGCTGTGGCTGCGCTTCAAGGAGCTCACCAATG<br>AGATGATCGTGACCAAGAACGGCAGGAGGATGTTTCCGGTGCT<br>GAAGGTGAACGTGTCTGGCCTGGACCCCAACGCCATGTACTCCT<br>TCCTGCTGGACTTCGTGGCGGCGGACAACCACCGCTGGAAGTAC<br>GTGAACGGGGAATGGGTGCCGGGGGGCAAGCCGGAGCCGCAGG<br>CGCCCAGCTGCGTCTACATCCACCCCGACTCGCCCAACTTCGGG<br>GCCCACTGGATGAAGGCTCCCGTCTCCTTCAGCAAAGTCAAGCT<br>CACCAACAAGCTCAACGGAGGGGGCCAGATCATGCTGAACTCC<br>TTGCATAAGTATGAGCCTCGAATCCACATAGTGAGAGTTGGGG<br>TCCACAGCGCATGATCACCAGCCACTGCTTCCCTGAGACCCAGT<br>TCATAGCGGTGACTGCTAGAAGTGATCACAAAGAGATGATGGA<br>GGAACCCGGAGACAGCCAGCAACCTGGGTACTCCCAATGGGGG<br>TGGCTTCTTCCTGGAACCAGCACCGTGTGTCCACCTGCAAATCC<br>TCATCCTCAGTTTGGAGGTGCCCTCTCCCTCCCCTCCACGCACAG<br>CTGTGACAGGTACCCAACCCTGAGGAGCCACCGGTCCTCACCCT<br>ACCCCAGCCCCTATGCTCATCGGAACAATTCTCCAACCTATTCT<br>GACAACTCACCTGCATGTTTATCCATGCTGCAATCCCATGACAA<br>TTGGTCCAGCCTTGGAATGCCTGCCCATCCCAGCATGCTCCCCG<br>TGAGCCACAATGCCAGCCCACCTACCAGCTCCAGTCAGTACCCC<br>AGCCTGTGGTCTGTGAGCAACGGCGCCGTCACCCCGGGCTCCCA<br>GGCAGCAGCCGTGTCAACGGGCTGGGGGCCCAGTTCTTCCGGG<br>GCTCCCCCGCGCACTACACACCCCTCACCCATCCGGTCTCGGCG<br>CCCTCTTCCTCGGGATCCCCACTGTACGAAGGGGCGGCCGCGGC<br>CACAGACATCGTGGACAGCCAGTACGACGCCGCAGCCCAAGGC<br>CGCCTCATAGCCTCATGGACACCTGTGTCGCCACCTTCCATGTG<br>AGATATCCGATCCACCGGATCTAGATAACTGATCATAATCAGCC<br>ATACCACATTTGTAGAGGTTTTACTTGCTTTAAAAAACCTCCCAC<br>ACCTCCCCCTGAACCTGAAACATAAAATGAATGCAATTGTTGTT |

| SEQ ID NO | Sequence |
|---|---|
| | GTTAACTTGTTTATTGCAGCTTATAATGGTTACAAATAAAGCAA
TAGCATCACAAATTTCACAAATAAAGCATTTTTTTCACTGCATTC
TAGTTGTGGTTTGTCCAAACTCATCAATGTATCTTAACGCGGATC
TGGAAGGTGCTGAGGTACGATGAGACCCGCACCAGGTGCAGAC
CCTGCGAGTGTGGCGGTAAACATATTAGGAACCAGCCTGTGATG
CTGGATGTGACCGAGGAGCTGAGGCCCGATCACTTGGTGCTGGC
CTGCACCCGCGCTGAGTTTGGCTCTAGCGATGAAGATACAGATT
GAGGTACTGAAATGTGTGGGCGTGGCTTAAGGGTGGGAAAGAA
TATATAAGGTGGGGGTCTTATGTAGTTTTGTATCTGTTTTGCAGC
AGCCGCCGCCGCCATGAGCACCAACTCGTTTGATGGAAGCATTG
TGAGCTCATATTTGACAACGCGCATGCCCCCATGGGCCGGGGTG
CGTCAGAATGTGATGGGCTCCAGCATTGATGGTCGCCCCGTCCT
GCCCGCAAACTCTACTACCTTGACCTACGAGACCGTGTCTGGAA
CGCCGTTGGAGACTGCAGCCTCCGCCGCCGCTTCAGCCGCTGCA
GCCACCGCCCGCGGGATTGTGACTGACTTTGCTTTCCTGAGCCC
GCTTGCAAGCAGTGCAGCTTCCCGTTCATCCGCCCGCGATGACA
AGTTGACGGCTCTTTTGGCACAATTGGATTCTTTGACCCGGGAA
CTTAATGTCGTTTCTCAGCAGCTGTTGGATCTGCGCCAGCAGGTT
TCTGCCCTGAAGGCTTCCTCCCCTCCCAATGCGGTTTAAAACAT
AAATAAAAAACCAGACTCTGTTTGGATTTGGATCAAGCAAGTGT
CTTGCTGTCTTTATTTAGGGGTTTTGCGCGCGGTAGGCCCGG
GACCAGCGGTCTCGGTCGTTGAGGGTCCTGTGTATTTTTTCCAG
GACGTGGTAAAGGTGACTCTGGATGTTCAGATACATGGGCATAA
GCCCGTCTCTGGGGTGGAGGTAGCACCACTGCAGAGCTTCATGC
TGCGGGGTGGTGTTGTAGATGATCCAGTCGTAGCAGGAGCGCTG
GGCGTGGTGCCTAAAAATGTCTTTCAGTAGCAAGCTGATTGCCA
GGGGCAGGCCCTTGGTGTAAGTGTTTACAAAGCGGTTAAGCTGG
GATGGGTGCATACGTGGGGATATGAGATGCATCTTGGACTGTAT
TTTTAGGTTGGCTATGTTCCCAGCCATATCCCTCCGGGGATTCAT
GTTGTGCAGAACCACCAGCACAGTGTATCCGGTGCACTTGGGAA
ATTTGTCATGTAGCTTAGAAGGAAATGCGTGGAAGAACTTGGAG
ACGCCCTTGTGACCTCCAAGATTTTCCATGCATTCGTCCATAATG
ATGGCAATGGGCCCACGGGCGGCGGCCTGGGCGAAGATATTTC
TGGGATCACTAACGTCATAGTTGTGTTCCAGGATGAGATCGTCA
TAGGCCATTTTTACAAAGCGCGGGCGGAGGGTGCCAGACTGCG
GTATAATGGTTCCATCCGGCCCAGGGGCGTAGTTACCCTCACAG
ATTTGCATTTCCCACGCTTTGAGTTCAGATGGGGGGATCATGTCT
ACCTGCGGGGCGATGAAGAAAACGGTTTCCGGGGTAGGGGAGA
TCAGCTGGGAAGAAAGCAGGTTCCTGAGCAGCTGCGACTTACC
GCAGCCGGTGGGCCCGTAAATCACACCTATTACCGGCTGCAACT
GGTAGTTAAGAGAGCTGCAGCTGCCGTCATCCCTGAGCAGGGG
GGCCACTTCGTTAAGCATGTCCCTGACTCGCATGTTTTCCCTGAC
CAAATCCGCCAGAAGGCGCTCGCCGCCCAGCGATAGCAGTTCTT
GCAAGGAAGCAAAGTTTTTCAACGGTTTGAGACCGTCCGCCGTA
GGCATGCTTTTGAGCGTTTGACCAAGCAGTTCCAGGCGGTCCCA
CAGCTCGGTCACCTGCTCTACGGCATCTCGATCCAGCATATCTC
CTCGTTTCGCGGGTTGGGCGGCTTTCGCTGTACGGCAGTAGTC
GGTGCTCGTCCAGACGGGCCAGGGTCATGTCTTTCCACGGGCGC
AGGGTCCTCGTCAGCGTAGTCTGGGTCACGGTGAAGGGGTGCGC
TCCGGGCTGCGCGCTGGCCAGGGTGCGCTTGAGGCTGGTCCTGC
TGGTGCTGAAGCGCTGCCGGTCTTCGCCCTGCGCGTCGGCCAGG
TAGCATTTGACCATGGTGTCATAGTCCAGCCCCTCCGCGGCGTG
GCCCTTGGCGCGCAGCTTGCCCTTGGAGGAGGCGCCGCACGAG
GGGCAGTGCAGACTTTTGAGGGCGTAGAGCTTGGGCGCGAGAA
ATACCGATTCCGGGGAGTAGGCATCCGCGCCGCAGGCCCCGCA
GACGGTCTCGCATTCCACGAGCCAGGTGAGCTCTGGCCGTTCGG
GGTCAAAAACCAGGTTTCCCCCATGCTTTTTGATGCGTTTCTTAC
CTCTGGTTTCCATGAGCCGGTGTCCACGCTCGGTGACGAAAAGG
CTGTCCGTGTCCCCGTATACAGACTTGAGAGGCCTGTCCTCGAG
CGGTGTTCCGCGGTCCTCCTCGTATAGAAACTCGGACCACTCTG
AGACAAAGGCTCGCGTCCAGGCCAGCACGAAGGAGGCTAAGTG
GGAGGGGTAGCGGTCGTTGTCCACTAGGGGGTCCACTCGCTCCA
GGGTGTGAAGACACATGTCGCCCTCTTCGGCATCAAGGAAGGTG
ATTGGTTTGTAGGTGTAGGCCACGTGACCGGGTGTTCCTGAAGG
GGGGCTATAAAAGGGGGTGGGGGCGCGTTCGTCCTCACTCTCTT
CCGCATCGCTGTCTGCGAGGGCCAGCTGTTGGGGTGAGTACTCC
CTCTGAAAAGCGGGCATGACTTCTGCGCTAAGATTGTCAGTTTC
CAAAAACGAGGAGGATTTGATATTCACCTGGCCCGCGGTGATGC
CTTTGAGGGTGGCCGCATCCATCTGGTCAGAAAAGACAATCTTT
TTGTTGTCAAGCTTGGTGGCAAACGACCCGTAGAGGGCGTTGGA
CAGCAACTTGGCGATGGAGCGCAGGGTTTGGTTTTTGTCGCGAT
CGGCGCGCTCCTTGGCCGCGATGTTTAGCTGCACGTATTCGCGC
GCAACGCACCGCCATTCGGGAAAGACGGTGGTGCGCTCGTCGG
GCACCAGGTGCACGCGCCAACCGCGGTTGTGCAGGGTGACAAG
GTCAACGCTGGTGGCTACCTCTCCGCGTAGGCGCTCGTTGGTCC
AGCAGAGGCGGCCGCCCTTGCGCGAGCAGAATGGCGGTAGGGG
GTCTAGCTGCGTCTCGTCCGGGGGGTCTGCGTTCCACGGTAAAGA |

| SEQ ID NO | Sequence |
| --- | --- |
| | CCCCGGGCAGCAGGCGCGCGTCGAAGTAGTCTATCTTGCATCCT
TGCAAGTCTAGCGCCTGCTGCCATGCGCGGGCGGCAAGCGCGC
GCTCGTATGGGTTGAGTGGGGGACCCCATGGCATGGGGTGGGT
GAGCGCGGAGGCGTACATGCCGCAAATGTCGTAAACGTAGAGG
GGCTCTCTGAGTATTCCAAGATATGTAGGGTAGCATCTTCCACC
GCGGATGCTGGCGCGCACGTAATCGTATAGTTCGTGCGAGGGA
GCGAGGAGGTCGGGACCGAGGTTGCTACGGGCGGGCTGCTCTG
CTCGGAAGACTATCTGCCTGAAGATGGCATGTGAGTTGGATGAT
ATGGTTGGACGCTGGAAGACGTTGAAGCTGGCGTCTGTGAGACC
TACCGCGTCACGCACGAAGGAGGCGTAGGAGTCGCGCAGCTTG
TTGACCAGCTCGGCGGTGACCTGCACGTCTAGGGCGCAGTAGTC
CAGGGTTTCCTTGATGATGTCATACTTATCCTGTCCCTTTTTTTC
CACAGCTCGCGGTTGAGGACAAACTCTTCGCGGTCTTTCCAGTA
CTCTTGGATCGGAAACCCGTCGGCCTCCGAACGGTAAGAGCCTA
GCATGTAGAACTGGTTGACGGCCTGGTAGGCGCAGCATCCCTTT
TCTACGGGTAGCGCGTATGCCTGCGCGGCCTTCCGGCATGACCA
GCATGAAGGGCACGAGCTGCTTCCCAAAGGCCCCCATCCAAGT
ATAGGTCTCTACATCGTAGGTGACAAAGAGACGCTCGGTGCGA
GGATGCGAGCCGATCGGGAAGAACTGGATCTCCCGCCACCAAT
TGGAGGAGTGGCTATTGATGTGGTGAAAGTAGAAGTCCCTGCG
ACGGGCCGAACACTCGTGCTGGCTTTTGTAAAAACGTGCGCAGT
ACTGGCAGCGGTGCACGGGCTGTACATCCTGCACGAGGTTGACC
TGACGACCGCGCACAAGGAAGCAGAGTGGGAATTTGAGCCCCT
CGCCTGGCGGGTTTGGCTGGTGGTCTTCTACTTCGGCTGCTTGTC
CTTGACCGTCTGGCTGCTCGAGGGGAGTTACGGTGGATCGGACC
ACCACGCCGCGCGAGCCCAAAGTCCAGATGTCCGCGCGCGGCG
GTCGGAGCTTGATGACAACATCGCGCAGATGGGAGCTGTCCATG
GTCTGGAGCTCCCGCGGCGTCAGGTCAGGCGGGAGCTCCTGCAG
GTTTACCTCGCATAGACGGGTCAGGGCGCGGGCTAGATCCAGGT
GATACCTAATTTCCAGGGGCTGGTTGGTGGCGGCGTCGATGGCT
TGCAAGAGGCCGCATCCCCGCGGCGCGACTACGGTACCGCGCG
GCGGGCGGTGGGCCGCGGGGGTGTCCTTGGATGATGCATCTAA
AAGCGGTGACGCGGGCGAGCCCCCGGAGGTAGGGGGGGCTCCG
GACCCGCCGGGAGAGGGGGCAGGGGCACGTCGGCGCCGCGCGC
GGGCAGGAGCTGGTGCTGCGCGCGTAGGTTGCTGGCGAACGCG
ACGACGCGGCGGTTGATCTCCTGAATCTGGCGCCTCTGCGTGAA
GACGACGGGCCCGGTGAGCTTGAACCTGAAAGAGAGTTCGACA
GAATCAATTTCGGTGTCGTTGACGGCGCCTGGCGCAAAATCTC
CTGCACGTCTCCTGAGTTGTCTTGATAGGCGATCTCGGCCATGA
ACTGCTCGATCTCTTCCTCCTGGAGATCTCCGCGTCCGGCTCGCT
CCACGGTGGCGGCGAGGTCGTTGGAAATGCGGGCCATGAGCTG
CGAGAAGGCGTTGAGGCCTCCCTCGTTCCAGACGCGGCTGTAGA
CCACGCCCCCTTCGGCATCGCGGGCGCGCATGACCACCTGCGCG
AGATTGAGCTCCACGTGCCGGGCGAAGACGGCGTAGTTTCGCA
GGCGCTGAAAGAGGTAGTTGAGGGTGGTGGCGGTGTGTTCTGCC
ACGAAGAAGTACATAACCCAGCGTCGCAACGTGGATTCGTTGAT
AATTGTTGTGTAGGTACTCCGCCGCCGAGGGACCTGAGCGAGTC
CGCATCGACCGGATCGGAAAACCTCTCGAGAAAGGCGTCTAAC
CAGTCACAGTCGCAAGGTAGGCTGAGCACCGTGGCGGGCGGCA
GCGGGCGGCGGTCGGGGTTGTTTCTGGCGGAGGTGCTGCTGATG
ATGTAATTAAAGTAGGCGGTCTTGAGACGGCGGATGGTCGACA
GAAGCACCATGTCCTTGGGTCCGGCCTGCTGAATGCGCAGGCGG
TCGGCCATGCCCCAGGCTTCGTTTTGACATCGGCGCAGGTCTTT
GTAGTAGTCTTGCATGAGCCTTTCTACCGGCACTTCTTCTTCTCC
TTCCTCTTGTCCTGCATCTCTTGCATCTATCGCTGCGGCGGCGGC
GGAGTTTGGCCGTAGGTGGCGCCCTCTTCCTCCCATGCGTGTGA
CCCCGAAGCCCCTCATCGGCTGAAGCAGGGCTAGGTCGGCGAC
AACGCGCTCGGCTAATATGGCCTGCTGCACCTGCGTGAGGGTAG
ACTGGAAGTCATCCATGTCCACAAAGCGGTGGTATGCGCCCGTG
TTGATGGTGTAAGTGCAGTTGGCCATAACGGACCAGTTAACGGT
CTGGTGACCCGGCTGCGAGAGCTCGGTGTACCTGAGACGCGAGT
AAGCCCTCGAGTCAAATACGTAGTCGTTGCAAGTCCGCACCAGG
TACTGGTATCCCACCAAAAAGTGCGGCGGCGGCTGGCGGTAGA
GGGGCCAGCGTAGGGTGGCCGGGCTCCGGGGCGAGATCTTC
CAACATAAGGCGATGATATCCGTAGATGTACCTGGACATCCAGG
TGATGCCGGCGGCGGTGGTGGAGGCGCGCGGAAAGTCGCGGAC
GCGGTTCCAGATGTTGCGCAGCGGCAAAAAGTGCTCCATGGTCG
GGACGCTCTGGCCGGTCAGGCGCGCAATCGTTGACGCTCTAG
CGTGCAAAAGGAGAGCCTGTAAGCGGGCACTCTTCCGTGGTCTG
GTGGATAAATTCGCAAGGGTATCATGGCGGACGACCGGGGTTC
GAGCCCCGTATCCGGCCGTCCGCCGTGATCCATGCGGTTACCGC
CCGCGTGTCGAACCCAGGTGTGCGACGTCAGACAACGGGGAG
TGCTCCTTTTGGCTTCCTTCCAGGCGCGGCGGCTGCTGCGCTAGC
TTTTTTGGCCACTGGCCGCGCGCAGCGTAAGCGGTTAGGCTGGA
AAGCGAAAGCATTAAGTGGCTCGCTCCCTGTAGCCGGAGGGTTA
TTTTCCAAGGGGTTGAGTCGCGGGACCCCCGGTTCGAGTCTCGGA
CCGGCCGGACTGCGGCGAACGGGGGTTTGCCTCCCCGTCATGCA |

| SEQ ID NO | Sequence |
| --- | --- |
| | AGACCCCGCTTGCAAATTCCTCCGGAAACAGGGACGAGCCCCTT
TTTTGCTTTTCCCAGATGCATCCGGTGCTGCGGCAGATGCGCCCC
CCTCCTCAGCAGCGGCAAGAGCAAGAGCAGCGGCAGACATGCA
GGGCACCCTCCCCTCCTCCTACCGCGTCAGGAGGGGCGACATCC
GCGGTTGACGCGGCAGCAGATGGTGATTACGAACCCCGCGGC
GCCGGGCCCGGCACTACCTGGACTTGGAGGAGGGCGAGGGCCT
GGCGCGGCTAGGAGCGCCCTCTCCTGAGCGGCACCCAAGGGTG
CAGCTGAAGCGTGATACGCGTGAGGCGTACGTGCCGCGGCAGA
ACCTGTTTCGCGACCGCGAGGGAGAGGAGCCCGAGGAGATGCG
GGATCGAAAGTTCCACGCAGGGCGCGAGCTGCGGCATGGCCTG
AATCGCGAGCGGTTGCTGCGCGAGGAGGACTTTGAGCCCGACG
CGCGAACCGGGATTAGTCCCGCGCGCGCACACGTGGCGGCCGC
CGACCTGGTAACCGCATACGAGCAGACGGTGAACCAGGAGATT
AACTTTCAAAAAAGCTTTAACAACCACGTGCGTACGCTTGTGGC
GCGCGAGGAGGTGGCTATAGGACTGATGCATCTGTGGGACTTTG
TAAGCGCGCTGGAGCAAAACCCAAATAGCAAGCCGCTCATGGC
GCAGCTGTTCCTTATAGTGCAGCACAGCAGGGACAACGAGGCA
TTCAGGGATGCGCTGCTAAACATAGTAGAGCCCGAGGGCCGCT
GGCTGCTCGATTTGATAAACATCCTGCAGAGCATAGTGGTGCAG
GAGCGCAGCTTGAGCCTGGCTGACAAGGTGGCCGCCATCAACT
ATTCCATGCTTAGCCTGGGCAAGTTTTACGCCCGCAAGATATAC
CATACCCCTTACGTTCCCATAGACAAGGAGGTAAAGATCGAGG
GGTTCTACATGCGCATGGCGCTGAAGGTGCTTACCTTGAGCGAC
GACCTGGGCGTTTATCGCAACGAGCGCATCCACAAGGCCGTGA
GCGTGAGCCGGCGGCGCGAGCTCAGCGACCGCGAGCTGATGCA
CAGCCTGCAAAGGGCCCTGGCTGGCACGGGCAGCGGCGATAGA
GAGGCCGAGTCCTACTTTGACGCGGGCGCTGACCTGCGCTGGGC
CCCAAGCCGACGCGCCCTGGAGGCAGCTGGGGCCGGACCTGGG
CTGGCGGTGGCACCCGCGCGCGCTGGCAACGTCGGCGGCGTGG
AGGAATATGACGAGGACGATGAGTACGAGCCAGAGGACGGCGA
GTACTAAGCGGTGATGTTTCTGATCAGATGATGCAAGACGCAAC
GGACCCGGCGGTGCGGGCGGCGCTGCAGAGCCAGCCGTCCGGC
CTTAACTCCACGGACGACTGGCGCCAGGTCATGGACCGCATCAT
GTCGCTGACTGCGCGCAATCCTGACGCGTTCCGGCAGCAGCCGC
AGGCCAACCGGCTCTCCGCAATTCTGGAAGCGGTGGTCCCGGCG
CGCGCAAACCCCACGCACGAGAAGGTGCTGGCGATCGTAAACG
CGCTGGCCGAAAACAGGGCCATCCGGCCCGACGAGGCCGGCCT
GGTCTACGACGCGCTGCTTCAGCGCGTGGCTCGTTACAACAGCG
GCAACGTGCAGACCAACCTGGACCGGCTGGTGGGGGATGTGCG
CGAGGCCGTGGCGCAGCGTGAGCGCGCGCAGCAGCAGGGCAAC
CTGGGCTCCATGGTTGCACTAAACGCCTTCCTGAGTACACAGCC
CGCCAACGTGCCGCGGGGACAGGAGGACTACACCAACTTTGTG
AGCGCACTGCGGCTAATGGTGACTGAGACACCGCAAAGTGAGG
TGTACCAGTCTGGGCCAGACTATTTTTTCCAGACCAGTAGACAA
GGCCTGCAGACCGTAAACCTGAGCCAGGCTTTCAAAAACTTGCA
GGGGCTGTGGGGGGTGCGGGCTCCCACAGGCGACCGCGCGACC
GTGTCTAGCTTGCTGACGCCCAACTCGCGCCTGTTGCTGCTGCTA
ATAGCGCCCTTCACGGACAGTGGCAGCGTGTCCCGGGACACATA
CCTAGGTCACTTGCTGACACTGTACCGCGAGGCCATAGGTCAGG
CGCATGTGGACGAGCATACTTTCCAGGAGATTACAAGTGTCAGC
CGCGCGCTGGGGCAGGAGGACACGGGCAGCCTGGAGGCAACCC
TAAACTACCTGCTGACCAACCGGCGGCAGAAGATCCCCTCGTTG
CACAGTTTAAACAGCGAGGAGGAGCGCATTTTGCGCTACGTGCA
GCAGAGCGTGAGCCTTAACCTGATGCGCGACGGGGTAACGCCC
AGCGTGGCGCTGGACATGACCGCGCGCAACATGGAACCGGGCA
TGTATGCCTCAAACCGGCCGTTTATCAACCGCCTAATGGACTAC
TTGCATCGCGCGGCCGCCGTGAACCCCGAGTATTTCACCAATGC
CATCTTGAACCCGCACTGGCTACCGCCCCCTGGTTTCTACACCG
GGGGATTCGAGGTGCCCGAGGGTAACGATGGATTCCTCTGGGA
CGACATAGACGACAGCGTGTTTTCCCCGCAACCGCAGACCCTGC
TAGAGTTGCAACAGCGCGAGCAGGCAGAGGCGGCGCTGCGAAA
GGAAAGCTTCCGCAGGCCAAGCAGCTTGTCCGATCTAGGCGCTG
CGGCCCCGCGGTCAGATGCTAGTAGCCCATTTCCAAGCTTGATA
GGGTCTCTTACCAGCACTCGCACCACCCGCCCGCGCCTGCTGGG
CGAGGAGGAGTACCTAAACAACTCGCTGCTGCAGCCGCAGCGC
GAAAAAAAACCTGCCTCCGGCATTTCCCAACAACGGGATAGAA
GCCTAGTGGACAAGATGAGTAGATGGAAGACGTACGCGCAGGA
GCACAGGGACGTGCCAGGCCCGCGCCCGCCCACCCGTCGTCAA
AGGCACGACCGTCAGCGGGGTCTGGTGTGGGAGGACGATGACT
CGGCAGACGACAGCAGCGTCCTGGATTTGGGAGGGAGTGGCAA
CCCGTTTGCGCACCTTCGCCCCAGGCTGGGGAGAATGTTTTAAA
AAAAAAAAAGCATGATGCAAAATAAAAAACTCACCAAGGCCAT
GGCACCGAGCGTTGGTTTTCTTGTATTCCCCTTAGTATGCGGCGC
GCGGCGATGTATGAGGAAGGTCCTCCTCCCTCCTACGAGAGTGT
GGTGAGCGCGGCGCCAGTGGCGGCGGCGCTGGGTTCTCCCTTCG
ATGCTCCCCTGGACCCGCCGTTTGTGCCTCCGCGGTACCTGCGG
CCTACCGGGGGGAGAAACAGCATCCGTTACTCTGAGTTGGCACC |

| SEQ ID NO | Sequence |
|---|---|
| | CCTATTCGACACCACCCGTGTGTACCTGGTGGACAACAAGTCAA |
| | CGGATGTGGCATCCCTGAACTACCAGAACGACCACAGCAACTTT |
| | CTGACCACGGTCATTCAAAACAATGACTACAGCCCGGGGGAGG |
| | CAAGCACACAGACCATCAATCTTGACGACCGGTCGCACTGGGG |
| | CGGCGACCTGAAAACCATCCTGCATACCAACATGCCAAATGTGA |
| | ACGAGTTCATGTTTACCAATAAGTTTAAGGCGCGGGTGATGGTG |
| | TCGCGCTTGCCTACTAAGGACAATCAGGTGGAGCTGAAATACGA |
| | GTGGGTGGAGTTCACGCTGCCCGAGGGCAACTACTCCGAGACC |
| | ATGACCATAGACCTTATGAACAACGCGATCGTGGAGCACTACTT |
| | GAAAGTGGGCAGACAGAACGGGGTTCTGGAAAGCGACATCGGG |
| | GTAAAGTTTGACACCCGCAACTTCAGACTGGGGTTTGACCCCGT |
| | CACTGGTCTTGTCATGCCTGGGGTATATACAAACGAAGCCTTCC |
| | ATCCAGACATCATTTTGCTGCCAGGATGCGGGGTGGACTTCACC |
| | CACACAGCCGCCTGAGCAACTTGTTGGGCATCCGCAAGCGGCAACC |
| | CTTCCAGGAGGGCTTTAGGATCACCTACGATGATCTGGAGGGTG |
| | GTAACATTCCCGCACTGTTGGATGTGGACGCCTACCAGGCGAGC |
| | TTGAAAGATGACACCGAACAGGGCGGGGGTGGCGCAGGCGGCA |
| | GCAACAGCAGTGGCAGCGGCGCGGAAGAGAACTCCAACGCGGC |
| | AGCCGCGGCAATGCAGCCGGTGGAGGACATGAACGATCATGCC |
| | ATTGCGCGCGACACCTTTGCCACACGGGCTGAGGAGAAGCGCG |
| | CTGAGGCCGAAGCAGCGGCCGAAGCTGCCGCCCCCGCTGCGCA |
| | ACCCGAGGTCGAGAAGCCTCAGAAGAAACCGGTGATCAAACCC |
| | CTGACAGAGGACAGCAAGAAACGCAGTTACAACCTAATAAGCA |
| | ATGACAGCACCTTCACCCAGTACCGCAGCTGGTACCTTGCATAC |
| | AACTACGGCGACCCTCAGACCGGAATCCGCTCATGGACCCTGCT |
| | TTGCACTCCTGACGTAACCTGCGGCTCGGAGCAGGTCTACTGGT |
| | CGTTGCCAGACATGATGCAAGACCCCGTGACCTTCCGCTCCACG |
| | CGCCAGATCAGCAACTTTCCGGTGGTGGGCGCCGAGCTGTTGCC |
| | CGTGCACTCCAAGAGCTTCTACAACGACCAGGCCGTCTACTCCC |
| | AACTCATCCGCCAGTTTACCTCTCTGACCCACGTGTTCAATCGCT |
| | TTCCCGAGAACCAGATTTTGGCGCGCCCGCCAGCCCCCACCATC |
| | ACCACCGTCAGTGAAAACGTTCCTGCTCTCACAGATCACGGGAC |
| | GCTACCGCTGCGCAACAGCATCGGAGGAGTCCAGCGAGTGACC |
| | ATTACTGACGCCAGACGCCGCACCTGCCCCTACGTTTACAAGGC |
| | CCTGGGCATAGTCTCGCCGCGCGTCCTATCGAGCCGCACTTTTT |
| | GAGCAAGCATGTCCATCCTTATATCGCCCAGCAATAACACAGGC |
| | TGGGGCCTGCGCTTCCCAAGCAAGATGTTTGGCGGGGCCAAGA |
| | AGCGCTCCGACCAACACCCAGTGCGCGTGCGCGGGCACTACCG |
| | CGCGCCCTGGGGCGCGCACAAACGCGGCCGCACTGGGCGCACC |
| | ACCGTCGATGACGCCATCGACGCGGTGGTGGAGGAGGCGCGCA |
| | ACTACACGCCCACGCCGCCACCAGTGTCCACAGTGGACGCGGCC |
| | ATTCAGACCGTGGTGCGCGGAGCCCGGCGCTATGCTAAAATGA |
| | AGAGACGGCGGAGGCGCGTAGCACGTCGCCACCGCCGCCGACC |
| | CGGCACTGCCGCCCAACGCGCGGCGGCGGCCCTGCTTAACCGCG |
| | CACGTCGCCACCGGCCGACGGGCGGCCATGCGGGCCGCTCGAAG |
| | GCTGGCCGCGGGTATTGTCACTGTGCCCCCCAGGTCCAGGCGAC |
| | GAGCGGCCGCCGCAGCAGCCGCGGCCATTAGTGCTATGACTCA |
| | GGGTCGCAGGGGCAACGTGTATTGGGTGCGCGACTCGGTTAGC |
| | GGCCTGCGCGTGCCCGTGCGCACCCGCCCCCCGCGCAACTAGAT |
| | TGCAAGAAAAAACTACTTAGACTCGTACTGTTGTATGTATCCAG |
| | CGGCGGCGGCGCGCAACGAAGCTATGTCCAAGCGCAAAATCAA |
| | AGAAGAGATGCTCCAGGTCATCGCGCCGGAGATCTATGGCCCCC |
| | CGAAGAAGGAAGAGCAGGATTACAAGCCCCGAAAGCTAAAGCG |
| | GGTCAAAAAGAAAAAGAAAGATGATGATGATGAACTTGACGAC |
| | GAGGTGGAACTGCTGCACGCTACCGCGCCCAGGCGACGGGTAC |
| | AGTGGAAAGGTCGACGCGTAAAACGTGTTTTGCGACCCGGCAC |
| | CACCGTAGTCTTTACGCCCGGTGAGCGCTCCACCCGCACCTACA |
| | AGCGCGTGTATGATGAGGTGTACGGCGACGAGGACCTGCTTGA |
| | GCAGGCCAACGAGCGCCTCGGGGAGTTTGCCTACGGAAAGCGG |
| | CATAAGGACATGCTGGCGTTGCCGCTGGACGAGGGCAACCCAA |
| | CACCTAGCCTAAAGCCCGTAACACTGCAGCAGGTGCTGCCCGCG |
| | CTTGCACCGTCCGAAGAAAAGCGCGGCCTAAAGCGCGAGTCTG |
| | GTGACTTGGCACCCACCGTGCAGCTGATGGTACCCAAGCGCCAG |
| | CGACTGGAAGATGTCTTGGAAAAAATGACCGTGGAACCTGGGC |
| | TGGAGCCCGAGGTCCGCGTGCGGCCAATCAAGCAGGTGGCGCC |
| | GGGACTGGGCGTGCAGACCGTGGACGTTCAGATACCCACTACC |
| | AGTAGCACCAGTATTGCCACCGCCACAGAGGGCATGGAGACAC |
| | AAACGTCCCCGGTTGCCTCAGCGGTGGCGGATGCCGCGGTGCAG |
| | GCGGTCGCTGCGGCCGCGTCCAAGACCTCTACGGAGGTGCAAA |
| | CGGACCCGTGGATGTTTCGCGTTTCAGCCCCCCGGCGCCCGCGC |
| | CGTTCGAGGAAGTACGGCGCCGCCAGCGCGCTACTGCCCGAAT |
| | ATGCCCTACATCCTTCCATTGCGCCTACCCCCGGCTATCGTGGCT |
| | ACACCTACCGCCCCAGAAGACGAGCAACTACCCGACGCCGAAC |
| | CACCCACTGGAACCCGCCGCCGCCGTCGCCGTCGCCAGCCCGTGC |
| | TGGCCCCGATTTCCGTGCGCAGGGTGGCTCGCGAAGGAGGCAG |
| | GACCCTGGTGCTGCCAACAGCGCGCTACCACCCCAGCATCGTTT |
| | AAAAGCCGGTCTTTGTGGTTCTTGCAGATATGGCCCTCACCTGC |

| SEQ ID NO | Sequence |
| --- | --- |
| | CGCCTCCGTTTCCCGGTGCCGGGATTCCGAGGAAGAATGCACCG |
| | TAGGAGGGGCATGGCCGGCCACGGCCTGACGGGCGGCATGCGT |
| | CGTGCGCACCACCGGCGGCGGCGCGCGTCGCACCGTCGCATGC |
| | GCGGCGGTATCCTGCCCCTCCTTATTCCACTGATCGCCGCGGCG |
| | ATTGGCGCCGTGCCCGGAATTGCATCCGTGGCCTTGCAGGCGCA |
| | GAGACACTGATTAAAAACAAGTTGCATGTGGAAAAATCAAAT |
| | AAAAAGTCTGGACTCTCACGCTCGCTTGGTCCTGTAACTATTTTG |
| | TAGAATGGAAGACATCAACTTTGCGTCTCTGGCCCCGCGACACG |
| | GCTCGCGCCCGTTCATGGGAAACTGGCAAGATATCGGCACCAGC |
| | AATATGAGCGGTGGCGCCTTCAGCTGGGGCTCGCTGTGGAGCGG |
| | CATTAAAAATTTCGGTTCCACCGTTAAGAACTATGGCAGCAAGG |
| | CCTGGAACAGCAGCACAGGCCAGATGCTGAGGGATAAGTTGAA |
| | AGAGCAAAATTTCCAACAAAAGGTGGTAGATGGCCTGGCCTCT |
| | GGCATTAGCGGGGTGGTGGACCTGGCCAACCAGGCAGTGCAAA |
| | ATAAGATTAACAGTAAGCTTGATCCCCGCCCTCCCGTAGAGGAG |
| | CCTCCACCGGCCGTGGAGACAGTGTCTCCAGAGGGGCGTGGCG |
| | AAAAGCGTCCGCGCCCCGACAGGGAAGAAACTCTGGTGACGCA |
| | AATAGACGAGCCTCCCTCGTACGAGGAGGCACTAAAGCAAGGC |
| | CTGCCCACCACCCGTCCCATCGCGCCCATGGCTACCGGAGTGCT |
| | GGGCCAGCACACACCCGTAACGCTGGACCTGCCTCCCCCCGCCG |
| | ACACCCAGCAGAAACCTGTGCTGCCAGGCCCGACCGCCGTTGTT |
| | GTAACCCGTCCTAGCCGCGCGTCCCTGCGCCGCGCCGCCAGCGG |
| | TCCGCGATCGTTGCGGCCCGTAGCCAGTGGCAACTGGCAAAGCA |
| | CACTGAACAGCATCGTGGGTCTGGGGGTGCAATCCTGAAGCGC |
| | CGACGATGCTTCTGATAGCTAACGTGTCGTATGTGTGTCATGTA |
| | TGCGTCCATGTCGCCGCCAGAGGAGCTGCTGAGCCGCCGCGCGC |
| | CCGCTTTCCAAGATGGCTACCCCTTCGATGATGCCGCAGTGGTC |
| | TTACATGCACATCTCGGGCCAGGACGCCTCGGAGTACCTGAGCC |
| | CCGGGCTGGTGCAGTTTGCCCGCGCCACCGAGACGTACTTCAGC |
| | CTGAATAACAAGTTTAGAAACCCCACGGTGGCGCCTACGCACG |
| | ACGTGACCACAGACCGGTCCCAGCGTTTGACGCTGCGGTTCATC |
| | CCTGTGGACCGTGAGGATACTGCGTACTCGTACAAGGCGCGGTT |
| | CACCCTAGCTGTGGGTGATAACCGTGTGCTGGACATGGCTTCCA |
| | CGTACTTTGACATCCGCGGCGTGCTGGACAGGGGCCCTACTTTT |
| | AAGCCCTACTCTGGCACTGCCTACAACGCCCTGGCTCCCAAGGG |
| | TGCCCCAAATCCTTGCGAATGGGATGAAGCTGCTACTGCTCTTG |
| | AAATAAACCTAGAAGAAGAGGACGATGACAACGAAGACGAAG |
| | TAGACGAGCAAGCTGAGCAGCAAAAAACTCACGTATTTGGGCA |
| | GGCGCCTTATTCTGGTATAAATATTACAAAGGAGGGTATTCAAA |
| | TAGGTGTCGAAGGTCAAACACCTAAATATGCCGATAAAACATTT |
| | CAACCTGAACCTCAAATAGGAGAATCTCAGTGGTACGAAACAG |
| | AAATTAATCATGCAGCTGGGAGAGTCCTAAAAAAGACTACCCC |
| | AATGAAACCATGTTACGGTTCATATGCAAAACCCCACAAATGAA |
| | AATGGAGGGCAAGGCATTCTTGTAAAGCAACAAAATGGAAAGC |
| | TAGAAAGTCAAGTGGAAATGCAATTTTTCTCAACTACTGAGGCA |
| | GCCGCAGGCAATGGTGATAACTTGACTCCTAAAGTGGTATTGTA |
| | CAGTGAAGATGTAGATATAGAAACCCCAGACACTCATATTTCTT |
| | ACATGCCCACTATTAAGGAAGGTAACTCACGAGAACTAATGGG |
| | CCAACAATCTATGCCCAACAGGCCTAATTACATTGCTTTTAGGG |
| | ACAATTTTATTGGTCTAATGTATTACAACAGCACGGGTAATATG |
| | GGTGTTCTGGCGGGCCAAGCATCGCAGTTGAATGCTGTTGTAGA |
| | TTTGCAAGACAGAAACACAGAGCTTTCATACCAGCTTTTGCTTG |
| | ATTCCATTGGTGATAGAACCAGGTACTTTTCTATGTGGAATCAG |
| | GCTGTTGACAGCTATGATCCAGATGTTAGAATTATTGAAAATCA |
| | TGGAACTGAAGATGAACTTCCAAATTACTGCTTTCCACTGGGAG |
| | GTGTGATTAATACAGAGACTCTTACCAAGGTAAAACCTAAAACA |
| | GGTCAGGAAAATGGATGGGAAAAAGATGCTACAGAATTTTCAG |
| | ATAAAAATGAAATAAGAGTTGGAAATAATTTTGCCATGGAAAT |
| | CAATCTAAATGCCAACCTGTGGAGAAATTTCCTGTACTCCAACA |
| | TAGCGCTGTATTTGCCCGACAAGCTAAAGTACAGTCCTTCCAAC |
| | GTAAAAATTTCTGATAACCCAAACACCTACGACTACATGAACAA |
| | GCGAGTGGTGGCTCCCGGGCTAGTGGACTGCTACATTAACCTTG |
| | GAGCACGCTGGTCCCTTGACTATATGGACAACGTCAACCCATTT |
| | AACCACCACCGCAATGCTGGCCTGCGCTACCGCTCAATGTTGCT |
| | GGGCAATGGTCGCTATGTGCCCTTCCACATCCAGGTGCCTCAGA |
| | AGTTCTTTGCCATTAAAAACCTCCTTCTCCTGCCGGGCTCATCA |
| | CCTACGAGTGGAACTTCAGGAAGGATGTTAACATGGTTCTGCAG |
| | AGCTCCCTAGGAAATGACCTAAGGGTTGACGGAGCCAGCATTA |
| | AGTTTGATAGCATTTGCCTTTACGCCACCTTCTTCCCCATGGCCC |
| | ACAACACCGCCTCCACGCTTGAGGCCATGCTTAGAAACGACACC |
| | AACGACCAGTCCTTTAACGACTATCTCTCCGCCGCCAACATGCT |
| | CTACCCTATACCCGCCAACGCTACCAACGTGCCCATATCCATCC |
| | CCTCCCGCAACTGGGCGGCTTTCCGCGGCTGGGCCTTCACGCGC |
| | CTTAAGACTAAGGAAACCCCATCACTGGGCTCGGGCTACGACCC |
| | TTATTACACCTACTCTGGCTCTATACCCTACCTAGATGGAACCTT |
| | TTACCTCAACCACACCTTTAAGAAGGTGGCCATTACCTTTGACT |
| | CTTCTGTCAGCTGGCCTGGCAATGACCGCCTGCTTACCCCCAAC |

| SEQ ID NO | Sequence |
|---|---|
| | GAGTTTGAAATTAAGCGCTCAGTTGACGGGGAGGGTTACAACGT |
| | TGCCCAGTGTAACATGACCAAAGACTGGTTCCTGGTACAAATGC |
| | TAGCTAACTATAACATTGGCTACCAGGGCTTCTATATCCCAGAG |
| | AGCTACAAGGACCGCATGTACTCCTTCTTTAGAAACTTCCAGCC |
| | CATGAGCCGTCAGGTGGTGGATGATACTAAATACAAGGACTAC |
| | CAACAGGTGGGCATCCTACACCAACACAACAACTCTGGATTTGT |
| | TGGCTACCTTGCCCCCACCATGCGCGAAGGACAGGCCTACCCTG |
| | CTAACTTCCCCTATCCGCTTATAGGCAAGACCGCAGTTGACAGC |
| | ATTACCCAGAAAAAGTTTCTTTGCGATCGCACCCTTTGGCGCAT |
| | CCCCATTCTCCAGTAACTTTATGTCCATGGGCGCACTCACAGACC |
| | TGGGCCAAAACCTTCTCTACGCCAACTCCGCCCACGCGCTAGAC |
| | ATGACTTTTGAGGTGGATCCCATGGACGAGCCCACCCTTCTTTA |
| | TGTTTTGTTTGAAGTCTTTGACGTGGTCCGTGTGCACCAGCCGCA |
| | CCGCGGCGTCATCGAAACCGTGTACCTGCGCACGCCCTTCTCGG |
| | CCGGCAACGCCACAACATAAAGAAGCAAGCAACATCAACAACA |
| | GCTGCCGCCATGGGCTCCAGTGAGCAGGAACTGAAAGCCATTGT |
| | CAAAGATCTTGGTTGTGGGCCATATTTTTTGGGCACCTATGACA |
| | AGCGCTTTCCAGGCTTTGTTTCTCCACACAAGCTCGCCTGCGCCA |
| | TAGTCAATACGGCCGGTCGCGAGACTGGGGGCGTACACTGGAT |
| | GGCCTTTGCCTGGAACCCGCACTCAAAAACATGCTACCTCTTTG |
| | AGCCCTTTGGCTTTTCTGACCAGCGACTCAAGCAGGTTTACCAG |
| | TTTGAGTACGAGTCACTCCTGCGCCGTAGCGCCATTGCTTCTTCC |
| | CCCGACCGCTGTATAACGCTGGAAAAGTCCACCCAAAGCGTAC |
| | AGGGGCCCAACTCGGCCGCCTGTGGACTATTCTGCTGCATGTTT |
| | CTCCACGCCTTTGCCAACTGGCCCCAAACTCCCATGGATCACAA |
| | CCCCACCATGAACCTTATTACCGGGGTACCCAACTCCATGCTCA |
| | ACAGTCCCCAGGTACAGCCCACCCTGCGTCGCAACCAGGAACA |
| | GCTCTACAGCTTCCTGGAGCGCCACTCGCCCTACTTCCGCAGCC |
| | ACAGTGCGCAGATTAGGAGCGCCACTTCTTTTTGTCACTTGAAA |
| | AACATGTAAAATAATGTACTAGAGACACTTTCAATAAAGGCA |
| | AATGCTTTTATTTGTACACTCTCGGGTGATTATTTACCCCCACCC |
| | TTGCCGTCTGCGCCGTTTAAAAATCAAAGGGGTTCTGCCGCGCA |
| | TCGCTATGCGCCACTGGCAGGGACACGTTGCGATACTGGTGTTT |
| | AGTGCTCCACTTAAACTCAGGCACAACCATCCGCGGCAGCTCGG |
| | TGAAGTTTTCACTCCACAGGCTGCGCACCATCACCAACGCGTTT |
| | AGCAGGTCGGGCGCCGATATCTTGAAGTCGCAGTTGGGGCCTCC |
| | GCCCTGCGCGCGCGAGTTGCGATACACAGGGTTGCAGCACTGG |
| | AACACTATCAGCGCCGGGTGGTGCACGCTGGCCAGCACGCTCTT |
| | GTCGGAGATCAGATCCGCGTCCAGGTCCTCCGCGTTGCTCAGGG |
| | CGAACGGAGTCAACTTTGGTAGCTGCCTTCCCAAAAAGGGCGCG |
| | TGCCCAGGCTTTGAGTTGCACTCGCACCGTAGTGGCATCAAAAG |
| | GTGACCGTGCCCGGTCTGGGCGTTAGGATACAGCGCCTGCATAA |
| | AAGCCTTGATCTGCTTAAAAGCCACCTGAGCCTTTGCGCCTTCA |
| | GAGAAGAACATGCCGCAAGACTTGCCGGAAAACTGATTGGCCG |
| | GACAGGCCGCGTCGTGCACGCAGCACCTTGCGTCGGTGTTGGAG |
| | ATCTGCACCACATTTCGGCCCCACCGGTTCTTCACGATCTTGGCC |
| | TTGCTAGACTGCTCCTTCAGCGCGCGCTGCCCGTTTTCGCTCGTC |
| | ACATCCATTTCAATCACGTGCTCCTTATTTATCATAATGCTTCCG |
| | TGTAGACACTTAAGCTCGCCTTCGATCTCAGCGCAGCGGTGCAG |
| | CCACAACGCGCAGCCCGTGGGCTCGTGATGCTTGTAGGTCACCT |
| | CTGCAAACGACTGCAGGTACGCCTGCAGGAATCGCCCCATCATC |
| | GTCACAAAGGTCTTGTTGCTGGTGAAGGTCAGCTGCAACCCGCG |
| | GTGCTCCTCGTTCAGCCAGGTCTTGCATACGGCCGCCAGAGCTT |
| | CCACTTGGTCAGGCAGTAGTTTGAAGTTCGCCTTTAGATCGTTAT |
| | CCACGTGGTACTTGTCCATCAGCGCGCGCGCAGCCTCCATGCCC |
| | TTCTCCCACGCAGACACGATCGGCACACTCAGCGGGTTCATCAC |
| | CGTAATTTCACTTTCCGCTTCGCTGGGCTCTTCCTCTTCCTCTTGC |
| | GTCCGCATACCACGCGCCACTGGGTCGTCTTCATTCAGCCGCCG |
| | CACTGTGCGCTTACCTCCTTTGCCATGCTTGATTAGCACCGGTGG |
| | GTTGCTGAAACCCACCATTTGTAGCGCCACATCTTCTCTTTCTTC |
| | CTCGCTGTCCACGATTACCTCTGGTGATGGCGGGCGCTCGGGCT |
| | TGGGAGAAGGGCGCTTCTTTTTCTTCTTGGGCGCAATGGCCAAA |
| | TCCGCCGCCGAGGTCGATGGCCGCGGGCTGGGTGTGCGCGGCA |
| | CCAGCGCGTCTTGTGATGAGTCTTCCTCGTCCTCGGACTCGATAC |
| | GCCGCCTCATCCGCTTTTTTGGGGGCGCCCGGGGAGGCGGCGGC |
| | GACGGGGACGGGGACGACACGTCCTCCATGGTTGGGGACGTC |
| | GCGCCGCACCGCGTCCGCGCTCGGGGGTGGTTTCGCGCTGCTCC |
| | TCTTCCCGACTGGCCATTTCCTTCTCCTATAGGCAGAAAAAGAT |
| | CATGGAGTCAGTCGAGAAGAAGGACAGCCTAACCGCCCCCTCT |
| | GAGTTCGCCACCACCGCCTCCACCGATGCCGCCAACGCGCCTAC |
| | CACCTTCCCCGTCGAGGCACCCCCGCTTGAGGAGGAGGAAGTG |
| | ATTATCGAGCAGGACCCAGGTTTTGTAAGCGAAGACGACGAGG |
| | ACCGCTCAGTACCAACAGAGGATAAAAAGCAAGACCAGGACAA |
| | CGCAGAGGCAAACGAGGAACAAGTCGGGCGGGGGACGAAAG |
| | GCATGGCGACTACCTAGATGTGGGAGACGACGTGCTGTTGAAG |
| | CATCTGCAGCGCCAGTGCGCCATTATCTGCGACGCGTTGCAAGA |
| | GCGCAGCGATGTGCCCCTCGCCATAGCGGATGTCAGCCTTGCCT |

| SEQ ID NO | Sequence |
|---|---|
| | ACGAACGCCACCTATTCTCACCGCGCGTACCCCCAAACGCCAA |
| | GAAAACGGCACATGCGAGCCCAACCCGCGCCTCAACTTCTACCC |
| | CGTATTTGCCGTGCCAGAGGTGCTTGCCACCTATCACATCTTTTT |
| | CCAAAACTGCAAGATACCCCTATCCTGCCGTGCCAACCGCAGCC |
| | GAGCGGACAAGCAGCTGGCCTTGCGGCAGGGCGCTGTCATACC |
| | TGATATCGCCTCGCTCAACGAAGTGCCAAAAATCTTTGAGGGTC |
| | TTGGACGCGACGAGAAGCGCGCGGCAAACGCTCTGCAACAGGA |
| | AAACAGCGAAAATGAAAGTCACTCTGGAGTGTTGGTGGAACTC |
| | GAGGGTGACAACGCGCGCCTAGCCGTACTAAAACGCAGCATCG |
| | AGGTCACCCACTTTGCCTACCCGGCACTTAACCTACCCCCAAG |
| | GTCATGAGCACAGTCATGAGTGAGCTGATCGTGCGCCGTGCGCA |
| | GCCCCTGGAGAGGGATGCAAATTTGCAAGAACAAACAGAGGAG |
| | GGCCTACCCGCAGTTGGCGACGAGCAGCTAGCGCGCTGGCTTCA |
| | AACGCGCGAGCCTGCCGACTTGGAGGAGCGACGCAAACTAATG |
| | ATGGCCGCAGTGCTCGTTACCGTGGAGCTTGAGTGCATGCAGCG |
| | GTTCTTTGCTGACCCGGAGATGCAGCGCAAGCTAGAGGAAACAT |
| | TGCACTACACCTTTCGACAGGGCTACGTACGCCAGGCCTGCAAG |
| | ATCTCCAACGTGGAGCTCTGCAACCTGGTCTCCTACCTTGGAAT |
| | TTTGCACGAAAACCGCCTTGGGCAAAACGTGCTTCATTCCACGC |
| | TCAAGGGCGAGGCGCGCCGCGACTACGTCCGCGACTGCGTTTAC |
| | TTATTTCTATGCTACACCTGGCAGACGGCCATGGGCGTTTGGCA |
| | GCAGTGCTTGGAGGAGTGCAACCTCAAGGAGCTGCAGAAACTG |
| | CTAAAGCAAAACTTGAAGGACCTATGGACGGCCTTCAACGAGC |
| | GCTCCGTGGCCGCGCACCTGGCGGACATCATTTTCCCCGAACGC |
| | CTGCTTAAAACCCTGCAACAGGGTCTGCCAGACTTCACCAGTCA |
| | AAGCATGTTGCAGAACTTTAGGAACTTTATCCTAGAGCGCTCAG |
| | GAATCTTGCCCGCCACCTGCTGTGCACTTCCTAGCGACTTTGTGC |
| | CCATTAAGTACCGCGAATGCCCTCCGCCGCTTTGGGGCCACTGC |
| | TACCTTCTGCAGCTAGCCAACTACCTTGCCTACCACTCTGACATA |
| | ATGGAAGACGTGAGCGGTGACGGTCTACTGGAGTGTCACTGTCG |
| | CTGCAACCTATGCACCCCGCACCGCTCCCTGGTTTGCAATTCGC |
| | AGCTGCTTAACGAAAGTCAAATTATCGGTACCTTTGAGCTGCAG |
| | GGTCCCTCGCCTGACGAAAAGTCCGCGGCTCCGGGGTTGAAACT |
| | CACTCCGGGGCTGTGGACGTCGGCTTACCTTCGCAAATTTGTAC |
| | CTGAGGACTACCACGCCCACGAGATTAGGTTCTACGAAGACCA |
| | ATCCCGCCCGCCTAATGCGGAGCTTACCGCCTGCGTCATTACCC |
| | AGGGCCACATTCTTGGCCAATTGCAAGCCATCAACAAAGCCCGC |
| | CAAGAGTTTCTGCTACGAAAGGGACGGGGGGTTTACTTGGACCC |
| | CCAGTCCGGCGAGGAGCTCAACCCAATCCCCCCGCCGCCGCAGC |
| | CCTATCAGCAGCAGCCGCGGGCCCTTGCTTCCCAGGATGGCACC |
| | CAAAAAGAAGCTGCAGCTGCCGCCGCCACCCACGGACGAGGAG |
| | GAATACTGGGACAGTCAGGCAGAGGAGGTTTTGGACGAGGAGG |
| | AGGAGGACATGATGGAAGACTGGGAGAGCCTAGACGAGGAAG |
| | CTTCCGAGGTCGAAGAGGTGTCAGACGAAACACCGTCACCCTCG |
| | GTCGCATTCCCCTCGCCGGCGCCCCAGAAATCGGCAACCGGTTC |
| | CAGCATGGCTACAACCTCCGCTCCTCAGGCGCCGCCGGCACTGC |
| | CCGTTCGCCGACCCAACCGTAGATGGGACACCACTGGAACCAG |
| | GGCCGGTAAGTCCAAGCAGCCGCCGCCGTTAGCCCAAGAGCAA |
| | CAACAGCGCCAAGGCTACCGCTCATGGCGCGGGCACAAGAACG |
| | CCATAGTTGCTTGCTTGCAAGACTGTGGGGGCAACATCTCCTTC |
| | GCCCGCCGCTTTCTTCTCTACCATCACGGCGTGGCCTTCCCCCGT |
| | AACATCCTGCATTACTACCGTCATCTCTACAGCCCATACTGCAC |
| | CGGCGGCAGCGGCAGCAACAGCAGCGGCCACACAGAAGCAAA |
| | GGCGACCGGATAGCAAGACTCTGACAAAGCCCAAGAAATCCAC |
| | AGCGGCGGCAGCAGCAGGAGGAGGAGCGCTGCGTCTGGCGCCC |
| | AACGAACCCGTATCGACCCGCGAGCTTAGAAACAGGATTTTTCC |
| | CACTCTGTATGCTATATTTCAACAGAGCAGGGGCCAAGAACAAG |
| | AGCTGAAAATAAAAAACAGGTCTCTGCGATCCCTCACCCGCAGC |
| | TGCCTGTATCACAAAAGCGAAGATCAGCTTCGGCGCACGCTGGA |
| | AGACGCGGAGGCTCTCTTCAGTAAATACTGCGCGCTGACTCTTA |
| | AGGACTAGTTTCGCGCCCTTTCTCAAATTTAAGCGCGAAAACTA |
| | CGTCATCTCCAGCGGCCACACCCGGCGCCAGCACCTGTTGTCAG |
| | CGCCATTATGAGCAAGGAAATTCCCACGCCCTACATGTGGAGTT |
| | ACCAGCCACAAATGGGACTTGCGGCTGGAGCTGCCCAAGACTA |
| | CTCAACCCGAATAAACTACATGAGCGCGGGACCCCACATGATAT |
| | CCCGGGTCAACGGAATACGCGCCCACCGAAACCGAATTCTCCTG |
| | GAACAGGCGGCTATTACCACCACACCTCGTAATAACCTTAATCC |
| | CCGTAGTTGGCCCGCTGCCCTGGTGTACCAGGAAAGTCCCGCTC |
| | CCACCACTGTGGTACTTCCCAGAGACGCCCAGGCCGAAGTTCAG |
| | ATGACTAACTCAGGGGCGCAGCTTGCGGGCGGCTTTCGTCACAG |
| | GGTGCGGTCGCCCGGGCAGGGTATAACTCACCTGACAATCAGA |
| | GGGCGAGGTATTCAGCTCAACGACGAGTCGGTGAGCTCCTCGCT |
| | TGGTCTCCGTCCGGACGGGACATTTCAGATCGGCGGCGCCGGCC |
| | GCTCTTCATTCACGCCTCGTCAGGCAATCCTAACTCTGCAGACCT |
| | CGTCCTCTGAGCCGCGCTCTGGAGGCATTGGAACTCTGCAATTT |
| | ATTGAGGAGTTTGTGCCATCGGTCTACTTTAACCCCTTCTCGGGA |
| | CCTCCCGGCCACTATCCGGATCAATTTATTCCTAACTTTGACGCG |

| SEQ ID NO | Sequence |
|---|---|
| | GTAAAGGACTCGGCGGACGGCTACGACTGAATGTTAAGTGGAG<br>AGGCAGAGCAACTGCGCCTGAAACACCTGGTCCACTGTCGCCGC<br>CACACAAGTGCTTTGCCCGCGACTCCGGTGAGTTTTGCTACTTTGA<br>ATTGCCCGAGGATCATATCGAGGGCCCGGCGCACGGCGTCCGG<br>CTTACCGCCCAGGGAGAGCTTGCCCGTAGCCTGATTCGGGAGTT<br>TACCCAGCGCCCCTGCTAGTTGAGCGGGACAGGGGACCCTGTG<br>TTCTCACTGTGATTTGCAACTGTCCTAACCCTGGATTACATCAAG<br>ATCCTCTAGTTAATGTCAGGTCGCCTAAGTCGATTAACTAGAGT<br>ACCCGGGGATCTTATTCCCTTTAACTAATAAAAAAAAATAATAA<br>AGCATCACTTACTTAAAATCAGTTAGCAAATTTCTGTCCAGTTTA<br>TTCAGCAGCACCTCCTTGCCCTCCTCCCAGCTCTGGTATTGCAGC<br>TTCCTCCTGGCTGCAAACTTTCTCCACAATCTAAATGGAATGTCA<br>GTTTCCTCCTGTTCCTGTCCATCCGCACCCACTATCTTCATGTTG<br>TTGCAGATGAAGCGCGCAAGACCGTCTGAAGATACCTTCAACCC<br>CGTGTATCCATATGACACGGAAACCGGTCCTCCAACTGTGCCTT<br>TTCTTACTCCTCCCTTTGTATCCCCCAATGGGTTTCAAGAGAGTC<br>CCCCTGGGGTACTCTCTTTGCGCCTATCCGAACCTCTAGTTACCT<br>CCAATGGCATGCTTGCGCTCAAAATGGGCAACGGCCTCTCTCTG<br>GACGAGGCCGGCAACCTTACCTCCCAAAATGTAACCACTGTGAG<br>CCCCACCTCTCAAAAAAACCAAGTCAAACATAAACCTGGAAATA<br>TCTGCACCCCTCACAGTTACCTCAGAAGCCCTAACTGTGGCTGC<br>CGCCGCACCTCTAATGGTCGCGGGCAACACACTCACCATGCAAT<br>CACAGGCCCCGCTAACCGTGCACGACTCCAAACTTAGCATTGCC<br>ACCCAAGGACCCCTCACAGTGTCAGAAGGAAAGCTAGCCCTGC<br>AAACATCAGGCCCCCTCACCACCACCGATAGCAGTACCCTTACT<br>ATCACTGCCTCACCCCCTCTAACTACTGCCACTGGTAGCTTGGG<br>CATTGACTTGAAAGAGCCCATTTATACACAAAATGGAAAACTAG<br>GACTAAAGTACGGGGCTCCTTTGCATGTAACAGACGACCTAAAC<br>ACTTTGACCGTAGCAACTGGTCCAGGTGTGACTATTAATAATAC<br>TTCCTTGCAAACTAAAGTTACTGGAGCCTTGGGTTTTGATTCACA<br>AGGCAATATGCAACTTAATGTAGCAGGAGGACTAAGGATTGAT<br>TCTCAAAACAGACGCCTTATACTTGATGTTAGTTATCCGTTTGAT<br>GCTCAAAACCAACTAAATCTAAGACTAGGACAGGGCCCTCTTTT<br>TATAAACTCAGCCCACAACTTGGATATTAACTACAACAAAGGCC<br>TTTACTTGTTTACAGCTTCAAACAATTCCAAAAAGCTTGAGGTT<br>AACCTAAGCACTGCCAAGGGGTTGATGTTTGACGCTACAGCCAT<br>AGCCATTAATGCAGGAGATGGGCTTGAATTTGGTTCACCTAATG<br>CACCAAACACAAATCCCCTCAAAACAAAATTGGCCATGGCCT<br>AGAATTTGATTCAAACAAGGCTATGGTTCCTAAACTAGGAACTG<br>GCCTTAGTTTTGACAGCACAGGTGCCATTACAGTAGGAAACAAA<br>AATAATGATAAGCTAACTTTGTGGACCACACCAGCTCCATCTCC<br>TAACTGTAGACTAAATGCAGAGAAAGATGCTAAACTCACTTTGG<br>TCTTAACAAAATGTGGCAGTCAAATACTTGCTACAGTTTCAGTT<br>TTGGCTGTTAAAGGCAGTTTGGCTCCAATATCTGGAACAGTTCA<br>AAGTGCTCATCTTATTATAAGATTTGACGAAAATGGAGTGCTAC<br>TAAACAATTCCTTCCTGGACCCAGAATATTGGAACTTTAGAAAT<br>GGAGATCTTACTGAAGGCACAGCCTATACAAACGCTGTTGGATT<br>TATGCCTAACCTATCAGCTTATCCAAAATCTCACGGTAAAACTG<br>CCAAAAGTAACATTGTCAGTCAAGTTTACTTAAACGGAGACAAA<br>ACTAAACCTGTAACACTAACCATTACACTAAACGGTACACAGGA<br>AACAGGAGACACAACTCCAAGTGCATACTCTATGTCATTTTCAT<br>GGGACTGGTCTGGCCACAACTACATTAATGAAATATTTGCCACA<br>TCCTCTTACACTTTTTCATACATTGCCCAAGAATAAAGAATCGTT<br>TGTGTTATGTTTCAACGTGTTTATTTTTCAATTGCAGAAAATTTC<br>AAGTCATTTTTCATTCAGTAGTATAGCCCCACCACCACATAGCTT<br>ATACAGATCACCGTACCTTAATCAAACTCACAGAACCCTAGTAT<br>TCAACCTGCCACCTCCCTCCCAACACACAGAGTACACAGTCCTT<br>TCTCCCCGGCTGGCCTTAAAAAGCATCATATCATGGGTAACAGA<br>CATATTCTTAGGTGTTATATTCCACACGGTTTCCTGTCGAGCAA<br>ACGCTCATCAGTGATATTAATAAACTCCCCGGGCAGCTCACTTA<br>AGTTCATGTCGCTGTCCAGCTGCTGAGCCACAGGCTGCTGTCCA<br>ACTTGCGGTTGCTTAACGGGCGGCGAAGGAGAAGTCCACGCCT<br>ACATGGGGGTAGAGTCATAATCGTGCATCAGGATAGGGCGGTG<br>GTGCTGCAGCAGCGCGCGAATAAACTGCTGCCGCCGCCGCTCCG<br>TCCTGCAGGAATACAACATGGCAGTGGTCTCCTCAGCGATGATT<br>CGCACCGCCCGCAGCATAAGGCGCCTTGTCCTCCGGGCACAGCA<br>GCGCACCCTGATCTCACTTAAATCAGCACAGTAACTGCAGCACA<br>GCACCACAATATTGTTCAAAATCCCACAGTGCAAGGCGCTGTAT<br>CCAAAGCTCATGGCGGGACCACAGAACCCACGTGGCCATCAT<br>ACCACAAGCGCAGGTAGATTAAGTGGCGACCCCTCATAAACAC<br>GCTGGACATAAACATTACCTCTTTTGGCATGTTGTAATTCACCAC<br>CTCCCGGTACCATATAAACCTCTGATTAAACATGGCGCCATCCA<br>CCACCATCCTAAACCAGCTGGCCAAAACCTGCCCGCCGGCTATA<br>CACTGCAGGGAACCGGGACTGGAACAATGACAGTGGAGAGCCC<br>AGGACTCGTAACCATGGATCATCATGCTCGTCATGATATCAATG<br>TTGGCACAACACAGGCACACGTGCATACACTTCCTCAGGATTAC<br>AAGCTCCTCCCGCGTTAGAACCATATCCCAGGGAACAACCCATT |

| SEQ ID NO | Sequence |
|---|---|
| | CCTGAATCAGCGTAAATCCCACACTGCAGGGAAGACCTCGCAC
GTAACTCACGTTGTGCATTGTCAAAGTGTTACATTCGGGCAGCA
GCGGATGATCCTCCAGTATGGTAGCGCGGGTTTCTGTCTCAAAA
GGAGGTAGACGATCCCTACTGTACGGAGTGCGCCGAGACAACC
GAGATCGTGTTGGTCGTAGTGTCATGCCAAATGGAACGCCGGAC
GTAGTCATATTTCCTGAAGCAAAACCAGGTGCGGGCGTGACAA
ACAGATCTGCGTCTCCGGTCTCGCCGCTTAGATCGCTCTGTGTA
GTAGTTGTAGTATATCCACTCTCTCAAAGCATCCAGGCGCCCCC
TGGCTTCGGGTTCTATGTAAACTCCTTCATGCGCCGCTGCCCTGA
TAACATCCACCACCGCAGAATAAGCCACACCCAGCCAACCTAC
ACATTCGTTCTGCGAGTCACACACGGGAGGAGCGGGAAGAGCT
GGAAGAACCATGTTTTTTTTTTATTCCAAAAGATTATCCAAAAC
CTCAAAATGAAGATCTATTAAGTGAACGCGCTCCCCTCCGGTGG
CGTGGTCAAACTCTACAGCCAAAGAACAGATAATGGCATTTGTA
AGATGTTGCACAATGGCTTCCAAAAGGCAAACGGCCCTCACGTC
CAAGTGGACGTAAAGGCTAAACCCTTCAGGGTGAATCTCCTCTA
TAAACATTCCAGCACCTTCAACCATGCCCAAATAATTCTCATCT
CGCCACCTTCTCAATATATCTCTAAGCAAATCCCGAATATTAAG
TCCGGCCATTGTAAAAATCTGCTCCAGAGCGCCCTCCACCTTCA
GCCTCAAGCAGCGAATCATGATTGCAAAAATTCAGGTTCCTCAC
AGACCTGTATAAGATTCAAAAGCGGAACATTAACAAAAATACC
GCGATCCCGTAGGTCCCTTCGCAGGGCCAGCTGAACATAATCGT
GCAGGTCTGCACGGACCAGCGCGGCCACTTCCCCGCCAGGAAC
CATGACAAAAGAACCCACACTGATTATGACACGCATACTCGGA
GCTATGCTAACCAGCGTAGCCCCGATGTAAGCTTGTTGCATGGG
CGGCGATATAAAATGCAAGGTGCTGCTCAAAAAATCAGGCAAA
GCCTCGCGCAAAAAGAAAGCACATCGTAGTCATGCTCATGCA
GATAAAGGCAGGTAAGCTCCGGAACCACCACAGAAAAAGACAC
CATTTTTCTCTCAAACATGTCTGCGGGTTTCTGCATAAACACAAA
ATAAAATAACAAAAAACATTTAAACATTAGAAGCCTGTCTTAC
AACAGGAAAAACAACCCTTATAAGCATAAGACGGACTACGGCC
ATGCCGGCGTGACCGTAAAAAAACTGGTCACCGTGATTAAAA
GCACCACCGACAGCTCCTCGGTCATGTCCGGAGTCATAATGTAA
GACTCGGTAAACACATCAGGTTGATTCACATCGGTCAGTGCTAA
AAAGCGACCGAAATAGCCCGGGGGAATACATACCCGCAGGCGT
AGAGACAACATTACAGCCCCCATAGGAGGTATAACAAAATTAA
TAGGAGAGAAAAACACATAAACACCTGAAAAACCCTCCTGCCT
AGGCAAAATAGCACCCTCCCGCTCCAGAACAACATACAGCGCTT
CCACAGCGGCAGCCATAACAGTCAGCCTTACCAGTAAAAAAGA
AAACCTATTAAAAAAACACCACTCGACACGGCACCAGCTCAAT
CAGTCACAGTGTAAAAAAGGGCCAAGTGCAGAGCGAGTATATA
TAGGACTAAAAAATGACGTAACGGTTAAAGTCCACAAAAAACA
CCCAGAAAAACCGCACGCGAACCTACGCCCAGAAACGAAAGCCA
AAAAACCCACAACTTCCTCAAATCGTCACTTCCGTTTTCCCACGT
TACGTCACTTCCCATTTTAAGAAAACTACAATTCCCAACACATA
CAAGTTACTCCGCCCTAAAACCTACGTCACCCGCCCCGTTCCCA
CGCCCCGCGCCACGTCACAAACTCCACCCCCTCATTATCATATT
GGCTTCAATCCAAATAAGGTATATTATTGATGAT |
| SEQ ID NO: 14 | MSSPGTESAGKSLQYRVDHLLSAVENELQAGSEKGDPTERELRVG
LEESELWLRFKELTNEMIVTKNGRRMFPVLKVNVSGLDPNAMYSF
LLDFVAADNHRWKYVNGEWVPGGKPEPQAPSCVYIHPDSPNFGA
HWMKAPVSFSKVKLTNKLNGGGQIMLNSLHKYEPRIHIVRVGGPQ
RMITSHCFPETQFIAVTARSDHKEMMEEPGDSQQPGYSQWGWLLP
GTSTVCPPANPHPQFGGALSLPSTHSCDRYPTLRSHRSSPYPSPYAH
RNNSPTYSDNSPACLSMLQSHDNWSSLGMPAHPSMLPVSHNASPP
TSSSQYPSLWSVSNGAVTPGSQAAAVSNGLGAQFFRGSPAHYTPLT
HPVSAPSSSGSPLYEGAAAATDIVDSQYDAAAQGRLIASWTPVSPP
SM |
| SEQ ID NO: 15 | WLLPGTSTV |
| SEQ ID NO: 16 | GCGGGGCAGCCTCACACAGAACACACACAGATATGGGTGTACC
CACTCAGCTCCTGTTGCTGTGGCTTACAGTCTAGTTGTCAGATG
TGACATCCAGATGACTCAGTCTCCAGCTTCACTGTCTGCATCTGT
GGGAGAAACTGTCACCATCACATGTGGAGCAAGTGAGAATATT
TACGGTGCTTTAAATTGGTATCAGCGGAAACAGGGAAAATCTCC
TCAGCTCCTGATTTATGCGCAAGTAATTTGGCAGATGGCATGT
CATCGAGGTTCAGTGGCAGTGGATCTGGTAGACAGTATTCTCTC
AAGATCAGTAGCCTGCATCCTGACGATTTTGCAACGTATTACTG
TCAAAATGTATTAAGTAGTCCGTACACGTTCGGAGGGGGGACCA
AGCTGGAAATAAAACGGGCTGATGCTGCACCAACTGTATCCATC
TTCCCACCATCCAGTGAGCAGTTAACATCTGGAGGTGCCTCAGT
CGTGTGCTTCTTGAACAACTTCTACCCCAAAGACATCAATGTCA
AGTGGAAGATTGATGGCAGTGAACGACAAAATGGCGTCCTGAA
CAGTTGGACTGATCAGGACAGCAAAGACAGCACCTACAGCATG
AGCAGCACCCTCACGTTGACCAAGGACGAGTATGAACGACATA |

| SEQ ID NO | Sequence |
|---|---|
| | ACAGCTATACCTGTGAGGCCACTCACAAGACACCAACTTCACCC<br>ATTGTCAAGAGCTTCAACAGGAATGAGTGTTAGAGACAAAGGT<br>CCTGAGACGCCACCACCAGCTCCCCAGCTCCATCCTATCTTCCT<br>TCTAAGGTCTTGGAGGCTTCCCCACAAGCGACCTACCACTGTTG<br>CGGTGCTCCAAACCTCCTCCCCACCTCCTTCTCCTCCTCCTCCCT<br>TTCCTTGGCTTTTATCATGCTAATATTTGCAGAAAATATTCAATA<br>AAGTGAGTCTTTGCACAAAAAAAAAAAAAAAAAAAAAAAAAA |
| SEQ ID NO: 17 | ACGCGGGACACAGTAGTCTCTACAGTCACAGGAGTACACAGGA<br>CATTGCCATGGGTTGGAGCTGTATCATCTTCTTTCTGGTAGCAA<br>CAGCTACAGGTGTGCACTCCCAGGTCCAGCTGCAGCAGTCTGGG<br>CCTGAGGTGGTGAGGCCTGGGGTCTCAGTGAAGATTTCCTGCAA<br>GGGTTCCGGCTACACATTCACTGATTATGCTATGCACTGGGTGA<br>AGCAGAGTCATGCAAAGAGTCTCGAGTGGATTGGACTTATTAGT<br>ACTTACAGTGGTGATACAAAGTACAACCAGAACTTTAAGGGCA<br>AGGCCACAATGACTGTAGACAAATCCTCCAACACAGCCTATATG<br>GAACTTGCCAGATTGACATCTGAGGATTCTGCCATCTATTACTG<br>TGCAAGAGGGGATTATTCCGGTAGTAGGTACTGGTTTGCTTACT<br>GGGGCCAAGGGACTCTGGTCACTGTCTCTGCAGCCAAAACGAC<br>ACCCCCATCTGTCTATCCACTGGCCCCTGGATCTGCTGCCCAAA<br>CTAACTCCATGGTGACCCTGGGATGCCTGGTCAAGGGCTATTTC<br>CCTGAGCCAGTGACAGTGACCTGGAACTCTGGATCCCTGTCCAG<br>CGGTGTGCACACCTTCCCAGCTGTCCTGCAGTCTGACCTCTACA<br>CTCTGAGCAGCTCAGTGACTGTCCCCTCCAGCACCTGGCCCAGC<br>GAGACCGTCACCTGCAACGTTGCCCACCCGGCCAGCAGCACCA<br>AGGTGGACAAGAAAATTGTGCCCAGGGATTGTGGTTGTAAGCCT<br>TGCATATGTACAGTCCCAGAAGTATCATCTGTCTTCATCTTCCCC<br>CCAAAGCCCAAGGATGTGCTCACCATTACTCTGACTCCTAAGGT<br>CACGTGTGTTGTGGTAGACATCAGCAAGGATGATCCCGAGGTCC<br>AGTTCAGCTGGTTTGTAGATGATGTGGAGGTGCACACAGCTCAG<br>ACGCAACCCCGGGAGGAGCAGTTCAACAGCACTTTCCGCTCAGT<br>CAGTGAACTTCCCATCATGCACCAGGACTGGCTCAATGGCAAGG<br>AGTTCAAATGCAGGGTCAACAGTGCAGCTTTCCCTGCCCCCATC<br>GAGAAAACCATCTCCAAAACCAAAGGCAGACCGAAGGCTCCAC<br>AGGTGTACACCATTCCACCTCCCAAGGAGCAGATGGCCAAGGA<br>TAAAGTCAGTCTGACCTGCATGATAACAGACTTCTTCCCTGAAG<br>ACATTACTGTGGAGTGGCAGTGGAATGGGCAGCCAGCGGAGAA<br>CTACAAGAACACTCAGCCCATCATGGACACAGATGGCTCTTACT<br>TCGTCTACAGCAAGCTCAATGTGCAGAAGAGCAACTGGGAGGC<br>AGGAAATACTTTCACCTGCTCTGTGTTACATGAGGGCCTGCACA<br>ACCACCATACTGAGAAGAGCCTCTCCCACTCTCCTGGTAAATGA<br>TCCCAGTGTCCTTGGAGCCCTCTGGCCCTACAGGACTTTGACAC<br>CTACCTCCACCCCTCCCTGTATAAATAAAGCACCCAGCACTGCC<br>TCGGGACCCTGCATAAAAAAAAAAAAAAAAAAAAAAAAAAAA |
| SEQ ID NO: 18 | LMTQSPASLSASVGETVTITCGASENIYGALNWYQRKQGKSPQLLI<br>YGASNLADGMSSRFSGSGSGRQYSLKISSLHPDDVATYYCQNVLS<br>SPYTFGGGTKLEIKKG |
| SEQ ID NO: 19 | MGVPTQLLLLWLTVVVRC/DIQMTQSPSSLSASVGDRVTITCQAS<br>ENIYGALNWYQRKPGKSPKLLIYGASNLATGMPSRFSGSGSGTDY<br>TFTISSLQPEDIATYYCQQVLSSPYTFGGGTKLEIKR/TVAAPSVFIFP<br>PSDEQLKSGTASVVCLINNFYPREAKVQWKVDNALQSGNSQESVT<br>EQDSKDSTYSLSSTLTLSKADYEKHKVYACEVTHQGLSSPVTKSFN<br>RGEC |
| SEQ ID NO: 20 | LEESGPEVVRPGVSVKISCKGSGYTFTDYAMHWVKQSHAKSLEWI<br>GLISTYSGDTKYNQNFKGKATMTVDKSSNTAYMELARLTSEDSAI<br>YYCARGDYSGSRYWFAYWGQGTTVTR |
| SEQ ID NO: 21 | GASENIYGALN |
| SEQ ID NO: 22 | GASNLAD |
| SEQ ID NO: 23 | QNVLSSPYT |
| SEQ ID NO: 24 | QASENIYGALN |
| SEQ ID NO: 25 | GASNLAT |
| SEQ ID NO: 26 | QQVLSSPYT |
| SEQ ID NO: 27 | GYTFTDYAMH |
| SEQ ID NO: 28 | LISTYSGDTKYNQNFKG |
| SEQ ID NO: 29 | GDYSGSRYWFAY |

| SEQ ID NO | Sequence |
|---|---|
| SEQ ID NO: 30 | LISTYSGDTKYNQKFQG |
| SEQ ID NO: 31 | GDYSGSRYWFAY |
| SEQ ID NO: 99 | MGWSCIIFFLVATATGVHS/QVQLVQSGAEVKKPGASVKVSCKASGYTFTDYAMHWVRQAPGQRLEWMGLISTYSGDTKYNQNFQGRVTMTVDKSASTAYMELSSLRSEDTAVYYCARGDYSGSRYWFAYWGQGTLVTVSS/ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK |
| SEQ ID NO: 100 | ATGGAGTCTCCCTCGGCCCCTCCCCACAGATGGTGCATCCCCTGGCAGAGGCTCCTGCTCACAGCCTCACTTCTAACCTTCTGGAACCCGCCCACCACTGCCAAGCTCACTATTGAATCCACGCCGTTCAATGTCGCAGAGGGGAAGGAGGTGCTTCTACTTGTCCACAATCTGCCCCAGCATCTTTTTGGCTACAGCTGGTACAAAGGTGAAAGAGTGGATGGCAACCGTCAAATTATAGGATATGTAATAGGAACTCAACAAGCTACCCCAGGGCCCGCATACAGTGGTCGAGAGATAATATACCCCAATGCATCCCTGCTGATCCAGAACATCATCCAGAATGACACAGGATTCTACACCCTACACGTCATAAAGTCAGATCTTGTGAATGAAGAAGCAACTGGCCAGTTCCGGGTATACCCGGAGCTGCCCAAGCCCTCCATCTCCAGCAACAACTCCAAACCCGTGGAGGACAAGGATGCTGTGGCCTTCACCTGTGAACCTGAGACTCAGGACGCAACCTACCTGTGGTGGGTAAACAATCAGAGCCTCCGGTCAGTCCCAGGCTGCAGCTGTCCAATGGCAACAGGACCCTCACTCTATTCAATGTCACAAGAAATGACACAGCAAGCTACAAATGTGAAACCCAGAACCCAGTGAGTGCCAGGCGCAGTGATTCAGTCATCCTGAATGTCCTCTATGGCCCGGATGCCCCCACCATTTCCCCTCTAAACACATCTTACAGATCAGGGGAAAATCTGAACCTCTCCTGCCACGCAGCCTCTAACCCACCTGCACAGTACTCTTGGTTTGTCAATGGGACTTTCCAGCAATCCACCCAAGAGCTCTTTATCCCCAACATCACTGTGAATAATAGTGGATCCTATACGTGCCAAGCCCATAACTCAGACACTGGCCTCAATAGGACCACAGTCACGACGATCACAGTCTATGCAGAGCCACCCAAACCCTTCATCACCAGCAACAACTCCAACCCCGTGGAGGATGAGGATGCTGTAGCCTTAACCTGTGAACCTGAGATTCAGAACACAACCTACCTGTGGTGGGTAAATAATCAGAGCCTCCGGTCAGTCCCAGGCTGCAGCTGTCCAATGACAACAGGACCCTCACTCTACTCAGTGTCACAAGGAATGATGTAGGACCCTATGAGTGTGGAATCCAGAACGAATTAAGTGTTGACCACAGCGACCCAGTCATCCTGAATGTCCTCTATGGCCCAGACGACCCCACCATTTCCCCTCATACACCTATTACCGTCCAGGGGTGAACCTCAGCCTCTCCTGCCATGCAGCCTCTAACCCACCTGCACAGTATTCTTGGCTGATTGATGGGAACATCAGCAACACACACAAGAGCTCTTTATCTCCAACATCACTGAGAAGAACAGCGGACTCTATACCTGCCAGGCCAATAACTCAGCCAGTGGCCACAGCAGGACTACAGTCAAGACAATCACAGTCTCTGCGGGAGCTGCCCAAGCCCTCCATCTCCAGCAACAACTCCAAACCCGTGGAGGACAAGGATGCTGTGGCCTTCACCTGTGAACCTGAGGCTCAGAACACAACCTACCTGTGGTGGGTAAATGGTCAGAGCCTCCCAGTCAGTCCCAGGCTGCAGCTGTCCAATGGCAACAGGACCCTCACTCTATTCAATGTCACAAGAAATGACGCAAGAGCCTATGTATGTGGAATCCAGAACTCAGTGAGTGCAAACCGCAGTGACCCAGTCACCCTGGATGTCCTCTATGGGCCGGACACCCCCATCATTTCCCCCCCAGACTCGTCTTACCTTTCGGGAGCGGACCTCAACCTCTCCTGCCACTCGGCCTCTAACCCATCCCCGCAGTATTCTTGGCGTATCAATGGGATACCGCAGCAACACACACAAGTTCTCTTTATCGCCAAAATCACGCCAAATAATAACGGGACCTATGCCTGTTTTGTCTCTAACTTGGCTACTGCCGCAATAATTCCATAGTCAAGAGCATCACAGTCTCTGCATCTGGAACTTCTCCTGGTCTCTCAGCTGGGGCCACTGTCGGCATCATGATTGGAGTGCTGGTTGGGGTTGCTCTGATATAG |
| SEQ ID NO: 101 | ATGACACCGGGCACCCAGTCTCCTTTCTTCCTGCTGCTGCTCCTCACAGTGCTTACAGTTGTTACGGGTTCTGGTCATGCAAGCTCTACCCCAGGTGGAGAAAAGGAGACTTCGGCTACCCAGAGAAGTTCAGTGCCCAGCTCTACTGAGAAGAATGCTGTGAGTATGACCAGCAGCGTACTCTCCAGCCACAGCCCCGGTTCAGGCTCCTCCACCACTCAGGGACAGGATGTCACTCTGGCCCCGGCCACGGAACCAGCTTCAGGTTCAGCTGCCCTTTGGGGACAGGATGTCACCTCGGTCCCAGTCACCGGCCAGCCCTGGGCTCCACCACCCGCCAGCCCACGATGTCACCTCAGCCCCGGACAACAAGCCAGCCCCGGGCTCCACCGCCCCCCCAGCCCACGGTGTCACCTCGTATCTTGACACCAGGCCGG |

| SEQ ID NO | Sequence |
|---|---|
| | CCCCGGTTTATCTTGCCCCCCCAGCCCATGGTGTCACCTCGGCCC<br>CGGACAACAGGCCCGCCTTGGGCTCCACCGCCCCTCCAGTCCAC<br>AATGTCACCTCGGCCTCAGGCTCTGCATCAGGCTCAGCTTCTAC<br>TCTGGTGCACAACGGCACCTCTGCCAGGGCTACCACAACCCCAG<br>CCAGCAAGAGCACTCCATTCTCAATTCCCAGCCACCACTCTGAT<br>ACTCCTACCACCCTTGCCAGCCATAGCACCAAGACTGATGCCAG<br>TAGCACTCACCATAGCACGGTACCTCCTCTCACCTCCTCCAATC<br>ACAGCACTTCTCCCCAGTTGTCTACTGGGGTCTCTTTCTTTTCC<br>TGTCTTTTCACATTTCAAACCTCCAGTTTAATTCCTCTCTGGAAG<br>ATCCCAGCACCGACTACTACCAAGAGCTGCAGAGAGACATTTCT<br>GAAATGTTTTTGCAGATTTATAAACAAGGGGGTTTTCTGGGCCT<br>CTCCAATATTAAGTTCAGGCCAGGATCTGTGGTGGTACAATTGA<br>CTCTGGCCTTCCGAGAAGGTACCATCAATGTCCACGACGTGGAG<br>ACACAGTTCAATCAGTATAAAACGGAAGCAGCCTCTCGATATAA<br>CCTGACGATCTCAGACGTCAGCGTGAGTGATGTGCCATTTCCTT<br>TCTCTGCCCAGTCTGGGGCTGGGGTGCCAGGCTGGGGCATCGCG<br>CTGCTGGTGCTGGTCTGTGTTCTGGTTTATCTGGCCATTGTCTAT<br>CTCATTGCCTTGGCTGTCGCTCAGGTTCGCCGAAAGAACTACGG<br>GCAGCTGGACATCTTTCCAGCCCGGGATAAATACCATCCTATGA<br>GCGAGTACGCTCTTTACCACACCCATGGGCGCTATGTGCCCCCT<br>AGCAGTCTTTTCCGTAGCCCCTATGAGAAGGTTTCTGCAGGTAA<br>TGGTGGCAGCTATCTCTCTTACACAAACCCAGCAGTGGCAGCCG<br>CTTCTGCCAACTTGTAG |
| SEQ ID NO: 102 | ATGAGCTCCCCTGGCACCGAGAGCGCGGGAAAGAGCCTGCAGT<br>ACCGAGTGGACCACCTGCTGAGCGCCGTGGAGAATGAGCTGCA<br>GGCGGGCAGCGAGAAGGGCGACCCCACAGAGCGCGAACTGCGC<br>GTGGGCCTGGAGGAGAGCGAGCTGTGGCTGCGCTTCAAGGAGC<br>TCACCAATGAGATGATCGTGACCAAGAACGGCAGGAGGATGTT<br>TCCGGTGCTGAAGGTGAACGTGTCTGGCCTGGACCCCAACGCCA<br>TGTACTCCTTCCTGCTGGACTTCGTGGCGGCGGACAACCACCGC<br>TGGAAGTACGTGAACGGGGAATGGGTGCCGGGGGGCAAGCCGG<br>AGCCGCAGGCGCCCAGCTGCGTCTACATCCACCCCGACTCGCCC<br>AACTTCGGGGCCCACTGGATGAAGGCTCCCGTCTCCTTCAGCAA<br>AGTCAAGCTCACCAACAAGCTCAACGGAGGGGGCCAGATCATG<br>CTGAACTCCTTGCATAAGTATGAGCCTCGAATCCACATAGTGAG<br>AGTTGGGGGTCCACAGCGCATGATCACCAGCCACTGCTTCCCTG<br>AGACCCAGTTCATAGCGGTGACTGCTAGAAGTGATCACAAAGA<br>GATGATGGAGGAACCCGGAGACAGCCAGCAACCTGGGTACTCC<br>CAATGGGGGTGGCTTCTTCCTGGAACCAGCACCGTGTGTCCACC<br>TGCAAATCCTCATCCTCAGTTTGGAGGTGCCCTCTCCCTCCCCTC<br>CACGCACAGCTGTGACAGGTACCCAACCCTGAGGAGCCACCGG<br>TCCTCACCCTACCCCAGCCCCTATGCTCATCGGAACAATTCTCCA<br>ACCTATTCTGACAACTCACCTGCATGTTTATCCATGCTGCAATCC<br>CATGACAATTGGTCCAGCCTTGGAATGCCTGCCCATCCCAGCAT<br>GCTCCCCGTGAGCCACAATGCCAGCCCACCTACCAGCTCCAGTC<br>AGTACCCCAGCCTGTGGTCTGTGAGCAACGGCGCCGTCACCCCG<br>GGCTCCCAGGCAGCAGCCGTGTCCAACGGGCTGGGGGCCCAGT<br>TCTTCCGGGGCTCCCCCGCGCACTACACACCCCTCACCCATCCG<br>GTCTCGGCGCCCTCTTCCTCGGGATCCCCACTGTACGAAGGGGC<br>GGCCGCGGCCACAGACATCGTGGACAGCCAGTACGACGCCGCA<br>GCCCAAGGCCGCCTCATAGCCTCATGGACACCTGTGTCGCCACC<br>TTCCATGTGA |

What is claimed is:

1. A composition comprising a first recombinant adenovirus subtype 5 (Ad5) vector comprising a deletion in an E1 gene region, a deletion in an E2b gene region, and a nucleic acid sequence encoding a carcinoembryonic antigen (CEA) according to SEQ ID NO:3 or SEQ ID NO:4, and:
   a) a second recombinant adenovirus vector comprising a nucleic acid sequence encoding an IL-15N72D domain of a human interleukin-15 (IL-15) superagonist complex and an IL-15RaSu/Fc fusion domain of the IL-15 superagonist complex; or
   b) a third recombinant adenovirus vector comprising a nucleic acid sequence encoding an IL-15N72D domain of a human IL-15 superagonist complex and fourth recombinant adenovirus vector comprising a nucleic acid sequence encoding an IL-15RαSu/Fc fusion domain of the IL-15 superagonist complex.

2. The composition of claim 1, wherein the CEA is SEQ ID NO: 3.

3. The composition of claim 1, wherein the nucleic acid sequence encoding CEA is SEQ ID NO: 1 or SEQ ID NO: 100.

4. The composition of claim 1, wherein the CEA is SEQ ID NO:4.

5. The composition of claim 1, wherein the IL-15 superagonist complex is ALT-803.

6. The composition of claim 1, wherein the composition comprises at least $1\times10^9$ viral particles in a single dose.

7. The composition of claim 6, wherein the composition comprises $1\times10^9$-$5\times10^{12}$ viral particles in a single dose.

8. The composition of claim 7, wherein the composition comprises $1\times10^{10}$-$5\times10^{12}$ viral particles in a single dose.

9. The composition of claim 8, wherein the composition-comprises $1\times10^{10}$-$5\times10^{11}$ viral particles in a single dose.

* * * * *

SEQUENCE LISTING

<160> NUMBER OF SEQ ID NOS: 113

<210> SEQ ID NO 1
<211> LENGTH: 2109
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
atggagtctc cctcggcccc tccccacaga tggtgcatcc cctggcagag gctcctgctc     60
acagcctcac ttctaacctt ctggaacccg cccaccactg ccaagctcac tattgaatcc    120
acgccgttca atgtcgcaga ggggaaggag gtgcttctac ttgtccacaa tctgccccag    180

```
catcttttg gctacagctg gtacaaaggt gaaagagtgg atggcaaccg tcaaattata      240
ggatatgtaa taggaactca acaagctacc ccagggcccg catacagtgg tcgagagata      300 atataccca atgcatccct gctgatccag aacatcatcc agaatgacac aggattctac      360
accctacacg tcataaagtc agatcttgtg aatgaagaag caactggcca gttccgggta      420
tacccggagc tgcccaagcc ctccatctcc agcaacaact ccaaacccgt ggaggacaag      480
gatgctgtgg ccttcacctg tgaacctgag actcaggacg caacctacct gtggtgggta      540
aacaatcaga gcctcccggt cagtcccagg ctgcagctgt ccaatggcaa caggaccctc      600
actctattca atgtcacaag aaatgacaca gcaagctaca aatgtgaaac ccagaaccca      660
gtgagtgcca ggcgcagtga ttcagtcatc ctgaatgtcc tctatggccc ggatgccccc      720
accatttccc ctctaaacac atcttacaga tcaggggaaa atctgaacct ctcctgccac      780
gcagcctcta acccacctgc acagtactct tggtttgtca atgggacttt ccagcaatcc      840
acccaagagc tctttatccc caacatcact gtgaataata gtggatccta tacgtgccaa      900
gcccataact cagacactgg cctcaatagg accacagtca cgacgatcac agtctatgca      960
gagccaccca aacccttcat caccagcaac aactccaacc ccgtggagga tgaggatgct     1020
gtagccttaa cctgtgaacc tgagattcag aacacaacct acctgtggtg ggtaaataat     1080
cagagcctcc cggtcagtcc caggctgcag ctgtccaatg acaacaggac cctcactcta     1140
ctcagtgtca caaggaatga tgtaggaccc tatgagtgtg aatccagaa cgaattaagt     1200 gttgaccaca cgcacccagt catcctgaat gtcctctatg cccagacga ccccaccatt     1260 tccccctcat acacctatta ccgtccaggg gtgaacctca gcctctcctg ccatgcagcc     1320
tctaacccac ctgcacagta ttcttggctg attgatggga acatccagca acacacacaa     1380 gagctctttta tctccaacat cactgagaag aacagcggac tctatacctg ccaggccaat     1440
aactcagcca gtggccacag caggactaca gtcaagacaa tcacagtctc tgcggagctg     1500
cccaagccct ccatctccag caacaactcc aaacccgtgg aggacaagga tgctgtggcc     1560
ttcacctgtg aacctgaggc tcagaacaca acctacctgt ggtgggtaaa tggtcagagc     1620
ctcccagtca gtcccaggct gcagctgtcc aatggcaaca ggaccctcac tctattcaat     1680
gtcacaagaa atgacgcaag agcctatgta tgtggaatcc agaactcagt gagtgcaaac     1740
cgcagtgacc cagtcacccc tggatgtcct atgggccgg acacccccat catttccccc     1800
ccagactcgt cttacctttc gggagcgaac ctcaacctct cctgccactc ggcctctaac     1860
ccatccccgc agtattcttg gcgtatcaat gggataccgc agcaacacac acaagttctc     1920
tttatcgcca aaatcacgcc aaataataac gggacctatg cctgttttgt ctctaacttg     1980
gctactggcc gcaataattc catagtcaag agcatcacag tctctgcatc tggaacttct     2040
cctggtctct cagctggggc cactgtcggc atcatgattg gagtgctggt tggggttgct     2100
ctgatatag                                                             2109

<210> SEQ ID NO 2
<211> LENGTH: 32315
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
catcatcaat aatataccctt attttggatt gaagccaata tgataatgag ggggtggagt       60
```

```
ttgtgacgtg gcgcggggcg tgggaacggg gcgggtgacg tagtagtgtg gcggaagtgt      120
gatgttgcaa gtgtggcgga acacatgtaa gcgacggatg tggcaaaagt gacgttttg       180 gtgtgcgccg gtgtacacag gaagtgacaa ttttcgcgcg gttttaggcg gatgttgtag      240
taaatttggg cgtaaccgag taagatttgg ccatttttcgc gggaaaactg aataagagga     300
agtgaaatct gaataatttt gtgttactca tagcgcgtaa tactgtaata gtaatcaatt      360
acggggtcat tagttcatag cccatatatg gagttccgcg ttacataact tacgtaaat       420 ggcccgcctg gctgaccgcc caacgacccc cgcccattga cgtcaataat gacgtatgtt      480
cccatagtaa cgccaatagg gactttccat tgacgtcaat gggtggagta tttacgtaa       540 actgcccact tggcagtaca tcaagtgtat catatgccaa gtacgccccc tattgacgtc      600
aatgacggta aatggcccgc ctggcattat gcccagtaca tgaccttatg gactttcct      660 acttggcagt acatctacgt attagtcatc gctattacca tggtgatgcg gttttggcag      720
tacatcaatg ggcgtggata gcggtttgac tcacggggat ttccaagtct ccaccccatt      780
gacgtcaatg ggagtttgtt ttggcaccaa aatcaacggg actttccaaa atgtcgtaac      840
aactccgccc cattgacgca aatgggcggt aggcgtgtac ggtgggaggt ctatataagc      900
agagctggtt tagtgaaccg tcagatccgc tagagatctg gtaccgtcga cgcggccgct      960
cgagcctaag cttggtaccg agctcggatc cactagtaac ggccgccagt gtgctggaat    1020
tcggcttaaa ggtacccaga gcagacagcc gccaccatgg agtctccctc ggcccctccc    1080
cacagatggt gcatccctg gcagaggctc ctgctcacag cctcacttct aaccttctgg      1140
aacccgccca ccactgccaa gctcactatt gaatccacgc cgttcaatgt cgcagagggg    1200
aaggaggtgc ttctacttgt ccacaatctg ccccagcatc tttttggcta cagctggtac    1260
aaaggtgaaa gagtggatgg caaccgtcaa attataggat atgtaatagg aactcaacaa    1320
gctaccccag ggcccgcata cagtggtcga gagataatat accccaatgc atccctgctg    1380
atccagaaca tcatccagaa tgacacagga ttctacaccc tacacgtcat aaagtcagat    1440
cttgtgaatg aagaagcaac tggccagttc cgggtatacc cggagctgcc caagccctcc    1500
atctccagca acaactccaa acccgtggag gacaaggatc tgtgggcctt cacctgtgaa    1560
cctgagactc aggacgcaac ctacctgtgg tgggtaaaca atcagagcct cccggtcagt    1620
cccaggctgc agctgtccaa tggcaacagg accctcactc tattcaatgt cacaagaaat    1680
gacacagcaa gctacaaatg tgaaacccag aacccagtga gtgccaggcg cagtgattca    1740
gtcatcctga atgtcctcta tggcccggat gcccccacca tttcccctct aaacacatct    1800
tacagatcag ggaaaatct gaacctctcc tgccacgcag cctctaaccc acctgcacag    1860
tactcttggt tgtcaatgg gactttccag caatccaccc aagagctctt tatcccaac     1920 atcactgtga ataatagtgg atcctatacg tgccaagccc ataactcaga cactggcctc    1980
aataggacca cagtcacgac gatcacagtc tatgcagagc cacccaaacc cttcatcacc    2040
agcaacaact ccaaccccgt ggaggatgag gatgctgtag ccttaacctg tgaacctgag    2100
attcagaaca caacctacct gtggtgggta aataatcaga gcctcccggt cagtcccagg    2160
ctgcagctgt ccaatgacaa caggaccctc actctactca gtgtcacaag gaatgatgta    2220
ggaccctatg agtgtggaat ccagaacgaa ttaagtgttg accacagcga cccagtcatc    2280
ctgaatgtcc tctatggccc agacgacccc accatttccc cctcatacac ctattaccgt    2340
ccaggggtga acctcagcct ctcctgccat gcagcctcta acccacctgc acagtattct    2400
```

-continued

```
tggctgattg atgggaacat ccagcaacac acacaagagc tctttatctc caacatcact    2460
gagaagaaca gcggactcta tacctgccag gccaataact cagccagtgg ccacagcagg    2520
actacagtca agacaatcac agtctctgcg gagctgccca agccctccat ctccagcaac    2580
aactccaaac ccgtggagga caaggatgct gtggccttca cctgtgaacc tgaggctcag    2640
aacacaacct acctgtggtg ggtaaatggt cagagcctcc cagtcagtcc caggctgcag    2700
ctgtccaatg gcaacaggac cctcactcta ttcaatgtca caagaaatga cgcaagagcc    2760
tatgtatgtg gaatccagaa ctcagtgagt gcaaaccgca gtgacccagt caccctggat    2820
gtcctctatg gccggacac ccccatcatt tccccccag actcgtctta cctttcggga    2880
gcggacctca acctctcctg ccactcggcc tctaacccat ccccgcagta ttcttggcgt    2940
atcaatggga taccgcagca acacacacaa gttctcttta tcgccaaaat cacgccaaat    3000
aataacggga cctatgcctg ttttgtctct aacttggcta ctggccgcaa taattccata    3060
gtcaagagca tcacagtctc tgcatctgga acttctcctg gtctctcagc tggggccact    3120
gtcggcatca tgattggagt gctggttggg gttgctctga tatagcagcc ctggtgtagt    3180
ttcttcattt caggaagact gacagttgtt ttgcttcttc cttaaagcat ttgcaacagc    3240
tacagtctaa aattgcttct ttaccaagga tatttacaga aaagactctg accagagatc    3300
gagaccatcc tctagataag atatccgatc caccggatct agataactga tcataatcag    3360
ccataccaca tttgtagagg ttttacttgc tttaaaaaac ctcccacacc tcccctgaa    3420 cctgaaacat aaaatgaatg caattgttgt tgttaacttg tttattgcag cttataatgg    3480
ttacaaataa agcaatagca tcacaaattt cacaaataaa gcattttttt cactgcattc    3540
tagttgtggt ttgtccaaac tcatcaatgt atcttaacgc ggatctgggc gtggttaagg    3600
gtgggaaaga atatataagg tgggggtctt atgtagtttt gtatctgttt tgcagcagcc    3660
gccgccgcca tgagcaccaa ctcgtttgat ggaagcattg tgagctcata tttgacaacg    3720
cgcatgcccc catgggccgg ggtgcgtcag aatgtgatgg gctccagcat tgatggtcgc    3780
cccgtcctgc ccgcaaactc tactaccttg acctacgaga ccgtgtctgg aacgccgttg    3840
gagactgcag cctccgccgc cgcttcagcc gctgcagcca ccgcccgcgg gattgtgact    3900
gactttgctt tcctgagccc gcttgcaagc agtgcagctt cccgttcatc cgcccgcgat    3960
gacaagttga cggctctttt ggcacaattg gattctttga cccgggaact taatgtcgtt    4020
tctcagcagc tgttggatct gcgccagcag gtttctgccc tgaaggcttc ctcccctccc    4080
aatgcggttt aaaacataaa taaaaaacca gactctgttt ggatttggat caagcaagtg    4140
tcttgctgtc tttatttagg ggttttgcgc gcgcggtagg cccgggacca gcggtctcgg    4200
tcgttgaggg tcctgtgtat ttttttccagg acgtggtaaa ggtgactctg gatgttcaga    4260
tacatgggca taagcccgtc tctggggtgg aggtagcacc actgcagagc ttcatgctgc    4320 gggggtggtgt tgtagatgat ccagtcgtag caggagcgct gggcgtggtg cctaaaaatg    4380
tctttcagta gcaagctgat tgccagggc aggcccttgg tgtaagtgtt tacaaagcgg    4440
ttaagctggg atgggtgcat acgtggggat atgagatgca tcttggactg tattttagg    4500 ttggctatgt tccagccat atccctccgg ggattcatgt tgtgcagaac caccagcaca    4560
gtgtatccgg tgcacttggg aaatttgtca tgtagcttag aaggaaatgc gtggaagaac    4620
ttggagacgc ccttgtgacc tccaagattt ccatgcatt cgtccataat gatggcaatg    4680
ggcccacggg cggcggcctg ggcgaagata tttctgggat cactaacgtc atagttgtgt    4740
tccaggatga gatcgtcata ggccattttt acaaagcgcg ggcggagggt gccagactgc    4800
```

```
ggtataatgg ttccatccgg cccaggggcg tagttaccct cacagatttg catttcccac   4860
gctttgagtt cagatggggg gatcatgtct acctgcgggg cgatgaagaa aacggtttcc   4920
ggggtagggg agatcagctg gaagaaagc aggttcctga gcagctgcga cttaccgcag    4980
ccggtgggcc cgtaaatcac acctattacc ggctgcaact ggtagttaag agagctgcag   5040
ctgccgtcat ccctgagcag gggggccact tcgttaagca tgtccctgac tcgcatgttt   5100
tccctgacca aatccgccag aaggcgctcg ccgcccagcg atagcagttc ttgcaaggaa   5160
gcaaagtttt tcaacggttt gagaccgtcc gccgtaggca tgcttttgag cgtttgacca   5220
agcagttcca ggcggtccca cagctcggtc acctgctcta cggcatctcg atccagcata   5280
tctcctcgtt tcgcgggttg gggcggcttt cgctgtacgg cagtagtcgg tgctcgtcca   5340
gacgggccag ggtcatgtct ttccacgggc gcagggtcct cgtcagcgta gtctgggtca   5400
cggtgaaggg gtgcgctccg ggctgcgcgc tggccagggt gcgcttgagg ctggtcctgc   5460
tggtgctgaa gcgctgccgg tcttcgccct gcgcgtcggc caggtagcat ttgaccatgg   5520
tgtcatagtc cagcccctcc gcggcgtggc ccttggcgcg cagcttgccc ttggaggagg   5580
cgccgcacga ggggcagtgc agacttttga gggcgtagag cttgggcgcg agaaataccg   5640
attccgggga gtaggcatcc gcgccgcagg ccccgcagac ggtctcgcat ccacgagcc    5700 aggtgagctc tggccgttcg gggtcaaaaa ccaggtttcc cccatgcttt ttgatgcgtt   5760
tcttacctct ggtttccatg agccggtgtc cacgctcggt gacgaaaagg ctgtccgtgt   5820
ccccgtatac agacttgaga ggcctgtcct cgagcggtgt tccgcggtcc tcctcgtata   5880
gaaactcgga ccactctgag acaaaggctc gcgtccaggc cagcacgaag gaggctaagt   5940
gggaggggta gcggtcgttg tccactaggg ggtccactcg ctccagggtg tgaagacaca   6000
tgtcgccctc ttcggcatca aggaaggtga ttggtttgta ggtgtaggcc acgtgaccgg   6060
gtgttcctga aggggggcta taaaggggg tgggggcgcg ttcgtcctca ctctcttccg    6120
catcgctgtc tgcgagggcc agctgttggg gtgagtactc cctctgaaaa gcgggcatga   6180
cttctgcgct aagattgtca gtttccaaaa acgaggagga tttgatattc acctggcccg   6240
cggtgatgcc tttgagggtg gccgcatcca tctggtcaga aaagacaatc tttttgttgt   6300
caagcttggt ggcaaacgac ccgtagaggg cgttggacag caacttggcg atggagcgca   6360
gggtttggtt tttgtcgcga tcggcgcgct ccttggccgc gatgtttagc tgcacgtatt   6420
cgcgcgcaac gcaccgccat tcgggaaaga cggtggtgcg ctcgtcgggc accaggtgca   6480
cgcgccaacc gcggttgtgc agggtgacaa ggtcaacgct ggtggctacc tctccgcgta   6540
ggcgctcgtt ggtccagcag aggcggccgc ccttgcgcga gcagaatggc ggtaggggt    6600 ctagctgcgt ctcgtccggg gggtctgcgt ccacggtaaa gaccccgggc agcaggcgcg   6660
cgtcgaagta gtctatcttg catccttgca agtctagcgc ctgctgccat gcgcgggcgg   6720
caagcgcgcg ctcgtatggg ttgagtgggg gaccccatgg catggggtgg gtgagcgcgg   6780
aggcgtacat gccgcaaatg tcgtaaacgt agaggggctc tctgagtatt ccaagatatg   6840
tagggtagca tcttccaccg cggatgctgg cgcgcacgta atcgtatagt tcgtgcgagg   6900
gagcgaggag gtcgggaccg aggttgctac gggcgggctg ctctgctcgg aagactatct   6960
gcctgaagat ggcatgtgag ttggatgata tggttggacg ctggaagacg ttgaagctgg   7020
cgtctgtgag acctaccgcg tcacgcacga aggaggcgta ggagtcgcgc agcttgttga   7080
ccagctcggc ggtgacctgc acgtctaggg cgcagtagtc cagggtttcc ttgatgatgt   7140
```

```
catacttatc ctgtcccttt tttttccaca gctcgcggtt gaggacaaac tcttcgcggt    7200 cttttccagta ctcttggatc ggaaacccgt cggcctccga acggtaagag cctagcatgt   7260
agaactggtt gacggcctgg taggcgcagc atcccttttc tacgggtagc gcgtatgcct   7320
gcgcggcctt ccggcatgac cagcatgaag ggcacgagct gcttcccaaa ggcccccatc   7380
caagtatagg tctctacatc gtaggtgaca aagagacgct cggtgcgagg atgcgagccg   7440
atcgggaaga actggatctc ccgccaccaa ttggaggagt ggctattgat gtggtgaaag   7500
tagaagtccc tgcgacgggc cgaacactcg tgctggcttt tgtaaaaacg tgcgcagtac   7560
tggcagcggt gcacgggctg tacatcctgc acgaggttga cctgacgacc cgcacaagg    7620 aagcagagtg ggaatttgag cccctcgcct ggcgggtttg gctggtggtc ttctacttcg   7680
gctgcttgtc cttgaccgtc tggctgctcg aggggagtta cggtggatcg gaccaccacg   7740
ccgcgcgagc ccaaagtcca gatgtccgcg cgcggcggtc ggagcttgat gacaacatcg   7800
cgcagatggg agctgtccat ggtctggagc tcccgcggcg tcaggtcagg cgggagctcc   7860
tgcaggttta cctcgcatag acgggtcagg cgcgggcta gatccaggtg atacctaatt    7920
tccaggggct ggttggtggc ggcgtcgatg gcttgcaaga ggccgcatcc ccgcggcgcg   7980
actacggtac cgcgcggcgg gcggtgggcc gcggggtgt ccttggatga tgcatctaaa    8040
agcggtgacg cgggcgagcc cccggaggta ggggggctc cggacccgcc gggagagggg    8100
gcaggggcac gtcggcgccg cgcgcggca ggagctggtg ctgcgcgcgt aggttgctgg    8160
cgaacgcgac gacgcggcgg ttgatctcct gaatctggcg cctctgcgtg aagacgacgg   8220
gcccggtgag cttgaacctg aaagagagtt cgacagaatc aatttcggtg tcgttgacgg   8280
cggcctggcg caaaatctcc tgcacgtctc ctgagttgtc ttgataggcg atctcggcca   8340
tgaactgctc gatctcttcc tcctggagat ctccgcgtcc ggctcgctcc acggtggcgg   8400
cgaggtcgtt ggaaatgcgg gccatgagct gcgagaaggc gttgaggcct ccctcgttcc   8460
agacgcggct gtagaccacg ccccttcgg catcgcgggc gcgcatgacc acctgcgcga    8520
gattgagctc cacgtgccgg gcgaagacgg cgtagtttcg caggcgctga agaggtagt    8580 tgagggtggt ggcggtgtgt tctgccacga agaagtacat aacccagcgt cgcaacgtgg   8640
attcgttgat aattgttgtg taggtactcc gccgccgagg gacctgagcg agtccgcatc   8700
gaccggatcg gaaaacctct cgagaaaggc gtctaaccag tcacagtcgc aaggtaggct   8760
gagcaccgtg gcgggcggca gcgggcggcg gtcggggttg tttctggcgg aggtgctgct   8820
gatgatgtaa ttaaagtagg cggtcttgag acggcggatg gtcgacagaa gcaccatgtc   8880
cttgggtccg gcctgctgaa tgcgcaggcg gtcggccatg ccccaggctt cgttttgaca   8940
tcggcgcagg tctttgtagt agtcttgcat gagcctttct accggcactt cttcttctcc   9000
ttcctcttgt cctgcatctc ttgcatctat cgctgcggcg gcggcggagt ttggccgtag   9060
gtggcgccct cttcctccca tgcgtgtgac cccgaagccc ctcatcggct gaagcagggc   9120
taggtcggcg acaacgcgct cggctaatat ggcctgctgc acctgcgtga gggtagactg   9180
gaagtcatcc atgtccacaa agcggtggta tgcgcccgtg ttgatggtgt aagtgcagtt   9240
ggccataacg gaccagttaa cggtctggtg accggctgc gagagctcgg tgtacctgag    9300
acgcgagtaa gccctcgagt caaatacgta gtcgttgcaa gtccgcacca ggtactggta   9360
tcccaccaaa aagtgcggcg gcggctggcg gtagagggc cagcgtaggg tggccggggc    9420 tccggggcg agatcttcca acataaggcg atgatatccg tagatgtacc tggacatcca   9480
ggtgatgccg gcgcggtgg tggaggcgcg cggaaagtcg cggacgcggt tccagatgtt    9540
```

```
gcgcagcggc aaaaagtgct ccatggtcgg gacgctctgg ccggtcaggc gcgcgcaatc   9600
gttgacgctc tagcgtgcaa aaggagagcc tgtaagcggg cactcttccg tggtctggtg   9660
gataaattcg caagggtatc atggcggacg accggggttc gagccccgta tccggccgtc   9720
cgccgtgatc catgcggtta ccgcccgcgt gtcgaaccca ggtgtgcgac gtcagacaac   9780
gggggagtgc tccttttggc ttccttccag gcgcggcggc tgctgcgcta gcttttttgg   9840
ccactggccg cgcgcagcgt aagcggttag gctggaaagc gaaagcatta agtggctcgc   9900
tccctgtagc cggagggtta ttttccaagg gttgagtcgc gggaccccg gttcgagtct   9960 cggaccggcc ggactgcggc gaacgggggt ttgcctcccc gtcatgcaag accccgcttg  10020
caaattcctc cggaaacagg gacgagcccc ttttttgctt ttcccagatg catccggtgc  10080
tgcggcagat gcgccccct cctcagcagc ggcaagagca agagcagcgg cagacatgca  10140 ggcaccctc ccctcctcct accgcgtcag gagggcgac atccgcggtt gacgcggcag  10200
cagatggtga ttacgaaccc ccgcggcgcc gggcccggca ctacctggac ttggaggagg  10260
gcgagggcct ggcgcggcta ggagcgccct ctcctgagcg gcacccaagg gtgcagctga  10320
agcgtgatac gcgtgaggcg tacgtgccgc ggcagaacct gtttcgcgac cgcgagggag  10380
aggagcccga ggagatgcgg gatcgaaagt tccacgcagg gcgcgagctg cggcatggcc  10440
tgaatcgcga gcggttgctg cgcgaggagg actttgagcc cgacgcgcga accgggatta  10500
gtcccgcgcg cgcacacgtg gcggccgccg acctggtaac cgcatacgag cagacggtga  10560
accaggagat taactttcaa aaaagcttta caaccacgt gcgtacgctt gtggcgcgcg  10620
aggaggtggc tataggactg atgcatctgt gggactttgt aagcgcgctg gagcaaaacc  10680
caaatagcaa gccgctcatg gcgcagctgt tccttatagt gcagcacagc agggacaacg  10740
aggcattcag ggatgcgctg ctaaacatag tagagcccga gggccgctgg ctgctcgatt  10800
tgataaacat cctgcagagc atagtggtgc aggagcgcag cttgagcctg gctgacaagg  10860
tggccgccat caactattcc atgcttagcc tgggcaagtt ttacgcccgc aagatatacc  10920 ataccccta cgttcccata gacaaggagg taaagatcga ggggttctac atgcgcatgg  10980
cgctgaaggt gcttaccttg agcgacgacc tgggcgttta tcgcaacgag cgcatccaca  11040
aggccgtgag cgtgagccgg cggcgcgagc tcagcgaccg cgagctgatg cacagcctgc  11100
aaagggccct ggctggcacg ggcagcggcg atagagaggc cgagtcctac tttgacgcgg  11160
gcgctgacct gcgctgggcc ccaagccgac gcgccctgga ggcagctggg gccggacctg  11220
ggctggcggt ggcacccgcg cgcgctggca acgtcggcgg cgtggaggaa tatgacgagg  11280
acgatgagta cgagccagag gacggcgagt actaagcggt gatgtttctg atcagatgat  11340
gcaagacgca acgacccgg cggtgcggc ggcgctgcag agccagccgt ccggccttaa  11400
ctccacggac gactggcgcc aggtcatgga ccgcatcatg tcgctgactg cgcgcaatcc  11460
tgacgcgttc cggcagcagc cgcaggccaa ccggctctcc gcaattctgg aagcggtggt  11520
cccggcgcgc gcaaacccca cgcacgagaa ggtgctggcg atcgtaaacg cgctggccga  11580
aaacagggcc atccgccccg acgaggccgg cctggtctac gacgcgctgc ttcagcgcgt  11640
ggctcgttac aacagcggca acgtgcagac caacctggac cggctggtgg gggatgtgcg  11700
cgaggccgtg gcgcagcgtg agcgcgcgca gcagcagggc aacctgggct ccatggttgc  11760
actaaacgcc ttcctgagta cacagcccgc caacgtgccg cggggacagg aggactacac  11820
caactttgtg agcgcactgc ggctaatggt gactgagaca ccgcaaagtg aggtgtacca  11880
```

-continued

```
gtctgggcca gactattttt tccagaccag tagacaaggc ctgcagaccg taaacctgag    11940
ccaggctttc aaaaacttgc aggggctgtg ggggtgcgg gctcccacag gcgaccgcgc    12000
gaccgtgtct agcttgctga cgcccaactc gcgcctgttg ctgctgctaa tagcgccctt    12060
cacggacagt ggcagcgtgt cccgggacac atacctaggt cacttgctga cactgtaccg    12120
cgaggccata ggtcaggcgc atgtggacga gcatactttc caggagatta caagtgtcag    12180
ccgcgcgctg gggcaggagg acacgggcag cctggaggca accctaaact acctgctgac    12240
caaccggcgg cagaagatcc cctcgttgca cagtttaaac agcgaggagg agcgcatttt    12300
gcgctacgtg cagcagagcg tgagccttaa cctgatgcgc gacggggtaa cgcccagcgt    12360
ggcgctggac atgaccgcgc gcaacatgga accgggcatg tatgcctcaa accggccgtt    12420
tatcaaccgc ctaatggact acttgcatcg cgcggccgcc gtgaaccccg agtatttcac    12480
caatgccatc ttgaacccgc actggctacc gcccctggt ttctacaccg ggggattcga    12540
ggtgcccgag ggtaacgatg gattcctctg ggacgacata gacgacagcg tgttttcccc    12600
gcaaccgcag accctgctag agttgcaaca gcgcgagcag gcagaggcgg cgctgcgaaa    12660
ggaaagcttc cgcaggccaa gcagcttgtc cgatctaggc gctgcggccc gcggtcaga    12720
tgctagtagc ccatttccaa gcttgatagg gtctcttacc agcactcgca ccacccgccc    12780
gcgcctgctg ggcgaggagg agtacctaaa caactcgctg ctgcagccgc agcgcgaaaa    12840
aaacctgcct ccggcatttc ccaacaacgg gatagagagc ctagtggaca agatgagtag    12900
atggaagacg tacgcgcagg agcacaggga cgtgccaggc ccgcgcccgc ccacccgtcg    12960
tcaaaggcac gaccgtcagc ggggtctggt gtgggaggac gatgactcgg cagacgacag    13020
cagcgtcctg gatttgggag ggagtggcaa cccgtttgcg caccttcgcc ccaggctggg    13080
gagaatgttt taaaaaaaaa aaagcatgat gcaaaataaa aaactcacca aggccatggc    13140
accgagcgtt ggttttcttg tattcccctt agtatgcggc gcgcggcgat gtatgaggaa    13200
ggtcctcctc cctcctacga gagtgtggtg agcgcggcgc cagtggcggc ggcgctgggt    13260
tctcccttcg atgctcccct ggacccgccg tttgtgcctc cgcggtacct gcggcctacc    13320
gggggagaa acagcatccg ttactctgag ttggcacccc tattcgacac cacccgtgtg    13380
tacctggtgg acaacaagtc aacggatgtg gcatccctga actaccagaa cgaccacagc    13440
aactttctga ccacggtcat tcaaaacaat gactacagcc ggggggaggc aagcacacag    13500
accatcaatc ttgacgaccg gtcgcactgg ggcggcgacc tgaaaaccat cctgcatacc    13560
aacatgccaa atgtgaacga gttcatgttt accaataagt ttaaggcgcg ggtgatggtg    13620
tcgcgcttgc ctactaagga caatcaggtg gagctgaaat acgagtgggt ggagttcacg    13680
ctgcccgagg gcaactactc cgagaccatg accatagacc ttatgaacaa cgcgatcgtg    13740
gagcactact tgaaagtggg cagacagaac ggggttctgg aaagcgacat cggggtaaag    13800
tttgacaccc gcaacttcag actggggttt gaccccgtca ctggtcttgt catgcctggg    13860
gtatatacaa acgaagcctt ccatccagac atcatttttgc tgccaggatg cggggtggac    13920
ttcacccaca gccgcctgag caacttgttg ggcatccgca gcggcaacc cttccaggag    13980
ggctttagga tcacctacga tgatctggag ggtggtaaca ttcccgcact gttggatgtg    14040
gacgcctacc aggcgagctt gaaagatgac accgaacagg gcggggtgg cgcaggcggc    14100
agcaacagca gtggcagcgg cgcggaagag aactccaacg cggcagccgc ggcaatgcag    14160
ccggtggagg acatgaacga tcatgccatt cgcggcgaca ccttgccac acgggctgag    14220
gagaagcgcg ctgaggccga agcagcggcc gaagctgccg cccccgctgc gcaacccgag    14280
```

```
gtcgagaagc ctcagaagaa accggtgatc aaaccccctga cagaggacag caagaaacgc    14340
agttacaacc taataagcaa tgacagcacc ttcacccagt accgcagctg gtaccttgca    14400
tacaactacg gcgaccctca gaccggaatc cgctcatgga ccctgctttg cactcctgac    14460
gtaacctgcg gctcggagca ggtctactgg tcgttgccag acatgatgca agaccccgtg    14520
accttccgct ccacgcgcca gatcagcaac tttccggtgg tgggcgccga gctgttgccc    14580
gtgcactcca agagcttcta caacgaccag gccgtctact cccaactcat ccgccagttt    14640
acctctctga cccacgtgtt caatcgcttt cccgagaacc agattttggc gcgcccgcca    14700 gccccccacca tcaccaccgt cagtgaaaac gttcctgctc tcacagatca cgggacgcta    14760
ccgctgcgca acagcatcgg aggagtccag cgagtgacca ttactgacgc cagacgccgc    14820 acctgccccct acgtttacaa ggccctgggc atagtctcgc cgcgcgtcct atcgagccgc    14880 acttttgag caagcatgtc catccttata tcgcccagca ataacacagg ctggggcctg    14940
cgcttcccaa gcaagatgtt tggcggggcc aagaagcgct ccgaccaaca cccagtgcgc    15000
gtgcgcgggc actaccgcgc ccctggggc gcgcacaaac gcggccgcac tgggcgcacc    15060
accgtcgatg acgccatcga cgcggtggtg gaggaggcgc gcaactacac gcccacgccg    15120
ccaccagtgt ccacagtgga cgcggccatt cagaccgtgg tgcgcggagc ccggcgctat    15180
gctaaaatga gagacggcg gaggcgcgta gcacgtcgcc accgccgccg acccggcact    15240
gccgcccaac gcgcggcggc ggccctgctt aaccgcgcac gtcgcaccgg ccgacgggcg    15300
gccatgcggg ccgctcgaag gctggccgcg ggtattgtca ctgtgccccc caggtccagg    15360
cgacgagcgg ccgccgcagc agccgcggcc attagtgcta tgactcaggg tcgcaggggc    15420
aacgtgtatt gggtgcgcga ctcggttagc ggcctgcgcg tgcccgtgcg cacccgcccc    15480
ccgcgcaact agattgcaag aaaaaactac ttagactcgt actgttgtat gtatccagcg    15540
gcggcggcgc gcaacgaagc tatgtccaag cgcaaaatca agaagagat gctccaggtc    15600 atcgcgccgg agatctatgg ccccccgaag aaggaagagc aggattacaa gccccgaaag    15660
ctaaagcggg tcaaaaagaa aaagaaagat gatgatgatg aacttgacga cgaggtggaa    15720
ctgctgcacg ctaccgcgcc caggcgacgg gtacagtgga aggtcgacg cgtaaaaacgt    15780 gttttgcgac ccggcaccac cgtagtcttt acgcccggtg agcgctccac ccgcacctac    15840
aagcgcgtgt atgatgaggt gtacggcgac gaggacctgc ttgagcaggc caacgagcgc    15900 ctcgggagt ttgcctacgg aaagcggcat aaggacatgc tggcgttgcc gctggacgag    15960
ggcaacccaa cacctagcct aaagcccgta acactgcagc aggtgctgcc cgcgcttgca    16020
ccgtccgaag aaaagcgcgg cctaaagcgc gagtctggtg acttggcacc caccgtgcag    16080
ctgatggtac ccaagcgcca gcgactggaa gatgtcttgg aaaaaatgac cgtggaacct    16140
gggctggagc ccgaggtccg cgtgcggcca atcaagcagg tggcgccggg actgggcgtg    16200
cagaccgtgg acgttcagat acccactacc agtagcacca gtattgccac cgccacagag    16260
ggcatggaga cacaaacgtc cccggttgcc tcagcggtgg cggatgccgc ggtgcaggcg    16320
gtcgctgcgg ccgcgtccaa gacctctacg gaggtgcaaa cggacccgtg atgtttcgc    16380 gtttcagccc ccggcgcccc gcgccgttcg aggaagtacg cgccgccag cgcgctactg    16440 cccgaatatg ccctacatcc ttccattgcg cctaccccg gctatcgtgg ctacacctac    16500
cgccccagaa gacgagcaac tacccgacgc cgaaccacca ctggaacccg ccgccgccgt    16560
cgccgtcgcc agcccgtgct ggcccccgatt tccgtgcgca gggtggctcg cgaaggaggc    16620
```

```
aggaccctgg tgctgccaac agcgcgctac caccccagca tcgtttaaaa gccggtcttt    16680
gtggttcttg cagatatggc cctcacctgc cgcctccgtt tcccggtgcc gggattccga    16740
ggaagaatgc accgtaggag gggcatggcc ggccacggcc tgacgggcgg catgcgtcgt    16800
gcgcaccacc ggcggcggcg cgcgtcgcac cgtcgcatgc gcggcggtat cctgcccctc    16860
cttattccac tgatcgccgc ggcgattggc gccgtgcccg gaattgcatc cgtggccttg    16920
caggcgcaga gacactgatt aaaaacaagt tgcatgtgga aaaatcaaaa taaaaagtct    16980
ggactctcac gctcgcttgg tcctgtaact attttgtaga atggaagaca tcaactttgc    17040
gtctctggcc ccgcgacacg gctcgcgccc gttcatggga aactggcaag atatcggcac    17100
cagcaatatg agcggtggcg cctttcagctg gggctcgctg tggagcggca ttaaaaattt    17160
cggttccacc gttaagaact atggcagcaa ggcctggaac agcagcacag gccagatgct    17220
gagggataag ttgaaagagc aaaatttcca acaaaaggtg gtagatggcc tggcctctgg    17280
cattagcggg gtggtggacc tggccaacca ggcagtgcaa aataagatta acagtaagct    17340
tgatccccgc cctcccgtag aggagcctcc accggccgtg gagacagtgt ctccagaggg    17400
gcgtggcgaa aagcgtccgc gccccgacag ggaagaaact ctggtgacgc aaatagacga    17460
gcctccctcg tacgaggagg cactaaagca aggcctgccc accacccgtc ccatcgcgcc    17520
catggctacc ggagtgctgg gccagcacac accgtaacg ctggacctgc ctccccccgc    17580
cgacacccag cagaaacctg tgctgccagg cccgaccgcc gttgttgtaa cccgtcctag    17640
ccgcgcgtcc ctgcgccgcg ccgccagcgg tccgcgatcg ttgcggcccg tagccagtgg    17700
caactggcaa agcacactga acagcatcgt gggtctgggg gtgcaatccc tgaagcgccg    17760
acgatgcttc tgatagctaa cgtgtcgtat gtgtgtcatg tatgcgtcca tgtcgccgcc    17820
agaggagctg ctgagccgcc gcgcgcccgc tttccaagat ggctacccct tcgatgatgc    17880
cgcagtggtc ttacatgcac atctcgggcc aggacgcctc ggagtacctg agccccgggc    17940
tggtgcagtt tgcccgcgcc accgagacgt acttcagcct gaataacaag tttagaaacc    18000
ccacggtggc gcctacgcac gacgtgacca cagaccggtc ccagcgtttg acgctgcggt    18060
tcatccctgt ggaccgtgag gatactgcgt actcgtacaa ggcgcggttc accctagctg    18120
tgggtgataa ccgtgtgctg gacatggctt ccacgtactt tgacatccgc ggcgtgctgg    18180
acaggggccc tactttttaag ccctactctg gcactgccta caacgccctg gctcccaagg    18240
gtgccccaaa tccttgcgaa tgggatgaag ctgctactgc tcttgaaata aacctagaag    18300
aagaggacga tgacaacgaa gacgaagtag acgagcaagc tgagcagcaa aaaactcacg    18360
tatttgggca ggcgccttat tctggtataa atattacaaa ggagggtatt caaataggtg    18420
tcgaaggtca aacacctaaa tatgccgata aaacatttca acctgaacct caaataggag    18480
aatctcagtg gtacgaaaca gaaattaatc atgcagctgg gagagtccta aaaaagacta    18540
ccccaatgaa accatgttac ggttcatatg caaaacccac aaatgaaaat ggagggcaag    18600
gcattcttgt aaagcaacaa aatggaaagc tagaaagtca agtggaaatg caattttttct    18660 caactactga ggcagccgca ggcaatggtg ataacttgac tcctaaagtg gtattgtaca    18720
gtgaagatgt agatatagaa accccagaca ctcatatttc ttacatgccc actattaagg    18780
aaggtaactc acgagaacta atgggccaac aatctatgcc caacaggcct aattacattg    18840 ctttttaggga caattttatt ggtctaatgt attacaacag cacgggtaat atgggtgttc    18900
tggcgggcca agcatcgcag ttgaatgctg ttgtagattt gcaagacaga aacacagagc    18960
tttcatacca gcttttgctt gattccattg gtgatagaac caggtacttt tctatgtgga    19020
```

```
atcaggctgt tgacagctat gatccagatg ttagaattat tgaaaatcat ggaactgaag   19080
atgaacttcc aaattactgc tttccactgg gaggtgtgat taatacagag actcttacca   19140
aggtaaaacc taaaacaggt caggaaaatg gatgggaaaa agatgctaca gaattttcag   19200
ataaaaatga aataagagtt ggaaataatt ttgccatgga aatcaatcta aatgccaacc   19260
tgtggagaaa tttcctgtac tccaacatag cgctgtattt gcccgacaag ctaaagtaca   19320
gtccttccaa cgtaaaaatt tctgataacc caaacaccta cgactacatg aacaagcgag   19380
tggtggctcc cgggctagtg gactgctaca ttaaccttgg agcacgctgg tcccttgact   19440
atatggacaa cgtcaaccca tttaaccacc accgcaatgc tggcctgcgc taccgctcaa   19500
tgttgctggg caatggtcgc tatgtgccct ccacatcca ggtgcctcag aagttctttg    19560
ccattaaaaa cctccttctc ctgccgggct catacaccta cgagtggaac ttcaggaagg   19620
atgttaacat ggttctgcag agctccctag gaaatgacct aagggttgac ggagccagca   19680
ttaagtttga tagcatttgc ctttacgcca ccttcttccc catggcccac aacaccgcct   19740
ccacgcttga ggccatgctt agaaacgaca ccaacgacca gtcctttaac gactatctct   19800
ccgccgccaa catgctctac cctatacccg ccaacgctac caacgtgccc atatccatcc   19860
cctcccgcaa ctgggcggct ttccgcggct gggccttcac gcgccttaag actaaggaaa   19920
ccccatcact gggctcgggc tacgacccct attacaccta ctctggctct atacactacc   19980
tagatggaac cttttacctc aaccacacct ttaagaaggt ggccattacc tttgactctt   20040
ctgtcagctg gcctggcaat gaccgcctgc ttacccccaa cgagtttgaa attaagcgct   20100
cagttgacgg ggagggttac aacgttgccc agtgtaacat gaccaaagac tggttcctgg   20160
tacaaatgct agctaactat aacattggct accagggctt ctatatccca gagagctaca   20220
aggaccgcat gtactccttc tttagaaact tccagcccat gagccgtcag gtggtggatg   20280
atactaaata caaggactac caacaggtgg gcatcctaca ccaacacaac aactctggat   20340
ttgttggcta ccttgccccc accatgcgcg aaggacaggc ctaccctgct aacttcccct   20400
atccgcttat aggcaagacc gcagttgaca gcattaccca gaaaaagttt ctttgcgatc   20460
gcaccctttg gcgcatccca ttctccagta actttatgtc catgggcgca ctcacagacc   20520
tgggccaaaa ccttctctac gccaactccg cccacgcgct agacatgact tttgaggtgg   20580
atcccatgga cgagcccacc cttctttatg ttttgtttga agtctttgac gtggtccgtg   20640
tgcaccagcc gcaccgcggc gtcatcgaaa ccgtgtacct gcgcacgccc ttctcggccg   20700
gcaacgccac aacataaaga agcaagcaac atcaacaaca gctgccgcca tgggctccag   20760
tgagcaggaa ctgaaagcca ttgtcaaaga tcttggttgt gggccatatt ttttgggcac   20820
ctatgacaag cgctttccag gctttgtttc tccacacaag ctcgcctgcg ccatagtcaa   20880
tacggccggt cgcgagactg ggggcgtaca ctggatggcc tttgcctgga acccgcactc   20940
aaaaacatgc tacctctttg agccctttgg cttttctgac cagcgactca agcaggttta   21000
ccagtttgag tacgagtcac tcctgcgccg tagcgccatt gcttcttccc ccgaccgctg   21060
tataacgctg gaaagtccca cccaaagcgt acaggggccc aactcggccg cctgtggact   21120
attctgctgc atgtttctcc acgcctttgc caactggccc caaactccca tggatcacaa   21180
ccccaccatg aaccttatta ccggggtacc caactccatg ctcaacagtc cccaggtaca   21240
gcccaccctg cgtcgcaacc aggaacagct ctacagcttc ctggagcgcc actcgcccta   21300
cttccgcagc cacagtgcgc agattaggag cgccacttct ttttgtcact tgaaaaacat   21360
```

```
gtaaaaataa tgtactagag acactttcaa taaaggcaaa tgcttttatt tgtacactct   21420
cgggtgatta tttaccccca cccttgccgt ctgcgccgtt taaaaatcaa aggggttctg   21480
ccgcgcatcg ctatgcgcca ctggcaggga cacgttgcga tactggtgtt tagtgctcca   21540
cttaaactca ggcacaacca tccgcggcag ctcggtgaag ttttcactcc acaggctgcg   21600
caccatcacc aacgcgttta gcaggtcggg cgccgatatc ttgaagtcgc agttggggcc   21660
tccgccctgc gcgcgcgagt tgcgatacac agggttgcag cactggaaca ctatcagcgc   21720
cgggtggtgc acgctggcca gcacgctctt gtcggagatc agatccgcgt ccaggtcctc   21780
cgcgttgctc agggcgaacg gagtcaactt tggtagctgc cttcccaaaa agggcgcgtg   21840
cccaggcttt gagttgcact cgcaccgtag tggcatcaaa aggtgaccgt gcccggtctg   21900
ggcgttagga tacagcgcct gcataaaagc cttgatctgc ttaaaagcca cctgagcctt   21960
tgcgccttca gagaagaaca tgccgcaaga cttgccggaa aactgattgg ccggacaggc   22020
cgcgtcgtgc acgcagcacc ttgcgtcggt gttggagatc tgcaccacat ttcggcccca   22080
ccggttcttc acgatcttgg ccttgctaga ctgctccttc agcgcgcgct gcccgttttc   22140
gctcgtcaca tccatttcaa tcacgtgctc cttatttatc ataatgcttc cgtgtagaca   22200
cttaagctcg ccttcgatct cagcgcagcg gtgcagccac aacgcgcagc ccgtgggctc   22260
gtgatgcttg taggtcacct ctgcaaacga ctgcaggtac gcctgcagga atcgccccat   22320
catcgtcaca aaggtcttgt tgctggtgaa ggtcagctgc aacccgcggt gctcctcgtt   22380
cagccaggtc ttgcatacgg ccgccagagc ttccacttgg tcaggcagta gtttgaagtt   22440
cgcctttaga tcgttatcca cgtggtactt gtccatcagc gcgcgcgcag cctccatgcc   22500
cttctcccac gcagacacga tcggcacact cagcgggttc atcaccgtaa tttcactttc   22560
cgcttcgctg ggctcttcct cttcctcttg cgtccgcata ccacgcgcca ctgggtcgtc   22620
ttcattcagc cgccgcactg tgcgcttacc tcctttgcca tgcttgatta gcaccggtgg   22680
gttgctgaaa cccaccattt gtagcgccac atcttctctt tcttcctcgc tgtccacgat   22740
tacctctggt gatggcgggc gctcgggctt gggagaaggg cgcttctttt tcttcttggg   22800
cgcaatggcc aaatccgccg ccgaggtcga tggccgcggg ctgggtgtgc gcggcaccag   22860
cgcgtcttgt gatgagtctt cctcgtcctc ggactcgata cgccgcctca tccgcttttt   22920
tgggggcgcc cggggaggcg gcggcgacgg ggacggggac gacacgtcct ccatggttgg   22980
gggacgtcgc gccgcaccgc gtccgcgctc ggggtggtt tcgcgctgct cctcttcccg   23040
actggccatt tccttctcct ataggcagaa aaagatcatg gagtcagtcg agaagaagga   23100
cagcctaacc gcccctctg agttcgccac caccgcctcc accgatgccg ccaacgcgcc   23160
taccaccttc cccgtcgagg cacccccgct tgaggaggag gaagtgatta tcgagcagga   23220
cccaggtttt gtaagcgaag acgacgagga ccgctcagta ccaacagagg ataaaaagca   23280
agaccaggac aacgcagagg caaacgagga acaagtcggg cgggggggacg aaaggcatgg   23340 cgactaccta gatgtgggag acgacgtgct gttgaagcat ctgcagcgcc agtgcgccat   23400
tatctgcgac gcgttgcaag agcgcagcga tgtgcccctc gccatagcgg atgtcagcct   23460
tgcctacgaa cgccacctat tctcaccgcg cgtaccccc aaacgccaag aaaacggcac   23520
atgcgagccc aacccgcgcc tcaacttcta ccccgtatt gccgtgccag aggtgcttgc   23580
cacctatcac atctttttcc aaaactgcaa gataccccta tcctgccgtg ccaaccgcag   23640
ccgagcggac aagcagctgg ccttgcggca gggcgctgtc atacctgata tcgcctcgct   23700
caacgaagtg ccaaaaatct ttgagggtct tggacgcgac gagaagcgcg cggcaaacgc   23760
```

```
tctgcaacag gaaaacagcg aaaatgaaag tcactctgga gtgttggtgg aactcgaggg    23820
tgacaacgcg cgcctagccg tactaaaacg cagcatcgag gtcacccact ttgcctaccc    23880
ggcacttaac ctacccccca aggtcatgag cacagtcatg agtgagctga tcgtgcgccg    23940
tgcgcagccc ctggagaggg atgcaaattt gcaagaacaa acagaggagg cctacccgc    24000 agttggcgac gagcagctag cgcgctggct tcaaacgcgc gagcctgccg acttggagga    24060
gcgacgcaaa ctaatgatgg ccgcagtgct cgttaccgtg gagcttgagt gcatgcagcg    24120
gttctttgct gacccggaga tgcagcgcaa gctagaggaa acattgcact acacctttcg    24180
acagggctac gtacgccagg cctgcaagat ctccaacgtg gagctctgca acctggtctc    24240
ctaccttgga attttgcacg aaaaccgcct tgggcaaaac gtgcttcatt ccacgctcaa    24300
gggcgaggcg cgccgcgact acgtccgcga ctgcgtttac ttatttctat gctacacctg    24360
gcagacggcc atgggcgttt ggcagcagtg cttggaggag tgcaacctca aggagctgca    24420
gaaactgcta aagcaaaact tgaaggacct atggacggcc ttcaacgagc gctccgtggc    24480
cgcgcacctg gcggacatca ttttcccccga acgcctgctt aaaaccctgc aacagggtct    24540 gccagcttc accagtcaaa gcatgttgca gaactttagg aactttatcc tagagcgctc    24600
aggaatcttg cccgccacct gctgtgcact tcctagcgac tttgtgccca ttaagtaccg    24660
cgaatgccct ccgccgcttt ggggccactg ctaccttctg cagctagcca actaccttgc    24720
ctaccactct gacataatgg aagacgtgag cggtgacggt ctactggagt gtcactgtcg    24780
ctgcaaccta tgcaccccgc accgctccct ggtttgcaat tcgcagctgc ttaacgaaag    24840
tcaaattatc ggtacctttg agctgcaggg tccctcgcct gacgaaaagt ccgcggctcc    24900
ggggttgaaa ctcactccgg ggctgtggac gtcggcttac cttcgcaaat ttgtacctga    24960
ggactaccac gcccacgaga ttaggttcta cgaagaccaa tcccgcccgc ctaatgcgga    25020
gcttaccgcc tgcgtcatta cccagggcca cattcttggc caattgcaag ccatcaacaa    25080
agcccgccaa gagtttctgc tacgaaaggg acgggggggtt tacttggacc cccagtccgg    25140
cgaggagctc aacccaatcc ccccgccgcc gcagccctat cagcagcagc cgcgggccct    25200
tgcttcccag gatggcaccc aaaaagaagc tgcagctgcc gccgccaccc acggacgagg    25260
aggaatactg ggacagtcag gcagaggagg ttttggacga ggaggaggag gacatgatgg    25320
aagactggga gagcctagac gaggaagctt ccgaggtcga gaggtgtca gacgaaacac    25380 cgtcacccctc ggtcgcattc ccctcgccgg cgccccagaa atcggcaacc ggttccagca    25440
tggctacaac ctccgctcct caggcgccgc cggcactgcc cgttcgccga cccaaccgta    25500
gatgggacac cactggaacc agggccggta agtccaagca gccgccgccg ttagcccaag    25560
agcaacaaca gcgccaaggc taccgctcat ggcgcgggca caagaacgcc atagttgctt    25620
gcttgcaaga ctgtgggggc aacatctcct tcgcccgccg cttcttctc taccatcacg    25680 gcgtggcctt cccccgtaac atcctgcatt actaccgtca tctctacagc ccatactgca    25740
ccggcggcag cggcagcaac agcagcggcc acacagaagc aaaggcgacc ggatagcaag    25800
actctgacaa agcccaagaa atccacagcg gcggcagcag caggaggagg agcgctgcgt    25860
ctggcgccca acgaacccgt atcgacccgc gagcttagaa acaggatttt tcccactctg    25920
tatgctatat ttcaacagag caggggccaa gaacaagagc tgaaaataaa aaacaggtct    25980
ctgcgatccc tcacccgcag ctgcctgtat cacaaaagcg aagatcagct tcggcgcacg    26040
ctggaagacg cggaggctct cttcagtaaa tactgcgcgc tgactcttaa ggactagttt    26100
```

```
cgcgcccttt ctcaaattta agcgcgaaaa ctacgtcatc tccagcggcc acacccggcg    26160
ccagcacctg ttgtcagcgc cattatgagc aaggaaattc ccacgcccta catgtggagt    26220
taccagccac aaatgggact tgcggctgga gctgcccaag actactcaac ccgaataaac    26280
tacatgagcg cgggacccca catgatatcc cgggtcaacg gaatacgcgc ccaccgaaac    26340
cgaattctcc tggaacaggc ggctattacc accacacctc gtaataacct taatccccgt    26400
agttggcccg ctgccctggt gtaccaggaa agtcccgctc ccaccactgt ggtacttccc    26460
agagacgccc aggccgaagt tcagatgact aactcagggg cgcagcttgc gggcggcttt    26520
cgtcacaggg tgcggtcgcc cgggcagggt ataactcacc tgacaatcag agggcgaggt    26580
attcagctca acgacgagtc ggtgagctcc tcgcttggtc tccgtccgga cgggacattt    26640
cagatcggcg gcgccggccg ctcttcattc acgcctcgtc aggcaatcct aactctgcag    26700
acctcgtcct ctgagccgcg ctctggaggc attggaactc tgcaatttat tgaggagttt    26760
gtgccatcgg tctactttaa ccccttctcg ggacctcccg gccactatcc ggatcaattt    26820
attcctaact ttgacgcggt aaaggactcg gcggacggct acgactgaat gttaagtgga    26880
gaggcagagc aactgcgcct gaaacacctg gtccactgtc gccgccacaa gtgctttgcc    26940
cgcgactccg gtgagttttg ctactttgaa ttgcccgagg atcatatcga gggcccggcg    27000
cacggcgtcc ggcttaccgc ccagggagag cttgcccgta gcctgattcg ggagtttacc    27060
cagcgccccc tgctagttga gcgggacagg ggaccctgtg ttctcactgt gatttgcaac    27120
tgtcctaacc ctggattaca tcaagatcct ctagttaatg tcaggtcgcc taagtcgatt    27180
aactagagta cccggggatc ttattccctt taactaataa aaaaaaataa taaagcatca    27240
cttacttaaa atcagttagc aaatttctgt ccagtttatt cagcagcacc tccttgccct    27300
cctcccagct ctggtattgc agcttcctcc tggctgcaaa cttctccac aatctaaatg    27360 gaatgtcagt ttcctcctgt tcctgtccat ccgcacccac tatcttcatg ttgttgcaga    27420
tgaagcgcgc aagaccgtct gaagatacct tcaaccccgt gtatccatat gacacggaaa    27480
ccggtcctcc aactgtgcct tttcttactc ctccctttgt atccccaat gggtttcaag    27540 agagtccccc tggggtactc tctttgcgcc tatccgaacc tctagttacc tccaatggca    27600
tgcttgcgct caaaatgggc aacggcctct ctctggacga ggccggcaac cttacctccc    27660
aaaatgtaac cactgtgagc ccacctctca aaaaaaccaa gtcaaacata aacctggaaa    27720
tatctgcacc cctcacagtt acctcagaag ccctaactgt ggctgccgcc gcacctctaa    27780
tggtcgcggg caacacactc accatgcaat cacaggcccc gctaaccgtg cacgactcca    27840
aacttagcat tgccacccaa ggacccctca cagtgtcaga aggaaagcta gccctgcaaa    27900
catcaggccc cctcaccacc accgatagca gtaccctta c tatcactgcc tcacccctc    27960 taactactgc cactggtagc ttgggcattg acttgaaaga gcccatttat acacaaaatg    28020
gaaaactagg actaaagtac ggggctcctt tgcatgtaac agacgaccta aacactttga    28080
ccgtagcaac tggtccaggt gtgactatta ataatacttc cttgcaaact aaagttactg    28140
gagccttggg ttttgattca caaggcaata tgcaacttaa tgtagcagga ggactaagga    28200
ttgattctca aaacagacgc cttatacttg atgttagtta ccgtttgat gctcaaaacc    28260 aactaaatct aagactagga cagggccctc tttttataaa ctcagcccac aacttggata    28320
ttaactacaa caaaggcctt tacttgttta cagcttcaaa caattccaaa agcttgagg    28380 ttaacctaag cactgccaag gggttgatgt ttgacgctac agcctagcc attaatgcag    28440 gagatgggct tgaatttggt tcacctaatg caccaaacac aaatcccctc aaaacaaaaa    28500
```

```
ttggccatgg cctagaattt gattcaaaca aggctatggt tcctaaacta ggaactggcc    28560
ttagttttga cagcacaggt gccattacag taggaaacaa aaataatgat aagctaactt    28620
tgtggaccac accagctcca tctcctaact gtagactaaa tgcagagaaa gatgctaaac    28680
tcactttggt cttaacaaaa tgtggcagtc aaatacttgc tacagtttca gttttggctg    28740
ttaaaggcag tttggctcca atatctggaa cagttcaaag tgctcatctt attataagat    28800
ttgacgaaaa tggagtgcta ctaaacaatt ccttcctgga cccagaatat tggaacttta    28860
gaaatggaga tcttactgaa ggcacagcct atacaaacgc tgttggattt atgcctaacc    28920
tatcagctta tccaaaatct cacgtaaaa ctgccaaaag taacattgtc agtcaagttt    28980
acttaaacgg agacaaaact aaacctgtaa cactaaccat tacactaaac ggtacacagg    29040
aaacaggaga cacaactcca agtgcatact ctatgtcatt tcatgggac tggtctggcc    29100 acaactacat taatgaaata tttgccacat cctcttacac ttttcatac attgcccaag    29160 aataaagaat cgtttgtgtt atgtttcaac gtgtttattt ttcaattgca gaaaatttca    29220 agtcatttt cattcagtag tatagcccca ccaccacata gcttatacag atcaccgtac    29280
cttaatcaaa ctcacagaac cctagtattc aacctgccac ctccctccca acacacagag    29340
tacacagtcc tttctccccg gctggcctta aaaagcatca tatcatgggt aacagacata    29400
ttcttaggtg ttatattcca cacggtttcc tgtcgagcca aacgctcatc agtgatatta    29460
ataaactccc cggcagctc acttaagttc atgtcgctgt ccagctgctg agccacaggc    29520
tgctgtccaa cttgcggttg cttaacgggc ggcgaaggag aagtccacgc ctacatgggg    29580
gtagagtcat aatcgtgcat caggataggg cggtggtgct gcagcagcgc gcgaataaac    29640
tgctgccgcc gccgctccgt cctgcaggaa tacaacatgg cagtggtctc ctcagcgatg    29700
attcgcaccg cccgcagcat aaggcgcctt gtcctccggg cacagcagcg caccctgatc    29760
tcacttaaat cagcacagta actgcagcac agcaccacaa tattgttcaa atcccacag    29820 tgcaaggcgc tgtatccaaa gctcatggcg gggaccacag aacccacgtg gccatcatac    29880
cacaagcgca ggtagattaa gtggcgaccc ctcataaaca cgctggacat aaacattacc    29940
tcttttggca tgttgtaatt caccacctcc cggtaccata taaacctctg attaaacatg    30000
gcgccatcca ccaccatcct aaaccagctg gccaaaacct gcccgccggc tatacactgc    30060
agggaaccgg gactggaaca atgacagtgg agagcccagg actcgtaacc atggatcatc    30120
atgctcgtca tgatatcaat gttggcacaa cacaggcaca cgtgcataca cttcctcagg    30180
attacaagct cctcccgcgt tagaaccata tcccagggaa caacccattc ctgaatcagc    30240
gtaaatccca cactgcaggg aagacctcgc acgtaactca cgttgtgcat tgtcaaagtg    30300
ttacattcgg gcagcagcgg atgatcctcc agtatggtag cgcgggtttc tgtctcaaaa    30360
ggaggtagac gatccctact gtacggagtg cgccgagaca accgagatcg tgttggtcgt    30420
agtgtcatgc caaatggaac gccggacgta gtcatatttc ctgaagcaaa accaggtgcg    30480
ggcgtgacaa acagatctgc gtctccggtc tcgccgctta gatcgctctg tgtagtagtt    30540
gtagtatatc cactctctca aagcatccag gcgcccctg gcttcgggtt ctatgtaaac    30600
tccttcatgc gccgctgccc tgataacatc caccaccgca gaataagcca cacccagcca    30660
acctacacat tcgttctgcg agtcacacac gggaggagcg ggaagagctg aagaaccat    30720 gtttttttt ttattccaaa agattatcca aaacctcaaa atgaagatct attaagtgaa    30780
cgcgctcccc tccggtggcg tggtcaaact ctacagccaa agaacagata atggcatttg    30840
```

```
taagatgttg cacaatggct tccaaaaggc aaacggccct cacgtccaag tggacgtaaa    30900
ggctaaaccc ttcagggtga atctcctcta taaacattcc agcaccttca accatgccca    30960
aataattctc atctcgccac cttctcaata tatctctaag caaatcccga atattaagtc    31020
cggccattgt aaaatctgc tccagagcgc cctccacctt cagcctcaag cagcgaatca    31080
tgattgcaaa aattcaggtt cctcacagac ctgtataaga ttcaaaagcg gaacattaac    31140
aaaaataccg cgatcccgta ggtcccttcg cagggccagc tgaacataat cgtgcaggtc    31200
tgcacggacc agcgcggcca cttccccgcc aggaaccatg acaaaagaac ccacactgat    31260
tatgacacgc atactcggag ctatgctaac cagcgtagcc ccgatgtaag cttgttgcat    31320
gggcggcgat ataaaatgca aggtgctgct caaaaaatca ggcaaagcct cgcgcaaaaa    31380
agaaagcaca tcgtagtcat gctcatgcag ataaaggcag gtaagctccg gaaccaccac    31440
agaaaaagac accattttc tctcaaacat gtctgcgggt ttctgcataa acacaaaata    31500
aaataacaaa aaacattta aacattagaa gcctgtctta caacaggaaa acaacccctt    31560
ataagcataa gacggactac ggccatgccg gcgtgaccgt aaaaaaactg gtcaccgtga    31620
ttaaaaagca ccaccgacag ctcctcggtc atgtccggag tcataatgta agactcggta    31680
aacacatcag gttgattcac atcggtcagt gctaaaaagc gaccgaaata gcccggggga    31740
atacataccc gcaggcgtag agacaacatt acagccccca taggaggtat aacaaaatta    31800
ataggagaga aaaacacata aacacctgaa aaaccctcct gcctaggcaa aatagcaccc    31860
tcccgctcca gaacaacata cagcgcttcc acagcggcag ccataacagt cagccttacc    31920
agtaaaaaag aaaacctatt aaaaaaacac cactcgacac ggcaccagct caatcagtca    31980
cagtgtaaaa aagggccaag tgcagagcga gtatatatag gactaaaaaa tgacgtaacg    32040
gttaaagtcc acaaaaaaca cccagaaaac cgcacgcgaa cctacgccca gaaacgaaag    32100
ccaaaaaacc cacaacttcc tcaaatcgtc acttccgttt tcccacgtta cgtcacttcc    32160
cattttaaga aaactacaat tcccaacaca tacaagttac tccgccctaa aacctacgtc    32220
acccgcccg ttcccacgcc ccgcgccacg tcacaaactc caccccctca ttatcatatt    32280
ggcttcaatc caaaataagg tatattattg atgat                              32315
```

<210> SEQ ID NO 3
<211> LENGTH: 9
<212> TYPE: PRT
<213> ORGANISM: Homo sapiens

<400> SEQUENCE: 3

Tyr Leu Ser Gly Ala Asn Leu Asn Leu
1               5

<210> SEQ ID NO 4
<211> LENGTH: 9
<212> TYPE: PRT
<213> ORGANISM: Homo sapiens

<400> SEQUENCE: 4

Tyr Leu Ser Gly Ala Asp Leu Asn Leu
1               5

<210> SEQ ID NO 5
<211> LENGTH: 1826
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

| | | | | | |
|---|---|---|---|---|---|
| cgctccacct | ctcaagcagc | cagcgcctgc | ctgaatctgt | tctgccccct | ccccacccat | 60 |
| ttcaccacca | ccatgacacc | gggcacccag | tctccttttct | tcctgctgct | gctcctcaca | 120 |
| gtgcttacag | ttgttacggg | ttctggtcat | gcaagctcta | ccccaggtgg | agaaaaggag | 180 |
| acttcggcta | cccagagaag | ttcagtgccc | agctctactg | agaagaatgc | tgtgagtatg | 240 |
| accagcagcg | tactctccag | ccacagcccc | ggttcaggct | cctccaccac | tcagggacag | 300 |
| gatgtcactc | tggccccggc | cacggaacca | gcttcaggtt | cagctgccac | ctggggacag | 360 |
| gatgtcacct | cggtcccagt | caccaggcca | gccctgggct | ccaccacccc | gccagcccac | 420 |
| gatgtcacct | cagccccgga | caacaagcca | gccccgggct | ccaccgcccc | ccagcccac | 480 |
| ggtgtcacct | cggccccgga | caccaggccg | gccccgggct | ccaccgcccc | ccagcccat | 540 |
| ggtgtcacct | cggccccgga | caacaggccc | gccttgggct | ccaccgcccc | tccagtccac | 600 |
| aatgtcacct | cggcctcagg | ctctgcatca | ggctcagctt | ctactctggt | gcacaacggc | 660 |
| acctctgcca | gggctaccac | aaccccagcc | agcaagagca | ctccattctc | aattcccagc | 720 |
| caccactctg | atactcctac | cacccttgcc | agccatagca | ccaagactga | tgccagtagc | 780 |
| actcaccata | gcacggtacc | tcctctcacc | tcctccaatc | acagcacttc | tccccagttg | 840 |
| tctactgggg | tctcttttctt | tttcctgtct | tttcacattt | caaacctcca | gtttaattcc | 900 |
| tctctggaag | atcccagcac | cgactactac | caagagctgc | agagagacat | ttctgaaatg | 960 |
| tttttgcaga | tttataaaca | aggggtttt | ctgggcctct | ccaatattaa | gttcaggcca | 1020 |
| ggatctgtgg | tggtacaatt | gactctggcc | ttccgagaag | gtaccatcaa | tgtccacgac | 1080 |
| gtggagacac | agttcaatca | gtataaaacg | gaagcagcct | ctcgatataa | cctgacgatc | 1140 |
| tcagacgtca | gcgtgagtga | tgtgccattt | cctttctctg | cccagtctgg | ggctggggtg | 1200 |
| ccaggctggg | gcatcgcgct | gctggtgctg | gtctgtgttc | tggttgcgct | ggccattgtc | 1260 |
| tatctcattg | ccttggctgt | ctgtcagtgc | cgccgaaaga | actacgggca | gctggacatc | 1320 |
| tttccagccc | gggataccta | ccatcctatg | agcgagtacc | ccacctacca | cacccatggg | 1380 |
| cgctatgtgc | cccctagcag | taccgatcgt | agcccctatg | agaaggtttc | tgcaggtaat | 1440 |
| ggtggcagca | gcctctctta | cacaaaccca | gcagtggcag | ccacttctgc | caacttgtag | 1500 |
| gggcacgtcg | cccgctgagc | tgagtggcca | gccagtgcca | ttccactcca | ctcaggttct | 1560 |
| tcagggccag | agccctgca | ccctgtttgg | gctggtgagc | tgggagttca | ggtgggctgc | 1620 |
| tcacagcctc | cttcagaggc | cccaccaatt | tctcggacac | ttctcagtgt | gtggaagctc | 1680 |
| atgtgggccc | ctgagggctc | atgcctggga | agtgttgtgg | tgggggctcc | caggaggact | 1740 |
| ggcccagaga | gccctgagat | agcggggatc | ctgaactgga | ctgaataaaa | cgtggtctcc | 1800 |
| cactgcgcca | aaaaaaaaaa | aaaaaa | | | | 1826 |

<210> SEQ ID NO 6
<211> LENGTH: 1826
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 6
cgctccacct ctcaagcagc cagcgcctgc ctgaatctgt tctgccccct ccccacccat    60

| | |
|---|---|
| ttcaccacca ccatgacacc gggcacccag tctcctttct tcctgctgct gctcctcaca | 120 |
| gtgcttacag ttgttacggg ttctggtcat gcaagctcta ccccaggtgg agaaaaggag | 180 |
| acttcggcta cccagagaag ttcagtgccc agctctactg agaagaatgc tgtgagtatg | 240 |
| accagcagcg tactctccag ccacagcccc ggttcaggct cctccaccac tcagggacag | 300 |
| gatgtcactc tggccccggc cacggaacca gcttcaggtt cagctgccct tggggacag | 360 |
| gatgtcacct cggtcccagt caccaggcca gccctgggct ccaccacccc gccagcccac | 420 |
| gatgtcacct cagccccgga caacaagcca gccccgggct ccaccgcccc ccagcccac | 480 |
| ggtgtcacct cgtatcttga caccaggccg ccccgggttt atcttgcccc ccagcccat | 540 |
| ggtgtcacct cggccccgga caacaggccc gccttgggct ccaccgcccc tccagtccac | 600 |
| aatgtcacct cggcctcagg ctctgcatca ggctcagctt ctactctggt gcacaacggc | 660 |
| acctctgcca gggctaccac aaccccagcc agcaagagca ctccattctc aattcccagc | 720 |
| caccactctg atactcctac cacccttgcc agcatagca ccaagactga tgccagtagc | 780 |
| actcaccata gcacggtacc tcctctcacc tcctccaatc acagcacttc tccccagttg | 840 |
| tctactgggg tctcttttctt tttcctgtct tttcacattt caaacctcca gtttaattcc | 900 |
| tctctggaag atcccagcac cgactactac caagagctgc agagagacat ttctgaaatg | 960 |
| tttttgcaga tttataaaca agggggtttt ctgggcctct ccaatattaa gttcaggcca | 1020 |
| ggatctgtgg tggtacaatt gactctggcc ttccgagaag gtaccatcaa tgtccacgac | 1080 |
| gtggagacac agttcaatca gtataaaacg gaagcagcct ctcgatataa cctgacgatc | 1140 |
| tcagacgtca gcgtgagtga tgtgccattt cctttctctg cccagtctgg ggctggggtg | 1200 |
| ccaggctggg gcatcgcgct gctggtgctg gtctgtgttc tggtttatct ggccattgtc | 1260 |
| tatctcattg ccttggctgt cgctcaggtt cgccgaaaga actacgggca gctggacatc | 1320 |
| tttccagccc gggataaata ccatcctatg agcgagtacg ctctttacca cacccatggg | 1380 |
| cgctatgtgc ccctagcag tcttttccgt agccccatg agaaggtttc tgcaggtaat | 1440 |
| ggtggcagct atctctctta cacaaaccca gcagtggcag ccgcttctgc caacttgtag | 1500 |
| gggcacgtcg cccgctgagc tgagtggcca gccagtgcca ttccactcca ctcaggttct | 1560 |
| tcagggccag agccctgca ccctgtttgg gctggtgagc tgggagttca ggtgggctgc | 1620 |
| tcacagcctc cttcagaggc cccaccaatt tctcggacac ttctcagtgt gtggaagctc | 1680 |
| atgtgggccc ctgagggctc atgcctggga agtgttgtgg tgggggctcc caggaggact | 1740 |
| ggcccagaga gccctgagat agcgggatc ctgaactgga ctgaataaaa cgtggtctcc | 1800 |
| cactgcgcca aaaaaaaaaa aaaaaa | 1826 |

<210> SEQ ID NO 7
<211> LENGTH: 475
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Thr Pro Gly Thr Gln Ser Pro Phe Phe Leu Leu Leu Leu Thr
1               5                   10                  15

Val Leu Thr Val Val Thr Gly Ser Gly His Ala Ser Ser Thr Pro Gly
            20                  25                  30

Gly Glu Lys Glu Thr Ser Ala Thr Gln Arg Ser Ser Val Pro Ser Ser
        35                  40                  45

```
Thr Glu Lys Asn Ala Val Ser Met Thr Ser Ser Val Leu Ser Ser His
    50                  55                  60
Ser Pro Gly Ser Gly Ser Ser Thr Gln Gly Gln Asp Val Thr Leu
65                      70                  75                  80
Ala Pro Ala Thr Glu Pro Ala Ser Gly Ser Ala Ala Leu Trp Gly Gln
                85                  90                  95
Asp Val Thr Ser Val Pro Val Thr Arg Pro Ala Leu Gly Ser Thr Thr
            100                 105                 110
Pro Pro Ala His Asp Val Thr Ser Ala Pro Asp Asn Lys Pro Ala Pro
                115                 120                 125
Gly Ser Thr Ala Pro Pro Ala His Gly Val Thr Ser Tyr Leu Asp Thr
        130                 135                 140
Arg Pro Ala Pro Val Tyr Leu Ala Pro Pro Ala His Gly Val Thr Ser
145                 150                 155                 160
Ala Pro Asp Asn Arg Pro Ala Leu Gly Ser Thr Ala Pro Pro Val His
                165                 170                 175
Asn Val Thr Ser Ala Ser Gly Ser Ala Ser Gly Ser Ala Ser Thr Leu
            180                 185                 190
Val His Asn Gly Thr Ser Ala Arg Ala Thr Thr Thr Pro Ala Ser Lys
        195                 200                 205
Ser Thr Pro Phe Ser Ile Pro Ser His His Ser Asp Thr Pro Thr Thr
    210                 215                 220
Leu Ala Ser His Ser Thr Lys Thr Asp Ala Ser Ser Thr His His Ser
225                 230                 235                 240
Thr Val Pro Pro Leu Thr Ser Ser Asn His Ser Thr Ser Pro Gln Leu
                245                 250                 255
Ser Thr Gly Val Ser Phe Phe Phe Leu Ser Phe His Ile Ser Asn Leu
            260                 265                 270
Gln Phe Asn Ser Ser Leu Glu Asp Pro Ser Thr Asp Tyr Tyr Gln Glu
        275                 280                 285
Leu Gln Arg Asp Ile Ser Glu Met Phe Leu Gln Ile Tyr Lys Gln Gly
    290                 295                 300
Gly Phe Leu Gly Leu Ser Asn Ile Lys Phe Arg Pro Gly Ser Val Val
305                 310                 315                 320
Val Gln Leu Thr Leu Ala Phe Arg Glu Gly Thr Ile Asn Val His Asp
                325                 330                 335
Val Glu Thr Gln Phe Asn Gln Tyr Lys Thr Glu Ala Ala Ser Arg Tyr
            340                 345                 350
Asn Leu Thr Ile Ser Asp Val Ser Val Ser Asp Val Pro Phe Pro Phe
        355                 360                 365
Ser Ala Gln Ser Gly Ala Gly Val Pro Gly Trp Gly Ile Ala Leu Leu
    370                 375                 380
Val Leu Val Cys Val Leu Val Tyr Leu Ala Ile Val Tyr Leu Ile Ala
385                 390                 395                 400
Leu Ala Val Ala Gln Val Arg Arg Lys Asn Tyr Gly Gln Leu Asp Ile
                405                 410                 415
Phe Pro Ala Arg Asp Lys Tyr His Pro Met Ser Glu Tyr Ala Leu Tyr
            420                 425                 430
His Thr His Gly Arg Tyr Val Pro Pro Ser Ser Leu Phe Arg Ser Pro
        435                 440                 445
Tyr Glu Lys Val Ser Ala Gly Asn Gly Gly Ser Tyr Leu Ser Tyr Thr
    450                 455                 460
```

Asn Pro Ala Val Ala Ala Ala Ser Ala Asn Leu
465                 470                 475

<210> SEQ ID NO 8
<211> LENGTH: 32040
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

| | | | | | |
|---|---|---|---|---|---|
| catcatcaat | aatatacctt | attttggatt | gaagccaata | tgataatgag | ggggtggagt | 60 |
| ttgtgacgtg | gcgcggggcg | tgggaacggg | gcgggtgacg | tagtagtgtg | gcggaagtgt | 120 |
| gatgttgcaa | gtgtggcgga | acacatgtaa | gcgacggatg | tggcaaaagt | gacgttttg | 180 |
| gtgtgcgccg | gtgtacacag | gaagtgacaa | ttttcgcgcg | gttttaggcg | gatgttgtag | 240 |
| taaatttggg | cgtaaccgag | taagatttgg | ccattttcgc | gggaaaactg | aataagagga | 300 |
| agtgaaatct | gaataatttt | gtgttactca | tagcgcgtaa | tactgtaata | gtaatcaatt | 360 |
| acggggtcat | tagttcatag | cccatatatg | gagttccgcg | ttacataact | tacggtaaat | 420 |
| ggcccgcctg | gctgaccgcc | caacgacccc | cgcccattga | cgtcaataat | gacgtatgtt | 480 |
| cccatagtaa | cgccaatagg | gactttccat | tgacgtcaat | gggtggagta | tttacggtaa | 540 |
| actgcccact | tggcagtaca | tcaagtgtat | catatgccaa | gtacgccccc | tattgacgtc | 600 |
| aatgacggta | aatggcccgc | ctggcattat | gcccagtaca | tgaccttatg | ggactttcct | 660 |
| acttggcagt | acatctacgt | attagtcatc | gctattacca | tggtgatgcg | gttttggcag | 720 |
| tacatcaatg | ggcgtggata | gcggtttgac | tcacggggat | ttccaagtct | ccaccccatt | 780 |
| gacgtcaatg | ggagtttgtt | ttggcaccaa | aatcaacggg | actttccaaa | atgtcgtaac | 840 |
| aactccgccc | cattgacgca | aatgggcggt | aggcgtgtac | ggtgggaggt | ctatataagc | 900 |
| agagctggtt | tagtgaaccg | tcagatccgc | tagagatctg | gtaccgtcga | cgcggccgct | 960 |
| cgagcctaag | cttctagatg | catgctcgag | cggccgccag | tgtgatggat | atctgcagaa | 1020 |
| ttcgcccttg | ctcgctccac | ctctcaagca | gccagcgcct | gcctgaatct | gttctgcccc | 1080 |
| ctccccaccc | atttcaccac | caccatgaca | ccgggcaccc | agtctccttt | cttcctgctg | 1140 |
| ctgctcctca | cagtgcttac | agttgttacg | ggttctggtc | atgcaagctc | taccccaggt | 1200 |
| ggagaaaagg | agacttcggc | tacccagaga | agttcagtgc | ccagctctac | tgagaagaat | 1260 |
| gctgtgagta | tgaccagcag | cgtactctcc | agccacagcc | ccggttcagg | ctcctccacc | 1320 |
| actcagggac | aggatgtcac | tctggccccg | gccacggaac | cagcttcagg | ttcagctgcc | 1380 |
| cttttgggac | aggatgtcac | ctcggtccca | gtcaccaggc | cagccctggg | ctccaccacc | 1440 |
| ccgccagccc | acgatgtcac | ctcagccccg | gacaacaagc | cagccccggg | ctccaccgcc | 1500 |
| ccccagcccc | acgtgtcac | ctcgtatctt | gacaccaggc | cggccccggt | ttatcttgcc | 1560 |
| cccccagccc | atggtgtcac | ctcggccccg | gacaacaggc | ccgccttggg | ctccaccgcc | 1620 |
| cctccagtcc | acaatgtcac | ctcggcctca | ggctctgcat | caggctcagc | ttctactctg | 1680 |
| gtgcacaacg | gcacctctgc | cagggctacc | acaacccag | ccagcaagag | cactccattc | 1740 |
| tcaattccca | gccaccactc | tgatactcct | accacccttg | ccagccatag | caccaagact | 1800 |
| gatgccagta | gcactcacca | tagcacggta | cctcctctca | cctcctccaa | tcacagcact | 1860 |
| tctcccccagt | tgtctactgg | ggtctctttc | ttttcctgt | cttttcacat | ttcaaacctc | 1920 |
| cagtttaatt | cctctctgga | agatcccagc | accgactact | accaagagct | gcagagagac | 1980 |

```
atttctgaaa tgttttttgca gatttataaa caaggggggtt ttctgggcct ctccaatatt   2040
aagttcaggc caggatctgt ggtggtacaa ttgactctgg ccttccgaga aggtaccatc   2100
aatgtccacg acgtggagac acagttcaat cagtataaaa cggaagcagc ctctcgatat   2160
aacctgacga tctcagacgt cagcgtgagt gatgtgccat ttcctttctc tgcccagtct   2220
ggggctgggg tgccaggctg gggcatcgcg ctgctggtgc tggtctgtgt tctggtttat   2280
ctggccattg tctatctcat tgccttggct gtcgctcagg ttcgccgaaa gaactacggg   2340
cagctggaca tctttccagc ccgggataaa taccatccta tgagcgagta cgctctttac   2400
cacacccatg gcgctatgt gcccctagc agtcttttcc gtagcccta tgagaaggtt   2460 tctgcaggta atggtggcag ctatctctct tacacaaacc cagcagtggc agccgcttct   2520
gccaacttgt aggggcacgt cgcccgctga gctgagtggc cagccagtgc cattccactc   2580
cactcaggtt cttcagggcc agagccctg caccctgttt gggctggtga ctgggagtt   2640 caggtgggct gctcacagcc tccttcagag gccccaccaa tttctcggac acttctcagt   2700
gtgtggaagc tcatgtgggc ccctgagggc tcatgcctgg gaagtgttgt ggtgggggct   2760
cccaggagga ctggcccaga gagccctgag atagcgggga tcctgaactg gactgaataa   2820
aacgtggtct cccactgcgc caaaaaaaaa aaaaaaaacg atccaccgga tctagataac   2880
tgatcataat cagccatacc acatttgtag aggttttact tgctttaaaa aacctcccac   2940 acctcccct gaacctgaaa cataaaatga atgcaattgt tgttgttaac ttgtttattg   3000
cagcttataa tggttacaaa taagcaata gcatcacaaa tttcacaaat aaagcattt   3060 tttcactgca ttctagttgt ggtttgtcca aactcatcaa tgtatcttaa cgcggatctg   3120
gaaggtgctg aggtacgatg agacccgcac caggtgcaga ccctgcgagt gtggcggtaa   3180
acatattagg aaccagcctg tgatgctgga tgtgaccgag gagctgaggc ccgatcactt   3240
ggtgctggcc tgcacccgcg ctgagtttgg ctctagcgat gaagatacag attgaggtac   3300
tgaaatgtgt gggcgtggct taagggtggg aaagaatata taaggtgggg gtcttatgta   3360
gttttgtatc tgttttgcag cagccgccgc cgccatgagc accaactcgt ttgatgaag   3420 cattgtgagc tcatattga caacgcgcat gcccccatgg gccggggtgc gtcagaatgt   3480
gatgggctcc agcattgatg gtcgccccgt cctgcccgca aactctacta ccttgaccta   3540
cgagaccgtg tctggaacgc cgttggagac tgcagcctcc gccgccgctt cagccgctgc   3600
agccaccgcc cgcgggattg tgactgactt tgctttcctg agcccgcttg caagcagtgc   3660
agcttcccgt tcatccgccc gcgatgacaa gttgacggc ctttttggcac aattggattc   3720 tttgacccgg gaacttaatg tcgtttctca gcagctgttg gatctgcgcc agcaggtttc   3780
tgccctgaag gcttcctccc ctcccaatgc ggtttaaaac ataaataaaa aaccagactc   3840
tgtttggatt tggatcaagc aagtgtcttg ctgtctttat ttaggggttt tgcgcgcgcg   3900
gtaggcccgg gaccagcggt ctcggtcgtt gagggtcctg tgtatttttt ccaggacgtg   3960
gtaaaggtga ctctggatgt tcagatacat gggcataagc ccgtctctgg ggtggaggta   4020
gcaccactgc agagcttcat gctgcggggt ggtgttgtag atgatccagt cgtagcagga   4080
gcgctgggcg tggtgcctaa aaatgtcttt cagtagcaag ctgattgcca ggggcaggcc   4140
cttggtgtaa gtgtttacaa agcggttaag ctgggatggg tgcatacgtg gggatatgag   4200
atgcatcttg gactgtattt ttaggttggc tatgttccca gccatatccc tccgggggatt   4260 catgttgtgc agaaccacca gcacagtgta tccggtgcac ttgggaaatt tgtcatgtag   4320
```

```
cttagaagga aatgcgtgga agaacttgga gacgcccttg tgacctccaa gattttccat    4380
gcattcgtcc ataatgatgg caatgggccc acgggcggcg gcctgggcga agatatttct    4440
gggatcacta acgtcatagt tgtgttccag gatgagatcg tcataggcca ttttttacaaa   4500
gcgcgggcgg agggtgccag actgcggtat aatggttcca tccggcccag gggcgtagtt    4560
accctcacag atttgcattt cccacgcttt gagttcagat gggggggatca tgtctacctg   4620
cggggcgatg aagaaaacgg tttccggggt aggggagatc agctgggaag aaagcaggtt    4680
cctgagcagc tgcgacttac cgcagccggt gggcccgtaa atcacaccta ttaccggctg    4740
caactggtag ttaagagagc tgcagctgcc gtcatccctg agcaggggggg ccacttcgtt   4800
aagcatgtcc ctgactcgca tgttttccct gaccaaatcc gccagaaggc gctcgccgcc    4860
cagcgatagc agttcttgca aggaagcaaa gtttttcaac ggtttgagac cgtccgccgt    4920
aggcatgctt ttgagcgttt gaccaagcag ttccaggcgg tcccacagct cggtcacctg    4980
ctctacggca tctcgatcca gcatatctcc tcgtttcgcg ggttggggcg gctttcgctg    5040
tacggcagta gtcggtgctc gtccagacgg gccagggtca tgtctttcca cgggcgcagg   5100
gtcctcgtca gcgtagtctg ggtcacggtg aaggggtgcg ctccgggctg cgcgctggcc    5160
agggtgcgct tgaggctggt cctgctggtg ctgaagcgct gccggtcttc gccctgcgcg    5220
tcggccaggt agcatttgac catggtgtca tagtccagcc cctccgcggc gtggcccttg    5280
gcgcgcagct tgcccttgga ggaggcgccg cacgagggggc agtgcagact tttgagggcg   5340
tagagcttgg gcgcgagaaa taccgattcc ggggagtagg catccgcgcc gcaggccccg    5400
cagacggtct cgcattccac gagccaggtg agctctggcc gttcggggtc aaaaaccagg    5460
tttcccccat gcttttttgat gcgtttctta cctctggttt ccatgagccg gtgtccacgc   5520
tcggtgacga aaaggctgtc cgtgtccccg tatacagact tgagaggcct gtcctcgagc    5580
ggtgttccgc ggtcctcctc gtatagaaac tcggaccact ctgagacaaa ggctcgcgtc    5640
caggccagca cgaaggaggc taagtgggag gggtagcggt cgttgtccac tagggggtcc    5700
actcgctcca gggtgtgaag acacatgtcg ccctcttcgg catcaaggaa ggtgattggt    5760
ttgtaggtgt aggccacgtg accgggtgtt cctgaagggg ggctataaaa gggggtgggg   5820
gcgcgttcgt cctcactctc ttccgcatcg ctgtctgcga gggccagctg ttggggtgag    5880
tactccctct gaaaagcggg catgacttct gcgctaagat tgtcagtttc caaaaacgag    5940
gaggatttga tattcacctg gcccgcggtg atgcctttga gggtggccgc atccatctgg   6000
tcagaaaaga caatcttttt gttgtcaagc ttggtggcaa acgacccgta gagggcgttg    6060
gacagcaact ggcgatgga gcgcagggtt tggttttttgt cgcgatcggc gcgctccttg   6120
gccgcgatgt ttagctgcac gtattcgcgc gcaacgcacc gccattcggg aaagacggtg    6180
gtgcgctcgt cgggcaccag gtgcacgcgc caaccgcggt tgtgcagggt gacaaggtca    6240
acgctggtgg ctacctctcc gcgtaggcgc tcgttggtcc agcagaggcg gccgcccttg    6300
cgcgagcaga atgcggtag ggggtctagc tgcgtctcgt ccgggggggtc tgcgtccacg    6360
gtaaagaccc cgggcagcag gcgcgcgtcg aagtagtcta tcttgcatcc ttgcaagtct    6420
agcgcctgct gccatgcgcg ggcggcaagc gcgcgctcgt atgggttgag tgggggaccc    6480
catggcatgg ggtgggtgag cgcggaggcg tacatgccgc aaatgtcgta aacgtagagg   6540
ggctctctga gtattccaag atatgtaggg tagcatcttc caccgcggat gctggcgcgc    6600
acgtaatcgt atagttcgtg cgaggagcg aggaggtcgg gaccgaggtt gctacgggcg    6660
ggctgctctg ctcggaagac tatctgcctg aagatggcat gtgagttgga tgatatggtt    6720
```

```
ggacgctgga agacgttgaa gctggcgtct gtgagaccta ccgcgtcacg cacgaaggag    6780
gcgtaggagt cgcgcagctt gttgaccagc tcggcggtga cctgcacgtc tagggcgcag    6840
tagtccaggg tttccttgat gatgtcatac ttatcctgtc ccttttttt ccacagctcg     6900 cggttgagga caaactcttc gcggtctttc cagtactctt ggatcggaaa cccgtcggcc    6960
tccgaacggt aagagcctag catgtagaac tggttgacgg cctggtaggc gcagcatccc    7020
ttttctacgg gtagcgcgta tgcctgcgcg gccttccggc atgaccagca tgaagggcac    7080
gagctgcttc ccaaaggccc ccatccaagt ataggtctct acatcgtagg tgacaaagag    7140
acgctcggtg cgaggatgcg agccgatcgg gaagaactgg atctcccgcc accaattgga    7200
ggagtggcta ttgatgtggt gaaagtagaa gtccctgcga cgggccgaac actcgtgctg    7260
gcttttgtaa aaacgtgcgc agtactggca gcggtgcacg ggctgtacat cctgcacgag    7320
gttgacctga cgaccgcgca caaggaagca gagtgggaat ttgagcccct cgcctggcgg    7380
gtttggctgt tggtcttcta cttcggctgc ttgtccttga ccgtctggct gctcgagggg    7440
agttacggtg gatcggacca ccacgccgcg cgagcccaaa gtccagatgt ccgcgcgcgg    7500
cggtcggagc ttgatgacaa catcgcgcag atgggagctg tccatggtct ggagctcccg    7560
cggcgtcagg tcaggcggga gctcctgcag gtttacctcg catagacggg tcagggcgcg    7620
ggctagatcc aggtgatacc taatttccag gggctggttg gtggcggcgt cgatggcttg    7680
caagaggccg catccccgcg gcgcgactac ggtaccgcgc ggcgggcggt gggccgcggg    7740
ggtgtccttg gatgatgcat ctaaaagcgg tgacgcgggc gagccccgg aggtaggggg     7800 ggctccggac ccgccgggag aggggcagg ggcacgtcgg cgccgcgcgc gggcaggagc     7860
tggtgctgcg cgcgtaggtt gctggcgaac gcgacgacgc ggcggttgat ctcctgaatc    7920
tggcgcctct gcgtgaagac gacgggcccg gtgagcttga acctgaaaga gagttcgaca    7980
gaatcaattt cggtgtcgtt gacggcggcc tggcgcaaaa tctcctgcac gtctcctgag    8040
ttgtcttgat aggcgatctc ggccatgaac tgctcgatct cttcctcctg gagatctccg    8100
cgtccggctc gctccacggt ggcggcgagg tcgttggaaa tgcgggccat gagctgcgag    8160
aaggcgttga ggcctccctc gttccagacg cggctgtaga ccacgccccc ttcggcatcg    8220
cgggcgcgca tgaccacctg cgcgagattg agctccacgt gccgggcgaa gacggcgtag    8280
tttcgcaggc gctgaaagag gtagttgagg gtggtggcgg tgtgttctgc cacgaagaag    8340
tacataaccc agcgtcgcaa cgtggattcg ttgataattg ttgtgtaggt actccgccgc    8400
cgagggacct gagcgagtcc gcatcgaccg gatcggaaaa cctctcgaga aaggcgtcta    8460
accagtcaca gtcgcaaggt aggctgagca ccgtggcggg cggcagcggg cggcggtcgg    8520
ggttgtttct ggcggaggtg ctgctgatga tgtaattaaa gtaggcggtc ttgagacggc    8580
ggatggtcga cagaagcacc atgtccttgg gtccggcctg ctgaatgcgc aggcggtcgg    8640
ccatgcccca ggcttcgttt tgacatcggc gcaggtcttt gtagtagtct tgcatgagcc    8700
tttctaccgg cacttcttct tctccttcct cttgtcctgc atctcttgca tctatcgctg    8760
cggcggcggc ggagtttggc cgtaggtggc gccctcttcc tcccatgcgt gtgaccccga    8820
agcccctcat cggctgaagc agggctaggt cggcgacaac gcgctcggct aatatggcct    8880
gctgcacctg cgtgagggta gactggaagt catccatgtc cacaaagcgg tggtatgcgc    8940
ccgtgttgat ggtgtaagtg cagttggcca taacggacca gttaacggtc tggtgacccg    9000
gctgcgagag ctcggtgtac ctgagacgcg agtaagccct cgagtcaaat acgtagtcgt    9060
```

```
tgcaagtccg caccaggtac tggtatccca ccaaaaagtg cggcggcggc tggcggtaga    9120
ggggccagcg tagggtggcc ggggctccgg gggcgagatc ttccaacata aggcgatgat    9180
atccgtagat gtacctggac atccaggtga tgccggcggc ggtggtggag gcgcgcggaa    9240
agtcgcggac gcggttccag atgttgcgca gcggcaaaaa gtgctccatg gtcgggacgc    9300
tctggccggt caggcgcgcg caatcgttga cgctctagcg tgcaaaagga gagcctgtaa    9360
gcgggcactc ttccgtggtc tggtggataa attcgcaagg gtatcatggc ggacgaccgg    9420
ggttcgagcc ccgtatccgg ccgtccgccg tgatccatgc ggttaccgcc cgcgtgtcga    9480
acccaggtgt gcgacgtcag acaacggggg agtgctcctt ttggcttcct tccaggcgcg    9540
gcggctgctg cgctagcttt tttggccact ggccgcgcgc agcgtaagcg gttaggctgg    9600
aaagcgaaag cattaagtgg ctcgctccct gtagccggag ggttattttc caagggttga    9660
gtcgcgggac ccccggttcg agtctcggac cggccggact gcggcgaacg ggggtttgcc    9720
tccccgtcat gcaagacccc gcttgcaaat tcctccggaa acaggacgac gcccctttt    9780
tgcttttccc agatgcatcc ggtgctgcgg cagatgcgcc ccctcctca gcagcggcaa    9840
gagcaagagc agcggcagac atgcagggca ccctccctc ctcctaccgc gtcaggaggg    9900
gcgacatccg cggttgacgc ggcagcagat ggtgattacg aaccccgcg gcgccgggcc    9960
cggcactacc tggacttgga ggagggcgag ggcctggcgc ggctaggagc gccctctcct   10020
gagcggcacc caagggtgca gctgaagcgt gatacgcgtg aggcgtacgt gccgcggcag   10080
aacctgtttc gcgaccgcga gggagaggag cccgaggaga tgcgggatcg aaagttccac   10140
gcagggcgcg agctgcggca tggcctgaat cgcgagcggt tgctgcgcga ggaggacttt   10200
gagcccgacg cgcgaaccgg gattagtccc gcgcgcgcac acgtggcggc cgccgacctg   10260
gtaaccgcat acgagcagac ggtgaaccag gagattaact ttcaaaaaag ctttaacaac   10320
cacgtgcgta cgcttgtggc gcgcgaggag gtggctatag gactgatgca tctgtgggac   10380
tttgtaagcg cgctggagca aaacccaaat agcaagccgc tcatggcgca gctgttcctt   10440
atagtgcagc acagcaggga caacgaggca ttcagggatg cgctgctaaa catagtagag   10500
cccgagggcc gctggctgct cgatttgata aacatcctgc agagcatagt ggtgcaggag   10560
cgcagcttga gcctggctga caaggtggcc gccatcaact attccatgct tagcctgggc   10620
aagttttacg cccgcaagat ataccatacc ccttacgttc ccatagacaa ggaggtaaag   10680
atcgagggt tctacatgcg catggcgctg aaggtgctta ccttgagcga cgacctgggc   10740
gtttatcgca acgagcgcat ccacaaggcc gtgagcgtga ccggcggcg cgagctcagc   10800
gaccgcgagc tgatgcacag cctgcaaagg ccctggctg cacgggcag cggcgataga   10860
gaggccgagt cctactttga cgcgggcgct gacctgcgct gggccccaag ccgacgcgcc   10920
ctggaggcag ctggggccgg acctgggctg gcggtggcac ccgcgcgcgc tggcaacgtc   10980
ggcggcgtgg aggaatatga cgaggacgat gagtacgagc agaggacgg cgagtactaa   11040
gcggtgatgt ttctgatcag atgatgcaag acgcaacgga cccggcggtg cggcggcgc   11100
tgcagagcca gccgtccggc cttaactcca cggacgactg cgccaggtc atggaccgca   11160
tcatgtcgct gactgcgcgc aatcctgacg cgttccggca gcagccgcag gccaaccggc   11220
tctccgcaat tctggaagcg gtggtccgg cgcgcgcaaa cccacgcac gagaaggtgc   11280
tggcgatcgt aaacgcgctg gccgaaaaca gggccatccg gcccgacgag ccggcctgg   11340
tctacgacgc gctgcttcag cgcgtggctc gttacaacag cggcaacgtg cagaccaacc   11400
tggaccggct ggtggggat gtgcgcgagg ccgtggcgca gcgtgagcgc gcgcagcagc   11460
```

```
agggcaacct gggctccatg gttgcactaa acgccttcct gagtacacag cccgccaacg    11520
tgccgcgggg acaggaggac tacaccaact ttgtgagcgc actgcggcta atggtgactg    11580
agacaccgca aagtgaggtg taccagtctg ggccagacta ttttttccag accagtagac    11640
aaggcctgca gaccgtaaac ctgagccagg ctttcaaaaa cttgcagggg ctgtgggggg    11700
tgcgggctcc cacaggcgac cgcgcgaccg tgtctagctt gctgacgccc aactcgcgcc    11760
tgttgctgct gctaatagcg cccttcacgg acagtggcag cgtgtcccgg acacatacc    11820 taggtcactt gctgacactg taccgcgagg ccataggtca ggcgcatgtg gacgagcata    11880 cttccagga gattacaagt gtcagccgcg cgctggggca ggaggacacg ggcagcctgg     11940
aggcaaccct aaactacctg ctgaccaacc ggcggcagaa gatcccctcg ttgcacagtt    12000
taaacagcga ggaggagcgc attttgcgct acgtgcagca gagcgtgagc cttaacctga    12060
tgcgcgacgg ggtaacgccc agcgtggcgc tggacatgac cgcgcgcaac atggaaccgg    12120
gcatgtatgc ctcaaaccgg ccgtttatca accgcctaat ggactacttg catcgcgcgg    12180
ccgccgtgaa ccccgagtat ttcaccaatg ccatcttgaa cccgcactgg ctaccgcccc    12240
ctggtttcta caccgggga ttcgaggtgc ccgagggtaa cgatggattc ctctgggacg      12300
acatagacga cagcgtgttt tccccgcaac cgcagaccct gctagagttg caacagcgcg    12360
agcaggcaga ggcggcgctg cgaaaggaaa gcttccgcag gccaagcagc ttgtccgatc    12420
taggcgctgc ggccccgcgg tcagatgcta gtagcccatt ccaagcttg ataggtctc      12480 ttaccagcac tcgcaccacc cgcccgcgcc tgctgggcga ggaggagtac ctaaacaact    12540
cgctgctgca gccgcagcgc gaaaaaaacc tgcctccggc atttcccaac aacgggatag    12600
agagcctagt ggacaagatg agtagatgga agacgtacgc gcaggagcac agggacgtgc    12660
caggcccgcg cccgcccacc cgtcgtcaaa ggcacgaccg tcagcggggt ctggtgtggg    12720
aggacgatga ctcggcagac gacagcagcg tcctggattt gggagggagt ggcaacccgt    12780
ttgcgcacct tcgcccagg ctggggagaa tgttttaaaa aaaaaaagc atgatgcaaa       12840 ataaaaaact caccaaggcc atggcaccga gcgttggttt tcttgtattc cccttagtat    12900
gcggcgcgcg gcgatgtatg aggaaggtcc tcctccctcc tacgagagtg tggtgagcgc    12960
ggcgccagtg gcggcggcgc tgggttctcc cttcgatgct ccctggacc cgccgtttgt     13020 gcctccgcgg tacctgcggc ctaccggggg gagaaacagc atccgttact ctgagttggc    13080
acccctattc gacaccaccc gtgtgtacct ggtggacaac aagtcaacgg atgtggcatc    13140
cctgaactac cagaacgacc acagcaactt tctgaccacg gtcattcaaa acaatgacta    13200
cagcccgggg gaggcaagca cacagaccat caatcttgac gaccggtcgc actgggcgg     13260 cgacctgaaa accatcctgc ataccaacat gccaaatgtg aacgagttca tgtttaccaa    13320
taagtttaag gcgcgggtga tggtgtcgcg cttgcctact aaggacaatc aggtggagct    13380
gaaatacgag tgggtggagt tcacgctgcc cgagggcaac tactccgaga ccatgaccat    13440
agaccttatg aacaacgcga tcgtggagca ctacttgaaa gtgggcagac agaacgggt     13500 tctggaaagc gacatcgggg taaagtttga caccgcaac ttcagactgg ggtttgaccc     13560
cgtcactggt cttgtcatgc ctgggtata tacaaacgaa gccttccatc cagacatcat    13620
tttgctgcca ggatgcgggg tggacttcac ccacagccgc ctgagcaact tgttgggcat    13680
ccgcaagcgc caacccttcc aggagggctt taggatcacc tacgatgatc tggagggtgg    13740
taacattccc gcactgttgg atgtggacgc ctaccaggcg agcttgaaag atgacaccga    13800
```

```
acagggcggg ggtggcgcag gcggcagcaa cagcagtggc agcggcgcgg aagagaactc   13860
caacgcggca gccgcggcaa tgcagccggt ggaggacatg aacgatcatg ccattcgcgg   13920
cgacaccttt gccacacggg ctgaggagaa gcgcgctgag gccgaagcag cggccgaagc   13980
tgccgccccc gctgcgcaac ccgaggtcga gaagcctcag aagaaaccgg tgatcaaacc   14040
cctgacagag gacagcaaga aacgcagtta caacctaata agcaatgaca gcaccttcac   14100
ccagtaccgc agctggtacc ttgcatacaa ctacggcgac cctcagaccg gaatccgctc   14160
atggaccctg ctttgcactc ctgacgtaac ctgcggctcg gagcaggtct actggtcgtt   14220
gccagacatg atgcaagacc ccgtgacctt ccgctccacg cgccagatca gcaacttttcc  14280 ggtggtgggc gccgagctgt tgcccgtgca ctccaagagc ttctacaacg accaggccgt   14340
ctactcccaa ctcatccgcc agtttacctc tctgacccac gtgttcaatc gctttcccga   14400
gaaccagatt ttggcgcgcc cgccagcccc caccatcacc accgtcagtg aaaacgttcc   14460
tgctctcaca gatcacggga cgctaccgct gcgcaacagc atcggaggag tccagcgagt   14520
gaccattact gacgccagac gccgcacctg ccccctacgtt tacaaggccc tgggcatagt   14580
ctcgccgcgc gtcctatcga gccgcacttt ttgagcaagc atgtccatcc ttatatcgcc   14640
cagcaataac acaggctggg gcctgcgctt cccaagcaag atgtttggcg gggccaagaa   14700
gcgctccgac caaacacccag tgcgcgtgcg cgggcactac cgcgcgccct ggggcgcgca   14760
caaacgcggc cgcactgggc gcaccaccgt cgatgacgcc atcgacgcgg tggtggagga   14820
ggcgcgcaac tacacgccca cgccgccacc agtgtccaca gtggacgcgg ccattcagac   14880
cgtggtcgcg ggagcccggc gctatgctaa aatgaagaga cggcggaggc gcgtagcacg   14940
tcgccaccgc cgccgacccg gcactgccgc ccaacgcgcg cggcggccc tgcttaaccg    15000 cgcacgtcgc accggccgac gggcggccat gcgggccgct cgaaggctgg ccgcgggtat   15060
tgtcactgtg ccccccaggt ccaggcgacg agcggccgcc gcagcagccg cggccattag   15120
tgctatgact cagggtcgca ggggcaacgt gtattgggtg cgcgactcgg ttagcggcct   15180
gcgcgtgccc gtgcgcaccc gccccccgcg caactagatt gcaagaaaaa actacttaga   15240
ctcgtactgt tgtatgtatc cagcggcggc ggcgcgcaac gaagctatgt ccaagcgcaa   15300
aatcaaagaa gagatgctcc aggtcatcgc gccggagatc tatggccccc cgaagaagga   15360
agagcaggat tacaagcccc gaaagctaaa gcgggtcaaa aagaaaaaga agatgatga    15420 tgatgaactt gacgacgagg tggaactgct gcacgctacc gcgcccaggc gacgggtaca   15480
gtggaaaggt cgacgcgtaa aacgtgtttt gcgaccccggc accaccgtag tctttacgcc   15540
cggtgagcgc tccacccgca cctacaagcg cgtgtatgat gaggtgtacg gcgacgagga   15600
cctgcttgag caggccaacg agcgcctcgg ggagtttgcc tacggaaagc ggcataagga   15660
catgctggcg ttgccgctgg acgagggcaa cccaacacct agcctaaagc ccgtaacact   15720
gcagcaggtg ctgcccgcgc ttgcaccgtc cgaagaaaag cgcggcctaa gcgcgagtc    15780 tggtgacttg gcacccaccg tgcagctgat ggtacccaag cgccagcgac tggaagatgt   15840
cttggaaaaa atgaccgtgg aacctgggct ggagcccgag gtccgcgtgc ggccaatcaa   15900
gcaggtggcg ccgggactgg gcgtgcagac cgtggacgtt cagataccca ctaccagtag   15960
caccagtatt gccaccgcca cagagggcat ggagacacaa acgtccccgg ttgcctcagc   16020
ggtggcggat gccgcggtgc aggcggtcgc tgcggccgcg tccaagacct ctacggaggt   16080
gcaaacggac ccgtggatgt ttcgcgtttc agccccccgg cgcccgcgcc gttcgaggaa   16140
gtacggcgcc gccagcgcgc tactgcccga atatgcccta catccttcca ttgcgcctac   16200
```

```
ccccggctat cgtggctaca cctaccgccc cagaagacga gcaactaccc gacgccgaac    16260
caccactgga acccgccgcc gccgtcgccg tcgccagccc gtgctggccc cgatttccgt    16320
gcgcagggtg gctcgcgaag gaggcaggac cctggtgctg ccaacagcgc gctaccaccc    16380
cagcatcgtt taaaagccgg tctttgtggt tcttgcagat atggccctca cctgccgcct    16440
ccgtttcccg gtgccgggat tccgaggaag aatgcaccgt aggaggggca tggccggcca    16500
cggcctgacg ggcggcatgc gtcgtgcgca ccaccggcgg cggcgcgcgt cgcaccgtcg    16560
catgcgcggc ggtatcctgc ccctccttat tccactgatc gccgcggcga ttggcgccgt    16620
gcccggaatt gcatccgtgg ccttgcaggc gcagagacac tgattaaaaa caagttgcat    16680
gtggaaaaat caaaataaaa agtctggact ctcacgctcg cttggtcctg taactatttt    16740
gtagaatgga agacatcaac tttgcgtctc tggccccgcg acacggctcg cgccgttca    16800 tgggaaactg gcaagatatc ggcaccagca atatgagcgg tggcgccttc agctggggct    16860
cgctgtggag cggcattaaa aatttcggtt ccaccgttaa gaactatggc agcaaggcct    16920
ggaacagcag cacaggccag atgctgaggg ataagttgaa agagcaaaat ttccaacaaa    16980
aggtggtaga tggcctggcc tctggcatta gcggggtggt ggacctggcc aaccaggcag    17040
tgcaaaataa gattaacagt aagcttgatc cccgccctcc cgtagaggag cctccaccgg    17100
ccgtggagac agtgtctcca gaggggcgtg gcgaaaagcg tccgcgcccc gacagggaag    17160
aaactctggt gacgcaaata gacgagcctc cctcgtacga ggaggcacta aagcaaggcc    17220
tgcccaccac ccgtcccatc gcgcccatgg ctaccggagt gctgggccag cacacacccg    17280
taacgctgga cctgcctccc cccgccgaca cccagcagaa acctgtgctg ccaggcccga    17340
ccgccgttgt tgtaacccgt cctagccgcg cgtccctgcg ccgcgccgcc agcggtccgc    17400
gatcgttgcg gcccgtagcc agtggcaact ggcaaagcac actgaacagc atcgtgggtc    17460
tgggggtgca atccctgaag cgccgacgat gcttctgata gctaacgtgt cgtatgtgtg    17520
tcatgtatgc gtccatgtcg ccgccagagg agctgctgag ccgccgcgcg cccgctttcc    17580
aagatggcta ccccttcgat gatgccgcag tggtcttaca tgcacatctc gggccaggac    17640
gcctcggagt acctgagccc cgggctggtg cagtttgccc gcgccaccga gacgtacttc    17700
agcctgaata caagtttag aaaccccacg gtggcgccta cgcacgacgt gaccacagac    17760
cggtcccagc gtttgacgct gcggttcatc cctgtgacc gtgaggatac tgcgtactcg    17820
tacaaggcgc ggttcaccct agctgtgggt gataaccgtg tgctggacat ggcttccacg    17880
tactttgaca tccgcggcgt gctggacagg ggccctactt ttaagcccta ctctggcact    17940
gcctacaacg ccctggctcc caagggtgcc ccaaatcctt gcgaatggga tgaagctgct    18000
actgctcttg aaataaacct agaagaagag gacgatgaca acgaagacga agtagacgag    18060
caagctgagc agcaaaaaac tcacgtattt gggcaggcgc ttattctgg tataaatatt    18120 acaaaggagg gtattcaaat aggtgtcgaa ggtcaaacac ctaaatatgc cgataaaaca    18180
tttcaacctg aacctcaaat aggagaatct cagtggtacg aaacagaaat taatcatgca    18240
gctgggagag tcctaaaaaa gactaccca atgaaaccat gttacggttc atatgcaaaa    18300
cccacaaatg aaaatggagg gcaaggcatt cttgtaaagc aacaaatgg aaagctagaa    18360 agtcaagtgg aaatgcaatt tttctcaact actgaggcag ccgcaggcaa tggtgataac    18420
ttgactccta aagtggtatt gtacagtgaa gatgtagata tagaaacccc agacactcat    18480
atttcttaca tgcccactat taaggaaggt aactcacgag aactaatggg ccaacaatct    18540
```

```
atgcccaaca ggcctaatta cattgctttt agggacaatt ttattggtct aatgtattac  18600
aacagcacgg gtaatatggg tgttctggcg ggccaagcat cgcagttgaa tgctgttgta  18660
gatttgcaag acagaaacac agagctttca taccagcttt tgcttgattc cattggtgat  18720
agaaccaggt acttttctat gtggaatcag gctgttgaca gctatgatcc agatgttaga  18780
attattgaaa atcatggaac tgaagatgaa cttccaaatt actgctttcc actgggaggt  18840
gtgattaata cagagactct taccaaggta aaacctaaaa caggtcagga aaatggatgg  18900
gaaaagatg ctacagaatt ttcagataaa aatgaaataa gagttggaaa taattttgcc  18960
atggaaatca atctaaatgc caacctgtgg agaaatttcc tgtactccaa catagcgctg  19020
tatttgcccg acaagctaaa gtacagtcct tccaacgtaa aaatttctga tacccaaac  19080
acctacgact acatgaacaa gcgagtggtg gctcccgggc tagtggactg ctacattaac  19140
cttggagcac gctggtccct tgactatatg gacaacgtca acccatttaa ccaccaccgc  19200
aatgctggcc tgcgctaccg ctcaatgttg ctgggcaatg gtcgctatgt gcccttccac  19260
atccaggtgc ctcagaagtt cttttgccatt aaaaacctcc ttctcctgcc gggctcatac  19320
acctacgagt ggaacttcag gaaggatgtt aacatggttc tgcagagctc cctaggaaat  19380
gacctaaggg ttgacggagc cagcattaag tttgatagca tttgccttta cgccaccttc  19440
ttccccatgg cccacaacac cgcctccacg cttgaggcca tgcttagaaa cgacaccaac  19500
gaccagtcct ttaacgacta tctctccgcc gccaacatgc tctaccctat acccgccaac  19560
gctaccaacg tgcccatatc catcccctcc cgcaactggg cggctttccg cggctgggcc  19620
ttcacgcgcc ttaagactaa ggaaacccca tcactgggct cgggctacga cccttattac  19680
acctactctg gctctatacc ctacctagat ggaaccttt acctcaacca cacctttaag  19740
aaggtggcca ttacctttga ctcttctgtc agctggcctg gcaatgaccg cctgcttacc  19800
cccaacgagt ttgaaattaa gcgctcagtt gacggggagg gttacaacgt tgcccagtgt  19860
aacatgacca agactggtt cctggtacaa atgctagcta actataacat tggctaccag  19920
ggcttctata tcccagagag ctacaaggac cgcatgtact ccttctttag aaacttccag  19980
cccatgagcc gtcaggtggt ggatgatact aaatacaagg actaccaaca ggtgggcatc  20040
ctacaccaac acaacaactc tggatttgtt ggctaccttg cccccaccat gcgcgaagga  20100
caggcctacc ctgctaactt ccccctatccg cttataggca agaccgcagt tgacagcatt  20160
acccagaaaa agtttctttg cgatcgcacc ctttggcgca tcccattctc cagtaacttt  20220
atgtccatgg gcgcactcac agacctgggc caaaaccttc tctacgccaa ctccgcccac  20280
gcgctagaca tgacttttga ggtggatccc atggacgagc ccacccttct ttatgttttg  20340
tttgaagtct ttgacgtggt ccgtgtgcac cagccgcacc gcggcgtcat cgaaaccgtg  20400
tacctgcgca cgcccttctc ggccggcaac gccacaacat aaagaagcaa gcaacatcaa  20460
caacagctgc cgccatgggc tccagtgagc aggaactgaa agccattgtc aaagatcttg  20520
gttgtgggcc atatttttg ggcacctatg acaagcgctt ccaggctttt gtttctccac  20580
acaagctcgc ctgcgccata gtcaatacgg ccggtcgcga actgggggc gtacactgga  20640
tggcctttgc ctggaacccg cactcaaaaa catgctacct cttttgagccc ttggctttt  20700
ctgaccagcg actcaagcag gtttaccagt ttgagtacga gtcactcctg cgccgtagcg  20760
ccattgcttc ttccccgac cgctgtataa cgctggaaaa gtccaccaa agcgtacagg  20820
ggcccaactc ggccgcctgt ggactattct gctgcatgtt tctccacgcc tttgccaact  20880
ggccccaaac tcccatggat cacaacccca ccatgaacct tattaccggg gtacccaact  20940
```

```
ccatgctcaa cagtccccag gtacagccca ccctgcgtcg caaccaggaa cagctctaca   21000
gcttcctgga gcgccactcg ccctacttcc gcagccacag tgcgcagatt aggagcgcca   21060 cttcttttg tcacttgaaa acatgtaaa aataatgtac tagagacact ttcaataaag    21120
gcaaatgctt ttatttgtac actctcgggt gattatttac ccccacccctt gccgtctgcg  21180 ccgtttaaaa atcaaagggg ttctgccgcg catcgctatg cgccactggc agggacacgt   21240
tgcgatactg tgtttagtg ctccacttaa actcaggcac aaccatccgc ggcagctcgg    21300
tgaagttttc actccacagg ctgcgcacca tcaccaacgc gtttagcagg tcgggcgccg   21360
atatcttgaa gtcgcagttg gggcctccgc cctgcgcgcg cgagttgcga tacacagggt   21420
tgcagcactg gaacactatc agcgccgggt ggtgcacgct ggccagcacg ctcttgtcgg   21480
agatcagatc cgcgtccagg tcctccgcgt tgctcagggc gaacggagtc aactttggta   21540
gctgccttcc caaaagggc gcgtgcccag gctttgagtt gcactcgcac cgtagtggca    21600
tcaaaaggtg accgtgcccg gtctgggcgt taggatacag cgcctgcata aaagccttga   21660
tctgcttaaa agccacctga gcctttgcgc cttcagagaa gaacatgccg caagacttgc   21720
cggaaaactg attggccgga caggccgcgt cgtgcacgca gcaccttgcg tcggtgttgg   21780
agatctgcac cacatttcgg ccccaccggt tcttcacgat cttggccttg ctagactgct   21840
ccttcagcgc gcgctgcccg ttttcgctcg tcacatccat ttcaatcacg tgctccttat   21900
ttatcataat gcttccgtgt agacacttaa gctcgccttc gatctcagcg cagcggtgca   21960
gccacaacgc gcagcccgtg ggctcgtgat gcttgtaggt cacctctgca aacgactgca   22020
ggtacgcctg caggaatcgc cccatcatcg tcacaaaggt cttgttgctg gtgaaggtca   22080
gctgcaaccc gcggtgctcc tcgttcagcc aggtcttgca tacggccgcc agagcttcca   22140
cttggtcagg cagtagtttg aagttcgcct ttagatcgtt atccacgtgg tacttgtcca   22200
tcagcgcgcg cgcagcctcc atgcccttct cccacgcaga cacgatcggc acactcagcg   22260
ggttcatcac cgtaatttca ctttccgctt cgctgggctc ttcctcttcc tcttgcgtcc   22320
gcataccacg cgccactggg tcgtcttcat tcagccgccg cactgtgcgc ttacctcctt   22380
tgccatgctt gattagcacc ggtgggttgc tgaaacccac catttgtagc gccacatctt   22440
ctctttcttc ctcgctgtcc acgattacct ctggtgatgg cgggcgctcg ggcttgggag   22500
aagggcgctt cttttcttc ttgggcgcaa tggccaaatc cgccgccgag gtcgatggcc   22560
gcgggctggg tgtgcgcggc accagcgcgt cttgtgatga gtcttcctcg tcctcggact   22620
cgatacgccg cctcatccgc ttttttgggg gcgcccgggg aggcggcggc gacggggacg   22680
gggacgacac gtcctccatg gttggggac gtcgcgccgc accgcgtccg cgctcggggg    22740
tggtttcgcg ctgctcctct tcccgactgg ccatttcctt ctcctatagg cagaaaaaga   22800
tcatggagtc agtcgagaag aaggacagcc taaccgcccc ctctgagttc gccaccaccg   22860
cctccaccga tgccgccaac gcgcctacca ccttccccgt cgaggcaccc ccgcttgagg   22920
aggaggaagt gattatcgag caggacccag gttttgtaag cgaagacgac gaggaccgct   22980
cagtaccaac agaggataaa aagcaagacc aggacaacgc agaggcaaac gaggaacaag   23040
tcgggcgggg ggacgaaagg catggcgact acctagatgt gggagacgac gtgctgttga   23100
agcatctgca gcgccagtgc gccattatct gcgacgcgtt gcaagagcgc agcgatgtgc   23160
ccctcgccat agcggatgtc agccttgcct acgaacgcca cctattctca ccgcgcgtac   23220 ccccccaaacg ccaagaaaac ggcacatgcg agcccaaccc gcgcctcaac ttctaccccg  23280
```

```
tatttgccgt gccagaggtg cttgccacct atcacatctt tttccaaaac tgcaagatac    23340
ccctatcctg ccgtgccaac cgcagccgag cggacaagca gctggccttg cggcagggcg    23400
ctgtcatacc tgatatcgcc tcgctcaacg aagtgccaaa aatctttgag ggtcttggac    23460
gcgacgagaa gcgcgcggca aacgctctgc aacaggaaaa cagcgaaaat gaaagtcact    23520
ctggagtgtt ggtggaactc gagggtgaca acgcgcgcct agccgtacta aaacgcagca    23580
tcgaggtcac ccactttgcc tacccggcac ttaacctacc ccccaaggtc atgagcacag    23640
tcatgagtga gctgatcgtg cgccgtgcgc agccctggaa gagggatgca aatttgcaag    23700
aacaaacaga ggagggccta cccgcagttg gcgacgagca gctagcgcgc tggcttcaaa    23760
cgcgcgagcc tgccgacttg gaggagcgac gcaaactaat gatggccgca gtgctcgtta    23820
ccgtggagct tgagtgcatg cagcggttct ttgctgaccc ggagatgcag cgcaagctag    23880
aggaaacatt gcactacacc tttcgacagg gctacgtacg ccaggcctgc aagatctcca    23940
acgtggagct ctgcaacctg gtctcctacc ttggaatttt gcacgaaaac cgccttgggc    24000
aaaacgtgct tcattccacg ctcaagggcg aggcgcgccg cgactacgtc cgcgactgcg    24060
tttacttatt tctatgctac acctggcaga cggccatggg cgtttggcag cagtgcttgg    24120
aggagtgcaa cctcaaggag ctgcagaaac tgctaaagca aaacttgaag gacctatgga    24180
cggccttcaa cgagcgctcc gtggccgcgc acctggcgga catcattttc cccgaacgcc    24240
tgcttaaaac cctgcaacag ggtctgccag acttcaccag tcaaagcatg ttgcagaact    24300
ttaggaactt tatcctagag cgctcaggaa tcttgcccgc cacctgctgt gcacttccta    24360
gcgactttgt gccattaag taccgcgaat gccctccgcc gctttgggc cactgctacc    24420 ttctgcagct agccaactac cttgcctacc actctgacat aatggaagac gtgagcggtg    24480
acggtctact ggagtgtcac tgtcgctgca acctatgcac cccgcaccgc tccctggttt    24540
gcaattcgca gctgcttaac gaaagtcaaa ttatcggtac ctttgagctg cagggtccct    24600
cgcctgacga aaagtccgcg gctccggggt tgaaactcac tccggggctg tggacgtcgg    24660
cttaccttcg caaatttgta cctgaggact accacgccca cgagattagg ttctacgaag    24720
accaatcccg cccgcctaat gcggagctta ccgcctgcgt cattacccag ggccacattc    24780
ttggccaatt gcaagccatc aacaaagccc gccaagagtt tctgctacga aagggacggg    24840
gggtttactt ggaccccag tccggcgagg agctcaaccc aatcccccg ccgccgcagc    24900 cctatcagca gcagccgcgg gcccttgctt cccaggatgg cacccaaaaa gaagctgcag    24960
ctgccgccgc cacccacgga cgaggaggaa tactgggaca gtcaggcaga ggaggttttg    25020
gacgaggagg aggaggacat gatggaagac tgggagagcc tagacgagga agcttccgag    25080
gtcgaagagg tgtcagacga acaccgtca ccctcggtcg cattcccctc gccggcgccc    25140
cagaaatcgg caaccggttc cagcatggct acaacctccg ctcctcaggc ccgccggca    25200 ctgcccgttc gccgacccaa ccgtagatgg gacaccactg gaaccagggc cggtaagtcc    25260
aagcagccgc cgccgttagc ccaagagcaa caacagcgcc aaggctaccg ctcatggcgc    25320
gggcacaaga acgccatagt tgcttgcttg caagactgtg ggggcaacat ctccttcgcc    25380
cgccgctttc ttctctacca tcacggcgtg gccttccccc gtaacatcct gcattactac    25440
cgtcatctct acagcccata ctgcaccggc ggcagcggca gcaacagcag cggccacaca    25500
gaagcaaagg cgaccggata gcaagactct gacaaagccc aagaaatcca cagcggcggc    25560
agcagcagga ggaggagcgc tgcgtctggc gcccaacgaa cccgtatcga cccgcgagct    25620
tagaaacagg atttttccca ctctgtatgc tatatttcaa cagagcaggg gccaagaaca    25680
```

```
agagctgaaa ataaaaaaca ggtctctgcg atccctcacc cgcagctgcc tgtatcacaa   25740
aagcgaagat cagcttcggc gcacgctgga agacgcggag gctctcttca gtaaatactg   25800
cgcgctgact cttaaggact agtttcgcgc cctttctcaa atttaagcgc gaaaactacg   25860
tcatctccag cggccacacc cggcgccagc acctgttgtc agcgccatta tgagcaagga   25920
aattcccacg ccctacatgt ggagttacca gccacaaatg ggacttgcgg ctggagctgc   25980
ccaagactac tcaacccgaa taaactacat gagcgcggga ccccacatga tatcccgggt   26040
caacggaata cgcgcccacc gaaaccgaat tctcctggaa caggcggcta ttaccaccac   26100
acctcgtaat aaccttaatc cccgtagttg gcccgctgcc ctggtgtacc aggaaagtcc   26160
cgctcccacc actgtggtac ttcccagaga cgcccaggcc gaagttcaga tgactaactc   26220
aggggcgcag cttgcgggcg gctttcgtca cagggtgcgg tcgcccgggc agggtataac   26280
tcacctgaca atcagagggc gaggtattca gctcaacgac gagtcggtga gctcctcgct   26340
tggtctccgt ccggacggga catttcagat cggcggcgcc ggccgctctt cattcacgcc   26400
tcgtcaggca atcctaactc tgcagacctc gtcctctgag ccgcgctctg gaggcattgg   26460
aactctgcaa tttattgagg agtttgtgcc atcggtctac tttaacccct tctcgggacc   26520
tcccggccac tatccggatc aatttattcc taactttgac gcggtaaagg actcggcgga   26580
cggctacgac tgaatgttaa gtggagaggc agagcaactg cgcctgaaac acctggtcca   26640
ctgtcgccgc cacaagtgct tgcccgcga ctccggtgag ttttgctact ttgaattgcc   26700
cgaggatcat atcgagggcc cggcgcacgg cgtccggctt accgcccagg gagagcttgc   26760
ccgtagcctg attcgggagt ttacccagcg ccccctgcta gttgagcggg acaggggacc   26820
ctgtgttctc actgtgattt gcaactgtcc taaccctgga ttacatcaag atcctctagt   26880
taatgtcagg tcgcctaagt cgattaacta gagtacccgg ggatcttatt ccctttaact   26940
aataaaaaaa aataataaag catcacttac ttaaaatcag ttagcaaatt tctgtccagt   27000
ttattcagca gcacctcctt gccctcctcc cagctctggt attgcagctt cctcctggct   27060
gcaaactttc tccacaatct aaatggaatg tcagtttcct cctgttcctg tccatccgca   27120
cccactatct tcatgttgtt gcagatgaag cgcgcaagac cgtctgaaga taccttcaac   27180
cccgtgtatc catatgacac ggaaaccggt cctccaactg tgccttttct tactcctccc   27240
tttgtatccc ccaatgggtt tcaagagagt cccctgggg tactctcttt gcgcctatcc   27300
gaacctctag ttacctccaa tggcatgctt gcgctcaaaa tgggcaacgg cctctctctg   27360
gacgaggccg gcaaccttac ctcccaaaat gtaaccactg tgagcccacc tctcaaaaaa   27420
accaagtcaa acataaacct ggaaatatct gcaccctca cagttacctc agaagcccta   27480
actgtggctg ccgccgcacc tctaatggtc gcgggcaaca cactcaccat gcaatcacag   27540
gccccgctaa ccgtgcacga ctccaaactt agcattgcca cccaaggacc cctcacagtg   27600
tcagaaggaa agctagccct gcaaacatca ggcccctca ccaccaccga tagcagtacc   27660
cttactatca ctgcctcacc ccctctaact actgccactg gtagcttggg cattgacttg   27720
aaagagccca tttatacaca aaatggaaaa ctaggactaa agtacggggc tcctttgcat   27780
gtaacagacg acctaaacac tttgaccgta gcaactggtc caggtgtgac tattaataat   27840
acttccttgc aaactaaagt tactggagcc ttgggttttg attcacaagg caatatgcaa   27900
cttaatgtag caggaggact aaggattgat tctcaaaaca gacgccttat acttgatgtt   27960
agttatccgt ttgatgctca aaaccaacta aatctaagac taggacaggg ccctcttttt   28020
```

```
ataaactcag cccacaactt ggatattaac tacaacaaag gcctttactt gtttacagct   28080
tcaaacaatt ccaaaaagct tgaggttaac ctaagcactg ccaagggggtt gatgtttgac   28140
gctacagcca tagccattaa tgcaggagat gggcttgaat ttggttcacc taatgcacca   28200
aacacaaatc ccctcaaaac aaaaattggc catggcctag aatttgattc aaacaaggct   28260
atggttccta aactaggaac tggccttagt tttgacagca caggtgccat tacagtagga   28320
aacaaaaata atgataagct aactttgtgg accacaccag ctccatctcc taactgtaga   28380
ctaaatgcag agaaagatgc taaactcact ttggtcttaa caaaatgtgg cagtcaaata   28440
cttgctacag tttcagtttt ggctgttaaa ggcagtttgg ctccaatatc tggaacagtt   28500
caaagtgctc atcttattat aagatttgac gaaaatggag tgctactaaa caattccttc   28560
ctggacccag aatattggaa ctttagaaat ggagatctta ctgaaggcac agcctataca   28620
aacgctgttg gatttatgcc taacctatca gcttatccaa atctcacgg taaaactgcc   28680
aaaagtaaca ttgtcagtca agtttactta aacggagaca aaactaaacc tgtaacacta   28740
accattacac taaacggtac acaggaaaca ggagacacaa ctccaagtgc atactctatg   28800
tcattttcat gggactggtc tggccacaac tacattaatg aaatatttgc cacatcctct   28860
tacactttt catacattgc ccaagaataa agaatcgttt gtgttatgtt tcaacgtgtt   28920
tatttttcaa ttgcagaaaa tttcaagtca tttttcattc agtagtatag ccccaccacc   28980
acatagctta tacagatcac cgtaccttaa tcaaactcac agaaccctag tattcaacct   29040
gccacctccc tcccaacaca cagagtacac agtcctttct ccccggctgg ccttaaaaag   29100
catcatatca tgggtaacag acatattctt aggtgttata ttccacacgg tttcctgtcg   29160
agccaaacgc tcatcagtga tattaataaa ctccccgggc agctcactta agttcatgtc   29220
gctgtccagc tgctgagcca caggctgctg tccaacttgc ggttgcttaa cgggcggcga   29280
aggagaagtc cacgcctaca tgggggtaga gtcataatcg tgcatcagga tagggcggtg   29340
gtgctgcagc agcgcgcgaa taaactgctg ccgccgccgc tccgtcctgc aggaatacaa   29400
catggcagtg gtctcctcag cgatgattcg caccgcccgc agcataaggc gccttgtcct   29460
ccgggcacag cagcgcaccc tgatctcact taaatcagca cagtaactgc agcacagcac   29520
cacaatattg ttcaaaatcc cacagtgcaa ggcgctgtat ccaaagctca tggcggggac   29580
cacagaaccc acgtggccat cataccacaa gcgcaggtag attaagtggc gaccctcat   29640
aaacacgctg gacataaaca ttacctcttt tggcatgttg taattcacca cctcccggta   29700
ccatataaac ctctgattaa acatggcgcc atccaccacc atcctaaacc agctggccaa   29760
aacctgcccg ccggctatac actgcaggga accgggactg gaacaatgac agtggagagc   29820
ccaggactcg taaccatgga tcatcatgct cgtcatgata tcaatgttgg cacaacacag   29880
gcacacgtgc atacacttcc tcaggattac aagctcctcc cgcgttagaa ccatatccca   29940
gggaacaacc cattcctgaa tcagcgtaaa tcccacactg cagggaagac ctcgcacgta   30000
actcacgttg tgcattgtca aagtgttaca ttcgggcagc agcggatgat cctccagtat   30060
ggtagcgcgg gtttctgtct caaaaggagg tagacgatcc ctactgtacg gagtgcgccg   30120
agacaaccga atcgtgttg gtcgtagtgt catgccaaat ggaacgccgg acgtagtcat   30180
atttcctgaa gcaaaaccag gtgcgggcgt gacaaacaga tctgcgtctc cggtctcgcc   30240
gcttagatcg ctctgtgtag tagttgtagt atatccactc tctcaaagca tccaggcgcc   30300
ccctggcttc gggttctatg taaactcctt catgcgccgc tgccctgata acatccacca   30360
ccgcagaata agccacaccc agccaaccta cacattcgtt ctgcgagtca cacacgggag   30420
```

-continued

| | | | |
|---|---|---|---|
| gagcgggaag agctggaaga accatgtttt ttttttttatt ccaaaagatt atccaaaacc | 30480 |
| tcaaaatgaa gatctattaa gtgaacgcgc tcccctccgg tggcgtggtc aaactctaca | 30540 |
| gccaaagaac agataatggc atttgtaaga tgttgcacaa tggcttccaa aaggcaaacg | 30600 |
| gccctcacgt ccaagtggac gtaaaggcta aacccttcag ggtgaatctc ctctataaac | 30660 |
| attccagcac cttcaaccat gcccaaataa ttctcatctc gccaccttct caatatatct | 30720 |
| ctaagcaaat cccgaatatt aagtccggcc attgtaaaaa tctgctccag agcgccctcc | 30780 |
| accttcagcc tcaagcagcg aatcatgatt gcaaaaattc aggttcctca cagacctgta | 30840 |
| taagattcaa aagcggaaca ttaacaaaaa taccgcgatc ccgtaggtcc cttcgcaggg | 30900 |
| ccagctgaac ataatcgtgc aggtctgcac ggaccagcgc ggccacttcc ccgccaggaa | 30960 |
| ccatgacaaa agaacccaca ctgattatga cacgcatact cggagctatg ctaaccagcc | 31020 |
| tagccccgat gtaagcttgt tgcatgggcg gcgatataaa atgcaaggtg ctgctcaaaa | 31080 |
| aatcaggcaa agcctcgcgc aaaaaagaaa gcacatcgta gtcatgctca tgcagataaa | 31140 |
| ggcaggtaag ctccggaacc accacagaaa aagacaccat ttttctctca aacatgtctg | 31200 |
| cgggtttctg cataaacaca aaataaaata acaaaaaaac atttaaacat tagaagcctg | 31260 |
| tcttacaaca ggaaaaacaa cccttataag cataagacgg actacggcca tgccggcgtg | 31320 |
| accgtaaaaa aactggtcac cgtgattaaa aagcaccacc gacagctcct cggtcatgtc | 31380 |
| cggagtcata atgtaagact cggtaaacac atcaggttga ttcacatcgg tcagtgctaa | 31440 |
| aaagcgaccg aaatagcccg ggggaataca tacccgcagg cgtagagaca acattacagc | 31500 |
| ccccatagga ggtataacaa aattaatagg agagaaaaac acataaacac ctgaaaaacc | 31560 |
| ctcctgccta ggcaaaatag caccctcccg ctccagaaca acatacagcg cttccacagc | 31620 |
| ggcagccata acagtcagcc ttaccagtaa aaaagaaaac ctattaaaaa aacaccactc | 31680 |
| gacacggcac cagctcaatc agtcacagtg taaaaagggg ccaagtgcag agcgagtata | 31740 |
| tataggacta aaaatgacg taacggttaa agtccacaaa aaacacccag aaaaccgcac | 31800 |
| gcgaacctac gcccagaaac gaaagccaaa aaacccacaa cttcctcaaa tcgtcacttc | 31860 |
| cgttttccca cgttacgtca cttcccattt taagaaaact acaattccca acacatacaa | 31920 |
| gttactccgc cctaaaacct acgtcacccg ccccgttccc acgccccgcg ccacgtcaca | 31980 |
| aactccaccc cctcattatc atattggctt caatccaaaa taaggtatat tattgatgat | 32040 |

<210> SEQ ID NO 9
<211> LENGTH: 2500
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 9

| | | | |
|---|---|---|---|
| ggaggacact tctcagaagg ggttgttttg cttttgctta tttccgtcca tttccctctc | 60 |
| tgcgcgcgga ccttccttt ccagatggtg agagccgcgg ggacacccga cgccggggca | 120 |
| ggctgatcca cgatcctggg tgtgcgtaac gccgcctggg gctccgtggg cgagggacgt | 180 |
| gtggggacag gtgcaccgga aactgccaga ctggagagtt gaggcatcgg aggcgcgaga | 240 |
| acagcactac tactgcggcg agacgagcgc ggcgcatccc aaagcccggc caaatgcgct | 300 |
| cgtccctggg aggggaggga ggcgcgcctg gagcggggac agtcttggtc cgcgccctcc | 360 |
| tcccgggtct gtgccgggac ccgggacccg ggagccgtcg caggtctcgg tccaaggggc | 420 |

```
cccttttctc ggaagggcgg cggccaagag cagggaaggt ggatctcagg tagcgagtct      480
gggcttcggg gacggcgggg aggggagccg gacgggagga tgagctcccc tggcaccgag      540
agcgcgggaa agagcctgca gtaccgagtg gaccacctgc tgagcgccgt ggagaatgag      600
ctgcaggcgg gcagcgagaa gggcgacccc acagagcgcg aactgcgcgt gggcctggag      660
gagagcgagc tgtggctgcg cttcaaggag ctcaccaatg agatgatcgt gaccaagaac      720
ggcaggagga tgtttccggt gctgaaggtg aacgtgtctg gcctggaccc caacgccatg      780
tactccttcc tgctggactt cgtggcggcg gacaaccacc gctggaagta cgtgaacggg      840
gaatgggtgc cggggggcaa gccggagccg caggcgccca gctgcgtcta catccacccc      900
gactcgccca acttcggggc ccactggatg aaggctcccg tctccttcag caaagtcaag      960
ctcaccaaca agctcaacgg aggggggccag atcatgctga actccttgca taagtatgag     1020
cctcgaatcc acatagtgag agttgggggt ccacagcgca tgatcaccag ccactgcttc     1080
cctgagaccc agttcatagc ggtgactgct tatcagaacg aggagatcac agctcttaaa     1140
attaagtaca atccatttgc aaaagctttc cttgatgcaa aggaaagaag tgatcacaaa     1200
gagatgatgg aggaacccgg agacagccag caacctgggt actcccaatg ggggtggctt     1260
cttcctggaa ccagcaccct gtgtccacct gcaaatcctc atcctcagtt tggaggtgcc     1320
ctctccctcc cctccacgca cagctgtgac aggtacccaa ccctgaggag ccaccggtcc     1380
tcaccctacc ccagccccta tgctcatcgg aacaattctc aacctattc tgacaactca      1440 cctgcatgtt tatccatgct gcaatcccat gacaattggt ccagccttgg aatgcctgcc     1500
catcccagca tgctccccgt gagccacaat gccagcccac ctaccagctc cagtcagtac     1560
cccagcctgt ggtctgtgag caacggcgcc gtcaccccgg gctcccaggc agcagccgtg     1620
tccaacgggc tgggggccca gttcttccgg ggctcccccg cgcactacac accccctcacc    1680 catccggtct cggcgccctc ttcctcggga tccccactgt acgaagggggc ggccgcggcc    1740 acagacatcg tggacagcca gtacgacgcc gcagcccaag gccgcctcat agcctcatgg     1800
acacctgtgt cgccaccttc catgtgaagc agcaaggccc aggtcccgaa agatgcagtg     1860 acttttttgtc gtggcagcca gtggtgactg gattgaccta ctaggtaccc agtggcagtc     1920
tcaggttaag aaggaaatgc agcctcagta acttccttt caaagcagtg gaggagcaca      1980 cggcacccttt ccccagagcc ccagcatccc ttgctcacac ctgcagtagc ggtgctgtcc     2040
caggtggctt acagatgaac ccaactgtgg agatgatgca gttggcccaa cctcactgac     2100
ggtgaaaaaa tgtttgccag ggtccagaaa cttttttttgg tttatttctc atacagtgta     2160
ttggcaactt tggcacacca gaatttgtaa actccaccag tcctacttta gtgagataaa     2220
aagcacactc ttaatcttct tccttgttgc tttcaagtag ttagagttga gctgttaagg     2280
acagaataaa atcatagttg aggacagcag gttttagttg aattgaaaat ttgactgctc     2340 tgcccctag aatgtgtgta ttttaagcat atgtagctaa tctcttgtgt tgttaaacta      2400
taactgtttc atattttct tttgacaaag tagccaaaga caatcagcag aaagcatttt      2460
ctgcaaaata aacgcaatat gcaaaaaaaa aaaaaaaaa                            2500
```

<210> SEQ ID NO 10
<211> LENGTH: 1251
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10

```
tctagagcca ccatgagctc ccctggcacc gagagcgcgg gaaagagcct gcagtaccga      60
gtggaccacc tgctgagcgc cgtggagaat gagctgcagg cgggcagcga aagggcgac      120
cccacagagc gcgaactgcg cgtgggcctg gaggagagcg agctgtggct gcgcttcaag     180
gagctcacca atgagatgat cgtgaccaag aacggcagga ggatgtttcc ggtgctgaag     240
gtgaacgtgt ctggcctgga ccccaacgcc atgtactcct tcctgctgga cttcgtggcg    300
gcggacaacc accgctggaa gtacgtgaac ggggaatggg tgccggggg caagccggag    360
ccgcaggcgc ccagctgcgt ctacatccac cccgactcgc caacttcgg ggcccactgg    420
atgaaggctc ccgtctcctt cagcaaagtc aagctcacca caagctcaa cggaggggc    480
cagatcatg tgaactcctt gcataagtat gagcctcgaa tccacatagt gagagttggg    540
ggtccacagc gcatgatcac cagccactgc ttccctgaga cccagttcat agcggtgact   600
gctagaagtg atcacaaaga gatgatggag gaacccggag acagccagca acctgggtac   660
tcccaatggg ggtggcttct tcctggaacc agcaccgtgt gtccacctgc aaatcctcat   720
cctcagtttg gaggtgccct ctccctcccc tccacgcaca gctgtgacag gtacccaacc    780
ctgaggagcc accggtcctc accctacccc agccctatg ctcatcggaa caattctcca   840
acctattctg acaactcacc tgcatgttta tccatgctgc aatcccatga caattggtcc   900
agccttggaa tgcctgccca tcccagcatg ctccccgtga gccacaatgc agcccacct   960
accagctcca gtcagtaccc cagcctgtgg tctgtgagca acggcgccgt caccccgggc  1020
tcccaggcag cagccgtgtc caacgggctg ggggcccagt tcttccgggg ctcccccgcg  1080
cactacacac ccctcaccca tccggtctcg gcgccctctt cctcgggatc cccactgtac  1140
gaagggcgg ccgcggccac agacatcgtg gacagccagt acgacgccgc agcccaaggc   1200
cgcctcatag cctcatggac acctgtgtcg ccaccttcca tgtgagatat c           1251
```

<210> SEQ ID NO 11
<211> LENGTH: 9
<212> TYPE: DNA
<213> ORGANISM: Gallus gallus
<220> FEATURE:
<221> NAME/KEY: modified_base
<222> LOCATION: (8)..(8)
<223> OTHER INFORMATION: a, c, t, g, unknown or other

<400> SEQUENCE: 11

```
tctctccna                                                              9
```

<210> SEQ ID NO 12
<211> LENGTH: 435
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
            20                  25                  30

Glu Lys Gly Asp Pro Thr Glu Arg Glu Leu Arg Val Gly Leu Glu Glu
        35                  40                  45
```

```
Ser Glu Leu Trp Leu Arg Phe Lys Glu Leu Thr Asn Glu Met Ile Val
 50                  55                  60
Thr Lys Asn Gly Arg Arg Met Phe Pro Val Leu Lys Val Asn Val Ser
 65                  70                  75                  80
Gly Leu Asp Pro Asn Ala Met Tyr Ser Phe Leu Leu Asp Phe Val Ala
                 85                  90                  95
Ala Asp Asn His Arg Trp Lys Tyr Val Asn Gly Glu Trp Val Pro Gly
            100                 105                 110
Gly Lys Pro Glu Pro Gln Ala Pro Ser Cys Val Tyr Ile His Pro Asp
            115                 120                 125
Ser Pro Asn Phe Gly Ala His Trp Met Lys Ala Pro Val Ser Phe Ser
        130                 135                 140
Lys Val Lys Leu Thr Asn Lys Leu Asn Gly Gly Gln Ile Met Leu
145                 150                 155                 160
Asn Ser Leu His Lys Tyr Glu Pro Arg Ile His Ile Val Arg Val Gly
                165                 170                 175
Asp Pro Gln Arg Met Ile Thr Ser His Cys Phe Pro Gly Thr Gln Phe
            180                 185                 190
Ile Ala Val Thr Ala Tyr Gln Asn Glu Glu Ile Thr Ala Leu Lys Ile
        195                 200                 205
Lys Tyr Asn Pro Phe Ala Lys Ala Phe Leu Asp Ala Lys Glu Arg Ser
210                 215                 220
Asp His Lys Glu Met Met Glu Glu Pro Gly Asp Ser Gln Gln Pro Gly
225                 230                 235                 240
Tyr Ser Gln Trp Gly Trp Leu Leu Pro Gly Thr Ser Thr Leu Cys Pro
                245                 250                 255
Pro Ala Asn Pro His Pro Gln Phe Gly Gly Ala Leu Ser Leu Pro Ser
            260                 265                 270
Thr His Ser Cys Asp Arg Tyr Pro Thr Leu Arg Ser His Arg Ser Ser
        275                 280                 285
Pro Tyr Pro Ser Pro Tyr Ala His Arg Asn Asn Ser Pro Thr Tyr Ser
290                 295                 300
Asp Asn Ser Pro Ala Cys Leu Ser Met Leu Gln Ser His Asp Asn Trp
305                 310                 315                 320
Ser Ser Leu Gly Met Pro Ala His Pro Ser Met Leu Pro Val Ser His
                325                 330                 335
Asn Ala Ser Pro Pro Thr Ser Ser Ser Gln Tyr Pro Ser Leu Trp Ser
            340                 345                 350
Val Ser Asn Gly Ala Val Thr Pro Gly Ser Gln Ala Ala Ala Val Thr
        355                 360                 365
Asn Gly Leu Gly Ala Gln Phe Phe Arg Gly Ser Pro Ala His Tyr Thr
370                 375                 380
Pro Leu Thr His Pro Val Ser Ala Pro Ser Ser Ser Gly Ser Pro Leu
385                 390                 395                 400
Tyr Glu Gly Ala Ala Ala Thr Asn Ile Val Asp Ser Gln Tyr Asp
                405                 410                 415
Ala Ala Ala Gln Gly Arg Leu Ile Ala Ser Trp Thr Pro Val Ser Pro
            420                 425                 430
Pro Ser Met
        435
```

<210> SEQ ID NO 13
<211> LENGTH: 31465
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 13

```
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgtttttg     180
gtgtgcgccg gtgtacacag gaagtgacaa ttttcgcgcg ttttaggcg gatgttgtag      240
taaatttggg cgtaaccgag taagatttgg ccattttcgc gggaaaactg aataagagga     300
agtgaaatct gaataatttt gtgttactca tagcgcgtaa tactgtaata gtaatcaatt     360
acggggtcat tagttcatag cccatatatg gagttccgcg ttacataact tacggtaaat     420
ggcccgcctg gctgaccgcc caacgacccc cgcccattga cgtcaataat gacgtatgtt     480
cccatagtaa cgccaatagg gactttccat tgacgtcaat gggtggagta tttacggtaa     540
actgcccact tggcagtaca tcaagtgtat catatgccaa gtacgccccc tattgacgtc     600
aatgacggta aatggcccgc ctggcattat gcccagtaca tgaccttatg gactttcct     660
acttggcagt acatctacgt attagtcatc gctattacca tggtgatgcg gttttggcag     720
tacatcaatg ggcgtggata gcggtttgac tcacggggat ttccaagtct ccaccccatt     780
gacgtcaatg ggagtttgtt ttggcaccaa aatcaacggg actttccaaa atgtcgtaac     840
aactccgccc cattgacgca aatgggcggt aggcgtgtac ggtgggaggt ctatataagc     900
agagctggtt tagtgaaccg tcagatccgc tagagatctg gtaccgtcga cgcggccgct     960
cgagcctaag cttctagatg catgctcgag cggccgccag tgtgatggat atctgcagaa    1020
ttcgcccttg cttctagagc caccatgagc tcccctggca ccgagagcgc gggaaagagc    1080
ctgcagtacc gagtggacca cctgctgagc gccgtggaga atgagctgca ggcgggcagc    1140
gagaagggcg accccacaga gcgcgaactg cgcgtgggcc tggaggagag cgagctgtgg    1200
ctgcgcttca aggagctcac caatgagatg atcgtgacca agaacggcag gaggatgttt    1260
ccggtgctga aggtgaacgt gtctggcctg gaccccaacg ccatgtactc cttcctgctg    1320
gacttcgtgg cggcgacaa ccaccgctgg aagtacgtga acggggaatg ggtgccgggg    1380
ggcaagccgg agccgcaggc gcccagctgc gtctacatcc ccccgactc gcccaacttc    1440
ggggcccact ggatgaaggc tcccgtctcc ttcagcaaag tcaagctcac caacaagctc    1500
aacggagggg gccagatcat gctgaactcc ttgcataagt atgagcctcg aatccacata    1560
gtgagagttg ggggtccaca gcgcatgatc accagccact gcttcctga cccagttc    1620
atagcggtga ctgctagaag tgatcacaaa gagatgatgg aggaacccgg agacagccag    1680
caacctgggt actcccaatg ggggtggctt cttcctggaa ccagcaccgt gtgtccacct    1740
gcaaatcctc atcctcagtt tggaggtgcc ctctccctcc cctccacgca cagctgtgac    1800
aggtacccaa ccctgaggag ccaccggtcc tcaccctacc ccagccccta tgctcatcgg    1860
aacaattctc caacctattc tgacaactca cctgcatgtt tatccatgct gcaatcccat    1920
gacaattggt ccagccttgg aatgcctgcc catcccagca tgctccccgt gagccacaat    1980
gccagcccac ctaccagctc cagtcagtac cccagcctgt ggtctgtgag caacggcgcc    2040
gtcaccccgg gctcccaggc agcagccgtg tccaacgggc tggggcccca gttcttccgg    2100
ggctcccccg cgcactacac acccctcacc catccggtct cggcgccctc ttcctcggga    2160
```

```
tccccactgt acgaaggggc ggccgcggcc acagacatcg tggacagcca gtacgacgcc    2220
gcagcccaag gccgcctcat agcctcatgg acacctgtgt cgccaccttc catgtgagat    2280
atccgatcca ccggatctag ataactgatc ataatcagcc ataccacatt tgtagaggtt    2340
ttacttgctt taaaaaacct cccacacctc cccctgaacc tgaaacataa aatgaatgca    2400
attgttgttg ttaacttgtt tattgcagct tataatggtt acaaataaag caatagcatc    2460
acaaatttca caaataaagc atttttttca ctgcattcta gttgtggttt gtccaaactc    2520
atcaatgtat cttaacgcgg atctggaagg tgctgaggta cgatgagacc cgcaccaggt    2580
gcagaccctg cgagtgtggc ggtaaacata ttaggaacca gcctgtgatg ctggatgtga    2640
ccgaggagct gaggcccgat cacttggtgc tggcctgcac ccgcgctgag tttggctcta    2700
gcgatgaaga tacagattga ggtactgaaa tgtgtgggcg tggcttaagg gtgggaaaga    2760
atatataagg tgggggtctt atgtagtttt gtatctgttt tgcagcagcc gccgccgcca    2820
tgagcaccaa ctcgtttgat ggaagcattg tgagctcata tttgacaacg cgcatgcccc    2880
catgggccgg ggtgcgtcag aatgtgatgg gctccagcat tgatggtcgc cccgtcctgc    2940
ccgcaaactc tactaccttg acctacgaga ccgtgtctgg aacgccgttg gagactgcag    3000
cctccgccgc cgcttcagcc gctgcagcca ccgcccgcgg gattgtgact gactttgctt    3060
tcctgagccc gcttgcaagc agtgcagctt cccgttcatc cgcccgcgat gacaagttga    3120
cggctctttt ggcacaattg gattctttga cccgggaact taatgtcgtt tctcagcagc    3180
tgttggatct gcgccagcag gtttctgccc tgaaggcttc ctcccctccc aatgcggttt    3240
aaaacataaa taaaaaacca gactctgttt ggatttggat caagcaagtg tcttgctgtc    3300
tttatttagg ggttttgcgc gcgcggtagg cccgggacca gcggtctcgg tcgttgaggg    3360
tcctgtgtat ttttccagg acgtggtaaa ggtgactctg gatgttcaga tacatgggca    3420
taagcccgtc tctggggtgg aggtagcacc actgcagagc ttcatgctgc ggggtggtgt    3480
tgtagatgat ccagtcgtag caggagcgct gggcgtggtg cctaaaaatg tctttcagta    3540
gcaagctgat tgccaggggc aggcccttgg tgtaagtgtt tacaaagcgg ttaagctggg    3600
atgggtgcat acgtggggat atgagatgca tcttggactg tattttaggg ttggctatgt    3660
tcccagccat atccctccgg ggattcatgt tgtgcagaac caccagcaca gtgtatccgg    3720
tgcacttggg aaatttgtca tgtagcttag aaggaaatgc gtggaagaac ttggagacgc    3780
ccttgtgacc tccaagattt tccatgcatt cgtccataat gatggcaatg ggcccacggg    3840
cggcggcctg ggcgaagata tttctgggat cactaacgtc atagttgtgt tccaggatga    3900
gatcgtcata ggccattttt acaaagcgcg gcggagggt gccagactgc ggtataatgg    3960
ttccatccgg cccaggggcg tagttaccct cacagatttg catttcccac gctttgagtt    4020
cagatggggg gatcatgtct acctgcgggg cgatgaagaa aacggtttcc ggggtagggg    4080
agatcagctg ggaagaaagc aggttcctga gcagctgcga cttaccgcag ccggtgggcc    4140
cgtaaatcac acctattacc ggctgcaact ggtagttaag agagctgcag ctgccgtcat    4200
ccctgagcag gggggccact tcgttaagca tgtccctgac tcgcatgttt ccctgaccca    4260
aatccgccaa aaggcgctcg ccgcccacg atagcagttc ttgcaaggaa gcaaagtttt    4320
tcaacggttt gagaccgtcc gccgtaggca tgcttttgag cgtttgacca agcagttcca    4380
ggcggtccca cagctcggtc acctgctcta cggcatctcg atccagcata tctcctcgtt    4440
tcgcggggttg gggcggcttt cgctgtacgg cagtagtcgg tgctcgtcca dacgggccag    4500
ggtcatgtct ttccacgggc gcagggtcct cgtcagcgta gtctgggtca cggtgaaggg    4560
```

```
gtgcgctccg ggctgcgcgc tggccagggt gcgcttgagg ctggtcctgc tggtgctgaa   4620
gcgctgccgg tcttcgccct gcgcgtcggc caggtagcat ttgaccatgg tgtcatagtc   4680
cagcccctcc gcggcgtggc ccttggcgcg cagcttgccc ttggaggagg cgccgcacga   4740
ggggcagtgc agacttttga gggcgtagag cttgggcgcg agaataccg attccgggga   4800 gtaggcatcc gcgccgcagg ccccgcagac ggtctcgcat tccacgagcc aggtgagctc   4860
tggccgttcg gggtcaaaaa ccaggtttcc cccatgcttt ttgatgcgtt tcttacctct   4920
ggtttccatg agccggtgtc cacgctcggt gacgaaaagg ctgtccgtgt ccccgtatac   4980
agacttgaga ggcctgtcct cgagcggtgt tccgcggtcc tcctcgtata gaaactcgga   5040
ccactctgag acaaaggctc gcgtccaggc cagcacgaag gaggctaagt gggaggggta   5100
gcggtcgttg tccactaggg ggtccactcg ctccagggtg tgaagacaca tgtcgccctc   5160
ttcggcatca aggaaggtga ttggtttgta ggtgtaggcc acgtgaccgg tgttcctga   5220 aggggggcta taaaagggggg tggggcgcg ttcgtcctca ctctcttccg catcgctgtc   5280
tgcgagggcc agctgttggg gtgagtactc cctctgaaaa gcgggcatga cttctgcgct   5340
aagattgtca gtttccaaaa acgaggagga tttgatattc acctggcccg cggtgatgcc   5400
tttgagggtg gccgcatcca tctggtcaga aaagacaatc tttttgttgt caagcttggt   5460
ggcaaacgac ccgtagaggg cgttggacag caacttggcg atggagcgca gggtttggtt   5520
tttgtcgcga tcggcgcgct ccttggccgc gatgtttagc tgcacgtatt cgcgcgcaac   5580
gcaccgccat tcgggaaaga cggtggtgcg ctcgtcgggc accaggtgca cgcgccaacc   5640
gcggttgtgc agggtgacaa ggtcaacgct ggtggctacc tctccgcgta ggcgctcgtt   5700
ggtccagcag aggcggccgc ccttgcgcga gcagaatggc ggtaggggt ctagctgcgt   5760 ctcgtccggg gggtctgcgt ccacggtaaa gaccccgggc agcaggcgcg cgtcgaagta   5820
gtctatcttg catccttgca agtctagcgc ctgctgccat gcgcgggcgg caagcgcgcg   5880
ctcgtatggg ttgagtgggg gaccccatgg catgggtgg gtgagcgcgg aggcgtacat   5940
gccgcaaatg tcgtaaacgt agaggggctc tctgagtatt ccaagatatg tagggtagca   6000
tcttccaccg cggatgctgg cgcgcacgta atcgtatagt tcgtgcgagg gagcgaggag   6060
gtcgggaccg aggttgctac gggcgggctg ctctgctcgg aagactatct gcctgaagat   6120
ggcatgtgag ttgatgata tggttggacg ctggaagacg ttgaagctgg cgtctgtgag   6180
acctaccgcg tcacgcacga aggaggcgta ggagtcgcgc agcttgttga ccagctcggc   6240
ggtgacctgc acgtctaggg cgcagtagtc cagggtttcc ttgatgatgt catacttatc   6300
ctgtcccttt tttttccaca gctcgcggtt gaggacaaac tcttcgcggt cttttccagta   6360 ctcttggatc ggaaacccgt cggcctccga acggtaagag cctagcatgt agaactggtt   6420
gacggcctgg taggcgcagc atccctttc tacgggtagc gcgtatgcct gcgcggcctt   6480
ccggcatgac cagcatgaag ggcacgagct gcttcccaaa ggcccccatc caagtatagg   6540
tctctacatc gtaggtgaca aagagacgct cggtgcgagg atgcgagccg atcgggaaga   6600
actggatctc ccgccaccaa ttggaggagt ggctattgat gtggtgaaag tagaagtccc   6660
tgcgacgggc cgaacactcg tgctggcttt tgtaaaaacg tgcgcagtac tggcagcggt   6720
gcacgggctg tacatcctgc acgaggttga cctgacgacc gcgcacaagg aagcagagtg   6780
ggaatttgag cccctcgcct ggcggggttg gctggtggtc ttctacttcg gctgcttgtc   6840
cttgaccgtc tggctgctcg aggggagtta cggtggatcg gaccaccacg ccgcgcgagc   6900
```

```
ccaaagtcca gatgtccgcg cgcggcggtc ggagcttgat gacaacatcg cgcagatggg      6960
agctgtccat ggtctggagc tcccgcggcg tcaggtcagg cgggagctcc tgcaggttta      7020
cctcgcatag acgggtcagg gcgcgggcta gatccaggtg atacctaatt tccaggggct      7080
ggttggtggc ggcgtcgatg gcttgcaaga ggccgcatcc ccgcggcgcg actacggtac      7140
cgcgcggcgg gcggtgggcc gcgggggtgt ccttggatga tgcatctaaa agcggtgacg      7200
cgggcgagcc cccggaggta ggggggggctc cggacccgcc gggagagggg caggggcac      7260
gtcggcgccg cgcgcgggca ggagctggtg ctgcgcgcgt aggttgctgg cgaacgcgac      7320
gacgcggcgg ttgatctcct gaatctggcg cctctgcgtg aagacgacgg gcccggtgag      7380
cttgaacctg aaagagagtt cgacagaatc aatttcggtg tcgttgacgg cggcctggcg      7440
caaaatctcc tgcacgtctc ctgagttgtc ttgataggcg atctcggcca tgaactgctc      7500
gatctcttcc tcctggagat ctccgcgtcc ggctcgctcc acggtggcgg cgaggtcgtt      7560
ggaaatgcgg gccatgagct gcgagaaggc gttgaggcct ccctcgttcc agacgcggct      7620
gtagaccacg ccccctttcgg catcgcgggc gcgcatgacc acctgcgcga gattgagctc      7680
cacgtgccgg gcgaagacgg cgtagtttcg caggcgctga agaggtagt tgagggtggt      7740
ggcggtgtgt tctgccacga agaagtacat aacccagcgt cgcaacgtgg attcgttgat      7800
aattgttgtg taggtactcc gccgccgagg gacctgagcg agtccgcatc gaccggatcg      7860
gaaaccctct cgagaaaggc gtctaaccag tcacagtcgc aaggtaggct gagcaccgtg      7920
gcgggcggca gcgggcggcg gtcgggggttg tttctggcgg aggtgctgct gatgatgtaa      7980
ttaaagtagg cggtcttgag acggcggatg gtcgacagaa gcaccatgtc cttgggtccg      8040
gcctgctgaa tgcgcaggcg gtcggccatg ccccaggctt cgttttgaca tcggcgcagg      8100
tctttgtagt agtcttgcat gagccttttct accggcactt cttcttctcc ttcctcttgt      8160
cctgcatctc ttgcatctat cgctgcggcg gcggcggagt ttggccgtag gtggcgccct      8220
cttcctccca tgcgtgtgac cccgaagccc ctcatcggct gaagcagggc taggtcggcg      8280
acaacgcgct cggctaatat ggcctgctgc acctgcgtga gggtagactg gaagtcatcc      8340
atgtccacaa agcggtggta tgcgcccgtg ttgatggtgt aagtgcagtt ggccataacg      8400
gaccagttaa cggtctggtg accggctgc gagagctcgg tgtacctgag acgcgagtaa      8460
gccctcgagt caaatacgta gtcgttgcaa gtccgcacca ggtactggta tcccaccaaa      8520
aagtgcggcg gcggctggcg gtagaggggc cagcgtaggg tggccggggc tccggggcg      8580
agatcttcca acataaggcg atgatatccg tagatgtacc tggacatcca ggtgatgccg      8640
gcggcggtgg tggaggcgcg cggaaagtcg cggacgcggt tccagatgtt gcgcagcggc      8700
aaaaagtgct ccatggtcgg gacgctctgg ccggtcaggc gcgcgcaatc gttgacgctc      8760
tagcgtgcaa aaggagagcc tgtaagcggg cactcttccg tggtctggtg gataaattcg      8820
caagggtatc atggcggacg accggggttc gagcccgta tccggccgtc cgccgtgatc      8880
catgcggtta ccgcccgcgt gtcgaaccca ggtgtgcgac gtcagacaac gggggagtgc      8940
tcctttttggc ttccttccag gcgcggcggc tgctgcgcta gcttttttgg ccactggccg      9000
cgcgcagcgt aagcggttag gctggaaagc gaaagcatta agtggctcgc tccctgtagc      9060
cggagggtta ttttccaagg gttgagtcgc gggacccccg gttcgagtct cggaccggcc      9120
ggactgcggc gaacgggggt ttgcctcccc gtcatgcaag accccgcttg caaattcctc      9180
cggaaacagg gacgagcccc ttttttgctt ttcccagatg catccggtgc tgcggcagat      9240
gcgcccccct cctcagcagc ggcaagagca agagcagcgg cagacatgca gggcaccctc      9300
```

```
ccctcctcct accgcgtcag gaggggcgac atccgcggtt gacgcggcag cagatggtga    9360
ttacgaaccc ccgcggcgcc gggcccggca ctacctggac ttggaggagg gcgagggcct    9420
ggcgcggcta ggagcgccct ctcctgagcg gcacccaagg gtgcagctga agcgtgatac    9480
gcgtgaggcg tacgtgccgc ggcagaacct gtttcgcgac cgcagggag aggagcccga    9540
ggagatgcgg gatcgaaagt tccacgcagg gcgcgagctg cggcatggcc tgaatcgcga    9600
gcggttgctg cgcgaggagg actttgagcc cgacgcgcga accgggatta gtcccgcgcg    9660
cgcacacgtg gcggccgccg acctggtaac cgcatacgag cagacggtga accaggagat    9720
taactttcaa aaaagcttta acaaccacgt gcgtacgctt gtggcgcgcg aggaggtggc    9780
tataggactg atgcatctgt gggactttgt aagcgcgctg gagcaaaacc caaatagcaa    9840
gccgctcatg gcgcagctgt tccttatagt gcagcacagc agggacaacg aggcattcag    9900
ggatgcgctg ctaaacatag tagagcccga gggccgctgg ctgctcgatt tgataaacat    9960
cctgcagagc atagtggtgc aggagcgcag cttgagcctg gctgacaagg tggccgccat   10020
caactattcc atgcttagcc tgggcaagtt ttacgcccgc aagatatacc atacccctta   10080
cgttcccata gacaaggagg taaagatcga ggggttctac atgcgcatgg cgctgaaggt   10140
gcttaccttg agcgacgacc tgggcgttta tcgcaacgag cgcatccaca aggccgtgag   10200
cgtgagccgg cggcgcgagc tcagcgaccg cgagctgatg cacagcctgc aaagggccct   10260
ggctggcacg ggcagcggcg atagagaggc cgagtcctac tttgacgcgg gcgctgacct   10320
gcgctgggcc ccaagccgac gcgccctgga ggcagctggg gccggacctg gctggcggt   10380
ggcacccgcg cgcgctggca acgtcggcgg cgtggaggaa tatgacgagg acgatgagta   10440
cgagccagag gacggcgagt actaagcggt gatgtttctg atcagatgat gcaagacgca   10500
acggacccgg cggtgcgggc ggcgctgcag agccagccgt ccggccttaa ctccacggac   10560
gactggcgcc aggtcatgga ccgcatcatg tcgctgactg cgcgcaatcc tgacgcgttc   10620
cggcagcagc cgcaggccaa ccggctctcc gcaattctgg aagcggtggt cccggcgcgc   10680
gcaaacccca cgcacgagaa ggtgctggcg atcgtaaacg cgctggccga aaacagggcc   10740
atccggcccg acgaggccgg cctggtctac gacgcgctgc ttcagcgcgt ggctcgttac   10800
aacagcggca acgtgcagac caacctggac cggctggtgg gggatgtgcg cgaggccgtg   10860
gcgcagcgtg agcgcgcgca gcagcagggc aacctgggct ccatggttgc actaaacgcc   10920
ttcctgagta cacagcccgc caacgtgccg cggggacagg aggactacac caactttgtg   10980
agcgcactgc ggctaatggt gactgagaca ccgcaaagtg aggtgtacca gtctgggcca   11040
gactattttt tccagaccag tagacaaggc ctgcagaccg taaacctgag ccaggctttc   11100
aaaaacttgc aggggctgtg gggggtgcgg gctcccacag gcgaccgcgc gaccgtgtct   11160
agcttgctga cgcccaactc gcgcctgttg ctgctgctaa tagcgcccct cacggacagt   11220
ggcagcgtgt cccgggacac ataccctaggt cacttgctga cactgtaccg cgaggccata   11280
ggtcaggcgc atgtggacga gcatactttc caggagatta caagtgtcag ccgcgcgctg   11340
gggcaggagg acacgggcag cctggaggca accctaaact acctgctgac caaccggcgg   11400
cagaagatcc cctcgttgca cagttttaaac agcgaggagg agcgcatttt gcgctacgtg   11460
cagcagagcg tgagccttaa cctgatgcgc gacggggtaa cgcccagcgt ggcgctggac   11520
atgaccgcgc gcaacatgga accgggcatg tatgcctcaa accggccgtt tatcaaccgc   11580
ctaatggact acttgcatcg cgcggccgcc gtgaaccccc agtatttcac caatgccatc   11640
```

```
ttgaacccgc actggctacc gccccctggt ttctacaccg ggggattcga ggtgcccgag    11700
ggtaacgatg gattcctctg ggacgacata gacgacagcg tgttttcccc gcaaccgcag    11760
accctgctag agttgcaaca gcgcgagcag gcagaggcgg cgctgcgaaa ggaaagcttc    11820
cgcaggccaa gcagcttgtc cgatctaggc gctgcggccc cgcggtcaga tgctagtagc    11880
ccatttccaa gcttgatagg gtctcttacc agcactcgca ccacccgccc gcgcctgctg    11940
ggcgaggagg agtacctaaa caactcgctg ctgcagccgc agcgcgaaaa aaacctgcct    12000
ccggcatttc ccaacaacgg gatagagagc ctagtggaca agatgagtag atggaagacg    12060
tacgcgcagg agcacaggga cgtgccaggc ccgcgcccgc ccacccgtcg tcaaaggcac    12120
gaccgtcagc ggggtctggt gtgggaggac gatgactcgg cagacgacag cagcgtcctg    12180
gatttgggag ggagtggcaa cccgtttgcg caccttcgcc ccaggctggg gagaatgttt    12240
taaaaaaaaa aaagcatgat gcaaaataaa aaactcacca aggccatggc accgagcgtt    12300
ggttttcttg tattcccctt agtatgcggc gcgcggcgat gtatgaggaa ggtcctcctc    12360
cctcctacga gagtgtggtg agcgcggcgc cagtggcggc ggcgctgggt tctcccttcg    12420
atgctcccct ggacccgccg tttgtgcctc cgcggtacct gcggcctacc gggggagaa    12480
acagcatccg ttactctgag ttggcacccc tattcgacac cacccgtgtg tacctggtgg    12540
acaacaagtc aacggatgtg gcatccctga actaccagaa cgaccacagc aactttctga    12600
ccacggtcat tcaaaacaat gactacagcc gggggaggc aagcacacag accatcaatc    12660
ttgacgaccg gtcgcactgg ggcggcgacc tgaaaaccat cctgcatacc aacatgccaa    12720
atgtgaacga gttcatgttt accaataagt ttaaggcgcg ggtgatggtg tcgcgcttgc    12780
ctactaagga caatcaggtg gagctgaaat acgagtgggt ggagttcacg ctgcccgagg    12840
gcaactactc cgagaccatg accatagacc ttatgaacaa cgcgatcgtg gagcactact    12900
tgaaagtggg cagacagaac ggggttctgg aaagcgacat cggggtaaag tttgacaccc    12960
gcaacttcag actggggttt gaccccgtca ctggtcttgt catgcctggg gtatatacaa    13020
acgaagcctt ccatccagac atcatttttc tgccaggatg cggggtggac ttcacccaca    13080
gccgcctgag caacttgttg ggcatccgca agcggcaacc cttccaggag gctttttagga    13140
tcacctacga tgatctggag ggtggtaaca ttcccgcact gttggatgtg gacgcctacc    13200
aggcgagctt gaaagatgac accgaacagg gcggggtgg cgcaggcggc agcaacagca    13260
gtggcagcgg cgcggaagag aactccaacg cggcagccgc ggcaatgcag ccggtggagg    13320
acatgaacga tcatgccatt cgcggcgaca cctttgccac acgggctgag gagaagcgcg    13380
ctgaggccga agcagcggcc gaagctgccg ccccccgctgc gcaacccgag gtcgagaagc    13440
ctcagaagaa accggtgatc aaaccccctga cagaggacag caagaaacgc agttacaacc    13500
taataagcaa tgacagcacc ttcacccagt accgcagctg gtaccttgca tacaactacg    13560
gcgaccctca gaccggaatc cgctcatgga ccctgctttg cactcctgac gtaacctgcg    13620
gctcggagca ggtctactgg tcgttgccag acatgatgca agacccgtg accttccgct    13680
ccacgcgcca gatcagcaac tttccggtgg tgggcgccga gctgttgccc gtgcactcca    13740
agagcttcta caacgaccag gccgtctact cccaactcat ccgccagttt acctctctga    13800
cccacgtgtt caatcgcttt cccgagaacc agattttggc gcgcccgcca gcccccacca    13860
tcaccaccgt cagtgaaaac gttcctgctc tcacagatca cgggacgcta ccgctgcgca    13920
acagcatcgg aggagtccag cgagtgacca ttactgacgc cagacgccgc acctgcccct    13980
acgtttacaa ggcctggggc atagtctcgc cgcgcgtcct atcgagccgc acttttttgag    14040
```

```
caagcatgtc catccttata tcgcccagca ataacacagg ctggggcctg cgcttcccaa    14100
gcaagatgtt tggcggggcc aagaagcgct ccgaccaaca cccagtgcgc gtgcgcgggc    14160
actaccgcgc gccctggggc gcgcacaaac gcggccgcac tgggcgcacc accgtcgatg    14220
acgccatcga cgcggtggtg gaggaggcgc gcaactacac gcccacgccg ccaccagtgt    14280
ccacagtgga cgcggccatt cagaccgtgg tgcgcggagc ccggcgctat gctaaaatga    14340
agagacggcg gaggcgcgta gcacgtcgcc accgccgccg accggcact gccgcccaac     14400 gcgcggcggc ggccctgctt aaccgcgcac gtcgcaccgg ccgacgggcg gccatgcggg    14460
ccgctcgaag gctggccgcg ggtattgtca ctgtgccccc caggtccagg cgacgagcgg    14520
ccgccgcagc agccgcggcc attagtgcta tgactcaggg tcgcagggc aacgtgtatt     14580 gggtgcgcga ctcggttagc ggcctgcgcg tgcccgtgcg cacccgcccc ccgcgcaact    14640
agattgcaag aaaaaactac ttagactcgt actgttgtat gtatccagcg gcggcggcgc    14700
gcaacgaagc tatgtccaag cgcaaaatca agaagagat gctccaggtc atcgcgccgg     14760
agatctatgg ccccccgaag aaggaagagc aggattacaa gccccgaaag ctaaagcggg    14820
tcaaaaagaa aaagaaagat gatgatgatg aacttgacga cgaggtggaa ctgctgcacg    14880
ctaccgcgcc caggcgacgg gtacagtgga aggtcgacg cgtaaaacgt gttttgcgac     14940
ccggcaccac cgtagtctttt acgcccggtg agcgctccac ccgcacctac aagcgcgtgt    15000
atgatgaggt gtacggcgac gaggacctgc ttgagcaggc caacgagcgc ctcggggagt    15060
ttgcctacgg aaagcggcat aaggacatgc tggcgttgcc gctggacgag ggcaacccca    15120
cacctagcct aaagcccgta acactgcagc aggtgctgcc cgcgcttgca ccgtccgaag    15180
aaaagcgcgg cctaaagcgc gagtctggtg acttggcacc caccgtgcag ctgatggtac    15240
ccaagcgcca gcgactggaa gatgtcttgg aaaaaatgac cgtggaacct gggctggagc    15300
ccgaggtccg cgtgcggcca atcaagcagg tggcgccggg actgggcgtg cagaccgtgg    15360
acgttcagat acccactacc agtagcacca gtattgccac cgccacagag ggcatggaga    15420
cacaaacgtc cccggttgcc tcagcggtgg cggatgccgc ggtgcaggcg gtcgctgcgg    15480
ccgcgtccaa gacctctacg gaggtgcaaa cggacccgtg gatgtttcgc gtttcagccc    15540
cccggcgccc gcgccgttcg aggaagtacg gcgccgccag cgcgctactg cccgaatatg    15600
ccctacatcc ttccattgcg cctaccccg gctatcgtgg ctacacctac cgccccagaa     15660
gacgagcaac tacccgacgc cgaaccacca ctggaacccg ccgccgccgt cgccgtcgcc    15720
agcccgtgct ggccccgatt tccgtgcgca gggtggctcg cgaaggaggc aggaccctgg    15780
tgctgccaac agcgcgctac caccccagca tcgtttaaaa gccggtcttt gtggttcttg    15840
cagatatggc cctcacctgc cgcctccgtt tccggtgcc gggattccga ggaagaatgc     15900
accgtaggag gggcatggcc ggccacggcc tgacgggcgg catgcgtcgt gcgcaccacc    15960 ggcggcggc cgcgtcgcac cgtcgcatgc gcggcggtat cctgcccctc cttattccac     16020
tgatcgccgc ggcgattggc gccgtgcccg gaattgcatc cgtggccttg caggcgcaga    16080
gacactgatt aaaacaagt tgcatgtgga aaaatcaaaa taaaagtct ggactctcac      16140 gctcgcttgg tcctgtaact attttgtaga atggaagaca tcaactttgc gtctctggcc    16200
ccgcgacacg gctcgcgccc gttcatggga aactggcaag atatcggcac cagcaatatg    16260
agcggtggcg ccttcagctg gggctcgctg tggagcggca ttaaaaattt cggttccacc    16320
gttaagaact atggcagcaa ggcctggaac agcagcacag gccagatgct gagggataag    16380
```

```
ttgaaagagc aaaatttcca acaaaaggtg gtagatggcc tggcctctgg cattagcggg   16440
gtggtggacc tggccaacca ggcagtgcaa aataagatta acagtaagct tgatccccgc   16500
cctcccgtag aggagcctcc accggccgtg gagacagtgt ctccagaggg gcgtggcgaa   16560
aagcgtccgc gccccgacag ggaagaaact ctggtgacgc aaatagacga gcctccctcg   16620
tacgaggagg cactaaagca aggcctgccc accacccgtc ccatcgcgcc catggctacc   16680
ggagtgctgg gccagcacac acccgtaacg ctggacctgc ctcccccgc cgacacccag    16740
cagaaacctg tgctgccagg cccgaccgcc gttgttgtaa cccgtcctag ccgcgcgtcc   16800
ctgcgccgcg ccgccagcgg tccgcgatcg ttgcggcccg tagccagtgg caactggcaa   16860
agcacactga acagcatcgt gggtctgggg gtgcaatccc tgaagcgccg acgatgcttc   16920
tgatagctaa cgtgtcgtat gtgtgtcatg tatgcgtcca tgtcgccgcc agaggagctg   16980
ctgagccgcc gcgcgcccgc tttccaagat ggctaccccct tcgatgatgc cgcagtggtc   17040
ttacatgcac atctcgggcc aggacgcctc ggagtacctg agcccgggc tggtgcagtt    17100
tgcccgcgcc accgagacgt acttcagcct gaataacaag tttagaaacc ccacggtggc   17160
gcctacgcac gacgtgacca cagaccggtc ccagcgtttg acgctgcggt tcatccctgt   17220
ggaccgtgag gatactgcgt actcgtacaa ggcgcggttc acccctagctg tgggtgataa   17280
ccgtgtgctg gacatggctt ccacgtactt tgacatccgc ggcgtgctgg acaggggccc   17340
tactttttaag ccctactctg gcactgccta caacgccctg gctcccaagg gtgccccaaa  17400
tccttgcgaa tgggatgaag ctgctactgc tcttgaaata aacctagaag aagaggacga   17460
tgacaacgaa gacgaagtag acgagcaagc tgagcagcaa aaaactcacg tatttgggca   17520
ggcgccttat tctggtataa atattacaaa ggagggtatt caaataggtg tcgaaggtca   17580
aacacctaaa tatgccgata aaacatttca acctgaacct caaataggag aatctcagtg   17640
gtacgaaaca gaaattaatc atgcagctgg gagagtccta aaaaagacta ccccaatgaa   17700
accatgttac ggttcatatg caaaacccac aaatgaaaat ggagggcaag gcattcttgt   17760
aaagcaacaa aatggaaagc tagaaagtca agtggaaatg caattttttct caactactga   17820
ggcagccgca ggcaatggtg ataacttgac tcctaaagtg gtattgtaca gtgaagatgt   17880
agatatagaa accccagaca ctcatatttc ttacatgccc actattaagg aaggtaactc   17940
acgagaacta atgggccaac aatctatgcc caacaggcct aattacattg cttttaggga   18000
caattttatt ggtctaatgt attacaacag cacgggtaat atgggtgttc tggcgggcca   18060
agcatcgcag ttgaatgctg ttgtagattt gcaagacaga aacacagagc tttcatacca   18120
gcttttgctt gattccattg gtgatagaac caggtacttt tctatgtgga atcaggctgt   18180
tgacagctat gatccagatg ttagaattat tgaaaatcat ggaactgaag atgaacttcc   18240
aaattactgc tttccactgg gaggtgtgat taatacagag actcttacca aggtaaaacc   18300
taaaacaggt caggaaaatg gatgggaaaa agatgctaca gaattttcag ataaaaatga   18360
aataagagtt ggaaataatt ttgccatgga aatcaatcta aatgccaacc tgtggagaaa   18420
tttcctgtac tccaacatag cgctgtattt gcccgacaag ctaaagtaca gtccttccaa   18480
cgtaaaaatt tctgataacc caaacaccta cgactacatg aacaagcgag tggtggctcc   18540
cgggctagtg gactgctaca ttaaccttgg agcacgctgg tcccttgact atatggacaa   18600
cgtcaaccca tttaaccacc accgcaatgc tggcctgcgc taccgctcaa tgttgctggg   18660
caatggtcgc tatgtgccct tccacatcca ggtgcctcag aagttctttg ccattaaaaa   18720
cctccttctc ctgccgggct catacaccta cgagtggaac ttcaggaagg atgttaacat   18780
```

```
ggttctgcag agctccctag gaaatgacct aagggttgac ggagccagca ttaagtttga   18840
tagcatttgc ctttacgcca ccttcttccc catgcccac aacaccgcct ccacgcttga    18900
ggccatgctt agaaacgaca ccaacgacca gtcctttaac gactatctct ccgccgccaa   18960
catgctctac cctatacccg ccaacgctac caacgtgccc atatccatcc cctcccgcaa   19020
ctgggcggct ttccgcggct gggccttcac gcgccttaag actaaggaaa ccccatcact   19080
gggctcgggc tacgacccct tattacaccta ctctggctct atacccctacc tagatggaac  19140 cttttacctc aaccacacct ttaagaaggt ggccattacc tttgactctt ctgtcagctg   19200
gcctggcaat gaccgcctgc ttaccccccaa cgagtttgaa attaagcgct cagttgacgg  19260
ggagggttac aacgttgccc agtgtaacat gaccaaagac tggttcctgg tacaaatgct   19320
agctaactat aacattggct accagggctt ctatatccca gagagctaca aggaccgcat   19380
gtactccttc tttagaaaact tccagcccat gagccgtcag gtggtggatg atactaaaata 19440 caaggactac caacaggtgg gcatcctaca ccaacacaac aactctggat tgttggcta    19500 ccttgccccc accatgcgcg aaggacaggc ctaccctgct aacttcccct atccgcttat   19560
aggcaagacc gcagttgaca gcattaccca gaaaaagttt ctttgcgatc gcacccttttg 19620 gcgcatccca ttctccagta actttatgtc catgggcgca ctcacagacc tgggccaaaa  19680
ccttctctac gccaactccg cccacgcgct agacatgact tttgaggtgg atcccatgga  19740
cgagcccacc cttctttatg ttttgtttga agtctttgac gtggtccgtg tgcaccagcc  19800
gcaccgcggc gtcatcgaaa ccgtgtacct gcgcacgccc ttctcggccg caacgccac    19860 aacataaaga agcaagcaac atcaacaaca gctgccgcca tgggctccag tgagcaggaa   19920
ctgaaagcca ttgtcaaaga tcttggttgt gggccatatt ttttgggcac ctatgacaag   19980
cgctttccag gctttgtttc tccacacaag ctcgcctgcg ccatagtcaa tacggccggt   20040
cgcgagactg ggggcgtaca ctggatggcc tttgcctgga acccgcactc aaaaacatgc   20100
tacctctttg agccctttgg ctttttctgac cagcgactca agcaggttta ccagtttgag  20160
tacgagtcac tcctgcgccg tagcgccatt gcttcttccc ccgaccgctg tataacgctg   20220
gaaaagtcca cccaaagcgt acagggggccc aactcggccg cctgtggact attctgctgc  20280
atgtttctcc acgcctttgc caactggccc caaactccca tggatcacaa ccccaccatg   20340
aaccttatta ccggggtacc caactccatg ctcaacagtc cccaggtaca gcccaccctg   20400
cgtcgcaacc aggaacagct ctacagcttc ctggagcgcc actcgcccta cttccgcagc   20460
cacagtgcgc agattaggag cgccacttct ttttgtcact tgaaaaacat gtaaaaataa   20520
tgtactagag cactttcaa taaaggcaaa tgcttttatt tgtacactct cgggtgatta   20580 tttacccccca cccttgccgt ctgcgccgtt taaaaatcaa aggggttctg ccgcgcatcg    20640
ctatgcgcca ctggcaggga cacgttgcga tactggtgtt tagtgctcca cttaaactca   20700
ggcacaacca tccgcggcag ctcggtgaag ttttcactcc acaggctgcg caccatcacc   20760
aacgcgttta gcaggtcggg cgccgatatc ttgaagtcgc agttggggcc tccgccctgc   20820
gcgcgcgagt tgcgatacac agggttgcag cactggaaca ctatcagcgc cgggtggtgc   20880
acgctggcca gcacgctctt gtcggagatc agatccgcgt ccaggtcctc cgcgttgctc   20940
agggcgaacg gagtcaactt tggtagctgc cttcccaaaa agggcgcgtg cccaggcttt   21000
gagttgcact cgcaccgtag tggcatcaaa aggtgaccgt gcccggtctg ggcgttagga   21060
tacagcgcct gcataaaagc cttgatctgc ttaaaagcca cctgagcctt tgcgccttca   21120
```

```
gagaagaaca tgccgcaaga cttgccggaa aactgattgg ccggacaggc cgcgtcgtgc   21180
acgcagcacc ttgcgtcggt gttggagatc tgcaccacat ttcggcccca ccggttcttc   21240
acgatcttgg ccttgctaga ctgctccttc agcgcgcgct gcccgttttc gctcgtcaca   21300
tccatttcaa tcacgtgctc cttatttatc ataatgcttc cgtgtagaca cttaagctcg   21360
ccttcgatct cagcgcagcg gtgcagccac aacgcgcagc ccgtgggctc gtgatgcttg   21420
taggtcacct ctgcaaacga ctgcaggtac gcctgcagga atcgcccat catcgtcaca    21480 aaggtcttgt tgctggtgaa ggtcagctgc aacccgcggt gctcctcgtt cagccaggtc   21540
ttgcatacgg ccgccagagc ttccacttgg tcaggcagta gtttgaagtt cgcctttaga   21600
tcgttatcca cgtggtactt gtccatcagc gcgcgcgcag cctccatgcc cttctcccac   21660
gcagacacga tcggcacact cagcgggttc atcaccgtaa tttcactttc cgcttcgctg   21720
ggctcttcct cttcctcttg cgtccgcata ccacgcgcca ctgggtcgtc ttcattcagc   21780
cgccgcactg tgcgcttacc tcctttgcca tgcttgatta gcaccggtgg gttgctgaaa   21840
cccaccattt gtagcgccac atcttctctt tcttcctcgc tgtccacgat tacctctggt   21900
gatggcgggc gctcgggctt gggagaaggg cgcttctttt tcttcttggg cgcaatggcc   21960
aaatccgccg ccgaggtcga tggccgcggg ctgggtgtgc gcggcaccag cgcgtcttgt   22020
gatgagtctt cctcgtcctc ggactcgata cgccgcctca tccgcttttt tgggggcgcc   22080
cggggaggcg gcggcgacgg ggacggggac gacacgtcct ccatggttgg gggacgtcgc   22140
gccgcaccgc gtccgcgctc gggggtggtt tcgcgctgct cctcttcccg actggccatt   22200
tccttctcct ataggcagaa aaagatcatg gagtcagtcg agaagaagga cagcctaacc   22260
gccccctctg agttcgccac caccgcctcc accgatgccg ccaacgcgcc taccaccttc   22320
cccgtcgagg caccccgct tgaggaggag gaagtgatta tcgagcagga cccaggtttt   22380
gtaagcgaag acgacgagga ccgctcagta ccaacagagg ataaaaagca agaccaggac   22440
aacgcagagg caaacgagga acaagtcggg cggggggacg aaaggcatgg cgactaccta   22500
gatgtgggag acgacgtgct gttgaagcat ctgcagcgcc agtgcgccat tatctgcgac   22560
gcgttgcaag agcgcagcga tgtgcccctc gccatagcgg atgtcagcct tgcctacgaa   22620
cgccacctat tctcaccgcg cgtacccccc aaacgccaag aaaacggcac atgcgagccc   22680
aacccgcgcc tcaacttcta ccccgtattt gccgtgccag aggtgcttgc cacctatcac   22740 atcttttcc aaaactgcaa gatacccta tcctgccgtg ccaaccgcag ccgagcggac   22800
aagcagctgg ccttgcggca gggcgctgtc atacctgata tcgcctcgct caacgaagtg   22860
ccaaaaatct ttgagggtct tggacgcgac gagaagcgcg cggcaaacgc tctgcaacag   22920
gaaaacagcg aaaatgaaag tcactctgga gtgttggtgg aactcgaggg tgacaacgcg   22980
cgcctagccg tactaaaacg cagcatcgag gtcacccact ttgcctaccc ggcacttaac   23040
ctacccccca aggtcatgag cacagtcatg agtgagctga tcgtgcgccg tgcgcagccc   23100
ctggagaggg atgcaaattt gcaagaacaa acagaggagg cctaccccgc agttggcgac   23160
gagcagctag cgcgctggct tcaaacgcgc gagcctgccg acttggagga gcgacgcaaa   23220
ctaatgatgg ccgcagtgct cgttaccgtg gagcttgagt gcatgcagcg gttcttttgct  23280 gacccggaga tgcagcgcaa gctagaggaa acattgcact acacctttcg acagggctac   23340
gtacgccagg cctgcaagat ctccaacgtg gagctctgca acctggtctc ctaccttgga   23400
attttgcacg aaaaccgcct tgggcaaaac gtgcttcatt ccacgctcaa gggcgaggcg   23460
cgccgcgact acgtccgcga ctgcgtttac ttatttctat gctacacctg gcagacggcc   23520
```

```
atgggcgttt ggcagcagtg cttggaggag tgcaacctca aggagctgca gaaactgcta   23580
aagcaaaact tgaaggacct atggacggcc ttcaacgagc gctccgtggc cgcgcacctg   23640
gcggacatca ttttccccga acgcctgctt aaaaccctgc aacagggtct gccagacttc   23700
accagtcaaa gcatgttgca gactttagg aactttatcc tagagcgctc aggaatcttg   23760
cccgccacct gctgtgcact tcctagcgac tttgtgccca ttaagtaccg cgaatgccct   23820
ccgccgcttt ggggccactg ctaccttctg cagctagcca actaccttgc ctaccactct   23880
gacataatgg aagacgtgag cggtgacggt ctactggagt gtcactgtcg ctgcaaccta   23940
tgcaccccgc accgctccct ggtttgcaat tcgcagctgc ttaacgaaag tcaaattatc   24000
ggtacctttg agctgcaggg tccctcgcct gacgaaaagt ccgcggctcc ggggttgaaa   24060
ctcactccgg ggctgtggac gtcggcttac cttcgcaaat ttgtacctga ggactaccac   24120
gcccacgaga ttaggttcta cgaagaccaa tcccgcccgc ctaatgcgga gcttaccgcc   24180
tgcgtcatta cccagggcca cattcttggc caattgcaag ccatcaacaa agcccgccaa   24240
gagtttctgc tacgaaaggg acgggggtt tacttggacc cccagtccgg cgaggagctc   24300
aacccaatcc ccccgccgcc gcagcccat cagcagcagc cgcgggccct tgcttcccag   24360
gatggcaccc aaaaagaagc tgcagctgcc gccgccaccc acggacgagg aggaatactg   24420
ggacagtcag gcagaggagg ttttggacga ggaggaggag gacatgatgg aagactggga   24480
gagcctagac gaggaagctt ccgaggtcga agaggtgtca gacgaaacac cgtcaccctc   24540
ggtcgcattc ccctcgccgg cgccccagaa atcggcaacc ggttccagca tggctacaac   24600
ctccgctcct caggcgccgc cggcactgcc cgttcgccga cccaaccgta gatgggacac   24660
cactggaacc agggccggta agtccaagca gccgccgccg ttagcccaag agcaacaaca   24720
gcgccaaggc taccgctcat ggcgcgggca caagaacgcc atagttgctt gcttgcaaga   24780
ctgtgggggc aacatctcct tcgcccgccg ctttcttctc taccatcacg gcgtggcctt   24840
cccccgtaac atcctgcatt actaccgtca tctctacagc ccatactgca ccggcggcag   24900
cggcagcaac agcagcggcc acacagaagc aaaggcgacc ggatagcaag actctgacaa   24960
agcccaagaa atccacagcg gcggcagcag caggaggagg agcgctgcgt ctggcgccca   25020
acgaacccgt atcgacccgc gagcttagaa acaggatttt tcccactctg tatgctatat   25080
ttcaacagag caggggccaa gaacaagagc tgaaaataaa aaacaggtct ctgcgatccc   25140
tcacccgcag ctgcctgtat cacaaaagcg aagatcagct tcggcgcacg ctggaagacg   25200
cggaggctct cttcagtaaa tactgcgcgc tgactcttaa ggactagttt cgcgcccttt   25260
ctcaaattta agcgcgaaaa ctacgtcatc tccagcggcc acaccggcg ccagcacctg   25320 ttgtcagcgc cattatgagc aaggaaattc ccacgcccta catgtggagt taccagccac   25380
aaatgggact tgcggctgga gctgcccaag actactcaac ccgaataaac tacatgagcg   25440
cgggacccca catgatatcc cgggtcaacg gaatacgcgc ccaccgaaac cgaattctcc   25500
tggaacaggc ggctattacc accacacctc gtaataacct taatcccgt agttggcccg   25560 ctgccctggt gtaccaggaa agtcccgctc ccaccactgt ggtacttccc agagacgccc   25620
aggccgaagt tcagatgact aactcagggg cgcagcttgc gggcggcttt cgtcacaggg   25680
tgcggtcgcc cgggcagggt ataactcacc tgacaatcag agggcgaggt attcagctca   25740
acgacgagtc ggtgagctcc tcgcttggtc tccgtccgga cgggacattt cagatcggcg   25800
gcgccggccg ctcttcattc acgcctcgtc aggcaatcct aactctgcag acctcgtcct   25860
```

```
ctgagccgcg ctctggaggc attggaactc tgcaatttat tgaggagttt gtgccatcgg    25920
tctactttaa cccttctcg ggacctcccg gccactatcc ggatcaattt attcctaact     25980
ttgacgcggt aaaggactcg gcggacggct acgactgaat gttaagtgga gaggcagagc    26040
aactgcgcct gaaacacctg gtccactgtc gccgccacaa gtgctttgcc cgcgactccg    26100
gtgagttttg ctactttgaa ttgcccgagg atcatatcga gggcccggcg cacggcgtcc    26160
ggcttaccgc ccagggagag cttgcccgta gcctgattcg ggagtttacc cagcgccccc    26220
tgctagttga gcgggacagg ggaccctgtg ttctcactgt gatttgcaac tgtcctaacc    26280
ctggattaca tcaagatcct ctagttaatg tcaggtcgcc taagtcgatt aactagagta    26340 cccgggatc ttattcccctt taactaataa aaaaaaataa taaagcatca cttacttaaa    26400
atcagttagc aaatttctgt ccagtttatt cagcagcacc tccttgccct cctcccagct    26460
ctggtattgc agcttcctcc tggctgcaaa ctttctccac aatctaaatg gaatgtcagt    26520
ttcctcctgt tcctgtccat ccgcaccac tatcttcatg ttgttgcaga tgaagcgcgc    26580
aagaccgtct gaagatacct tcaacccccgt gtatccatat gacacggaaa ccggtcctcc    26640
aactgtgcct tttcttactc ctcccttttgt atccccaat gggtttcaag agagtcccc     26700 tggggtactc tctttgcgcc tatccgaacc tctagttacc tccaatggca tgcttgcgct    26760
caaaatgggc aacggcctct ctctggacga ggccggcaac cttacctccc aaaatgtaac    26820
cactgtgagc ccacctctca aaaaaccaa gtcaaacata aacctggaaa tatctgcacc    26880
cctcacagtt acctcagaag ccctaactgt ggctgccgcc gcacctctaa tggtcgcggg    26940
caacacactc accatgcaat cacaggcccc gctaaccgtg cacgactcca aacttagcat    27000
tgccacccaa ggaccctca cagtgtcaga aggaaagcta gccctgcaaa catcaggccc    27060
cctcaccacc accgatagca gtacccttac tatcactgcc tcaccccctc taactactgc    27120
cactggtagc ttgggcattg acttgaaaga gcccatttat acacaaaatg gaaaactagg    27180
actaaagtac ggggctcctt tgcatgtaac agacgaccta acactttga ccgtagcaac     27240 tggtccaggt gtgactatta ataatacttc cttgcaaact aaagttactg gagccttggg    27300
ttttgattca caaggcaata tgcaacttaa tgtagcagga ggactaagga ttgattctca    27360
aaacagacgc cttatacttg atgttagtta tccgtttgat gctcaaaacc aactaaatct    27420
aagactagga cagggccctc tttttataaa ctcagcccac aacttggata ttaactacaa    27480
caaaggcctt tacttgttta cagcttcaaa caattccaaa aagcttgagg ttaacctaag    27540
cactgccaag gggttgatgt ttgacgctac agccatagcc attaatgcag gagatgggct    27600
tgaatttggt tcacctaatg caccaaacac aaatcccctc aaaacaaaaa ttggccatgg    27660
cctagaattt gattcaaaca aggctatggt tcctaaacta ggaactggcc ttagtttga    27720 cagcacaggt gccattacag taggaaacaa aaataatgat aagctaactt tgtggaccac    27780
accagctcca tctcctaact gtagactaaa tgcagagaaa gatgctaaac tcactttggt    27840
cttaacaaaa tgtggcagtc aaatacttgc tacagtttca gttttggctg ttaaaggcag    27900
tttggctcca atatctggaa cagttcaaag tgctcatctt attataagat tgacgaaaa     27960 tggagtgcta ctaaacaatt ccttcctgga cccagaatat tggaactta gaatggaga     28020 tcttactgaa ggcacagcct atacaaacgc tgttggattt atgcctaacc tatcagctta    28080
tccaaaatct cacggtaaaa ctgccaaaag taacattgtc agtcaagttt acttaaacgg    28140
agacaaaact aaacctgtaa cactaaccat tacactaaac ggtacacagg aaacaggaga    28200
cacaactcca agtgcatact ctatgtcatt ttcatgggac tggtctggcc acaactacat    28260
```

```
taatgaaata tttgccacat cctcttacac tttttcatac attgcccaag aataaagaat    28320
cgtttgtgtt atgtttcaac gtgtttattt ttcaattgca gaaaatttca agtcattttt    28380
cattcagtag tatagcccca ccaccacata gcttatacag atcaccgtac cttaatcaaa    28440
ctcacagaac cctagtattc aacctgccac ctccctccca acacacagag tacacagtcc    28500
tttctccccg gctggcctta aaaagcatca tatcatgggt aacagacata ttcttaggtg    28560
ttatattcca cacggtttcc tgtcgagcca aacgctcatc agtgatatta ataaactccc    28620
cgggcagctc acttaagttc atgtcgctgt ccagctgctg agccacaggc tgctgtccaa    28680
cttgcggttg cttaacgggc ggcgaaggag aagtccacgc ctacatgggg gtagagtcat    28740
aatcgtgcat caggataggg cggtggtgct gcagcagcgc gcgaataaac tgctgccgcc    28800
gccgctccgt cctgcaggaa tacaacatgg cagtggtctc ctcagcgatg attcgcaccg    28860
cccgcagcat aaggcgcctt gtcctccggg cacagcagcg caccctgatc tcacttaaat    28920
cagcacagta actgcagcac agcaccacaa tattgttcaa aatcccacag tgcaaggcgc    28980
tgtatccaaa gctcatggcg gggaccacag aacccacgtg gccatcatac cacaagcgca    29040
ggtagattaa gtggcgaccc ctcataaaca cgctggacat aaacattacc tcttttggca    29100
tgttgtaatt caccacctcc cggtaccata taaacctctg attaaacatg gcgccatcca    29160
ccaccatcct aaaccagctg gccaaaacct gcccgccggc tatacactgc agggaaccgg    29220
gactggaaca atgacagtgg agagcccagg actcgtaacc atggatcatc atgctcgtca    29280
tgatatcaat gttggcacaa cacaggcaca cgtgcataca cttcctcagg attacaagct    29340
cctcccgcgt tagaaccata tcccagggaa caacccattc ctgaatcagc gtaaatccca    29400
cactgcaggg aagacctcgc acgtaactca cgttgtgcat tgtcaaagtg ttacattcgg    29460
gcagcagcgg atgatcctcc agtatggtag cgcgggtttc tgtctcaaaa ggaggtagac    29520
gatccctact gtacggagtg cgccgagaca accgagatcg tgttggtcgt agtgtcatgc    29580
caaatggaac gccggacgta gtcatatttc ctgaagcaaa accaggtgcg ggcgtgacaa    29640
acagatctgc gtctccggtc tcgccgctta gatcgctctg tgtagtagtt gtagtatatc    29700
cactctctca aagcatccag gcgccccctg gcttcgggtt ctatgtaaac tccttcatgc    29760
gccgctgccc tgataacatc caccaccgca gaataagcca cacccagcca acctacacat    29820
tcgttctgcg agtcacacac gggaggagcg ggaagagctg gaagaaccat gtttttttt    29880
ttattccaaa agattatcca aaacctcaaa atgaagatct attaagtgaa cgcgctcccc    29940
tccggtggcg tggtcaaact ctacagccaa agaacagata atggcatttg taagatgttg    30000
cacaatggct tccaaaaggc aaacggccct cacgtccaag tggacgtaaa ggctaaaccc    30060
ttcagggtga atctcctcta taaacattcc agcaccttca accatgccca aataattctc    30120
atctcgccac cttctcaata tatctctaag caaatcccga atattaagtc cggccattgt    30180
aaaaatctgc tccagagcgc cctccaacctt cagcctcaag cagcgaatca tgattgcaaa    30240
aattcaggtt cctcacagac ctgtataaga ttcaaaagcg gaacattaac aaaaataccg    30300
cgatcccgta ggtcccttcg cagggccagc tgaacataat cgtgcaggtc tgcacggacc    30360
agcgcggcca cttcccgcc aggaaccatg acaaagaac ccacactgat tatgacacgc    30420
atactcggag ctatgctaac cagcgtagcc ccgatgtaag cttgttgcat gggcggcgat    30480
ataaaatgca aggtgctgct caaaaaatca ggcaaagcct cgcgcaaaaa agaaagcaca    30540
tcgtagtcat gctcatgcag ataaaggcag gtaagctccg gaaccaccac agaaaaagac    30600
```

```
accattttc tctcaaacat gtctgcgggt ttctgcataa acacaaaata aaataacaaa    30660
aaaacattta aacattagaa gcctgtctta caacaggaaa aacaacccct ataagcataa    30720
gacggactac ggccatgccg gcgtgaccgt aaaaaaactg gtcaccgtga ttaaaaagca    30780
ccaccgacag ctcctcggtc atgtccggag tcataatgta agactcggta aacacatcag    30840
gttgattcac atcggtcagt gctaaaaagc gaccgaaata gcccggggga atacataccc    30900
gcaggcgtag agacaacatt acagcccca taggaggtat aacaaaatta ataggagaga    30960
aaaacacata aacacctgaa aaaccctcct gcctaggcaa aatagcaccc tcccgctcca    31020
gaacaacata cagcgcttcc acagcggcag ccataacagt cagccttacc agtaaaaaag    31080
aaaacctatt aaaaaaacac cactcgacac ggcaccagct caatcagtca cagtgtaaaa    31140
aagggccaag tgcagagcga gtatatatag gactaaaaaa tgacgtaacg gttaaagtcc    31200
acaaaaaaca cccagaaaac cgcacgcgaa cctacgccca gaaacgaaag ccaaaaaacc    31260
cacaacttcc tcaaatcgtc acttccgttt tcccacgtta cgtcacttcc cattttaaga    31320
aaactacaat tcccaacaca tacaagttac tccgccctaa aacctacgtc acccgccccg    31380
ttcccacgcc ccgcgccacg tcacaaactc cacccctca ttatcatatt ggcttcaatc    31440
caaaataagg tatattattg atgat                                          31465
```

<210> SEQ ID NO 14
<211> LENGTH: 410
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Met Ser Ser Pro Gly Thr Glu Ser Ala Gly Lys Ser Leu Gln Tyr Arg
1               5                   10                  15

Val Asp His Leu Leu Ser Ala Val Glu Asn Glu Leu Gln Ala Gly Ser
                20                  25                  30

Glu Lys Gly Asp Pro Thr Glu Arg Glu Leu Arg Val Gly Leu Glu Glu
            35                  40                  45

Ser Glu Leu Trp Leu Arg Phe Lys Glu Leu Thr Asn Glu Met Ile Val
        50                  55                  60

Thr Lys Asn Gly Arg Arg Met Phe Pro Val Leu Lys Val Asn Val Ser
65                  70                  75                  80

Gly Leu Asp Pro Asn Ala Met Tyr Ser Phe Leu Leu Asp Phe Val Ala
                85                  90                  95

Ala Asp Asn His Arg Trp Lys Tyr Val Asn Gly Glu Trp Val Pro Gly
            100                 105                 110

Gly Lys Pro Glu Pro Gln Ala Pro Ser Cys Val Tyr Ile His Pro Asp
        115                 120                 125

Ser Pro Asn Phe Gly Ala His Trp Met Lys Ala Pro Val Ser Phe Ser
    130                 135                 140

Lys Val Lys Leu Thr Asn Lys Leu Asn Gly Gly Gln Ile Met Leu
145                 150                 155                 160

Asn Ser Leu His Lys Tyr Glu Pro Arg Ile His Ile Val Arg Val Gly
                165                 170                 175

Gly Pro Gln Arg Met Ile Thr Ser His Cys Phe Pro Glu Thr Gln Phe
            180                 185                 190

Ile Ala Val Thr Ala Arg Ser Asp His Lys Glu Met Met Glu Glu Pro
        195                 200                 205

Gly Asp Ser Gln Gln Pro Gly Tyr Ser Gln Trp Gly Trp Leu Leu Pro
    210                 215                 220

Gly Thr Ser Thr Val Cys Pro Pro Ala Asn Pro His Pro Gln Phe Gly
225                 230                 235                 240

Gly Ala Leu Ser Leu Pro Ser Thr His Ser Cys Asp Arg Tyr Pro Thr
                245                 250                 255

Leu Arg Ser His Arg Ser Ser Pro Tyr Pro Ser Pro Tyr Ala His Arg
            260                 265                 270

Asn Asn Ser Pro Thr Tyr Ser Asp Asn Ser Pro Ala Cys Leu Ser Met
        275                 280                 285

Leu Gln Ser His Asp Asn Trp Ser Ser Leu Gly Met Pro Ala His Pro
    290                 295                 300

Ser Met Leu Pro Val Ser His Asn Ala Ser Pro Pro Thr Ser Ser Ser
305                 310                 315                 320

Gln Tyr Pro Ser Leu Trp Ser Val Ser Asn Gly Ala Val Thr Pro Gly
                325                 330                 335

Ser Gln Ala Ala Ala Val Ser Asn Gly Leu Gly Ala Gln Phe Phe Arg
            340                 345                 350

Gly Ser Pro Ala His Tyr Thr Pro Leu Thr His Pro Val Ser Ala Pro
        355                 360                 365

Ser Ser Ser Gly Ser Pro Leu Tyr Glu Gly Ala Ala Ala Thr Asp
    370                 375                 380

Ile Val Asp Ser Gln Tyr Asp Ala Ala Gln Gly Arg Leu Ile Ala
385                 390                 395                 400

Ser Trp Thr Pro Val Ser Pro Pro Ser Met
                405                 410

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Trp Leu Leu Pro Gly Thr Ser Thr Val
1               5

<210> SEQ ID NO 16
<211> LENGTH: 965
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
gcggggcagc ctcacacaga acacacacag atatgggtgt acccactcag ctcctgttgc      60
tgtggcttac agtcgtagtt gtcagatgtg acatccagat gactcagtct ccagcttcac     120
tgtctgcatc tgtgggagaa actgtcacca tcacatgtgg agcaagtgag aatatttacg     180
gtgctttaaa ttggtatcag cggaaacagg gaaaatctcc tcagctcctg atttatggcg     240
caagtaattt ggcagatggc atgtcatcga ggttcagtgg cagtggatct ggtagacagt     300
attctctcaa gatcagtagc ctgcatcctg acgattttgc aacgtattac tgtcaaaatg     360
tattaagtag tccgtacacg ttcggagggg ggaccaagct ggaaataaaa cgggctgatg     420

```
ctgcaccaac tgtatccatc ttcccaccat ccagtgagca gttaacatct ggaggtgcct    480
cagtcgtgtg cttcttgaac aacttctacc ccaaagacat caatgtcaag tggaagattg    540
atggcagtga acgacaaaat ggcgtcctga acagttggac tgatcaggac agcaaagaca    600
gcacctacag catgagcagc accctcacgt tgaccaagga cgagtatgaa cgacataaca    660
gctatacctg tgaggccact cacaagacac caacttcacc cattgtcaag agcttcaaca    720
ggaatgagtg ttagagacaa aggtcctgag acgccaccac cagctcccca gctccatcct    780
atcttcccct taaggtcttt ggaggcttcc ccacaagcga cctaccactg ttgcggtgct    840
ccaaacctcc tccccacctc cttctcctcc tcctcccttt ccttggcttt tatcatgcta    900
atatttgcag aaaatattca ataaagtgag tctttgcaca aaaaaaaaaa aaaaaaaaa     960 aaaaa                                                                965
```

<210> SEQ ID NO 17
<211> LENGTH: 1575
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 17

```
acgcgggaca cagtagtctc tacagtcaca ggagtacaca ggacattgcc atgggttgga     60
gctgtatcat cttctttctg gtagcaacag ctacaggtgt gcactcccag gtccagctgc    120
agcagtctgg gcctgaggtg gtgaggcctg gggtctcagt gaagatttcc tgcaaggggt    180
ccggctacac attcactgat tatgctatgc actgggtgaa gcagagtcat gcaaagagtc    240
tcgagtggat tggacttatt agtacttaca gtggtgatac aaagtacaac cagaacttta    300
agggcaaggc cacaatgact gtagacaaat cctccaacac agcctatatg aacttgcca     360 gattgacatc tgaggattct gccatctatt actgtgcaag aggggattat tccggtagta    420
ggtactggtt tgcttactgg ggccaaggga ctctggtcac tgtctctgca gccaaaacga    480
cacccccatc tgtctatcca ctggcccctg gatctgctgc ccaaactaac tccatggtga    540
ccctgggatg cctggtcaag ggctatttcc ctgagccagt gacagtgacc tggaactctg    600
gatccctgtc cagcggtgtg cacaccttcc cagctgtcct gcagtctgac ctctacactc    660
tgagcagctc agtgactgtc ccctccagca cctggcccag cgagaccgtc acctgcaacg    720
ttgcccaccc ggccagcagc accaaggtgg acaagaaaat tgtgcccagg gattgtggtt    780
gtaagccttg catatgtaca gtcccagaag tatcatctgt cttcatcttc cccccaaagc    840
ccaaggatgt gctcaccatt actctgactc ctaaggtcac gtgtgttgtg gtagacatca    900
gcaaggatga tcccgaggtc cagttcagct ggtttgtaga tgatgtggag gtgcacacag    960
ctcagacgca accccgggag gagcagttca acagcacttt ccgctcagtc agtgaacttc   1020
ccatcatgca ccaggactgg ctcaatggca aggagttcaa atgcagggtc aacagtgcag   1080 cttttccctgc ccccatcgag aaaaccatct ccaaaaccaa aggcagaccg aaggctccac   1140
aggtgtacac cattccacct cccaaggagc agatggccaa ggataaagtc agtctgacct   1200
gcatgataac agacttcttc cctgaagaca ttactgtgga gtggcagtgg aatgggcagc   1260
cagcggagaa ctacaagaac actcagccca tcatggacac agatggctct tacttcgtct   1320
acagcaagct caatgtgcag aagagcaact gggaggcagg aaatactttc acctgctctg   1380
tgttacatga gggcctgcac aaccaccata ctgagaagag cctctcccac tctcctggta   1440
```

```
aatgatccca gtgtccttgg agccctctgg ccctacagga ctttgacacc tacctccacc      1500
cctccctgta taaataaagc acccagcact gcctcgggac cctgcataaa aaaaaaaaaa      1560
aaaaaaaaaa aaaaa                                                        1575
```

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Leu Met Thr Gln Ser Pro Ala Ser Leu Ser Ala Ser Val Gly Glu Thr
1               5                   10                  15

Val Thr Ile Thr Cys Gly Ala Ser Glu Asn Ile Tyr Gly Ala Leu Asn
            20                  25                  30

Trp Tyr Gln Arg Lys Gln Gly Lys Ser Pro Gln Leu Leu Ile Tyr Gly
        35                  40                  45

Ala Ser Asn Leu Ala Asp Gly Met Ser Ser Arg Phe Ser Gly Ser Gly
    50                  55                  60

Ser Gly Arg Gln Tyr Ser Leu Lys Ile Ser Ser Leu His Pro Asp Asp
65                  70                  75                  80

Val Ala Thr Tyr Tyr Cys Gln Asn Val Leu Ser Ser Pro Tyr Thr Phe
                85                  90                  95

Gly Gly Gly Thr Lys Leu Glu Ile Lys Lys Gly
            100                 105
```

<210> SEQ ID NO 19
<211> LENGTH: 233
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Met Gly Val Pro Thr Gln Leu Leu Leu Trp Leu Thr Val Val
1               5                   10                  15

Val Arg Cys Asp Ile Gln Met Thr Gln Ser Pro Ser Ser Leu Ser Ala
            20                  25                  30

Ser Val Gly Asp Arg Val Thr Ile Thr Cys Gln Ala Ser Glu Asn Ile
        35                  40                  45

Tyr Gly Ala Leu Asn Trp Tyr Gln Arg Lys Pro Gly Lys Ser Pro Lys
    50                  55                  60

Leu Leu Ile Tyr Gly Ala Ser Asn Leu Ala Thr Gly Met Pro Ser Arg
65                  70                  75                  80

Phe Ser Gly Ser Gly Ser Gly Thr Asp Tyr Thr Phe Thr Ile Ser Ser
                85                  90                  95

Leu Gln Pro Glu Asp Ile Ala Thr Tyr Tyr Cys Gln Asn Val Leu Ser
            100                 105                 110

Ser Pro Tyr Thr Phe Gly Gly Gly Thr Lys Leu Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Ile Asn Asn Phe Tyr Pro
145                 150                 155                 160
```

```
Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230

<210> SEQ ID NO 20
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Leu Glu Glu Ser Gly Pro Glu Val Val Arg Pro Gly Val Ser Val Lys
1               5                   10                  15

Ile Ser Cys Lys Gly Ser Gly Tyr Thr Phe Thr Asp Tyr Ala Met His
            20                  25                  30

Trp Val Lys Gln Ser His Ala Lys Ser Leu Glu Trp Ile Gly Leu Ile
        35                  40                  45

Ser Thr Tyr Ser Gly Asp Thr Lys Tyr Asn Gln Asn Phe Lys Gly Lys
    50                  55                  60

Ala Thr Met Thr Val Asp Lys Ser Ser Asn Thr Ala Tyr Met Glu Leu
65                  70                  75                  80

Ala Arg Leu Thr Ser Glu Asp Ser Ala Ile Tyr Tyr Cys Ala Arg Gly
                85                  90                  95

Asp Tyr Ser Gly Ser Arg Tyr Trp Phe Ala Tyr Trp Gly Gln Gly Thr
            100                 105                 110

Thr Val Thr Arg
        115

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Ala Ser Glu Asn Ile Tyr Gly Ala Leu Asn
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ala Ser Asn Leu Ala Asp
1               5
```

```
<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Asn Val Leu Ser Ser Pro Tyr Thr
1               5

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Ala Ser Glu Asn Ile Tyr Gly Ala Leu Asn
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Ala Ser Asn Leu Ala Thr
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gln Gln Val Leu Ser Ser Pro Tyr Thr
1               5

<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Tyr Thr Phe Thr Asp Tyr Ala Met His
1               5                   10

<210> SEQ ID NO 28
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28
```

```
Leu Ile Ser Thr Tyr Ser Gly Asp Thr Lys Tyr Asn Gln Asn Phe Lys
1               5                   10                  15

Gly

<210> SEQ ID NO 29
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Asp Tyr Ser Gly Ser Arg Tyr Trp Phe Ala Tyr
1               5                   10

<210> SEQ ID NO 30
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Leu Ile Ser Thr Tyr Ser Gly Asp Thr Lys Tyr Asn Gln Lys Phe Gln
1               5                   10                  15

Gly

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Asp Tyr Ser Gly Ser Arg Tyr Trp Phe Ala Tyr
1               5                   10

<210> SEQ ID NO 32
<211> LENGTH: 132
<212> TYPE: PRT
<213> ORGANISM: Mycobacterium sp.

<400> SEQUENCE: 32

Thr Ala Ala Ser Asp Asn Phe Gln Leu Ser Gln Gly Gln Gly Phe
1               5                   10                  15

Ala Ile Pro Ile Gly Gln Ala Met Ala Ile Ala Gly Gln Ile Arg Ser
                20                  25                  30

Gly Gly Gly Ser Pro Thr Val His Ile Gly Pro Thr Ala Phe Leu Gly
            35                  40                  45

Leu Gly Val Val Asp Asn Asn Gly Asn Gly Ala Arg Val Gln Arg Val
        50                  55                  60

Val Gly Ser Ala Pro Ala Ala Ser Leu Gly Ile Ser Thr Gly Asp Val
65                  70                  75                  80

Ile Thr Ala Val Asp Gly Ala Pro Ile Asn Ser Ala Thr Ala Met Ala
                85                  90                  95

Asp Ala Leu Asn Gly His His Pro Gly Asp Val Ile Ser Val Thr Trp
                100                 105                 110
```

```
Gln Thr Lys Ser Gly Gly Thr Arg Thr Gly Asn Val Thr Leu Ala Glu
            115                 120                 125

Gly Pro Pro Ala
        130

<210> SEQ ID NO 33
<211> LENGTH: 230
<212> TYPE: PRT
<213> ORGANISM: Mycobacterium sp.

<400> SEQUENCE: 33

Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
                20                  25                  30

Ile Ala Gly Gln Ile Arg Ser Gly Gly Gly Ser Pro Thr Val His Ile
                35                  40                  45

Gly Pro Thr Ala Phe Leu Gly Leu Gly Val Val Asp Asn Asn Gly Asn
        50                  55                  60

Gly Ala Arg Val Gln Arg Val Val Gly Ser Ala Pro Ala Ala Ser Leu
65                  70                  75                  80

Gly Ile Ser Thr Gly Asp Val Ile Thr Ala Val Asp Gly Ala Pro Ile
                        85                  90                  95

Asn Ser Ala Thr Ala Met Ala Asp Ala Leu Asn Gly His His Pro Gly
                100                 105                 110

Asp Val Ile Ser Val Thr Trp Gln Thr Lys Ser Gly Gly Thr Arg Thr
            115                 120                 125

Gly Asn Val Thr Leu Ala Glu Gly Pro Pro Ala Glu Phe Asp Asp Asp
        130                 135                 140

Asp Lys Asp Pro Pro Asp Pro His Gln Pro Asp Met Thr Lys Gly Tyr
145                 150                 155                 160

Cys Pro Gly Gly Arg Trp Gly Phe Gly Asp Leu Ala Val Cys Asp Gly
                        165                 170                 175

Glu Lys Tyr Pro Asp Gly Ser Phe Trp His Gln Trp Met Gln Thr Trp
                180                 185                 190

Phe Thr Gly Pro Gln Phe Tyr Phe Asp Cys Val Ser Gly Gly Glu Pro
        195                 200                 205

Leu Pro Gly Pro Pro Pro Gly Gly Cys Gly Gly Ala Ile Pro Ser
    210                 215                 220

Glu Gln Pro Asn Ala Pro
225                 230

<210> SEQ ID NO 34
<211> LENGTH: 578
<212> TYPE: PRT
<213> ORGANISM: Mycobacterium sp.

<400> SEQUENCE: 34

Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
                20                  25                  30

Ile Ala Gly Gln Ile Arg Ser Gly Gly Gly Ser Pro Thr Val His Ile
                35                  40                  45

Gly Pro Thr Ala Phe Leu Gly Leu Gly Val Val Asp Asn Asn Gly Asn
        50                  55                  60
```

-continued

```
Gly Ala Arg Val Gln Arg Val Val Gly Ser Ala Pro Ala Ala Ser Leu
 65                  70                  75                  80

Gly Ile Ser Thr Gly Asp Val Ile Thr Ala Val Asp Gly Ala Pro Ile
                 85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Thr Arg Thr
        115                 120                 125

Gly Asn Val Thr Leu Ala Glu Gly Pro Ala Glu Phe Pro Leu Val
    130                 135                 140

Pro Arg Gly Ser Pro Met Gly Ser Asp Val Arg Asp Leu Asn Ala Leu
145                 150                 155                 160

Leu Pro Ala Val Pro Ser Leu Gly Gly Gly Gly Cys Ala Leu Pro
                165                 170                 175

Val Ser Gly Ala Ala Gln Trp Ala Pro Val Leu Asp Phe Ala Pro Pro
            180                 185                 190

Gly Ala Ser Ala Tyr Gly Ser Leu Gly Gly Pro Ala Pro Pro Ala
        195                 200                 205

Pro Pro Pro Pro Pro Pro Pro Pro His Ser Phe Ile Lys Gln Glu
210                 215                 220

Pro Ser Trp Gly Gly Ala Glu Pro His Glu Glu Gln Cys Leu Ser Ala
225                 230                 235                 240

Phe Thr Val His Phe Ser Gly Gln Phe Thr Gly Thr Ala Gly Ala Cys
                245                 250                 255

Arg Tyr Gly Pro Phe Gly Pro Pro Pro Ser Gln Ala Ser Ser Gly
            260                 265                 270

Gln Ala Arg Met Phe Pro Asn Ala Pro Tyr Leu Pro Ser Cys Leu Glu
        275                 280                 285

Ser Gln Pro Ala Ile Arg Asn Gln Gly Tyr Ser Thr Val Thr Phe Asp
    290                 295                 300

Gly Thr Pro Ser Tyr Gly His Thr Pro Ser His His Ala Ala Gln Phe
305                 310                 315                 320

Pro Asn His Ser Phe Lys His Glu Asp Pro Met Gly Gln Gln Gly Ser
                325                 330                 335

Leu Gly Glu Gln Gln Tyr Ser Val Pro Pro Val Tyr Gly Cys His
            340                 345                 350

Thr Pro Thr Asp Ser Cys Thr Gly Ser Gln Ala Leu Leu Leu Arg Thr
        355                 360                 365

Pro Tyr Ser Ser Asp Asn Leu Tyr Gln Met Thr Ser Gln Leu Glu Cys
    370                 375                 380

Met Thr Trp Asn Gln Met Asn Leu Gly Ala Thr Leu Lys Gly His Ser
385                 390                 395                 400

Thr Gly Tyr Glu Ser Asp Asn His Thr Thr Pro Ile Leu Cys Gly Ala
                405                 410                 415

Gln Tyr Arg Ile His Thr His Gly Val Phe Arg Gly Ile Gln Asp Val
            420                 425                 430

Arg Arg Val Pro Gly Val Ala Pro Thr Leu Val Arg Ser Ala Ser Glu
        435                 440                 445

Thr Ser Glu Lys Arg Pro Phe Met Cys Ala Tyr Ser Gly Cys Asn Lys
    450                 455                 460

Arg Tyr Phe Lys Leu Ser His Leu Gln Met His Ser Arg Lys His Thr
465                 470                 475                 480

Gly Glu Lys Pro Tyr Gln Cys Asp Phe Lys Asp Cys Glu Arg Arg Phe
```

```
                        485                 490                 495
Phe Arg Ser Asp Gln Leu Lys Arg His Gln Arg Arg His Thr Gly Val
                    500                 505                 510

Lys Pro Phe Gln Cys Lys Thr Cys Gln Arg Lys Phe Ser Arg Ser Asp
                515                 520                 525

His Leu Lys Thr His Thr Arg Thr His Thr Gly Glu Lys Pro Phe Ser
            530                 535                 540

Cys Arg Trp Pro Ser Cys Gln Lys Lys Phe Ala Arg Ser Asp Glu Leu
545                 550                 555                 560

Val Arg His His Asn Met His Gln Arg Asn Met Thr Lys Leu Gln Leu
                565                 570                 575

Ala Leu

<210> SEQ ID NO 35
<211> LENGTH: 220
<212> TYPE: PRT
<213> ORGANISM: Mycobacterium sp.

<400> SEQUENCE: 35

Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
                20                  25                  30

Ile Ala Gly Gln Ile Arg Ser Gly Gly Ser Pro Thr Val His Ile
            35                  40                  45

Gly Pro Thr Ala Phe Leu Gly Leu Gly Val Val Asp Asn Asn Gly Asn
        50                  55                  60

Gly Ala Arg Val Gln Arg Val Val Gly Ser Ala Pro Ala Ala Ser Leu
65                  70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Ile Glu Gly
    130                 135                 140

Arg Gly Ser Gly Cys Pro Leu Leu Glu Asn Val Ile Ser Lys Thr Ile
145                 150                 155                 160

Asn Pro Gln Val Ser Lys Thr Glu Tyr Lys Glu Leu Leu Gln Glu Phe
                165                 170                 175

Ile Asp Asp Asn Ala Thr Thr Asn Ala Ile Asp Glu Leu Lys Glu Cys
            180                 185                 190

Phe Leu Asn Gln Thr Asp Glu Thr Leu Ser Asn Val Glu Val Phe Met
        195                 200                 205

Gln Leu Ile Tyr Asp Ser Ser Leu Cys Asp Leu Phe
    210                 215                 220

<210> SEQ ID NO 36
<211> LENGTH: 729
<212> TYPE: PRT
<213> ORGANISM: Mycobacterium sp.

<400> SEQUENCE: 36

Met His His His His His His Thr Ala Ala Ser Asp Asn Phe Gln Leu
1               5                   10                  15
```

```
Ser Gln Gly Gly Gln Gly Phe Ala Ile Pro Ile Gly Gln Ala Met Ala
            20                  25                  30

Ile Ala Gly Gln Ile Arg Ser Gly Gly Ser Pro Thr Val His Ile
        35                  40                  45

Gly Pro Thr Ala Phe Leu Gly Leu Gly Val Val Asp Asn Asn Gly Asn
    50                  55                  60

Gly Ala Arg Val Gln Arg Val Val Gly Ser Ala Pro Ala Ser Leu
65              70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
                100                 105                 110

Asp Val Ile Ser Val Thr Trp Gln Thr Lys Ser Gly Gly Thr Arg Thr
            115                 120                 125

Gly Asn Val Thr Leu Ala Glu Gly Pro Pro Ala Glu Phe Met Val Asp
    130                 135                 140

Phe Gly Ala Leu Pro Pro Glu Ile Asn Ser Ala Arg Met Tyr Ala Gly
145                 150                 155                 160

Pro Gly Ser Ala Ser Leu Val Ala Ala Gln Met Trp Asp Ser Val
                165                 170                 175

Ala Ser Asp Leu Phe Ser Ala Ala Ser Ala Phe Gln Ser Val Val Trp
                180                 185                 190

Gly Leu Thr Val Gly Ser Trp Ile Gly Ser Ser Ala Gly Leu Met Val
            195                 200                 205

Ala Ala Ala Ser Pro Tyr Val Ala Trp Met Ser Val Thr Ala Gly Gln
210                 215                 220

Ala Glu Leu Thr Ala Ala Gln Val Arg Val Ala Ala Ala Tyr Glu
225                 230                 235                 240

Thr Ala Tyr Gly Leu Thr Val Pro Pro Pro Val Ile Ala Glu Asn Arg
                245                 250                 255

Ala Glu Leu Met Ile Leu Ile Ala Thr Asn Leu Leu Gly Gln Asn Thr
                260                 265                 270

Pro Ala Ile Ala Val Asn Glu Ala Glu Tyr Gly Glu Met Trp Ala Gln
            275                 280                 285

Asp Ala Ala Ala Met Phe Gly Tyr Ala Ala Ala Thr Ala Thr Ala Thr
    290                 295                 300

Ala Thr Leu Leu Pro Phe Glu Glu Ala Pro Glu Met Thr Ser Ala Gly
305                 310                 315                 320

Gly Leu Leu Glu Gln Ala Ala Val Glu Glu Ala Ser Asp Thr Ala
                325                 330                 335

Ala Ala Asn Gln Leu Met Asn Asn Val Pro Gln Ala Leu Gln Gln Leu
                340                 345                 350

Ala Gln Pro Thr Gln Gly Thr Thr Pro Ser Ser Lys Leu Gly Gly Leu
        355                 360                 365

Trp Lys Thr Val Ser Pro His Arg Ser Pro Ile Ser Asn Met Val Ser
    370                 375                 380

Met Ala Asn Asn His Met Ser Met Thr Asn Ser Gly Val Ser Met Thr
385                 390                 395                 400

Asn Thr Leu Ser Ser Met Leu Lys Gly Phe Ala Pro Ala Ala Ala
            405                 410                 415

Gln Ala Val Gln Thr Ala Ala Gln Asn Gly Val Arg Ala Met Ser Ser
            420                 425                 430
```

Leu Gly Ser Ser Leu Gly Ser Ser Gly Leu Gly Gly Val Ala Ala
            435                 440                 445

Asn Leu Gly Arg Ala Ala Ser Val Gly Ser Leu Ser Val Pro Gln Ala
450                 455                 460

Trp Ala Ala Ala Asn Gln Ala Val Thr Pro Ala Ala Arg Ala Leu Pro
465                 470                 475                 480

Leu Thr Ser Leu Thr Ser Ala Ala Glu Arg Gly Pro Gly Gln Met Leu
            485                 490                 495

Gly Gly Leu Pro Val Gly Gln Met Gly Ala Arg Ala Gly Gly Leu
            500                 505                 510

Ser Gly Val Leu Arg Val Pro Pro Arg Pro Tyr Val Met Pro His Ser
            515                 520                 525

Pro Ala Ala Gly Asp Ile Ala Pro Pro Ala Leu Ser Gln Asp Arg Phe
530                 535                 540

Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
            565                 570                 575

Ala Val Gly Ala Gly Thr Gly Ile Val Ile Asp Pro Asn Gly Val Val
            580                 585                 590

Leu Thr Asn Asn His Val Ile Ala Gly Ala Thr Asp Ile Asn Ala Phe
            595                 600                 605

Ser Val Gly Ser Gly Gln Thr Tyr Gly Val Asp Val Gly Tyr Asp
            610                 615                 620

Arg Thr Gln Asp Val Ala Val Leu Gln Leu Arg Gly Ala Gly Gly Leu
625                 630                 635                 640

Pro Ser Ala Ala Ile Gly Gly Val Ala Val Gly Glu Pro Val Val
            645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
            675                 680                 685

Thr Gly Ala Glu Glu Thr Leu Asn Gly Leu Ile Gln Phe Asp Ala Ala
            690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser
            725

<210> SEQ ID NO 37
<211> LENGTH: 30
<212> TYPE: PRT
<213> ORGANISM: Mycobacterium sp.

<400> SEQUENCE: 37

Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile
            20                  25                  30

<210> SEQ ID NO 38
<211> LENGTH: 128
<212> TYPE: PRT
<213> ORGANISM: Mycobacterium sp.

<400> SEQUENCE: 38

```
Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile Lys Leu
            20                  25                  30

Pro Thr Val His Ile Gly Pro Thr Ala Phe Leu Gly Leu Gly Val Val
            35                  40                  45

Asp Asn Asn Gly Asn Gly Ala Arg Val Gln Arg Val Val Gly Ser Ala
        50                  55                  60

Pro Ala Ala Ser Leu Gly Ile Ser Thr Gly Asp Val Ile Thr Ala Val
65                  70                  75                  80

Asp Gly Ala Pro Ile Asn Ser Ala Thr Ala Met Ala Asp Ala Leu Asn
                85                  90                  95

Gly His His Pro Gly Asp Val Ile Ser Val Thr Trp Gln Thr Lys Ser
            100                 105                 110

Gly Gly Thr Arg Thr Gly Asn Val Thr Leu Ala Glu Gly Pro Pro Ala
            115                 120                 125
```

<210> SEQ ID NO 39
<211> LENGTH: 128
<212> TYPE: PRT
<213> ORGANISM: Mycobacterium sp.

<400> SEQUENCE: 39

```
Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile Arg Ser
            20                  25                  30

Gly Gly Gly Ser Pro Thr Val His Ile Gly Pro Thr Ala Phe Leu Gly
            35                  40                  45

Leu Gly Val Val Asp Asn Asn Gly Asn Gly Ala Arg Val Gln Arg Val
        50                  55                  60

Val Gly Ser Ala Pro Ala Ala Ser Leu Gly Ile Ser Thr Gly Asp Val
65                  70                  75                  80

Ile Thr Ala Val Asp Gly Ala Pro Ile Asn Ser Ala Thr Ala Met Ala
                85                  90                  95

Asp Ala Leu Asn Gly His His Pro Gly Asp Val Ile Ser Val Thr Trp
            100                 105                 110

Gln Thr Lys Ser Gly Gly Thr Arg Thr Gly Asn Val Thr Leu Ala Glu
            115                 120                 125
```

<210> SEQ ID NO 40
<211> LENGTH: 355
<212> TYPE: PRT
<213> ORGANISM: Mycobacterium sp.

<400> SEQUENCE: 40

```
Met Ser Asn Ser Arg Arg Arg Ser Leu Arg Trp Ser Trp Leu Leu Ser
1               5                   10                  15

Val Leu Ala Ala Val Gly Leu Gly Leu Ala Thr Ala Pro Ala Gln Ala
            20                  25                  30

Ala Pro Pro Ala Leu Ser Gln Asp Arg Phe Ala Asp Phe Pro Ala Leu
            35                  40                  45

Pro Leu Asp Pro Ser Ala Met Val Ala Gln Val Gly Pro Gln Val Val
        50                  55                  60

Asn Ile Asn Thr Lys Leu Gly Tyr Asn Asn Ala Val Gly Ala Gly Thr
65                  70                  75                  80
```

Gly Ile Val Ile Asp Pro Asn Gly Val Val Leu Thr Asn Asn His Val
            85                  90                  95

Ile Ala Gly Ala Thr Asp Ile Asn Ala Phe Ser Val Gly Ser Gly Gln
            100                 105                 110

Thr Tyr Gly Val Asp Val Val Gly Tyr Asp Arg Thr Gln Asp Val Ala
            115                 120                 125

Val Leu Gln Leu Arg Gly Ala Gly Gly Leu Pro Ser Ala Ala Ile Gly
            130                 135                 140

Gly Gly Val Ala Val Gly Glu Pro Val Val Ala Met Gly Asn Ser Gly
145                 150                 155                 160

Gly Gln Gly Gly Thr Pro Arg Ala Val Pro Gly Arg Val Val Ala Leu
            165                 170                 175

Gly Gln Thr Val Gln Ala Ser Asp Ser Leu Thr Gly Ala Glu Glu Thr
            180                 185                 190

Leu Asn Gly Leu Ile Gln Phe Asp Ala Ala Ile Gln Pro Gly Asp Ser
            195                 200                 205

Gly Gly Pro Val Val Asn Gly Leu Gly Gln Val Val Gly Met Asn Thr
            210                 215                 220

Ala Ala Ser Asp Asn Phe Gln Leu Ser Gln Gly Gln Gly Phe Ala
225                 230                 235                 240

Ile Pro Ile Gly Gln Ala Met Ala Ile Ala Gly Gln Ile Arg Ser Gly
            245                 250                 255

Gly Gly Ser Pro Thr Val His Ile Gly Pro Thr Ala Phe Leu Gly Leu
            260                 265                 270

Gly Val Val Asp Asn Asn Gly Asn Gly Ala Arg Val Gln Arg Val Val
            275                 280                 285

Gly Ser Ala Pro Ala Ala Ser Leu Gly Ile Ser Thr Gly Asp Val Ile
            290                 295                 300

Thr Ala Val Asp Gly Ala Pro Ile Asn Ser Ala Thr Ala Met Ala Asp
305                 310                 315                 320

Ala Leu Asn Gly His His Pro Gly Asp Val Ile Ser Val Thr Trp Gln
            325                 330                 335

Thr Lys Ser Gly Gly Thr Arg Thr Gly Asn Val Thr Leu Ala Glu Gly
            340                 345                 350

Pro Pro Ala
        355

<210> SEQ ID NO 41
<211> LENGTH: 364
<212> TYPE: PRT
<213> ORGANISM: Haemophilus influenzae

<400> SEQUENCE: 41

Met Lys Leu Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
            20                  25                  30

Ser Asp Lys Ile Ile Ile Ala His Arg Gly Ala Ser Gly Tyr Leu Pro
            35                  40                  45

Glu His Thr Leu Glu Ser Lys Ala Leu Ala Phe Ala Gln Gln Ala Asp
            50                  55                  60

Tyr Leu Glu Gln Asp Leu Ala Met Thr Lys Asp Gly Arg Leu Val Val
65                  70                  75                  80

Ile His Asp His Phe Leu Asp Gly Leu Thr Asp Val Ala Lys Lys Phe
            85                  90                  95

```
Pro His Arg His Arg Lys Asp Gly Arg Tyr Tyr Val Ile Asp Phe Thr
                100                 105                 110

Leu Lys Glu Ile Gln Ser Leu Glu Met Thr Glu Asn Phe Glu Thr Lys
                115                 120                 125

Asp Gly Lys Gln Ala Gln Val Tyr Pro Asn Arg Phe Pro Leu Trp Lys
            130                 135                 140

Ser His Phe Arg Ile His Thr Phe Glu Asp Glu Ile Glu Phe Ile Gln
145                 150                 155                 160

Gly Leu Glu Lys Ser Thr Gly Lys Lys Val Gly Ile Tyr Pro Glu Ile
                165                 170                 175

Lys Ala Pro Trp Phe His His Gln Asn Gly Lys Asp Ile Ala Ala Glu
            180                 185                 190

Thr Leu Lys Val Leu Lys Lys Tyr Gly Tyr Asp Lys Lys Thr Asp Met
                195                 200                 205

Val Tyr Leu Gln Thr Phe Asp Phe Asn Glu Leu Lys Arg Ile Lys Thr
            210                 215                 220

Glu Leu Leu Pro Gln Met Gly Met Asp Leu Lys Leu Val Gln Leu Ile
225                 230                 235                 240

Ala Tyr Thr Asp Trp Lys Glu Thr Gln Glu Lys Asp Pro Lys Gly Tyr
                245                 250                 255

Trp Val Asn Tyr Asn Tyr Asp Trp Met Phe Lys Pro Gly Ala Met Ala
            260                 265                 270

Glu Val Val Lys Tyr Ala Asp Gly Val Gly Pro Gly Trp Tyr Met Leu
                275                 280                 285

Val Asn Lys Glu Glu Ser Lys Pro Asp Asn Ile Val Tyr Thr Pro Leu
            290                 295                 300

Val Lys Glu Leu Ala Gln Tyr Asn Val Glu Val His Pro Tyr Thr Val
305                 310                 315                 320

Arg Lys Asp Ala Leu Pro Ala Phe Phe Thr Asp Val Asn Gln Met Tyr
                325                 330                 335

Asp Val Leu Leu Asn Lys Ser Gly Ala Thr Gly Val Phe Thr Asp Phe
            340                 345                 350

Pro Asp Thr Gly Val Glu Phe Leu Lys Gly Ile Lys
                355                 360

<210> SEQ ID NO 42
<211> LENGTH: 313
<212> TYPE: PRT
<213> ORGANISM: Streptococcus pneumoniae

<400> SEQUENCE: 42

Met Glu Ile Asn Val Ser Lys Leu Arg Thr Asp Leu Pro Gln Val Gly
1               5                   10                  15

Val Gln Pro Tyr Arg Gln Val His Ala His Ser Thr Gly Asn Pro His
                20                  25                  30

Ser Thr Val Gln Asn Glu Ala Asp Tyr His Trp Arg Lys Asp Pro Glu
            35                  40                  45

Leu Gly Phe Phe Ser His Ile Val Gly Asn Gly Cys Ile Met Gln Val
        50                  55                  60

Gly Pro Val Asp Asn Gly Ala Trp Asp Val Gly Gly Trp Asn Ala
65                  70                  75              80

Glu Thr Tyr Ala Ala Val Glu Leu Ile Glu Ser His Ser Thr Lys Glu
                85                  90                  95

Glu Phe Met Thr Asp Tyr Arg Leu Tyr Ile Glu Leu Leu Arg Asn Leu
```

```
                100             105             110
Ala Asp Glu Ala Gly Leu Pro Lys Thr Leu Asp Thr Gly Ser Leu Ala
            115                 120                 125
Gly Ile Lys Thr His Glu Tyr Cys Thr Asn Asn Gln Pro Asn Asn His
        130                 135                 140
Ser Asp His Val Asp Pro Tyr Pro Tyr Leu Ala Lys Trp Gly Ile Ser
145                 150                 155                 160
Arg Glu Gln Phe Lys His Asp Ile Glu Asn Gly Leu Thr Ile Glu Thr
                165                 170                 175
Gly Trp Gln Lys Asn Asp Thr Gly Tyr Trp Tyr Val His Ser Asp Gly
            180                 185                 190
Ser Tyr Pro Lys Asp Lys Phe Glu Lys Ile Asn Gly Thr Trp Tyr Tyr
        195                 200                 205
Phe Asp Ser Ser Gly Tyr Met Leu Ala Asp Arg Trp Arg Lys His Thr
210                 215                 220
Asp Gly Asn Trp Tyr Trp Phe Asp Asn Ser Gly Glu Met Ala Thr Gly
225                 230                 235                 240
Trp Lys Lys Ile Ala Asp Lys Trp Tyr Tyr Phe Asn Glu Glu Gly Ala
                245                 250                 255
Met Lys Thr Gly Trp Val Lys Tyr Lys Asp Thr Trp Tyr Tyr Leu Asp
            260                 265                 270
Ala Lys Glu Gly Ala Met Val Ser Asn Ala Phe Ile Gln Ser Ala Asp
        275                 280                 285
Gly Thr Gly Trp Tyr Tyr Leu Lys Pro Asp Gly Thr Leu Ala Asp Arg
    290                 295                 300
Pro Glu Phe Arg Met Ser Gln Met Ala
305                 310

<210> SEQ ID NO 43
<211> LENGTH: 166
<212> TYPE: PRT
<213> ORGANISM: Homo sapiens

<400> SEQUENCE: 43

Met Lys Tyr Thr Ser Tyr Ile Leu Ala Phe Gln Leu Cys Ile Val Leu
1               5                   10                  15
Gly Ser Leu Gly Cys Tyr Cys Gln Asp Pro Tyr Val Lys Glu Ala Glu
            20                  25                  30
Asn Leu Lys Lys Tyr Phe Asn Ala Gly His Ser Asp Val Ala Asp Asn
        35                  40                  45
Gly Thr Leu Phe Leu Gly Ile Leu Lys Asn Trp Lys Glu Glu Ser Asp
    50                  55                  60
Arg Lys Ile Met Gln Ser Gln Ile Val Ser Phe Tyr Phe Lys Leu Phe
65                  70                  75                  80
Lys Asn Phe Lys Asp Asp Gln Ser Ile Gln Lys Ser Val Glu Thr Ile
                85                  90                  95
Lys Glu Asp Met Asn Val Lys Phe Phe Asn Ser Asn Lys Lys Lys Arg
            100                 105                 110
Asp Asp Phe Glu Lys Leu Thr Asn Tyr Ser Val Thr Asp Leu Asn Val
        115                 120                 125
Gln Arg Lys Ala Ile His Glu Leu Ile Gln Val Met Ala Glu Leu Ser
    130                 135                 140
Pro Ala Ala Lys Thr Gly Lys Arg Lys Arg Ser Gln Met Leu Phe Arg
145                 150                 155                 160
```

Gly Arg Arg Ala Ser Gln
                165

<210> SEQ ID NO 44
<211> LENGTH: 233
<212> TYPE: PRT
<213> ORGANISM: Homo sapiens

<400> SEQUENCE: 44

Met Ser Thr Glu Ser Met Ile Arg Asp Val Glu Leu Ala Glu Ala
1               5                   10                  15

Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 45
<211> LENGTH: 153
<212> TYPE: PRT
<213> ORGANISM: Homo sapiens

<400> SEQUENCE: 45

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

```
Glu Glu Leu Lys Pro Leu Glu Glu Val Leu Asn Leu Ala Gln Ser Lys
            85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
            115                 120                 125

Asp Glu Thr Ala Thr Ile Val Glu Phe Leu Asn Arg Trp Ile Thr Phe
            130                 135                 140

Cys Gln Ser Ile Ile Ser Thr Leu Thr
145                 150
```

<210> SEQ ID NO 46
<211> LENGTH: 99
<212> TYPE: PRT
<213> ORGANISM: Homo sapiens

<400> SEQUENCE: 46

```
Met Thr Ser Lys Leu Ala Val Ala Leu Leu Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
            35                  40                  45

Ile Lys Glu Leu Arg Val Ile Glu Ser Gly Pro His Cys Ala Asn Thr
50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
            85                  90                  95

Glu Asn Ser
```

<210> SEQ ID NO 47
<211> LENGTH: 662
<212> TYPE: PRT
<213> ORGANISM: Homo sapiens

<400> SEQUENCE: 47

```
Met Glu Pro Leu Val Thr Trp Val Val Pro Leu Leu Phe Leu Phe Leu
1               5                   10                  15

Leu Ser Arg Gln Gly Ala Ala Cys Arg Thr Ser Glu Cys Cys Phe Gln
            20                  25                  30

Asp Pro Pro Tyr Pro Asp Ala Asp Ser Gly Ser Ala Ser Gly Pro Arg
            35                  40                  45

Asp Leu Arg Cys Tyr Arg Ile Ser Ser Asp Arg Tyr Glu Cys Ser Trp
50                  55                  60

Gln Tyr Glu Gly Pro Thr Ala Gly Val Ser His Phe Leu Arg Cys Cys
65                  70                  75                  80

Leu Ser Ser Gly Arg Cys Cys Tyr Phe Ala Ala Gly Ser Ala Thr Arg
            85                  90                  95

Leu Gln Phe Ser Asp Gln Ala Gly Val Ser Val Leu Tyr Thr Val Thr
            100                 105                 110

Leu Trp Val Glu Ser Trp Ala Arg Asn Gln Thr Glu Lys Ser Pro Glu
            115                 120                 125

Val Thr Leu Gln Leu Tyr Asn Ser Val Lys Tyr Glu Pro Pro Leu Gly
            130                 135                 140

Asp Ile Lys Val Ser Lys Leu Ala Gly Gln Leu Arg Met Glu Trp Glu
```

-continued

```
           145                 150                 155                 160
       Thr Pro Asp Asn Gln Val Gly Ala Glu Val Gln Phe Arg His Arg Thr
                       165                 170                 175

Pro Ser Ser Pro Trp Lys Leu Gly Asp Cys Gly Pro Gln Asp Asp Asp
                       180                 185                 190

Thr Glu Ser Cys Leu Cys Pro Leu Glu Met Asn Val Ala Gln Glu Phe
                       195                 200                 205

Gln Leu Arg Arg Gln Leu Gly Ser Gln Ser Ser Trp Ser Lys
           210                 215                 220

Trp Ser Ser Pro Val Cys Val Pro Pro Glu Asn Pro Gln Pro Gln
       225                 230                 235                 240

Val Arg Phe Ser Val Glu Gln Leu Gly Gln Asp Gly Arg Arg Leu
                       245                 250                 255

Thr Leu Lys Glu Gln Pro Thr Gln Leu Glu Leu Pro Glu Gly Cys Gln
                       260                 265                 270

Gly Leu Ala Pro Gly Thr Glu Val Thr Tyr Arg Leu Gln Leu His Met
                       275                 280                 285

Leu Ser Cys Pro Cys Lys Ala Lys Ala Thr Arg Thr Leu His Leu Gly
           290                 295                 300

Lys Met Pro Tyr Leu Ser Gly Ala Ala Tyr Asn Val Ala Val Ile Ser
       305                 310                 315                 320

Ser Asn Gln Phe Gly Pro Gly Leu Asn Gln Thr Trp His Ile Pro Ala
                       325                 330                 335

Asp Thr His Thr Glu Pro Val Ala Leu Asn Ile Ser Val Gly Thr Asn
                       340                 345                 350

Gly Thr Thr Met Tyr Trp Pro Ala Arg Ala Gln Ser Met Thr Tyr Cys
                       355                 360                 365

Ile Glu Trp Gln Pro Val Gly Gln Asp Gly Gly Leu Ala Thr Cys Ser
                       370                 375                 380

Leu Thr Ala Pro Gln Asp Pro Asp Pro Ala Gly Met Ala Thr Tyr Ser
       385                 390                 395                 400

Trp Ser Arg Glu Ser Gly Ala Met Gly Gln Glu Lys Cys Tyr Tyr Ile
                       405                 410                 415

Thr Ile Phe Ala Ser Ala His Pro Glu Lys Leu Thr Leu Trp Ser Thr
                       420                 425                 430

Val Leu Ser Thr Tyr His Phe Gly Gly Asn Ala Ser Ala Ala Gly Thr
                       435                 440                 445

Pro His His Val Ser Val Lys Asn His Ser Leu Asp Ser Val Ser Val
       450                 455                 460

Asp Trp Ala Pro Ser Leu Leu Ser Thr Cys Pro Gly Val Leu Lys Glu
       465                 470                 475                 480

Tyr Val Val Arg Cys Arg Asp Glu Asp Ser Lys Gln Val Ser Glu His
                       485                 490                 495

Pro Val Gln Pro Thr Glu Thr Gln Val Thr Leu Ser Gly Leu Arg Ala
                       500                 505                 510

Gly Val Ala Tyr Thr Val Gln Val Arg Ala Asp Thr Ala Trp Leu Arg
                       515                 520                 525

Gly Val Trp Ser Gln Pro Gln Arg Phe Ser Ile Glu Val Gln Val Ser
                       530                 535                 540

Asp Trp Leu Ile Phe Phe Ala Ser Leu Gly Ser Phe Leu Ser Ile Leu
       545                 550                 555                 560

Leu Val Gly Val Leu Gly Tyr Leu Gly Leu Asn Arg Ala Ala Arg His
                       565                 570                 575
```

```
Leu Cys Pro Pro Leu Pro Thr Pro Cys Ala Ser Ser Ala Ile Glu Phe
            580                 585                 590

Pro Gly Gly Lys Glu Thr Trp Gln Trp Ile Asn Pro Val Asp Phe Gln
            595                 600                 605

Glu Glu Ala Ser Leu Gln Glu Ala Leu Val Val Glu Met Ser Trp Asp
610                 615                 620

Lys Gly Glu Arg Thr Glu Pro Leu Glu Lys Thr Glu Leu Pro Glu Gly
625                 630                 635                 640

Ala Pro Glu Leu Ala Leu Asp Thr Glu Leu Ser Leu Glu Asp Gly Asp
            645                 650                 655

Arg Cys Lys Ala Lys Met
            660

<210> SEQ ID NO 48
<211> LENGTH: 193
<212> TYPE: PRT
<213> ORGANISM: Homo sapiens

<400> SEQUENCE: 48

Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
            85                  90                  95

Ala Val Thr Ile Ser Val Lys Cys Glu Lys Ile Ser Thr Leu Ser Cys
        100                 105                 110

Glu Asn Lys Ile Ile Ser Phe Lys Glu Met Asn Pro Pro Asp Asn Ile
    115                 120                 125

Lys Asp Thr Lys Ser Asp Ile Ile Phe Phe Gln Arg Ser Val Pro Gly
130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
            165                 170                 175

Glu Asp Glu Leu Gly Asp Arg Ser Ile Met Phe Thr Val Gln Asn Glu
        180                 185                 190

Asp

<210> SEQ ID NO 49
<211> LENGTH: 177
<212> TYPE: PRT
<213> ORGANISM: Homo sapiens

<400> SEQUENCE: 49

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
            20                  25                  30
```

```
Asp Gly Lys Gln Tyr Glu Ser Val Leu Met Val Ser Ile Asp Gln Leu
            35                  40                  45

Leu Asp Ser Met Lys Glu Ile Gly Ser Asn Cys Leu Asn Asn Glu Phe
 50                  55                  60

Asn Phe Phe Lys Arg His Ile Cys Asp Ala Asn Lys Glu Gly Met Phe
65                   70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110

Ile Leu Leu Asn Cys Thr Gly Gln Val Lys Gly Arg Lys Pro Ala Ala
            115                 120                 125

Leu Gly Glu Ala Gln Pro Thr Lys Ser Leu Glu Glu Asn Lys Ser Leu
130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His

<210> SEQ ID NO 50
<211> LENGTH: 152
<212> TYPE: PRT
<213> ORGANISM: Homo sapiens

<400> SEQUENCE: 50

Met Ser Arg Leu Pro Val Leu Leu Leu Leu Gln Leu Leu Val Arg Pro
1               5                   10                  15

Gly Leu Gln Ala Pro Met Thr Gln Thr Thr Ser Leu Lys Thr Ser Trp
            20                  25                  30

Val Asn Cys Ser Asn Met Ile Asp Glu Ile Ile Thr His Leu Lys Gln
            35                  40                  45

Pro Pro Leu Pro Leu Leu Asp Phe Asn Asn Leu Asn Gly Glu Asp Gln
 50                  55                  60

Asp Ile Leu Met Glu Asn Asn Leu Arg Arg Pro Asn Leu Glu Ala Phe
65                   70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
            115                 120                 125

Lys Leu Thr Phe Tyr Leu Lys Thr Leu Glu Asn Ala Gln Ala Gln Gln
130                 135                 140

Thr Thr Leu Ser Leu Ala Ile Phe
145                 150

<210> SEQ ID NO 51
<211> LENGTH: 153
<212> TYPE: PRT
<213> ORGANISM: Homo sapiens

<400> SEQUENCE: 51

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
```

```
                20                  25                  30
Glu Ile Ile Lys Thr Leu Asn Ser Leu Thr Glu Gln Lys Thr Leu Cys
            35                  40                  45
Thr Glu Leu Thr Val Thr Asp Ile Phe Ala Ala Ser Lys Asn Thr Thr
        50                  55                  60
Glu Lys Glu Thr Phe Cys Arg Ala Ala Thr Val Leu Arg Gln Phe Tyr
65                  70                  75                  80
Ser His His Glu Lys Asp Thr Arg Cys Leu Gly Ala Thr Ala Gln Gln
                85                  90                  95
Phe His Arg His Lys Gln Leu Ile Arg Phe Leu Lys Arg Leu Asp Arg
            100                 105                 110
Asn Leu Trp Gly Leu Ala Gly Leu Asn Ser Cys Pro Val Lys Glu Ala
        115                 120                 125
Asn Gln Ser Thr Leu Glu Asn Phe Leu Glu Arg Leu Lys Thr Ile Met
    130                 135                 140
Arg Glu Lys Tyr Ser Lys Cys Ser Ser
145                 150
```

<210> SEQ ID NO 52
<211> LENGTH: 134
<212> TYPE: PRT
<213> ORGANISM: Homo sapiens

<400> SEQUENCE: 52

```
Met Arg Met Leu Leu His Leu Ser Leu Leu Ala Leu Gly Ala Ala Tyr
1               5                   10                  15
Val Tyr Ala Ile Pro Thr Glu Ile Pro Thr Ser Ala Leu Val Lys Glu
                20                  25                  30
Thr Leu Ala Leu Leu Ser Thr His Arg Thr Leu Leu Ile Ala Asn Glu
            35                  40                  45
Thr Leu Arg Ile Pro Val Pro Val His Lys Asn His Gln Leu Cys Thr
        50                  55                  60
Glu Glu Ile Phe Gln Gly Ile Gly Thr Leu Glu Ser Gln Thr Val Gln
65                  70                  75                  80
Gly Gly Thr Val Glu Arg Leu Phe Lys Asn Leu Ser Leu Ile Lys Lys
                85                  90                  95
Tyr Ile Asp Gly Gln Lys Lys Lys Cys Gly Glu Glu Arg Arg Arg Val
            100                 105                 110
Asn Gln Phe Leu Asp Tyr Leu Gln Glu Phe Leu Gly Val Met Asn Thr
        115                 120                 125
Glu Trp Ile Ile Glu Ser
    130
```

<210> SEQ ID NO 53
<211> LENGTH: 212
<212> TYPE: PRT
<213> ORGANISM: Homo sapiens

<400> SEQUENCE: 53

```
Met Asn Ser Phe Ser Thr Ser Ala Phe Gly Pro Val Ala Phe Ser Leu
1               5                   10                  15
Gly Leu Leu Leu Val Leu Pro Ala Ala Phe Pro Ala Pro Val Pro Pro
                20                  25                  30
Gly Glu Asp Ser Lys Asp Val Ala Ala Pro His Arg Gln Pro Leu Thr
            35                  40                  45
Ser Ser Glu Arg Ile Asp Lys Gln Ile Arg Tyr Ile Leu Asp Gly Ile
```

```
                    50                  55                  60

Ser Ala Leu Arg Lys Glu Thr Cys Asn Lys Ser Asn Met Cys Glu Ser
 65                  70                  75                  80

Ser Lys Glu Ala Leu Ala Glu Asn Asn Leu Asn Leu Pro Lys Met Ala
                     85                  90                  95

Glu Lys Asp Gly Cys Phe Gln Ser Gly Phe Asn Glu Glu Thr Cys Leu
                100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
        130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 54
<211> LENGTH: 140
<212> TYPE: PRT
<213> ORGANISM: Homo sapiens

<400> SEQUENCE: 54

Met Val Leu Thr Ser Ala Leu Leu Leu Cys Ser Val Ala Gly Gln Gly
  1               5                  10                  15

Cys Pro Thr Leu Ala Gly Ile Leu Asp Ile Asn Phe Leu Ile Asn Lys
                 20                  25                  30

Met Gln Glu Asp Pro Ala Ser Lys Cys His Cys Ser Ala Asn Val Thr
             35                  40                  45

Ser Cys Leu Cys Leu Gly Ile Pro Ser Asp Asn Cys Thr Arg Pro Cys
         50                  55                  60

Phe Ser Glu Arg Leu Ser Gln Met Thr Asn Thr Thr Met Gln Thr Arg
 65                  70                  75                  80

Tyr Pro Leu Ile Phe Ser Arg Val Lys Lys Ser Val Glu Val Leu Lys
                 85                  90                  95

Asn Asn Lys Cys Pro Tyr Phe Ser Cys Glu Gln Pro Cys Asn Gln Thr
                100                 105                 110

Thr Ala Gly Asn Ala Leu Thr Phe Leu Lys Ser Leu Leu Glu Ile Phe
            115                 120                 125

Gln Lys Glu Lys Met Arg Gly Met Arg Gly Lys Ile
        130                 135                 140

<210> SEQ ID NO 55
<211> LENGTH: 178
<212> TYPE: PRT
<213> ORGANISM: Homo sapiens

<400> SEQUENCE: 55

Met His Ser Ser Ala Leu Leu Cys Cys Leu Val Leu Leu Thr Gly Val
  1               5                  10                  15

Arg Ala Ser Pro Gly Gln Gly Thr Gln Ser Glu Asn Ser Cys Thr His
```

```
                20              25              30

Phe Pro Gly Asn Leu Pro Asn Met Leu Arg Asp Leu Arg Asp Ala Phe
                35              40              45

Ser Arg Val Lys Thr Phe Phe Gln Met Lys Asp Gln Leu Asp Asn Leu
        50              55              60

Leu Leu Lys Glu Ser Leu Glu Asp Phe Lys Gly Tyr Leu Gly Cys
65              70              75              80

Gln Ala Leu Ser Glu Met Ile Gln Phe Tyr Leu Glu Glu Val Met Pro
                85              90              95

Gln Ala Glu Asn Gln Asp Pro Asp Ile Lys Ala His Val Asn Ser Leu
            100             105             110

Gly Glu Asn Leu Lys Thr Leu Arg Leu Arg Leu Arg Arg Cys His Arg
            115             120             125

Phe Leu Pro Cys Glu Asn Lys Ser Lys Ala Val Glu Gln Val Lys Asn
        130             135             140

Ala Phe Asn Lys Leu Gln Glu Lys Gly Ile Tyr Lys Ala Met Ser Glu
145             150             155             160

Phe Asp Ile Phe Ile Asn Tyr Ile Glu Ala Tyr Met Thr Met Lys Ile
                165             170             175

Arg Asn

<210> SEQ ID NO 56
<211> LENGTH: 145
<212> TYPE: PRT
<213> ORGANISM: Homo sapiens

<400> SEQUENCE: 56

Met Ala Leu Leu Leu Thr Thr Val Ile Ala Leu Thr Cys Leu Gly Gly
1               5               10              15

Phe Ala Ser Pro Gly Pro Val Pro Ser Thr Ala Leu Arg Glu Leu
            20              25              30

Ile Glu Glu Leu Val Asn Ile Thr Gln Asn Gln Lys Ala Pro Leu Cys
            35              40              45

Asn Gly Ser Met Val Trp Ser Ile Asn Leu Thr Ala Gly Met Tyr Cys
        50              55              60

Ala Ala Leu Glu Ser Leu Ile Asn Val Ser Gly Cys Ser Ala Ile Glu
65              70              75              80

Lys Thr Gln Arg Met Leu Ser Gly Phe Cys Pro His Lys Val Ser Ala
                85              90              95

Gly Gln Phe Ser Ser Leu His Val Arg Asp Thr Lys Ile Glu Val Ala
            100             105             110

Gln Phe Val Lys Asp Leu Leu Leu His Leu Lys Lys Leu Phe Arg Glu
        115             120             125

Gly Gln Phe Asn Arg Asn Phe Glu Ser Ile Ile Cys Arg Asp Arg
    130             135             140

Thr
145

<210> SEQ ID NO 57
<211> LENGTH: 136
<212> TYPE: PRT
<213> ORGANISM: Homo sapiens

<400> SEQUENCE: 57

Met Asp Phe Gln Val Gln Ile Phe Ser Phe Leu Leu Ile Ser Ala Ser
1               5               10              15
```

```
Val Ile Met Ser Arg Ala Asn Trp Val Asn Val Ile Ser Asp Leu Lys
            20                  25                  30

Lys Ile Glu Asp Leu Ile Gln Ser Met His Ile Asp Ala Thr Leu Tyr
        35                  40                  45

Thr Glu Ser Asp Val His Pro Ser Cys Lys Val Thr Ala Met Lys Cys
    50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
                85                  90                  95

Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
        115                 120                 125

Val Gln Met Phe Ile Asn Thr Ser
    130                 135

<210> SEQ ID NO 58
<211> LENGTH: 656
<212> TYPE: PRT
<213> ORGANISM: Homo sapiens

<400> SEQUENCE: 58

Met Glu Gly Asp Gly Ser Asp Pro Glu Pro Asp Ala Gly Glu Asp
1               5                   10                  15

Ser Lys Ser Glu Asn Gly Glu Asn Ala Pro Ile Tyr Cys Ile Cys Arg
            20                  25                  30

Lys Pro Asp Ile Asn Cys Phe Met Ile Gly Cys Asp Asn Cys Asn Glu
        35                  40                  45

Trp Phe His Gly Asp Cys Ile Arg Ile Thr Glu Lys Met Ala Lys Ala
    50                  55                  60

Ile Arg Glu Trp Tyr Cys Arg Glu Cys Arg Glu Lys Asp Pro Lys Leu
65                  70                  75                  80

Glu Ile Arg Tyr Arg His Lys Lys Ser Arg Glu Arg Asp Gly Asn Glu
                85                  90                  95

Arg Asp Ser Ser Glu Pro Arg Asp Glu Gly Gly Gly Arg Lys Arg Pro
            100                 105                 110

Val Pro Asp Pro Asn Leu Gln Arg Arg Ala Gly Ser Gly Thr Gly Val
        115                 120                 125

Gly Ala Met Leu Ala Arg Gly Ser Ala Ser Pro His Lys Ser Ser Pro
    130                 135                 140

Gln Pro Leu Val Ala Thr Pro Ser Gln His His Gln Gln Gln Gln Gln
145                 150                 155                 160

Gln Ile Lys Arg Ser Ala Arg Met Cys Gly Glu Cys Glu Ala Cys Arg
                165                 170                 175

Arg Thr Glu Asp Cys Gly His Cys Asp Phe Cys Arg Asp Met Lys Lys
            180                 185                 190

Phe Gly Gly Pro Asn Lys Ile Arg Gln Lys Cys Arg Leu Arg Gln Cys
        195                 200                 205

Gln Leu Arg Ala Arg Glu Ser Tyr Lys Tyr Phe Pro Ser Ser Leu Ser
    210                 215                 220

Pro Val Thr Pro Ser Glu Ser Leu Pro Arg Pro Arg Arg Pro Leu Pro
225                 230                 235                 240

Thr Gln Gln Gln Pro Gln Pro Ser Gln Lys Leu Gly Arg Ile Arg Glu
```

```
            245                 250                 255
Asp Glu Gly Ala Val Ala Ser Ser Thr Val Lys Glu Pro Pro Glu Ala
            260                 265                 270

Thr Ala Thr Pro Glu Pro Leu Ser Asp Glu Asp Leu Pro Leu Asp Pro
        275                 280                 285

Asp Leu Tyr Gln Asp Phe Cys Ala Gly Ala Phe Asp Asp Asn Gly Leu
    290                 295                 300

Pro Trp Met Ser Asp Thr Glu Glu Ser Pro Phe Leu Asp Pro Ala Leu
305                 310                 315                 320

Arg Lys Arg Ala Val Lys Val Lys His Val Lys Arg Glu Lys Lys
            325                 330                 335

Ser Glu Lys Lys Lys Glu Glu Arg Tyr Lys Arg His Arg Gln Lys Gln
            340                 345                 350

Lys His Lys Asp Lys Trp Lys His Pro Glu Arg Ala Asp Ala Lys Asp
        355                 360                 365

Pro Ala Ser Leu Pro Gln Cys Leu Gly Pro Gly Cys Val Arg Pro Ala
    370                 375                 380

Gln Pro Ser Ser Lys Tyr Cys Ser Asp Asp Cys Gly Met Lys Leu Ala
385                 390                 395                 400

Ala Asn Arg Ile Tyr Glu Ile Leu Pro Gln Arg Ile Gln Gln Trp Gln
            405                 410                 415

Gln Ser Pro Cys Ile Ala Glu Glu His Gly Lys Lys Leu Leu Glu Arg
            420                 425                 430

Ile Arg Arg Glu Gln Gln Ser Ala Arg Thr Arg Leu Gln Glu Met Glu
        435                 440                 445

Arg Arg Phe His Glu Leu Glu Ala Ile Ile Leu Arg Ala Lys Gln Gln
    450                 455                 460

Ala Val Arg Glu Asp Glu Glu Ser Asn Glu Gly Asp Ser Asp Asp Thr
465                 470                 475                 480

Asp Leu Gln Ile Phe Cys Val Ser Cys Gly His Pro Ile Asn Pro Arg
            485                 490                 495

Val Ala Leu Arg His Met Glu Arg Cys Tyr Ala Lys Tyr Glu Ser Gln
            500                 505                 510

Thr Ser Phe Gly Ser Met Tyr Pro Thr Arg Ile Glu Gly Ala Thr Arg
        515                 520                 525

Leu Phe Cys Asp Val Tyr Asn Pro Gln Ser Lys Thr Tyr Cys Lys Arg
    530                 535                 540

Leu Gln Val Leu Cys Pro Glu His Ser Arg Asp Pro Lys Val Pro Ala
545                 550                 555                 560

Asp Glu Val Cys Gly Cys Pro Leu Val Arg Asp Val Phe Glu Leu Thr
            565                 570                 575

Gly Asp Phe Cys Arg Leu Pro Lys Arg Gln Cys Asn Arg His Tyr Cys
        580                 585                 590

Trp Glu Lys Leu Arg Arg Ala Glu Val Asp Leu Glu Arg Val Arg Val
    595                 600                 605

Trp Tyr Lys Leu Asp Glu Leu Phe Glu Gln Glu Arg Asn Val Arg Thr
    610                 615                 620

Ala Met Thr Asn Arg Ala Gly Leu Leu Ala Leu Met Leu His Gln Thr
625                 630                 635                 640

Ile Gln His Asp Pro Leu Thr Thr Asp Leu Arg Ser Ser Ala Asp Arg
            645                 650                 655

<210> SEQ ID NO 59
```

```
<211> LENGTH: 124
<212> TYPE: PRT
<213> ORGANISM: Vibrio cholerae

<400> SEQUENCE: 59

Met Ile Lys Leu Lys Phe Gly Val Phe Phe Thr Val Leu Leu Ser Ser
1               5                   10                  15

Ala Tyr Ala His Gly Thr Pro Gln Asn Ile Thr Asp Leu Cys Ala Glu
            20                  25                  30

Tyr His Asn Thr Gln Ile Tyr Thr Leu Asn Asp Lys Ile Phe Ser Tyr
        35                  40                  45

Thr Glu Ser Leu Ala Gly Lys Arg Glu Met Ala Ile Ile Thr Phe Lys
    50                  55                  60

Asn Gly Ala Ile Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn
        115                 120

<210> SEQ ID NO 60
<211> LENGTH: 258
<212> TYPE: PRT
<213> ORGANISM: Vibrio sp.

<400> SEQUENCE: 60

Met Val Lys Ile Ile Phe Val Phe Phe Ile Phe Leu Ser Ser Phe Ser
1               5                   10                  15

Tyr Ala Asn Asp Asp Lys Leu Tyr Arg Ala Asp Ser Arg Pro Pro Asp
            20                  25                  30

Glu Ile Lys Gln Ser Gly Gly Leu Met Pro Arg Gly Gln Asn Glu Tyr
        35                  40                  45

Phe Asp Arg Gly Thr Gln Met Asn Ile Asn Leu Tyr Asp His Ala Arg
    50                  55                  60

Gly Thr Gln Thr Gly Phe Val Arg His Asp Asp Gly Tyr Val Ser Thr
65                  70                  75                  80

Ser Ile Ser Leu Arg Ser Ala His Leu Val Gly Gln Thr Ile Leu Ser
                85                  90                  95

Gly His Ser Thr Tyr Tyr Ile Tyr Val Ile Ala Thr Ala Pro Asn Met
            100                 105                 110

Phe Asn Val Asn Asp Val Leu Gly Ala Tyr Ser Pro His Pro Asp Glu
        115                 120                 125

Gln Glu Val Ser Ala Leu Gly Gly Ile Pro Tyr Ser Gln Ile Tyr Gly
    130                 135                 140

Trp Tyr Arg Val His Phe Gly Val Leu Asp Glu Gln Leu His Arg Asn
145                 150                 155                 160

Arg Gly Tyr Arg Asp Arg Tyr Tyr Ser Asn Leu Asp Ile Ala Pro Ala
                165                 170                 175

Ala Asp Gly Tyr Gly Leu Ala Gly Phe Pro Pro Glu His Arg Ala Trp
            180                 185                 190

Arg Glu Glu Pro Trp Ile His His Ala Pro Pro Gly Cys Gly Asn Ala
        195                 200                 205

Pro Arg Ser Ser Met Ser Asn Thr Cys Asp Glu Lys Thr Gln Ser Leu
    210                 215                 220
```

```
Gly Val Lys Phe Leu Asp Glu Tyr Gln Ser Lys Val Lys Arg Gln Ile
225                 230                 235                 240

Phe Ser Gly Tyr Gln Ser Asp Ile Asp Thr His Asn Arg Ile Lys Asp
                245                 250                 255

Glu Leu

<210> SEQ ID NO 61
<211> LENGTH: 124
<212> TYPE: PRT
<213> ORGANISM: Vibrio cholerae

<400> SEQUENCE: 61

Met Ile Lys Leu Lys Phe Gly Val Phe Phe Thr Val Leu Leu Ser Ser
1               5                   10                  15

Ala Tyr Ala His Gly Thr Pro Gln Asn Ile Thr Asp Leu Cys Ala Glu
                20                  25                  30

Tyr His Asn Thr Gln Ile His Thr Leu Asn Asp Lys Ile Leu Ser Tyr
            35                  40                  45

Thr Glu Ser Leu Ala Gly Asn Arg Glu Met Ala Ile Ile Thr Phe Lys
        50                  55                  60

Asn Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
                100                 105                 110

Thr Pro His Ala Ile Ala Ala Ile Ser Met Ala Asn
            115                 120

<210> SEQ ID NO 62
<211> LENGTH: 18
<212> TYPE: PRT
<213> ORGANISM: Homo sapiens

<400> SEQUENCE: 62

Asp Pro Asn Ala Pro Lys Arg Pro Pro Ser Ala Phe Phe Leu Phe Cys
1               5                   10                  15

Ser Glu

<210> SEQ ID NO 63
<211> LENGTH: 96
<212> TYPE: PRT
<213> ORGANISM: Homo sapiens

<400> SEQUENCE: 63

Met Cys Cys Thr Lys Ser Leu Leu Leu Ala Ala Leu Met Ser Val Leu
1               5                   10                  15

Leu Leu His Leu Cys Gly Glu Ser Glu Ala Ala Ser Asn Phe Asp Cys
                20                  25                  30

Cys Leu Gly Tyr Thr Asp Arg Ile Leu His Pro Lys Phe Ile Val Gly
            35                  40                  45

Phe Thr Arg Gln Leu Ala Asn Glu Gly Cys Asp Ile Asn Ala Ile Ile
        50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95
```

<210> SEQ ID NO 64
<211> LENGTH: 92
<212> TYPE: PRT
<213> ORGANISM: Homo sapiens

<400> SEQUENCE: 64

Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
            20                  25                  30

Cys Cys Phe Ser Tyr Thr Ser Arg Gln Ile Pro Gln Asn Phe Ile Ala
        35                  40                  45

Asp Tyr Phe Glu Thr Ser Ser Gln Cys Ser Lys Pro Gly Val Ile Phe
    50                  55                  60

Leu Thr Lys Arg Ser Arg Gln Val Cys Ala Asp Pro Ser Glu Glu Trp
65                  70                  75                  80

Val Gln Lys Tyr Val Ser Asp Leu Glu Leu Ser Ala
                85                  90

<210> SEQ ID NO 65
<211> LENGTH: 144
<212> TYPE: PRT
<213> ORGANISM: Homo sapiens

<400> SEQUENCE: 65

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 66
<211> LENGTH: 204
<212> TYPE: PRT
<213> ORGANISM: Homo sapiens

<400> SEQUENCE: 66

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

```
Glu Gln Val Arg Lys Ile Gln Gly Asp Gly Ala Ala Leu Gln Glu Lys
 50                  55                  60
Leu Cys Ala Thr Tyr Lys Leu Cys His Pro Glu Glu Leu Val Leu Leu
 65                  70                  75                  80
Gly His Ser Leu Gly Ile Pro Trp Ala Pro Leu Ser Ser Cys Pro Ser
                 85                  90                  95
Gln Ala Leu Gln Leu Ala Gly Cys Leu Ser Gln Leu His Ser Gly Leu
             100                 105                 110
Phe Leu Tyr Gln Gly Leu Leu Gln Ala Leu Glu Gly Ile Ser Pro Glu
         115                 120                 125
Leu Gly Pro Thr Leu Asp Thr Leu Gln Leu Asp Val Ala Asp Phe Ala
130                 135                 140
Thr Thr Ile Trp Gln Gln Met Glu Glu Leu Gly Met Ala Pro Ala Leu
145                 150                 155                 160
Gln Pro Thr Gln Gly Ala Met Pro Ala Phe Ala Ser Ala Phe Gln Arg
                165                 170                 175
Arg Ala Gly Gly Val Leu Val Ala Ser His Leu Gln Ser Phe Leu Glu
            180                 185                 190
Val Ser Tyr Arg Val Leu Arg His Leu Ala Gln Pro
        195                 200
```

```
<210> SEQ ID NO 67
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Glu Ile Asn Ser Ser Tyr
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Ser His Pro Arg Leu Ser Ala
1               5

<210> SEQ ID NO 69
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Met Pro Asn Pro Met Val
1               5

<210> SEQ ID NO 70
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 70

Gly Leu Gln Gln Val Leu Leu
1               5

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

His Glu Leu Ser Val Leu Leu
1               5

<210> SEQ ID NO 72
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Tyr Ala Pro Gln Arg Leu Pro
1               5

<210> SEQ ID NO 73
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Thr Pro Arg Thr Leu Pro Thr
1               5

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Pro Val His Ser Ser Ile
1               5

<210> SEQ ID NO 75
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Pro Pro His Ala Leu Ser
1               5

<210> SEQ ID NO 76

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Thr Phe Ser Asn Arg Phe Ile
1               5

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Val Val Pro Thr Pro Pro Tyr
1               5

<210> SEQ ID NO 78
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Glu Leu Ala Pro Asp Ser Pro
1               5

<210> SEQ ID NO 79
<211> LENGTH: 69
<212> TYPE: PRT
<213> ORGANISM: Shigella dysenteria 1

<400> SEQUENCE: 79

Thr Pro Asp Cys Val Thr Gly Lys Val Glu Tyr Thr Lys Tyr Asn Asp
1               5                   10                  15

Asp Asp Thr Phe Thr Val Lys Val Gly Asp Lys Glu Leu Phe Thr Asn
                20                  25                  30

Arg Trp Asn Leu Gln Ser Leu Leu Leu Ser Ala Gln Ile Thr Gly Met
            35                  40                  45

Thr Val Thr Ile Lys Gln Asn Ala Cys His Asn Gly Gly Gly Phe Ser
        50                  55                  60

Glu Val Ile Phe Arg
65

<210> SEQ ID NO 80
<211> LENGTH: 560
<212> TYPE: PRT
<213> ORGANISM: Corynephage omega

<400> SEQUENCE: 80

Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
                20                  25                  30

Ser Ser Lys Ser Phe Val Met Glu Asn Phe Ser Ser Tyr His Gly Thr
            35                  40                  45
```

```
Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Val Val Lys Val Thr Tyr Pro Gly
                100                 105                 110

Leu Thr Lys Val Leu Ala Leu Lys Val Asp Asn Ala Glu Thr Ile Lys
            115                 120                 125

Lys Glu Leu Gly Leu Ser Leu Thr Glu Pro Leu Met Glu Gln Val Gly
        130                 135                 140

Thr Glu Glu Phe Ile Lys Arg Phe Gly Asp Gly Ala Ser Arg Val Val
145                 150                 155                 160

Leu Ser Leu Pro Phe Ala Glu Gly Ser Ser Val Glu Tyr Ile Asn
                165                 170                 175

Asn Trp Glu Gln Ala Lys Ala Leu Ser Val Glu Leu Glu Ile Asn Phe
                180                 185                 190

Glu Thr Arg Gly Lys Arg Gly Gln Asp Ala Met Tyr Glu Tyr Met Ala
            195                 200                 205

Gln Ala Cys Ala Gly Asn Arg Val Arg Arg Ser Val Gly Ser Ser Leu
        210                 215                 220

Ser Cys Ile Asn Leu Asp Trp Asp Val Ile Arg Asp Lys Thr Lys Thr
225                 230                 235                 240

Lys Ile Glu Ser Leu Lys Glu His Gly Pro Ile Lys Asn Lys Met Ser
                245                 250                 255

Glu Ser Pro Asn Lys Thr Val Ser Glu Glu Lys Ala Lys Gln Tyr Leu
                260                 265                 270

Glu Glu Phe His Gln Thr Ala Leu Glu His Pro Glu Leu Ser Glu Leu
            275                 280                 285

Lys Thr Val Thr Gly Thr Asn Pro Val Phe Ala Gly Ala Asn Tyr Ala
        290                 295                 300

Ala Trp Ala Val Asn Val Ala Gln Val Ile Asp Ser Glu Thr Ala Asp
305                 310                 315                 320

Asn Leu Glu Lys Thr Thr Ala Ala Leu Ser Ile Leu Pro Gly Ile Gly
                325                 330                 335

Ser Val Met Gly Ile Ala Asp Gly Ala Val His His Asn Thr Glu Glu
                340                 345                 350

Ile Val Ala Gln Ser Ile Ala Leu Ser Ser Leu Met Val Ala Gln Ala
            355                 360                 365

Ile Pro Leu Val Gly Glu Leu Val Asp Ile Gly Phe Ala Ala Tyr Asn
        370                 375                 380

Phe Val Glu Ser Ile Ile Asn Leu Phe Gln Val Val His Asn Ser Tyr
385                 390                 395                 400

Asn Arg Pro Ala Tyr Ser Pro Gly His Lys Thr Gln Pro Phe Leu His
                405                 410                 415

Asp Gly Tyr Ala Val Ser Trp Asn Thr Val Glu Asp Ser Ile Ile Arg
            420                 425                 430

Thr Gly Phe Gln Gly Glu Ser Gly His Asp Ile Lys Ile Thr Ala Glu
        435                 440                 445

Asn Thr Pro Leu Pro Ile Ala Gly Val Leu Leu Pro Thr Ile Pro Gly
    450                 455                 460
```

Lys Leu Asp Val Asn Lys Ser Lys Thr His Ile Ser Val Asn Gly Arg
465                 470                 475                 480

Lys Ile Arg Met Arg Cys Arg Ala Ile Asp Gly Asp Val Thr Phe Cys
            485                 490                 495

Arg Pro Lys Ser Pro Val Tyr Val Gly Asn Gly Val His Ala Asn Leu
        500                 505                 510

His Val Ala Phe His Arg Ser Ser Glu Lys Ile His Ser Asn Glu
    515                 520                 525

Ile Ser Ser Asp Ser Ile Gly Val Leu Gly Tyr Gln Lys Thr Val Asp
            530                 535                 540

His Thr Lys Val Asn Ser Lys Leu Ser Leu Phe Phe Glu Ile Lys Ser
545                 550                 555                 560

<210> SEQ ID NO 81
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asp Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 82
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Pro Lys Ser Cys Asp Lys Thr His Thr Cys Pro Pro Cys Pro
65                  70                  75                  80

Ala Pro Glu Leu Leu Gly Gly Pro Ser Val Phe Leu Phe Pro Pro Lys

```
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160
Gln Asp Trp Leu Asn Gly Lys Glu Tyr Lys Cys Lys Val Ser Asn Lys
                165                 170                 175
Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Asp Glu Leu
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240
Tyr Lys Thr Thr Pro Pro Val Leu Asp Ser Asp Gly Ser Phe Phe Leu
                245                 250                 255
Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295

<210> SEQ ID NO 83
<211> LENGTH: 535
<212> TYPE: PRT
<213> ORGANISM: Corynebacterium diphtheriae

<400> SEQUENCE: 83

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160
```

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
    530                 535

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 84

Met Ala Val Pro Met Gln Leu Ser Cys Ser Arg
1               5                   10

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Arg Ser Thr Gly
1

<210> SEQ ID NO 86
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Thr Arg
1

<210> SEQ ID NO 87
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Arg Ser Gln
1

<210> SEQ ID NO 88
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Arg Ser Ala Gly Glu
1               5

<210> SEQ ID NO 89
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Ser
1

<210> SEQ ID NO 90

```
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Gly
1

<210> SEQ ID NO 91
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Gly Ser Gly Gly Ser Gly Gly Ser Gly
1               5

<210> SEQ ID NO 92
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Gly Ser Gly Gly Ser Gly Gly Ser Gly Gly
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Gly Ser Gly Gly Ser Gly Gly Ser Gly Gly Ser Gly Gly
1               5                   10

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gly Gly Ser Gly Gly Ser Gly Gly Ser Gly Gly Ser Gly Gly Ser Gly
1               5                   10                  15

Gly

<210> SEQ ID NO 95
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 95

Gly Gly Ser Gly Gly Ser Gly Gly Ser Gly Gly Ser Gly
1               5                   10                  15

Gly Ser Gly Gly
            20

<210> SEQ ID NO 96
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Gly Ser Gly Gly Ser Gly Gly Ser Gly Gly Ser Gly
1               5                   10                  15

Gly Ser Gly Gly Ser Gly Gly
            20

<210> SEQ ID NO 97
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Ser Gly Gly Ser Gly Gly Ser Gly Gly Ser Gly
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Ser Gly Gly Ser Gly Gly Ser Gly Gly Ser Gly Gly
1               5                   10                  15

<210> SEQ ID NO 99
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Met Gly Trp Ser Cys Ile Ile Phe Phe Leu Val Ala Thr Ala Thr Gly
1               5                   10                  15

Val His Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asp Tyr Ala Met His Trp Val Arg Gln Ala Pro Gly Gln Arg Leu
    50                  55                  60

Glu Trp Met Gly Leu Ile Ser Thr Tyr Ser Gly Asp Thr Lys Tyr Asn
65                  70                  75                  80

Gln Asn Phe Gln Gly Arg Val Thr Met Thr Val Asp Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Gly Asp Tyr Ser Gly Ser Arg Tyr Trp Phe Ala
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 100
<211> LENGTH: 2109
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 100

| | |
|---|---|
| atggagtctc cctcggcccc tccccacaga tggtgcatcc cctggcagag gctcctgctc | 60 |
| acagcctcac ttctaacctt ctggaacccg cccaccactg ccaagctcac tattgaatcc | 120 |
| acgccgttca atgtcgcaga ggggaaggag gtgcttctac ttgtccacaa tctgccccag | 180 |
| catcttttg gctacagctg gtacaaaggt gaaagagtgg atggcaaccg tcaaattata | 240 |
| ggatatgtaa taggaactca acaagctacc ccagggcccg catacagtgg tcgagagata | 300 |
| atataccca atgcatccct gctgatccag aacatcatcc agaatgacac aggattctac | 360 |
| accctacacg tcataaagtc agatcttgtg aatgaagaag caactggcca gttccgggta | 420 |
| tacccggagc tgcccaagcc ctccatctcc agcaacaact ccaaaccgt ggaggacaag | 480 |
| gatgctgtgg ccttcacctg tgaacctgag actcaggacg caacctacct gtggtgggta | 540 |
| aacaatcaga gcctcccggt cagtcccagg ctgcagctgt ccaatggcaa caggaccctc | 600 |
| actctattca atgtcacaag aaatgacaca gcaagctaca aatgtgaaac ccagaaccca | 660 |
| gtgagtgcca ggcgcagtga ttcagtcatc ctgaatgtcc tctatggccc ggatgccccc | 720 |
| accatttccc ctctaaacac atcttacaga tcaggggaaa atctgaacct ctcctgccac | 780 |
| gcagcctcta acccacctgc acagtactct tggtttgtca atgggacttt ccagcaatcc | 840 |
| acccaagagc tctttatccc caacatcact gtgaataata gtggatccta tacgtgccaa | 900 |
| gcccataact cagacactgg cctcaatagg accacagtca cgacgatcac agtctatgca | 960 |
| gagccaccca acccttcat caccagcaac aactccaacc cgtggaggga tgaggatgct | 1020 |
| gtagccttaa cctgtgaacc tgagattcag aacacaacct acctgtggtg ggtaaataat | 1080 |
| cagagcctcc cggtcagtcc caggctgcag ctgtccaatg caacaggac cctcactcta | 1140 |
| ctcagtgtca caaggaatga tgtaggaccc tatgagtgtg aatccagaa cgaattaagt | 1200 |
| gttgaccaca gcgacccagt catcctgaat gtcctctatg gcccagacga ccccaccatt | 1260 |
| tcccctcat acacctatta ccgtccaggg gtgaacctca gcctctcctg ccatgcagcc | 1320 |
| tctaacccac tgcacagta ttcttggctg attgatggga acatccagca acacacaa | 1380 |
| gagctctta tctccaacat cactgagaag aacagcggac tctatacctg ccaggccaat | 1440 |
| aactcagcca gtggccacag caggactaca gtcaagacaa tcacagtctc tgcggagctg | 1500 |
| cccaagccct ccatctccag caacaactcc aaaccgtgg aggacaagga tgctgtggcc | 1560 |
| ttcacctgtg aacctgaggc tcagaacaca acctacctgt ggtgggtaaa tggtcagagc | 1620 |
| ctcccagtca gtcccaggct gcagctgtcc aatggcaaca ggaccctcac tctattcaat | 1680 |
| gtcacaagaa atgacgcaag agcctatgta tgtggaatcc agaactcagt gagtgcaaac | 1740 |
| cgcagtgacc cagtcaccct ggatgtcctc tatgggccgg acacccccat catttccccc | 1800 |
| ccagactcgt cttacctttc gggagcggac ctcaacctct cctgccactc ggcctctaac | 1860 |
| ccatccccgc agtattcttg gcgtatcaat gggataccgc agcaacacac acaagttctc | 1920 |
| tttatcgcca aaatcacgcc aaataataac gggacctatg cctgttttgt ctctaacttg | 1980 |
| gctactggcc gcaataattc catagtcaag agcatcacag tctctgcatc tggaacttct | 2040 |
| cctggtctct cagctggggc cactgtcggc atcatgattg gagtgctggt tggggttgct | 2100 |
| ctgatatag | 2109 |

<210> SEQ ID NO 101
<211> LENGTH: 1428
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 101

```
atgacaccgg gcacccagtc tcctttcttc ctgctgctgc tcctcacagt gcttacagtt      60
gttacgggtt ctggtcatgc aagctctacc ccaggtggag aaaaggagac ttcggctacc     120
cagagaagtt cagtgcccag ctctactgag aagaatgctg tgagtatgac cagcagcgta     180
ctctccagcc acagccccgg ttcaggctcc tccaccactc agggacagga tgtcactctg     240
gccccggcca cggaaccagc ttcaggttca gctgcccttt ggggacagga tgtcacctcg     300
gtcccagtca ccaggccagc cctgggctcc accacccgc cagcccacga tgtcacctca     360
gccccggaca caagccagc cccgggctcc accgccccc cagcccacgg tgtcacctcg     420
tatcttgaca ccaggccggc cccggtttat cttgccccc cagcccatgg tgtcacctcg     480
gccccggaca caggcccgc cttgggctcc accgcccctc cagtccacaa tgtcacctcg     540
gcctcaggct ctgcatcagg ctcagcttct actctggtgc acaacggcac ctctgccagg     600
gctaccacaa cccagccag caagagcact ccattctcaa ttcccagcca ccactctgat     660
actcctacca cccttgccag ccatagcacc aagactgatg ccagtagcac tcaccatagc     720
acggtacctc ctctcacctc ctccaatcac agcacttctc cccagttgtc tactggggtc     780 tcttttctttt tcctgtcttt tcacatttca aacctccagt ttaattcctc tctggaagat     840
cccagcaccg actactacca agagctgcag agagacattt ctgaaatgtt tttgcagatt     900
tataaacaag ggggttttct gggcctctcc aatattaagt tcaggccagg atctgtggtg     960
gtacaattga ctctggcctt ccgagaaggt accatcaatg tccacgacgt ggagacacag    1020
ttcaatcagt ataaaacgga agcagcctct cgatataacc tgacgatctc agacgtcagc    1080
gtgagtgatg tgccatttcc tttctctgcc cagtctgggg ctggggtgcc aggctggggc    1140
atcgcgctgc tggtgctggt ctgtgttctg gtttatctgg ccattgtcta tctcattgcc    1200
ttggctgtcg ctcaggttcg ccgaaagaac tacgggcagc tggacatctt tccagcccgg    1260
gataaatacc atcctatgag cgagtacgct ctttaccaca cccatgggcg ctatgtgccc    1320
cctagcagtc ttttccgtag cccctatgag aaggtttctg caggtaatgg tggcagctat    1380
ctctcttaca caaacccagc agtggcagcc gcttctgcca acttgtag                 1428
```

<210> SEQ ID NO 102
<211> LENGTH: 1233
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 102

```
atgagctccc ctggcaccga gagcgcggga aagagcctgc agtaccgagt ggaccacctg      60
ctgagcgccg tggagaatga gctgcaggcg ggcagcgaga agggcgaccc cacagagcgc     120
gaactgcgcg tgggcctgga ggagagcgag ctgtggctgc gcttcaagga gctcaccaat     180
gagatgatcg tgaccaagaa cggcaggagg atgtttccgg tgctgaaggt gaacgtgtct     240
ggcctggacc ccaacgccat gtactccttc ctgctggact tcgtggcggc ggacaaccac     300
```

```
cgctggaagt acgtgaacgg ggaatgggtg ccggggggca agccggagcc gcaggcgccc      360
agctgcgtct acatccaccc cgactcgccc aacttcgggg cccactggat gaaggctccc      420
gtctccttca gcaaagtcaa gctcaccaac aagctcaacg gagggggcca gatcatgctg      480
aactccttgc ataagtatga gcctcgaatc cacatagtga gagttggggg tccacagcgc      540
atgatcacca gccactgctt ccctgagacc cagttcatag cggtgactgc tagaagtgat      600
cacaaagaga tgatggagga acccggagac agccagcaac tgggtactcc caatggggg       660 tggcttcttc ctggaaccag caccgtgtgt ccacctgcaa atcctcatcc tcagtttgga      720
ggtgccctct ccctccccctc cacgcacagc tgtgacaggt acccaaccct gaggagccac     780
cggtcctcac cctaccccag cccctatgct catcggaaca attctccaac ctattctgac      840
aactcacctg catgtttatc catgctgcaa tcccatgaca attggtccag ccttggaatg      900
cctgcccatc ccagcatgct ccccgtgagc acaatgcca gcccacctac cagctccagt       960
cagtacccca gcctgtggtc tgtgagcaac ggcgccgtca cccgggctc ccaggcagca      1020 gccgtgtcca acgggctggg ggcccagttc ttccggggct ccccgcgca ctacacaccc      1080 ctcacccatc cggtctcggc gccctcttcc tcgggatccc cactgtacga aggggcggcc      1140
gcggccacag acatcgtgga cagccagtac gacgccgcag cccaaggccg cctcatagcc     1200
tcatggacac ctgtgtcgcc accttccatg tga                                  1233
```

<210> SEQ ID NO 103
<211> LENGTH: 1331
<212> TYPE: PRT
<213> ORGANISM: Homo sapiens

<400> SEQUENCE: 103

```
Met Glu Ser His Ser Arg Ala Gly Lys Ser Arg Lys Ser Ala Lys Phe
1               5                   10                  15

Arg Ser Ile Ser Arg Ser Leu Met Leu Cys Asn Ala Lys Thr Ser Asp
            20                  25                  30

Asp Gly Ser Ser Pro Asp Glu Lys Tyr Pro Asp Pro Phe Glu Ile Ser
        35                  40                  45

Leu Ala Gln Gly Lys Glu Gly Ile Phe His Ser Ser Val Gln Leu Ala
    50                  55                  60

Asp Thr Ser Glu Ala Gly Pro Ser Ser Val Pro Asp Leu Ala Leu Ala
65                  70                  75                  80

Ser Glu Ala Ala Gln Leu Gln Ala Ala Gly Asn Asp Arg Gly Lys Thr
                85                  90                  95

Cys Arg Arg Ile Phe Phe Met Lys Glu Ser Ser Thr Ala Ser Ser Arg
            100                 105                 110

Glu Lys Pro Gly Lys Leu Glu Ala Gln Ser Ser Asn Phe Leu Phe Pro
        115                 120                 125

Lys Ala Cys His Gln Arg Ala Arg Ser Asn Ser Thr Ser Val Asn Pro
    130                 135                 140

Tyr Cys Thr Arg Glu Ile Asp Phe Pro Met Thr Lys Lys Ser Ala Ala
145                 150                 155                 160

Pro Thr Asp Arg Gln Pro Tyr Ser Leu Cys Ser Asn Arg Lys Ser Leu
                165                 170                 175

Ser Gln Gln Leu Asp Cys Pro Ala Gly Lys Ala Ala Gly Thr Ser Arg
            180                 185                 190

Pro Thr Arg Ser Leu Ser Thr Ala Gln Leu Val Gln Pro Ser Gly Gly
        195                 200                 205
```

-continued

Leu Gln Ala Ser Val Ile Ser Asn Ile Val Leu Met Lys Gly Gln Ala
    210                 215                 220

Lys Gly Leu Gly Phe Ser Ile Val Gly Gly Lys Asp Ser Ile Tyr Gly
225                 230                 235                 240

Pro Ile Gly Ile Tyr Val Lys Thr Ile Phe Ala Gly Gly Ala Ala Ala
                245                 250                 255

Ala Asp Gly Arg Leu Gln Glu Gly Asp Glu Ile Leu Glu Leu Asn Gly
            260                 265                 270

Glu Ser Met Ala Gly Leu Thr His Gln Asp Ala Leu Gln Lys Phe Lys
        275                 280                 285

Gln Ala Lys Lys Gly Leu Leu Thr Leu Thr Val Arg Thr Arg Leu Thr
290                 295                 300

Ala Pro Pro Ser Leu Cys Ser His Leu Ser Pro Pro Leu Cys Arg Ser
305                 310                 315                 320

Leu Ser Ser Ser Thr Cys Ile Thr Lys Asp Ser Ser Phe Ala Leu
                325                 330                 335

Glu Ser Pro Ser Ala Pro Ile Ser Thr Ala Lys Pro Asn Tyr Arg Ile
            340                 345                 350

Met Val Glu Val Ser Leu Gln Lys Glu Ala Gly Val Gly Leu Gly Ile
        355                 360                 365

Gly Leu Cys Ser Val Pro Tyr Phe Gln Cys Ile Ser Gly Ile Phe Val
370                 375                 380

His Thr Leu Ser Pro Gly Ser Val Ala His Leu Asp Gly Arg Leu Arg
385                 390                 395                 400

Cys Gly Asp Glu Ile Val Glu Ile Ser Asp Ser Pro Val His Cys Leu
                405                 410                 415

Thr Leu Asn Glu Val Tyr Thr Ile Leu Ser Arg Cys Asp Pro Gly Pro
            420                 425                 430

Val Pro Ile Ile Val Ser Arg His Pro Asp Pro Gln Val Ser Glu Gln
        435                 440                 445

Gln Leu Lys Glu Ala Val Ala Gln Ala Val Glu Asn Thr Lys Phe Gly
450                 455                 460

Lys Glu Arg His Gln Trp Ser Leu Glu Gly Val Lys Arg Leu Glu Ser
465                 470                 475                 480

Ser Trp His Gly Arg Pro Thr Leu Glu Lys Glu Arg Glu Lys Asn Ser
                485                 490                 495

Ala Pro Pro His Arg Arg Ala Gln Lys Val Met Ile Arg Ser Ser Ser
            500                 505                 510

Asp Ser Ser Tyr Met Ser Gly Ser Pro Gly Gly Ser Pro Gly Ser Gly
        515                 520                 525

Ser Ala Glu Lys Pro Ser Ser Asp Val Asp Ile Ser Thr His Ser Pro
530                 535                 540

Ser Leu Pro Leu Ala Arg Glu Pro Val Val Leu Ser Ile Ala Ser Ser
545                 550                 555                 560

Arg Leu Pro Gln Glu Ser Pro Leu Pro Glu Ser Arg Asp Ser His
                565                 570                 575

Pro Pro Leu Arg Leu Lys Lys Ser Phe Glu Ile Leu Val Arg Lys Pro
            580                 585                 590

Met Ser Ser Lys Pro Lys Pro Pro Arg Lys Tyr Phe Lys Ser Asp
        595                 600                 605

Ser Asp Pro Gln Lys Ser Leu Glu Glu Arg Glu Asn Ser Ser Cys Ser
610                 615                 620

Ser Gly His Thr Pro Pro Thr Cys Gly Gln Glu Ala Arg Glu Leu Leu
625                 630                 635                 640

Pro Leu Leu Leu Pro Gln Glu Asp Thr Ala Gly Arg Ser Pro Ser Ala
            645                 650                 655

Ser Ala Gly Cys Pro Gly Pro Gly Ile Gly Pro Gln Thr Lys Ser Ser
        660                 665                 670

Thr Glu Gly Glu Pro Gly Trp Arg Arg Ala Ser Pro Val Thr Gln Thr
    675                 680                 685

Ser Pro Ile Lys His Pro Leu Leu Lys Arg Gln Ala Arg Met Asp Tyr
690                 695                 700

Ser Phe Asp Thr Thr Ala Glu Asp Pro Trp Val Arg Ile Ser Asp Cys
705                 710                 715                 720

Ile Lys Asn Leu Phe Ser Pro Ile Met Ser Glu Asn His Gly His Met
            725                 730                 735

Pro Leu Gln Pro Asn Ala Ser Leu Asn Glu Glu Glu Gly Thr Gln Gly
        740                 745                 750

His Pro Asp Gly Thr Pro Pro Lys Leu Asp Thr Ala Asn Gly Thr Pro
    755                 760                 765

Lys Val Tyr Lys Ser Ala Asp Ser Ser Thr Val Lys Lys Gly Pro Pro
770                 775                 780

Val Ala Pro Lys Pro Ala Trp Phe Arg Gln Ser Leu Lys Gly Leu Arg
785                 790                 795                 800

Asn Arg Ala Ser Asp Pro Arg Gly Leu Pro Asp Pro Ala Leu Ser Thr
            805                 810                 815

Gln Pro Ala Pro Ala Ser Arg Glu His Leu Gly Ser His Ile Arg Ala
        820                 825                 830

Ser Ser Ser Ser Ser Ile Arg Gln Arg Ile Ser Ser Phe Glu Thr
    835                 840                 845

Phe Gly Ser Ser Gln Leu Pro Asp Lys Gly Ala Gln Arg Leu Ser Leu
850                 855                 860

Gln Pro Ser Ser Gly Glu Ala Ala Lys Pro Leu Gly Lys His Glu Glu
865                 870                 875                 880

Gly Arg Phe Ser Gly Leu Leu Gly Arg Gly Ala Ala Pro Thr Leu Val
            885                 890                 895

Pro Gln Gln Pro Glu Gln Val Leu Ser Ser Gly Ser Pro Ala Ala Ser
        900                 905                 910

Glu Ala Arg Asp Pro Gly Val Ser Glu Ser Pro Pro Gly Arg Gln
    915                 920                 925

Pro Asn Gln Lys Thr Leu Pro Pro Gly Pro Asp Pro Leu Leu Arg Leu
930                 935                 940

Leu Ser Thr Gln Ala Glu Glu Ser Gln Gly Pro Val Leu Lys Met Pro
945                 950                 955                 960

Ser Gln Arg Ala Arg Ser Phe Pro Leu Thr Arg Ser Gln Ser Cys Glu
            965                 970                 975

Thr Lys Leu Leu Asp Glu Lys Thr Ser Lys Leu Tyr Ser Ile Ser Ser
        980                 985                 990

Gln Val Ser Ser Ala Val Met Lys Ser Leu Leu Cys Leu Pro Ser Ser
    995                 1000                1005

Ile Ser Cys Ala Gln Thr Pro Cys Ile Pro Lys Glu Gly Ala Ser
    1010                1015                1020

Pro Thr Ser Ser Ser Asn Glu Asp Ser Ala Ala Asn Gly Ser Ala
    1025                1030                1035

Glu Thr Ser Ala Leu Asp Thr Gly Phe Ser Leu Asn Leu Ser Glu

```
                1040                1045                1050

Leu Arg Glu Tyr Thr Glu Gly Leu Thr Glu Ala Lys Glu Asp Asp
        1055                1060                1065

Asp Gly Asp His Ser Ser Leu Gln Ser Gly Gln Ser Val Ile Ser
    1070                1075                1080

Leu Leu Ser Ser Glu Glu Leu Lys Lys Leu Ile Glu Glu Val Lys
        1085                1090                1095

Val Leu Asp Glu Ala Thr Leu Lys Gln Leu Asp Gly Ile His Val
    1100                1105                1110

Thr Ile Leu His Lys Glu Glu Gly Ala Gly Leu Gly Phe Ser Leu
    1115                1120                1125

Ala Gly Gly Ala Asp Leu Glu Asn Lys Val Ile Thr Val His Arg
    1130                1135                1140

Val Phe Pro Asn Gly Leu Ala Ser Gln Glu Gly Thr Ile Gln Lys
    1145                1150                1155

Gly Asn Glu Val Leu Ser Ile Asn Gly Lys Ser Leu Lys Gly Thr
    1160                1165                1170

Thr His His Asp Ala Leu Ala Ile Leu Arg Gln Ala Arg Glu Pro
    1175                1180                1185

Arg Gln Ala Val Ile Val Thr Arg Lys Leu Thr Pro Glu Ala Met
    1190                1195                1200

Pro Asp Leu Asn Ser Ser Thr Asp Ser Ala Ala Ser Ala Ser Ala
    1205                1210                1215

Ala Ser Asp Val Ser Val Glu Ser Thr Glu Ala Thr Val Cys Thr
    1220                1225                1230

Val Thr Leu Glu Lys Met Ser Ala Gly Leu Gly Phe Ser Leu Glu
    1235                1240                1245

Gly Gly Lys Gly Ser Leu His Gly Asp Lys Pro Leu Thr Ile Asn
    1250                1255                1260

Arg Ile Phe Lys Gly Ala Ala Ser Glu Gln Ser Glu Thr Val Gln
    1265                1270                1275

Pro Gly Asp Glu Ile Leu Gln Leu Gly Gly Thr Ala Met Gln Gly
    1280                1285                1290

Leu Thr Arg Phe Glu Ala Trp Asn Ile Ile Lys Ala Leu Pro Asp
    1295                1300                1305

Gly Pro Val Thr Ile Val Ile Arg Arg Lys Ser Leu Gln Ser Lys
    1310                1315                1320

Glu Thr Thr Ala Ala Gly Asp Ser
    1325                1330

<210> SEQ ID NO 104
<211> LENGTH: 155
<212> TYPE: PRT
<213> ORGANISM: Homo sapiens

<400> SEQUENCE: 104

Met Thr Pro Gly Lys Thr Ser Leu Val Ser Leu Leu Leu Leu Ser
1               5                   10                  15

Leu Glu Ala Ile Val Lys Ala Gly Ile Thr Ile Pro Arg Asn Pro
                20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Asn Pro Lys Arg Ser Ser
    50                  55                  60
```

```
Asp Tyr Tyr Asn Arg Ser Thr Ser Pro Trp Asn Leu His Arg Asn Glu
 65                  70                  75                  80

Asp Pro Glu Arg Tyr Pro Ser Val Ile Trp Glu Ala Lys Cys Arg His
                 85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155
```

<210> SEQ ID NO 105
<211> LENGTH: 476
<212> TYPE: PRT
<213> ORGANISM: Homo sapiens

<400> SEQUENCE: 105

```
Arg Ala Val Pro Gly Gly Ser Ser Pro Ala Trp Thr Gln Cys Gln Gln
 1               5                  10                  15

Leu Ser Gln Lys Leu Cys Thr Leu Ala Trp Ser Ala His Pro Leu Val
                 20                  25                  30

Gly His Met Asp Leu Arg Glu Glu Gly Asp Glu Thr Thr Asn Asp
             35                  40                  45

Val Pro His Ile Gln Cys Gly Asp Gly Cys Asp Pro Gln Gly Leu Arg
         50                  55                  60

Asp Asn Ser Gln Phe Cys Leu Gln Arg Ile His Gln Gly Leu Ile Phe
 65                  70                  75                  80

Tyr Glu Lys Leu Leu Gly Ser Asp Ile Phe Thr Gly Glu Pro Ser Leu
                 85                  90                  95

Leu Pro Asp Ser Pro Val Gly Gln Leu His Ala Ser Leu Leu Gly Leu
            100                 105                 110

Ser Gln Leu Leu Gln Pro Glu Gly His His Trp Glu Thr Gln Gln Ile
        115                 120                 125

Pro Ser Leu Ser Pro Ser Gln Pro Trp Gln Arg Leu Leu Leu Arg Phe
    130                 135                 140

Lys Ile Leu Arg Ser Leu Gln Ala Phe Val Ala Val Ala Ala Arg Val
145                 150                 155                 160

Phe Ala His Gly Ala Ala Thr Leu Ser Pro Ile Trp Glu Leu Lys Lys
                165                 170                 175

Asp Val Tyr Val Val Glu Leu Asp Trp Tyr Pro Asp Ala Pro Gly Glu
            180                 185                 190

Met Val Val Leu Thr Cys Asp Thr Pro Glu Glu Asp Gly Ile Thr Trp
        195                 200                 205

Thr Leu Asp Gln Ser Ser Glu Val Leu Gly Ser Gly Lys Thr Leu Thr
    210                 215                 220

Ile Gln Val Lys Glu Phe Gly Asp Ala Gly Gln Tyr Thr Cys His Lys
225                 230                 235                 240

Gly Gly Glu Val Leu Ser His Ser Leu Leu Leu Leu His Lys Lys Glu
                245                 250                 255

Asp Gly Ile Trp Ser Thr Asp Ile Leu Lys Asp Gln Lys Glu Pro Lys
            260                 265                 270

Asn Lys Thr Phe Leu Arg Cys Glu Ala Lys Asn Tyr Ser Gly Arg Phe
        275                 280                 285
```

```
Thr Cys Trp Trp Leu Thr Thr Ile Ser Thr Asp Leu Thr Phe Ser Val
            290                 295                 300

Lys Ser Ser Arg Gly Ser Ser Asp Pro Gln Gly Val Thr Cys Gly Ala
305                 310                 315                 320

Ala Thr Leu Ser Ala Glu Arg Val Arg Gly Asp Asn Lys Glu Tyr Glu
                325                 330                 335

Tyr Ser Val Glu Cys Gln Glu Asp Ser Ala Cys Pro Ala Ala Glu Glu
                340                 345                 350

Ser Leu Pro Ile Glu Val Met Val Asp Ala Val His Lys Leu Lys Tyr
            355                 360                 365

Glu Asn Tyr Thr Ser Ser Phe Phe Ile Arg Asp Ile Ile Lys Pro Asp
370                 375                 380

Pro Pro Lys Asn Leu Gln Leu Lys Pro Leu Lys Asn Ser Arg Gln Val
385                 390                 395                 400

Glu Val Ser Trp Glu Tyr Pro Asp Thr Trp Ser Thr Pro His Ser Tyr
                405                 410                 415

Phe Ser Leu Thr Phe Cys Val Gln Val Gln Gly Lys Ser Lys Arg Glu
            420                 425                 430

Lys Lys Asp Arg Val Phe Thr Asp Lys Thr Ser Ala Thr Val Ile Cys
            435                 440                 445

Arg Lys Asn Ala Ser Ile Ser Val Arg Ala Gln Asp Arg Tyr Tyr Ser
450                 455                 460

Ser Ser Trp Ser Glu Trp Ala Ser Val Pro Cys Ser
465                 470                 475

<210> SEQ ID NO 106
<211> LENGTH: 234
<212> TYPE: PRT
<213> ORGANISM: Homo sapiens

<400> SEQUENCE: 106

Met Cys Phe Pro Lys Val Leu Ser Asp Asp Met Lys Lys Leu Lys Ala
1               5                   10                  15

Arg Met Val Met Leu Leu Pro Thr Ser Ala Gln Gly Leu Gly Ala Trp
                20                  25                  30

Val Ser Ala Cys Asp Thr Glu Asp Thr Val Gly His Leu Gly Pro Trp
            35                  40                  45

Arg Asp Lys Asp Pro Ala Leu Trp Cys Gln Leu Cys Leu Ser Ser Gln
        50                  55                  60

His Gln Ala Ile Glu Arg Phe Tyr Asp Lys Met Gln Asn Ala Glu Ser
65                  70                  75                  80

Gly Arg Gly Gln Val Met Ser Ser Leu Ala Glu Leu Glu Asp Asp Phe
                85                  90                  95

Lys Glu Gly Tyr Leu Glu Thr Val Ala Ala Tyr Tyr Glu Glu Gln His
            100                 105                 110

Pro Glu Leu Thr Pro Leu Leu Glu Lys Glu Arg Asp Gly Leu Arg Cys
        115                 120                 125

Arg Gly Asn Arg Ser Pro Val Pro Asp Val Glu Asp Pro Ala Thr Glu
130                 135                 140

Glu Pro Gly Glu Ser Phe Cys Asp Lys Val Met Arg Trp Phe Gln Ala
145                 150                 155                 160

Met Leu Gln Arg Leu Gln Thr Trp Trp His Gly Val Leu Ala Trp Val
                165                 170                 175

Lys Glu Lys Val Val Ala Leu Val His Ala Val Gln Ala Leu Trp Lys
```

180                 185                 190
Gln Phe Gln Ser Phe Cys Cys Ser Leu Ser Glu Leu Phe Met Ser Ser
                195                 200                 205

Phe Gln Ser Tyr Gly Ala Pro Arg Gly Asp Lys Glu Glu Leu Thr Pro
    210                 215                 220

Gln Lys Cys Ser Glu Pro Gln Ser Ser Lys
225                 230

<210> SEQ ID NO 107
<211> LENGTH: 345
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 107
aactgggtga atgtaataag tgatttgaaa aaaattgaag atcttattca atctatgcat     60
attgatgcta ctttatatac ggaaagtgat gttcacccca gttgcaaagt aacagcaatg    120
aagtgctttc tcttggagtt acaagttatt tcacttgagt ccggagatgc aagtattcat    180
gatacagtag aaaatctgat catcctagca acgacagtt tgtcttctaa tgggaatgta    240
acagaatctg gatgcaaaga atgtgaggaa ctggaggaaa aaatattaa agaattttg     300 cagagttttg tacatattgt ccaaatgttc atcaacactt cttaa                   345

<210> SEQ ID NO 108
<211> LENGTH: 894
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 108
atcacgtgcc ctcccccat gtccgtggaa cacgcagaca tctgggtcaa gagctacagc     60
ttgtactcca gggagcggta catttgtaac tctggtttca gcgtaaagc cggcacgtcc    120 agcctgacgg agtgcgtgtt gaacaaggcc acgaatgtcg cccactggac aaccccagt   180 ctcaaatgta ttagagagcc caaatcttgt gacaaaactc acacatgccc accgtgccca    240
gcacctgaac tcctgggggg accgtcagtc ttcctcttcc ccccaaaacc caaggacacc    300
ctcatgatct cccggacccc tgaggtcaca tgcgtggtgg tggacgtgag ccacgaagac    360
cctgaggtca agttcaactg gtacgtggac ggcgtggagg tgcataatgc caagacaaag    420
ccgcgggagg agcagtacaa cagcacgtac cgtgtggtca gcgtcctcac cgtcctgcac    480
caggactggc tgaatggcaa ggagtacaag tgcaaggtct ccaacaaagc cctcccagcc    540
cccatcgaga aaaccatctc caaagccaaa gggcagcccc gagaaccaca ggtgtacacc    600 ctgccccat cccgggatga gctgaccaag aaccaggtca gcctgacctg cctggtcaaa    660
ggcttctatc ccagcgacat cgccgtggag tgggagagca atgggcagcc ggagaacaac    720
tacaagacca cgcctcccgt gctggactcc gacggctcct tcttcctcta cagcaagctc    780
accgtggaca agagcaggtg gcagcagggg aacgtcttct catgctccgt gatgcatgag    840
gctctgcaca accactacac gcagaagagc ctctccctgt ctccgggtaa ataa          894

<210> SEQ ID NO 109
<211> LENGTH: 1416
<212> TYPE: DNA

<213> ORGANISM: Artificial Sequence
<220> FEATURE:
<223> OTHER INFORMATION: Description of Artificial Sequence: Synthetic polynucleotide

<400> SEQUENCE: 109

```
atggaaaccg acaccctgct gctgtgggtg ctgctgctgt gggtgccagg cagcacaggc    60
aactgggtca acgtgatcag cgacctgaag aagatcgagg acctgatcca gagcatgcac   120
atcgacgcca ccctgtacac cgagagcgac gtgcacccca gctgcaaagt gaccgccatg   180
aagtgctttc tgctggaact gcaagtgatc agcctggaaa gcggcgacgc cagcatccac   240
gacaccgtgg aaaacctgat catcctggcc aacgacagcc tgagcagcaa cggcaacgtg   300
accgagtccg gctgcaaaga gtgcgaggaa ctggaagaga gaatatcaa agagttcctg   360
cagagcttcg tgcacatcgt gcagatgttc atcaacacca gcggctctgg cgagggcaga   420
ggcagcctgc tgacatgcgg agatgtggaa gagaaccctg gccccatgga ccggctgacc   480
agctcttttc tgctgctgat cgtgcccgcc tacgtgctga gcatcacctg tcccccaccc   540
atgagcgtgg aacacgccga catctgggtc aagagctaca gcctgtacag ccgggaacgg   600
tacatctgca cagcggctt caagcggaag gccggcacca gcagcctgac cgagtgtgtg   660
ctgaacaagg ccaccaacgt ggcccactgg accaccccta gcctgaagtg catcagagag   720
cccaagagct gcgacaagac ccacacatgc ccccttgtc ctgcccctga actgctggga   780
ggccctagcg tgttcctgtt cccccaaag cccaaggaca cctgatgat cagccggacc   840
cccgaagtga cctgcgtggt ggtggatgtg tcccacgagg accctgaagt gaagttcaat   900
tggtacgtgg acggcgtgga agtgcacaac gccaagacca gcccagaga ggaacagtac   960
aacagcaccct accgggtggt gtccgtgctg accgtgctgc accaggactg gctgaacggc  1020
aaagagtaca agtgcaaggt gtccaacaag gccctgcctg ccccatcga aaaaccatc   1080
agcaaggcca agggccagcc ccgcgaaccc caggtgtaca cactgccccc tagcagggac  1140
gagctgacca agaaccaggt gtccctgacc tgtctcgtga agggcttcta ccccagcgac  1200
attgccgtgg aatgggagag caacggccag cccgagaaca actacaagac caccccccct  1260
gtgctggaca gcgacggctc attcttcctg tactccaagc tgacagtgga caagagccgg  1320
tggcagcagg gcaacgtgtt cagctgcagc gtgatgcacg aggccctgca caaccactac  1380
acccagaagt ccctgagcct gagccccggc aaatga                             1416
```

<210> SEQ ID NO 110
<211> LENGTH: 471
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

```
Met Glu Thr Asp Thr Leu Leu Leu Trp Val Leu Leu Leu Trp Val Pro
1               5                   10                  15

Gly Ser Thr Gly Asn Trp Val Asn Val Ile Ser Asp Leu Lys Lys Ile
                20                  25                  30

Glu Asp Leu Ile Gln Ser Met His Ile Asp Ala Thr Leu Tyr Thr Glu
            35                  40                  45

Ser Asp Val His Pro Ser Cys Lys Val Thr Ala Met Lys Cys Phe Leu
        50                  55                  60

Leu Glu Leu Gln Val Ile Ser Leu Glu Ser Gly Asp Ala Ser Ile His
```

```
            65                  70                  75                  80
Asp Thr Val Glu Asn Leu Ile Ile Leu Ala Asn Asp Ser Leu Ser Ser
                    85                  90                  95

Asn Gly Asn Val Thr Glu Ser Gly Cys Lys Glu Cys Glu Glu Leu Glu
                100                 105                 110

Glu Lys Asn Ile Lys Glu Phe Leu Gln Ser Phe Val His Ile Val Gln
            115                 120                 125

Met Phe Ile Asn Thr Ser Gly Ser Gly Glu Gly Arg Gly Ser Leu Leu
    130                 135                 140

Thr Cys Gly Asp Val Glu Glu Asn Pro Gly Pro Met Asp Arg Leu Thr
145                 150                 155                 160

Ser Ser Phe Leu Leu Leu Ile Val Pro Ala Tyr Val Leu Ser Ile Thr
                165                 170                 175

Cys Pro Pro Pro Met Ser Val Glu His Ala Asp Ile Trp Val Lys Ser
                180                 185                 190

Tyr Ser Leu Tyr Ser Arg Glu Arg Tyr Ile Cys Asn Ser Gly Phe Lys
            195                 200                 205

Arg Lys Ala Gly Thr Ser Ser Leu Thr Glu Cys Val Leu Asn Lys Ala
    210                 215                 220

Thr Asn Val Ala His Trp Thr Thr Pro Ser Leu Lys Cys Ile Arg Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
                260                 265                 270

Asp Thr Leu Met Ile Ser Arg Thr Pro Glu Val Thr Cys Val Val Val
            275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
                340                 345                 350

Pro Ala Pro Ile Glu Lys Thr Ile Ser Lys Ala Lys Gly Gln Pro Arg
            355                 360                 365

Glu Pro Gln Val Tyr Thr Leu Pro Pro Ser Arg Asp Glu Leu Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
                420                 425                 430

Lys Leu Thr Val Asp Lys Ser Arg Trp Gln Gln Gly Asn Val Phe Ser
            435                 440                 445

Cys Ser Val Met His Glu Ala Leu His Asn His Tyr Thr Gln Lys Ser
    450                 455                 460

Leu Ser Leu Ser Pro Gly Lys
465                 470

<210> SEQ ID NO 111
```

```
<211> LENGTH: 18
<212> TYPE: PRT
<213> ORGANISM: Thosea asigna virus

<400> SEQUENCE: 111

Glu Gly Arg Gly Ser Leu Leu Thr Cys Gly Asp Val Glu Glu Asn Pro
1               5                   10                  15

Gly Pro

<210> SEQ ID NO 112
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Ala Leu Trp Gly Gln Asp Val Thr Ser Val
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Lys Tyr His Pro Met Ser Glu Tyr Ala Leu
1               5                   10
```